United States Patent
Askew et al.

(10) Patent No.: US 6,878,714 B2
(45) Date of Patent: Apr. 12, 2005

(54) SUBSTITUTED ALKYLAMINE DERIVATIVES AND METHODS OF USE

(75) Inventors: Benny Askew, Newbury Park, CA (US); Jeffrey Adams, Thousand Oaks, CA (US); Shon Booker, Thousand Oaks, CA (US); Guoqing Chen, Thousand Oaks, CA (US); Lucian V. DiPietro, Gloucester, MA (US); Daniel Elbaum, Newton, MA (US); Julie Germain, Medford, MA (US); Stephanie D. Geuns-Meyer, Medford, MA (US); Gregory J. Habgood, Merrimac, MA (US); Michael Handley, Greenbrae, CA (US); Qi Huang, Moorpark, CA (US); Tae-Seong Kim, Thousand Oaks, CA (US); Aiwen Li, Westlake Village, CA (US); Nobuko Nishimura, West Hills, CA (US); Rana Nomak, Istanbul (TR); Vinod F. Patel, Acton, MA (US); Babak Riahi, Woodland Hills, CA (US); Joseph L. Kim, Wayland, MA (US); Ning Xi, Thousand Oaks, CA (US); Kevin Yang, San Gabriel, CA (US); Chester Chenguang Yuan, Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 94 days.

(21) Appl. No.: 10/197,974

(22) Filed: Jul. 17, 2002

(65) Prior Publication Data

US 2003/0225106 A1 Dec. 4, 2003

Related U.S. Application Data

(63) Continuation-in-part of application No. 10/046,681, filed on Jan. 10, 2002.
(60) Provisional application No. 60/323,764, filed on Sep. 19, 2001, and provisional application No. 60/261,339, filed on Jan. 12, 2001.

(51) Int. Cl.$^7$ .................. A61K 31/4427; C07D 401/12
(52) U.S. Cl. ...................... 514/256; 514/300; 514/314; 514/333; 514/336; 514/337; 544/333; 546/113; 546/175; 546/256; 546/262; 546/271.7; 546/282.1; 546/282.7
(58) Field of Search .......................... 544/333; 546/113, 546/175, 256, 262, 271.7, 282.1, 282.7; 514/256, 300, 314, 333, 336, 337

(56) References Cited

U.S. PATENT DOCUMENTS

| | | | |
|---|---|---|---|
| 3,226,394 A | 12/1965 | Schipper et al. | 260/295 |
| 5,532,358 A | 7/1996 | Kelly | 540/495 |
| 6,140,351 A | 10/2000 | Arnaiz et al. | 514/336 |
| 6,506,747 B1 * | 1/2003 | Betageri et al. | 514/228.8 |
| 6,624,174 B2 * | 9/2003 | Manley et al. | 514/310 |

FOREIGN PATENT DOCUMENTS

| | | |
|---|---|---|
| EP | 0 947 500 A1 | 10/1999 |
| EP | 1219609 A1 | 7/2002 |
| FR | 2 168 227 | 8/1973 |
| JP | 2000 256358 | 9/2000 |
| WO | WO 96/41795 | 12/1996 |
| WO | WO 98/24771 | 6/1998 |
| WO | WO 98/45268 | 10/1998 |
| WO | WO 99/32477 | 7/1999 |
| WO | WO 99/62885 | 12/1999 |
| WO | WO 00/02851 | 1/2000 |
| WO | WO 00/27819 | 5/2000 |
| WO | WO 00/27820 | 5/2000 |
| WO | WO 00/39111 | 7/2000 |
| WO | WO 00/39117 | 7/2000 |
| WO | WO 00/47212 | 8/2000 |
| WO | WO 01/29009 A1 | 4/2001 |
| WO | WO 01/30745 A1 | 5/2001 |
| WO | WO 01/55114 A1 | 8/2001 |
| WO | WO 01/55115 A1 | 8/2001 |
| WO | WO 01/81311 A1 | 11/2001 |
| WO | WO 01/85671 A2 | 11/2001 |
| WO | WO 01/85691 A1 | 11/2001 |
| WO | WO 01/85715 A2 | 11/2001 |
| WO | WO 02/055501 A2 | 7/2002 |
| WO | WO 02/066470 A1 | 8/2002 |

OTHER PUBLICATIONS

Betageri et al., Chemical Abstracts, vol. 132:22963, 1999.*
Singh, et al., "Substituted Imidazolines and Their CNS Activity" Ind.J.Het.Chem. 2: 129–132 (1992).
Seto, et al., "Molecular Self–Assembly through Hydrogen Bonding: Supramolecular Aggregates Based on the Cyanuric Acid•Melamine Lattice" J.Am.Chem.Soc. 115: 905–916 (1993).
Bold et al., "New Anilinophthalazines as Potent and Orally Well Absorbed Inhibitors of the VEGF Receptor Tyrosine Kinases Useful as Antagonists of Tumor–Driven Angiogenesis", J. Med. Chem . . . , 43:2310–2323 (2000).
Breier et al., "The role of vascular endothelial growth factor in blood vessel formation", Trends in Cell Biology, 6:454–456 (1996).
Connell et al., "Patent focus on cancer chemotherapeutics. II Angiogenesis agents: Apr. 2000—Sep. 2000", Exp. Opin. Ther. Patents, 11:77–114 (2001).

(Continued)

Primary Examiner—Richard L. Raymond
(74) Attorney, Agent, or Firm—Joseph W. Bulock

(57) ABSTRACT

Selected amines are effective for prophylaxis and treatment of diseases, such as angiogenesis mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

39 Claims, No Drawings

OTHER PUBLICATIONS

Hennequin et al., "Design and Structure–Activity Relationship of a New Class of Potent VEGF Receptor Tyrosine Kinase Inhibitor", J. Med. Chem., 42:5369–5389 (1999).

Konshin et al., Synthesis and antimicrobial activity of arylamides of N–(4–pyridyl)anthranilic acid, Chem. Abstr., 97:109837 (1981).

Sun et al., "Design, Synthesis and Evaluations of substituted 3–[(3– or 4–Carboxyethylpyrrol–2–yl)methylidenyl]indolin– 2–ones as Inhibitors of VEGF, FGF, PDGF Receptor Tyrosine Kinases", J. Med. Chem., 42:5120–5130 (1999).

* cited by examiner

SUBSTITUTED ALKYLAMINE DERIVATIVES AND METHODS OF USE

This application is a continuation-in-part of U.S. patent application Ser. No. 10/046,681 filed Jan. 10, 2002 which claims benefit of U.S. Provisional Application No. 60/261,339, filed Jan. 12, 2001, and No. 60/323,764 filed Sep. 19, 2001 which are hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Atk, bcr-ab1, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6, 454–6 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1–2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11, 77–114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Schipper U.S. Pat. No. 3,226,394, issued Dec. 28, 1965, describes anthranilamides as CNS depressants. Japanese patent JP2000256358 describes pyrazole derivatives that block the calcium release-activated calcium channel. EP application 9475000, published 6 Oct. 1999, describes compounds as $PGE_2$ antagonists. PCT publication WO96/41795, published 27 Dec. 1996, describes benzamides as vasopressin antagonists. WO01/29009 describes aminopyridines as KDR inhibitors. WO01/30745 describes anthranilic acids as CGMP phosphodiesterase inhibitors. WO00/02851, published 20 Jan 2000 describes arylsulfonylamnoaryl amides as guanylate cyclase activators. WO98/45268 describes nicotinamide derivatives as PDE4 inhibitors. WO98/24771 describes benzamides as vasopressin antagonists.

U.S. Pat. No. 5,532,358, issued Jul. 2, 1996, describes the preparation of 2-(cyclopropylamino)-N-(2-methoxy-4-methyl-3-pyridinyl)-3-pyridinecarboxamide as an intermediate for HIV inhibitors. Triazine-substituted amines are described for their aggregating ability (J. Amer. Chem. Soc., 115, 905–16 (1993). Substituted imidazolines were tested for their antidepressant activity in Ind. J. Het. Chem., 2, 129–32 (1992). N-(4-Pyridyl)anthranilic amides were described in Chem Abstr. 97:109837 (1981). PCT publication WO99/32477, published 1 Jul. 1999, describes anthranilamides as anti-coagulants. U.S. Pat. No. 6,140,351 describes anthranilamides as anti-coagulants. PCT publication WO99/62885, published 9 Dec. 1999, describes 1-(4-aminophenyl)pyrazoles as antiinflammatories. PCT publication WO00/39111, published 6 Jul. 2000, describes amides as factor Xa inhibitors. PCT publication WO00/39117, published 6 Jul. 2000, describes heteroaromatic amides as factor Xa inhibitors. PCT publication WO00/27819, published 18 May 2000, describes anthranilic acid amides as VEGF inhibitors. PCT publication WO00/27820 published 18 May 2000, describes N-aryl anthranilic acid amides as VEGF inhibitors. 7-Chloroquinolinylamines are described in FR2168227 as antiinflammatories. WO01/55114, published 2 Aug. 2001, describes nicotinamides for the treatment of cancer. WO01/55115, published 2 Aug. 2001, describes nicotinamides as inducers of apoptosis. WO01/85715, published 15 Nov. 2001, describes substituted pyridines and pyrimidines as anti-angiogenesis agents. PCT publication WO01/85691 published 15 Nov. 2001, describes anthranilic amides as VEGF inhibitors. PCT publication WO01/85671 published 15 Nov. 2001, describes anthranyl amides as VEGF inhibitors. PCT publication WO01/81311 published 1 Nov. 2001, describes anthranilic amides as VEGF inhibitors. However, compounds of the current invention have not been described as inhibitors of angiogenesis such as for the treatment of cancer.

DESCRIPTION OF THE INVENTION

A class of compounds useful in treating cancer and angiogenesis is defined by Formula I:

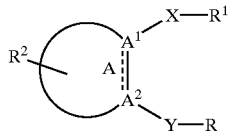

I wherein each of $A^1$ and $A^2$ is independently C, CH or N;
wherein ring A is selected from
  a) 5- or 6-membered partially saturated heterocyclyl,
    preferably dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl,
  b) 5- or 6-membered heteroaryl,
    preferably
    I) 5-membered heteroaryl selected from thienyl, furanyl, pyrrolyl, thiazolyl, oxazolyl, imidazolyl, pyrazolyl, isoxazolyl, triazolyl and isothiazolyl, even more preferably 5-membered heteroaryl selected from:

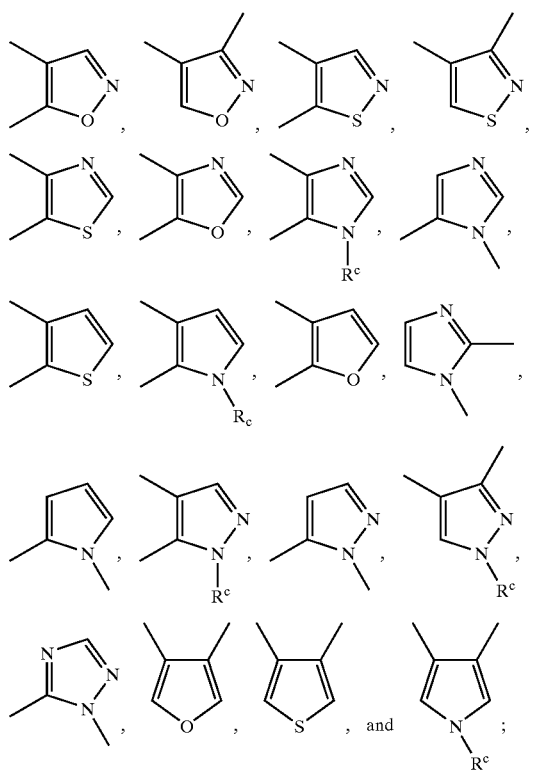

specifically

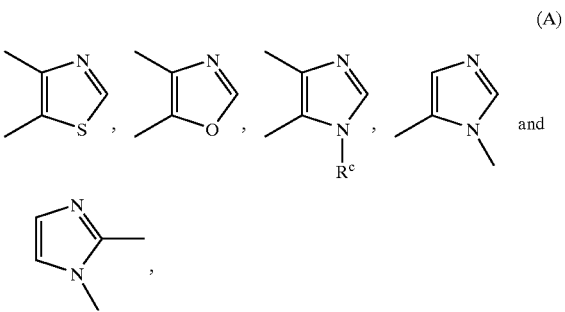

(A)

and

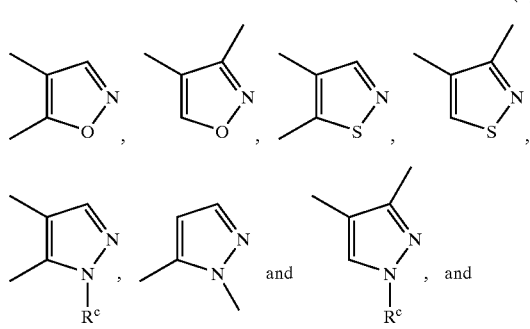

(B)

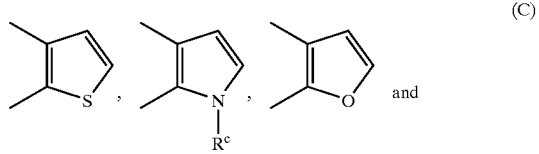

(C)

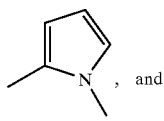, and

II) preferably 6-membered heteroaryl selected from pyridyl, pyrazinyl, pyrimidinyl, pyridazinyl, and triazinyl,
even more preferably 6-membered heteroaryl selected from:

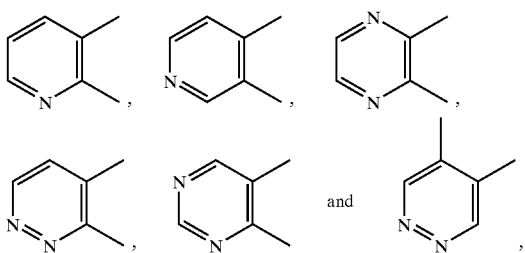

more specifically:

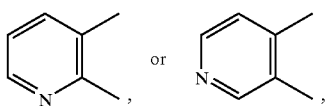

c) 9-, 10- or 11-membered fused partially saturated heterocyclyl
preferably tetrahydroquinolinyl,
d) 9- or 10-membered fused heteroaryl,
preferably
i) fused 9-membered fused heteroaryl selected from benzothienyl, benzothiazolyl, indolyl, benzimidazolyl, benzoxazolyl, benzofuryl, indazolyl and isoindolyl, and
ii) fused 10-membered heteroaryl selected from quinolyl, isoquinolyl, naphthpyridinyl, quinoxalinyl and quinazolinyl,
e) naphthyl, and
f) 4-, 5- or 6-membered cycloalkenyl,
preferably 5-membered cycloalkenyl,
more preferably cyclopentadienyl or cyclopentenyl;
wherein X is selected from:

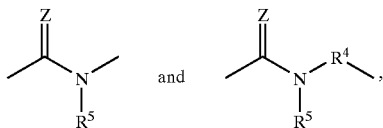

preferably X is selected from:

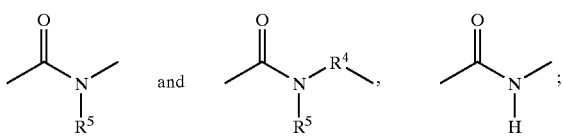

more preferably X is
wherein Z is oxygen or sulfur;
wherein Y is selected from:

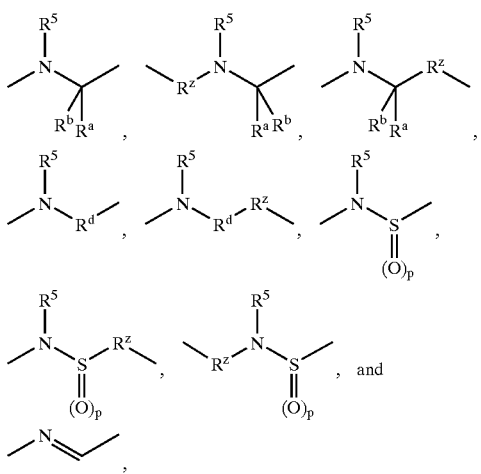

preferably Y is selected from:

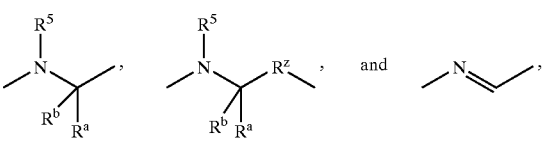

more preferably Y is selected from:

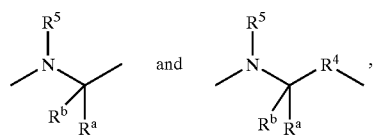

even more preferably Y is —NH—CH$_2$—;
wherein R$^a$ and R$^b$ are independently selected from H, halo, cyano and C$_{1-4}$-alkyl substituted with R$^2$, or wherein R$^a$ and R$^b$ together form C$_3$–C$_4$ cycloalkyl,
preferably H, halo, cyano and C$_{1-2}$-alkyl substituted with R$^2$, or wherein R$^a$ and R$^b$ together form C$_3$–C$_4$ cycloalkyl,
more preferably H, halo and C$_1$-C$_2$-alkyl,
even more preferably H;
wherein R$^z$ is selected from C$_1$–C$_4$ alkylenyl, where one of the CH$_2$ groups may be substituted with an oxygen atom or an —NH—,
preferably C$_1$–C$_2$ alkylenyl, where one of the CH$_2$ groups may be substituted with an oxygen atom or an —NH—
more preferably C$_1$–C$_2$ alkylenyl;
wherein R$^d$ is cycloalkyl,
preferably C$_3$–C$_6$ cycloalkyl;
wherein R is selected from
a) substituted or unsubstituted 5–6 membered heterocyclyl,
preferably substituted or unsubstituted 5–6 membered heteroaryl comprising one or more nitrogen atoms,
more preferably 4-pyrazolyl, triazolyl, 4-pyridyl, 4-pyrimidinyl, 5-pyrimidinyl, 6-pyrimidinyl, 4-pyridazinyl, or 6-pyridazinyl,
even more preferably 4-pyridyl, 4-pyrimidinyl and 4-pyridazinyl, even more preferably 4-pyridyl, and
b) substituted or unsubstituted fused 9-, 10- or 11-membered heterocyclyl,
   preferably substituted or unsubstituted 9–10 membered fused heteroaryl comprising one or more nitrogen atoms,
      more preferably indazolyl, quinolinyl, isoquinolinyl, or quinazolinyl,
         even more preferably indazolyl, 4-quinolyl, 5-quinolyl, 6-quinolyl, 4-isoquinolyl, 5-isoquinolyl, and 6-isoquinolyl,
   wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, cycloalkyl, optionally substituted 5–6 membered heterocyclyl, optionally substituted phenyl, lower alkyl substituted with $R^2$, cyano, nitro, lower alkenyl and lower alkynyl;
      preferably halo, —$OR^3$, —$SR^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, —$NR^3C(O)NR^3R^3$, cycloalkyl, optionally substituted 5–6 membered heterocyclyl, optionally substituted phenyl, $C_{1-2}$-alkyl, cyano, $C_{1-2}$-hydroxyalkyl, nitro and $C_{1-2}$-haloalkyl;
wherein $R^1$ is selected from
a) substituted or unsubstituted 6–10 membered aryl,
   preferably phenyl, naphthyl, indenyl, or tetrahydronaphthyl,
      more preferably phenyl,
b) substituted or unsubstituted 5–6 membered heterocyclyl,
   preferably 5–6 membered heteroaryl,
      more preferably thienyl, pyridyl, pyrimidinyl, pyridazinyl, pyrazolyl, imidazolyl, oxazolyl, thiazolyl, thiadiazolyl, furyl, or pyrrolyl,
c) substituted or unsubstituted 9–10 membered fused heterocyclyl,
   preferably 9–10 membered fused heteroaryl,
      more preferably indazolyl, indolyl, 2,1,3-benzothiadiazolyl, isoquinolyl, quinolyl, tetrahydroquinolyl, benzodioxanyl, or quinazolinyl,
d) cycloalkyl, and
e) cycloalkenyl
   wherein substituted $R^1$ is substituted with one or more substituents independently selected from halo, —$OR^3$, —$SR^3$, —$CO_2R^3$, —$CONR^3R^3$, —$COR^3$, —$NR^3R^3$, —$NH(C_1-C_4$ alkylenyl$R^{14}$), —$SO_2R^3$, —$SO_2NR^3R^3$, —$NR^3C(O)OR^3$, —$NR^3C(O)R^3$, optionally substituted cycloalkyl, optionally substituted 5–6 membered heterocyclyl, optionally substituted phenyl, lower alkyl substituted with $R^2$, cyano, nitro, lower alkenyl and lower alkynyl,
      preferably $R^1$ is unsubstituted or substituted with one or more substituents independently selected from halo, —$OR^3$, —$SR^3$, —$SO_2R^3$, —$CO_2R^3$, —$CONR^3R^3$, —$COR^3$, —$NR^3R^3$, —$NH(C_1-C_2$ alkylenyl$R^3$), —$(C_1-C_2$ alkylenyl)$NR^3R^3$, —$SO_2NR^3R^3$, —$NR^3C(O)OR^3$, —$NR^3C(O)R^3$, optionally substituted cycloalkyl, optionally substituted 5–6 membered heterocyclyl, optionally substituted phenyl, optionally substituted phenyl-$C_{1-2}$-alkylenyl, optionally substituted 5–6 membered heterocyclyl-$C_1-C_2$-alkylenyl, $C_{1-2}$-alkyl, cyano, $C_{1-2}$-hydroxyalkyl, nitro and $C_{1-2}$-haloalkyl,
         more preferably $R^1$ is unsubstituted or substituted with one or more substituents selected from chloro, fluoro, bromo, methoxy, phenyloxy, benzyl, methylthio, methyl, ethyl, trifluoromethyl, difluoromethyl, pentafluoroethyl, hydroxymethyl, cyano, carboxy, aminocarbonyl, methylcarbonyl, amino, methylamino, cyclopropyl, cyclohexyl, piperidinyl, morpholinyl, N-methylpiperazinyl, N-ethylpiperazinyl, morpholinylmethyl, methylpiperdinylmethyl, methylpiperazinylmethyl, methylaminothiocarbonyl, N-methylamino-methylenyl, optionally substituted phenyl, N,N-diethylamino, or N,N-dimethylamino;
wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$, —$NR^3C(O)OR^3$, —$NR^3C(O)R^3$, cycloalkyl, optionally substituted phenylalkylenyl, optionally substituted 5–6 membered heterocyclyl, optionally substituted heteroarylalkylenyl, optionally substituted phenyl, lower alkyl, cyano, lower hydroxyalkyl, lower carboxyalkyl, nitro, lower alkenyl, lower alkynyl, lower aminoalkyl, lower alkylaminoalkyl and lower haloalkyl,
   preferably $R^2$ is one or more substituents independently selected from H, halo, —$OR^3$, oxo, —$SR^3$, —$CO_2R^3$—$CONR^3R^3$, —$COR^3$, —$NR^3R^3$, —$SO_2NR^3R^3$, —$NR^3C(O)OR^3$, —$NR^3C(O)R^3$, cycloalkyl, optionally substituted 5–6 membered heterocyclyl, optionally substituted phenyl, $C_{1-2}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl;
wherein $R^3$ is selected from H, lower alkyl, phenyl, 5–6 membered heterocyclyl, $C_3-C_6$ cycloalkyl, and lower haloalkyl,
   preferably H, $C_{1-2}$-alkyl, phenyl, $C_3-C_6$ cycloalkyl, and $C_{1-2}$-haloalkyl,
      more preferably H, methyl, phenyl, cyclopropyl, cyclohexyl, and trifluoromethyl;
wherein $R^4$ is independently selected from $C_{2-4}$-alkylenyl, $C_{2-4}$-alkenylenyl and $C_{2-4}$-alkynylenyl, where one of the $CH_2$ groups may be substituted with an oxygen atom or an —NH—,
   preferably $C_{2-3}$-alkylenyl where one of the $CH_2$ groups may be substituted with an oxygen atom or an —NH—,
      more preferably $C_2-C_3$ alkylenyl;
wherein $R^5$ is selected from H, lower alkyl, phenyl and lower aralkyl,
   preferably H, methyl or ethyl;
wherein $R^6$ is selected from H or $C_{1-6}$-alkyl,
   preferably H or $C_{1-2}$ alkyl; and
wherein $R^c$ is selected from H, methyl and optionally substituted phenyl;
wherein $R^{14}$ is selected from H, phenyl, 5–6 membered heterocyclyl and $C_3-C_6$ cycloalkyl;
wherein p is 0 to 2, preferably p is 2;
and pharmaceutically acceptable salts thereof; provided A is not naphthyl when X is —C(O)NH— and when $R^1$ is phenyl when Y is —$NHCH_2$— and when R is 4-pyridyl; further provided A is not pyridyl when X is —C(O)NH— and when $R^1$ is 4-[3,5-bis(trifluoromethyl)-1H-pyrazol-1-yl]phenyl when Y is —$N(CH_3)$— and when R is 4-methylpiperidinyl; further provided A is not pyridyl when X is —C(O)NH— and when Y is —$NHCH_2$— and when R is 4-pyridylpiperidin-4-yl, 1-tertbutylpiperidin-4- yl, 1-isopropylpiperidin-4-yl or 1-cycloalkylpiperidin-4-yl; further provided A is not pyridyl when X is —C(O)NH— and when $R^1$ is 4-[3-(3-pyridyl)-5-(trifluoromethyl)-1H-pyrazol-1-yl]phenyl when Y is —NHCH$_2$— and when R is 4-pyridyl; and further provided R is not unsubstituted 2-thienyl, 2-pyridyl or 3-pyridyl.

The invention also relates to compounds of Formula II:

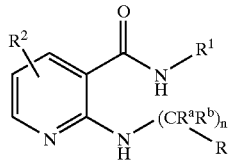

II wherein $R^a$ and $R^b$ are independently selected from H, halo, $C_{1-4}$-alkyl and —N($R^6$)$_2$,
preferably H;
wherein n is 0–2;
preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, triazolyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, $C_{1-6}$-alkyl, $C_{1-6}$-haloalkyl and $C_{1-6}$-alkoxy,
    preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula III:

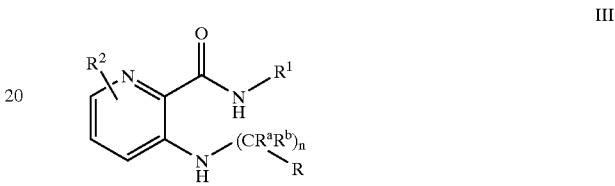

III wherein $R^a$ and $R^b$ are independently selected from H, halo, $C_{1-4}$-alkyl and —N($R^6$)$_2$,
preferably H;
wherein n is 0–2;
preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, $C_{1-6}$-alkyl, $C_{1-6}$-haloalkyl and $C_{1-6}$-alkoxy,
    preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
  H,
  halo,
  $C_{1-6}$-alkyl,
  $C_{1-6}$-haloalkyl,
  $C_{1-6}$-alkoxy,
  $C_{1-6}$-haloalkoxy,
  $C_{1-6}$-carboxyalkyl,
  unsubstituted or substituted aryl and
  unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula IV:

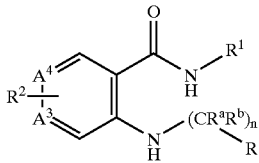

IV wherein $A^3$ is selected from $CR^2$ and N;
wherein $A^4$ is selected from $CR^2$ and N; provided one of $A^3$ and $A^4$ is not $CR^2$;
wherein $R^a$ and $R^b$ are independently selected from H, halo, $C_{1-4}$-alkyl and —$N(R^6)_2$,
  preferably H;
wherein n is 0–2;
  preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, $C_{1-6}$-alkyl, $C_{1-6}$-haloalkyl and $C_{1-6}$-alkoxy,
    preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
    preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
  H,
  halo,
  $C_{1-6}$-alkyl,
  $C_{1-6}$-haloalkyl,
  $C_{1-6}$-alkoxy,
  $C_{1-6}$-haloalkoxy,
  $C_{1-6}$-carboxyalkyl,
  unsubstituted or substituted aryl and
  unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula V:

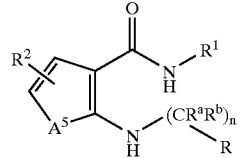

V wherein $A^5$ is selected from S, O and $NR^6$;
wherein $R^a$ and $R^b$ are independently selected from H, halo, $C_{1-4}$-alkyl and —$N(R^6)_2$,
  preferably H;
wherein n is 0–2;
  preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, $C_{1-6}$-alkyl, $C_{1-6}$-haloalkyl and $C_{1-6}$-alkoxy,
    preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
  wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
    preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
  H,
  halo,
  $C_{1-6}$-alkyl,
  $C_{1-6}$-haloalkyl,
  $C_{1-6}$-alkoxy,
  $C_{1-6}$-haloalkoxy,
  $C_{1-6}$-carboxyalkyl,
  unsubstituted or substituted aryl and
  unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula VI:

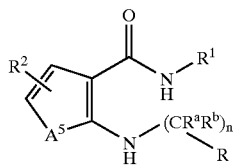

VI wherein $A^5$ is selected from S, O and $NR^6$;
wherein $R^a$ and $R^b$ are independently selected from H, halo, $C_{1-4}$-alkyl and —$N(R^6)_2$,
  preferably H;
wherein n is 0–2;
  preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, $C_{1-6}$-alkyl, $C_{1-6}$-haloalkyl and $C_{1-6}$-alkoxy,
    preferably substituted with one or more substituents selected from chloro, fluoro, amino, hydroxy, methyl, ethyl, propyl, trifluoromethyl, methoxy and ethoxy;

wherein $R^1$ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein $R^2$ is one or more substituents independently selected from
  H,
  halo,
  $C_{1-6}$-alkyl,
  $C_{1-6}$-haloalkyl,
  $C_{1-6}$-alkoxy,
  $C_{1-6}$-haloalkoxy,
  $C_{1-6}$-carboxyalkyl,
  unsubstituted or substituted aryl and
  unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula VII:

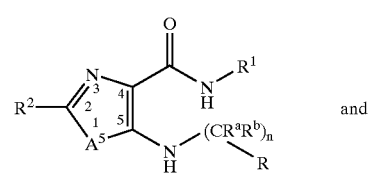

VII and

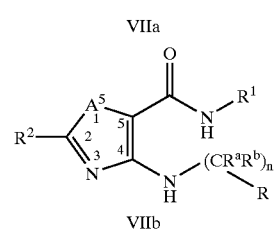

VIIa

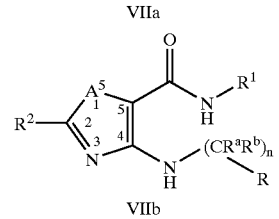

VIIb wherein A⁵ is selected from S, O and NR⁶;
wherein R^a and R^b are independently selected from H, halo, C_{1-4}-alkyl and —N(R⁶)₂,
  preferably H;
wherein n is 0–2;
  preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, C_{1-6}-alkyl, C_{1-6}-haloalkyl and C_{1-6}-alkoxy,
    preferably substituted with one or more substituents selected from chloro, fluoro, amino, hydroxy, methyl, ethyl, propyl, trifluoromethyl, methoxy and ethoxy;
wherein R¹ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein R¹ is substituted with one or more substituents selected from halo, C_{1-6}-alkyl, optionally substituted C_{3-6}-cycloalkyl, optionally substituted phenyl, C_{1-6}-haloalkoxy, optionally substituted phenyloxy, benzyl, optionally substituted 5–6 membered heterocyclyl-C_{1}-C_{2}-alkylenyl, optionally substituted heteroaryl, optionally substituted heteroaryloxy, C_{1-6}-haloalkyl, and C_{1-6}-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein R² is one or more substituents independently selected from
  H,
  halo,
  C_{1-6}-alkyl,
  C_{1-6}-haloalkyl,
  C_{1-6}-alkoxy,
  C_{1-6}-haloalkoxy,
  C_{1-6}-carboxyalkyl,
  unsubstituted or substituted aryl and
  unsubstituted or substituted 5–6 membered heteroaryl;
  preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl; and
wherein R⁶ is H or C_{1-2}-alkyl;
and pharmaceutically acceptable isomers and salts thereof.

The invention also relates to compounds of Formula

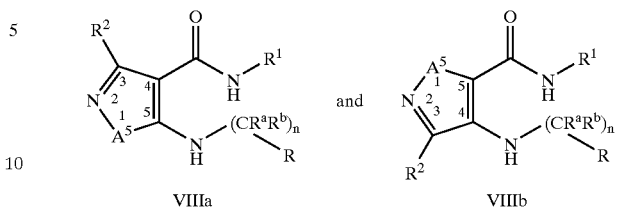

VIII

VIIIa    VIIIb wherein A⁵ is selected from S, O and NR⁶;
wherein R^a and R^b are independently selected from H, halo, C_{1-4}-alkyl and —N(R⁶)₂,
  preferably H;
wherein n is 0–2;
  preferably 1–2;
wherein R is selected from
  a) unsubstituted or substituted 5- or 6-membered nitrogen-containing heteroaryl, and
  b) unsubstituted or substituted 9- or 10-membered fused nitrogen-containing heteroaryl,
    preferably 4-pyridyl, pyrimidinyl, pyridazinyl, indolyl, isoindolyl, indazolyl, quinolyl, isoquinolyl, naphthyridinyl or quinozalinyl,
  where R is substituted with one or more substituents selected from halo, amino, hydroxy, C_{1-6}-alkyl, C_{1-6}-haloalkyl and C_{1-6}-alkoxy,
    preferably substituted with one or more substituents selected from chloro, fluoro, amino, hydroxy, methyl, ethyl, propyl, trifluoromethyl, methoxy and ethoxy;
wherein R¹ is selected from unsubstituted or substituted aryl, 5–6-membered heteroaryl and 9–10 membered fused heteroaryl,
  preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
    wherein R¹ is substituted with one or more substituents selected from halo, C_{1-6}-alkyl, optionally substituted C_{3-6}-cycloalkyl, optionally substituted phenyl, C_{1-6}-haloalkoxy, optionally substituted phenyloxy, benzyl, optionally substituted 5–6 membered heterocyclyl-C_{1}-C_{2}-alkylenyl, optionally substituted heteroaryl, optionally substituted heteroaryloxy, C_{1-6}-haloalkyl, and C_{1-6}-alkoxy,
      preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;
wherein R² is one or more substituents independently selected from
  H,
  halo,
  C_{1-6}-alkyl,
  C_{1-6}-haloalkyl,
  C_{1-6}-alkoxy,
  C_{1-6}-haloalkoxy,
  C_{1-6}-carboxyalkyl, unsubstituted or substituted aryl and
unsubstituted or substituted 5–6 membered heteroaryl;
preferably one or more substituents independently
selected from H, chloro, fluoro, bromo, amino,
hydroxy, methyl, ethyl, propyl, trifluoromethyl,
methoxy, ethoxy, trifluoromethoxy, carboxymethyl,
unsubstituted or substituted phenyl and unsubstituted
or substituted heteroaryl selected from thienyl, furanyl,
pyridyl, imidazolyl, and pyrazolyl; and
wherein $R^6$ is H or $C_{1-2}$-alkyl;
and pharmaceutically acceptable isomers and salts thereof.

The invention also relates to compounds of Formula IX:

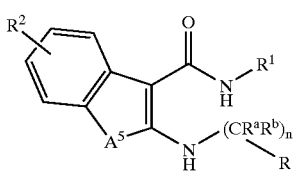

IX wherein $A^5$ is selected from S, O and $NR^6$;
wherein $R^a$ and $R^b$ are independently selected from H, halo, $C_{1-4}$-alkyl and $—N(R^6)_2$,
preferably H;
wherein n is 0–2;
preferably 1–2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy,
preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5–6 membered heteroaryl;
preferably one or more substituents independently
selected from H, chloro, fluoro, bromo, amino,
hydroxy, methyl, ethyl, propyl, trifluoromethyl,
methoxy, ethoxy, trifluoromethoxy, carboxymethyl,
unsubstituted or substituted phenyl and unsubstituted
or substituted heteroaryl selected from thienyl,
furanyl, pyridyl, imidazolyl, and pyrazolyl; and
wherein $R^6$ is H or $C_{1-2}$-alkyl;
and pharmaceutically acceptable isomers and salts thereof.

The invention also relates to compounds of Formula X:

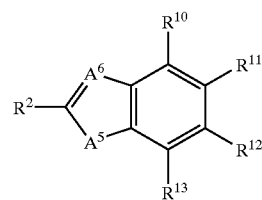

X wherein $A^5$ is selected from S, O and $NR^6$;
wherein $A^6$ is selected from N and $CR^2$;
wherein $R^a$ and $R^b$ are independently selected from H, halo, $C_{1-4}$-alkyl and $—N(R^6)_2$,
preferably H;
wherein n is 0–2;
preferably 1–2;
wherein R is selected from
a) unsubstituted or substituted 5- or 6-membered nitrogen-containing heteroaryl, and
b) unsubstituted or substituted 9- or 10-membered fused nitrogen-containing heteroaryl,
preferably 4-pyridyl, pyrimidinyl, pyridazinyl, indolyl, isoindolyl, indazolyl, quinolyl, isoquinolyl, naphthyridinyl or quinozalinyl,
where R is substituted with one or more substituents selected from halo, amino, hydroxy, $C_{1-6}$-alkyl, $C_{1-6}$-haloalkyl and $C_{1-6}$-alkoxy,
preferably substituted with one or more substituents selected from chloro, fluoro, amino, hydroxy, methyl, ethyl, propyl, trifluoromethyl, methoxy and ethoxy;
wherein $R^1$ is selected from unsubstituted or substituted aryl, 5–6-membered heteroaryl and 9–10 membered fused heteroaryl,
preferably unsubstituted or substituted phenyl, tetrahydronaphthyl, naphthyl, isoquinolyl, quinolyl, pyridyl, pyrimidinyl, pyridazinyl, indolyl, isoindolyl, naphthyridinyl, quinozalinyl, tetrahydroquinolinyl, indazolyl, benzothienyl, benzofuryl, benzimidazolyl, benzoxazolyl, or benzthiazolyl,
wherein $R^1$ is substituted with one or more substituents selected from halo, $C_{1-6}$-alkyl, optionally substituted $C_{3-6}$-cycloalkyl, optionally substituted phenyl, $C_{1-6}$-haloalkoxy, optionally substituted phenyloxy, benzyl, optionally substituted 5–6 membered heterocyclyl-$C_1$-$C_2$-alkylenyl, optionally substituted heteroaryl, optionally substituted heteroaryloxy, $C_{1-6}$-haloalkyl, and $C_{1-6}$-alkoxy,
preferably chloro, fluoro, amino, hydroxy, cyclohexyl, phenylmethyl, morpholinylmethyl, methylpiperdinylmethyl, methylpiperazinylmethyl, ethyl, propyl, trifluoromethyl, phenyloxy, methoxy and ethoxy;

wherein $R^2$ is one or more substituents independently selected from
H,
halo,
$C_{1-6}$-alkyl,
$C_{1-6}$-haloalkyl,
$C_{1-6}$-alkoxy,
$C_{1-6}$-haloalkoxy,
$C_{1-6}$-carboxyalkyl,
unsubstituted or substituted aryl and
unsubstituted or substituted 5–6 membered heteroaryl;
preferably one or more substituents independently selected from H, chloro, fluoro, bromo, amino, hydroxy, methyl, ethyl, propyl, trifluoromethyl, methoxy, ethoxy, trifluoromethoxy, carboxymethyl, unsubstituted or substituted phenyl and unsubstituted or substituted heteroaryl selected from thienyl, furanyl, pyridyl, imidazolyl, and pyrazolyl;

wherein:

a) $R^{10}$ is

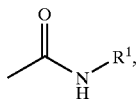

$R^{11}$ is

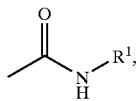

$R^{12}$ is H, and $R^{13}$ is H; or b) $R^{10}$ is

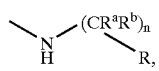

$R^{11}$ is

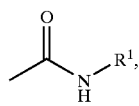

$R^{12}$ is H, and $R^{13}$ is H; or c) $R^{10}$ is H, $R^{11}$ is

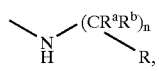

$R^{12}$ is

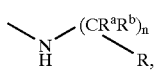

and $R^{13}$ is H; or d) $R^{10}$ is H, $R^{11}$ is

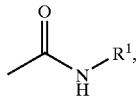

$R^{12}$ is

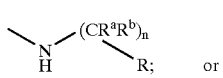

and $R^{13}$ is H; or e) $R^{10}$ is H, $R^{11}$ is H, $R^{12}$ is

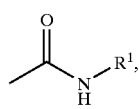

and $R^{13}$ is

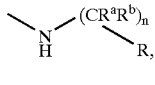; or or f) $R^{10}$ is H, $R^{11}$ is H, $R^{12}$ is

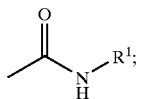

and $R^{13}$ is

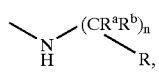; and wherein $R^6$ is H or $C_{1-2}$-alkyl;
and pharmaceutically acceptable isomers and salts thereof.

The invention also relates to compounds of Formula II':

II'

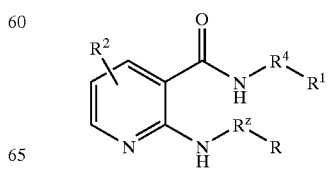

wherein R is selected from
- a) unsubstituted or substituted 5- or 6-membered nitrogen-containing heteroaryl,
  preferably 4-pyridyl, 3-pyridyl, 2-pyridyl, pyrimidinyl, triazolyl, and pyridazinyl,
  more preferably 4-pyridyl, and
- b) unsubstituted or substituted 9- or 10-membered fused heterocyclyl
  preferably indolyl, isoindolyl, indazolyl, quinolyl, isoquinolyl, benzotriazolyl, 2,3-dihydrobenzofuryl, 2-oxo-1,2-dihydroquinol-7-yl, naphthyridinyl and quinozalinyl,
  where substituted R is substituted with one or more substituents selected from halo, amino, hydroxy, oxo, $C_{1-6}$-alkyl, $C_{1-6}$-haloalkyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl,
    preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;

wherein $R^1$ is selected from unsubstituted or substituted
  aryl, preferably phenyl, tetrahydronaphthyl, indanyl, indenyl, and naphthyl,
  cycloalkyl, preferably cyclohexyl,
  5–6 membered heteroaryl, preferably isoxazolyl, pyrazolyl, thiazolyl, thiadiazolyl, thienyl, pyridyl, pyrimidinyl, and pyridazinyl, and
  9–10 membered bicyclic and 13–14 membered tricyclic heterocyclyl, preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, dihydro-benzimidazolyl, benzimidazolyl, benzoxazolyl and benzthiazolyl;

wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted 4–6 membered heterocyclyl-$C_1$-$C_4$-alkylenyl, optionally substituted 4–6 membered heterocyclyl-$C_2$-$C_4$-alkenylenyl, optionally substituted 4–6 membered heterocyclyl, optionally substituted phenyloxy, optionally substituted 4–6 membered heterocyclyloxy, optionally substituted 4–6 membered heterocyclyl-$C_{1-4}$-alkyloxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, $C_{1-2}$-haloalkyl, $C_{1-4}$-aminoalkyl, nitro, amino, —NHC(O)NH$_2$, alkylcarbonylamino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

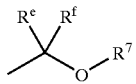

and $C_{1-4}$-alkoxy, preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from
  H,
  halo,
  hydroxy,
  amino,
  $C_{1-6}$-alkyl,
  $C_{1-6}$-haloalkyl,
  $C_{1-6}$-alkoxy,
  $C_{1-2}$-alkylamino,
  aminosulfonyl,
  $C_{3-6}$-cycloalkyl,
  cyano,
  $C_{1-2}$-hydroxyalkyl,
  nitro,
  $C_{2-3}$-alkenyl, C$_{2-3}$-alkynyl,
C$_{1-6}$-haloalkoxy,
C$_{1-6}$-carboxyalkyl,
5–6-membered heterocyclyl-C$_{1-6}$-alkylamino,
unsubstituted or substituted phenyl and
unsubstituted or substituted 5–6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl;
wherein R$^4$ is selected from a direct bond, C$_{1-4}$-alkyl, and
preferably a direct bond, ethyl, butyl, and

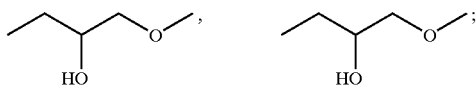

wherein R$^z$ is selected from C$_{1-2}$-alkyl, C$_{2-6}$-branched alkyl, C$_{2-4}$-branched haloalkyl, amino-C$_{1-4}$-alkyl and C$_{1-2}$-alkylamino-C$_{1-2}$-alkyl,
preferably methylenyl, ethylenyl,

and aminoethylenyl;
wherein R$^e$ and R$^f$ are independently selected from H and C$_{1-2}$-haloalkyl,
preferably trifluoromethyl; and
wherein R$^7$ is selected from H, C$_{1-3}$-alkyl, optionally substituted phenyl, optionally substituted phenyl-C$_{1-3}$-alkyl, optionally substituted 4–6 membered heterocyclyl, optionally substituted 4–6 membered heterocyclyl-C$_1$-C$_3$-alkyl, C$_{1-3}$-alkylamino-C$_{1-3}$-alkyl, C$_{1-3}$-alkoxy-C$_{1-2}$-alkyl and C$_{1-3}$-alkoxy-C$_{1-3}$-alkoxy-C$_{1-3}$-alkyl;
provided R$^2$ is not H, or provided R$^1$ is not heteroaryl or aryl or provided R is substituted with optionally substituted heterocyclyl-C$_{1-6}$-alkoxy, optionally substituted heterocyclyl-C$_{1-6}$-alkylamino, optionally substituted heterocyclyl-C$_{1-6}$-alkyl, C$_{1-6}$-alkylamino-C$_{2-4}$-alkynyl, C$_{1-6}$-alkylamino-C$_{1-6}$-alkoxy, C$_{1-6}$-alkylamino-C$_{1-6}$-alkoxy-C$_{1-6}$-alkoxy, or optionally substituted heterocyclyl-C$_{2-4}$-alkynyl, or R$^1$ is substituted with optionally substituted phenyloxy, optionally substituted 5–6 membered heterocyclyloxy, optionally substituted 5–6 membered heterocyclylsulfonyl, optionally substituted 5–6 membered heterocyclylamino, optionally substituted 5–6 membered heterocyclylcarbonyl, optionally substituted 5–6 membered heterocyclyl-C$_{1-4}$-alkylcarbonyl, C$_{1-3}$-alkylamino-C$_{1-3}$-alkoxy, or C$_{1-3}$-alkylamino-C$_{1-3}$-alkoxy-C$_{1-3}$-alkoxy; further provided R is not 3-pyridyl when R$^z$ is CH$_2$;
and pharmaceutically acceptable isomers and derivatives thereof.

The invention also relates to compounds of Formula XI

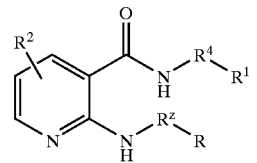

XI wherein R is selected from
a) unsubstituted or substituted 5- or 6-membered nitrogen-containing heteroaryl,
preferably 4-pyridyl, 3-pyridyl, 2-pyridyl, pyrimidinyl, triazolyl, and pyridazinyl, more preferably 4-pyridyl, and
b) unsubstituted or substituted 9- or 10-membered fused heteroaryl
preferably indolyl, isoindolyl, indazolyl, quinolyl, isoquinolyl, benzotriazolyl, naphthyridinyl and quinozalinyl,
where substituted R is substituted with one or more substituents selected from halo, amino, hydroxy, C$_{1-6}$-alkyl, C$_{1-6}$-haloalkyl, C$_{1-6}$-alkoxy, optionally substituted heterocyclyl-C$_{1-6}$-alkoxy, optionally substituted heterocyclyl-C$_{1-6}$-alkylamino, optionally substituted heterocyclyl-C$_{1-6}$-alkyl, C$_{1-6}$-alkylamino-C$_{2-4}$-alkynyl, C$_{1-6}$-alkylamino-C$_{1-6}$-alkoxy, C$_{1-6}$-alkylamino-C$_{1-6}$-alkoxy-C$_{1-6}$-alkoxy, and optionally substituted heterocyclyl-C$_{2-4}$-alkynyl,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein R$^1$ is selected from unsubstituted or substituted
aryl,
cycloalkyl,
5–6 membered heteroaryl and
9–10 membered bicyclic and 13–14 membered tricyclic heterocyclyl,
preferably phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, dihydro-benzimidazolyl, benzimidazolyl, benzoxazolyl and benzthiazolyl,
specifically 4–6 membered saturated or partially un-saturated monocyclic heterocyclyl,
9–10 membered saturated or partially un-saturated bicyclic heterocyclyl, and
13–14 membered saturated or partially un-saturated tricyclic heterocyclyl,
more specifically 1,2-dihydroquinolyl, 1,2,3,4-tetrahydro-isoquinolyl, 2,3-dihydro-1H-indolyl, benzo[d]isothiazolyl, dihydro-benzimidazolyl, 2,3,4,4a,9,9a-hexahydro-1H-3-aza-fluorenyl, 5,6,7-trihydro-1,2,4-triazolo[3,4-a]isoquinolyl, and tetrahydroquinolinyl, wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted 4–6 membered heterocyclyl-$C_1$-$C_4$-alkyl, optionally substituted 4–6 membered heterocyclyl-$C_2$-$C_4$-alkenyl, optionally substituted 4–6 membered heterocyclyl, optionally substituted phenyloxy, optionally substituted 4–6 membered heterocyclyloxy, optionally substituted 4–6 membered heterocyclyl-$C_1$-$C_4$-alkoxy, optionally substituted 4–6 membered heterocyclylsulfonyl, optionally substituted 4–6 membered heterocyclylamino, optionally substituted 4–6 membered heterocyclylcarbonyl, optionally substituted 5–6 membered heterocyclyl-$C_{1-4}$-alkylcarbonyl, $C_{1-2}$-haloalkyl, $C_{1-4}$-aminoalkyl, nitro, amino, hydroxy, oxo, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

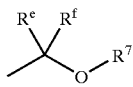

and $C_{1-4}$-alkoxy,
preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 5–6 membered heterocyclyl,
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinyl-ethylamino, propynyl, unsubstituted or substituted phenyl and unsubstituted or substituted
heteroaryl selected from thienyl, furanyl, pyridyl, imidazolyl, and pyrazolyl,
specifically chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinyl-ethylamino, propynyl, unsubstituted or substituted phenyl and unsubstituted or substituted
heteroaryl selected from thienyl, furanyl, pyridyl, imidazolyl, and pyrazolyl;
wherein $R^4$ is selected from a direct bond, $C_{1-4}$-alkyl, and preferably a direct bond, ethyl, butyl, and

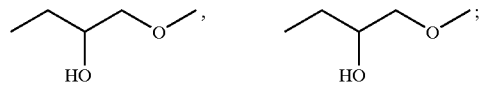

wherein $R^z$ is selected from $C_{1-2}$-alkyl, $C_{2-6}$-branched alkyl, $C_{2-4}$-branched haloalkyl, amino-$C_{1-4}$-alkyl and $C_{1-2}$-alkylamino-$C_{1-2}$-alkyl,
preferably methylenyl, ethylenyl,

and aminoethylenyl;
wherein $R^e$ and $R^f$ are independently selected from H and $C_{1-2}$-haloalkyl,
preferably trifluoromethyl; and
wherein $R^7$ is selected from H, $C_{1-3}$-alkyl, optionally substituted phenyl, optionally substituted phenyl-$C_{1-3}$-alkyl, optionally substituted 4–6 membered heterocyclyl, optionally substituted 4–6 membered heterocyclyl-C$_{1-}$C$_3$-alkyl, C$_{1-3}$-alkoxy-C$_{1-2}$-alkyl and C$_{1-3}$-alkoxy-C$_{1-3}$-alkoxy-C$_{1-3}$-alkyl;

provided R$^1$ is substituted with optionally substituted phenyloxy, optionally substituted 4–6 membered heterocyclyloxy, optionally substituted 4–6 membered heterocyclyl-C$_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-C$_{1-4}$-alkylcarbonyl, C$_{1-3}$-alkylamino-C$_{1-3}$-alkoxy, or C$_{1-3}$-alkylamino-C$_{1-3}$-alkoxy-C$_{1-3}$-alkoxy; further provided R is not 3-pyridyl when R$^5$ is CH$_2$;

and pharmaceutically acceptable isomers and derivatives thereof.

The invention also relates to compounds of Formula XII

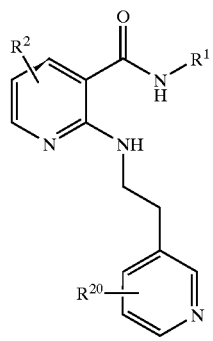

XII wherein R$^1$ is selected from unsubstituted or substituted
aryl, preferably phenyl, tetrahydronaphthyl, indanyl, indenyl, and naphthyl,
cycloalkyl, preferably cyclohexyl,
5–6 membered heteroaryl, preferably isoxazolyl, pyrazolyl, thiazolyl, thiadiazolyl, thienyl, pyridyl, pyrimidinyl, and pyridazinyl, and
9–10 membered bicyclic and 13–14 membered tricyclic heterocyclyl, preferably 1,2-dihydroquinolyl, 1,2,3,4-tetrahydro-isoquinolyl, isoquinolyl, quinolyl, indolyl, isoindolyl, 2,3-dihydro-1H-indolyl, naphthyridinyl, quinozalinyl, benzo[d]isothiazolyl, 2,3,4,4a,9,9a-hexahydro-1H-3-aza-fluorenyl, 5,6,7-trihydro-1,2,4-triazolo [3,4-a]isoquinolyl, tetrahydroquinolinyl, indazolyl, 2,1,3-benzothiadiazolyl, benzodioxanyl, benzothienyl, benzofuryl, benzimidazolyl, benzoxazolyl and benzthiazolyl;

wherein substituted R$^1$ is substituted with one or more substituents selected from halo, C$_{1-6}$-alkyl, optionally substituted C$_{3-6}$-cycloalkyl, optionally substituted phenyl, optionally substituted phenyl-C$_{1-}$C$_4$-alkylenyl, C$_{1-2}$-haloalkoxy, optionally substituted 4–6 membered heterocyclyl-C$_{1-}$C$_4$-alkyl, optionally substituted 4–6 membered heterocyclyl-C$_{2-}$C$_4$-alkenyl, optionally substituted 4–6 membered heterocyclyl, optionally substituted phenyloxy, optionally substituted 4–6 membered heterocyclyloxy, optionally substituted 4–6 membered heterocyclyl-C$_{1-}$C$_4$-alkoxy, optionally substituted 4–6 membered heterocyclylsulfonyl, optionally substituted 4–6 membered heterocyclylamino, optionally substituted 4–6 membered heterocyclylcarbonyl, optionally substituted 5–6 membered heterocyclyl-C$_{1-4}$-alkylcarbonyl, C$_{1-2}$-haloalkyl, C$_{1-4}$-aminoalkyl, nitro, amino, hydroxy, oxo, cyano, aminosulfonyl, C$_{1-2}$-alkylsulfonyl, halosulfonyl, C$_{1-4}$-alkylcarbonyl, C$_{1-3}$-alkylamino-C$_{1-3}$-alkyl, C$_{1-3}$-alkylamino-C$_{1-3}$-alkoxy, C$_{1-3}$-alkylamino-C$_{1-3}$-alkoxy-C$_{1-3}$-alkoxy, C$_{1-4}$-alkoxycarbonyl, C$_{1-4}$-alkoxycarbonylamino-C$_{1-4}$-alkyl, C$_{1-4}$-hydroxyalkyl,

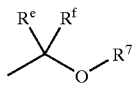

and C$_{1-4}$-alkoxy, preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein R$^2$ is one or more substituents independently selected from
H,
halo,
hydroxy,
amino,
C$_{1-6}$-alkyl,
C$_{1-6}$-haloalkyl,
C$_{1-6}$-alkoxy,
C$_{1-2}$-alkylamino,
aminosulfonyl,
C$_{3-6}$-cycloalkyl,
cyano, $C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
5–6-membered heterocyclyl-$C_{1-6}$-alkylamino,
unsubstituted or substituted phenyl and
unsubstituted or substituted 5–6 membered heterocyclyl,
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, fury, pyridyl, imidazolyl, and pyrazolyl;
wherein $R^e$ and $R^f$ are independently selected from H and $C_{1-2}$-haloalkyl,
preferably trifluoromethyl;
wherein $R^7$ is selected from H, $C_{1-3}$-alkyl, optionally substituted phenyl, optionally substituted phenyl-$C_{1-3}$-alkyl, optionally substituted 4–6 membered heterocyclyl, optionally substituted 4–6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl; and
wherein $R^{20}$ is one or more substituents selected from halo, amino, hydroxy, $C_{1-6}$-alkyl, $C_{1-6}$-haloalkyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
and pharmaceutically acceptable isomers and derivatives thereof.

The invention also relates to compounds of Formula XIII:

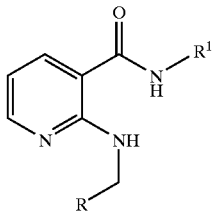

XIII wherein R is selected from
a) unsubstituted or substituted 5- or 6-membered nitrogen-containing heteroaryl selected from 4-pyridyl, 2-pyridyl, 4-pyrimidinyl, and tetrahydro-2H-pyran-4-yl, and
b) unsubstituted or substituted 9- or 10-membered fused heteroaryl selected from 4-quinolyl, 6-quinolyl, 2,3-dihydro-5-benzofuryl, 5-benzoxazolyl, 1H-pyrrolo[2,3-b]pyridin-4-yl, and 2,3-dihydro-1H-pyrrolo[2,3-b]pyridin-4-yl,
where substituted R is substituted with one or more substituents selected from halo, amino, hydroxy, oxo, $C_{1-6}$-alkyl, $C_{1-6}$-haloalkyl, $C_{1-6}$-alkylaminocarbonyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl;
preferably 2-methylamino-4-pyrimidinyl, 4-pyrimidinyl, 4-quinolyl, 2-methylamino-4-pyridyl, 1H-pyrrolo[2,3-b]pyridin-4-yl, 4-pyridyl, 2-amino-4-pyridyl, 2-methoxy-4-pyrimidinyl, 6-quinolyl, 2-methoxy-4-pyridyl, 2-morpholino-4-pyridyl, and 2-trifluoromethoxy-4-pyridyl;
more preferably 4-quinolyl, 2-methylamino-4-pyridyl, 4-pyridyl and N-oxides thereof, 4-pyrimidinyl, 2-methoxy-4-pyrimidinyl, 2-methoxy-4-pyridyl, 2-methylaminocarbonyl-4-pyridyl and 2-methylamino-4-pyrimidinyl;
wherein $R^1$ is selected from unsubstituted or substituted aryl,
cycloalkyl,
5–6 membered heteroaryl and
9–10 membered bicyclic and 11–14 membered tricyclic heterocyclyl,
preferably phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-6'-yl, isoquinolyl, quinolyl, indolyl, isoindolyl, 2,3-dihydro-1H-indolyl, naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydroquinazolinyl, 2,3,4,4a,9,9a-hexahydro-1H-3-azafluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl,
more preferably phenyl, 1,2,3,4-tetrahydroisoquinolyl, 2,3-dihydro-1H-indolyl, 1,2,3,4-tetrahydro-[1,8]naphthyridinyl, 1',2'-dihydro-spiro[cyclopropane-1,3'-[3H]indol]-6'-yl, and tetrahydroquinolinyl,
even more preferably
phenyl substituted with one or more substituents selected from chloro, 2-methyl-2-(1-methylpiperidin-4-yl)ethyl, 2-methyl-2-(5-methyloxadiazol-2-yl)ethyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, isopropyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonylpyrrolidin-2-ylmethoxy, 1-methyl-pyrrolindin-2-ylmethoxy, pyrrolindin-1-ylethoxy, 1-isopropyl-pyrrolindin-2-ylmethoxy, 3-tetrahydrofurylmethoxy, azetidin-3-ylmethoxy, and methylsulfonylaminoethoxy,
4,4-dimethyl-3,4-dihydro-2-oxo-1H-quinolinyl;
4,4-dimethyl-1,2,3,4-tetrahydro-1H-quinolinyl;

4,4-dimethyl-3,4-dihydro-2-oxo-1H-[1,8]
naphthyridinyl;
2-oxo-3,3-bis(trifluoromethyl)-2,3-dihydro-1H-
indol-6-yl;
2-oxo-2,3-dihydro-1H-indol-6-yl;
1',2'-dihydro-spiro[cyclopropane-1,3'-[3H]
indol]-6'-yl;
3,3-dimethyl-2,3-dihydro-1H-indolyl optionally
substituted with a substituent selected from
pyrrolidin-1-yl-carbonyl, methylcarbonyl, and
methylsulfonyl; and
4,4-dimethyl-1,2,3,4-tetrahydro-1H-
isoquinolinyl;

wherein substituted $R^1$ is substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4–6 membered heterocyclyl-$C_1$-$C_6$-alkyl, optionally substituted 4–6 membered heterocyclyl-$C_2$-$C_4$-alkenyl, optionally substituted 4–6 membered heterocyclyl, optionally substituted 4–6 membered heterocyclyloxy, optionally substituted 4–6 membered heterocyclyl-$C_{1-4}$-alkoxy, optionally substituted 4–6 membered heterocyclylsulfonyl, optionally substituted 4–6 membered heterocyclylamino, optionally substituted 4–6 membered heterocyclylcarbonyl, optionally substituted 4–6 membered heterocyclyl-$C_{1-4}$-alkylcarbonyl, optionally substituted 4–6 membered heterocyclylcarbonyl-$C_{1-4}$-alkyl, optionally substituted 4–6 membered heterocyclyl-$C_{1-4}$-alkylcarbonylamino, optionally substituted 4–6 membered heterocyclyloxycarbonylamino, $C_{1-2}$-haloalkyl, $C_{1-4}$-aminoalkyl, nitro, amino, $C_{1-3}$-alkylsulfonylamino, hydroxy, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

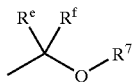

and $C_{1-4}$-alkoxy;
preferably bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl) ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl) ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, 4-methylpiperazin-1-ylcarbonylethyl, $CH_3O$—C(=O)—$CH_2$—, methoxycarbonyl, aminomethylcarbonyl, dimethylaminomethylcarbonyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, cyclohexyl-N($CH_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino) ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperdin-4-ylmethoxy, (1-pyrrolidinyl)ethoxy, piperdin-4-ylmethoxy, piperdin-3-ylmethoxy, 1-methylpiperdin-4-yloxy, methylsulfonylaminoethoxy, isopropoxy, methoxy and ethoxy;
more preferably chloro, oxo, methylsulfonyl, 2-methyl-2-(1-methylpiperidin-4-yl)ethyl, 2-methyl-2-(5-methyloxadiazol-2-yl)ethyl, methylcarbonyl, pyrrolidin-1-yl-carbonyl, 4-pyridylcarbonyl, methylsulfonylamino, dimethylaminomethyl-carbonylamino, 1-pyrrolidinyl-$CH_2$—C(=O)—NH—, 4-morpholinyl-$CH_2$—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 4-pyridylmethyl, 2-pyrrolidinylmethyl, 3-tetrahydrofurylmethoxy, azetidin-3-ylmethoxy, 3-tetrahydrofuryloxy, piperdin-3-ylmethoxy, 1-methylcarbonyl-pyrrolidin-2-ylmethoxy, 1-methyl-pyrrolidin-2-ylmethoxy, 1-isopropyl-pyrrolidin-2-ylmethoxy and methylsulfonylaminoethoxy;
particularly 2-methyl-2-(1-ethoxycarbonyl-1,2,3,6-tetrahydropyridin-4-yl)ethyl, 2-methyl-2-(5-methyloxadiazol-2-yl)ethyl, 1-(4-morpholinyl)-2,2-dimethylethyl, pyrrolidin-1-yl-carbonyl, $CH_3O$—C(=O)—$CH_2$—, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, 1,1-di(trifluoromethyl)-1-(pyrrolidin-2-ylmethoxy) methyl, 3-tetrahydrofuryloxy, 1-methylcarbonyl-pyrrolidin-2-ylmethoxy, and methylsulfonylaminoethoxy; and wherein R$^e$ and R$^f$ are independently selected from H and C$_{1-2}$-haloalkyl; preferably —CF$_3$; and wherein R$^7$ is selected from H, C$_{1-3}$-alkyl, optionally substituted phenyl, optionally substituted phenyl-C$_{1-3}$-alkyl, 4–6 membered heterocyclyl, optionally substituted 4–6 membered heterocyclyl-C$_1$C$_3$-alkyl, C$_{1-3}$-alkoxy-C$_{1-2}$-alkyl and C$_{1-3}$-alkoxy-C$_{1-3}$-alkoxy-C$_{1-3}$-alkyl; and pharmaceutically acceptable derivatives thereof.

A family of specific compounds of particular interest within Formula I consists of compounds and pharmaceutically-acceptable derivatives thereof as follows:

N-(4-Isopropylphenyl){2-[(4-pyridylmethyl)amino](3-pyridyl)}carboxamide;
N-[3-(Isopropyl)phenyl]{2-[(4-pyridylmethyl)amino](3-pyridyl)}carboxamide;
N-(3-Isoquinolyl){2-[(4-pyridylmethyl)amino](3-pyridyl)}carboxamide;
N-[4-Isopropylphenyl]{2-[(2-(3-pyridyl)ethyl)amino](3-pyridyl)}carboxamide;
N-[4-(tert-Butyl)phenyl]{2-[(2-(3-pyridyl)ethyl)amino](3-pyridyl)}carboxamide;
N-[4-(Methylpropyl)phenyl]{2-[(2-(3-pyridyl)ethyl)amino](3-pyridyl))carboxamide;
{2-[(2-(3-Pyridyl)ethyl)amino](3-pyridyl)}-N-[3-(trifluoromethyl)phenyl]carboxamide;
{2-[(4-Pyridylmethyl)amino](3-pyridyl)}-N-{4-[2,2,2-trifluoro-1-hydroxy-1-(trifluoromethyl)ethyl]phenyl}carboxamide;
N-[5-(tert-Butyl)isoxazol-3-yl]{2-[(4-pyridylmethyl)amino](3-pyridyl)}carboxamide;
N-[5-(tert-Butyl)-1-methylpyrazol-3-yl]{2-[(4-pyridylmethyl)amino](3-pyridyl)}carboxamide;
N-[4-(tert-Butyl)(1,3-thiazol-2-yl)]{2-[(4-pyridylmethyl)amino](3-pyridyl)}carboxamide;
N-[5-(tert-Butyl)(1,3,4-thiadiazol-2-yl)]{2-[(4-pyridylmethyl)amino](3-pyridyl)}carboxamide;
N-[4-(4-Hydroxybutyl)phenyl]{2-[(4-pyridylmethyl)amino](3-pyridyl)}carboxamide;
N-[2-(4-Chlorophenyl)ethyl]-2-[(pyridin-4-ylmethyl)amino](3-pyridyl)carboxamide;
5-Bromo-N-[2-(4-chlorophenyl)ethyl]-2-[(pyridin-4-ylmethyl)amino](3-pyridyl)carboxamide;
N-[2-(4-Phenoxyphenyl)ethyl]-2-[(pyridin-4-ylmethyl)amino](3-pyridyl)carboxamide;
N-[2-(4-Methoxyphenyl)ethyl]-2-[(pyridin-4-ylmethyl)amino](3-pyridyl)carboxamide;
N-[2-(3,4-Dimethoxyphenyl)ethyl]-2-[(pyridin-4-ylmethyl)amino](3-pyridyl)carboxamide;
N-[2-(4-Hydroxy-3-ethoxyphenyl)ethyl]-2-[(pyridin-4-ylmethyl)amino](3-pyridyl)carboxamide;
N-[2-(4-Fluorophenyl)ethyl]-2-[(pyridin-4-ylmethyl)amino](3-pyridyl)carboxamide;
N-[2-(4-(tert-Butyl)phenyl)ethyl]-2-[(pyridin-4-ylmethyl)amino](3-pyridyl)carboxamide;
N-[2-(3-Fluorophenyl)ethyl]-2-[(pyridin-4-ylmethyl)amino](3-pyridyl)carboxamide;
N-[2-(3-Chlorophenyl)ethyl]-2-[(pyridin-4-ylmethyl)amino](3-pyridyl)carboxamide;
N-[2-(3-(Trifluoromethyl)phenyl)ethyl]-2-[(pyridin-4-ylmethyl)amino](3-pyridyl)carboxamide;
N-[2-(3-Ethoxyphenyl)ethyl]-2-[(pyridin-4-ylmethyl)amino](3-pyridyl)carboxamide;
N-[2-(3,4-Dimethylphenyl)ethyl]-2-[(pyridin-4-ylmethyl)amino](3-pyridyl)carboxamide;
N-[2-(1,3-Benzodioxol-5-yl)ethyl]-2-[(pyridin-4-ylmethyl)amino](3-pyridyl)carboxamide;
N-[2-(4-Methylphenyl)ethyl]-2-[(pyridin-4-ylmethyl)amino](3-pyridyl)carboxamide;
N-[2-(4-Hydroxyphenyl)ethyl]-2-[(pyridin-4-ylmethyl)amino](3-pyridyl)carboxamide;
N-[2-(3,4-Dimethoxyphenyl)ethyl]-2-[(pyridin-4-ylmethyl)amino](3-pyridyl)carboxamide;
N-[2-(4-Bromophenyl)ethyl]-2-[(pyridin-4-ylmethyl)amino](3-pyridyl)carboxamide;
N-[2-(3,4-Dichlorophenyl)ethyl]-2-[(pyridin-4-ylmethyl)amino](3-pyridyl)carboxamide;
N-[2-(4-(Fluorosulfonyl)phenyl)ethyl]-2-[(pyridin-4-ylmethyl)amino](3-pyridyl)carboxamide;
N-[2-(3,5-(Dimethoxy)phenyl)ethyl]-2-[(pyridin-4-ylmethyl)amino](3-pyridyl)carboxamide;
N-[2-(2,4-Dichlorophenyl)ethyl]-2-[(pyridin-4-ylmethyl)amino](3-pyridyl)carboxamide;
N-[2-(2-Fluorophenyl)ethyl]-2-[(pyridin-4-ylmethyl)amino](3-pyridyl)carboxamide;
N-[2-(2-Chlorophenyl)ethyl]-2-[(pyridin-4-ylmethyl)amino](3-pyridyl)carboxamide;
N-[2-(4-(Aminosulphonyl)phenyl)ethyl]-2-[(pyridin-4-ylmethyl)amino](3-pyridyl)carboxamide;
N-[2-(2-Thienyl)ethyl]-2-[(pyridin-4-ylmethyl)amino](3-pyridyl)carboxamide;
N-[2-(Pyridin-2-yl)ethyl]-2-[(pyridin-4-ylmethyl)amino](3-pyridyl)}carboxamide;
N-[2-(Pyridin-3-yl)ethyl]-2-[(pyridin-4-ylmethyl)amino](3-pyridyl)carboxamide;
N-[2-(Pyridin-4-yl)ethyl]-2-[(pyridin-4-ylmethyl)amino](3-pyridyl)carboxamide;
N-(4-Phenylbutyl)-2-[(pyridin-4-ylmethyl)amino](3-pyridyl)carboxamide;
N-(2-Hydroxy-3-phenoxypropyl)-2-[(pyridin-4-ylmethyl)amino](3-pyridyl)carboxamide;
{6-Chloro-5-fluoro-2-[(4-pyridylmethyl)amino](3-pyridyl)}-N-[4-(isopropyl)phenyl]carboxamide;
{5-Fluoro-2-[(4-pyridylmethyl)amino](3-pyridyl)}-N-[4-(isopropyl)phenyl]carboxamide;
2-[(Pyridin-4-ylmethyl)amino]-N-[4-tert-butyl-3-(1,2,3,6-tetrahydropyridin-4-yl)phenyl](3-pyridyl)carboxamide;
N-(3,4-Dichlorophenyl){6-[(2-morpholin-4-ylethyl)amino]-2-[(4-pyridylmethyl)amino](3-pyridyl)}carboxamide;
N-[4-(Morpholin-4-ylmethyl)phenyl]{2-[(4-pyridylmethyl)amino](3-pyridyl))carboxamide;
N-{4-{2-[(tert-Butoxy)carbonylamino]ethyl}phenyl){2-[(4-pyridylmethyl)amino](3-pyridyl)}carboxamide;
N-[4-(2-Aminoethyl)phenyl]{2-[(4-pyridylmethyl)amino](3-pyridyl)}carboxamide;
N-[4-(tert-Butyl)-3-nitrophenyl]{2-[(2-pyridylmethyl)amino](3-pyridyl)}carboxamide;
N-[3-Amino-4-(tert-butyl)phenyl]{2-[(2-pyridylmethyl)amino](3-pyridyl)}carboxamide;
N-[4-(Isopropyl)phenyl]{2-[(2-pyridylmethyl)amino](3-pyridyl)}carboxamide;
N-(3-Aminosulfonyl-4-chlorophenyl){2-[(4-pyridylmethyl)amino](3-pyridyl)}carboxamide;
N-{3-[(4-Methylpiperazinyl)sulfonyl]phenyl}{2-[(4-pyridylmethyl)amino](3-pyridyl)}carboxamide;
N-[4-(1,1,2,2,2-Pentafluoroethyl)phenyl]{2-[(4-pyridylmethyl)amino](3-pyridyl)}carboxamide;
N-[4-(1,1,2,2,3,3,4,4,4-Nonafluorobutyl)phenyl]{2-[(4-pyridylmethyl)amino](3-pyridyl)}carboxamide;

N-[4-(Isopropyl)phenyl]{2-[(2-(1,2,4-triazolyl)ethyl)amino](3-pyridyl)}carboxamide;
(2-{[2-(2-Pyridylamino)ethyl]amino}(3-pyridyl))-N-[3-(trifluoromethyl)phenyl]carboxamide;
{2-[(1-(2-Pyridyl)pyrrolidin-3-yl)amino](3-pyridyl)}-N-[3-(trifluoromethyl)phenyl]carboxamide;
2-[(Pyridin-4-ylmethyl)-amino]-N-(3-trifluoromethyl-phenyl)-nicotinamide
{2-[(4-Pyridylmethyl)amino](3-pyridyl)}-N-(8-quinolyl)carboxamide hydrochloride;
N-[4-(4-Chlorophenoxy)phenyl]{2-[(4-pyridylmethyl)amino](3-pyridyl)}carboxamide hydrochloride;
{2-[(4-Pyridylmethyl)amino](3-pyridyl)}-N-(2,3,4-trifluorophenyl)carboxamide hydrochloride;
N-(2-Naphthyl){2-[(4-pyridylmethyl)amino](3-pyridyl)}carboxamide hydrochloride;
N-(2-Phenoxyphenyl){2-[(4-pyridylmethyl)amino](3-pyridyl)}carboxamide hydrochloride;
{2-[(4-Pyridylmethyl)amino](3-pyridyl)}-N-(5,6,7,8-tetrahydronaphthyl) carboxamide hydrochloride;
N-(2H-Benzo[3,4-d]1,3-dioxolen-5-yl){2-[(4-pyridylmethyl)amino](3-pyridyl)}carboxamide hydrochloride;
N-Naphthyl{2-[(4-pyridylmethyl)amino](3-pyridyl)}carboxamide hydrochloride;
N-[3-Benzylphenyl]{2-[(4-pyridylmethyl)amino](3-pyridyl)}carboxamide hydrochloride;
N-(Cyclohexylethyl){2-[(4-pyridylmethyl)amino](3-pyridyl)}carboxamide hydrochloride;
N-(Cyclohexylethyl){2-[(4-pyridylmethyl)amino](3-pyridyl)}carboxamide hydrochloride;
N-Indan-2-yl{2-[(4-pyridylmethyl)amino](3-pyridyl)}carboxamide hydrochloride;
N-[4-(tert-Butyl)phenyl]{2-[(4-pyridylmethyl)amino](3-pyridyl)}carboxamide;
N-(4-sec-Butyl-phenyl)-2-[(pyridin-4-ylmethyl)-amino]-nicotinamide;
N-(4-Methylphenyl){2-[(4-pyridylmethyl)amino](3-pyridyl)}carboxamide;
{2-[(4-Pyridylmethyl)amino](3-pyridyl)}-N-[4-trifluoromethoxy)phenyl]carboxamide;
N-(4-Ethylphenyl){2-[(4-pyridylmethyl)amino](3-pyridyl)}carboxamide;
N-(4-Butylphenyl){2-[(4-pyridylmethyl)amino](3-pyridyl)}carboxamide;
N-(4-Iodophenyl){2-[(4-pyridylmethyl)amino](3-pyridyl)}carboxamide;
N-[3-(Hydroxyethyl)phenyl]{2-[(4-pyridylmethyl)amino](3-pyridyl)}carboxamide;
N-(3-Ethylphenyl){2-[(4-pyridylmethyl)amino](3-pyridyl)}carboxamide;
Ethyl 2-methyl-5-[3-({2-[(4-pyridylmethyl)amino](3-pyridyl)}carbonylamino)phenyl]furan-3-carboxylate;
N-(3-Phenylphenyl){2-[(4-pyridylmethyl)amino](3-pyridyl)}carboxamide;
N-[4-Benzylphenyl]{2-[(4-pyridylmethyl)amino](3-pyridyl)}carboxamide;
N-(6-Ethyl(2-pyridyl)){2-[(4-pyridylmethyl)amino](3-pyridyl)}carboxamide;
N-(6-Propyl(2-pyridyl)){2-[(4-pyridylmethyl)amino](3-pyridyl)}carboxamide;
N-[4-(tert-Butyl)(2-pyridyl)]{2-[(4-pyridylmethyl)amino](3-pyridyl)}carboxamide;
N-(3-Hydroxyphenyl){2-[(4-pyridylmethyl)amino](3-pyridyl)}carboxamide;
N-[4-(Methylethyl)(2-pyridyl)]{2-[(4-pyridylmethyl)amino](3-pyridyl)}carboxamide;
N-[3,5-bis(Trifluoromethyl)phenyl]{2-[(4-pyridylmethyl)amino](3-pyridyl)}carboxamide hydrochloride;
N-[4-Chloro-3-(trifluoromethyl)phenyl]{2-[(4-pyridylmethyl)amino](3-pyridyl)}carboxamide hydrochloride;
N-(3-Chlorophenyl){2-[(2-(4-pyridyl)ethyl)amino](3-pyridyl)}carboxamide hydrochloride;
N-(4-Phenoxyphenyl){2-[(2-(2-pyridyl)ethyl)amino](3-pyridyl)}carboxamide;
2-[(Benzo[b]thiophen-3-ylmethyl)amino](3-pyridyl)}-N-(4-phenoxyphenyl)carboxamide;
N-(4-Phenoxyphenyl){2-[(2-(3-pyridyl)ethyl)amino](3-pyridyl)}carboxamide;
N-[4-(Methylsulfonyl)phenyl]{2-[(4-pyridylmethyl)amino](3-pyridyl)}carboxamide;
N-(1-Acetylindolin-6-yl){2-[(4-pyridylmethyl)amino](3-pyridyl)}carboxamide;
N-Indolin-6-yl{2-[(4-pyridylmethyl)amino](3-pyridyl)}carboxamide;
N-Indol-6-yl{2-[(4-pyridylmethyl)amino](3-pyridyl)}carboxamide;
N-Indol-5-yl{2-[(4-pyridylmethyl)amino](3-pyridyl)}carboxamide;
N-Indol-7-yl{2-[(4-pyridylmethyl)amino](3-pyridyl)}carboxamide;
N-[3-(tert-Butyl)pyrazol-5-yl]{2-[(4-pyridylmethyl)amino](3-pyridyl)}carboxamide;
N-(3-Phenylpyrazol-5-yl){2-[(4-pyridylmethyl)amino](3-pyridyl)}carboxamide;
N-{2-[2-(dimethylamino)ethoxy]-5-(tert-butyl)phenyl}{2-[(4-pyridylmethyl)amino](3-pyridyl)}carboxamide;
N-[4-(tert-Butyl)-3-(4-methylpiperazinyl)phenyl]{2-[(4-pyridylmethyl)amino](3-pyridyl)}carboxamide;
N-[3-(4-Methylpiperazinyl)phenyl]{2-[(4-pyridylmethyl)amino](3-pyridyl)}carboxamide;
N-[4-(4-Methylpiperazinyl)phenyl]{2-[(4-pyridylmethyl)amino](3-pyridyl)}formamide;
N-[1-(1-Methyl-(4-piperidyl))indolin-6-yl]{2-[(4-pyridylmethyl)amino](3-pyridyl)}carboxamide;
N-[1-(1-Methyl-(4-piperidyl))indolin-6-yl]{2-[(2-(3-pyridyl)ethyl)amino](3-pyridyl)}carboxamide;
N-[1-(2-Piperidylethyl)indolin-6-yl]{2-[(4-pyridylmethyl)amino](3-pyridyl)}carboxamide;
N-[1-(2-Piperidylacetyl)indolin-6-yl]{2-[(4-pyridylmethyl)amino](3-pyridyl)}carboxamide;
N-[3,3-Dimethyl-1-(1-methyl(4-piperidyl))indolin-6-yl]{2-[(4-pyridylmethyl)amino](3-pyridyl))carboxamide;
N-(3,3-Dimethylindolin-6-yl){2-[(4-pyridylmethyl)amino](3-pyridyl)}carboxamide;
N-[3-(1-Methyl-(4-piperidyl))indol-5-yl]{2-[(4-pyridylmethyl)amino](3-pyridyl)}carboxamide;
N-[4-(1,1-Dimethyl-3-morpholin-4-ylpropyl)phenyl]{2-[(4-pyridylmethyl)amino](3-pyridyl)}carboxamide;
N-[4-(tert-Butyl)phenyl]{2-[({2-[(1-methyl(4-piperidyl))-methoxy](4-pyridyl)}methyl)amino](3-pyridyl)}carboxamide;
N-(4-Bromo-2-fluorophenyl){2-[(4-pyridylmethyl)amino](3-pyridyl)}carboxamide;
N-[4-(tert-Butyl)phenyl](2-{[((2-chloro(4-pyridyl))methyl]amino}(3-pyridyl))carboxamide;
{(2-[({2-[3-(Dimethylamino)prop-1-ynyl](4-pyridyl)}methyl)amino](3-pyridyl)}-N-[4-(tert-butyl)phenyl]carboxamide;
(2-{[(2-Methoxy(4-pyridyl))methyl]amino}(3-pyridyl))-N-[4-(methylethyl)phenyl]carboxamide;
N-{3-[3-(Dimethylamino)propyl]-5-(trifluoromethyl)phenyl}-{2-[(4-pyridylmethyl)amino](3-pyridyl)}carboxamide;

N-[4-(tert-Butyl)-3-(3-piperid-1-ylpropyl)phenyl]{2-[(4-pyridylmethyl)amino](3-pyridyl)}carboxamide;
N-[4-(tert-Butyl)-3-(3-pyrrolidin-1-ylpropyl)phenyl]{2-[(4-pyridylmethyl)amino](3-pyridyl)}carboxamide;
N-[3-((1E)-4-Pyrrolidin-1-ylbut-1-enyl)-4-(tert-butyl)phenyl]{2-[(4-pyridylmethyl)amino](3-pyridyl)}carboxamide;
N-[4-(tert-Butyl)-3-(3-morpholin-4-ylpropyl)phenyl]{2-[(4-pyridylmethyl)amino](3-pyridyl)}carboxamide;
N-[1-(2-Morpholin-4-ylethyl)indol-6-yl]{2-[(4-pyridylmethyl)amino](3-pyridyl)}carboxamide;
N-[4-(tert-Butyl)phenyl]{2-[(pyrimidin-4-ylmethyl)amino](3-pyridyl)}carboxamide;
N-(4-Chlorophenyl){2-[(pyrimidin-4-ylmethyl)amino](3-pyridyl)}carboxamide;
{2-[(Pyrimidin-4-ylmethyl)amino](3-pyridyl)}-N-[3-(trifluoromethyl)phenyl]carboxamide;
N-[4-(Isopropyl)phenyl]{4-[(4-pyridylmethyl)amino]pyrimidin-5-yl}carboxamide;
(2-{[(2-{2-[2-(Dimethylamino)ethoxy]ethoxy}(4-pyridyl))methyl]amino}(3-pyridyl))-N-[4-(tert-butyl)phenyl]carboxamide;
{2-[(4-Pyridylmethyl)amino](3-pyridyl)}-N-{4-[2,2,2-trifluoro-1-(2-piperidylethoxy)-1-(trifluoromethyl)ethyl]phenyl}carboxamide;
(2-{[(2-{2-[2-(Dimethylamino)ethoxy]ethoxy}(4-pyridyl))methyl]amino}-6-fluoro(3-pyridyl))-N-[3-(trifluoromethyl)phenyl]carboxamide;
N-[4-(tert-Butyl)phenyl]{6-fluoro-2-[(4-pyridylmethyl)amino](3-pyridyl)}carboxamide;
(6-Fluoro-2-[(4-pyridylmethyl)amino](3-pyridyl)}-N-[4-(isopropyl)phenyl]carboxamide;
{6-Fluoro-2-[(4-pyridylmethyl)amino](3-pyridyl)}-N-[3-(trifluoromethyl)phenyl]carboxamide;
N-(1-Bromo(3-isoquinolyl)){6-fluoro-2-[(4-pyridylmethyl)amino](3-pyridyl)}-carboxamide;
N-(4-Phenoxyphenyl){2-[(4-pyridylmethyl)amino](3-pyridyl)}carboxamide hydrochloride;
N-(4-Phenylphenyl){2-[(4-pyridylmethyl)amino](3-pyridyl)}carboxamide hydrochloride;
N-(3-Phenoxyphenyl){2-[(4-pyridylmethyl)amino](3-pyridyl)}carboxamide hydrochloride;
N-(4-Cyclohexylphenyl){2-[(4-pyridylmethyl)amino](3-pyridyl)}carboxamide hydrochloride;
N-(4-Imidazol-1-ylphenyl){2-[(4-pyridylmethyl)amino](3-pyridyl)}carboxamide hydrochloride;
N-(4-Morpholin-4-ylphenyl){2-[(4-pyridylmethyl)amino](3-pyridyl)}carboxamide hydrochloride;
N-(4-Cyanonaphthyl){2-[(4-pyridylmethyl)amino](3-pyridyl)}carboxamide hydrochloride;
{2-[(4-Pyridylmethyl)amino](3-pyridyl)}-N-[4-(trifluoromethyl)phenyl]carboxamide hydrochloride;
Methyl-4-({2-[(4-pyridylmethyl)amino]-3-pyridyl}carbonylamino)benzoate hydrochloride;
N-[4-(Isopropyl)phenyl]{2-[(4-quinolylmethyl)amino](3-pyridyl)}carboxamide;
N-[4-(tert-Butyl)phenyl]{2-[(6-quinolylmethyl)amino](3-pyridyl)}carboxamide;
{2-[(6-Quinolylmethyl)amino](3-pyridyl)}-N-[3-(trifluoromethyl)phenyl]carboxamide;
N-(4-chlorophenyl){3-[(4-pyridylmethyl)amino](2-thienyl)}carboxamide;
N-phenyl{3-[(4-pyridylmethyl)amino](2-thienyl)}carboxamide;
N-(4-chlorophenyl)-3-[(4-pyridinylmethylene)amino]-4-pyridinecarboxamide;
N-(4-chlorophenyl){2-[(4-pyridylmethyl)amino](3-pyridyl)}carboxamide;
N-(3,4-dichlorophenyl){2-[(4-pyridylmethyl)amino](3-pyridyl)}-carboxamide;
N-(3-chlorophenyl){2-[(4-pyridylmethyl)amino](3-pyridyl)}carboxamide;
N-(4-chlorophenyl){3-[(4-pyridylmethyl)amino](2-pyridyl)}carboxamide;
N-(4-chlorophenyl){3-[(6-quinolylmethyl)amino](2-pyridyl)}carboxamide;
N-(3,4-dichlorophenyl){2-[(6-quinolylmethyl)amino](3-pyridyl)}-carboxamide;
N-(4-chlorophenyl){6-methyl-2-[(4-pyridylmethyl)amino](3-pyridyl)}carboxamide;
N-(3,4-dichlorophenyl){6-methyl-2-[(4-pyridylmethyl)amino](3-pyridyl)}carboxamide;
N-(3-fluoro-4-methylphenyl){6-methyl-2-[(4-pyridylmethyl)amino](3-pyridyl)}carboxamide;
N-(3,4-dichlorophenyl){6-chloro-2-[(4-pyridylmethyl)amino](3-pyridyl)}carboxamide;
N-(4-chlorophenyl){6-chloro-2-[(4-pyridylmethyl)amino](3-pyridyl)}carboxamide;
{6-chloro-2-[(4-pyridylmethyl)amino](3-pyridyl)}-N-(3-fluorophenyl)carboxamide;
N-(3-chlorophenyl){6-chloro-2-[(4-pyridylmethyl)amino](3-pyridyl)}carboxamide;
N-(4-chlorophenyl){3-[(4-pyridylmethyl)amino](4-pyridyl)}carboxamide;
N-(3-fluoro-4-methylphenyl){2-[(4-pyridylmethyl)amino](3-pyridyl)}carboxamide;
N-(4-chlorophenyl){2-[(4-quinolylmethyl)amino](3-pyridyl)}carboxamide;
N-(4-chlorophenyl){2-[(5-quinolylmethyl)amino](3-pyridyl)}carboxamide;
N-(4-chlorophenyl){2-[(4-pyridylethyl)amino]-5-(3-thienyl)-(3-pyridyl)}carboxamide;
N-(4-chlorophenyl){5-(4-methoxyphenyl)-2-[(4-pyridylmethyl)amino]-(3-pyridyl)}carboxamide; and
N-(4-chlorophenyl){5-bromo-2-[(4-pyridylmethyl)amino]-(3-pyridyl)}carboxamide.

A family of specific compounds of particular interest within Formula II' consists of compounds and pharmaceutically-acceptable derivatives thereof as follows:
2-{[2-(1-Isopropyl-azetidin-3-ylmethoxy)-pyridin-4-ylmethyl]-amino}-N-(4-trifluoromethyl-phenyl)-nicotinamide;
N-(4-tert-Butyl-phenyl)-2-{[2-(1-isopropyl-azetidin-3-ylmethoxy)-pyridin-4-ylmethyl]-amino}-nicotinamide;
2-[(2,3-Dihydro-benzofuran-5-ylmethyl)-amino]-N-{4-[1-methyl-1-(1-methyl-piperidin-4-yl)-ethyl]-phenyl}-nicotinamide;
N-(1-Acetyl-3,3-dimethyl-2,3-dihydro-1H-indol-6-yl)-2-[(2,3-dihydro-benzofuran-5-ylmethyl)-amino]-nicotinamide;
2-[(2,3-Dihydro-benzofuran-5-ylmethyl)-amino]-N-[3,3-dimethyl-1-(1-Boc-piperidin-4-ylmethyl)-2,3-dihydro-1H-indol-6-yl]-nicotinamide;
2-[(2,3-Dihydro-benzofuran-5-ylmethyl)-amino]-N-[3,3-dimethyl-1-(1-methylpiperidin-4-ylmethyl)-2,3-dihydro-1H-indol-6-yl]-nicotinamide;
N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide;
2-({2-[2-(1-Methyl-piperidin-4-yl)-ethoxy]-pyridin-4-ylmethyl}-amino)-N-(3-trifluoromethyl-phenyl)-nicotinamide;
N-(4-tert-Butyl-phenyl)-2-{[2-ethylpyridin-4-ylmethyl]-amino}-nicotinamide;
N-(4-tert-Butyl-phenyl)-2-({2-[2-(1-methyl-pyrrolidin-2-yl)-ethoxy]-pyridin-4-ylmethyl}-amino)-nicotinamide;

2-({2-[2-(1-Methyl-pyrrolidin-2-yl)-ethoxy]-pyridin-4-ylmethyl}-amino)-N-(4-pentafluoroethyl-phenyl)-nicotinamide;
N-(4-Pentafluoroethyl-phenyl)-2-{[2-(2-pyrrolidin-1-yl-ethoxy)-pyridin-4-ylmethyl]-amino}-nicotinamide;
N-(4-tert-Butyl-phenyl)-2-{[2-(2-pyrrolidin-1-yl-ethoxy)-pyridin-4-ylmethyl]-amino}-nicotinamide;
N-[3-(4-Boc-piperazin-1-ylmethyl)-5-trifluoromethyl-phenyl]-2-[(pyridin-4-ylmethyl)-amino]-nicotinamide;
N-[3-(4-Boc-piperazine-1-carbonyl)-5-trifluoromethyl-phenyl]-2-[(pyridin-4-ylmethyl)-amino]-nicotinamide;
N-[3-(4-Boc-piperazine-1-carbonyl)-5-trifluoromethyl-phenyl]-2-(2-pyridin-4-yl-ethylamino)-nicotinamide;
N-[3-(4-Methyl-piperazin-1-ylmethyl)-4-pentafluoroethyl-phenyl]-2-[(pyridin-4-ylmethyl)-amino]-nicotinamide;
N-[3-(4-Boc-piperazin-1-ylmethyl)-4-pentafluoroethyl-phenyl]-2-[(pyridin-4-ylmethyl)-amino]-nicotinamide;
2-{[2-(1-Methyl-piperidin-4-ylmethoxy)-pyridin-4-ylmethyl]-amino}-N-(4-trifluoromethyl-phenyl)-nicotinamide;
N-(4-tert-Butyl-phenyl)-2-{[2-(1-methyl-piperidin-4-ylmethoxy)-pyridin-4-ylmethyl]-amino}-nicotinamide;
2-({2-[3-(1-Methyl-piperidin-4-yl)-propoxy]-pyridin-4-ylmethyl}-amino)-N-(4-pentafluoroethyl-phenyl)-nicotinamide;
N-(1-Acetyl-3,3-dimethyl-2,3-dihydro-1H-indol-6-yl)-2-[(2-methoxy-pyridin-4-ylmethyl)-amino]-nicotinamide;
N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide;
N-(1-Boc-3,3-dimethyl-2,3-dihydro-1H-indol-6-yl)-2-[(2-methoxy-pyridin-4-ylmethyl)-amino]-nicotinamide;
N-[3,3-Dimethyl-1-(1-Boc-piperidin-4-ylmethyl)-2,3-dihydro-1H-indol-6-yl]-2-[(2-methoxy-pyridin-4-ylmethyl)-amino]-nicotinamide;
N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide;
N-[1-(2-Dimethylamino-acetyl)-3,3-dimethyl-2,3-dihydro-1H-indol-6-yl]-2-[(2-methoxy-pyridin-4-ylmethyl)-amino]-nicotinamide;
N-[1-(2-Dimethylamino-acetyl)-3,3-dimethyl-2,3-dihydro-1H-indol-6-yl]-2-[(pyridin-4-ylmethyl)-amino]-nicotinamide;
2-[(2-Methoxy-pyridin-4-ylmethyl)-amino]-N-[3-(1-Boc-piperidin-4-ylmethoxy)-5-trifluoromethyl-phenyl]-nicotinamide;
N-[3,3-Dimethyl-1-(1-Boc-pyrrolidin-2-ylmethoxy)-2,3-dihydro-1H-indol-6-yl]-2-[(2-methoxy-pyridin-4-ylmethyl)-amino]-nicotinamide;
N-[3,3-Dimethyl-1-(2-Boc-amino-acetyl)-2,3-dihydro-1H-indol-6-yl]-2-[(2-methoxy-pyridin-4-ylmethyl)-amino]-nicotinamide;
N-[3,3-Dimethyl-1-(2-Boc-amino-acetyl)-2,3-dihydro-1H-indol-6-yl]-2-[(pyridin-4-ylmethyl)-amino]-nicotinamide;
2-[(2-Methoxy-pyridin-4-ylmethyl)-amino]-N-[3-(1-methyl-pyrrolidin-2-ylmethoxy)-5-trifluoromethyl-phenyl]-nicotinamide;
2-[(2-Methoxy-pyridin-4-ylmethyl)-amino]-N-[3-(1-Boc-piperidin-4-ylmethyl)-5-trifluoromethyl-phenyl]-nicotinamide;
2-[(2-Methoxy-pyridin-4-ylmethyl)-amino]-N-[3-(4-Boc-piperazin-1-ylmethyl)-5-trifluoromethyl-phenyl]-nicotinamide;
2-{[2-(3-Morpholin-4-yl-propoxy)-pyridin-4-ylmethyl]-amino}-N-(4-pentafluoroethyl-phenyl)-nicotinamide;
(S) 2-{[2-(1-Methyl-pyrrolidin-2-ylmethoxy)-pyridin-4-ylmethyl]-amino}-N-(4-pentafluoroethyl-phenyl)-nicotinamide;
N-(3-tert-Butyl-isoxazol-5-yl)-2-{[2-(3-morpholin-4-yl-propoxy)-pyridin-4-ylmethyl]-amino}-nicotinamide;
N-(1-Acetyl-3,3-dimethyl-2,3-dihydro-1H-indol-6-yl)-2-{[2-(3-morpholin-4-yl-propylamino)-pyridin-4-ylmethyl]-amino}-nicotinamide;
N-(4-tert-Butyl-phenyl)-2-{[2-(3-morpholin-4-yl-propoxy)-pyridin-4-ylmethyl]-amino}-nicotinamide;
N-(4-tert-Butyl-phenyl)-2-{[2-(2-morpholin-4-yl-ethoxy)-pyridin-4-ylmethyl]-amino}-nicotinamide;
2-{[2-(2-Morpholin-4-yl-ethoxy)-pyridin-4-ylmethyl]-amino}-N-(4-trifluoromethyl-phenyl)-nicotinamide;
2-{[2-(2-Morpholin-4-yl-ethoxy)-pyridin-4-ylmethyl]-amino}-N-(3-trifluoromethyl-phenyl)-nicotinamide;
2-{[2-(2-Morpholin-4-yl-ethoxy)-pyridin-4-ylmethyl]-amino}-N-(4-pentafluoroethyl-phenyl)-nicotinamide;
N-(3-tert-Butyl-isoxazol-5-yl)-2-{[2-(2-morpholin-4-yl-ethoxy)-pyridin-4-ylmethyl]-amino}-nicotinamide;
N-(1-Acetyl-3,3-dimethyl-2,3-dihydro-1H-indol-6-yl)-2-{[2-(2-morpholin-4-yl-ethoxy)-pyridin-4-ylmethyl]-amino}-nicotinamide;
N-(1-Acetyl-3,3-dimethyl-2,3-dihydro-1H-indol-6-yl)-2-{[2-(1-methyl-piperidin-4-yloxy)-pyridin-4-ylmethyl]-amino}-nicotinamide;
2-{[2-(1-Methyl-piperidin-4-yloxy)-pyridin-4-ylmethyl]-amino}-N-(4-trifluoromethyl-phenyl)-nicotinamide;
2-{[2-(1-Methyl-piperidin-4-yloxy)-pyridin-4-ylmethyl]-amino}-N-(4-pentafluoroethyl-phenyl)-nicotinamide;
2-{[2-(1-Methyl-piperidin-4-yloxy)-pyridin-4-ylmethyl]-amino}-N-(4-tert-butyl-phenyl)-nicotinamide;
(R) N-(4-tert-Butyl-phenyl)-2-{[2-(1-methyl-pyrrolidin-2-ylmethoxy)-pyridin-4-ylmethyl]-amino}-nicotinamide;
(R) N-[3-(1-Boc-pyrrolidin-2-ylmethoxy)-5-trifluoromethyl-phenyl]-2-[(pyridin-4-ylmethyl)-amino]-nicotinamide;
(R) N-[3-(1-Methyl-pyrrolidin-2-ylmethoxy)-5-trifluoromethyl-phenyl]-2-[(pyridin-4-ylmethyl)-amino]-nicotinamide;
N-[3-(1-Methyl-piperidin-4-yloxy)-5-trifluoromethyl-phenyl]-2-[(pyridin-4-ylmethyl)-amino]-nicotinamide;
N-[3-(1-Methyl-piperidin-4-ylmethyl)-5-trifluoromethyl-phenyl]-2-[(pyridin-4-ylmethyl)-amino]-nicotinamide;
N-[3-tert-Butyl-4-(1-Boc-pyrrolidin-2-ylmethoxy)-phenyl]-2-[(pyridin-4-ylmethyl)-amino]-nicotinamide;
N-(3,3-Dimethyl-2,3-dihydro-benzofuran-6-yl)-2-{[2-(1-methyl-piperidin-4-ylmethoxy)-pyridin-4-ylmethyl]-amino}-nicotinamide;
2-({2-[3-(1-Methyl-piperidin-4-yl)-propoxy]-pyridin-4-ylmethyl}-amino)-N-(4-trifluoromethyl-phenyl)-nicotinamide;
2-({2-[3-(1-Methyl-piperidin-4-yl)-propoxy]-pyridin-4-ylmethyl}-amino)-N-(3-trifluoromethyl-phenyl)-nicotinamide;
2-({2-[3-(1-Methyl-piperidin-4-yl)-propoxy]-pyridin-4-ylmethyl}-amino)-N-(4-tert-butyl-phenyl)-nicotinamide;
2-({2-[3-(1-Methyl-piperidin-4-yl)-propoxy]-pyridin-4-ylmethyl}-amino)-N-(3-tert-butyl-isoxazol-5-yl)-nicotinamide;
N-(3,3-Dimethyl-2,3-dihydro-1H-indol-6-yl)-2-({2-[3-(1-methyl-piperidin-4-yl)-propoxy]-pyridin-4-ylmethyl}-amino)-nicotinamide;
2-[(Pyridin-4-ylmethyl)-amino]-N-(3,9,9-trimethyl-2,3,4,4a,9,9a-hexahydro-1H-3-aza-fluoren-6-yl)-nicotinamide;
N-[3,3-Dimethyl-1-(1-Boc-piperidin-4-ylmethyl)-2,3-dihydro-1H-indol-6-yl]-2-[(pyridin-4-ylmethyl)-amino]-nicotinamide;

N-(4-Imidazol-1-ylphenyl){2-[(4-pyridylmethyl)amino](3-pyridyl)}carboxamide hydrochloride;
N-[3,3-Dimethyl-1-(1-methyl-piperidin-4-ylmethyl)-2,3-dihydro-1H-indol-6-yl]-2-[(pyridine-4-ylmethyl)-amino]-nicotinamide;
2-{[2-(1-Methyl-piperidin-4-ylmethoxy)-pyridin-4-ylmethyl]-amino}-N-(4-pentafluoroethyl-phenyl)-nicotinamide;
N-(3-tert-Butyl-isoxazol-5-yl)-2-{[2-(1-methyl-piperidin-4-ylmethoxy)-pyridin-4-ylmethyl]-amino}-nicotinamide;
N-(1-Acetyl-3,3-dimethyl-2,3-dihydro-1H-indol-6-yl)-2-{[2-(1-methyl-piperidin-4-ylmethoxy)-pyridin-4-ylmethyl]-amino}-nicotinamide;
N-(4-tert-Butyl-phenyl)-2-{[2-(3-morpholin-4-yl-propylamino)-pyrimidin-4-ylmethyl]-amino}-nicotinamide;
2-{[2-(3-Morpholin-4-yl-propylamino)-pyrimidin-4-ylmethyl]-amino}-N-(4-pentafluoroethyl-phenyl)-nicotinamide;
2-{[2-(3-Morpholin-4-yl-propylamino)-pyrimidin-4-ylmethyl]-amino}-N-(3-trifluoromethyl-phenyl)-nicotinamide;
N-(4-tert-Butyl-phenyl)-2-({2-[2-(1-methyl-pyrrolidin-2-yl)-ethylamino]-pyrimidin-4-ylmethyl}-amino)-nicotinamide;
N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide;
N-(4-Phenoxyphenyl){2-[(4-pyridylmethyl)amino](3-pyridyl)}carboxamide hydrochloride;
2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide;
N-(3-tert-Butyl-isoxazol-5-yl)-2-{[2-(1-methyl-piperidin-4-ylmethoxy)-pyridin-4-ylmethyl]-amino}-nicotinamide;
N-[3-(1-Boc-azetidin-3-ylmethoxy)-5-trifluoromethyl-phenyl]-2-[(pyridin-4-ylmethyl)-amino]-nicotinamide;
2-[(2-Methoxy-pyridin-4-ylmethyl)-amino]-N-[3-(1-Boc-azetidin-3-ylmethoxy)-5-trifluoromethyl-phenyl]-nicotinamide;
N-(3,3-Dimethylindolin-6-yl){2-[(4-pyridylmethyl)amino](3-pyridyl)}carboxamide phosphate salt;
N-(4-Morpholin-4-ylphenyl){2-[(4-pyridylmethyl)amino](3-pyridyl)}carboxamide hydrochloride;
N-(4-Cyanonaphthyl){2-[(4-pyridylmethyl)amino](3-pyridyl)}carboxamide hydrochloride;
{2-[(4-Pyridylmethyl)amino](3-pyridyl)}-N-[4-(trifluoromethyl)phenyl]carboxamide hydrochloride;
Methyl-({2-[(4-pyridylmethyl)amino]-3-pyridyl}carbonylamino)benzoate, hydrochloride;
2-[(Pyridin-4-ylmethyl)-amino]-N-(2,2,4-trimethyl-3,4-dihydro-2H-benzo[1,4]oxazin-6-yl)-nicotinamide;
N-(4-Acetyl-2,2-dimethyl-3,4-dihydro-2H-benzo[1,4]oxazin-6-yl)-2-[(pyridin-4-ylmethyl)-amino]-nicotinamide;
N-(2,2-Dimethyl-3-oxo-3,4-dihydro-2H-benzo[1,4]oxazin-6-yl)-2-[(pyridin-4-ylmethyl)-amino]-nicotinamide;
2-{[2-(1-Benzhydryl-azetidin-3-yloxy)-pyridin-4-ylmethyl]-amino}-N-(4-tert-butyl-phenyl)-nicotinamide;
N-(4,4-Dimethyl-1-oxo-1,2,3,4-tetrahydro-isoquinolin-7-yl)-2-[(pyridin-4-ylmethyl)-amino]-nicotinamide;
N-(4-tert-Butyl-phenyl)-2-({2-[2-(1-methyl-piperidin-4-yl)-ethoxy]-pyridin-4-ylmethyl}-amino)-nicotinamide;
N-(3-tert-Butyl-isoxazol-5-yl)-2-({2-[2-(1-methyl-piperidin-4-yl)-ethoxy]-pyridin-4-ylmethyl}-amino)-nicotinamide;
N-(3-trifluoromethylphenyl)-2-({2-[2-(1-methyl-piperidin-4-yl)-ethoxy]-pyridin-4-ylmethyl}-amino)-nicotinamide;
2-[(2,3-Dihydro-benzofuran-6-ylmethyl)-amino]-N-[3-(1-Boc-pyrrolidin-2-ylmethoxy)-4-pentafluoroethyl-phenyl]-nicotinamide;
N-[3-(1-Methyl-piperidin-4-ylmethoxy)-4-pentafluoroethyl-phenyl]-2-[(pyridin-4-ylmethyl)-amino]-nicotinamide hydrochloride;
(R) N-[3-(2-Hydroxy-3-pyrrolidin-1-yl-propoxy)-4-pentafluoroethyl-phenyl]-2-[(pyridin-4-ylmethyl)-amino]-nicotinamide;
(S) N-[3-(2-Hydroxy-3-pyrrolidin-1-yl-propoxy)-4-pentafluoroethyl-phenyl]-2-[(pyridin-4-ylmethyl)-amino]-nicotinamide;
N-[4-tert-Butyl-3-(1-methyl-piperidin-4-ylmethoxy)-phenyl]-2-[(pyridin-4-ylmethyl)-amino]-nicotinamide;
N-[3-(1-Methyl-piperidin-4-ylmethoxy)-4-pentafluoroethyl-phenyl]-2-[(pyridin-4-ylmethyl)-amino]-nicotinamide;
N-[4-Pentafluoroethyl-3-(2-piperidin-1-yl-ethoxy)-phenyl]-2-[(pyridin-4-ylmethyl)-amino]-nicotinamide;
2-[(Pyridin-4-ylmethyl)-amino]-N-(3-trifluoromethyl-phenyl)-nicotinamide hydrochloride;
N-(4-Imidazol-1-ylphenyl){2-[(4-pyridylmethyl)amino](3-pyridyl)}carboxamide hydrochloride;
N-(3,3-Dimethyl-2,3-dihydro-benzofuran-6-yl)-2-[(pyridin-4-ylmethyl)-amino]-nicotinamide hydrochloride;
2-[(Pyridin-4-ylmethyl)-amino]-N-(4-tert-butyl-phenyl)-nicotinamide hydrochloride;
N-[4-Trifluoromethyl-3-(2-piperidin-1-yl-ethoxy)-phenyl]-2-[(pyridin-4-ylmethyl)-amino]-nicotinamide;
(S) N-[3-(1-Boc-pyrrolidin-2-ylmethoxy)-4-pentafluoroethyl-phenyl]-2-[(pyridin-4-ylmethyl)-amino]-nicotinamide;
(R) N-[3-(1-Boc-pyrrolidin-2-ylmethoxy)-4-trifluoromethyl-phenyl]-2-[(pyridin-4-ylmethyl)-amino]-nicotinamide;
(R) N-[3-(1-Boc-pyrrolidin-2-ylmethoxy)-4-pentafluoroethyl-phenyl]-2-[(pyridin-4-ylmethyl)-amino]-nicotinamide;
N-(4-tert-Butyl-phenyl)-2-{[2-(1-methyl-piperidin-4-yloxy)-pyridin-4-ylmethyl]-amino}-nicotinamide;
N-(3-Trifluoromethyl-phenyl)-2-{[2-(1-methyl-piperidin-4-yloxy)-pyridin-4-ylmethyl]-amino}-nicotinamide;
N-(3-tert-Butyl-isoxazol-5-yl)-2-{[2-(1-methyl-piperidin-4-yloxy)-pyridin-4-ylmethyl]-amino}-nicotinamide;
N-[3-(3-Piperidin-1-yl-propyl)-5-trifluoromethyl-phenyl]-2-[(pyridin-4-ylmethyl)-amino]-nicotinamide;
N-[3-(3-Morpholin-4-yl-propyl)-5-trifluoromethyl-phenyl]-2-[(pyridin-4-ylmethyl)-amino]-nicotinamide;
2-[(2-Methoxy-pyridin-4-ylmethyl)-amino]-N-[3-(1-Boc-piperidin-4-yloxy)-5-trifluoromethyl-phenyl]-nicotinamide;
N-(3,3-Dimethylindolin-6-yl){2-[(4-pyridylmethyl)amino](3-pyridyl)}carboxamide edisylate;
N-{4-tert-Butyl-3-[2-(1-Boc-piperidin-4-yl)-ethyl]-phenyl}-2-[(pyridin-4-ylmethyl)-amino]-nicotinamide;
N-[4-tert-Butyl-3-(1-methyl-azetidin-3-ylmethoxy)-phenyl]-2-[(pyridin-4-ylmethyl)-amino]-nicotinamide;
N-(3,3-Dimethyl-1,1-dioxo-2,3-dihydro-1H-1λ-benzo[d]isothiazol-6-yl)-2-[(pyridin-4-ylmethyl)-amino]-nicotinamide;
N-[1,1,4,4-Tetramethyl-1,2,3,4-tetrahydro-naphth-6-yl]-2-[(pyridin-4-ylmethyl)-amino]-nicotinamide;
N-{4-[1-Methyl-1-(1-methyl-piperidin-4-yl)-ethyl]-phenyl}-2-[(pyridin-4-ylmethyl)-amino]-nicotinamide;
2-[(2-Methoxy-pyridin-4-ylmethyl)-amino]-N-{4-[1-methyl-1-(1-methyl-piperidin-4-yl)-ethyl]-phenyl}-nicotinamide;

N-(3,3-Dimethyl-2,3-dihydro-benzofuran-6-yl)-2-[(pyridin-4-ylmethyl)-amino]-nicotinamide;

N-(3,3-Dimethyl-2,3-dihydro-1H-indol-6-yl)-2-({2-[2-(1-methyl-piperidin-4-yl)-ethoxy]-pyridin-4-ylmethyl}-amino)-nicotinamide;

2-[(Pyridin-4-ylmethyl)-amino]-N-[3-(2-pyrrolidin-1-yl-ethoxy)-4-trifluoromethyl-phenyl]-nicotinamide hydrochloride;

N-(2,2-Dimethyl-3,4-dihydro-2H-benzo[1,4]oxazin-6-yl)-2-[(pyridin-4-ylmethyl)-amino]-nicotinamide;

N-(4,4-Dimethyl-1,2,3,4-tetrahydro-isoquinolin-7-yl)-2-[(pyridin-4-ylmethyl)-amino]-nicotinamide;

N-(3,3-Dimethyl-2,3-dihydro-1H-indol-6-yl)-2-{[2-(1-methyl-piperidin-4-ylmethoxy)-pyridin-4-ylmethyl]-amino}-nicotinamide;

N-(3,3-Dimethylindolin-6-yl){2-[(4-pyridylmethyl)amino](3-pyridyl)}carboxamide hydrochloride;

N-(3,3-Dimethyl-1-piperidin-4-yl-2,3-dihydro-1H-indol-6-yl)-2-[(pyridin-4-ylmethyl)-amino]-nicotinamide;

N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide;

N-(3,3-dimethyl-2,3-dihydro-1H-indol-6-yl)-2-[(2-methoxy-pyridin-4-ylmethyl)-amino]-nicotinamide;

N-[3,3-Dimethyl-1-(piperidin-4-ylmethyl)-2,3-dihydro-1H-indol-6-yl]-2-[(2-methoxy-pyridin-4-ylmethyl)-amino]-nicotinamide;

N-(3,3-Dimethyl-1-piperidin-4-yl-2,3-dihydro-1H-indol-6-yl)-2-[(2-methoxy-pyridin-4-ylmethyl)-amino]-nicotinamide;

2-[(2-Methoxy-pyridin-4-ylmethyl)-amino]-N-[3-(piperidin-4-ylmethoxy)-5-trifluoromethyl-phenyl]-nicotinamide;

N-[3,3-Dimethyl-1-(pyrrolidin-2-ylmethoxy)-2,3-dihydro-1H-indol-6-yl]-2-[(2-methoxy-pyridin-4-ylmethyl)-amino]-nicotinamide;

2-[(2-Methoxy-pyridin-4-ylmethyl)-amino]-N-[3-(piperazin-1-ylmethyl)-5-trifluoromethyl-phenyl]-nicotinamide;

N-(3,3-dimethyl-2,3-dihydro-1H-indol-6-yl)-2-{[2-(2-morpholin-4-yl-ethoxy)-pyridin-4-ylmethyl]-amino}-nicotinamide;

N-(3,3-dimethyl-2,3-dihydro-1H-indol-6-yl)-2-{[2-(2-morpholin-4-yl-propylamino)-pyridin-4-ylmethyl]-amino}-nicotinamide hydrochloride;

N-(3,3-dimethyl-2,3-dihydro-1H-indol-6-yl)-2-{[2-(1-methyl-piperidin-4-yloxy)-pyridin-4-ylmethyl]-amino}-nicotinamide;

N-(3,3-dimethyl-2,3-dihydro-1H-indol-6-yl)-2-{[2-(2-morpholin-4-yl-propoxy)-pyridin-4-ylmethyl]-amino}-nicotinamide;

N-(4-Pentafluoroethyl-phenyl)-2-[(pyrimidin-4-ylmethyl)-amino]-nicotinamide;

2-{[2-(Azetidin-3-yloxy)-pyridin-4-ylmethyl]-amino}-N-(4-tert-butyl-phenyl)nicotinamide;

N-(2,3,3-Trimethyl-1,1-dioxo-2,3-dihydro-1H-1λ-benzo[d]isothiazol-6-yl)-2-[(pyridin-4-ylmethyl)-amino]-benzamide;

N-(4,4-Dimethyl-1-oxo-1,2,3,4-tetrahydro-isoquinolin-7-yl)-2-[(pyridin-4-ylmethyl)-amino]-nicotinamide hydrochloride;

N-[3,3-Dimethyl-1,1-dioxo-2-(2-piperidin-1-yl-ethyl)-2,3-dihydro-1H-1λ'-benzo[d]isothiazol-6-yl]-2-[(pyridin-4-ylmethyl)-amino]-nicotinamide; and N-[2-(2-Dimethylamino-ethyl)-3,3-dimethyl-1,1-dioxo-2,3-dihydro-1H-1λ'-benzo[d]isothiazol-6-yl]-2-[(pyridin-4-ylmethyl)-amino]-nicotinamide.

Another family of specific compounds of particular interest within Formula I consists of compounds and pharmaceutically-acceptable derivatives thereof as follows:

2-[(2,3-Dihydro-benzofuran-5-ylmethyl)-amino]-N-(1-Boc-4,4-dimethyl-1,2,3,4-tetrahydro-isoquinolin-7-yl)-nicotinamide;

2-[(2,3-Dihydro-benzofuran-5-ylmethyl)-amino]-N-(4,4-dimethyl-1,2,3,4-tetrahydro-isoquinolin-7-yl)-nicotinamide;

2-[(2,3-Dihydro-benzofuran-5-ylmethyl)-amino]-N-[4-pentafluoroethyl-3-(pyrrolidin-2-ylmethoxy)-phenyl]-nicotinamide;

N-(3,3-Dimethyl-2,3-dihydro-1H-indol-6-yl)-2-[(tetrahydro-pyran-4-ylmethyl)-amino]-nicotinamide;

N-(1-Acetyl-3,3-dimethyl-2,3-dihydro-1H-indol-6-yl)-2-[(tetrahydro-pyran-4-ylmethyl)-amino]-nicotinamide;

N-(4-Pentafluoroethyl-phenyl)-2-[(tetrahydro-pyran-4-ylmethyl)-amino]-nicotinamide;

N-(3-((2-(1-pyrrolidinyl)ethyl)oxy)-4-(trifluoromethyl)phenyl)-2-((4-quinolinylmethyl)amino)-3-pyridinecarboxamide;

N-(1-acetyl-3,3-dimethyl-2,3-dihydro-1H-indol-6-yl)-2-((4-pyrimidinylmethyl)amino)-3-pyridinecarboxamide;

N-(3,3-dimethyl-2,3-dihydro-1H-indol-6-yl)-2-((4-quinolinylmethyl)amino)-3-pyridinecarboxamide;

2-((4-pyrimidinylmethyl)amino)-N-(3-((2-(1-pyrrolidinyl)ethyl)oxy)-4-(trifluoromethyl)phenyl)-3-pyridinecarboxamide;

N-(3-((((2S)-1-methyl-2-pyrrolidinyl)methyl)oxy)-5-(trifluoromethyl)phenyl)-2-((4-pyrimidinylmethyl)amino)-3-pyridinecarboxamide;

N-(3-((3-azetidinylmethyl)oxy)-4-(pentafluoroethyl)phenyl)-2-((4-pyrimidinylmethyl)amino)-3-pyridinecarboxamide;

N-(4-(1-methyl-1-(1-methyl-4-piperidinyl)ethyl)phenyl)-2-((4-pyrimidinylmethyl)amino)-3-pyridinecarboxamide;

N-(4-(1-methyl-1-(1-methyl-4-piperidinyl)ethyl)phenyl)-2-((4-quinolinylmethyl)amino)-3-pyridinecarboxamide;

N-(3,3-dimethyl-2,3-dihydro-1H-indol-6-yl)-2-((4-pyrimidinylmethyl)amino)-3-pyridinecarboxamide;

N-(1-(N,N-dimethylglycyl)-3,3-dimethyl-2,3-dihydro-1H-indol-6-yl)-2-((4-quinolinylmethyl)amino)-3-pyridinecarboxamide;

N-(3-((2-((methylsulfonyl)amino)ethyl)oxy)-4-(pentafluoroethyl)phenyl)-2-((4-pyridinylmethyl)amino)-3-pyridinecarboxamide;

N-(3-((2-((methylsulfonyl)amino)ethyl)oxy)-4-(trifluoromethyl)phenyl)-2-((4-pyridinylmethyl)amino)-3-pyridinecarboxamide;

2-(((2-(methylamino)-4-pyrimidinyl)methyl)amino)-N-(3-((2-((methylsulfonyl)amino)ethyl)oxy)-4-(trifluoromethyl)phenyl)-3-pyridinecarboxamide;

N-(2-oxo-3,3-bis(trifluoromethyl)-2,3-dihydro-1H-indol-6-yl)-2-((4-pyridinylmethyl)amino)-3-pyridinecarboxamide;

2-(((2-(methylamino)-4-pyridinyl)methyl)amino)-N-(2-oxo-3,3-bis(trifluoromethyl)-2,3-dihydro-1H-indol-6-yl)-3-pyridinecarboxamide;

2-(((2-(methylamino)-4-pyrimidinyl)methyl)amino)-N-(2-oxo-3,3-bis(trifluoromethyl)-2,3-dihydro-1H-indol-6-yl)-3-pyridinecarboxamide;

2-(((2-(methyloxy)-4-pyridinyl)methyl)amino)-N-(2-oxo-3,3-bis(trifluoromethyl)-2,3-dihydro-1H-indol-6-yl)-3-pyridinecarboxamide;

N-(4,4-dimethyl-1,2,3,4-tetrahydro-7-isoquinolinyl)-2-(((2-(methylamino)-4-pyrimidinyl)methyl)amino)-3-pyridinecarboxamide;

N-(1-(N,N-dimethylglycyl)-3,3-dimethyl-2,3-dihydro-1H-indol-6-yl)-2-(((2-(methylamino)-4-pyrimidinyl)methyl)amino)-3-pyridinecarboxamide;

N-(3,3-dimethyl-2,3-dihydro-1H-indol-6-yl)-2-(((2-(methylamino)-4-pyrimidinyl)methyl)amino)-3-pyridinecarboxamide;

2-(((2-(methylamino)-4-pyrimidinyl)methyl)amino)-N-(2,4,4-trimethyl-1,2,3,4-tetrahydro-7-isoquinolinyl)-3-pyridinecarboxamide;

2-(((6-(methylamino)-4-pyrimidinyl)methyl)amino)-N-(4-(1-methyl-1-(1-methyl-4-piperidinyl)ethyl)phenyl)-3-pyridinecarboxamide;

2-(((2-(methylamino)-4-pyrimidinyl)methyl)amino)-N-(4-(1-methyl-1-(1-methyl-4-piperidinyl)ethyl)phenyl)-3-pyridinecarboxamide;

2-(((2-(methylamino)-4-pyrimidinyl)methyl)amino)-N-(3-(((2R)-1-methyl-2-pyrrolidinyl)methyl)oxy)-5-(trifluoromethyl)phenyl)-3-pyridinecarboxamide;

N-(1-acetyl-3,3-dimethyl-2,3-dihydro-1H-indol-6-yl)-2-(((2-(methylamino)-4-pyrimidinyl)methyl)amino)-3-pyridinecarboxamide;

N-(1-acetyl-3,3-dimethyl-2,3-dihydro-1H-indol-6-yl)-2-(((2-(methyloxy)-4-pyrimidinyl)methyl)amino)-3-pyridinecarboxamide;

2-(((2-(methyloxy)-4-pyrimidinyl)methyl)amino)-N-(3-(((2S)-1-methyl-2-pyrrolidinyl)methyl)oxy)-5-(trifluoromethyl)phenyl)-3-pyridinecarboxamidel;

2-(((2-((2-((2R,S)-1-methyl-2-pyrrolidinyl)ethyl)amino)-4-pyrimidinyl)methyl)amino)-N-(3-(trifluoromethyl)phenyl)-3-pyridinecarboxamide;

2-[(2-Amino-pyridin-4-ylmethyl)-amino]-N-{4-[1-methyl-1-(5-methyl-[1,3,4]oxadiazol-2-yl)-ethyl]-phenyl}-nicotinamide;

2-[(2,3-Dihydro-benzofuran-5-ylmethyl)-amino]-N-{4-[1-methyl-1-(5-methyl-[1,3,4]oxadiazol-2-yl)-ethyl]-phenyl}-nicotinamide;

2-[(2-Methylamino-pyridin-4-ylmethyl)-amino]-N-{4-[1-methyl-1-(5-methyl-[1,3,4]oxadiazol-2-yl)-ethyl]-phenyl}-nicotinamide;

2-(((2-(methylamino)-4-pyrimidinyl)methyl)amino)-N-(4-(1-methyl-1-(5-methyl-1,3,4-oxadiazol-2-yl)ethyl)phenyl)-3-pyridinecarboxamide;

N-(4-(1-methyl-1-(5-methyl-1,3,4-oxadiazol-2-yl)ethyl)phenyl)-2-((4-pyrimidinylmethyl)amino)-3-pyridinecarboxamide;

2-(((2-(methylamino)-4-pyrimidinyl)methyl)amino)-N-(4-(1-methyl-1-(4-pyrimidinyl)ethyl)phenyl)-3-pyridinecarboxamide;

2-[(2-Methylamino-pyrimidin-4-ylmethyl)-amino]-N-{4-[1-methyl-1-(2H-pyrazol-3-yl)-ethyl]-phenyl}-nicotinamide;

N-(3-((((2R)-1-methyl-2-pyrrolidinyl)methyl)oxy)-4-(trifluoromethyl)phenyl)-2-((6-quinolinylmethyl)amino)-3-pyridinecarboxamide;

N-(3-((((2R)-1-methyl-2-pyrrolidinyl)methyl)oxy)-5-(trifluoromethyl)phenyl)-2-((6-quinolinylmethyl)amino)-3-pyridinecarboxamide;

N-(3,3-dimethyl-1-(methylsulfonyl)-2,3-dihydro-1H-indol-6-yl)-2-(((2-(methylamino)-4-pyrimidinyl)methyl)amino)-3-pyridinecarboxamide;

2-(((2-amino-4-pyridinyl)methyl)amino)-N-(3,3-dimethyl-1-(methylsulfonyl)-2,3-dihydro-1H-indol-6-yl)-3-pyridinecarboxamide;

N-(3,3-dimethyl-1-(methylsulfonyl)-2,3-dihydro-1H-indol-6-yl)-2-(((2-(methylamino)-4-pyrimidinyl)methyl)amino)-3-pyridinecarboxamide;

N-(4,4-dimethyl-1,2,3,4-tetrahydro-7-isoquinolinyl)-2-((6-quinolinylmethyl)amino)-3-pyridinecarboxamide;

1,1-dimethylethyl(2S)-2-(((2-(1,1-dimethylethyl)-5-(((2-(((2-(methyloxy)-4-pyridinyl)methyl)amino)-3-pyridinyl)carbonyl)amino)phenyl)oxy)methyl)-1-pyrrolidinecarboxylate;

2-((6-quinolinylmethyl)amino)-N-(3-((tetrahydro-2-furanylmethyl)oxy)-5-(trifluoromethyl)phenyl)-3-pyridinecarboxamide;

N-(4-(1,1-dimethylethyl)-3-((N,N-dimethylglycyl)amino)phenyl)-2-((6-quinolinylmethyl)amino)-3-pyridinecarboxamide;

2-((6-quinolinylmethyl)amino)-N-(3-((3R)-tetrahydro-3-furanyloxy)-5-(trifluoromethyl)phenyl)-3-pyridinecarboxamide;

N-(2-oxo-3,3-bis(trifluoromethyl)-2,3-dihydro-1H-indol-6-yl)-2-((6-quinolinylmethyl)amino)-3-pyridinecarboxamide;

N-(4-(1,1-dimethylethyl)-3-(((2S)-2-pyrrolidinylmethyl)oxy)phenyl)-2-(((2-(methyloxy)-4-pyridinyl)methyl)amino)-3-pyridinecarboxamide;

N-(3,3-dimethyl-1-(methylsulfonyl)-2,3-dihydro-1H-indol-6-yl)-2-((4-pyridinylmethyl)amino)-3-pyridinecarboxamide;

1-methyl-5-[(pyridin-4-ylmethyl)-amino]-1H-pyrazole-4-carboxylic acid (4-tert-butyl-phenyl)-amide;

1-Methyl-5-[(pyridin-4-ylmethyl)-amino]-1H-pyrazole-4-carboxylic acid [3-(pyrrolidin-2-ylmethoxy)-5-trifluoromethyl-phenyl]-amide;

N-(4-(1,1-dimethylethyl)-3-((N,N-dimethylglycyl)amino)phenyl)-2-(((2-(methyloxy)-4-pyridinyl)methyl)amino)-3-pyridinecarboxamide;

N-(4-(1,1-dimethylethyl)-3-((N,N-dimethylglycyl)amino)phenyl)-2-((4-quinolinylmethyl)amino)-3-pyridinecarboxamide;

N-(4-(1,1-dimethylethyl)-3-((N,N-dimethylglycyl)amino)phenyl)-2-((4-pyrimidinylmethyl)amino)-3-pyridinecarboxamide;

N-(4-(1,1-dimethylethyl)-3-((N,N-dimethylglycyl)amino)phenyl)-2-(((2-(methyloxy)-4-pyrimidinyl)methyl)amino)-3-pyridinecarboxamide;

N-(4-(1,1-dimethylethyl)-3-((1-pyrrolidinylacetyl)amino)phenyl)-2-((4-quinolinylmethyl)amino)-3-pyridinecarboxamide;

N-(4-(1,1-dimethylethyl)-3-((1-pyrrolidinylacetyl)amino)phenyl)-2-(((2-(methyloxy)-4-pyridinyl)methyl)amino)-3-pyridinecarboxamide;

N-(4-(1,1-dimethylethyl)-3-((N,N-dimethylglycyl)amino)phenyl)-2-(((2-(methylamino)-4-pyrimidinyl)methyl)amino)-3-pyridinecarboxamide;

N-(3-((3R)-tetrahydro-3-furanyloxy)-5-(trifluoromethyl)phenyl)-2-((tetrahydro-2H-pyran-4-ylmethyl)amino)-3-pyridinecarboxamide;

2-(((2-(methyloxy)-4-pyridinyl)methyl)amino)-N-(3-(((2S)-tetrahydro-2-furanylmethyl)oxy)-5-(trifluoromethyl)phenyl)-3-pyridinecarboxamide;

2-(((2-(methyloxy)-4-pyridinyl)methyl)amino)-N-(3-(((2R)-tetrahydro-2-furanylmethyl)oxy)-5-(trifluoromethyl)phenyl)-3-pyridinecarboxamide;

2-(((2-(methylamino)-4-pyridinyl)methyl)amino)-N-(3-(((2S)-tetrahydro-2-furanylmethyl)oxy)-5-(trifluoromethyl)phenyl)-3-pyridinecarboxamide;

2-(((2-(methylamino)-4-pyridinyl)methyl)amino)-N-(3-(((2R)-tetrahydro-2-furanylmethyl)oxy)-5-(trifluoromethyl)phenyl)-3-pyridinecarboxamide;

2-(((2-(methylamino)-4-pyrimidinyl)methyl)amino)-N-(3-(((2S)-tetrahydro-2-furanylmethyl)oxy)-5-(trifluoromethyl)phenyl)-3-pyridinecarboxamide;

2-(((2-(methylamino)-4-pyrimidinyl)methyl)amino)-N-(3-(((2R)-tetrahydro-2-furanylmethyl)oxy)-5-(trifluoromethyl)phenyl)-3-pyridinecarboxamide;

2-(((2-(methyloxy)-4-pyridinyl)methyl)amino)-N-(3-((3R)-tetrahydro-3-furanyloxy)-5-(trifluoromethyl)phenyl)-3-pyridinecarboxamide;

2-(((2-(methylamino)-4-pyridinyl)methyl)amino)-N-(3-((3R)-tetrahydro-3-furanyloxy)-5-(trifluoromethyl)phenyl)-3-pyridinecarboxamide;

2-(((2-(methylamino)-4-pyrimidinyl)methyl)amino)-N-(3-((3R)-tetrahydro-3-furanyloxy)-5-(trifluoromethyl)phenyl)-3-pyridinecarboxamide;

N-(3-((((2R)-1-acetyl-2-pyrrolidinyl)methyl)oxy)-5-(trifluoromethyl)phenyl)-2-(((2-(methylamino)-4-pyrimidinyl)methyl)amino)-3-pyridinecarboxamide;

(3S)-tetrahydro-3-furanyl 3-(((2-((4-pyrimidinylmethyl)amino)-3-pyridinyl)carbonyl)amino)-5-(trifluoromethyl)phenylcarbamate;

N-(3-((2-((methylsulfonyl)amino)ethyl)oxy)-5-(trifluoromethyl)phenyl)-2-((4-pyrimidinylmethyl)amino)-3-pyridinecarboxamide;

(3S)-tetrahydro-3-furanyl 3-(((2-((4-pyridinylmethyl)amino)-3-pyridinyl)carbonyl)amino)-5-(trifluoromethyl)phenylcarbamate;

(3S)-tetrahydro-3-furanyl 3-(((2-(((2-(methylamino)-4-pyrimidinyl)methyl)amino)-3-pyridinyl)carbonyl)amino)-5-(trifluoromethyl)phenylcarbamate;

N-(3-((2-((methylsulfonyl)amino)ethyl)oxy)-5-(trifluoromethyl)phenyl)-2-((4-pyridinylmethyl)amino)-3-pyridinecarboxamide;

2-(((2-(methylamino)-4-pyrimidinyl)methyl)amino)-N-(3-((2-((methylsulfonyl)amino)ethyl)oxy)-5-(trifluoromethyl)phenyl)-3-pyridinecarboxamide;

2-(((2-(methyloxy)-4-pyridinyl)methyl)amino)-N-(3-((methylsulfonyl)amino)-5-(trifluoromethyl)phenyl)-3-pyridinecarboxamide;

2-(((2-(methylamino)-4-pyrimidinyl)methyl)amino)-N-(3-((methylsulfonyl)amino)-5-(trifluoromethyl)phenyl)-3-pyridinecarboxamide;

2-(((2-(methylamino)-4-pyridinyl)methyl)amino)-N-(3-((methylsulfonyl)amino)-5-(trifluoromethyl)phenyl)-3-pyridinecarboxamide;

N-(3-((methylsulfonyl)amino)-5-(trifluoromethyl)phenyl)-2-((4-pyridinylmethyl)amino)-3-pyridinecarboxamide;

N-(3-((((2S)-1-(1-methylethyl)-2-pyrrolidinyl)methyl)oxy)-5-(trifluoromethyl)phenyl)-2-((4-pyridinylmethyl)amino)-3-pyridinecarboxamide;

N-{4-[1-Methyl-1-(1-methyl-piperidin-4-yl)-ethyl]-phenyl}-2-[(1-oxy-pyridin-4-ylmethyl)-amino]-nicotinamide;

4-{1-Methyl-1-[4-({2-[(pyridin-4-ylmethyl)-amino]-pyridine-3-carbonyl}-amino)-phenyl]-ethyl}-3,6-dihydro-2H-pyridine-1-carboxylic acid ethyl ester;

N-[3,3-Dimethyl-1-(1-oxy-pyridin-4-ylmethyl)-2,3-dihydro-1H-indol-6-yl]-2-[(pyridin-4-ylmethyl)-amino]-nicotinamide;

N-[3,3-Dimethyl-1-(1-oxy-pyridine-4-carbonyl)-2,3-dihydro-1H-indol-6-yl]-2-[(pyridin-4-ylmethyl)-amino]-nicotinamide;

2-[(2-Amino-pyridin-4-ylmethyl)-amino]-N-{4-[1-methyl-1-(1-methyl-piperidin-4-yl)-ethyl]-phenyl}-nicotinamide;

N-(1-Acetyl-3,3-dimethyl-2,3-dihydro-1H-indol-6-yl)-2-[(2-methylamino-pyridin-4-ylmethyl)-amino]-nicotinamide;

N-(3,3-Dimethyl-2,3-dihydro-1H-indol-6-yl)-2-[(2-methylamino-pyridin-4-ylmethyl)-amino]-nicotinamide;

2-[(2-Methylamino-pyrimidin-4-ylmethyl)-amino]-N-{4-[1-methyl-1-(1-methyl-piperidin-4-yl)-ethyl]-phenyl}-nicotinamide;

Ethyl [1,2-dihydro-6-({2-[(2-methylamino-pyridin-4-ylmethyl)-amino]-pyridine-3-carbonyl}-amino)-3-spiro-1'-cyclopropyl-1H-indole]-1-carbamate;

N-(1,2-dihydroindol-3-spiro-1'-cyclopropane-6-yl)-2-[(2-methylaminopyridin-4-ylmethyl)-amino]-nicotinamide;

Ethyl [1,2-dihydro-6-({2-[(2-methylamino-pyrimidin-4-ylmethyl)-amino]-pyridine-3-carbonyl}-amino)-3-spiro-1'-cyclopropyl-1H-indole]-1-carbamate;

N-(4,4-Dimethyl-1,2,3,4-tetrahydro-quinolin-7-yl)-2-[(pyridin-4-ylmethyl)-amino]-nicotinamide;

N-(4,4-Dimethyl-1,2,3,4-tetrahydro-quinolin-7-yl)-2-[(pyrimidin-4-ylmethyl)-amino]-nicotinamide;

2-[(2-Amino-pyridin-4-ylmethyl)-amino]-N-(4,4-dimethyl-1,2,3,4-tetrahydro-quinolin-7-yl)-nicotinamide;

N-(4,4-Dimethyl-1,2,3,4-tetrahydro-quinolin-7-yl)-2-[(2-methylamino-pyrimidin-4-ylmethyl)-amino]-nicotinamide;

N-(4,4-Dimethyl-1,2,3,4-tetrahydro-quinolin-7-yl)-2-[(2-methoxy-pyridin-4-ylmethyl)-amino]-nicotinamide;

N-(4,4-Dimethyl-2-oxo-1,2,3,4-tetrahydro-quinolin-7-yl)-2-[(pyridin-4-ylmethyl)-amino]-nicotinamide;

N-(4,4-Dimethyl-2-oxo-1,2,3,4-tetrahydro-quinolin-7-yl)-2-[(2-methylamino-pyrimidin-4-ylmethyl)-amino]-nicotinamide;

N-(4,4-Dimethyl-2-oxo-1,2,3,4-tetrahydro-quinolin-7-yl)-2-[(2-methoxy-pyridin-4-ylmethyl)-amino]-nicotinamide;

N-(4,4-Dimethyl-2-oxo-1,2,3,4-tetrahydro-quinolin-7-yl)-2-{[2-(2,2,2-trifluoro-ethoxy)-pyridin-4-ylmethyl]-amino}-nicotinamide;

2-[(2-Amino-pyridin-4-ylmethyl)-amino]-N-(4,4-dimethyl-2-oxo-1,2,3,4-tetrahydro-quinolin-7-yl)-nicotinamide;

N-(4,4-Dimethyl-2-oxo-1,2,3,4-tetrahydro-quinolin-7-yl)-2-[(2-methylamino-pyridin-4-ylmethyl)-amino]-nicotinamide;

N-(4,4-Dimethyl-2-oxo-1,2,3,4-tetrahydro-quinolin-7-yl)-2-[(2-methylamino-pyridin-4-ylmethyl)-amino]-nicotinamide;

N-(4,4-Dimethyl-2-oxo-1,2,3,4-tetrahydro-quinolin-7-yl)-2-[(3-fluoro-pyridin-2-ylmethyl)-amino]-nicotinamide;

tert-Butyl N-[7-({2-[(5-fluoro-pyridin-2-ylmethyl)-amino]-pyridine-3-carbonyl}-amino)-4,4-dimethyl-3,4-dihydro-1H-isoquinoline]carbamate;

N-(4,4-Dimethyl-1,2,3,4-tetrahydro-isoquinolin-7-yl)-2-[(5-fluoro-pyridin-2-ylmethyl)-amino]-nicotinamide;

N-(1-Ethyl-4,4-dimethyl-1,2,3,4-tetrahydro-quinolin-7-yl)-2-[(pyridin-4-ylmethyl)-amino]-nicotinamide;

2-[(2-Amino-pyridin-4-ylmethyl)-amino]-N-(1-ethyl-4,4-dimethyl-1,2,3,4-tetrahydro-quinolin-7-yl)-nicotinamide;

2-[(2-Methoxy-pyridin-4-ylmethyl)-amino]-N-(1,4,4-trimethyl-1,2,3,4-tetrahydro-quinolin-7-yl)-nicotinamide;

tert-Butyl N-[7-({2-[(2-methoxy-pyridin-4-ylmethyl)-amino]-pyridine-3-carbonyl}-amino)-4-spiro-1'-cyclopropane-3,4-dihydro-1H-isoquinoline]carbamate;

N-(4-Spiro-1'-cyclopropane-1,2,3,4-tetrahydroisoquinolin-7-yl)-2-[(2-methoxy-pyridin-4-ylmethyl)-amino]-nicotinamide;

N-(4,4-Dimethyl-1,2,3,4-tetrahydro-isoquinolin-7-yl)-2-{[2-(2,2,2-trifluoro-ethoxy)-pyridin-4-ylmethyl]-amino}-nicotinamide;

N-(4,4-Dimethyl-1,2,3,4-tetrahydro-isoquinolin-7-yl)-2-[(2-methylamino-pyridin-4-ylmethyl)-amino]-nicotinamide;

N-(4,4-Dimethyl-1,2,3,4-tetrahydro-isoquinolin-7-yl)-2-[(quinolin-6-ylmethyl)-amino]-nicotinamide;

N-(4,4-Dimethyl-1,2,3,4-tetrahydro-isoquinolin-7-yl)-2-[(2-methoxy-pyrimidin-4-ylmethyl)-amino]-nicotinamide;

N-(2-Chloro-pyridin-4-yl)-2-[(2-methylamino-pyridin-4-ylmethyl)-amino]-nicotinamide;

2-[(2-Methoxy-pyridin-4-ylmethyl)-amino]-N-[4-methyl-6-(1-methyl-pyrrolidin-2-ylmethoxy)-pyrimidin-2-yl]-nicotinamide;

N-(5,5-Dimethyl-7-oxo-5,6,7,8-tetrahydro-[1,8]naphthyridin-2-yl)-2-[(2-methylamino-pyrimidin-4-ylmethyl)-amino]-nicotinamide;

N-(5,5-Dimethyl-5,6-dihydro-[1,7]naphthyridin-2-yl)-2-[(2-methoxy-pyridin-4-ylmethyl)-amino]-nicotinamide;

2-{2,2,2-Trifluoro-1-[3-({2-[(pyridin-4-ylmethyl)-amino]-pyridine-3-carbonyl}-amino)-phenyl]-1-trifluoromethyl-ethoxymethyl}-pyrrolidine-1-carboxylic acid tert-butyl ester;

2-[(Pyridin-4-ylmethyl)-amino]-N-{3-[2,2,2-trifluoro-1-(pyrrolidin-2-ylmethoxy)-1-trifluoromethyl-ethyl]-phenyl}-nicotinamide;

2-[(2-Methoxy-pyridin-4-ylmethyl)-amino]-N-{3-[2,2,2-trifluoro-1-(pyrrolidin-2-ylmethoxy)-1-trifluoromethyl-ethyl]-phenyl}-nicotinamide;

2-{2,2,2-Trifluoro-1-[4-({2-[(pyridin-4-ylmethyl)-amino]-pyridine-3-carbonyl}-amino)-phenyl]-1-trifluoromethyl-ethoxymethyl}-pyrrolidine-1-carboxylic acid tert-butyl ester;

2-[(Pyridin-4-ylmethyl)-amino]-N-{4-[2,2,2-trifluoro-1-(pyrrolidin-2-ylmethoxy)-1-trifluoromethyl-ethyl]-phenyl}-nicotinamide;

2-[(2-Methoxy-pyridin-4-ylmethyl)-amino]-N-{4-[2,2,2-trifluoro-1-(pyrrolidin-2-ylmethoxy)-1-trifluoromethyl-ethyl]-phenyl}-nicotinamide;

2-[(2-Methylamino-pyridin-4-ylmethyl)-amino]-N-[3-(1-methyl-pyrrolidin-2-ylmethoxy)-5-trifluoromethyl-phenyl]-nicotinamide;

2-[(2-Methylamino-pyrimidin-4-ylmethyl)-amino]-N-[3-(1-methyl-pyrrolidin-2-ylmethoxy)-5-trifluoromethyl-phenyl]-nicotinamide;

N-(4,4-Dimethyl-1,2,3,4-tetrahydro-isoquinolin-7-yl)-2-[(1H-pyrrolo[2,3-b]pyridin-4-ylmethyl)-amino]-nicotinamide;

7-({2-[(2,3-Dihydro-1H-pyrrolo[2,3-b]pyridin-4-ylmethyl)-amino]-pyridine-3-carbonyl}-amino)-4,4-dimethyl-3,4-dihydro-1H-isoquinoline-2-carboxylic acid tert-butyl ester;

2-[(2,3-Dihydro-1H-pyrrolo[2,3-b]pyridin-4-ylmethyl)-amino]-N-(4,4-dimethyl-1,2,3,4-tetrahydro-isoquinolin-7-yl)-nicotinamide;

2 2-[(2-Methoxy-pyridin-4-ylmethyl)-amino]-N-[3-(1-methyl-piperidin-3-yloxy)-5-trifluoromethyl-phenyl]-nicotinamide;

N-[3-Chloro-5-(2-dimethylamino-acetylamino)-phenyl]-2-[(2-methylamino-pyridin-4-ylmethyl)-amino]-nicotinamide;

2-[(2-Amino-pyridin-4-ylmethyl)-amino]-N-[3-chloro-5-(2-dimethylamino-acetylamino)-phenyl]-nicotinamide;

N-[6-(4-Methyl-piperazin-1-yl)-pyridin-2-yl]-2-[(pyridin-4-ylmethyl)-amino]-nicotinamide;

2-[(Pyridin-4-ylmethyl)-amino]-N-(3,4,5,6-tetrahydro-2H-[1,2']bipyridinyl-6'-yl)-nicotinamide;

N-(5,5-Dimethyl-7-oxo-5,6,7,8-tetrahydro-[1,8]naphthyridin-2-yl)-2-[(2-methylamino-pyridin-4-ylmethyl)-amino]-nicotinamide;

N-(4,4-Dimethyl-1,2,3,4-tetrahydro-quinolin-7-yl)-2-[(2-morpholin-4-yl-pyridin-4-ylmethyl)-amino]-nicotinamide;

2-[(2-Morpholin-4-yl-pyridin-4-ylmethyl)-amino]-N-(4-pentafluoroethyl-phenyl)-nicotinamide;

tert-Butyl N-[4,4-Dimethyl-7-({2-[(2-morpholin-4-yl-pyridin-4-ylmethyl)-amino]-pyridine-3-carbonyl}-amino)-3,4-dihydro-1H-isoquinoline]carbamate;

N-(4,4-Dimethyl-1,2,3,4-tetrahydro-isoquinolin-7-yl)-2-[(2-morpholin-4-yl-pyridin-4-ylmethyl)-amino]-nicotinamide;

N-(4,4-Dimethyl-1,2,3,4-tetrahydro-quinolin-7-yl)-2-[(2-pyrrolidin-1-yl-pyridin-4-ylmethyl)-amino]-nicotinamide;

tert-Butyl N-[4,4-Dimethyl-7-({2-[(2-pyrrolidin-1-yl-pyridin-4-ylmethyl)-amino]-pyridine-3-carbonyl}-amino)-3,4-dihydro-1H-isoquinoline]carbamate;

N-(4,4-Dimethyl-1,2,3,4-tetrahydro-isoquinolin-7-yl)-2-[(2-pyrrolidin-1-yl-pyridin-4-ylmethyl)-amino]-nicotinamide;

N-{4-[1-Methyl-1-(1-methyl-piperidin-4-yl)-ethyl]-phenyl}-2-[(2-pyrrolidin-1-yl-pyridin-4-ylmethyl)-amino]-nicotinamide;

2-[(2-Pyrrolidin-1-yl-pyridin-4-ylmethyl)-amino]-N-(4-trifluoromethyl-phenyl)-nicotinamide;

N-(4-Pentafluoroethyl-phenyl)-2-[(2-pyrrolidin-1-yl-pyridin-4-ylmethyl)-amino]-nicotinamide;

N-{4-[1-Methyl-1-(1-methyl-piperidin-4-yl)-ethyl]-phenyl}-2-[(2-morpholin-4-yl-pyridin-4-ylmethyl)-amino]-nicotinamide;

2-[(2-Morpholin-4-yl-pyridin-4-ylmethyl)-amino]-N-(4-trifluoromethyl-phenyl)-nicotinamide;

N-[3-(1-Methyl-pyrrolidin-2-ylmethoxy)-5-trifluoromethyl-phenyl]-2-[(2-morpholin-4-yl-pyridin-4-ylmethyl)-amino]-nicotinamide;

N-[3-(1-Methyl-pyrrolidin-2-ylmethoxy)-5-trifluoromethyl-phenyl]-2-[(2-pyrrolidin-1-yl-pyridin-4-ylmethyl)-amino]-nicotinamide;

2-[(2-Amino-pyridin-4-ylmethyl)-amino]-N-{4-[1-methyl-1-(5-methyl-[1,3,4]oxadiazol-2-yl)-ethyl]phenyl}-nicotinamide;

2-[(2,3-Dihydro-benzofuran-5-ylmethyl)-amino]-N-{4-[1-methyl-1-(5-methyl-[1,3,4]oxadiazol-2-yl)-ethyl]-phenyl}-nicotinamide;

2-[(2-Methylamino-pyridin-4-ylmethyl)-amino]-N-{4-[1-methyl-1-(5-methyl-[1,3,4]oxadiazol-2-yl)-ethyl]-phenyl}-nicotinamide;

2-[(2-Methylamino-pyrimidin-4-ylmethyl)-amino]-N-{4-[1-methyl-1-(5-methyl-[1,3,4]oxadiazol-2-yl)-ethyl]-phenyl}-nicotinamide;

N-{4-[1-Methyl-1-(5-methyl-[1,3,4]oxadiazol-2-yl)-ethyl]-phenyl}-2-[(pyrimidin-4-ylmethyl)-amino]-nicotinamide;

2-[(2-Methylamino-pyrimidin-4-ylmethyl)-amino]-N-[4-(1-methyl-1-pyrimidin-4-yl-ethyl)-phenyl]-nicotinamide;

2-[(2-Methylamino-pyrimidin-4-ylmethyl)-amino]-N-{4-[1-methyl-1-(2H-pyrazol-3-yl)-ethyl]-phenyl}-nicotinamide;

N-(3,3-Dimethyl-1-pyrrolidin-(2S)-ylmethyl-2,3-dihydro-1H-indol-6-yl)-2-[(2-methoxy-pyridin-4-ylmethyl)-amino]-nicotinamide;

N (3,3-Dimethyl-1-pyrrolidin-(2S)-ylmethyl-2,3-dihydro-1H-indol-6-yl)-2-[(pyridin-4-ylmethyl)-amino]-nicotinamide;

N-(4,4-Dimethyl-1,2,3,4-tetrahydro-isoquinolin-7-yl)-2-[(2-methoxy-pyridin-4-ylmethyl)-amino]-nicotinamide;

N-[3,3-Dimethyl-1-L-(pyrrolidine-2-carbonyl)-2,3-dihydro-1H-indol-6-yl]-2-[(2-methoxy-pyridin-4-ylmethyl)-amino]-nicotinamide;

2-[(2-Methoxy-pyridin-4-ylmethyl)-amino]-N-[3-(1-methyl-pyrrolidin-(2R)-ylmethoxy)-5-trifluoromethylphenyl]-nicotinamide;

3-[(2-Methoxy-pyridin-4-ylmethyl)-amino]-pyridazine-4-carboxylic acid (4-tert-butylphenyl)-amide;

3-{[2-(2,2,2-Trifluoro-ethoxy)-pyridin-4-ylmethyl]-amino}-1,2,5,6-tetrahydro-pyridazine-4-carboxylic acid (4-tert-butyl-phenyl)-amide;

N-{4-[1-Methyl-1-(1-methyl-piperidin-4-yl)-ethyl]-phenyl}-2-{[2-(2,2,2-trifluoro-ethoxy)-pyridin-4-ylmethyl]-amino}-nicotinamide;

N-[1-(2-Dimethylamino-acetyl)-3,3-dimethyl-2,3-dihydro-1H-indol-6-yl]-2-{[2-(2,2,2-trifluoro-ethoxy)-pyridin-4-ylmethyl]-amino}-nicotinamide;

2-[(Pyridin-4-ylmethyl)-amino]-N-(1,3,3-trimethyl-2,3-dihydro-1H-indol-6-yl)-nicotinamide;

N-[3-(Azetidin-3-ylmethoxy)-4-chloro-phenyl]-2-[(2-methoxy-pyridin-4-ylmethyl)-amino]-nicotinamide;

N-[4-(1,1-Dimethyl-2-pyrrolidin-1-yl-ethyl)-phenyl]-2-[(pyrimidin-4-ylmethyl)-amino]-nicotinamide;

N-[4-(1,1-Dimethyl-2-morpholin-4-yl-ethyl)-phenyl]-2-[(pyrimidin-4-ylmethyl)-amino]-nicotinamide;

N-[4-(1,1-Dimethyl-2-morpholin-4-yl-ethyl)-phenyl]-2-[(pyridin-4-ylmethyl)-amino]-nicotinamide;

2-[(2-Methylamino-pyridin-4-ylmethyl)-amino]-N-{4-[1-methyl-1-(2-methylsulfanyl-pyrimidin-4-ylamino)-ethyl]-phenyl}-nicotinamide;

N-(1-Acetyl-3,3-dimethyl-2,3-dihydro-1H-indol-6-yl)-2-[(tetrahydro-pyran-4-ylmethyl)-amino]-nicotinamide;

N-(3,3-Dimethyl-2,3-dihydro-1H-indol-6-yl)-2-[(tetrahydro-pyran-4-ylmethyl)-amino]-nicotinamide;

2-[(2-N-{4,4-Dimethyl-1,2,3,4-tetrahydro-quinolin-7-yl)-2-[(2-methylamino-pyridin-4-ylmethyl}-amino]-nicotinamide;

2-[(2-Amino-pyridin-4-ylmethyl)-amino]-N-(4,4-dimethyl-1,2,3,4-tetrahydro-isoquinolin-7-yl)-nicotinamide; and N-(4,4-Dimethyl-1,2,3,4-tetrahydro-isoquinolin-7-yl)-2-[(quinolin-4-ylmethyl)-amino]-nicotinamide.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anaemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of this invention may also act as inhibitors of other protein kinases, e.g. p38, EGFR, CDK-2, CDK-5, IKK, JNK3, bFGFR, PDGFR and RAF and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "heterocyclylalkylenyl" embraces heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S-$).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$–$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$–$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The phrase "Formula I–XIII" includes sub formulas such as II'.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I–XIII in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I:

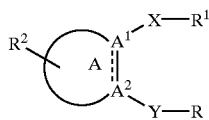

I wherein each of $A^1$ and $A^2$ is independently C, CH or N;
wherein ring A is selected from
  a) 5- or 6-membered partially saturated heterocyclyl,
  b) 5- or 6-membered heteroaryl,
  c) 9-, 10- or 11-membered fused partially saturated heterocyclyl,
  d) 9-, 10- or 11-membered fused heteroaryl;
  e) naphthyl, and
  f) 4-, 5- or 6-membered cycloalkenyl;
wherein X is

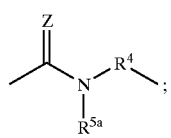

wherein Z is oxygen or sulfur;

wherein Y is selected from:

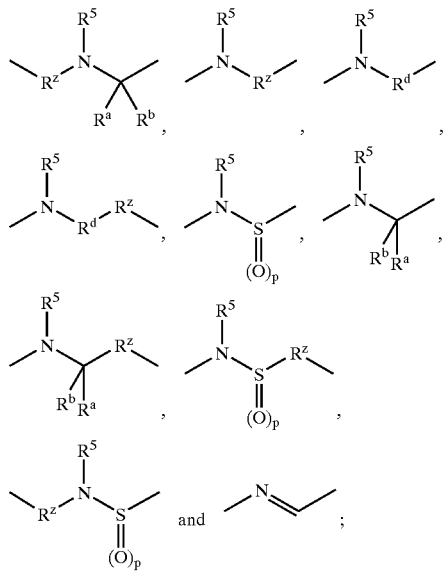

wherein p is 0 to 2,
wherein $R^a$ and $R^b$ are independently selected from H, halo, cyano, —$NHR^6$ and $C_{1-4}$-alkyl substituted with $R^2$, or wherein $R^a$ and $R^b$ together form $C_3$–$C_6$ cycloalkyl;
wherein $R^z$ is selected from $C_2$–$C_6$-alkylenyl, where one of the $CH_2$ groups may be replaced with an oxygen atom or an —NH—; wherein one of the $CH_2$ groups may be substituted with one or two radicals selected from halo, cyano, —$NHR^6$ and $C_{1-4}$-alkyl substituted with $R^2$;
wherein $R^d$ is cycloalkyl;
wherein R is selected from
  a) substituted or unsubstituted 5–6 membered heterocyclyl, b) substituted aryl, and
  c) substituted or unsubstituted fused 9–14-membered bicyclic or tricyclic heterocyclyl;
    wherein substituted R is substituted with one or more substituents independently selected from halo, —$OR^3$, —$SR^3$, —$SO_2R^3$, —$CO_2R^3$, —$CONR^3R^3$, —$COR^3$, —$NR^3R^3$, —$SO_2NR^3R^3$, —$NR^3C(O)OR^3$, —$NR^3C(O)R^3$, cycloalkyl, optionally substituted 5–6 membered heterocyclyl, optionally substituted phenyl, nitro, alkylaminoalkoxyalkoxy, cyano, alkylaminoalkoxy, lower alkyl substituted with $R^2$, lower alkenyl substituted with $R^2$, and lower alkynyl substituted with $R^2$;
wherein $R^1$ is selected from
  a) substituted or unsubstituted 6–10 membered aryl,
  b) substituted or unsubstituted 5–6 membered heterocyclyl,
  c) substituted or unsubstituted 9–14 membered bicyclic or tricyclic heterocyclyl,
  d) cycloalkyl, and
  e) cycloalkenyl,
    wherein substituted $R^1$ is substituted with one or more substituents independently selected from halo, —$OR^3$, —$SR^3$, —$CO_2R^3$, —$CONR^3R^3$, —$COR^3$, —$NR^3R^3$, —$NH(C_1$–$C_4$ alkylenylR$^{14}$), —$SO_2R^3$, —$SO_2NR^3R^3$, —$NR^3C(O)OR^3$, —$NR^3C(O)R^3$, optionally substituted cycloalkyl, optionally substituted 5–6 membered heterocyclyl, optionally substituted phenyl, halosulfonyl, cyano, alkylaminoalkoxy, alkylaminoalkoxyalkoxy, nitro, lower alkyl substituted with $R^2$, lower alkenyl substituted with $R^2$, and lower alkynyl substituted with $R^2$;

wherein $R^2$ is one or more substituents independently selected from H, halo, —$OR^3$, oxo, —$SR^3$, —$CO_2R^3$, —$COR^3$, —$CONR^3R^3$, —$NR^3R^3$, —$SO_2NR^3R^3$, —$NR^3C(O)OR^3$, —$NR^3C(O)R^3$, cycloalkyl, optionally substituted phenylalkylenyl, optionally substituted 5–6 membered heterocyclyl, optionally substituted heteroarylalkylenyl, optionally substituted phenyl, lower alkyl, cyano, lower hydroxyalkyl, lower carboxyalkyl, nitro, lower alkenyl, lower alkynyl, lower aminoalkyl, lower alkylaminoalkyl and lower haloalkyl;

wherein $R^3$ is selected from H, lower alkyl, phenyl, heterocyclyl, $C_3$–$C_6$-cycloalkyl, phenylalkyl, heterocyclylalkyl, $C_3$–$C_6$ cycloalkylalkyl, and lower haloalkyl;

wherein $R^4$ is selected from a direct bond, $C_{2-4}$-alkylenyl, $C_{2-4}$-alkenylenyl and $C_{2-4}$-alkynylenyl, where one of the $CH_2$ groups may be substituted with an oxygen atom or an —NH—, wherein $R^4$ is optionally substituted with hydroxy;

wherein $R^5$ is selected from H, lower alkyl, phenyl and lower aralkyl;

wherein $R^{5a}$ is selected from H, lower alkyl, phenyl and lower aralkyl;

wherein $R^6$ is selected from H or $C_{1-6}$-alkyl; and wherein $R^{14}$ is selected from H, phenyl, 5–6 membered heterocyclyl and $C_3$–$C_6$ cycloalkyl;

and pharmaceutically acceptable derivatives thereof; provided A is not naphthyl when X is —C(O)NH— and when $R^1$ is phenyl when Y is —$NCH_2$— and when R is 4-pyridyl; and further provided R is not unsubstituted 2-thienyl, 2-pyridyl or 3-pyridyl when Y is —$NHCH_2$—.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with, or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR- 456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I–XIII.

Also included in the family of compounds of Formula I–XIII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–XIII may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, $\beta$-hydroxybutyric, salicylic, galactaric and galacturonic acid. Suitable pharmaceutically-acceptable base addition salts of compounds of Formula I–XIII include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I–XIII.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases. Preferred salts include hydrochloride, phosphate and edisylate.

Additional examples of such salts can be found in Berge et al., J. Pharm. Sci., 66, 1 (1977).

General Synthetic Procedures

The compounds of the invention can be synthesized according to the following procedures of Schemes 1–48, wherein the substituents are as defined for Formulas I–XIII, above, except where further noted.

Scheme 1

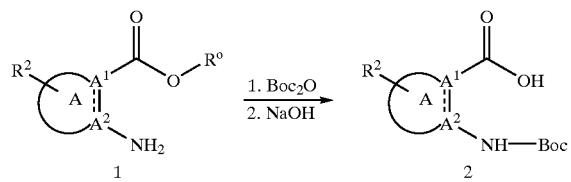

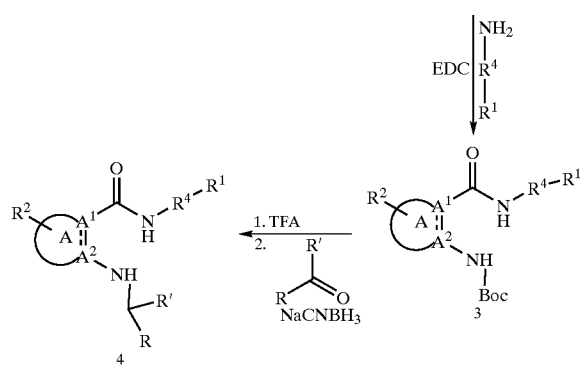

Scheme 2

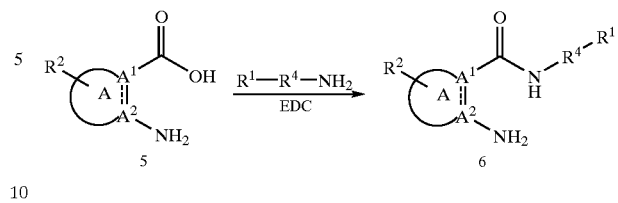

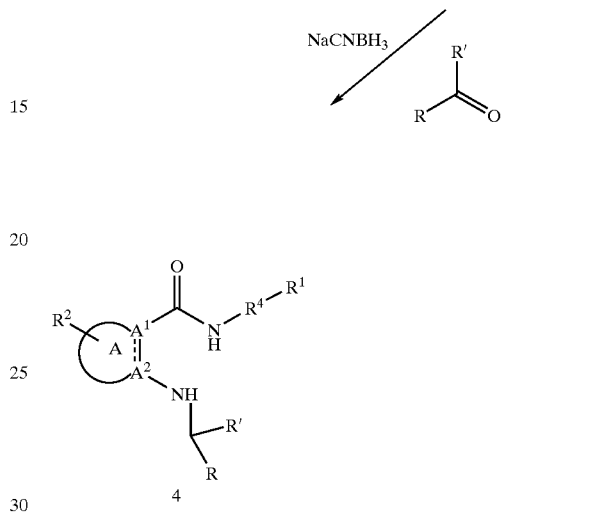

Cyclic amides can be prepared according to the method set out in Scheme 1. The amino group of compound 1 (where $R^o$ is alkyl, aryl, and the like) is protected, such as with Boc anhydride, followed by treatment, to remove the ester, such as with base, forming the protected amine/free acid 2. Alternatively, other amino protecting groups known in the art can be used. Substituted amines are coupled with the free acid, such as with EDC, to form the protected amine/amide 3. The protected amine moiety is deprotected, such as with acid, and reacted via one step reductive alkylation with carbonyl-containing compounds (where R' is H, halo, cyano, —NHR$^6$ and $C_{1-4}$ alkyl) to form the 1-amido-2-substituted amino-compounds 4. Preferably the amination is in an alcohol, such as MeOH, EtOH or propanol, and at a temperature between about 0–50° C., such as RT. Aldehydes or ketones are preferred carbonyl-containing compounds. Alternative carbonyl-containing compounds are, for example, bisulfite adducts or hemiacetals, acetals, hemiketals or ketals of compounds with alcohols, for example lower hydroxyalkyl compounds; or thioacetals or thioketals of compounds with mercaptans, for example lower alkylthio compounds. The reductive alkylation is preferably carried out with hydrogenation in the presence of a catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkylcarboxylic acids, especially acetic acid, or a sulfonic acid, such as p-toluenesulfonic acid; in customary solvents, for example alcohols, such as MeOH or EtOH, or ethers, for example cyclic ethers, such as THF, in the presence or absence of water.

Alternatively, compounds 4 can be prepared from mixed acid/amines 5 as shown in Scheme 2. Substituted amines are coupled with the mixed acid/amines 5 such as with a coupling reagent, for example EDC, to form the mixed amine/amide 6. Substituted carbonyl compounds, such as acid halides, anhydrides, carboxylic acids, esters, ketones, aldehydes and the like, are added to the mixed amine/amide 6 followed with reduction to give the substituted amide/substituted amine compounds 4.

Scheme 3

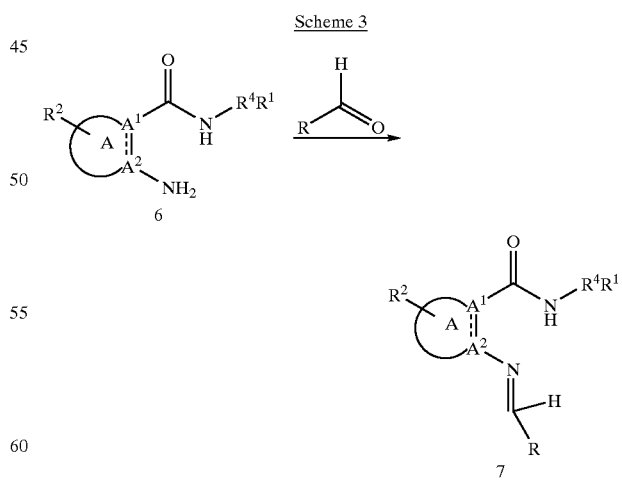

Imino compounds 7 can be formed from the mixed amine/amides 6, such as by reacting with a substituted carbonyl compound.

Scheme 4

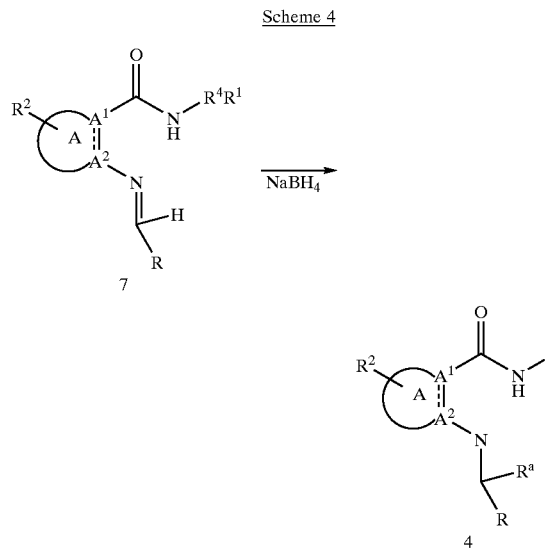

Substituted cyclic carboxamides can be prepared from the corresponding imino analogs by the process outlined in Scheme 4. Treatment of the imino compound 7 with a reducing agent yields compound 4. Reagents which can be used to add hydrogen to an imine double bond include borane in THF, LiAlH$_4$, NaBH$_4$, sodium in EtOH and hydrogen in the presence of a catalyst, and others.

Scheme 5

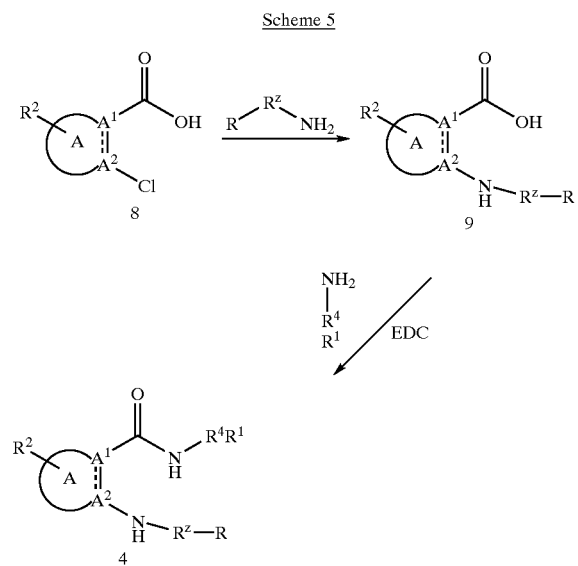

Substituted carboxamides 4 can be prepared from the corresponding halo analogs 8 by the process outlined in Scheme 5. Substituted amino acids 9 are prepared from the corresponding chloro compounds 8 such as by reacting with an amine at a suitable temperature, such as about 80° C. The acid 9 is coupled with an amine, preferably in the presence of a coupling agent such as EDC, to form the corresponding amide 4.

The amination process can be carried out as an Ullmann type reaction using a copper catalyst, such as copper[0] or a copper[I] compound such as copper[I]oxide, copper[I] bromide or copper[I]iodide in the presence of a suitable base (such as a metal carbonate, for example K$_2$CO$_3$) to neutralize the acid generated in the reaction. This reaction is reviewed in Houben-Weyl "Methoden der Organischen Chemie", Band 11/1, page 32–33, 1958, in Organic Reactions, 14, page 19–24, 1965 and by J. Lindley (1984) in Tetrahedron, 40, page 1433–1456. The amount of catalyst is typically in the range of 1 to 20 mole percent. The reaction is carried out in an inert, aprotic solvent such as an ether (for example dimethoxyethane or dioxane) or an amide (for example dimethylformamide or N-methylpyrrolidone), under an inert atmosphere in the temperature range of 60–180° C.

An alternative amination process involves using a Group VIII element, where the metal core of the catalyst should be a zero-valent transition metal, such as palladium or nickel, which has the ability to undergo oxidative addition to the aryl-halogen bond. The zero valent state of the metal may be generated in situ from the M[II] state. The catalyst complexes may include chelating ligands, such as alkyl, aryl or heteroaryl derivatives of phosphines or biphosphines, imines or arsines. Preferred catalysts contain palladium or nickel. Examples of such catalysts include palladium[II]chloride, palladium[II]acetate, tetrakis(triphenyl-phosphine) palladium[0] and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl)phosphine, and triheteroaryl phosphines, such as tri-2-furylphosphine; or they may be bidentate such as in the case of 2,2'-bis (diphenylphosphino)-1,1'binaphthyl, 1,2-bis (diphenylphosphino)ethane, 1,1'-bis(diphenylphosphino) ferrocene and 1-(N,N-dimethyl-amino)-1'-(dicyclohexylphosphino)biphenyl. The supporting ligand may be complexed to the metal center in the form of a metal complex prior to being added to the reaction mixture or may be added to the reaction mixture as a separate compound. The supporting ligand is typically present in the range 0.01 to 20 mole percent. It is often necessary to add a suitable base to the reaction mixture, such as a trialkylamine (for example DIEA or 1,5-diazabicyclo[5,4,0]undec-5-ene), a Group I alkali metal alkoxide (for example potassium tert-butoxide) or carbonate (for example cesium carbonate) or potassium phosphate. The reaction is typically carried out in an inert aprotic solvent such as an ether (for example dimethoxyethane or dioxane) or an amide (for example, DMF or N-methylpyrrolidone), under an inert atmosphere in the temperature range of 60–180° C.

The amination is preferably carried out in an inert, aprotic, preferably anhydrous, solvent or solvent mixture, for example in a carboxylic acid amide, for example DMF or dimethylacetamide, a cyclic ether, for example THF or dioxane, or a nitrile, for example CH$_3$CN, or in a mixture thereof, at an appropriate temperature, for example in a temperature range of from about 40° C. to about 180° C., and if necessary under an inert gas atmosphere, for example a nitrogen or argon atmosphere.

Scheme 6

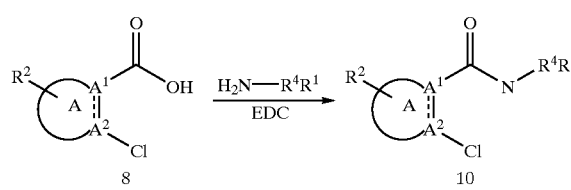

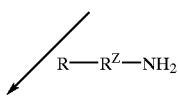

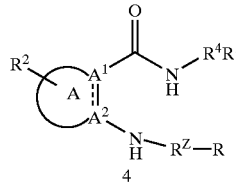

Substituted carboxamides 4 can be prepared from the corresponding halo analogs 8 by the process outlined in Scheme 6. The chloro acid 8 is coupled with an amine, preferably in the presence of a coupling agent such as EDC, to form the corresponding chloro amide 10. Substituted amino-amides 4 are prepared from the corresponding chloro compounds 10 such as by reacting with an amine at a suitable temperature, such as about 80° C. The amination reaction can be run in the presence of an appropriate catalyst such as a palladium catalyst, in the presence of an aprotic base such as sodium t-butoxide or cesium carbonate, or a nickel catalyst, or a copper catalyst.

Scheme 7

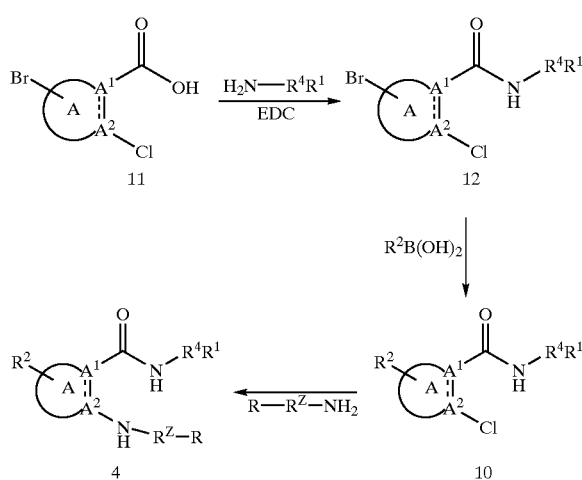

Substituted carboxamides 4 can be prepared from the corresponding bromo/chloro analogs 11 by the process outlined in Scheme 7. The bromo/chloro acid 11 is coupled with an amine, preferably in the presence of a coupling agent such as EDC, to form the corresponding bromo substituted amide 12. Suzuki coupling with the bromo amide 12 and suitable boronic acids provides the substituted amide 10. Substituted amino-amides 4 are prepared from the corresponding chloro compounds 10 as described in Scheme 6.

Scheme 8

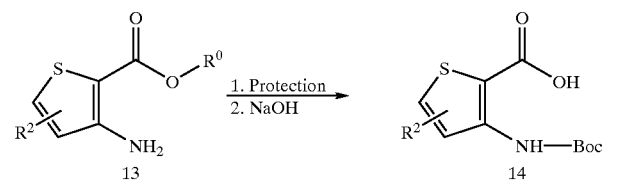

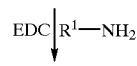

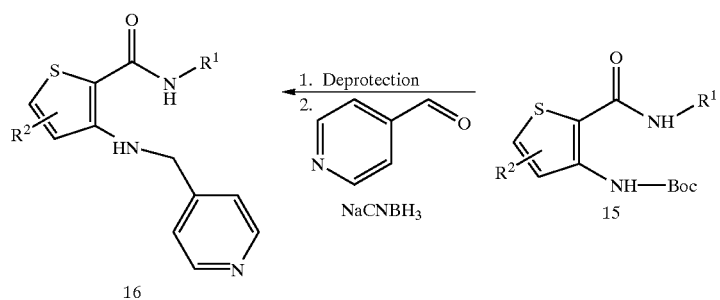

Substituted thiophenes 16 can be prepared by the method of Scheme 8. The free amino group of a 3-amino-2-thiophenecarboxylic acid ester 13 can be protected such as by the addition of $Boc_2O$ in a suitable solvent such as $CH_2Cl_2$ and DMAP. The ester is removed such as with base to form the free acid 14. The thiophene amide 15 is formed from the acid 14 such as by coupling with a substituted amine in the presence of DIEA, EDC and HOBt. The 2-protected-amino-thiophene amide 15 is deprotected, such as with 25% $TFA/CH_2Cl_2$. The free amine is alkylated such as with a substituted carboxaldehyde or similar active carbonyl compound, in the presence of a reducing agent $NaCNBH_3$ and the like, to form compounds 16.

Scheme 9

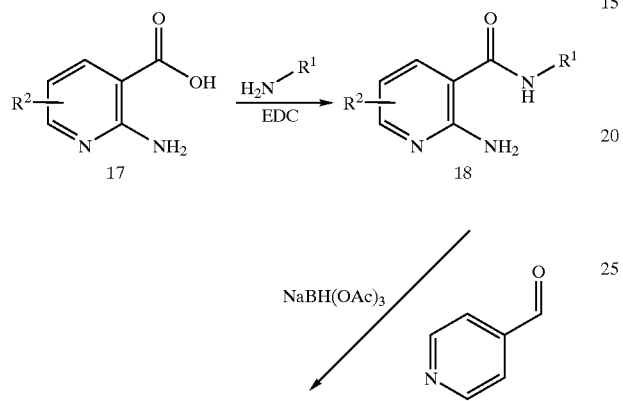

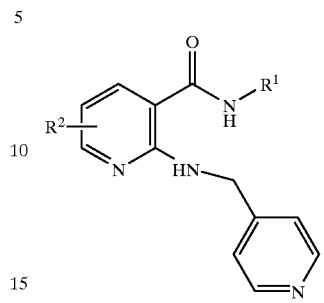

Substituted pyridines can be prepared such as by the method found in Scheme 9. 2-Aminonicotinic acid 17 is coupled with a substituted amine at a suitable temperature, nonprotic solvent such as $CH_2Cl_2$, such as with EDC and HOBt, to form the nicotinamide 18. The nicotinamide 18 is reductively alkylated such as with 4-pyridinecarboxaldehyde and $NaBH(OAc)_3$, to yield the 2-substituted aminopyridyl carboxamides 19.

Scheme 10

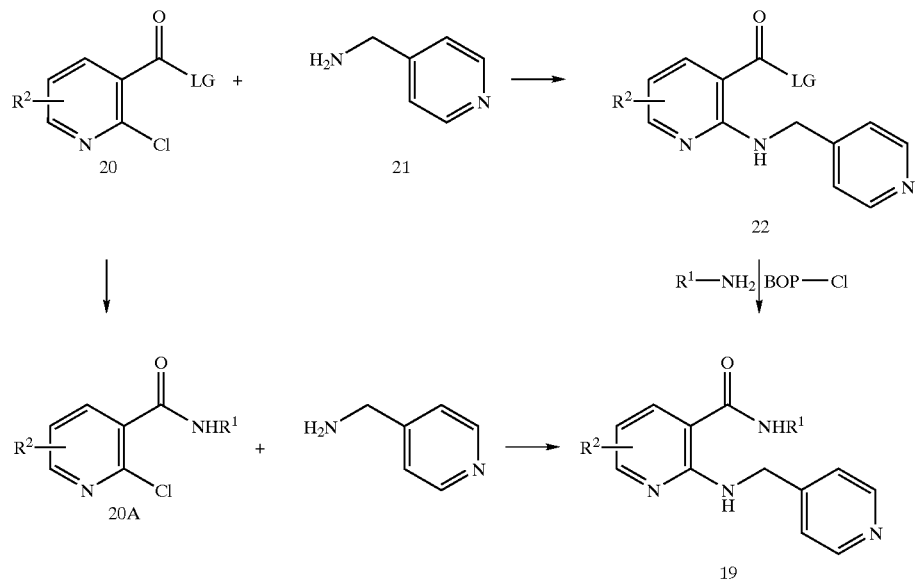

Substituted pyridines may be prepared by the method found in Scheme 10. 2-Chloro-nicotinic acid 20 is coupled with an amine 21 at a suitable temperature, such as a temperature over about 100° C. to give the 2-substituted amino-nicotinic acid 22. The 2-substituted amino-nicotinic acid 22 is reacted with a substituted amine in the presence of a coupling reagent, such as BOP—Cl and base, such as TEA to form the 2-substituted amino-nicotinamide 19.

Alternatively, 2-chloro-nicotinoyl chloride (LG is Cl) is coupled first with $R^1$—$NH_2$ such as in the presence of base, e.g., $NaHCO_3$, in a suitable solvent, such as $CH_2Cl_2$, to form the amide 20A, then coupling with a pyridylmethylamine to yield the 2-substituted amino-nicotinamide 19.

Scheme 11

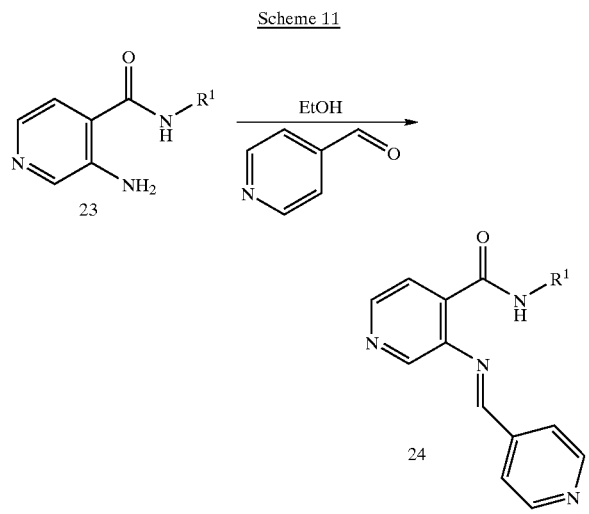

Imino-substituted pyridines may be prepared by the method found in Scheme 11. (2-Amino-(4-pyridyl))-carboxamide 23 is reacted with 4-pyridine-carboxaldehyde, such as in the presence of p-toluenesulfonic acid monohydrate to yield the imino compound 24.

Scheme 12

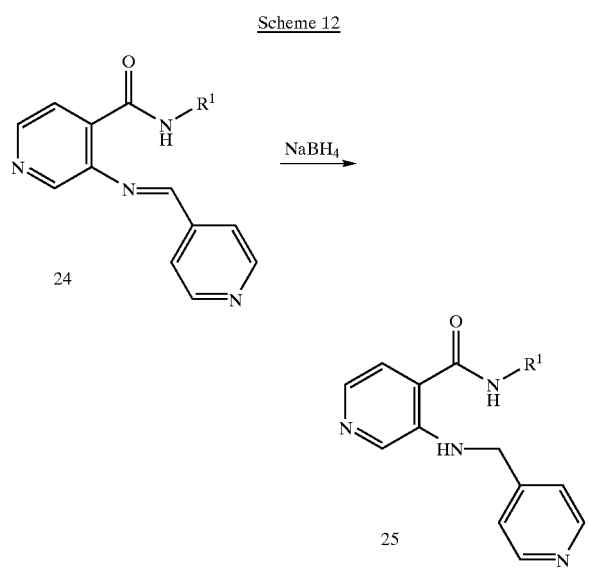

Substituted pyridines alternatively may be prepared by the method found in Scheme 12. The imino compound 24 is reduced, such as with $NaBH_4$, to form the substituted amine 25.

Scheme 13

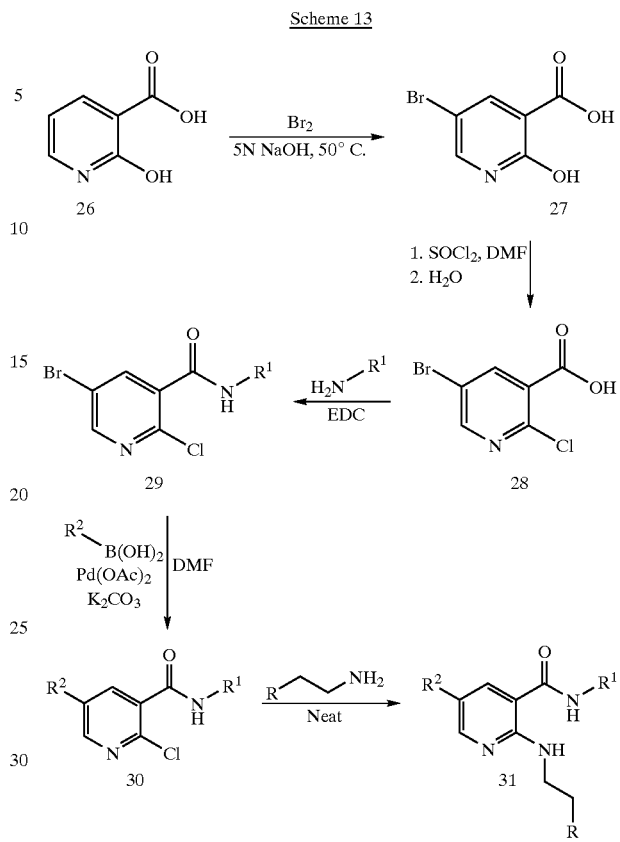

Substituted pyridines can be prepared by the process outlined in Scheme 13. A solution of sodium hypobromide is freshly prepared and added to 2-hydroxynicotinic acid 26 and heated, preferably at a temperature at about 50° C. Additional sodium hypobromide may be needed to form the bromo compound 27. The 5-bromo-2-hydroxynicotinic acid 27 is reacted with thionyl chloride, preferably at a temperature >RT, more preferably at about 80° C. to form the 2-chloro-nicotinic acid analog 28. The acid is coupled with an amine, preferably in the presence of EDC, HOBT, and DIEA to form the corresponding substituted amide 29. Suzuki coupling with the bromo amide and suitable boronic acids, provides the substituted nicotinamide 30. 2-Amino-nicotinamides 31 are prepared from the corresponding chloro compounds 30 such as by reacting with substituted amines at a suitable temperature, such as about 80° C.

Scheme 14

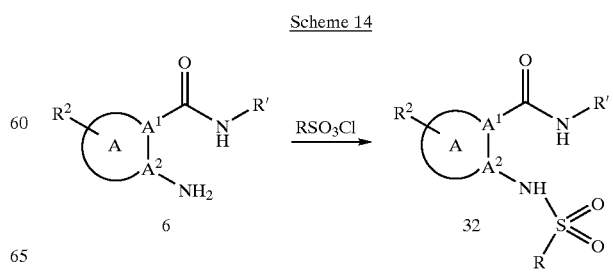

Sulfonamides 32 can be prepared from amines 6 as shown in Scheme 14. Substituted sulfonyl compounds, such as sulfonyl halides, preferably chloro or bromo, sulfonic acids, an activated ester or reactive anhydride, or in the form of a cyclic amide, and the like, are added to the amine 6 to give the sulfonamide compounds 32.

The reaction is carried out in a suitable solvent, such as $CH_2Cl_2$, at a temperature between about RT to about the reflux temperature of the solvent, in the presence of a suitable base, such as DIEA or DMAP.

The amino group of compounds 6 is preferably in free form, especially when the sulfonyl group reacting therewith is present in reactive form. The amino group may, however, itself be a derivative, for example by reaction with a phosphite, such as diethylchlorophosphite, 1,2-phenylene chlorophosphite, ethyldichlorophosphite, ethylene chlorophosphite or tetraethylpyrophosphite. A derivative of such a compound having an amino group also can be a carbamic acid halide or an isocyanate.

The condensation of activated sulfonic esters, reactive anhydrides or reactive cyclic amides with the corresponding amines is customarily carried out in the presence of an inorganic base, such as an alkaline metal hydrogen carbonate of carbonate, or especially an organic base, for example simple lower (alkyl)$_3$-amines, for example TEA or tributylamine, or one of the above-mentioned organic bases. If desired, a condensation agent is additionally used, for example as described for free carboxylic acids.

The condensation is preferably carried out in an inert, aprotic, preferably anhydrous, solvent or solvent mixture, for example in a carboxylic acid amide, for example formamide or DMF, a halogenated hydrocarbon, for example $CH_2Cl_2$, $CCl_4$ or chlorobenzene, a ketone, for example acetone, a cyclic ether, for example THF or dioxane, an ester, for example EtOAc, or a nitrile, for example $CH_3CN$, or in a mixture thereof, as appropriate at reduced or elevated temperature, for example in a temperature range of from about −40° C. to about +100° C., preferably from about −10° C. to about 70° C., and when arylsulfonyl esters are used, also at temperatures of from about 10–30° C., and if necessary under an inert gas atmosphere, for example a nitrogen or argon atmosphere.

Alcoholic solvents, for example EtOH, or aromatic solvents, for example benzene or toluene, may also be used. When alkali metal hydroxides are present as bases, acetone may also be added where appropriate.

Scheme 15

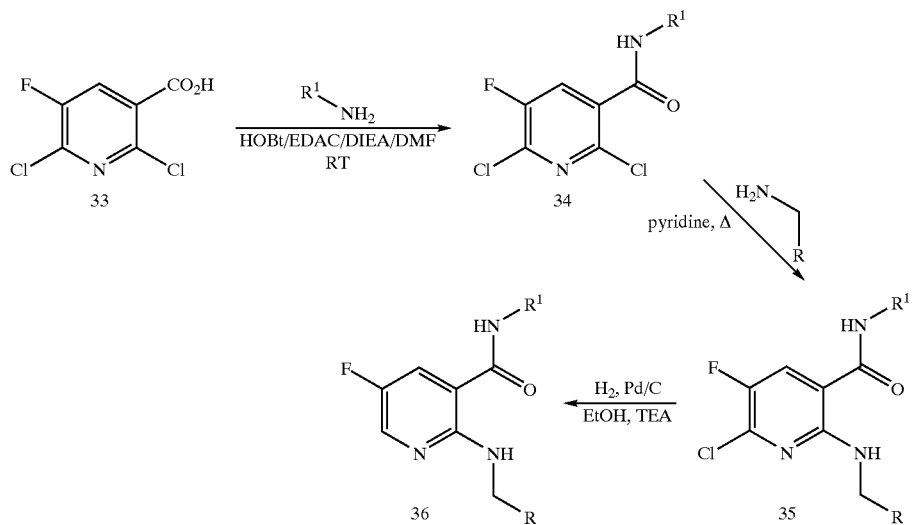

Substituted pyridines can be prepared by the process outlined in Scheme 15. 2-Chloronicotinic acid 33 and substituted amine are coupled under conditions similar to that described in the previous schemes to give the amide 34. 6-Chloro-2-aminopyridines 35 are prepared from the amide 34, such as by reacting with substituted amines at a suitable temperature, such as above about 80° C., preferably above about 100° C., more preferably at about 130° C., neat. 6-Chloro-2-aminopyridines 35 are de-chlorinated such as by hydrogenation, for example by treatment with $H_2$ in the presence of Pd/C, to yield other compounds of the present invention 36.

Scheme 16

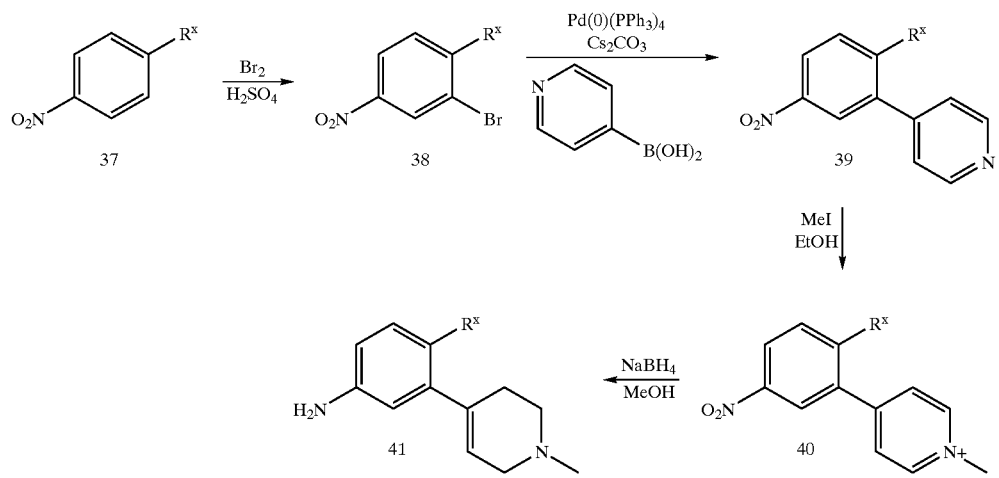

1,2,3,6-Tetrahydro-pyridyl substituted anilines are prepared such as by the procedure described in Scheme 16 (where $R^x$ is a substituent selected from those available for substituted $R^1$). Nitrobenzenes 37 are brominated, such as with bromine in the presence of acid, $H_2SO_4$ for example, or with NBS to yield the 3-bromo derivative 38. Suzuki coupling of the bromo-derivative 38 and a substituted pyridyl-boronic acid, in an appropriate solvent such as toluene, such as at a temperature above RT, preferably above about 50° C., and more preferably at about 80° C., yields the pyridyl derivative 39. Alkylation of the nitrophenyl-pyridine 39, such as by treatment with iodomethane, preferably above about 50° C., and more preferably at about 80° C., yields the pyridinium compound 40, which upon reduction, such as by $NaBH_4$, yields the tetrahydropyridine 41.

-continued

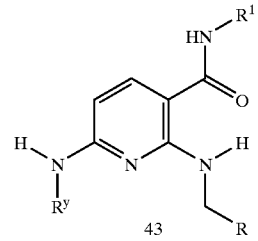

6-Amino substituted pyridines are prepared such as by the procedure described in Scheme 17. Similar to the method of Scheme 13, chloropyridine 42 and is reacted with an amine, preferably above about 50° C., and more preferably at about 80° C., to yield the 6-aminopyridines 43.

Scheme 17

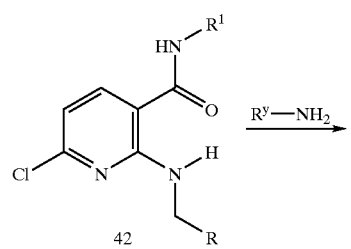

Scheme 18

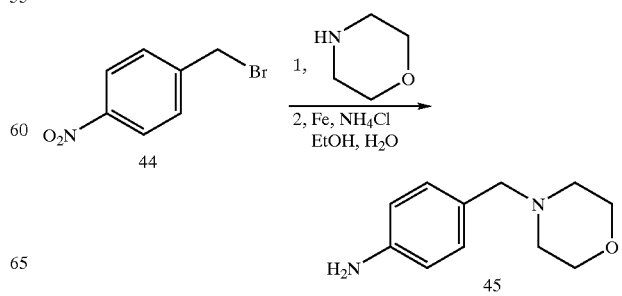

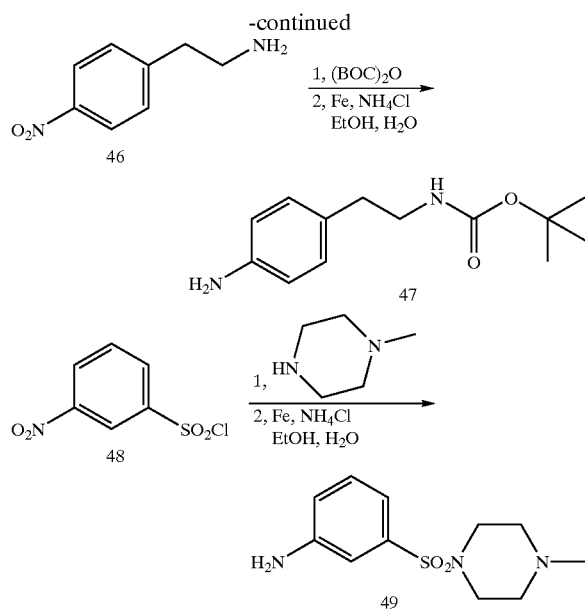

A series of substituted anilines are prepared such as by the procedure described in Scheme 18. A nitrobenzyl bromide 44 is coupled with morpholine, such as at a temperature at about RT, to yield the heterocyclylmethyl nitrobenzene derivative. Reduction of the nitro compound, such as with iron powder, preferably above about 50° C., and more preferably at about 80° C., yields the heterocyclylmethyl substituted aniline 45.

Protected alkylamine substituted anilines can be prepared from the nitro free amines 46, such as with standard protecting agents and chemistry known in the art, such as BOC chemistry. Reduction of the protected nitro compound, such as with iron powder, preferably above about 50° C., and more preferably at about 80° C., yields the aniline 47.

Sulfonamide substituted anilines can be prepared from nitrobezenesulfonyl chlorides 48. Coupling of nitrobezenesulfonyl chlorides 48 with reactive heterocyclic compounds, such as substituted piperazines, piperidines, and the like, in a protic solvent such as EtOH, such as at a temperature about RT, yields the nitrobezenesulfonamides 48. Reduction of the nitro benzenesulfonamide, such as with iron powder, preferably above about 50° C., and more preferably at about 80° C., yields the aniline 49.

Scheme 19

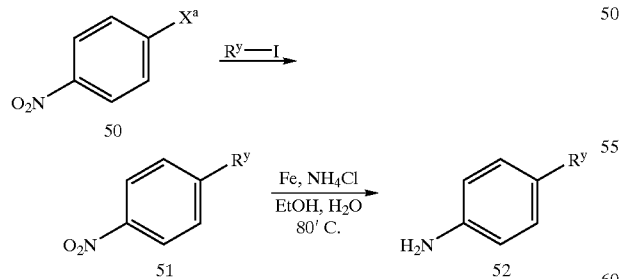

A series of perhaloalkyl-substituted anilines 52, where $R^y$ represents perhaloalkyl radicals, are prepared such as by the procedure described in Scheme 19. 1-Nitro-4-(perfluoroethyl)benzene can be synthesized by the method described in the reference [John N. Freskos, Synthetic Communications, 18(9), 965–972 (1988)]. Alternatively, 1-Nitro-4-(perfluoroalkyl)benzene can be synthesized from the nitro compound, where $X^a$ is a leaving group, such as iodo, by the method described by W. A. Gregory, et al. [J. Med. Chem., 1990, 33, 2569–2578].

Reduction of the nitrobenzenes 51, such as with iron powder, at a temperature above about 50° C., and preferably at about 80° C., yields the aniline 52. Hydrogenation, such as with $H_2$ in the presence of catalyst, such as Pd/C, is also possible.

Scheme 20

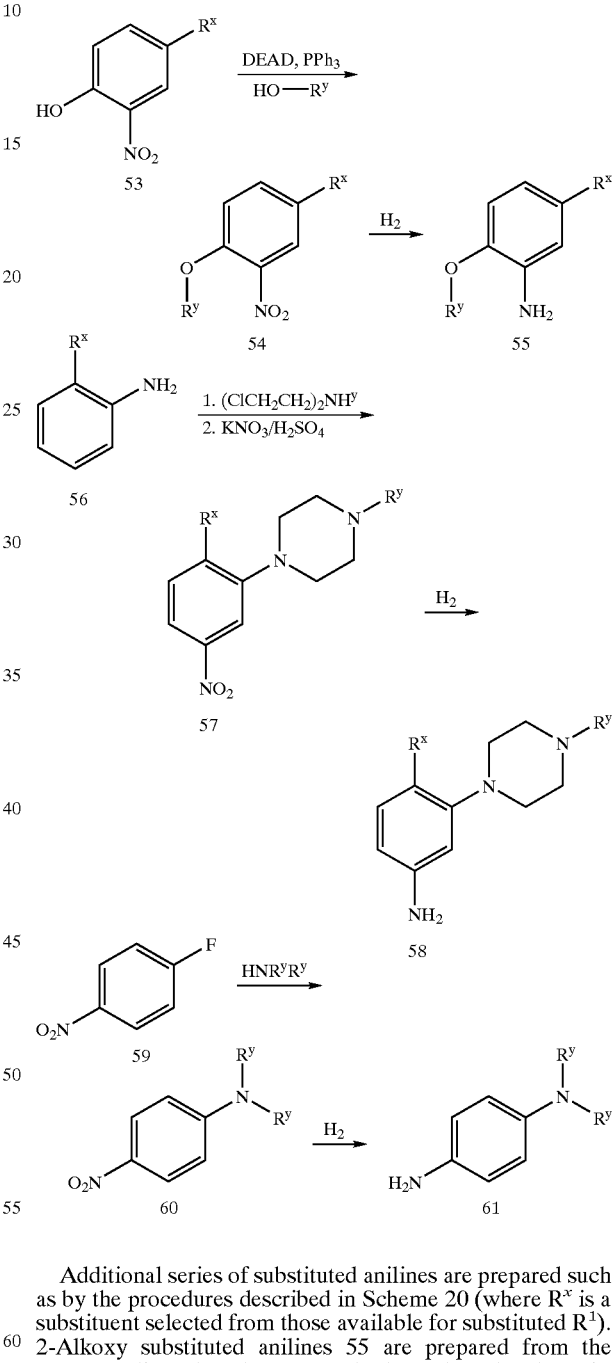

Additional series of substituted anilines are prepared such as by the procedures described in Scheme 20 (where $R^x$ is a substituent selected from those available for substituted $R^1$). 2-Alkoxy substituted anilines 55 are prepared from the corresponding phenol compounds 53 such as by the Mitsunobu reaction, including treatment with a N,N-dialkylethanolamine and $PPh_3$ and DEAD to give the corresponding nitro compound 54, followed by hydrogenation, such as with $H_2$ to give the aniline 55.

Alternatively, piperazinyl substituted anilines 58 can be prepared by the treatment of an aniline 56 with an N-substituted-bis(2-chloroethyl)amine, base, such as K$_2$CO$_3$ and NaI, at a temperature above about 50° C., preferably above about 100° C., and more preferably at about 170° C., to give the piperazinylbenzene compound 57. Nitration, such as with H$_2$SO$_4$ and HNO$_3$, at a temperature above 0° C., and preferably at about RT, followed by hydrogenation, such as with H$_2$ atmosphere gives the substituted aniline 58.

Alternatively, piperazinyl substituted anilines 61 can be prepared by the treatment of a fluoro-nitro-substituted aryl compounds 59. The fluoro-nitro-substituted aryl compounds 59 and 1-substituted piperazines are heated, preferably neat, at a temperature above about 50° C., and preferably at about 90° C., to yield the piperazinyl-nitroaryl compounds 60. Hydrogenation, such as with H$_2$ atmosphere in the presence of a catalyst, such as 10% Pd/C, gives the substituted aniline 61.

64 are prepared from the nitroindoline 62 and a ketone in the presence of NaHB(OAc)$_3$ to form the 1-substituted indoline 63. The nitroindoline 63 is hydrogenated, such as with H$_2$ in the presence of a catalyst, such as Pd/C, to yield the amino-indoline 64.

Alternatively, substituted amino-indolines 67 are prepared from the nitroindoline 62. Nitroindoline 62, is reacted with an acid chloride to form an amide. Further treatment with a primary or secondary amine, preferably a secondary amine, such as in the presence of NaI, at a temperature above about 50° C., and preferably at about 70° C. yields the nitroindoline 65. The nitro compound 65 is hydrogenated, such as with H$_2$ in the presence of a catalyst, such as Pd/C,

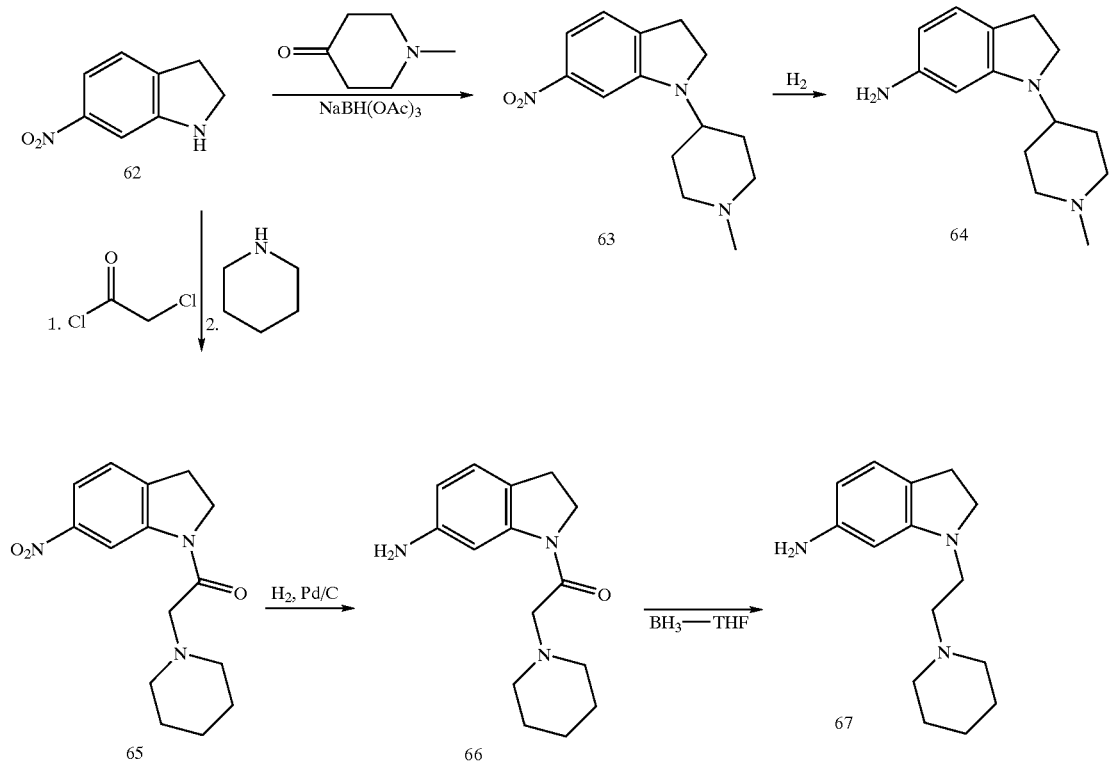

Scheme 21

Substituted indolines are prepared such as by the procedures described in Scheme 21. Substituted amino-indolines to yield the amino-indoline 66. The carbonyl is reduced, such as with BH$_3$-THF yields 1-aminoalkyl-indolines 67.

Scheme 22

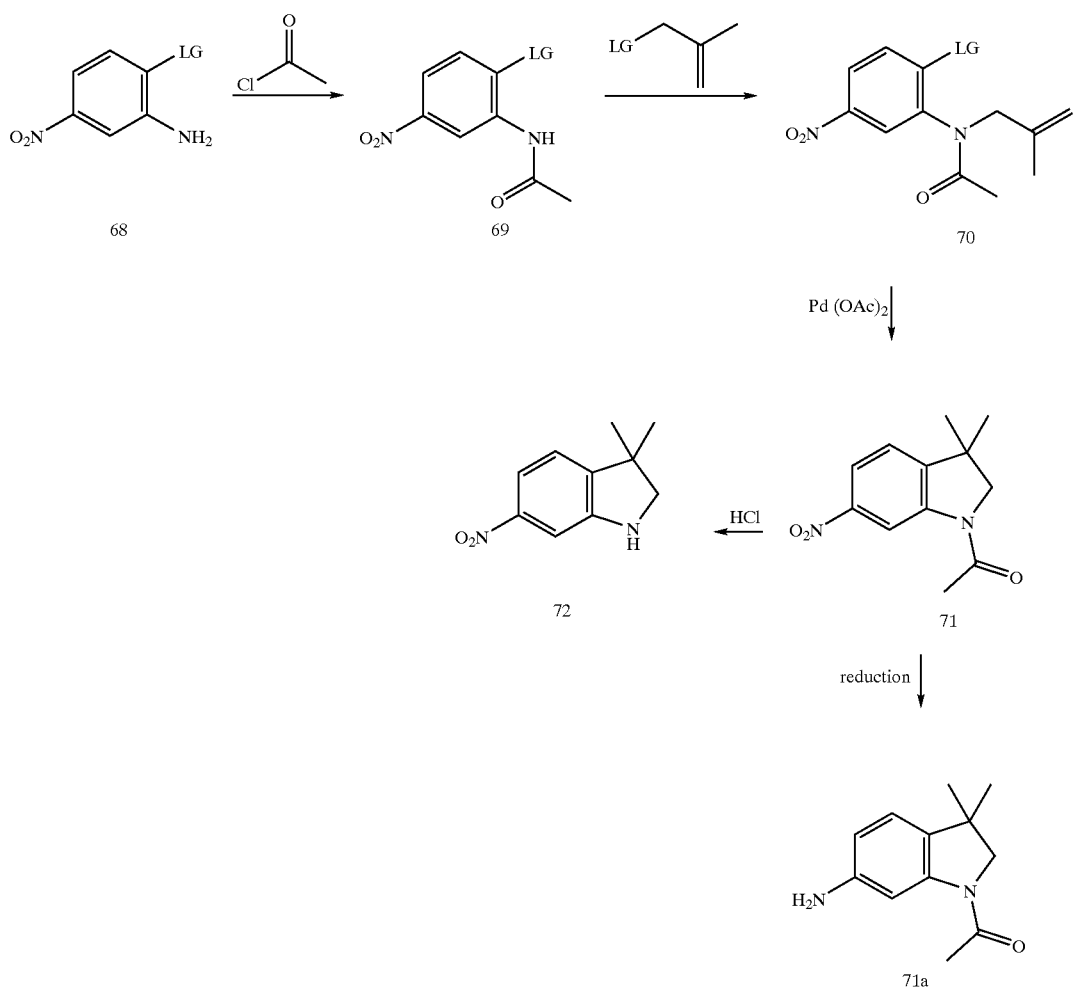

Substituted indolines are prepared such as by the procedures described in Scheme 22. Substituted acetamides 69 are prepared from the acylation of halo-5-nitroanilines 68 (where LG is bromo or chloro, preferably chloro) with an acylating agent, such as acetyl chloride or acetic anhydride, under standard coupling chemistry, such as with DIEA, and DMAP, at a temperature of about RT, in a suitable solvent, such as $CH_2Cl_2$, DMF and/or DMAC. The N-(2-methylprop-2-enyl)acetamide 70 is prepared from the acetamide 69, such as by the treatment of base, such as NaH in anhydrous DMF and a 3-halo-2-methylpropene such as 3-bromo-2-methylpropene or 3-chloro-2-methylpropene, at a temperature between about 0° C. and RT, and preferably at about RT; or with $CsCO_3$ at a temperature above RT, preferably above about 50° C. and more preferably above about 60° C. Cyclization of the N-(2-methylprop-2-enyl) acetamide 70, such as by the Heck-type reaction (treatment with $Pd(OAc)_2$ in the presence of base, for example tetraethyl-ammonium chloride, sodium formate, and NaOAc) at a temperature above about 50° C., and preferably at about 80° C., yields the protected (3,3-dimethyl-2,3-dihydro-indol-1-yl)ethanone 71. Deprotection, such as with strong acid such as AcOH on HCl at a temperature above about 50° C., and preferably at about 70–80° C., yields the 3,3-dimethyl-6-nitro-2,3-dihydro-indol-1-yl 72. Alternatively, the protected dihydro-6-nitro indoline 71 can be reduced, such as with Fe, or with 10% Pd/C in the presence of an excess of $NH_4CO_2H$, or with $H_2$ in the presence of a catalyst to form the protected dihydro-6-amino indoline 71a.

Scheme 23

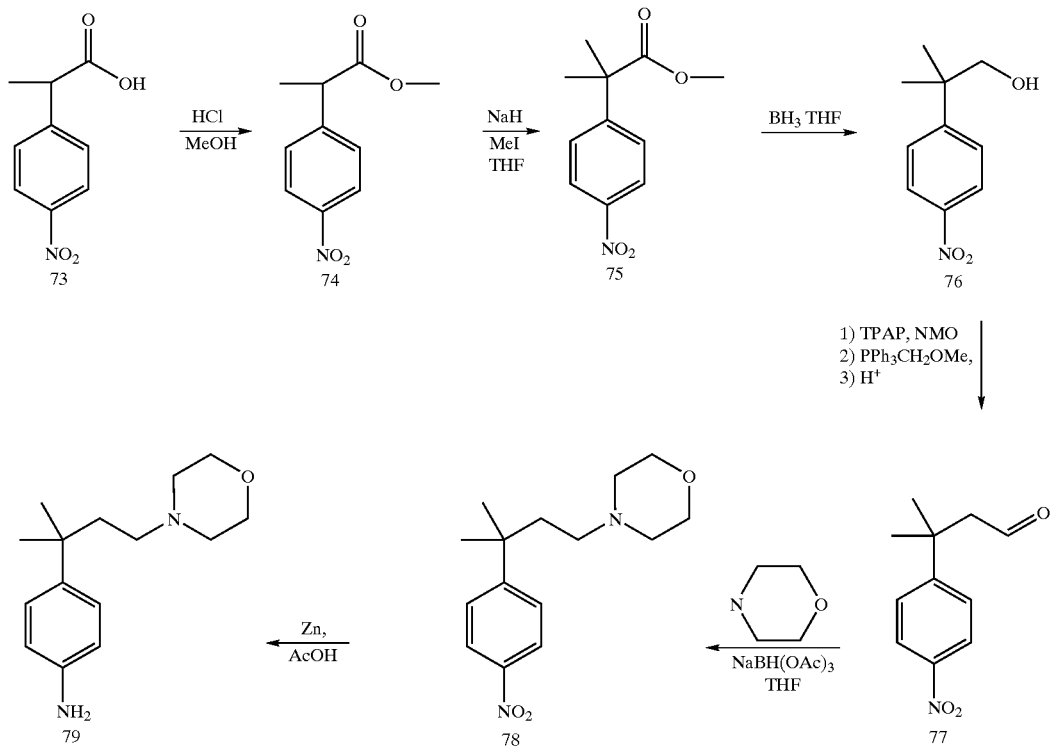

Substituted anilines are prepared such as by the procedures described in Scheme 23. Nitrophenyl esters 74 are formed from the acid 73, such as by treatment with MeOH and acid. Alkylation of the ester 74, such as by treatment with base, followed by alkyl halide, yields the branched alkyl compounds 75. Reduction of the ester 75, such as with BH₃, yields the alcohol 76. The aldehyde 77 is prepared from the alcohol 76, such as by treatment with TPAP in the presence of N-methylmorpholine-N-oxide. Subsequent treatment with methoxymethyltriphenylphosphonium chloride and KHMDS yields 77. Coupling of the aldehyde 77 with morpholine, such as with NaBH(OAc)₃ yields the tertiary amine 78. Reduction of the nitro compound, such as with acid, for example AcOH, and zinc yields the aniline 79.

Scheme 24

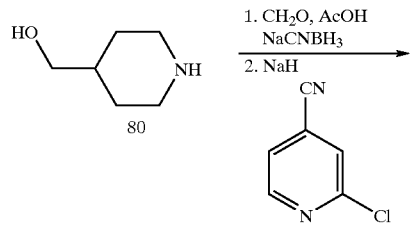

-continued

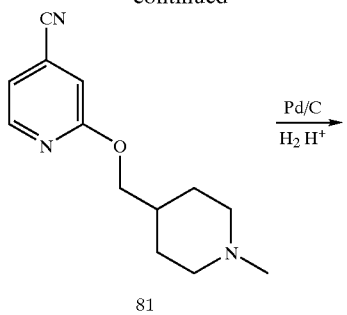

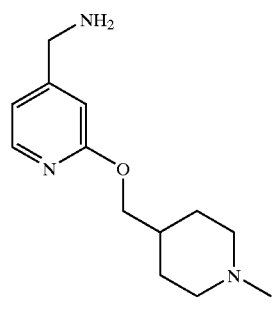

Substituted aminomethyl compounds are prepared such as by the procedure described in Scheme 24. A piperidinemethanol 80 is reacted with formaldehyde and NaCNBH₃. Subsequently, base, such as sodium hydride, and a halo substituted cyclic nitrile gives the ether 81. Hydrogenation of 81 under conditions described above, furnishes the aminomethyl compound 82.

Scheme 25

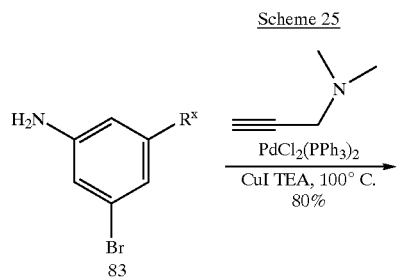

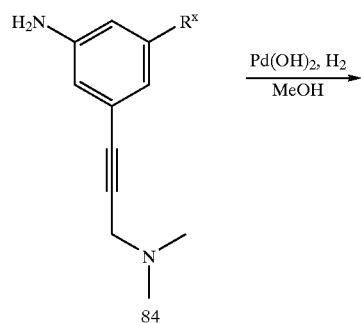

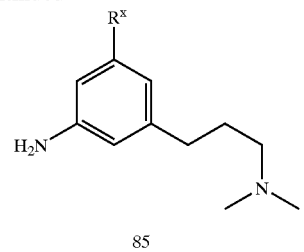

Substituted aniline compounds are prepared such as by the procedure described in Scheme 25 (where $R^x$ is a substituent selected from those available for substituted $R^1$, preferably haloalkyl or alkyl). Alkynyl-aniline 84, prepared similar to that described in Scheme 46, is hydrogenated such as with $H_2$ in the presence of a catalyst, such as $Pd(OH)_2$, to yield the substituted alkyl 85.

Scheme 26

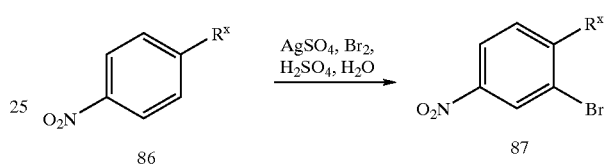

Substituted bromophenyl compounds are prepared such as by the procedure described in Scheme 26. Bromine is added to a optionally substituted nitrobenzene 86, silver(II) sulfate and acid, such as $H_2SO_4$, to provide the bromo derivative 87.

Scheme 27

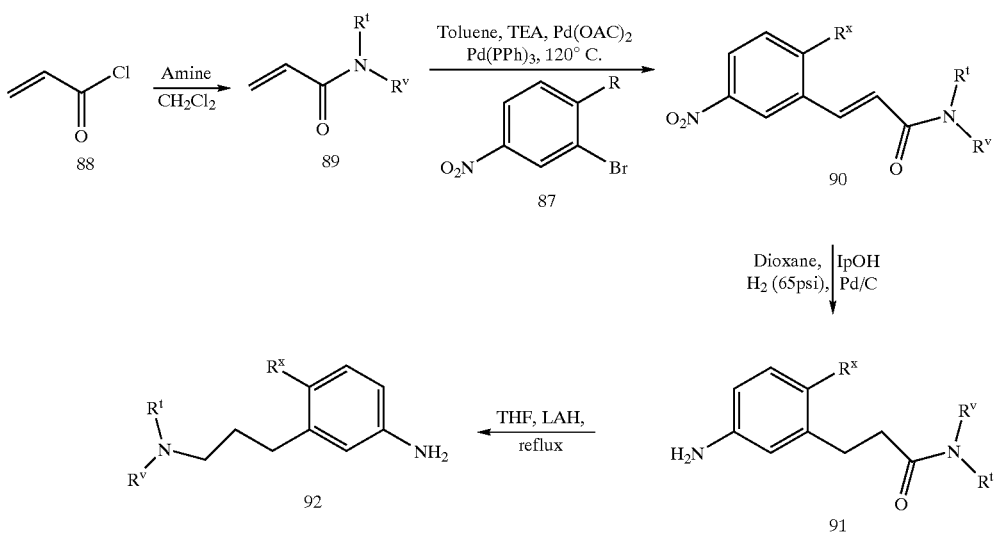

Substituted anilines are prepared such as by the procedure described in Scheme 27 (where $R^t$ and $R^v$ are alkyl, or together with the nitrogen atom form a 4–6 membered heterocyclic ring). Acryloyl chloride 88 is reacted with an amine, preferably a secondary amine, such as at a temperature between about 0° C. and about RT, to form the amide 89. A bromo-nitrobenzene 87 is reacted with the amide 89, such as in the presence of base, for example TEA, together with $Pd(OAc)_2$ and $Pd(PPh_3)_4$, at a temperature above about 50° C., and preferably at about 120° C., such as in a sealed container, to form the substituted alkene 90. Hydrogenation of the alkene 90, such as with $H_2$-in the presence of a catalyst, for example Pd/C catalyst yields the substituted aniline 91. Reduction of the amide 91, such as with $LiAlH_4$, at a temperature above about 50° C., and preferably at about 80° C. yields the aniline 92.

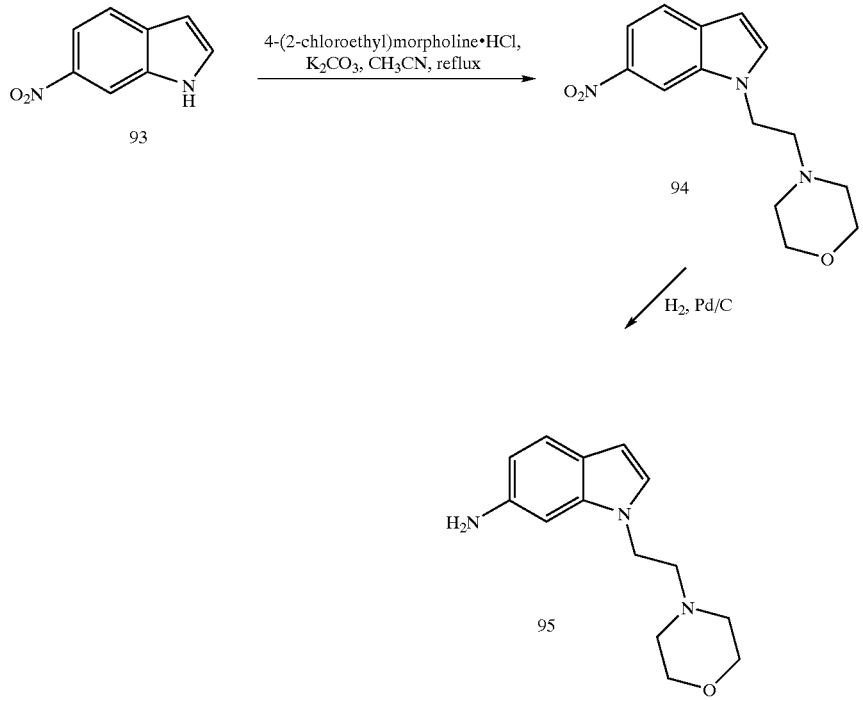

Substituted indoles are prepared such as by the procedure described in Scheme 28. A nitroindole 93 is coupled with a halo compound, in the presence of base, for example $K_2CO_3$. Heating at a temperature above about 50° C., and preferably at about reflux yields the substituted-nitro-1H-indole 94. Hydrogenation similar to conditions described above yield the amino derivative 95.

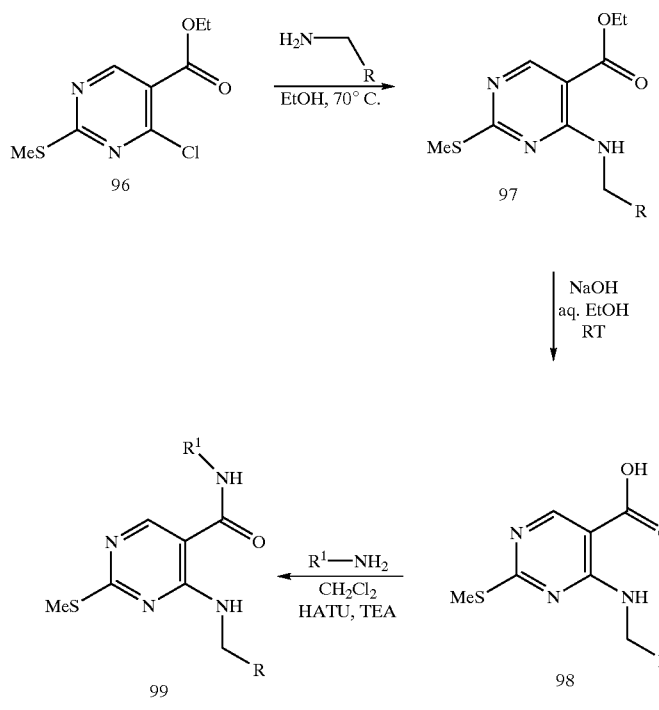

Scheme 29

Substituted pyrimidines are prepared such as by the procedure described in Scheme 29. 2-Methylthio-5-pyrimidyl acids 98 are prepared from the corresponding esters 96 similar to procedures described above. The amides 99 are formed from the acids 98 by coupling with the amine such as in the presence of HATU and base, TEA for example. The methylthio group can be removed, such as with Raney-Ni and heat, preferably at about reflux temperature, to form the pyrimidine 100.

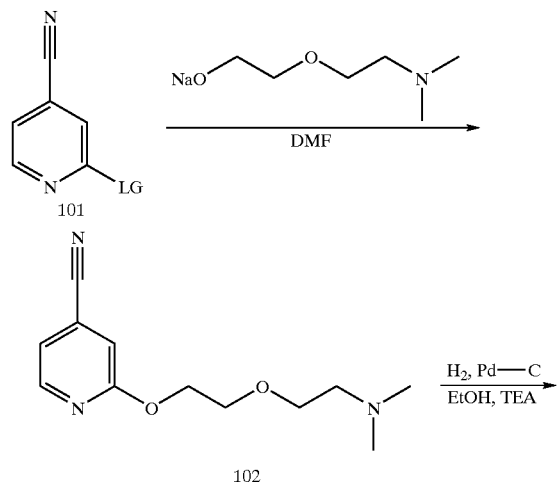

Scheme 30

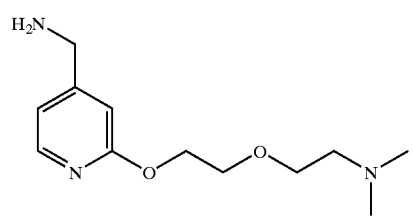

Substituted aminomethyl compounds are prepared such as by the procedure described in Scheme 30 (where LG is a leaving group, such as Cl). Strong base, such as NaH is added to an alcohol and heated at about 50° C. to form the sodium alkoxide, which is added to a halo compound, such as 2-chloro-4-cyanopyridine and heated at a temperature above about 50° C., and preferably at about 70° C. to form the ether 102. Hydrogenation yields the aminomethyl derivative 103.

Scheme 31

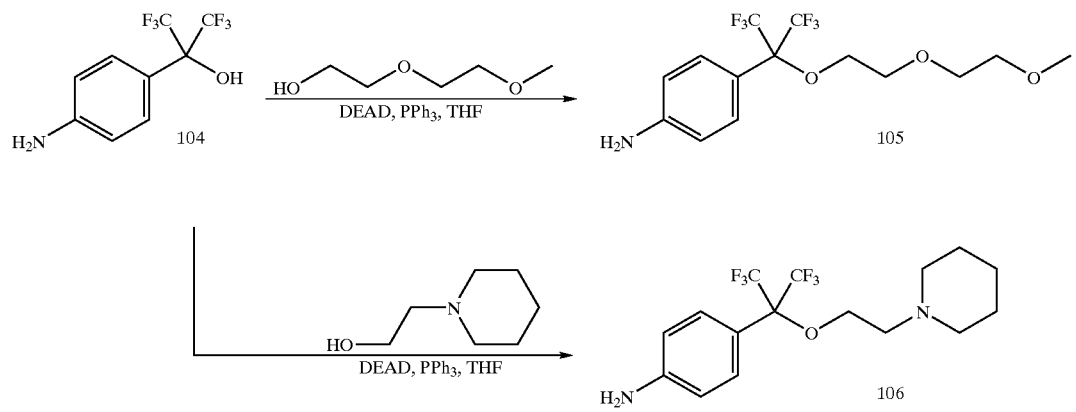

Substituted anilines are prepared such as by the procedure described in Scheme 31. Treatment with the haloalkyl alcohol 104 with an alcohol, such as in the presence of DEAD and PPh₃ yields the ether 105 or 106.

Scheme 32

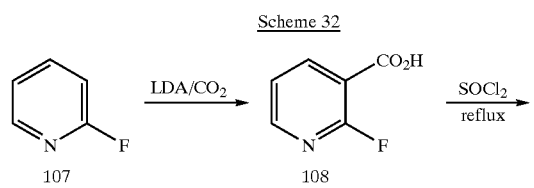

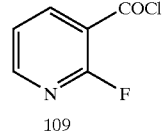

Functionalized pyridines are prepared such as by the procedure described in Scheme 32. 2-Fluoropyridine 107 is treated with base, such as LDA at a temperature below about 0° C., and preferably at about −78° C., and quenched with a stream of dry $CO_2$ to form the nicotinic acid 108. Alternatively, solid $CO_2$ (dry ice) can be used, preferably dried with $N_2$ prior to use. The acid 108 is converted to the acid halide 109, such as by treatment with thionyl chloride and heating at a temperature above about 50° C., and preferably at about reflux.

Scheme 33

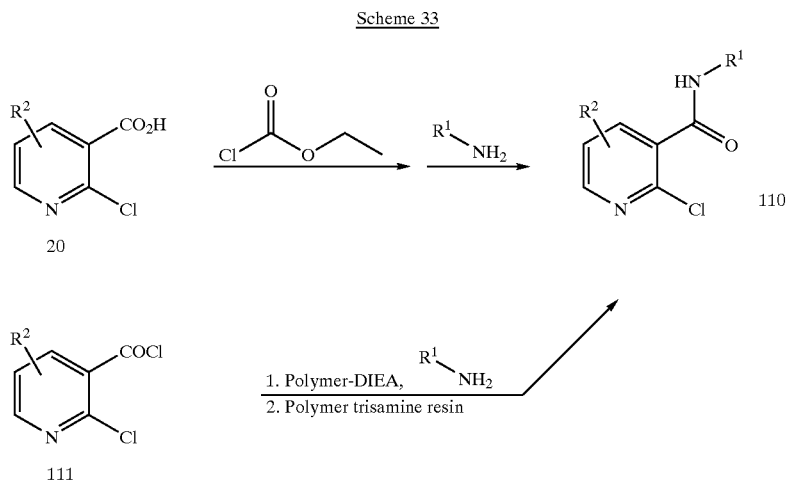

Chloro-substituted pyridines 110 are prepared such as by the procedure described in Scheme 33. 2-Chloronicotinic acid is activated with ethyl chloroformate, in the presence of base, such as TEA, at a temperature of about RT. Reaction with an amine produces amide 110. Alternatively, the amine can be coupled with the acid chloride 111, such as with polymer-supported DIEA, to form amide 110. Excess acid chloride is removed by treating the reaction mixture with polymer-supported trisamine resin.

Scheme 35

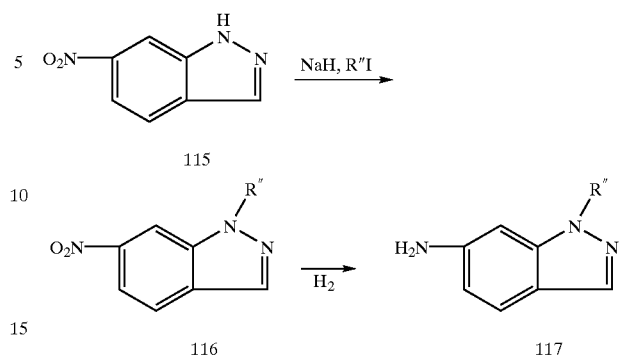

Alkylated indazoles can be prepared by the process outlined in Scheme 35. To a solution of 6-nitroindazole 115 in a solvent such as THF is added strong base, such as NaH at a temperature below RT, preferably at about 0° C. Alkylhalides, such as where R" is methyl, are added and reacted at a temperature about RT to give 1-alkyl-6-nitro-1H-indazole 116. The nitro indazole 116 is hydrogenated, such as with an $H_2$ atmosphere in the presence of a catalyst, such as Pd/C to give the 1-substituted-6-amino-1H-indazole 117.

Scheme 34

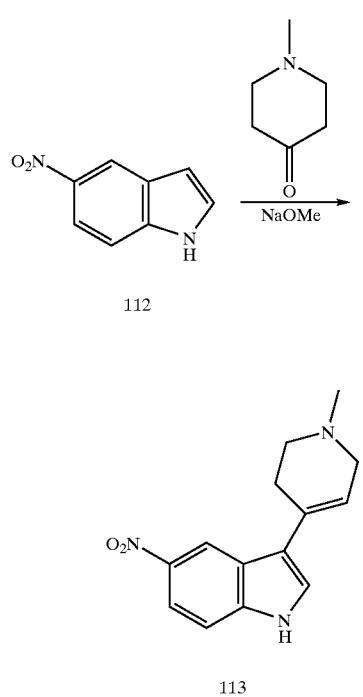

Scheme 36

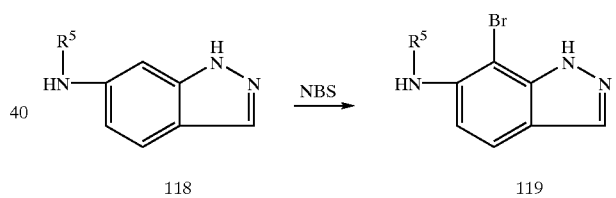

Brominated indazoles can be prepared by the process outlined in Scheme 36. NBS is slowly added to an acidic solution, such as a mixture of TFA:$H_2SO_4$ (5:1) and tert-butyl-4-nitrobenzene 118 at a temperature of about RT to yield the brominated compound 119.

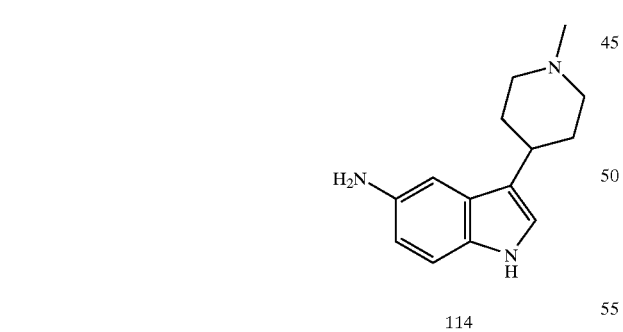

Scheme 37

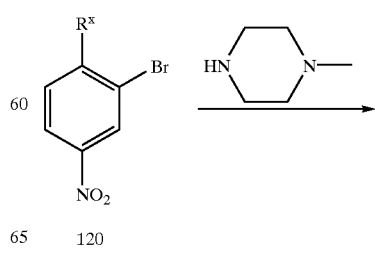

Amino-substituted indoles 110 are prepared such as by the procedure described in Scheme 34. Nitroindoline 112 is reacted with N-methyl-4-piperidone in the presence of NaOMe at a temperature above about 50° C., and preferably at about reflux, to form the 3-substituted indole 113. Hydrogenation as previously discussed yields the amino indole 114.

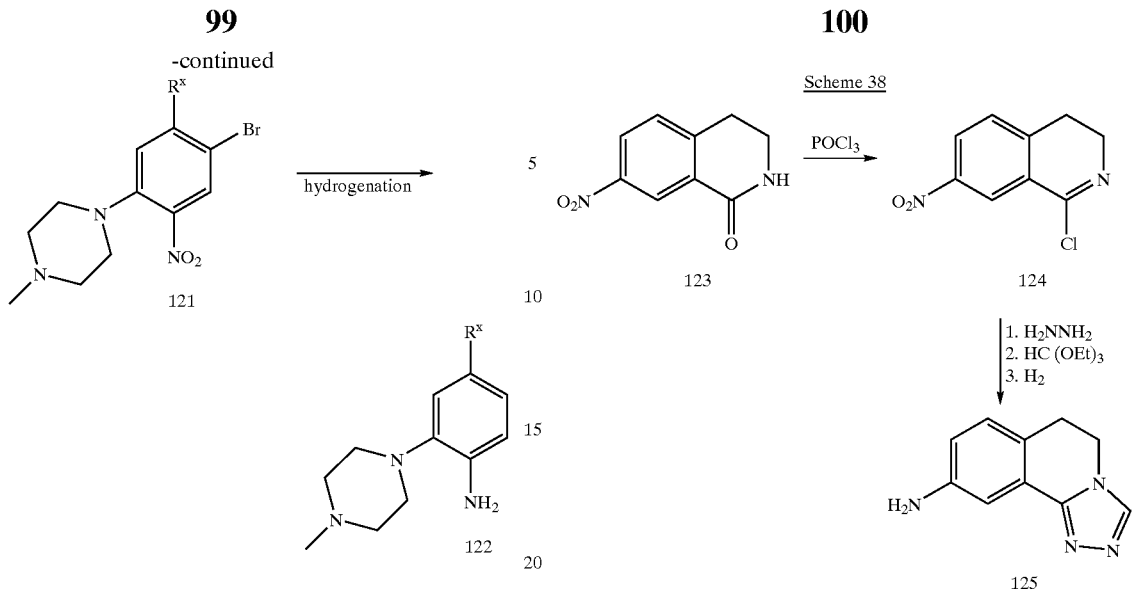

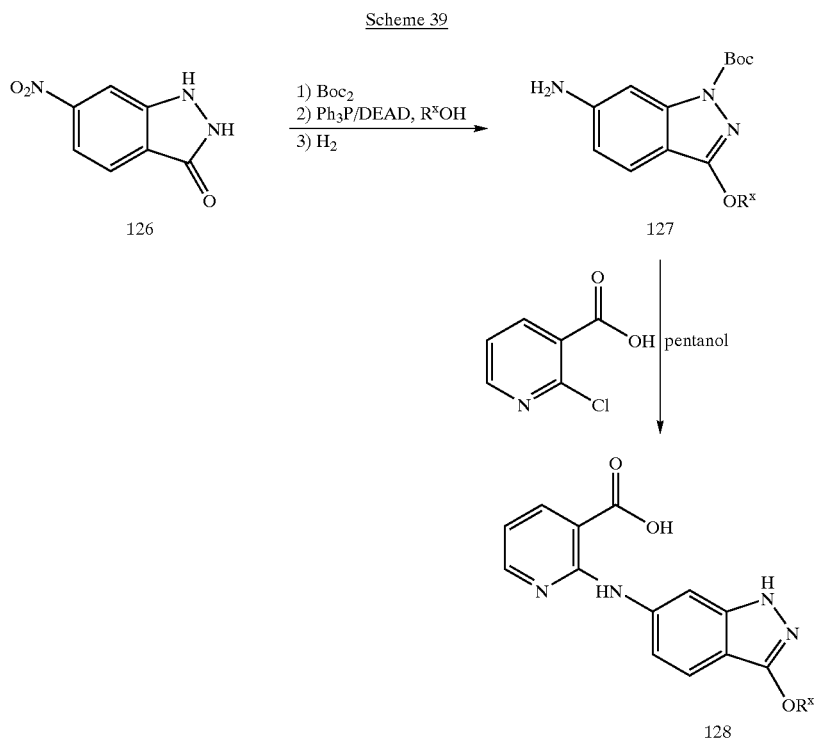

Substituted anilines can be prepared by the process outlined in Scheme 38. A mixture of 1-(substituted)-2-bromo-4-nitrobenzene 120 (where R$^x$ is a substituent selected from those available for substituted R$^1$) and N-methylpiperazine is heated, such as with or without solvent, preferably without solvent, at a temperature above RT, preferably at a temperature above about 100° C., and more preferably at a temperature at about 130° C. to give the 1-[5-(substituted)-2-nitrophenyl]-4-methylpiperazine 121. The nitro compound 121 is hydrogenated, such as with an H$_2$ atmosphere in the presence of a catalyst, such as Pd/C to furnish 4-(substituted)-2-(4-methylpiperazinyl)phenylamine 122.

Tricyclic heterocycles can be prepared by the process outlined in Scheme 38. 7-Nitro-2,3,4-trihydroisoquinolin-1-one 123 is heated in POCl$_3$ at a temperature above RT, preferably at a temperature sufficient for reflux, to form the 1-chloro-7-nitro-3,4-dihydroisoquinoline 124. The 1-chloro-7-nitro-3,4-dihydroisoquinoline 124 is dissolved in a solvent, such as THF, and H$_2$NNH$_2$ is added. The reaction is evaporated to a residue, then heated with HC(OEt)$_3$ at a temperature above RT, preferably at a temperature above about 75° C., and more preferably at a temperature at about 115° C. to give the nitro-substituted tricyclic. Hydrogenation, such as with an H$_2$ atmosphere in the presence of a catalyst, such as Pd/C, gives 2-amino-5,6,7-trihydro-1,2,4-triazolo[3,4-a]isoquinoline 125.

Indazolyl ethers can be prepared by the process outlined in Scheme 39. 6-Nitro-1H-2-hydroindazol-3-one 126 is protected such as with $Boc_2O$ and DMAP in $CH_2Cl_2$ at a temperature of about RT, to give the protected 6-nitro-2-hydroindazol-3-one. The protected 6-nitro-2-hydroindazol-3-one is reacted with an alcohol (where $R^x$ is an appropriate substituent selected from the possible substituents on R) and $Ph_3P$ in a solvent, such as THF, and DEAD, at a temperature of about RT, to give the protected 6-nitro(indazol-3-yl) ether. The nitro intermediate is hydrogenated, such as with an $H_2$ atmosphere in the presence of a catalyst, such as Pd/C, to give the protected 6-amino(indazol-3-yl) ether 127. The amine 127 is coupled and 2-chloronicotinic acid in a solvent, such as an alcohol, preferably pentanol, at a temperature above RT, preferably at a temperature above about 75° C., and more preferably at a temperature at about 130° C. to give the coupled and deprotected compound 128.

Indolinyl substituted carboxamides can be prepared from the corresponding nitro indoline 129 by the process outlined in Scheme 40. For example, 3,3-dimethyl-6-nitroindoline 129 is alkylated, such as with N-protected-4-formylpiperidine in the presence of $NaHB(OAc)_3$ and acid, such as glacial AcOH, and solvent, such as dichloromethane, at a temperature of about RT, to afford the alkylated indane 130. Hydrogenation of the alkylated indane 130, such as with an $H_2$ atmosphere in the presence of a catalyst, such as Pd/C, in the presence of a solvent, such as an alcohol, preferably MeOH, to give the amino intermediate 131. Alternatively, other hydrogenation methods can be used, such as Fe powder with $NH_4Cl$. Coupling of the amine 131, such as with 2-chloronicotinic acid and DIEA, HOBt and EDC, in a solvent such as $CH_2Cl_2$ at a temperature of about RT provides the protected carboxamide 132, which upon deprotection and alkylation yields other compounds of the

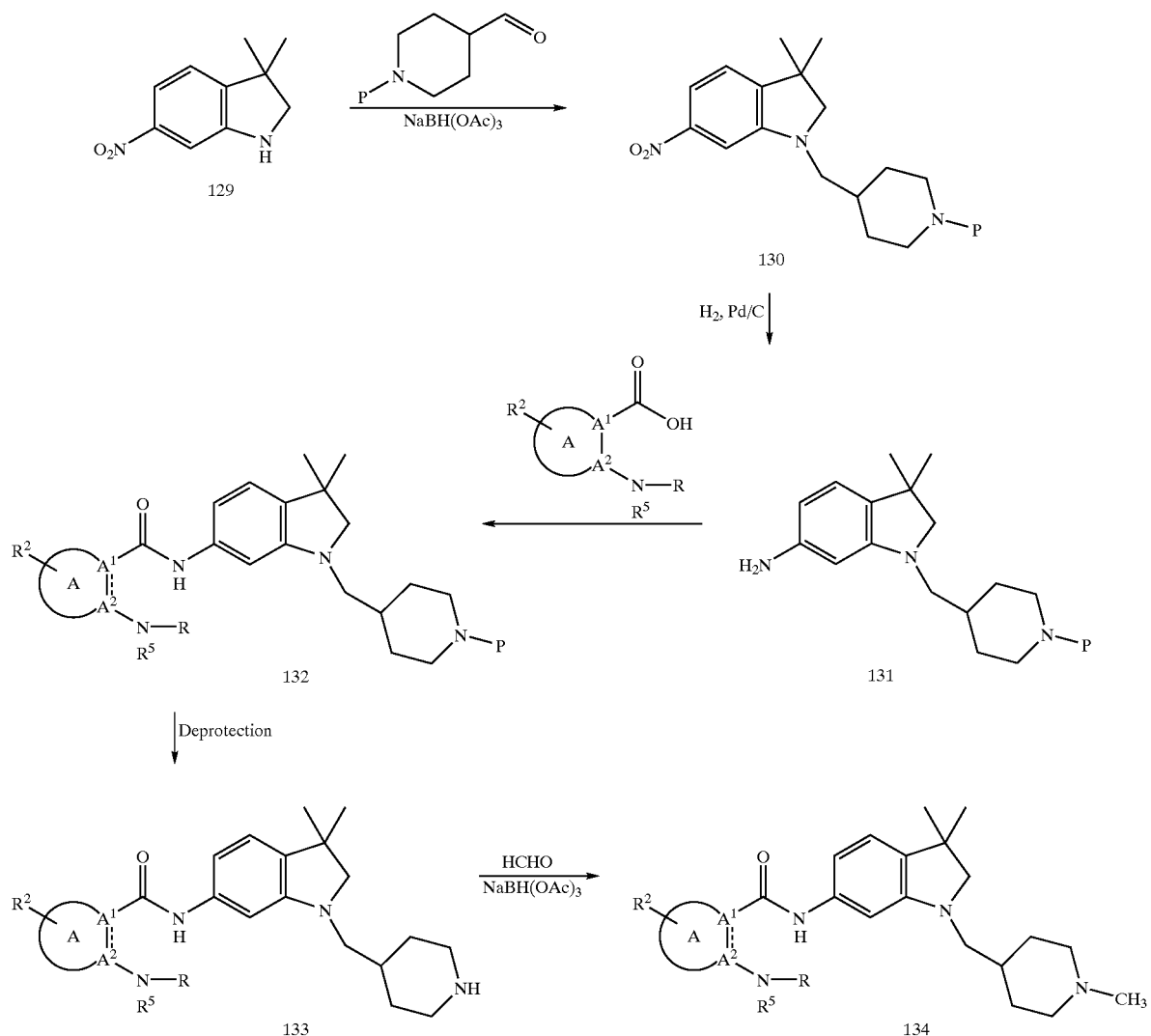

invention, 133 and 134, respectively. Alternatively, amine 131 is reacted with 2-fluoronicotinoyl chloride to form a 2-fluoronicotinamide, which can be alkylated, such as in Scheme 10.

Scheme 41

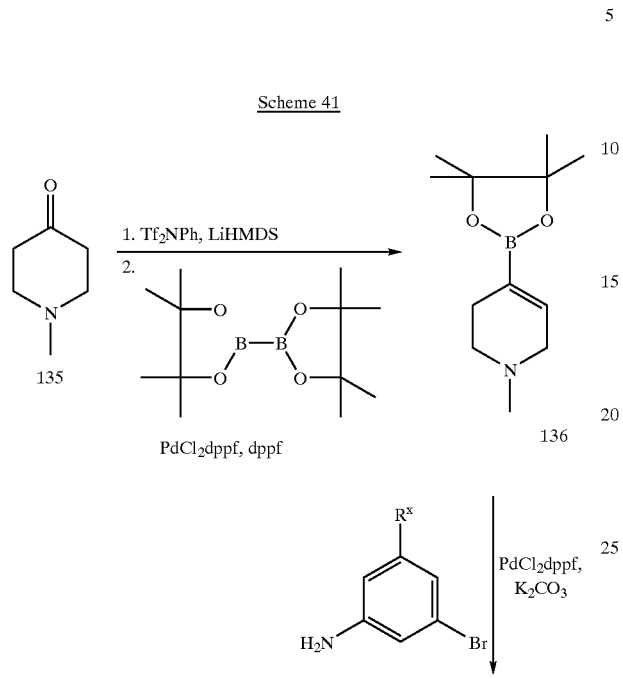

-continued

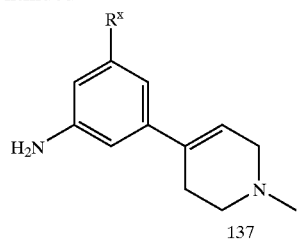

Substituted anilines can be prepared by the process outlined in Scheme 41. 1-Methyl-4-piperidinone 135 is added to a solution of strong base such as LiHMDS, in a solvent such as THF, at a temperature below RT, preferably lower than about −50° C., more preferably at about −78° C. Tf$_2$NPh is reacted with the enolate at a temperature of about RT, to give 1-methyl-4-(1,2,5,6-tetrahydro)pyridyl-(trifluoromethyl)sulfonate. A mixture of the triflate intermediate, bis(pinacolato)diboron, potassium acetate, PdCl$_2$dppf, and dppf in a solvent such as dioxane is heated at a temperature above RT, preferably at a temperature above about 50° C., and more preferably at a temperature at about 80° C. to give 4,4,5,5-tetramethyl-2-(1-methyl(4-1,2,5,6-tetrahydropyridyl))-1,3,2-dioxaborolane 136. The substituted aniline 137 is formed from the 1,3,2-dioxaborolane 136 such as with treatment with an amine in the presence of 1,1'-bis(diphenyphosphino)ferrocene-palladium dichloride and base, such as K$_2$CO$_3$, in a solvent such as DMF at a temperature above RT, preferably at a temperature above about 50° C., and more preferably at a temperature at about 80° C.

Scheme 42

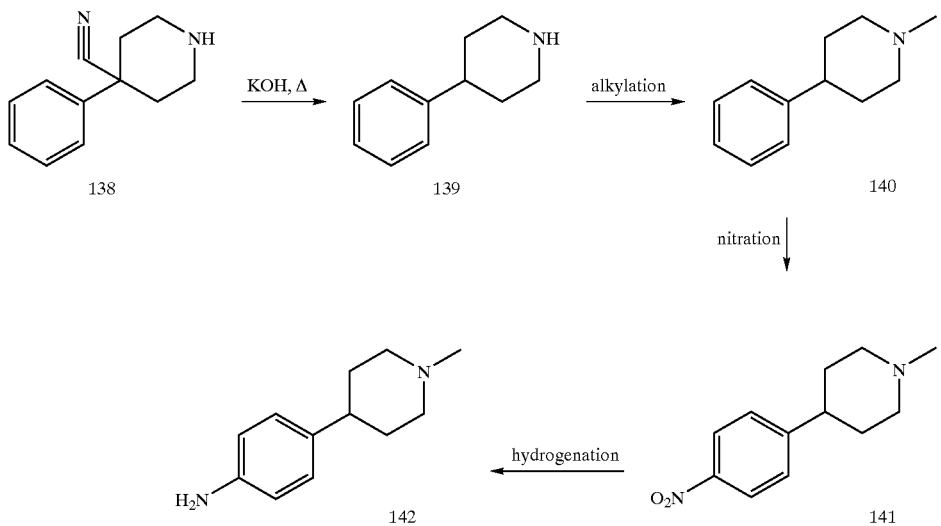

Substituted anilines can be prepared by the process outlined in Scheme 42. 4-Cyano-4-phenylpiperidine hydrochloride 138 is treated with base, such as KOH, at a temperature above RT, preferably at a temperature above about 100° C., and more preferably at a temperature at about 160° C., to provide the phenyl piperidine 139. Alkylation of the phenyl piperidine 139, such as with formaldehyde and NaCNBH$_3$ in a solvent such as CH$_3$CN, with sufficient acid to maintain the reaction pH near 7, to provide the alkylated piperidine 140. Nitration of the phenylpiperidine 140, such as with H$_2$SO$_4$ and fuming HNO$_3$ at a temperature below RT, and preferably at about 0° C., gives the nitro intermediate 141. Hydrogenation of the nitro intermediate 141, such as with an H$_2$ atmosphere in the presence of a catalyst, such as Pd/C, in the presence of a solvent, such as an alcohol, preferably MeOH, to give the amino intermediate 142.

Substituted benzylamines can be prepared by the process outlined in Scheme 44. A substituted bromobenzylamine 145 where $R^{1a}$ is a substituent described for $R^1$ is protected such as with Boc$_2$O in the presence of base, such as TEA in an appropriate solvent such as CH$_2$Cl$_2$. The protected bromobenzylamine 146 is alkylated, such as with 1-dimethylamino-2-propyne in the presence of catalyst, such as PdCl$_2$(PPh$_3$)$_2$, and CuI, in the presence of base, such as TEA, at a temperature above RT, preferably at a temperature above about 50° C., and more preferably at a temperature at about 100° C., such as in a sealed tube, to form the propynylbenzylamine 147. The propynylbenzylamine is hydrogenated such as with H$_2$ in the presence of Pd(OH)$_2$ and MeOH to provide the propylbenzylamine 148. Deprotection, such as with strong acid, such as TFA, for removal of a Boc protecting group, yields the propylbenzylamine 149.

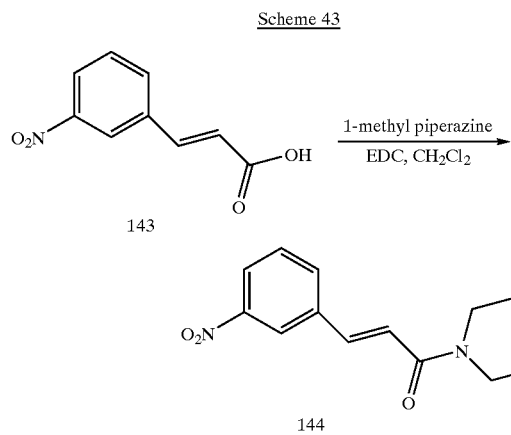

Scheme 43

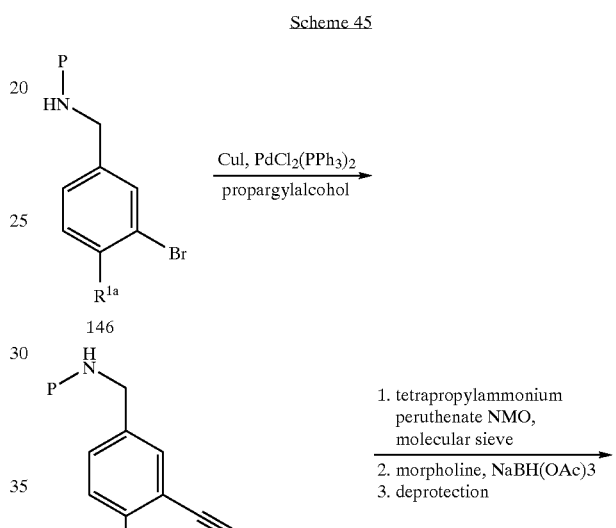

Scheme 45

Substituted amides can be prepared by the process outlined in Scheme 43. 3-Nitrocinnamic acid 143 is coupled with 1-methylpiperazine in the presence of EDC and a solvent such as CH$_2$Cl$_2$, at a temperature of about RT gives the carboxamide 144.

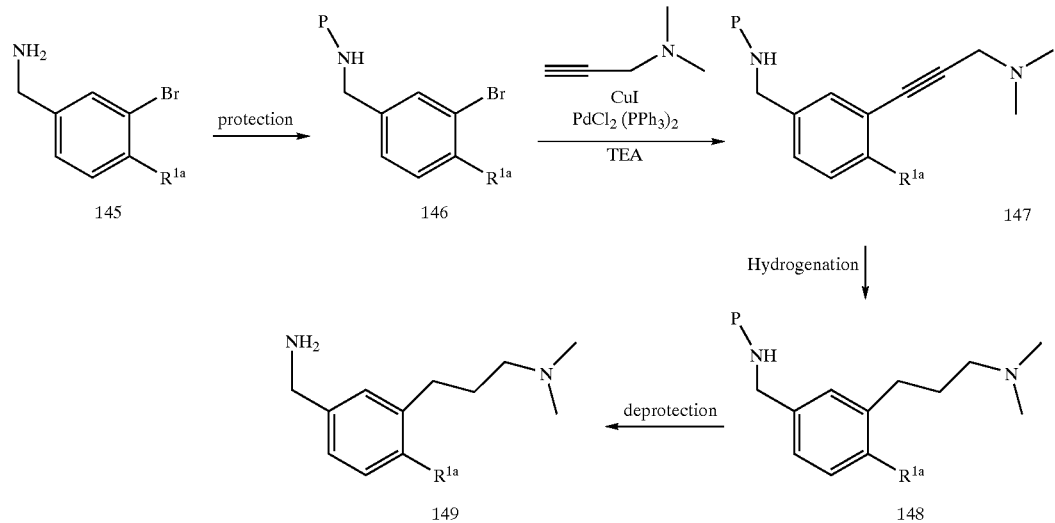

Scheme 44

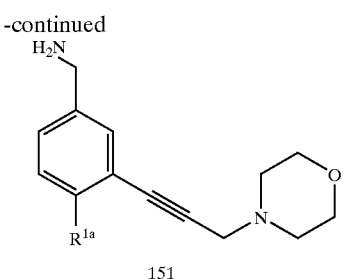

151

Substituted benzylamines can be prepared by the process outlined in Scheme 45. The protected bromobenzylamine 146 is alkylated, such as with propargyl alcohol in the presence of catalyst, such as PdCl₂(PPh₃), and CuI, in the presence of base, such as TEA, at a temperature above RT, preferably at a temperature above about 50° C., and more preferably at a temperature at about 100° C., such as in a sealed tube, to form the protected hydroxypropynylbenzylamine 150. The protected hydroxypropynylbenzylamine is treated with N-methylmorpholine oxide in the presence of a catalyst, such as tetrapropylammonium perruthenate, to form the aldehyde intermediate. Reductive amination, such as with the addition of morpholine and NaBH(OAc)₃ provides the morpholinyl derivative. Deprotection, such as with strong acid, such as TFA, for removal of a Boc protecting group, yields the propylbenzylamine 151.

Scheme 46

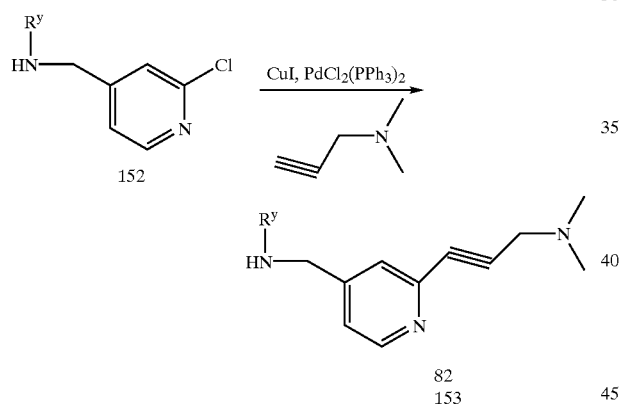

Substituted aminomethyl compounds are prepared such as by the procedure described in Scheme 46. A halo compound 152, is reacted with an alkyne in the presence of PdCl₂ (PPh₃)₂ and CuI, with base is heated at a temperature above about 50° C., and preferably at about 100° C., such as in a sealed container, to provide the substituted alkyne 153.

Scheme 47

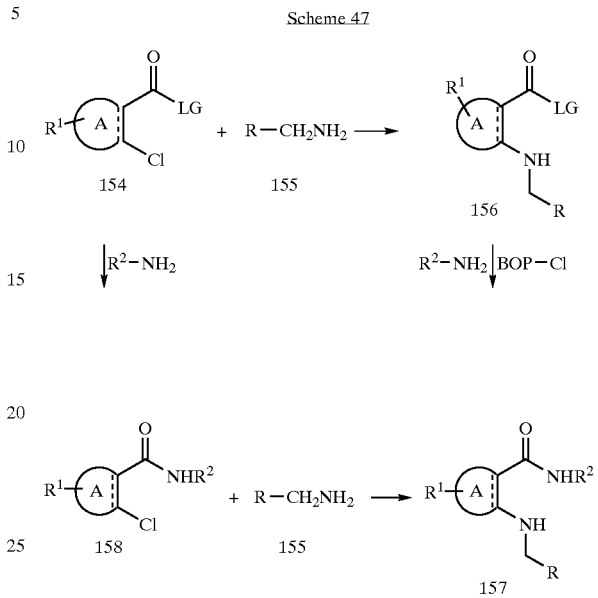

Substituted heterocycles may be prepared by the method found in Scheme 47. Chloro-heterocycles 154 (where LG is OH) is coupled with an amine 155 at a suitable temperature, such as a temperature over about 100° C. to give the 2-substituted amino-nicotinic acid 156. The 2-substituted amino-nicotinic acid 156 is reacted with a substituted amine in the presence of a coupling reagent, such as BOP—Cl and base, such as TEA to form the 2-substituted amino-nicotinamide 157.

Alternatively, 2-chloro-nicotinoyl chloride 154 (where LG is Cl) is coupled first with R²—NH₂, such as in the presence of base, e.g., NaHCO₃, in a suitable solvent, such as IpOH or CH₂Cl₂, to form the amide 158, then coupled with an amine 155 to yield the 2-substituted amino-nicotinamide 157. Where A is a pi-electron rich heterocycle, the addition of KF, such as 40% KF on alumina in IpOH, at a temperature over about 100° C., preferably about 160° C., can be used in the formation of 157 from 158.

Scheme 48

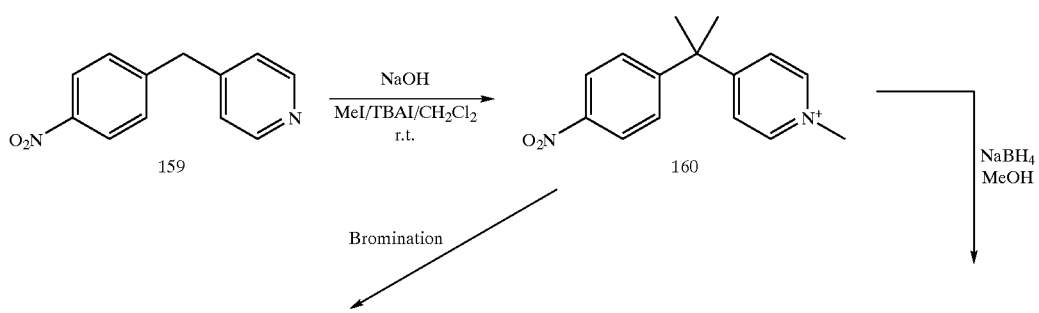

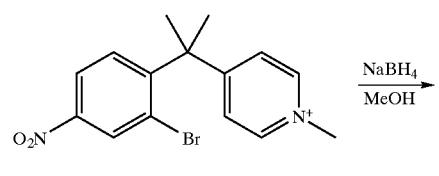
161

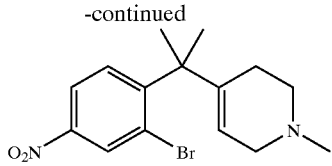
162

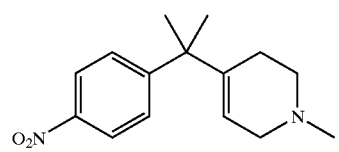
165

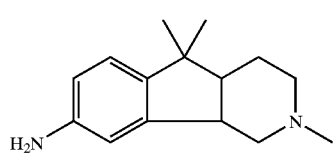
164

163

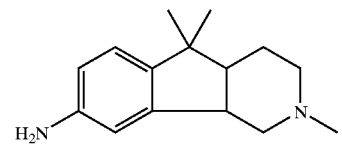
166

2,3,4,4a,9,9a-hexahydro-1H-3-aza-fluoren-6-ylamine may be prepared by the method found in Scheme 48. Nitrobenzylpyridines 159 are alkylated, such as with MeI, in the presence of TBAI and base to form the pyridinium compound 160. The pyridinium compounds 160 are halogenated, such as brominated with NBS, to form the brominated pyridinium compounds 161 which are reduced such as with NaBH$_4$ to form the tetrahydro-pyridines 162. Heck-Type Coupling delivers the tricyclic compound 163, which was reduced via catalytic hydrogenation such as by using Pd—C to form the hexahydro-fluorenes 164. Alternatively, pyridinium salt 160 can be reduced to tetrahydropyridine 165 via such as NaBH$_4$ in a solvent such as MeOH. The nitrophenyl comnpound 165 can be reduced, such as with catalytic hydrogenation, to yield the bicyclic aniline 166.

The starting compounds defined in Schemes 1–48 may also be present with functional groups in protected form if necessary and/or in the form of salts, provided a salt-forming group is present and the reaction in salt form is possible. If so desired, one compound of formulas I–XIII can be converted into another compound of formulas I–XIII or a N-oxide thereof; a compound of formulas I–XIII can be converted into a salt; a salt of a compound of formulas I–XIII can be converted into the free compound or another salt; and/or a mixture of isomeric compounds of formulas I–XIII can be separated into the individual isomers.

N-Oxides can be obtained in a known matter by reacting a compound of formulas I–XIII with hydrogen peroxide or a peracid, e.g. 3-chloroperoxy-benzoic acid, in an inert solvent, e.g. dichloromethane, at a temperature between about –10–35° C., such as about 0° C.-RT.

If one or more other functional groups, for example carboxy, hydroxy, amino, or mercapto, are or need to be protected in a compound of formulas I–XIII or in the synthesis of a compound of formulas I–XIII, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas I–XIII with a salt-forming group may be prepared in a manner known per se. Acid addition salts of compounds of formulas I–XIII may thus be obtained by treatment with an acid or with a suitable anion exchange reagent. A salt with two acid molecules (for example a dihalogenide of a compound of formulas I–XIII) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas I–XIII.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

A compound of formulas I–XIII, wherein Z is oxygen, can be converted into the respective compound wherein Z is sulfur, for example, by using an appropriate sulfur compound, e.g. using reaction with Lawesson's reagent (2,4-bis-(4-methoxyphenyl)-1,3-dithia-2,4-diphosphetane-2,4-disulfide) in a halogenated hydrocarbon, such as $CH_2Cl_2$, or an aprotic solvent, such as toluene or xylene, at temperatures from about 30° C. to reflux.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas I–XIII, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

For example, amine 1 can be prepared by reduction of the corresponding nitro. The reduction preferably takes place in the presence of a suitable reducing agent, such as tin(II) chloride or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as MeOH. The reaction temperature is preferably between about 0° C. and about 80° C., especially about 15° C. to about 30° C.

It would also be possible to reduce the nitro compound after forming the amide compound under reaction conditions analogous to those for the reduction of nitro compounds described above. This would eliminate the need to protect the free amino group as described in Scheme 1.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

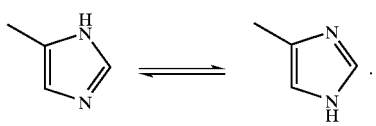

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necesssary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, 2$^{nd}$ Ed. (2001); M. Bodanszky, A. Bodanszky: *The practice of Peptide Synthesis* Springer-Verlag, Berlin Heidelberg 1984; J. Seyden-Penne: *Reductions by the Alumino-and Borohydrides in Organic Synthesis*, 2$^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I–XIII. These detailed descriptions fall within the scope, and serve to exemplify, the above described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200–400 mesh, 60A) or Biotage pre-packed column. Thin-layer chromatography (TLC) was performed with Analtech gel TLC plates (250μ). Preparative TLC was performed with Analtech silica gel plates (1000–2000μ). Preparative HPLC was conducted on Beckman or Waters HPLC system with 0.1% $TFA/H_2O$ and 0.1% $TFA/CH_3CN$ as mobile phase. The flow rate was at 20 ml/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer—SCIEX API 165 electrospray mass spectrometer (positive and, or negative) or an HP 1100 MSD LC-MS with eletrospray ionization and quadrupole detection. All parts are by weight and temperatures are in Degrees centigrade unless otherwise indicated.

The following abbreviations are used:

| | |
|---|---|
| AcOH - | acetic acid |
| $Ac_2O$ - | acetic anhydride |
| AIBN - | 2,2'-azobisisobutyronitrile |
| Ar - | argon |
| $AgSO_4$ - | silver sulfate |
| $AlCl_3$ - | aluminum trichloride |
| ATP - | adenosine triphosphate |
| $BH_3$ - | borane |
| Boc - | tert-butyloxycarbonyl |
| $Boc_2O$ - | Boc anhydride |
| BOP-Cl - | bis(2-oxo-3-oxazolidinyl)phosphinic chloride |
| $Br_2$ - | bromine |
| BSA - | bovine serum albumin |
| t-BuOH - | tert-butanol |
| CAN - | ammonium cerium (IV) nitrate |

| | |
|---|---|
| CH₃CN, AcCN - | acetonitrile |
| CH₂Cl₂ - | dichloromethane |
| CH₃I, MeI - | iodomethane, methyl iodide |
| CCl₄ - | carbon tetrachloride |
| CCl₃ - | chloroform |
| CO₂ - | carbon dioxide |
| Cs₂CO₃ - | cesium carbonate |
| DIEA - | diisopropylethylamine |
| CuI - | copper iodide |
| CuCN - | copper cyanide |
| DCE - | 1,2-dichloroethane |
| DEAD - | diethyl azodicarboxylate |
| DIEA - | diisopropylethylamine |
| dppf - | 1,1-diphenylphosphinoferrocene |
| DMAP - | 4-(dimethylamino)pyridine |
| DMAC - | N,N-dimethylacetamide |
| DMF - | dimethylformamide |
| DMSO - | dimethylsulfoxide |
| DTT - | dithiothreitol |
| EDC, EDAC - | 1-(3-dimethylaminopropyl)-3-ethylcarbodiimide hydrochloride |
| EGTA - | ethylene glycol-bis(β-aminoethyl ether)-N,N,N',N'-tetraacetic acid |
| EtOAc - | ethyl acetate |
| EtOH - | ethanol |
| Et₂O - | diethyl ether |
| Fe - | iron |
| g - | gram |
| h - | hour |
| HATU - | O-(7-azabenzotriazol-1-yl)-N,N,N',N'-tetramethyluronium hexafluorophosphate |
| H₂ - | hydrogen |
| H₂O - | water |
| HCl - | hydrochloric acid |
| H₂SO₄ - | sulfuric acid |
| H₂NNH₂ - | hydrazine |
| HC(OEt)₃ - | triethylorthoformate |
| HCHO, H₂CO - | formaldehyde |
| HCO₂Na - | sodium formate |
| HOAc, AcOH - | acetic acid |
| HOAt - | 1-hydroxy-7-azabenzotriazole |
| HOBt - | hydroxybenzotriazole |
| IpOH - | isopropanol |
| KF - | potassium fluoride |
| K₂CO₃ - | potassium carbonate |
| KHMDS - | potassium hexamethylsilazane |
| KNO₃ - | potassium nitrate |
| KOAc - | potassium acetate |
| KOH - | potassium hydroxide |
| LAH, LiAlH₄ - | lithium aluminum hydride |
| LDA - | lithium diisopropylamide |
| LiCl - | lithium chloride |
| LiHMDS - | lithium hexamethyldisilazide |
| MeOH - | methanol |
| MgCl₂ - | magnesium chloride |
| MgSO₄ - | magnesium sulfate |
| mg - | milligram |
| ml - | milliliter |
| MnCl₂ - | manganese chloride |
| NBS - | N-bromosuccinimide |
| NMO - | 4-methylmorpholine, N-oxide |
| NMP - | N-methylpyrrolidone |
| Na₂SO₄ - | sodium sulfate |
| Na₂S₂O₅ - | sodium metabisulfite |
| NaHSO₃ - | sodium bisulfite |
| NaHCO₃ - | sodium bicarbonate |
| Na₂CO₃ - | sodium carbonate |
| NaCl - | sodium chloride |
| NaH - | sodium hydride |
| NaI - | sodium iodide |
| NaOH - | sodium hydroxide |
| NaOMe - | sodium methoxide |
| NaOEt - | sodium ethoxide |
| NaCNBH₃ - | sodium cyanoborohydride |
| NaBH₄ - | sodium borohydride |
| NaNO₂ - | sodium nitrate |
| NaBH(OAc)₃ - | sodium triacetoxyborohydride |
| NH₄Cl - | ammonium chloride |
| N₂ - | nitrogen |
| Pd/C - | palladium on carbon |
| PdCl₂(PPh₃)₂ - | palladium chloride bis(triphenylphosphine) |
| PdCl₂(dppf) - | 1,1-bis(diphenylphosphino)ferrocene palladium chloride |
| Pd(PPh₃)₄ - | palladium tetrakis triphenylphosphine |
| Pd(OH)₂ - | palladium hydroxide |
| Pd(OAc)₂ - | palladium acetate |
| PMB - | para methoxybenzyl |
| POCl₃ - | phosphorus oxychloride |
| PPh₃ - | triphenylphosphine |
| PtO₂ - | platinum oxide |
| RT - | room temperature |
| SiO₂ - | silica |
| SOCl₂ - | thionyl chloride |
| TBAI - | tetrabutylammonium iodide |
| TBTU - | O-(1H-benzotriazol-1-yl)-N,N,N',N'-tetramethyluronium tetrafluoroborate |
| TEA - | triethylamine |
| Tf₂NPh - | N-phenyltrifluoromethanesulfonimide |
| TFA - | trifluoroacetic acid |
| THF - | tetrahydrofuran |
| TPAP - | tetrapropylammoniumperruthenate |
| Tris-HCl - | Tris(hydroxymethyl)aminomethane hydrochloride salt |
| Zn - | zinc |

Preparation I—3-nitro-5-trifluoromethyl-phenol

1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h the mixture was cooled to RT and partitioned between 1N HCl and EtOAc. The EtOAc fraction was washed with 1N HCl (4×), brine (1×), dried with Na₂SO₄, filtered and concentrated in vacuo to form 3-nitro-5-trifluoromethyl-phenol as an off-white solid.

Preparation II—1-Boc-4-(3-nitro-5-trifluoromethyl-phenoxy)-piperidine

3-Nitro-5-trifluoromethyl-phenol (8.81 g) was dissolved in THF (76 ml). 1-Boc-4-hydroxy-piperidine (8.81 g, Aldrich) and Ph₃P (11.15 g) were added and the solution was cooled to −20° C. A solution of DEAD (6.8 ml, Aldrich) in THF (36 ml) was added dropwise, maintaining the temperature between −20 and −10° C. The reaction was warmed to RT and stirred overnight. The reaction was concentrated in vacuo and triturated with hexane. The yellow solid was removed by filtration and washed with Et₂O (25 ml), and hexane. The white filtrate was washed with 1N NaOH (2×), brine (1×) and the hexane layer was dried over Na₂SO₄, filtered and concentrated in vacuo. The crude material was purified with flash chromatography (SiO₂, 5–10% EtOAc/hexane) to obtain 1-Boc-4-(3-nitro-5-trifluoromethyl-phenoxy)-piperidine.

The following compounds were prepared similarly to the procedure outlined above:

a) (S)-1-Boc-[2-(5-nitro-2-trifluoromethylphenoxymethyl]-pyrrolidine b) (R)-1-Boc-[2-(5-nitro-2-trifluoromethylphenoxymethyl]-pyrrolidine.

c) (R) 1-Boc-2-(3-Nitro-5-trifluoromethyl-phenoxymethyl)-pyrrolidine d) 4-(2-tert-Butyl-5-nitro-phenoxymethyl)-1-methyl-piperidine.

e) (S) 1-Boc-2-(3-Nitro-5-trifluoromethyl-phenoxymethyl)-pyrrolidine f) 1-Boc-3-(5-nitro-2-pentafluoroethyl-phenoxymethyl)-azetidine.

g) N-Boc-[2-(5-nitro-2-pentafluoroethyl-phenoxy)-ethyl] amine.

h) (R) 3-(2-tert-Butyl-5-nitro-phenoxymethyl)-1-Boc-pyrrolidine.

i) 3-(2-tert-Butyl-5-nitro-phenoxymethyl)-1-Boc-azetidine.
j) (S)-1-Boc-[2-(5-nitro-2-tert-butylphenoxymethyl]-pyrrolidine
k) (S) 3-(2-tert-Butyl-5-nitro-phenoxymethyl)-1-Boc-pyrrolidine.
l) (R)-1-Boc-[2-(5-nitro-2-tert-butylphenoxymethyl]-pyrrolidine Preparation III— 1-Boc-4-(3-amino-5-trifluoromethyl-phenoxy)-piperidine:

1-Boc-4-(3-nitro-5-trifluoromethyl-phenoxy)-piperidine (470 mg) was dissolved in MeOH (12 ml) and Pd/C (10 mg) was added. After sparging briefly with $H_2$, the mixture was stirred under $H_2$ for 6 H. The catalyst was removed by filtration and the MeOH solution was concentrated in vacuo to yield 1-Boc-4-(3-amino-5-trifluoromethyl-phenoxy)-piperidine as an off-white foam.

The following compounds were prepared similarly to the procedure outlined above:

a) 1-Boc-2-(3-Amino-5-trifluoromethyl-phenoxymethyl)-pyrrolidine.
b) 2-(3-Amino-5-trifluoromethyl-phenoxymethyl)-1-methyl-pyrrolidine.
c) [2-(1-Methylpiperidin-4-yloxy)-pyridin-4-yl] methylamine. ESI (M+H)=222.
d) [2-(2-Morpholin-4-yl-ethoxy)-pyridin-4-yl]methylamine.
e) [2-(2-Morpholin-4-yl-propoxy)-pyridin-4-yl] methylamine.
f) [2-(1-Methyl-pyrrolidin-2-ylmethoxy)-pyridin-4-yl] methylamine. ESI MS: (M+H)=222.
g) (4-Aminomethyl-pyridin-2-yl)-(3-morpholin-4-yl-propyl)-amine. ESI MS: (M+H)=251.
h) 4-tert-Butyl-3-(1-methyl-piperidin-4-ylmethoxy)-phenylamine.
i) 4-tert-Butyl-3-(2-piperidin-1-yl-ethoxy)-phenylamine.
j) 3-(1-Methyl-piperidin-4-ylmethoxy)-4-pentafluoroethyl-phenylamine.
k) 3-(1-Isopropyl-piperidin-4-ylmethoxy)-4-pentafluoroethyl-phenylamine.
l) (S) 3-Oxiranylmethoxy-4-pentafluoroethyl-phenylamine.
m) 3-(2-Pyrrolidin-1-yl-ethoxy)-4-trifluoromethyl-phenylamine.
n) 3-(2-Piperidin-1-yl-ethoxy)-4-trifluoromethyl-phenylamine.
o) (S) 3-(1-Boc-pyrrolidin-2-ylmethoxy)-4-pentafluoroethyl-phenylamine.
p) (R) 3-(1-Boc-pyrrolidin-2-ylmethoxy)-4-pentafluoroethyl-phenylamine.
q) (R) 3-(1-Methyl-pyrrolidin-2-ylmethoxy)-5-trifluoromethyl-phenylamine.
r) (S) 3-(1-Methyl-pyrrolidin-2-ylmethoxy)-5-trifluoromethyl-phenylamine
s) (R) 3-Oxiranylmethoxy-4-pentafluoroethyl-phenylamine.
t) (R) 2-(5-Amino-2-pentafluoroethyl-phenoxy)-1-pyrrolidin-1-yl-ethanol.
u) 3-(1-Boc-azetidin-3-ylmethoxy)-4-pentafluoroethyl-phenylamine.
v) 3-(2-(Boc-amino)ethoxy)-4-pentafluoroethyl-phenylamine.
w) 6-Amino-2,2-dimethyl-4H-benzo[1,4]oxazin-3-one. M+H 193.2. Calc'd 192.1.
x) 2,2,4-Trimethyl-3,4-dihydro-2H-benzo[1,4]oxazin-6-ylamine.
y) 1-(6-Amino-2,2-dimethyl-2,3-dihydro-benzo[1,4]oxazin-4-yl)-ethanone. M+H 221.4. Calc'd 220.3.
z) [2-(1-Benzhydryl-azetidin-3-yloxy)-pyridin-4-yl]-methylamine.
aa) [2-(1-Methyl-piperidin-4-ylmethoxy)-pyridin-4-yl]-methylamine. M+H 236.3. Calc'd 235.2.
ab) 3-(4-Boc-piperazin-1-ylmethyl)-5-trifluoromethyl-phenylamine. M+H 360.3.
ac) 2-Boc-4,4-dimethyl-1,2,3,4-tetrahydro-isoquinolin-7-ylamine.
ad) 3-Morpholin-4-ylmethyl-4-pentafluoroethyl-phenylamine.
ae) 3-(4-Methyl-piperazin-1-ylmethyl)-4-pentafluoroethyl-phenylamine. M+H 410.3. Calc'd 409.4.
af) 7-Amino-2-(4-methoxy-benzyl)-4,4-dimethyl-3,4-dihydro-2H-isoquinolin-1-one. M+H 311.1.
ag) 7-Amino-4,4-dimethyl-3,4-dihydro-2H-isoquinolin-1-one.
ah) (3-Amino-5-trifluoromethyl-phenyl)-(4-Boc-piperazin-1-yl)-methanone. M+H 374.3; Calc'd 373.
ai) 3-(4-Boc-Piperazin-1-ylmethyl)-5-trifluoromethyl-phenylamine.
aj) 1-(7-Amino-4,4-dimethyl-3,4-dihydro-1H-isoquinolin-2-yl)-ethanone. M+H 219.2.
ak) {2-[2-(1-Methylpiperidin-4-yl)ethoxy]-pyridin-4-yl}-methylamine.
al) {2-[2-(1-Pyrrolidinyl)ethoxy]-pyridin-4-yl}-methylamine.
am) {2-[2-(1-Methylpyrrolin-2-yl)ethoxy]-pyridin-4-yl}-methylamine.
an) (2-Chloro-pyrimidin-4-yl)-methylamine.
ao) 3-(1-Boc-azetidin-3-ylmethoxy)-5-trifluoromethyl-phenylamine.
ap) 4-tert-Butyl-3-(1-Boc-pyrrolidin-3-ylmethoxy)-phenylamine. M+H 385.
aq) 4-tert-Butyl-3-(1-Boc-azetidin-3-ylmethoxy)-phenylamine. M+Na 357.
ar) (S) 4-tert-Butyl-3-(1-Boc-pyrrolidin-2-ylmethoxy)-phenylamine. M+Na 371.
as) 3-tert-Butyl-4-(4-Boc-piperazin-1-yl)-phenylamine
at) 3-(1-Methyl-piperidin-4-yl)-5-trifluoromethyl-phenylamine.
au) 3,3-Dimethyl-2,3-dihydro-benzofuran-6-ylamine.
av) 3,9,9-Trimethyl-2,3,4,4a,9,9a-hexahydro-1H-3-aza-fluoren-6-ylamine.
aw) 4-[1-Methyl-1-(1-methyl-piperidin-4-yl)-ethyl]-phenylamine was prepared using EtOH as the solvent.
ax) 4-tert-Butyl-3-(4-pyrrolidin-1-yl-but-1-enyl)-phenylamine.
ay) (R) 3-(1-Boc-pyrrolidin-2-ylmethoxy)-5-trifluoromethyl-phenylamine.
az) (S) 3-(1-Boc-pyrrolidin-2-ylmethoxy)-5-trifluoromethyl-phenylamine.

Preparation IV—1-Boc-4-{3-[(2-fluoro-pyridine-3-carbonyl)-amino]-5-trifluoromethyl-phenoxy}-piperidine:

1-Boc-4-(3-amino-5-trifluoromethyl-phenoxy)-piperidine (4.37 g) was dissolved in $CH_2Cl_2$ (100 ml) and $NaHCO_3$ (2.4 g, Baker) was added. 2-Fluoropyridine-3-carbonyl chloride (2.12 g) was added an the reaction was stirred at RT for 2.5 h. The reaction was filtered and concentrated in vacuo to yield a yellow foam. (30%) EtOAc/Hexane was added and 1-Boc-4-{3-[(2-fluoro-pyridine-3-carbonyl)-amino]-5-trifluoromethyl-phenoxy}-piperidine precipitated as an off white solid.

The following compounds were prepared similarly to the procedure outlined above:

a) 2-Fluoro-N-[3-(3-piperidin-1-yl-propyl)-5-trifluoromethyl-phenyl]-nicotinamide.
b) N-[4-tert-Butyl-3-(2-piperidin-1-yl-ethoxy)-phenyl]-2-fluoro-nicotinamide.
c) N-[3,3-Dimethyl-1-(1-methyl-piperidin-4-ylmethyl)-2,3-dihydro-1H-indol-6-yl]-2-fluoro-nicotinamide.
d) N-[1-(2-Dimethylamino-acetyl)-3,3-dimethyl-2,3-dihydro-1H-indol-6-yl]-2-fluoro-nicotinamide e) N-[3,3-Dimethyl-1-(2-(Boc-amino)acetyl)-2,3-dihydro-1H-indol-6-yl]-2-fluoro-nicotinamide.
f) N-(4-Acetyl-2,2-dimethyl-3,4-dihydro-2H-benzo[1,4]oxazin-6-yl)-2-fluoro-nicotinamide. M+H 344.5. Calc'd 343.4.
g) 2-Fluoro-N-(2,2,4-trimethyl-3,4-dihydro-2H-benzo[1,4]oxazin-6-yl)-nicotinamide. M+H 316.2. Calc'd 315.1.
h) N-(2,2-Dimethyl-3-oxo-3,4-dihydro-2H-benzo[1,4]oxazin-6-yl)-2-fluoro-nicotinamide. M+H 316.1. Calc'd 315.10.
i) 2-Fluoro-N-[3-(4-methyl-piperazin-1-ylmethyl)-5-trifluoromethyl-phenyl]-nicotinamide. M+H 481. Calc'd 480.
j) 2-Fluoro-N-(2-Boc-4,4-dimethyl-1,2,3,4-tetrahydro-isoquinolin-7-yl)-nicotinamide. M+H 400.
k) 2-Fluoro-N-[3-(4-methyl-piperazin-1-ylmethyl)-4-pentafluoroethyl-phenyl]-nicotinamide. M+H 447.0. Calc'd 446.
l) 2-Fluoro-N-(3-morpholin-4-ylmethyl-4-pentafluoroethyl-phenyl)-nicotinamide.
m) 2-Fluoro-N-[4-iodophenyl]-nicotinamide.
n) 2-Fluoro-N-(4,4-dimethyl-1-oxo-1,2,3,4-tetrahydro-isoquinolin-7-yl)-nicotinamide. M+H 314.0, Calc'd 311.
o) 2-Fluoro-N-[3-(4-Boc-piperazine-1-carbonyl)-5-trifluoromethyl-phenyl]-nicotinamide. M+H 495.
p) 2-Fluoro-N-[3-(4-Boc-piperazin-1-ylmethyl)-5-trifluoromethyl-phenyl]-nicotinamide. M+H 483.3; Calc'd 482.
q) N-(2-Acetyl-4,4-dimethyl-1,2,3,4-tetrahydro-isoquinolin-7-yl)-2-fluoro-nicotinamide. M+H 430.0.
r) N-[3,3-Dimethyl-1-(1-methyl-piperidin-4-yl)-2,3-dihydro-1H-indol-6-yl]-2-fluoro-nicotinamide. M+H 383.2; Calc'd 382.5.
s) N-(4-tert-Butylphenyl)-2-fluoronicotinamide.
t) N-(4-Trifluoromethylphenyl)-2-fluoronicotinamide.
u) 2-Fluoro-N-[3-(1-Boc-azetidin-3-ylmethoxy)-5-trifluoromethyl-phenyl]-nicotinamide. M−H 468.2; Calc'd 469.16.
v) 2-Fluoro-N-[3-(1-Boc-azetidin-3-ylmethoxy)-4-tert-butyl-phenyl]-nicotinamide.
w) (S) N-[4-tert-Butyl-3-(1-Boc-pyrrolidin-2-ylmethoxy)-phenyl]-2-fluoro-nicotinamide. M+Na 494.
x) N-[3-(1-Methyl-piperidin-4-yl)-5-trifluoromethyl-phenyl]-2-fluoro-nicotinamide was prepared with $K_2CO_3$. instead of $NaHCO_3$.
y) N-(3-Bromo-5-trifluoromethyl-phenyl)-2-fluoro-nicotinamide.
z) 2-Fluoro-N-(3,9,9-trimethyl-2,3,4,4a,9,9a-hexahydro-1H-3-aza-fluoren-6-yl)-nicotinamide.
aa) 2-Fluoro-N-{4-[1-methyl-1-(1-methyl-piperidin-4-yl)-ethyl]-phenyl}-nicotinamide
ab) N-[3,3-Dimethyl-1-(1-Boc-piperidin-4-ylmethyl)-2,3-dihydro-1H-indol-6-yl]-2-fluoro-nicotinamide.

Preparation V—1-Boc-4-{3-[(2-chloro-pyridine-3-carbonyl)-amino]-5-trifluoromethyl-phenoxy}-piperidine 1-Boc-4-{3-[(2-chloro-pyridine-3-carbonyl)-amino]-5-trifluoromethyl-phenoxy}-piperidine was prepared from 1-Boc-4-(3-amino-5-trifluoromethyl-phenoxy)-piperidine and 2-chloropyridine-3-carbonyl chloride by a procedure similar to that described in the preparation of 1-Boc-4-{3-[(2-fluoro-pyridine-3-carbonyl)-amino]-5-trifluoromethyl-phenoxy}-piperidine.

The following compounds were prepared similarly to the procedure outlined above:
a) N-(4-tert-Butyl-3-nitro-phenyl)-2-chloro-nicotinamide.
b) 2-Chloro-N-[3-(3-piperidin-1-yl-propyl)-5-trifluoromethyl-phenyl]-nicotinamide.
c) 2-Chloro-N-[3-(3-morpholin-4-yl-propyl)-5-trifluoromethyl-phenyl]-nicotinamide.
d) 2-Chloro-N-[3-(1-methylpiperidin-4-yl)-5-trifluoromethyl-phenyl]-nicotinamide.
e) 2-Chloro-N-[3-(1-methyl-piperidin-4-ylmethoxy)-4-pentafluoroethyl-phenyl]-nicotinamide.
f) 2-Chloro-N-[3-(1-isopropyl-piperidin-4-ylmethoxy)-4-pentafluoroethyl-phenyl]-nicotinamide.
g) (S) 2-Chloro-N-[4-(oxiranylmethoxy)-3-pentafluoroethyl-phenyl]-nicotinamide.
h) 2-Chloro-N-[3-(2-pyrrolidin-1-yl-ethoxy)-4-trifluoromethyl-phenyl]-nicotinamide.
i) 2-Chloro-N-[3-(2-piperidin-1-yl-ethoxy)-4-pentafluoroethyl-phenyl]-nicotinamide.
j) (R) 2-Chloro-N-[3-(1-Boc-pyrrolidin-2-ylmethoxy)-4-pentafluoroethyl-phenyl]-nicotinamide.
k) (S) 2-Chloro-N-[3-(1-Boc-pyrrolidin-2-ylmethoxy)-4-pentafluoroethyl-phenyl]-nicotinamide.
l) (R) 2-Chloro-N-[3-(1-methyl-pyrrolidin-2-ylmethoxy)-5-trifluoromethyl-phenyl]-nicotinamide.
m) (S) 2-Chloro-N-[3-(1-methyl-pyrrolidin-2-ylmethoxy)-5-trifluoromethyl-phenyl]-nicotinamide.
n) (R) 2-Chloro-N-[4-(oxiranylmethoxy)-3-pentafluoroethyl-phenyl]-nicotinamide.
o) (R) Acetic acid 2-{5-[(2-chloro-pyridine-3-carbonyl)-amino]-2-pentafluoroethyl-phenoxy}-1-pyrrolidin-1-yl-ethyl ester.
p) 2-Chloro-N-[3-(4-methyl-piperazin-1-ylmethyl)-5-trifluoromethyl-phenyl]-nicotinamide.
q) 2-Chloro-N-[2-(4-methoxy-benzyl)-4,4-dimethyl-1-oxo-1,2,3,4-tetrahydro-isoquinolin-7-yl]-nicotinamide. M+H 450.2. Calc'd 449.
r) 2-Chloro-N-(4,4-dimethyl-1-oxo-1,2,3,4-tetrahydro-isoquinolin-7-yl)-nicotinamide. M+H 330.1, Calc'd 329.
s) 2-Chloro-N-[3-(4-Boc-piperazin-1-ylmethyl)-5-trifluoromethyl-phenyl]-nicotinamide.
t) 2-{3-[(2-Chloro-pyridine-3-carbonyl)-amino]-phenyl}-2-methyl-propionic acid methyl ester. M+H 405
u) N-{4-tert-Butyl-3-[2-(1-Boc-piperidin-4-yl)-ethyl]-phenyl}-2-chloro-nicotinamide. M+Na 524. Calc'd 501.1.
v) N-[3,3-Dimethyl-1,1-dioxo-2,3-dihydro-1H-benzo[d]isothiazol-6-yl]-2-chloro-nicotinamide.
w) N-[1,1,4,4-Tetramethyl-1,2,3,4-tetrahydro-naphth-6-yl]-2-chloro-nicotinamide.
x) 2-Chloro-N-[3,3-dimethyl-2,3-dihydro-benzofuran-6-yl]-2-chloro-nicotinamide.
y) 2-Chloro-N-[3-(1-Boc-piperidin-4-yloxy)-5-trifluoromethyl-phenyl]-nicotinamide.
z) 2-Chloro-N-[3-(1-methyl-piperidin-4-ylmethyl)-5-trifluoromethyl-phenyl]-nicotinamide.
aa) 2-Chloro-N-[3-(3-piperidin-1-yl-propyl)-5-trifluoromethyl-phenyl]-nicotinamide.
ab) N-[4-tert-Butyl-3-(4-pyrrolidin-1-yl-but-1-enyl)-phenyl]-2-chloro-nicotinamide.
ac) (R) 2-Chloro-N-[3-(1-Boc-pyrrolidin-2-ylmethoxy)-5-trifluoromethyl-phenyl]-nicotinamide.
ad) (S) 2-Chloro-N-[3-(1-Boc-pyrrolidin-2-ylmethoxy)-5-trifluoromethyl-phenyl]-nicotinamide.

Preparation VI—1-Boc-2-{3-[(2-fluoro-pyridine-3-carbonyl)-amino]-5-trifluoromethyl-phenoxymethyl}-pyrrolidine 1-Boc-2-{3-[(2-Fluoro-pyridine-3-carbonyl)-amino]-5-trifluoromethyl-phenoxymethyl}-pyrrolidine was prepared from 1-Boc-2-(3-amino-5-trifluoromethyl-phenoxymethyl)-pyrrolidine by a procedure similar to that described in the preparation of 1-Boc-4-{3-[(2-fluoro-pyridine-3-carbonyl)-amino]-5-trifluoromethyl-phenoxy}-piperidine.

Preparation VII—2-(3-nitro-5-trifluoromethyl-phenoxymethyl)-pyrrolidine

1-Boc-2-(3-nitro-5-trifluoromethyl-phenoxymethyl)-pyrrolidine (2.35 g) was dissolved in $CH_2Cl_2$ (60 ml) and TFA (20 ml) was added. After stirring for 1 h at RT, the mixture was concentrated in vacuo to yield 2-(3-nitro-5-trifluoromethyl-phenoxymethyl)-pyrrolidine as an oil that solidified upon standing. The material was used as is without further purification.

The following compounds were prepared similarly to the procedure outlined above:
a) (4-Aminomethyl-pyrimidin-2-yl)-(3-morpholin-4-yl-propyl)-amine.
b) (4-Aminomethyl-pyrimidin-2-yl)-[2-(1-methyl-pyrrolidin-2-yl)-ethyl]-amine.

Preparation VIII—1-methyl-2-(3-nitro-5-trifluoromethyl-phenoxymethyl)-pyrrolidine 2-(3-Nitro-5-trifluoromethyl-phenoxymethyl)-pyrrolidine (6 mmol) was dissolved in $CH_3CN$ (20 ml) and formaldehyde (2.4 ml, 37% aqueous) was added. $NaBH_3CN$ (607 mg) was added, an exotherm was observed. The pH is monitored every 15 min and adjusted to ~7 with AcOH. After 45 min, the mixture was concentrated in vacuo and the residue is dissolved in EtOAc, washed with 6N NaOH, 1N NaOH, and 2N HCl (3×). The acid washings were combined, adjusted to ~pH 10 with solid $Na_2CO_3$ and extracted with EtOAc (2×). The EtOAc fractions were combined, dried with $Na_2SO_4$, and purified with flash chromatography ($SiO_2$, 95:5:0.5 $CH_2Cl_2$:MeOH:$NH_4OH$) to afford 1-methyl-2-(3-nitro-5-trifluoromethyl-phenoxymethyl)-pyrrolidine.

The following compounds were prepared similarly to the procedure outlined above:
a) 2-(1-Methylpiperidin-4-yl)-ethanol.
b) 2-{3-[(2-Fluoro-pyridine-3-carbonyl)-amino]-5-trifluoromethyl-phenoxymethyl}-1-methylpyrrolidine.

Preparation IX—4-tert-butyl-3-nitro-phenylamine

A mixture of 1,3-dinitro-4-tert-butylbenzene (10.0 g) in $H_2O$ (56 ml) was heated to reflux. A mixture of $Na_2S$ (21.42 g) and sulfur (2.85 g) in $H_2O$ (34 ml) was added over 1 h via an addition funnel. The reaction maintained at reflux for 1.5 h then cooled to RT and extracted with EtOAc. The organic extracts were combined and washed with $H_2O$, brine, dried over $MgSO_4$ and concentrated in vacuo to afford 4-tert-butyl-3-nitro-phenylamine which was used as is without further purification.

Preparation X—N-(3-bromo-5-trifluoromethyl-phenyl)-acetamide

3-Bromo-5-(trifluoromethyl)phenylamine (5 g, Alfa-Aesar) was dissolved in AcOH (140 ml) and $Ac_2O$ (5.9 ml, Aldrich) was added. The reaction was stirred at RT overnight. The mixture was added slowly to $H_2O$ (~700 ml) forming a white precipitate. The solid was isolated by filtration, washed with $H_2O$ and dried under vacuum to yield N-(3-bromo-5-trifluoromethyl-phenyl)-acetamide.

Preparation XI—N-[3-(3-piperidin-1-yl-propyl)-5-trifluoromethyl-phenyl]-acetamide Allylpiperidine (1.96 g, Lancaster) was degassed under vacuum, dissolved in 0.5 M 9-BBN in THF (31.2 ml, Aldrich), and heated to reflux for 1 h, then cooled to RT. $PD(dppf)Cl_2/CH_2Cl_2$ was added to a degassed mixture of N-(3-bromo-5-trifluoromethyl-phenyl)-acetamide, $K_2CO_3$ (9.8 g) DMF (32.1 ml and $H_2O$ (3 ml). The allyl piperidine solution was added heated to 60° C. for 3 h. After cooling to RT and reheating at 60° C. for 6 h, the mixture was cooled to RT and poured into $H_2O$. The mixture was extracted with EtOAc (2×), and the EtOAc portion was washed with 2 N HCl (2×) and brine. The aqueous phases were combined and the pH was adjusted to ~11 with NaOH (15%) forming a cloudy suspension. The cloudy suspension was extracted with EtOAc (2×) and the EtOAc portion was dried with $Na_2SO_4$, filtered and concentrated in vacuo. The crude material was purified by flash chromatography ($SiO_2$, 95:5:0.5 $CH_2Cl_2$:MeOH:$NH_4OH$) to afford N-[3-(3-piperidin-1-yl-propyl)-5-trifluoromethyl-phenyl]-acetamide as a brown oil that solidified under vacuum.

The following compounds were prepared similarly to the procedure outlined above:
a) N-(3-Morpholin-4-ylpropyl-5-trifluoromethyl-phenyl)-acetamide from 4-allyl-morpholine.
b) N-(3-(1-methylpiperdin-4-ylmethyl-5-trifluoromethyl-phenyl)-acetamide from 1-Methyl-4-methylene-piperidine.

Preparation XII—3-(3-piperidin-1-yl-propyl)-5-trifluoromethyl-phenylamine

N-[3-(3-Piperidin-1-yl-propyl)-5-trifluoromethyl-phenyl]-acetamide (1.33 g) was dissolved in EtOH (40 ml) and 12 N HCl (40 ml) was added. After stirring overnight at 70° C. and RT, the mixture was concentrated in vacuo, affording 3-(3-piperidin-1-yl-propyl)-5-trifluoromethyl-phenylamine as a brown oil.

The following compounds were prepared similarly to the procedure outlined above:
a) 3,3-Dimethyl-6-nitro-2,3-dihydro-1H-indole. M+H 193.1; Calc'd 192.2.
b) 3-(1-Methyl-piperidin-4-ylmethyl)-5-trifluoromethyl-phenylamine.
c) 3-Morpholin-4-ylmethyl-5-trifluoromethyl-phenylamine.

Preparation XIII—3,3-Dimethyl-6-nitro-1-piperidin-4-ylmethyl-2,3-dihydro-1H-indole 3,3-Dimethyl-1-(1-Boc-piperidin-4-ylmethyl)-6-nitro-2,3-dihydro-1H-indole was dissolved in HCl/EtOAc and stirred for 2 h. The mixture was concentrated in vacuo and partitioned between 1,2-dichloroethane and 1N NaOH. The organic layer was removed, washed with brine, dried ($Na_2SO_4$) and filtered. The material was used without further purification.

Preparation XIV—N-[3-(3-morpholin-4-yl-propyl)-5-trifluoromethyl-phenyl]-acetamide N-[3-(3-Morpholin-4-yl-propyl)-5-trifluoromethyl-phenyl]-acetamide was prepared from allyl morpholine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XV—3-(3-morpholin-4-yl-propyl)-5-trifluoromethyl-phenylamine 3-(3-Morpholin-4-yl-propyl)-5-trifluoromethyl-phenylamine was prepared from N-[3-(3-morpholin-4-yl-propyl)-5-trifluoromethyl-phenyl]-acetamide similar to that described in the preparation of 3-(3-piperidin-1-yl-propyl)-5-trifluoromethyl-phenylamine.

Preparation XVI—1-methyl-4-methylene-piperidine $Ph_3PCH_3I$ (50 g, Aldrich) was suspended in $Et_2O$ (20 ml) and butyllithium (77.3 ml, 1.6 M in hexanes, Aldrich) was added dropwise. The reaction was stirred for 2 h at RT then 1-methylpiperidone (12.3 ml, Aldrich) was added slowly. The mixture was stirred at RT overnight. The solid was removed by filtration, the volume was reduced to ~400 ml and additional solid was removed by filtration. The $Et_2O$ was washed with $H_2O$ (2×) and 2N HCl (4×). The pH of the acid washings was adjusted to ~11 with 6 N NaOH, then they were extracted with $CH_2Cl_2$ (4×). The $CH_2Cl_2$ washings were dried over $Na_2SO_4$ and concentrated cold in vacuo to provide 1-methyl-4-methylene-piperidine which was used as is.

Preparation XVII—N-[3-(1-methylpiperidin-4-yl)-5-trifluoromethyl-phenyl]-acetamide N-[3-(1-Methylpiperidin-4-yl)-5-trifluoromethyl-phenyl]-acetamide was prepared from 1-methyl-4-methylene-piperidine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XVIII—3-(1-methylpiperidin-4-yl)-5-trifluoromethyl-phenylamine 3-(1-Methylpiperidin-4-yl)-5-trifluoromethyl-phenylamine was prepared from N-[3-(1-methylpiperidin-4-yl)-5-trifluoromethyl-phenyl]-acetamide similar to the procedure described in the preparation of 3-(3-piperidin-1-yl-propyl)-5-trifluoromethyl-phenylamine.

Preparation XIX—2-(1-methylpiperidin-4-yloxy)-4-pyridylcarbonitrile

4-Hydroxy-1-methylpiperidine (25.4 g) was dissolved in THF (50 ml) in a 100 mL r.b. flask. NaH/mineral oil mixture (9.58 g) was slowly added to the flask and stirred for 20 min. 2-Chloro-4-cyanopyridine was added to the mixture and stirred at RT until completion. Diluted mixture with EtOAc and added $H_2O$ to quench mixture, then transferred contents to a sep. funnel. The organic phase was collected while the aqueous phase was washed two times with EtOAc. The combined organics were dried over $Na_2SO_4$, filtered, then concentrated in vacuo. Then redissolved mixture in $CH_2Cl_2$, 10% HCl (300 ml) was added and the mixture was transferred to sep. funnel. The org. was extracted, while EtOAc along with 300 mL 5N NaOH was added to the sep. funnel. The organic phases were collected, dried over $Na_2SO_4$, filtered and concentrated in vacuo affording 2-(1-methylpiperidin-4-yloxy)-4-pyridylcarbonitrile as a brown solid. ESI (M+H)=218.

The following compounds were prepared similarly to the procedure outlined above:
a) 2-(1-methylpiperidin-4-ylmethoxy)-4-pyridylcarbonitrile. M+H 232.1. Calc'd 231.1.
b) 2-(1-Benzhydryl-azetidin-3-yloxy)-4-pyridylcarbonitrile. M+H 342.2. Calc'd 341.2.
c) 2-(1-methylpiperidin-4-ylethoxy)-4-pyridylcarbonitrile.
d) 2-(1-pyrrolidinylethoxy)-4-pyridylcarbonitrile.
e) 2-(1-methylpyrrolin-2-ylethoxy)-4-pyridylcarbonitrile.
f) 2-[2-(1-Boc-azetidin-3-yl)-ethoxy]-4-pyridylcarbonitrile.

Preparation XX—[2-(1-methylpiperidin-4-yloxy)-pyridin-4-yl]methylamine bis hydrochloride

[2-(1-Methylpiperidin-4-yloxy)-pyridin-4-yl] methylamine was diluted with $Et_2O$ (50 ml) and 1M HCl/$Et_2O$ (47 ml) was added. The vessel was swirled until precipitate formed.

Preparation XXI—2-(2-morpholin-4-yl-ethoxy)-4-pyridylcarbonitrile 2-(2-Morpholin-4-yl-ethoxy)-4-pyridylcarbonitrile was prepared from 2-chloro-4-cyanopyridine and 2-morpholin-4-yl-ethanol by a procedure similar to that described in the preparation of 2-(1-methylpiperidin-4-yloxy)-4-pyridylcarbonitrile. The hydrochloride salt was prepared similar to that described for [2-(1-methylpiperidin-4-yloxy)-pyridin-4-yl]methylamine bis hydrochloride.

Preparation XXII—2-morpholin-4-yl-propanol

LAH powder (1.6 g) was added to a flask while under $N_2$ atmosphere, immediately followed by THF (50 ml). The mixture was chilled to 0° C., methyl 2-morpholin-4-yl-propionate (5 g) was added dropwise to the reaction mixture and stirred at 0° C. After 1 h, the mixture was worked up by adding $H_2O$ (44 mL), 2N NaOH (44 mL), then $H_2O$ (44 mL, 3×). After 30 min of stirring, the mixture was filtered through Celite® and the organic portion was concentrated in vacuo providing 2-morpholin-4-yl-propanol as a colorless oil.

The following compounds were prepared similarly to the procedure outlined above:
a) (1-Methyl-piperidin-4-yl)-methanol. M+H 130.2. Calc'd 129.1.

Preparation XXIII—2-(2-morpholin-4-yl-propoxy)-4-pyridylcarbonitrile 2-(2-Morpholin-4-yl-propoxy)-4-pyridylcarbonitrile was prepared from 2-chloro-4-cyanopyridine and 2-morpholin-4-yl-propanol by a procedure similar to that described in the preparation of 2-(1-methylpiperidin-4-yloxy)-4-pyridylcarbonitrile.

Preparation XXIV—2-(1-Methyl-pyrrolidin-2-ylmethoxy)-4-pyridylcarbonitrile 2-(1-Methyl-pyrrolidin-2-ylmethoxy)-4-pyridylcarbonitrile was prepared from 2-chloro-4-cyanopyridine and 1-methyl-pyrrolidin-2-ylmethanol by a procedure similar to that described in the preparation of 2-(1-methylpiperidin-4-yloxy)-4-pyridylcarbonitrile. ESI MS: (M+H)=218.

Preparation XXV—2-(3-morpholin-4-yl-propylamino)-4-pyridylcarbonitrile

To a flask charged with 2-chloro-4-cyanopyridine (2.0 g), was added the aminopropyl morpholine (2.11 ml). The mixture was heated to 79° C. for 5 h and stirred. After 5 h the reaction was incomplete. The mixture was then heated at 60° C. overnight. The crude compound was purified on silica gel (1–5% MeOH/$CH_2Cl_2$ gradient). EST MS: (M+H)=247, (M−H)=245.

Preparation XXVI—5-Nitro-2-pentafluoroethylphenol

Combined 2-methoxy-4-nitro-1-pentafluoroethylbenzene (9.35 g) and pyridine hydrochloride in a round bottom flask and heated at 210° C. for 1 h then cooled to RT. The mixture was diluted with EtOAc and 2N HCl (>500 ml) until all residue dissolved. The organic layer was removed, washed with 2N HCl (2×) and concentrated in vacuo. The residue was dissolved in hexanes and $Et_2O$, washed with 2N HCl, then brine. Dried organic layer over $Na_2SO_4$, filtered, concentrated in vacuo and dried under high vacuum to provide 5-nitro-2-pentafluoromethylphenol.

Preparation XXVII—2-tert-Butyl-5-nitro-aniline

To $H_2SO_4$ (98%, 389 mL) in a 500 mL 3-neck flask was added 2-tert-butyl aniline (40.6 mL). The reaction was cooled to −10° C. and $KNO_3$ in 3.89 g aliquots was added every 6 min for a total of 10 aliquots. Tried to maintain temperature at −5° C. to −10° C. After final addition of $KNO_3$, stirred the reaction for five min then it was poured onto ice (50 g). The black mix was diluted with $H_2O$ and extracted with EtOAc. The aqueous layer was basified with solid NaOH slowly then extracted with EtOAc (2×). The combined organic layers were washed with 6N NaOH and then with a mix of 6N NaOH and brine, dried over $Na_2SO_4$, filtered and concentrated in vacuo to obtain crude 2-tert-butyl-5-nitro-aniline as a dark red-black oil which solidified when standing at RT. The crude material was triturated with about 130 mL hexanes. After decanting the hexanes, the material was dried to obtain a dark-red black solid.

Preparation XXVIII—2-tert-Butyl-5-nitrophenol

In a 250 ml round bottom flask, 20 mL concentrated H2SO4 was added to 2-tert-butyl-5-nitro-aniline (7.15 g) by adding 5 mL aliquots of acid and sonicating with occasional heating until all of the starting aniline went into solution. $H_2O$ (84 ml) was added with stirring, then the reaction was cooled to 0° C. forming a yellow-orange suspension. A solution of $NaNO_2$ (2.792 g) in $H_2O$ (11.2 mL) was added dropwise to the suspension and stirred for 5 min. Excess NaNO$_2$ was neutralized with urea, then the cloudy solution was transferred to 500 ml 3-necked round bottom flask then added 17 mL of 1:2 H$_2$SO$_4$:H$_2$O solution, and heated at reflux. Two additional 5 mL aliquots of 1:2 H$_2$SO$_4$:H$_2$O solution, a 7 mL aliquot of 1:2 H$_2$SO$_4$:H$_2$O solution and another 10 mL of 1:2 H$_2$SO$_4$:H$_2$O were added while heating at reflux. The mixture was cooled to RT forming a black layer floating on top of the aqueous layer. The black layer was diluted with EtOAc (300 mL) and separated. The organic layer was washed with H$_2$O then brine, dried over Na$_2$SO$_4$ and concentrated in vacuo. Crude oil was purified on silica gel column with 8% EtOAc/Hexanes. Upon drying under vacuum, the 2-tert-butyl-5-nitrophenol was isolated as a brown solid.

Preparation XXIX—1-methylpiperidine-4-carboxylic acid ethyl ester

Piperidine-4-carboxylic acid ethyl ester (78 g) was dissolved in MeOH (1.2 L) at RT then formaldehyde (37%, 90 ml) and acetic acid (42 ml) were added and stirred for 2 h. The mixture was cooled to 0° C., NaCNBH$_3$ (70 g) was added, and the mix was stirred for 20 min at 0° C., then overnight at RT. The mixture was cooled to 0° C. then quenched with 6N NaOH. The mixture was concentrated in vacuo to an aqueous layer, which was extracted with EtOAc (4×), brine-washed, dried over Na$_2$SO$_4$, and concentrated in vacuo to provide 1-methylpiperidine-4-carboxylic acid ethyl ester.

The following compounds were prepared similarly to the procedure outlined above:
a) (1-Methyl-piperidin-4-yl)-methanol. M+H 130.2. Calc'd 129.1.

Preparation XXX—N-[4-tert-Butyl-3-(1-methyl-piperidin-4-ylmethoxy)-phenyl]-2-chloro-nicotinamide N-[4-tert-Butyl-3-(1-methyl-piperidin-4-ylmethoxy)-phenyl]-2-chloro-nicotinamide was prepared from 4-tert-butyl-3-(1-methyl-piperidin-4-ylmethoxy)-phenylamine by a procedure similar to that described in the preparation of 1-Boc-4-{3-[(2-chloro-pyridine-3-carbonyl)-amino]-5-trifluoromethyl-phenoxy}-piperidine.

Preparation XXXI—1-[2-(2-tert-Butyl-5-nitro-phenoxy)-ethyl]-piperidine

To 2-tert-butyl-5-nitrophenol (1.01 g) and K$_2$CO$_3$ (1.72 g) was added acetone (35 ml) and H$_2$O (10.5 mL), then 1-(2-chloroethyl)piperidine HCl (1.909 g) and TBAI (153 mg). The mixture was stirred at reflux overnight. Additional K$_2$CO$_3$ (850 mg) and 1-(2-chloroethyl)-piperidine HCl (950 mg) were added and the mixture was heated at reflux for 6 h. The mixture was concentrated in vacuo to an aqueous layer which was acidified with 2N HCl and extracted with EtOAc. The aqueous layer was basified with 6N NaOH and washed with CH$_2$Cl$_2$ (3×). The combined organic layers were washed with brine/1N NaOH and dried over Na$_2$SO$_4$. Washed the EtOAc layer with 2N NaOH/brine and dried over Na$_2$SO$_4$. The crude material was purified by silica gel column chromatography with 15% EtOAc/Hexanes to yield 1-[2-(2-tert-butyl-5-nitro-phenoxy)-ethyl]-piperidine as a light tan solid. (M+1)=307.3.

Preparation XXXII—1-Boc-Piperidine-4-carboxylic acid ethyl ester

To a stirred solution of piperidine-4-carboxylic acid ethyl ester (23.5 g) in EtOAc (118 ml) at 0° C. was added dropwise Boc$_2$O in EtOAc (60 ml). The reaction was warmed to RT and stirred overnight. Washed reaction with H$_2$O, 0.1N HCl, H$_2$O, NaHCO$_3$ and brine. The organic layer was dried over Na$_2$SO$_4$, filtered and concentrated in vacuo. The liquid was dried under vacuum to provide 1-Boc-piperidine-4-carboxylic acid ethyl ester.

The following compounds were prepared similarly to the procedure outlined above:
a) N-Boc-(2-chloropyrimidin-4-yl)-methylamine.
b) 1-(2-tert-Butyl-4-nitrophenyl)-4-Boc-piperazine.
c) 1-Boc-azetidine-3-carboxylic acid
d) 1-Boc-4-Hydroxymethyl-piperidine using TEA.

Preparation XXXIII—1-Boc-4-hydroxymethyl-piperidine

1-Boc-4-Hydroxymethyl-piperidine was prepared from 1-Boc-piperidine-4-carboxylic acid ethyl ester by a procedure similar to that described in the preparation of 2-morpholin-4-yl-propanol.

Preparation XXXIV—1-Boc-4-Methylsulfonyloxymethyl-piperidine

Dissolved 1-Boc-4-hydroxymethyl-piperidine in anhydrous CH$_2$Cl$_2$ (50 ml) and TEA (4.5 ml) and cooled to 0° C. Mesyl chloride (840 µl) was added and the mixture was stirred for 15 min then at RT for 45 min. The mixture was washed with brine/1N HCl and then brine, dried over Na$_2$SO$_4$, concentrated in vacuo and dried under high vacuum to provide 1-Boc-4-methylsulfonyloxymethyl-piperidine as a yellow orange thick oil.

The following compounds were prepared similarly to the procedure outlined above:
a) 1-Boc-3-methylsulfonyloxymethyl-azetidine.

Preparation XXXV—1-Boc-4-(3-nitro-6-pentafluoroethyl-phenoxymethyl)-piperidine

To a slurry of 60% NaH suspension in DMF (30 mL) at RT added a solution of 5-nitro-2-pentafluoroethyl-phenol (3.6 g) in 5 mL DMF. The dark red mixture was stirred at RT for 10 min then added a solution of 1-Boc-4-methylsulfonyloxymethyl-piperidine (3.1 g) in 5 mL DMF. The reaction was stirred at 60° C. and 95° C. After 1 h, added 2.94 g K$_2$CO$_3$ and stirred overnight at 105° C. After cooling to RT, the reaction was diluted with hexanes and 1N NaOH. Separated layers, and washed organic layer with 1N NaOH and with brine, dried over Na$_2$SO$_4$, filtered and concentrated in vacuo. Purification with silica gel column chromatography with 8% EtOAc/Hexanes yielded 1-Boc-4-(3-nitro-6-pentafluoroethyl-phenoxymethyl)-piperidine as a light yellow thick oil.

Preparation XXXVI—4-(3-nitro-6-pentafluoroethyl-phenoxymethyl)-piperidine 4-(3-Nitro-6-pentafluoroethyl-phenoxymethyl)-piperidine was prepared from 1-Boc-4-(3-nitro-6-pentafluoroethyl-phenoxymethyl)-piperidine by a procedure similar to that described in the preparation of 2-(3-nitro-5-trifluoromethyl-phenoxymethyl)-pyrrolidine.

Preparation XXXVII—1-methyl-4-(3-nitro-6-pentafluoroethyl-phenoxymethyl)-piperidine 4-(3-Nitro-6-pentafluoroethyl-phenoxymethyl)-piperidine (316.5 mg) was dissolved in 2.7 mL acetonitrile, then added 37% formaldehyde/H$_2$O (360 ul) and then NaBH$_3$CN (90 mg). Upon addition of NaCNBH$_3$ the reaction exothermed slightly. The reaction was stirred at RT and pH was maintained at ~7 by addition of drops of glacial acetic acid. After about 1 h, the mixture was concentrated in vacuo, treated with 8 mL 2N KOH and extracted two times with 10 mL Et$_2$O. The organic layers were washed with 0.5N KOH and then the combined organic layers were extracted two times with 1N HCl. The aqueous layer was basified with solid KOH and extracted two times with Et$_2$O. This organic layer was then washed with brine/1N NaOH, dried over Na$_2$SO$_4$, filtered, concentrated in vacuo and dried under high vacuum to give pure compound.

Preparation XXXVIII—1-Isopropyl-4-(5-nitro-2-pentafluoroethyl-phenoxymethyl)-piperidine Dissolved 4-(5-nitro-2-pentafluoroethyl-phenoxymethyl)-piperidine (646 mg) in 1,2-dichloroethane (6.4 ml), then added acetone (136 ul), NaBH(OAc)$_3$ (541 mg) and finally acetic acid (105 ul). Stirred the cloudy yellow solution under N$^2$ at RT overnight. Added another 130 uL acetone and stirred at RT over weekend. Quenched the reaction with 30 mL N NaOH/H$_2$O and stirred 10 min. Extracted with Et$_2$O and the organic layer was brine-washed, dried over Na$_2$SO$_4$, filtered and concentrated in vacuo. Dried under high vacuum for several h to obtain 1-isopropyl-4-(5-nitro-2-pentafluoroethyl-phenoxymethyl)-piperidine as a yellow orange solid.

The following compounds were prepared similarly to the procedure outlined above:
a) 3,3-Dimethyl-1-(1-methyl-piperidin-4-yl)-6-nitro-2,3-dihydro-1H-indole was prepared using 1-methyl-piperidin-4-one. M+H 290; Calc'd 289.4.
b) 3,3-Dimethyl-1-(1-Boc-piperidin-4-ylmethyl)-6-nitro-2,3-dihydro-1H-indole using 1-Boc-4-formyl-piperidine.

Preparation XXXIX—3,3-Dimethyl-1-(1-methyl-piperidin-4-ylmethyl)-6-nitro-2,3-dihydro-1H-indole 3,3-Dimethyl-1-piperidin-4-ylmethyl-6-nitro-2,3-dihydro-1H-indole was treated with an excess of formaldehyde and NaBH(OAc)$_3$ and stirred overnight at RT. The reaction was quenched with MeOH and concentrated in vacuo. The residue was partitioned between EtOAc and 1N NaOH. The organic layer was removed, washed with brine, dried (Na$_2$SO$_4$), filtered and concentrated to provide the compound.

Preparation XL—(S) 2-(5-Nitro-2-pentafluoroethyl-phenoxymethyl)-oxirane

Combined 5-nitro-2-pentafluoromethylphenol (2.69 g), DMF (25 ml) K$_2$CO$_3$ (3.03 g) and (S) toluene-4-sulfonic acid oxiranyl-methyl ester (2.27 g) and stirred the mixture at 90° C. After about 4 hours, the mix was cooled, diluted with EtOAc, washed with H$_2$O, 1N NaOH (2x), 1N HCl and then with brine. Dried over Na$_2$SO$_4$, filtered and concentrated in vacuo. Purified the crude on silica gel column with 5% EtOAc/hexane and drying under high vacuum provided the (S)-2-(5-nitro-2-pentafluoroethyl-phenoxymethyl)-oxirane.

The following compounds were prepared similarly to the procedure outlined above:
a) (R)-2-(5-Nitro-2-pentafluoroethyl-phenoxymethyl)-oxirane.

Preparation XLI—(S) 2-Chloro-N-[3-(2-hydroxy-3-pyrrolidin-1-yl-propoxy)-4-pentafluoroethyl-phenyl]-nicotinamide (S) 2-Chloro-N-[4-(2-oxiranylmethoxy-)-3-pentafluoroethyl-phenyl]-nicotinamide (1.11 g) in a sealed tube and added pyrrolidine (285 µl). Stirred after sealing tube at 60° C. After 12 h, the mix was concentrated in vacuo and purified on a silica gel column (5:95:0.5 MeOH:CH$_2$Cl$_2$:NH$_4$OH—8:92:1, MeOH:CH$_2$Cl$_2$:NH$_4$OH). Concentrated in vacuo and dried under high vacuum to obtain pure compound.

The following compounds were prepared similarly to the procedure outlined above:
a) (R) 1-(5-Nitro-2-pentafluoroethyl-phenoxy)-3-pyrrolidin-1-yl-propan-2-ol.

Preparation XLII—5-nitro-2-trifluoromethylanisole

Cooled 140 mL pyridine in a large sealable vessel to −40° C. Bubbled in trifluoromethyl iodide from a gas cylinder which had been kept in freezer overnight. After adding ICF$_3$ for 20 min, added 2-iodo-5-nitroanisole (24.63 g) and copper powder (67.25 g). Sealed vessel and stirred vigorously for 22 h at 140° C. After cooling to −50° C., carefully unsealed reaction vessel and poured onto ice and Et$_2$O. Repeatedly washed with Et$_2$O and H$_2$O. Allowed the ice—Et$_2$O mixture to warm to RT. Separated layers, washed organic layer with 1N HCl (3x), then brine, dried over Na$_2$SO$_4$, filtered and concentrated in vacuo. Eluted material through silica gel plug (4.5:1 Hex:CH$_2$Cl$_2$) to provide 5-nitro-2-trifluoromethylanisole.

Preparation XLIII—1-[2-(5-nitro-2-trifluoromethyl-phenoxy)ethyl]pyrrolidine

1-[2-(5-Nitro-2-trifluoromethylphenoxy)ethyl]-pyrrolidine was prepared from 5-nitro-2-trifluoromethyl-phenol and 1-(2-chloroethyl)pyrrolidine by a procedure similar to that described for 1-[2-(2-tert-butyl-5-nitro-phenoxy)-ethyl]-piperidine.

Preparation XLIV—1-[2-(5-Nitro-2-pentafluoroethyl-phenoxy)-ethyl]-piperidine

1-[2-(5-Nitro-2-pentafluoroethyl-phenoxy)-ethyl]-piperidine was prepared from 5-nitro-2-pentafluoroethylphenol and 1-(2-chloroethyl)piperidine by a procedure similar to that described in the preparation of 1-[2-(2-tert-butyl-5-nitro-phenoxy)-ethyl]-piperidine.

Preparation XLV—3-(1-Boc-pyrrolidin-2-ylmethoxy)-4-pentafluoroethyl-phenylamine 3-(2-Pyrrolidin-1-yl-methoxy)-4-trifluoromethyl-phenylamine was prepared from 1-[2-(5-nitro-2-trifluoromethylphenoxy)methyl]-pyrrolidine by a procedure similar to that described in the preparation of 1-Boc-4-(3-amino-5-trifluoromethyl-phenoxy)-piperidine.

Preparation XLVI—2-Chloro-N-[3-(2-pyrrolidin-1-yl-ethoxy)-4-trifluoromethyl-phenyl]-nicotinamide 2-Chloro-N-[3-(2-pyrrolidin-1-yl-ethoxy)-4-trifluoromethyl-phenyl]-nicotinamide was prepared from 3-(2-pyrrolidin-1-yl-ethoxy)-4-trifluoromethyl-phenylamine and 2-chloropyridine-3-carbonyl chloride by a procedure similar to that described in the preparation of 1-Boc-4-{3-[(2-chloro-pyridine-3-carbonyl)-amino]-5-trifluoromethyl-phenoxy}-piperidine.

Preparation XLVII—(R) Acetic acid 2-(5-nitro-2-pentafluoroethyl-phenoxy)-1-pyrrolidin-1-ylmethyl-ethyl ester Dissolved 1-(5-nitro-2-pentafluoroethyl-phenoxy)-3-pyrrolidin-1-yl-propan-2-ol (3.5 g) in CH$_2$Cl$_2$ (15 ml), added TEA (2.55 ml) and cooled to 0° C. Acetyl chloride (781.3 µl) was added dropwise, forming a suspension. The mixture was warmed to RT and stirred for 1.5 h. Additional acetyl chloride (200 µl) was added and the mix was stirred for another h. The mixture was diluted with CH$_2$Cl$_2$ and washed with sat. NaHCO$_3$. The organic layer was removed, washed with brine and back extracted with CH$_2$Cl$_2$. Dried the combined organic layers over Na$_2$SO$_4$, filtered and concentrated in vacuo. The residue was purified over silica gel column (5:94.5:0.5 MeOH:CH$_2$Cl$_2$:NH$_4$OH) to provide acetic acid 2-(5-nitro-2-pentafluoroethyl-phenoxy)-1-pyrrolidin-1-ylmethyl-ethyl ester as a yellow brown oil.

The following compounds were prepared similarly to the procedure outlined above:
a) (R) Acetic acid 2-(5-amino-2-pentafluoroethyl-phenoxy)-1-pyrrolidin-1-yl-methyl-ethyl ester.
b) 1-(2,2-Dimethyl-6-nitro-2,3-dihydro-benzo[1,4]oxazin-4-yl)-ethanone. M—NO$_2$ 206.4; Calc'd 250.1.

Preparation XLVIII—(R) 2-Chloro-N-[3-(2-hydroxy-2-pyrrolidin-1-yl-propoxy)-4-pentafluoroethyl-phenyl]-nicotinamide (R) Acetic acid 2-{5-[(2-chloro-pyridine-3-carbonyl)-amino]-2-pentafluoroethyl-phenoxy}-1-pyrrolidin-1-yl-ethyl ester (408 mg) was dissolved in MeOH (15 ml) and NH$_4$OH (6 ml) was added and the mixture was stirred at RT for 6 h. The reaction was concentrated in vacuo and dried under high vacuum. The residue was purified over silica gel column (8:92:0.6 MeOH:CH$_2$Cl$_2$:NH$_4$OH). The purified fractions were concentrated in vacuo and dried again to provide (R)-2-chloro-N-[3-(2-hydroxy-2-pyrrolidin-1-yl-ethoxy)-4-pentafluoroethyl-phenyl]-nicotinamide as a white foam.

Preparation XLIX—2-Dimethylamino-1-(3,3-dimethyl-6-nitro-2,3-dihydro-indol-1-yl)-ethanone 3,3-Dimethyl-6-nitro-2,3-dihydro-1H-indole (5 g) was dissolved in DMF (100 ml) and HOAt (3.89 g) dimethylamino-acetic acid (5.83 g) and EDC (3.89 g) were added. The reaction was stirred overnight. The mixture was diluted with $CH_2Cl_2$ (1 L) and washed with sat'd $NaHCO_3$ (3×200 ml). The organic layer was washed with brine, dried over $Na_2SO_4$, filtered and concentrated in vacuo. The residue was purified by flash chromatography ($SiO_2$, EtOAc to 5% MeOH/EtOAc) to afford the title compound.

The following compounds were prepared similarly to the procedure outlined above:
a) 1-(3,3-Dimethyl-6-nitro-2,3-dihydro-indol-1-yl)-2-(N-Boc-amino)-ethanone.

Preparation L—1-(6-Amino-3,3-dimethyl-2,3-dihydro-indol-1-yl)-2-(N-Boc-amino)-ethanone 1-(3,3-Dimethyl-6-nitro-2,3-dihydro-indol-1-yl)-2-(N-Boc-amino)-ethanone (3.9 g) was dissolved in EtOH (30 ml) and Fe powder (3.1 g) $NH_4Cl$ (299 mg) and $H_2O$ (5 ml) were added. The reaction was stirred at 80° C. overnight. The reaction was filtered through Celite® and evaporated off the MeOH. The residue was partitioned between $CH_2Cl_2$ and sat'd $NaHCO_3$. The organic layer was removed, washed with brine, dried over $Na_2SO_4$, filtered and concentrated in vacuo. The residue was purified by flash chromatography ($SiO_2$, 25% EtOAc/hexane). The purified fractions were concentrated in vacuo to afford the compound as a white powder.

The following compounds were prepared similarly to the procedure outlined above:
a) 1-(6-Amino-3,3-dimethyl-2,3-dihydro-indol-1-yl)-2-dimethylamino-ethanone.
b) 3,3-Dimethyl-1-(1-methyl-piperidin-4-ylmethyl)-2,3-dihydro-1H-indol-6-ylamine.
c) 3-(4-Methyl-piperazin-1-ylmethyl)-4-pentafluoroethyl-phenylamine. M+H 324.2. Calc'd 323.
d) 3,3-Dimethyl-1-(1-methyl-piperidin-4-yl)-2,3-dihydro-1H-indol-6-ylamine. M+H 259.6; Calc'd 259.3.
e) 3,3-Dimethyl-1,1-dioxo-2,3-dihydro-1H-1λ6-benzo[d]isothiazol-6-ylamine
f) 1,1,4,4-Tetramethyl-1,2,3,4-tetrahydro-naphth-6-ylamine.
g) 3,3-Dimethyl-1-(1-Boc-piperidin-4-ylmethyl)-2,3-dihydro-1H-indol-6-ylamine.

Preparation LI—2-Boc-4,4-dimethyl-7-nitro-1,2,3,4-tetrahydro-isoquinoline 4,4-Dimethyl-7-nitro-1,2,3,4-tetrahydro-isoquinoline (150 mg) was dissolved with $CH_2Cl_2$ (3 ml) DIEA (100 ul) DMAP (208 mg and $Boc_2O$ (204 mg) and the mixture was stirred for 6 h at RT. The reaction was diluted with $CH_2Cl_2$, washed with sat'd $NaHCO_3$ and dried over $MgSO_4$, filtered and concentrated to provide the compound which was used without further purification.

The following compounds were prepared similarly to the procedure outlined above substituting $Ac_2O$:
a) 1-(4,4-Dimethyl-7-nitro-3,4-dihydro-1H-isoquinolin-2-yl)-ethanone. M+H 249.3.

Preparation LII—2-Bromo-N-(4-methoxy-benzyl)-5-nitro-benzamide

PMB-amine (5.35 ml) in $CH_2Cl_2$ (130 ml) was slowly added to 2-bromo-5-nitro-benzoyl chloride (10.55 g) and $NaHCO_3$ (9.6 g) and the mixture was stirred at RT for 1 h. The mixture was diluted with $CH_2Cl_2$ (1 L), filtered, washed with dilute HCl, dried, filtered again, concentrated and dried under vacuum to provide the compound as a white solid. M+H 367. Calc'd 366.

Preparation LIII—2-Bromo-N-(4-methoxy-benzyl)-N-(2-methyl-allyl)-5-nitro-benzamide To a suspension of NaH (1.22 g) in DMF (130 ml) was added 2-bomo-N-(4-methoxy-benzyl)-5-nitro-benzamide (6.2 g) in DMF (60 ml) at −78 C. The mixture was warmed to 0° C., 3-bromo-2-methyl-propene (4.57 g) was added and the mixture was stirred for 2 h at 0° C. The reaction was poured into ice water, extracted with EtOAc (2×400 ml), dried over $MgSO_4$, filtered and concentrated to a DMF solution which was used without further purification.

Preparation LIV—of 2-(4-Methoxy-benzyl)-4,4-dimethyl-7-nitro-3,4-dihydro-2H-isoquinolin-1-one 2-Bromo-N-(4-methoxy-benzyl)-N-(2-methyl-allyl)-5-nitro-benzamide (23.4 mmol) was dissolved in DMF (150 ml) and $Et_4NCl$ (4.25 g), $HCO_2Na$ (1.75 g) and NaOAc (4.99 g) were added. $N_2$ was bubbled through the solution for 10 min, then $Pd(OAc)_2$ (490 mg) was added and the mixture was stirred overnight at 70° C. The mixture was extracted with EtOAc, washed with sat'd $NH_4Cl$, dried over $MgSO_4$, filtered and concentrated until the compound precipitated as a white solid.

The following compounds were prepared similarly to the procedure outlined above:
a) 3,3-Dimethyl-6-nitro-2,3-dihydro-benzofuran was prepared from 1-bromo-2-(2-methyl-allyloxy)-4-nitro-benzene.
b) 3,9,9-Trimethyl-6-nitro-4,9-dihydro-3H-3-aza-fluorene was prepared from 4-[1-(2-bromo-4-nitro-phenyl)-1-methyl-ethyl]-1-methyl-1,2,3,6-tetrahydro-pyridine.

Preparation LV—4,4-Dimethyl-7-nitro-3,4-dihydro-2H-isoquinolin-1-one 2-(4-Methoxy-benzyl)-4,4-dimethyl-7-nitro-3,4-dihydro-2H-isoquinolin-1-one (2.0 g) was dissolved in $CH_3CN$ (100 ml) and $H_2O$ (50 ml) and cooled to 0° C. CAN (9.64 g) was added and the reaction was stirred at 0° C. for 30 min, then warmed to RT and stirred for 6 h. The mixture was extracted with $CH_2Cl_2$ (2×300 ml) washed with sat'd $NH_4Cl$, dried over $MgSO_4$, filtered and concentrated. The crude material was recrystallized in $CH_2Cl_2$/EtOAc (1:1) to give 4,4-dimethyl-7-nitro-3,4-dihydro-2H-isoquinolin-1-one as a white solid.

Preparation LVI—4,4-Dimethyl-7-nitro-1,2,3,4-tetrahydro-isoquinoline 4,4-Dimethyl-7-nitro-3,4-dihydro-2H-isoquinolin-1-one (230 mg) was dissolved in THF (10 ml) and $BH_3Me_2S$ (400 ul) was added and the reaction was stirred overnight at RT. The reaction was quenched with MeOH (10 ml) and NaOH (200 mg) and heating at reflux for 20 min. The mixture was extracted with EtOAc, washed with sat'd $NH_4Cl$, extracted with 10% HCl (20 ml). The acidic solution was treated with 5N NaOH (15 ml), extracted with EtOAc (30 ml) dried, filtered and evaporated to give the compound as a yellow solid. M+H 207.2, Calc'd 206.

The following compounds were prepared similarly to the procedure outlined above:
a) 4-Boc-2,2-dimethyl-6-nitro-3,4-dihydro-2H-benzo[1,4]oxazine.

Preparation LVII—2-Bromomethyl-4-nitro-1-pentafluoroethyl-benzene

2-Methyl-4-nitro-1-pentafluoroethyl-benzene (2.55 g) was dissolved in $CCl_4$ (30 ml) and AIBN (164 mg) and NBS (1.96 g) were added. The reaction was heated to reflux and stirred for 24 h. The mix was diluted with $CH_2Cl_2$, washed with sat'd $NaHCO_3$, dried over $MgSO_4$ and concentrated to give the compound as an oil which was used without further purification.

Preparation LVIII—1-Methyl-4-(5-nitro-2-pentafluoroethyl-benzyl)-piperazine

2-Bromomethyl-4-nitro-1-pentafluoroethyl-benzene (2.6 g) was added to N-methylpiperazine (5 ml) and stirred at RT for 3 h. The mixture was filtered and the filtrate was treated with 1-chlorobutane, extracted with 2N HCl (100 ml). The acidic solution was treated with 5N NaOH (6 ml) then extracted with EtOAc. The organic layer was removed, dried over $MgSO_4$ and concentrated to give the compound as an oil.

The following compounds were prepared similarly to the procedure outlined above:
a) 4-(5-Nitro-2-pentafluoroethyl-benzyl)-morpholine.

Preparation LIX—1-Boc-4-(5-nitro-2-pentafluoroethyl-benzyl)-piperazine.

2-Bromomethyl-4-nitro-1-pentafluoroethyl-benzene (2.5 g) was dissolved in $CH_2Cl_2$ and added to N-Boc-piperazine (2.5 g) and $NaHCO_3$ (1 g) and stirred at RT overnight. The mixture was diluted with $CH_2Cl_2$ (100 ml), washed with sat'd $NH_4Cl$, dried over $MgSO_4$, filtered and concentrated. The residue was purified by silica gel chromatography (hexane, $CH_2Cl_2$:hexane 2:8) to give the compound as an yellow solid.

Preparation LX—(4-Boc-piperazin-1-yl)-(3-nitro-5-trifluoromethyl-phenyl)-methanone A mixture of 3-nitro-5-trifluoromethyl-benzoic acid (4.13 g), 4-Boc-piperazine (2.97 g), EDC (3.88 g), HOBt (2.74 g), DIEA (3.33 ml) in $CH_2Cl_2$ (120 ml) was stirred at RT for 3 h. The mixture was diluted with $CH_2Cl_2$ (100 ml), washed with sat'd $NH_4Cl$, dried over $MgSO_4$, filtered and concentrated. The residue was purified by silica gel chromatography (hexane, $CH_2Cl_2$:hexane 1:2) to give the compound as a white solid.

Preparation LXI—1-Boc-4-(3-nitro-5-trifluoromethyl-benzyl)-piperazine (4-Boc-piperazin-1-yl)-(3-nitro-5-trifluoromethyl-phenyl)-methanone (403 mg) was dissolved in THF (6 ml) and $BH_3Me_2S$ (300 μl) was added and the reaction was stirred for 3 h at 60° C. and 2 h at RT. The reaction was quenched with MeOH (5 ml) and NaOH (100 mg) and stirred at RT for 1 h. The mixture was concentrated and dissolved in $CH_2Cl_2$, washed with sated $NH_4Cl/NaHCO_3$, dried ($MgSO_4$), filtered and evaporated to give the compound as an oil. M+H 390.3.

Preparation LXII—2-Ethyl-4-aminomethyl pyridine

To a solution of 2-ethyl-4-thiopyridylamide (10 g) in MeOH (250 ml) was added Raney 2800 Nickel (5 g, Aldrich) in one portion. The mixture was stirred at RT for 2 days then at 60° C. for 16 h. The mixture was filtered, concentrated to provide the desired compound.

Preparation LXIII—N-Boc-[2-(4-morpholin-4-yl-butyl)-pyrimidin-4-ylmethyl]-amine

N-Boc-(2-chloropyrimidine)-methylamine (663 mg) and 4-(aminopropyl)morpholine (786 mg) were dissolved in MeOH and concentrated in vacuo. The residue was heated at 100° C. for 15 min, forming a solid which was dissolved in $CH_2Cl_2$/MeOH then concentrated again and heated 15 min more. Concentrated in vacuo and dried under high vacuum. Triturated with a small amount of IpOH and allowed to settle over a weekend. Filtered, rinsing with a small amount of IpOH to provide the compound as a white solid.

The following compounds were prepared similarly to the procedure outlined above:
a) (4-Bocaminomethyl-pyrimidin-2-yl)-[2-(1-methyl-pyrrolidin-2-yl)-ethyl]-amine. M+H 336.5; Calc'd 335.45.

Preparation LXIV—2-fluoronicotinic acid

In a flame dried 3-necked round bottom flask equipped with a dropping funnel and thermometer, under $N_2$, THF (250 ml) was added via cannula. LDA (2M in cyclohexane, 54 ml) was added via cannula as the flask was cooled to −78° C. At −78° C., 2-fluoropyridine (8.87 ml) was added dropwise over 10 min. The reaction was stirred for 3 h. Condensation was blown off (with $N_2$) a few cubes of solid $CO_2$ and they were added to the mixture. The mixture was warmed to RT once the solution turned yellow, and it was stirred overnight. The reaction was cooled to 0° C. and the pH was adjusted to ~2.5 with 5N HCl. The mixture was concentrated in vacuo and extracted with EtOAc. The EtOAc layer was washed with brine, dried over $MgSO_4$, filtered and concentrated to dryness. The resulting solid was slurried in EtOAc (100 ml), filtered, washed with cold EtOAc and dried at 50° C. for 1 h to afford 2-fluoronictinic acid. M+H 142.1; Calc'd 141.0.

Preparation LXV—4-cyano-2-methoxypyridine

Under a stream of $N_2$ and with cooling, Na metal (2.7 g) was added to MeOH (36 ml) with a considerable exotherm. After the Na is dissolved, a solution of 2-chloro-4-cyanopyridine (15 g) in dioxane:MeOH (1:1, 110 ml) was added via dropping funnel over a 10 min period. The reaction was heated to reflux for 3.5 h then cooled at ~10° C. overnight. Solid was filtered off and the solid was washed with MeOH. The filtrate was concentrated to ~60 ml and $H_2O$ (60 ml) was added to redissolve a precipitate. Upon further concentration, a precipitate formed which was washed with $H_2O$. Further concentration produced additional solids. The solids were combined and dried in vacuo overnight at 35° C. to provide 4-cyano-2-methoxypyridine which was used as is.

Preparation LXVI—(2-methoxypyridin-4-yl)methylamine

4-Cyano-2-methoxypyridine (1.7 g) was dissolved in MeOH (50 ml) and conc. HCl (4.96 ml) was added. Pd/C (10%) was added and $H_2$ was added and let stand overnight. The solids were filtered through Celite® and the cake was washed with MeOH (~250 ml). Concentration in vacuo produced an oil which was dissolved in MeOH (~20 ml). $Et_2O$ (200 ml) was added and stirred for 1 h. The resulting precipitate was filtered and washed with $Et_2O$ to afford (2-methoxypyridin-4-yl)methylamine (hydrochloride salt) as an off-white solid.

Preparation LXVII—2-(4-Amino-phenyl)-2-methyl-propionic acid methyl ester

2-Methyl-2-(4-nitro-phenyl)-propionic acid methyl ester (2.1 g) was dissolved in THF (70 ml) and acetic acid (5 ml) and Zn (10 g) were added. The mixture was stirred for 1 h and filtered through Celite®. The filtrate was rinsed with EtOAc and the organics were evaporated to a residue which was purified on silica gel chromatography (40% EtOAc/hexanes) to provide the desired compound as a yellow oil. M+H 194.

Preparation LXVIII—1-(2-tert-Butyl-phenyl)-4-methyl-piperazine 2-tert-Butyl-phenylamine and bis-(2-chloro-ethyl)-methylamine were mixed together with $K_2CO_3$ (25 g), NaI (10 g) and diglyme (250 mL) and heated at 170° C. for 8 h. Cooled and filtered solid and evaporated solvent. Diluted with EtOAc, washed with $NaHCO_3$ solution, extracted twice more with EtOAc, washed with brine, dried over $Na_2SO_4$ and evaporated to give the compound as a dark solid.

The following compounds were prepared similarly to the procedure outlined above:
a) 1-Bromo-2-(2-methyl-allyloxy)-4-nitro-benzene was prepared from methallyl bromide.

Preparation LXIX 3-(1-Methyl-1,2,3,6-tetrahydro-pyridin-4-yl)-5-trifluoromethyl-phenylamine 3-(5,5-Dimethyl-[1,3,2]dioxaborinan-2-yl)-5-trifluoromethyl-phenylamine (8.8 g, 0.032 mol) was added to trifluoro-methanesulfonic acid 1-methyl-1,2,3,6-tetrahydro-pyridin-4-yl ester (7.91 g, 0.032 mol) and 2N $Na_2CO_3$ aqueous solution (25 mL) was bubbled through $N_2$ for 5 min. $Pd(PPh_3)_4$ (3.7 g, 3.2 mmol) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 ml) followed by brine (25 mL). The organic phase was dried over $Na_2SO_4$ and concentrated in vacuo. The desired product was isolated by passing through silica gel column chromatography (EtOAc, then (2M $NH_3$) in MeOH/EtOAc) to provide a yellow oil.

Preparation LXX—3,3-Dimethyl-6-nitro-2,3-dihydro-benzo[d]isothiazole 1,1-dioxide 3,3-Dimethyl-2,3-dihydro-benzo[d]isothiazole 1,1-dioxide was added to $KNO_3$ in $H_2SO_4$ cooled to 0° C. and stirred for 15 min. The reaction was warmed to RT and stirred overnight. The mix was poured into ice and extracted with EtOAc (3×), washed with $H_2O$ and brine, dried and evaporated to give the product which was used without further purification.

The following compounds were prepared similarly to the procedure outlined above:
a) 1,1,4,4-Tetramethyl-6-nitro-1,2,3,4-tetrahydro-naphthalene Preparation LXXI—3-(1-Methyl-1,2,3,4-tetrahydro-pyridin-4-yl)-5-trifluoromethyl-phenylamine 3-(5,5-Dimethyl-[1,3,2]dioxaborinan-2-yl)-5-trifluoromethyl-phenylamine (1.2 g) was added to trifluoro-methanesulfonic acid 1-methyl-1,2,3,6-tetrahydro-pyridin-4-yl ester (1.0 g), LiCl (500 mg, Aldrich), $PPh_3$ (300 mg, Aldrich) and 2M $Na_2CO_3$ aqueous solution (6 ml) and was bubbled with $N_2$ for 5 min. $Pd(PPH_3)_4$ (300 mg, Aldrich) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 ml) followed by brine (25 mL). The organic phase was dried over $Na_2SO_4$ and concentrated in vacuo. The desired compound was isolated by silica gel column chromatography (EtOAc 10% (2M $NH_3$) in MeOH/EtOAc) to provide yellow oil. M+H 257.2; Calc'd 256.1.

Preparation LXXII—Trifluoromethylsulfonic acid 1-methyl-1,2,3,6-tetrahydro-pyridin-4-yl ester In a three-necked round bottom flask equipped with a thermometer and an additional funnel was placed anhydrous THF (200 mL) and 2M LDA (82.8 mL). The solution was cooled to −78° C. and a solution of 1-methyl-piperidin-4-one (20 mL) in anhydrous THF (70 mL) was added dropwise. The reaction was warmed to −10° C. over 30 min and cooled down again to −78° C. $Tf_2NPh$ (54.32 g) in 200 mL of anhydrous THF was added through the additional funnel over 30 min and anhydrous THF (30 mL) was added to rinse the funnel. The reaction was warmed to RT and the reaction solution was concentrated in vacuo. The residue was dissolved in $Et_2O$ purified on neutral $Al_2O_3$ column chromatography ($Et_2O$ as elutant). The product was obtained as orange oil. (20 g)

Preparation LXXIII—3-(5,5-Dimethyl-[1,3,2]dioxaborinan-2-yl)-5-trifluoromethyl-phenylamine $N_2$ was bubbled through a solution of 3-bromo-5-trifluoromethyl-phenylamine (2.38 g), 5,5,5',5'-tetramethyl-[2,2']bi[[1,3,2]dioxaborinanyl](2.24 g, Frontier Scientific) and KOAc (2.92 g), dppf (165 mg, Aldrich) in anhydrous dioxane (50 ml) for 2 min. $PdCl_2$ (dppf) (243 mg, Aldrich) was added and the reaction was heated to 80° C. for 4 h. After cooling to RT, the mix was diluted with 50 mL of $Et_2O$, filtered through Celite®, and the filtrate was concentrated in vacuo. The residue was dissolved in $Et_2O$ (100 mL), washed with sat. $NaHCO_3$ aqueous solution (50 mL) followed by brine (50 mL). The organic phase was dried over $Na_2SO_4$ and concentrated in vacuo. The residue was dissolved in 3:2 $Et_2O$/Hex (100 mL), filtered through Celite® and the filtrate was concentrated in vacuo to afford a dark brown semi-solid.

Preparation LXXIV—1-Boc-3-Hydroxymethyl-azetidine

A solution of 1-Boc-azetidine-3-carboxylic acid (1.6 g) and $Et_3N$ (2 ml) in anhydrous THF (60 ml) was cooled to 0° C. Isopropyl chloroformate (1.3 g) was added via a syringe slowly; forming a white precipitate almost immediately. The reaction was stirred for 1 h at 0° C. and the precipitate was filtered out. The filtrate was cooled to 0° C. again and aqueous $NaBH_4$ solution (900 mg, 5 ml) was added via pipette and stirred for 1 h. The reaction was quenched with $NaHCO_3$ solution (50 mL) and the product was extracted with EtOAc (200 mL). The organic phase was washed with brine (50 mL), dried over $Na_2SO_4$ and concentrated in vacuo. The residue was dissolved in EtOAc and passed through a short silica gel pad. Concentrating the filtrate in vacuo provided the compound as a light yellow oil.

Preparation LXXV—1-Boc-3-(3-nitro-5-trifluoromethyl-phenoxymethyl)-azetidine

A mixture of 1-Boc-3-methylsulfonyloxymethyl-azetidine (1.47 g), 3-nitro-5-trifluoromethyl-phenol (1.15 g) and $K_2CO_3$ (1.15 g) in DMF (20 ml) at 80° C. was stirred overnight. The reaction was cooled to RT and diluted with 25 mL of sat. $NaHCO_3$ and 50 mL of EtOAc. The organic phase was separated and washed with brine (25 mL), dried over $Na_2SO_4$ and concentrated in vacuo. The crude compound was purified by column chromatography (50% EtOAc/hex).

Preparation LXXVI—2,2-Dimethyl-6-nitro-3,4-dihydro-2H-benzo[1,4]oxazine 2,2-Dimethyl-6-nitro-4H-benzo[1,4]oxazin-3-one was added to $BH_3$—THF complex (Aldrich) in THF with ice cooling. The mixture was heated to reflux for 2 h then carefully diluted with 12 mL of MeOH and heated to reflux for an additional 1 h. Concentrated HCl (12 mL) was added and heated to reflux for 1 h. The mixture was concentrated and the resulting solid was suspended in a dilute aqueous solution of NaOH (1 M) and extracted with EtOAc (100 mL×4). The organic layers were washed with $H_2O$ and dried over $MgSO_4$. Evaporation of solvent gave a yellow solid.

Preparation LXXVII—2,2,4-Trimethyl-6-nitro-4H-benzo[1,4]oxazin-3-one 2,2-Dimethyl-6-nitro-4H-benzo[1,4]oxazin-3-one (1.1 g) was mixed with MeI (850 mg, Aldrich), $K_2CO_3$ (1.38 g, Aldrich) and DMF (30 ml, Aldrich) at 40° C. for 48 h. The DMF was removed in vacuo and the residue was diluted with EtOAc (80 ml). The organic phase was washed with $H_2O$ (50 ml), aqueous $Na_2SO_3$ (50 ml) and brine (50 ml). The resulting solution was dried ($MgSO_4$) and concentrated to provide the compound which was used as is.

Preparation LXXVIII—2-Bromo-N-(2-hydroxy-5-nitro-phenyl)-2-methyl-propionamide

2-Amino-4-nitro-phenol (3.08 g, Aldrich) was stirred with THF (30 ml, Aldrich) in an ice bath. 2-Bromo-2-methyl-propionyl bromide (2.47 ml, Aldrich) and $Et_3N$ (2.0 g, Aldrich) was slowly added via syringe. The mixture was stirred for 45 min then poured into ice. The aqueous phase was extracted by EtOAc (50 mL×4). The organic layer was dried and concentrated. The desired product was crystallized from EtOAc. (*Chem. Pharm. Bull* 1996, 44(1) 103–114).

Preparation LXXIX—2,2-Dimethyl-6-nitro-4H-benzo[1,4]oxazin-3-one

2-Bromo-N-(2-hydroxy-5-nitro-phenyl)-2-methyl-propionamide was mixed with $K_2CO_3$ in 20 mL of DMF and stirred overnight at 50° C. The reaction mixture was poured into ice water. The precipitate was collected by filtration and washed with $H_2O$. The crude compound was recrystallized from EtOH.

Preparation LXXX—4-[1-(2-Bromo-4-nitro-phenyl)-1-methyl-ethyl]-1-methyl-pyridinium iodide 1-Methyl-4-[1-methyl-1-(4-nitro-phenyl)-ethyl]-pyridinium (8 g) was dissolved in glacial HOAc (10 ml) then diluted with $H_2SO_4$ (50 ml), then NBS (3.8 g) was added. After 1 h, additional NBS (1.2 g) was added, 30 min later another 0.5 g of NBS, then 15 min later 200 mg more NBS. After 1 h, the mixture was neutralized with $NH_4OH$ (conc.) with ice bath cooling. The neutralized mixture was then concentrated and used as is.

Preparation LXXXI—4-[1-(2-Bromo-4-nitro-phenyl)-1-methyl-ethyl]-1-methyl-1,2,3,6-tetrahydro-pyridine 4-[1-(2-Bromo-4-nitro-phenyl)-1-methyl-ethyl]-1-methyl-pyridiniumiodide was mixed with MeOH (400 ml) and $CH_2Cl_2$ (200 ml), then treated with $NaBH_4$ (2.5 g) in portions. After stirring at RT for 2 h, the mixture was extracted with $CH_2Cl_2$ (300 mL×3). The $CH_2Cl_2$ layer was washed with brine, dried over $Na_2SO_4$ and concentrated in vacuo, to provide the desired product.

Preparation LXXXII—1-Methyl-4-[1-methyl-1-(4-nitro-phenyl)-ethyl]-pyridinium iodide 4-(4-nitrobenzyl)pyridine (64 g, 300 mmol) and $Bu_4NI$ (6 g, 16.2 mmol) were dissolved in $CH_2Cl_2$ (500 mL) and the solution was suspended with NaOH (aq. 5N, 450 mL). With vigorous stirring, MeI (213 g, 1500 mmol) was added. The resulting solution was placed under $N_2$ and stirred vigorously at RT for 60 h until blue color disappears. (MS: $M^+$=257). The reaction mixture was used in the next step without any further purification.

Preparation LXXXIII—1-Methyl-4-(4-nitrobenzyl)-1,2,3,6-tetrahydro-pyridine

1-Methyl-4-[1-methyl-1-(4-nitro-phenyl)-ethyl]-pyridinium was treated with DEA (100 mL) in MeOH (300 mL) for 2 h. $NaBH_4$ (19 g, 500 mmole) was added in small portions. The resulting mixture was stirred for 30 min at RT, then partitioned between $CH_2Cl_2/H_2O$ (500 mL/500 mL). The lower layer (organic) was collected and the upper layer was washed with $CH_2Cl_2$ (300 mL×3). The combined organic layer was washed with brine then concentrated in vacuo. The residue was purified on a silica washed-column (7% TEA in EtOAc). The desired fractions were combined and concentrated under vacuum to give the desired compound as a dark gray solid. (MS: M+1=261).

Preparation LXXXIV—1-Boc-4-formylpiperidine

4A Molecular sieves were heated to 100° C. and a vacuum was applied. They were cooled to RT and purged with N2. $CH_2Cl_2$ (420 ml) and $CH_3CN$ (40 ml), NMO (40 g) and 1-Boc-4-hydroxymethylpiperidine (50 g) were added and the mix was stirred for 5 min then cooled to 15° C. TPAP (4.1 g) is added and an exotherm was observed. The reaction was maintained at RT with external cooling. The reaction was stirred at RT for 3 h, filtered, concentrated, diluted with 50% EtOAc/hexanes and purified on a silica gel plug (50% EtOAc/hexanes). The eluant fractions were concentrated to afford a yellow oil.

Preparation LXXXV 2-Chloro-4-cyanopyridine

2-Chloro-4-cyanopyridine was prepared similar to the method described by Daves et al., J. Het. Chem., 1, 130–32 (1964).

Preparation LXXXVI 4-(2-tert-Butyl-5-nitro-phenyl)-but-3-en-1-ol

A mix of 1-(tert-butyl)-2-bromo-4-nitrobenzene (3.652 g), TEA (5.92 ml), 3-buten-1-ol (5.48 ml), $Pd(OAc)_2$ (32 mg), $Pd(PPh_3)_4$ (327 mg) and toluene (40 ml) was degassed with nitrogen and heated in a sealed vessel for 16 h at 120° C. The next day, the reaction mixture was cooled to RT, filtered, and concentrated in vacuo. The crude was eluted on a silica gel column with 15% to 22% EtOAc/hexanes gradient system to yield a yellow-brown oil.

Preparation LXXXVII 4-(2-tert-Butyl-5-nitro-phenyl)-but-3-enal 4-(2-tert-Butyl-5-nitro-phenyl)-but-3-en-1-ol (1.024 g) was dissolved in 10 ml of $CH_2Cl_2$ and added dropwise over 5 min to a −78° C. mix of oxalyl chloride (0.645 ml), DMSO (0.583 ml), and 10 ml $CH_2Cl_2$. The reaction was stirred at −78° C. for 1 h, then treated with a solution of TEA (1.52 ml) in 7 ml $CH_2Cl_2$ and stirred at −78° C. for an additional 25 min, then warmed to −30° C. for 35 min. The reaction was treated with 50 ml of saturated aqueous $NH_4Cl$, diluted with $H_2O$ and extracted with EtOAc. The organic layer was brine-washed, dried over $Na_2SO_4$, filtered, and concentrated in vacuo to yield a yellow oil.

Preparation LXXXVIII 1-[4-(2-tert-Butyl-5-nitro-phenyl)-but-3-enyl]-pyrrolidine 4-(2-tert-Butyl-5-nitro-phenyl)-but-3-enal (895 mg) was dissolved in 40 ml THF, and to the solution was added pyrrolidine (0.317 ml). To the deep orange solution was added $NaBH(OAc)_3$ (1.151 g) and glacial AcOH (0.207 ml). The reaction was stirred at RT overnight, then treated with saturated aqueous $NaHCO_3$ and diluted with $Et_2O$ and some 1N NaOH. The layers were separated, and the organic layer was extracted with aqueous 2N HCl. The acidic aqueous layer was basified to pH>12 with 6 N NaOH, extracted with $Et_2O$, brine-washed, dried over $Na_2SO_4$, filtered, and concentrated in vacuo to provide 1-[4-(2-tert-butyl-5-nitro-phenyl)-but-3-enyl]-pyrrolidine as a orange-brown oil.

Preparation LXXXVIX N-Boc-(2-chloropyrimidin-4-yl)-methylamine

To 2-chloropyrimidine-4-carbonitrile [2.5 g, prepared by the procedure of Daves et. al. (J. Het. Chem. 1964, 1, 130–132)] in EtOH (250 ml) under $N_2$ was added $Boc_2O$ (7.3 g). After the mixture was briefly placed under high vacuum and flushed with $N_2$, 10% Pd/C (219 mg) was added. $H_2$ was bubbled though the mixture (using balloon pressure with a needle outlet) as it stirred 4.2 h at RT. After filtration through Celite®, addition of 1.0 g additional $Boc_2O$, and concentration, the residue was purified by silica gel chromatography (5:1→4:1 hexanes/EtOAc) to obtain N-Boc-(2-chloropyrimidin-4-yl)-methylamine.

Preparation XC Methanesulfonic acid 1-Boc-azetidin-3-ylmethyl ester

To a solution of (1-Boc-azetidin-3-yl)-methanol (1.06 g, 5.7 mmol), TEA (1.18 mL, 8.52 mmol) in $CH_2Cl_2$ at 0° C. was added $MeSO_2Cl$ (0.53 mL, 6.82 mmol) via a syringe. The reaction was warmed to RT over 2 h and stirring was continued at RT for 2 h. The white solid formed was removed by filtration and the filtrate was washed with 25 mL of $H_2O$. The organic phase was dried over $Na_2SO_4$, and concentrated in vacuo to afford yellow oil.

Preparation XC—Methanesulfonic acid 1-Boc-azetidin-3-ylmethyl ester

To a solution of (1-Boc-azetidin-3-yl)-methanol (1.06 g, 5.7 mmol), TEA (1.18 mL, 8.52 mmol) in $CH_2Cl_2$ at 0° C. was added $MeSO_2Cl$ (0.53 mL, 6.82 mmol) via a syringe. The reaction was warmed to RT over 2 h and stirring was continued at RT for 2 h. The white solid formed was removed by filtration and the filtrate was washed with 25 mL of $H_2O$. The organic phase was dried over $Na_2SO_4$, and concentrated in vacuo to afford yellow oil.

Preparation XCI—N-(2-bromo-5-nitrophenyl)acetamide

2-Bromo-5-nitroaniline (10 g) was dissolved in 500 mL of $CH_2Cl_2$, DIEA (6.6 g) was added to the mixture, followed by DMAP (100 mg). The mixture was cooled to 0° C. in ice bath. Acetyl chloride (4 g in 50 mL $CH_2Cl_2$) was added dropwise to the reaction mixture. After the mixture was stirred at RT over 3 h, extracted once with saturated $NaHCO_3$ solution and once with brine, the resulting organic layer was dried over $MgSO_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M−1). Calc'd. for $C_8H_7BrN_2O_3$—259.06.

Preparation XCII—N-(2-bromo-5-nitrophenyl)-N-(2-methylprop-2-enyl)acetamide

A suspension of 2 g NaH (95% powder) in anhydrous DMF (100 mL) was cooled to −78° C., N-(2-bromo-5-nitrophenyl)acetamide (7 g) in dry DMF (50 mL) was added to the mixture under $N_2$ atmosphere. After the mixture was warmed to 0° C., 3-bromo-2-methylpropene (7.3 g in 20 dry DMF) was added to the mixture. The mixture was stirred at RT overnight. The mixture was poured into a container of ice and extracted between saturated $NaHCO_3$ solution and EtOAc. The resulting organic layer was dried over $MgSO_4$, filtered and concentrated in vacuo. The crude material was purified by flash chromatography on silica gel with 7:2 hexane:EtOAc to afford the title compound as a yellow gum. MS: 314 (M+1). Calc'd. for $C_{12}H_{13}BrN_2O_3$—313.15.

Preparation XCIII—1-(3,3-dimethyl-6-nitro-2,3-dihydro-indol-1-yl)ethanone

N-(2-Bromo-5-nitrophenyl)-N-(2-methylprop-2-enyl) acetamide (4.5 g) was dissolved in anhydrous DMF (50 mL), tetraethyl-ammonium chloride (2.5 g), sodium formate (1.2 g), NaOAc (3 g) were added, and the resulting mixture was bubbled with $N_2$ gas for 10 min. $Pd(OAc)_2$ (350 mg) was added and the mixture was heated at 80° C. under $N_2$ atmosphere overnight. After the mixture was concentrated in vacuo, it was partitioned between saturated $NaHCO_3$ solution and EtOAc, the resulting organic layer was dried over $MgSO_4$, filtered and concentrated in vacuo. The crude material was purified by flash chromatography on silica gel with 2:1 Hexane:EtOAc to afford the title compound as a yellow gum. MS: 235 (M+1). Calc'd. for $C_{12}H_{14}N_2O_3$—234.25.

Preparation XCIV—3,3-dimethyl-6-nitroindoline 1-(3,3-Dimethyl-6-nitro-2,3-dihydro-indol-1-yl)ethanone (1.8 g) was dissolved in EtOH (50 mL), 12N HCl (50 mL) was added and the resulting mixture was heated at 70° C. overnight. After the mixture was concentrated in vacuo, it was partitioned between saturated $NaHCO_3$ solution and EtOAc, the resulting organic layer was dried over $MgSO_4$, filtered and concentrated in vacuo to afford a yellow solid. MS: 193 (M+1). Calc'd. for $C_{10}H_{12}N_2O_2$—192.21.

Preparation XCV—1-Acetyl-6-amino-3,3-dimethylindoline 1-(3,3-Dimethyl-6-nitro-2,3-dihydro-indol-1-yl)ethanone (250 mg) was dissolved in MeOH (20 mL), the mixture was bubbled with $H_2$ for 10 min. 10% Pd/C (50 mg) was added and the mixture was stirred under $H_2$ overnight. The mixture was filtered through Celite® and concentrated in vacuo. The crude material was purified by flash chromatography on silica gel with 1:1 EtOAc:$CH_2Cl_2$ to afford the title compound as a white crystalline material. MS: 205 (M+1). Calc'd. for $C_{12}H_{16}N_2O$—204.27.

Preparation XCVI—4-(1,1,2,2,3,3,4,4,4-nonafluorobutyl) phenylamine

4-Nitro-(1,1,2,2,3,3,4,4,4-nonafluorobutyl)benzene was synthesized by a method analogous to that described by Gregory, W. A. et al. (J. Med. Chem, 1990, 33(9) 2569–2578). The mixture of the above nitro intermediate (1.0 mmol), iron powder (5.0 mmol) and $NH_4Cl$ (0.7 mmol) in EtOH (3 mL) and $H_2O$ (3 ml) was stirred for 4 h at 80° C. Filtration and concentration gave the crude title compound, which was used without further purification.

Preparation XCVII—2-bromo-1-tert-butyl-4-nitrobenzene

NBS (125.0 g, 697.5 mmol, 1.5 eq) was slowly added to a solution of TFA:$H_2SO_4$ (5:1, 750 mL) and tert-butyl-4-nitrobenzene (100.0 g, 558.0 mmol) at RT. The solution was stirred for 24 h and poured over 5 kg of ice. The resulting suspension was filtered and washed with a 1:1 MeOH:$H_2O$ solution (200 mL) and dried in a vacuum oven. MS (ES+): 258.1, 260.1 (M+H)$^+$. Calc'd for $C_{10}H_{12}BrNO_2$: 257.0.

Preparation XCVIII—4-(2-tert-butyl-5-nitrophenyl) pyridine

To a solution of 2-bromo-1-tert-butyl-4-nitrobenzene (8.6 g, 33.3 mmol) and toluene (70 mL) in a 150 mL round bottom flask, 4-pyridylboronic acid (4.5 g, 36.6 mmol, 1.1 eq), $Pd(PPh_3)_4$ (3.8 g, 3.3 mmol, 0.1 eq) and $K_2CO_3$ (13.8 g, 99.9 mmol, 3 eq) were added. The solution was stirred for 24 h at 80° C. before cooling to RT. The solution was filtered through a pad of Celite® and purified by silica flash chromatography (30% EtOAc/Hexanes). This afforded the desired compound as a yellow solid. MS (ES+): 257.2 (M+H)$^+$; (ES−): 255.2 (M−H)$^-$. Calc'd for $C_{15}H_{16}N_2O_2$: 256.1.

Preparation XCIX—4-(2-tert-butyl-5-nitrophenyl)-1-methylpyridinium 4-(2-tert-Butyl-5-nitrophenyl)pyridine (2.0 g, 7.8 mmol) was added to a round-bottom flask and dissolved in EtOH (10 mL). $CH_3I$ (30 mL) was added to the flask which was placed in a 80° C. sand bath and heated to reflux. After 6 h, the solution was cooled to RT and the excess $CH_3I$ and EtOH were stripped-off under reduced pressure resulting in the desired compound as a light brown solid. MS (ES+): 271.2 (M+H)$^+$; (ES−): 269.2 (M−H)$^-$. Calc'd for $C_{16}H_{19}N_2O_2^+$: 271.1.

Preparation C—4-tert-butyl-3-(1-methyl-1,2,3,6-tetrahydroyridin-4-yl)aniline 4-(2-tert-Butyl-5-nitrophenyl)-1-methylpyridinium (2.1 g, 7.8 mmol) was added to a 100 mL round-bottom flask and dissolved in a 10% $H_2O$/EtOH mixture. To the flask iron dust (1.31 g, 23.4 mmol, 3 eq) and $NH_4Cl$ (460 mg, 8.6 mmol, 1.1 eq) were added. The flask was placed in a 100° C. sand bath and heated to reflux. After 2 h, the solution was cooled to RT and filtered through a pad of Celite®. The resulting solution was stripped down to a yellow solid and redissolved in MeOH (20 mL, anhydrous). The solution was cooled to 0° C. by placing it in an ice bath and slowly adding $NaBH_4$ (450 mg, 11.7 mmol, 1.5 eq). After addition of the $NaBH_4$, the solution was cooled to RT and stirred for 30 min. The solvent was stripped-off under vacuum and the solid was redissolved in $CH_2Cl_2$ and filtered. The solution was concentrated in vacuo to afford an amorphous clear yellow solid. MS (ES+): 245.2 (M+H)$^+$. Calc'd for $C_{16}H_{24}N_2$: 244.2.

Preparation CI—[1-(4-amino-phenyl)-ethyl]carbamic acid tert-butyl ester

A mixture of 1-(S)-1-(4-nitrophenyl)ethylamine hydrochloride (2 g), $Boc_2O$ (2.6 g) and $NaHCO_3$ (3 g) in MeOH/$H_2O$ (1:1, 200 ml) was stirred at RT overnight. The reaction was extracted with EtOAc twice then washed with H2O followed by brine. The organic layer was dried with $Na_2SO_4$ and evaporated under reduced pressure to give the protected nitrophenyl ethylamine. Boc-1-(S)-1-(4 nitrophenyl) ethylamine (1 g) was hydrogenated by $H_2$ atmosphere in the presence of Pd/C (200 mg) to give Boc protected aniline (0.8 g). The intermediate was deprotected with 4N HCl/dioxane to give the title compound as the HCl salt.

Preparation CII—1-[2-(tert-butyl)-5-aminophenyl]-4-methylpiperazine

A mixture of 2-t-butylaniline (5.4 g) and methylchlorethylamine hydrochloride (7 g) and $K_2CO_3$ (5 g) in NaI (2 g) in diglyme (150 m) was heated at 170° C. for 8 h. The reaction was filtered and the filtrate was evaporated under high vacuum. The residue was mixed with EtOAc (200 ml) and $H_2O$ (200 ml) and extracted with EtOAc twice. The combined organic layer was washed with brine and dried over $Na_2SO_4$ and evaporated to give crude 1-[2-(tert-butylphenyl]-4-methylpiperazine. The crude 1-[2-(tert-butylphenyl]-4-methylpiperazine (260 mg) was stirred with $H_2SO_4$ (3 ml) at 0° C. and $HNO_3$ (1.2 ml, 70%) was slowly added to the reaction. The reaction was warmed to RT, stirred for 30 min, poured on ice and basified with $K_2CO_3$ slowly. The solution was extracted with EtOAc three times, washed with $H_2O$, followed by brine, dried over $Na_2SO_4$ and evaporated under reduced pressure. The residue was purified by column chromatography to give 1-[2-(tert-butyl)-5-nitrophenyl]-4-methylpiperazine (260 mg), which was hydrogenated under $H_2$ atmosphere to give 1-[2-(tert-butyl)-5-aminophenyl]-4-methylpiperazine.

The following compounds were prepared similarly to the procedure outlined above:

a) 1-(5-aminophenyl)-4-methylpiperazine

Preparation CIII—4-(tert-butyl)-2-(4-methylpiperazinyl) phenylamine

A mixture of 1-(tert-butyl)-2-bromo-4-nitrobenzene (3 g) and N-methylpiperazine (8 g) was heated neat at 130° C. for 4 h. The residue was purified by column chromatography to give 1-[4-bromo-5-(tert-butyl)-2-nitrophenyl]-4-methylpiperazine, which was hydrogenated to furnish 4-(tert-butyl)-2-(4-methylpiperazinyl)-phenylamine.

Preparation CIV—{2-[4-(tert-butyl)-2-aminophenoxy]ethyl}dimethylamine

DEAD (2.6 ml) was added to a mixture of 2-nitro-4-tert-butylphenol (2 g) and N,N-dimethylethanolamine (1.3 g) and $Ph_3P$ (4 g) in THF (50 ml). The reaction was stirred at RT for 1 h, diluted with EtOAc (50 ml) and washed with 1 N HCl twice. The aqueous layer was basified with $NaHCO_3$, extracted with EtOAc twice and washed with $H_2O$ and brine. The organic layer was dried over $Na_2SO_4$ and evaporated to give {2-[4-(tert-butyl)-2-nitrophenoxy]ethyl}-dimethylamine. It was hydrogenated under $H_2$ atmosphere to give {2-[4-(tert-butyl)-2-aminophenoxy]ethyl}-dimethylamine.

The following compounds were prepared similarly to the procedure outlined above:

a) [2-(2-aminophenoxy)ethyl]-dimethylamine.

Preparation CV—2-amino-5,6,7-trihydro-1,2,4-triazolo[3,4-a]isoquinoline

7-Nitro-2,3,4-trihydroisoquinolin-1-one (500 mg) was heated in $POCl_3$ (10 ml) to reflux for 8 h. The mixture was evaporated, mixed with toluene and evaporated again. The residue was dissolved in THF, $H_2NNH_2$ (1 ml) was slowly added to the reaction and stirred for 2 h. The reaction was evaporated, heated with HC(OEt)$_3$ (15 ml) at 115° C. for 2 h, extracted with EtOAc and hydrogenated to give 2-amino-5,6,7-trihydro-1,2,4-triazolo[3,4-a]isoquinoline.

Preparation CVI—tert-butyl 4-[(6-nitro-3,3-dimethylindolinyl)methyl]piperidinecarboxylate 3,3-Dimethyl-6-nitroindoline (450 mg) was dissolved in 20 mL of dichloroethane, N-boc-4-formylpiperidine (750 mg) was added to the mixture, followed by 2 g NaHB(OAc)$_3$ and 1 mL of glacial AcOH. The mixture was stirred at RT overnight. Saturated $NaHCO_3$ solution (20 mL) was added to the reaction mixture and stirred for 1 h. The resulting mixture was separated by separation funnel, the organic layer was extracted once with saturated $NaHCO_3$ solution and once with brine. The resulting organic layer was dried over $MgSO_4$, filtered and concentrated in vacuo. The crude material was purified by flash chromatography on silica gel with 9:1 Hexane:EtOAc to afford an orange oil. MS: 290 (M−99). Calc'd. for $C_{21}H_{31}N_3O_4$—389.5.

Preparation CVII—3,3-dimethyl-1-piperidin-4-ylmethyl-2,3-dihydro-1H-indol-6-ylamine tert-Butyl 4-[(6-nitro-3,3-dimethylindolinyl)-methyl] piperidinecarboxylate (900 mg) was dissolved in 10 mL MeOH, the mixture was bubbled with $H_2$ for 10 min. 10% Pd/C (30 mg) was added and the mixture was stirred under $H_2$ overnight. The mixture was filtered through Celite® and concentrated in vacuo. The crude material was purified by flash chromatography on silica gel with 1:1 Hexane:EtOAc to afford a colorless oil. MS: 360 (M+1). Calc'd. for $C_{21}H_{33}N_3O_2$— 359.5.

Preparation CVIII—(2-chloro-(3-pyridyl))-N-(4-phenoxyphenyl)carboxamide

2-Chloronicotinoyl chloride (9.15 g, 0.052 mol) was added to a stirred solution of 4-phenoxyaniline (10 g, 0.054 mol) and DIEA (10 ml, 0.057 mol) in $CH_2Cl_2$ (100 ml) at RT. The mixture was stirred for 48 h before removal of solvent under reduced pressure. The resulting residue was dissolved in EtOAc and washed several times with saturated $NaHCO_3$ aqueous solution and brine, respectively. The organic layer was dried over $Na_2SO_4$ and evaporated to leave a solid. This material was re-crystallized from EtOAc/Hexane mixture, followed by filtration and rinsing with $Et_2O$ to give the desired compound as a white solid. MS m/z: 325 (M+1); 323 (M−1)

Preparation CIX—1-(1-methyl(4-piperidyl))-6-nitroindoline

6-Nitroindoline (5 g) was dissolved in 200 mL of DCE. N-Methyl-4-piperidone (5 g) was added to the mixture, followed by NaHB(OAc)$_3$ (12 g) and 1 mL of glacial AcOH. The mixture was stirred at RT overnight. A saturated $NaHCO_3$ (200 mL) solution was added to the reaction mixture and stirred for 1 h. The mixture was separated by separation funnel. The organic layer was extracted once with saturated $NaHCO_3$ solution and once with brine. The resulting organic layer was dried over $MgSO_4$, filtered and concentrated in vacuo. The crude material was purified by flash chromatography on silica gel with 2:1 EtOAc:MeOH to afford an orange oil. MS: 262 (M+1). Calc'd. for $C_{14}H_{19}N_3O_2$—261.3.

Preparation CX—1-(1-methyl-4-piperidyl)indoline-6-ylamine 1-(1-Methyl(4-piperidyl))-6-nitroindoline (3 g) was dissolved in 100 mL MeOH and the mixture was bubbled with $H_2$ for 10 min. 10% Pd/C (200 mg) was added and the mixture was stirred under $H_2$ overnight. The mixture was filtered through Celite® and concentrated in vacuo to afford light yellow oil. MS: 232 (M+1). Calc'd. for $C_{14}H_{21}N_3$—231.3.

Preparation CXI—N-(2-bromo-5-nitrophenyl)acetamide

2-Bromo-5-nitroaniline (10 g) was dissolved in $CH_2Cl_2$ (500 mL), DIEA (6.6 g) was added to the mixture, followed by 100 mg of DMAP. The mixture was cooled to 0° C. in ice bath. Acetyl chloride (4 g in 50 mL $CH_2Cl_2$) was added dropwise to the reaction mixture. After the mixture was stirred at RT over 3 h, and extracted once with saturated $NaHCO_3$ solution and once with brine. The resulting organic layer was dried over MgSO$_4$, filtered and concentrated in vacuo. The crude material was purified by flash chromatography on silica gel with 1:1 EtOAc:Hexane to 100% EtOAc to afford a white solid. MS: 258 (M−1). Calc'd. for C$_8$H$_7$BrN$_2$O$_3$—259.1.

Preparation CXII—N-(2-bromo-5-nitrophenyl)-N-(2-methylprop-2-enyl)acetamide

A suspension of NaH (2 g) (95% powder) in 100 mL anhydrous DMF was cooled to −78° C., and N-(2-bromo-5-nitrophenyl) acetamide (7 g) in 50 mL dry DMF was added to the mixture under N$_2$. After the mixture was warmed to 0° C., 3-bromo-2-methylpropene (7.3 g in 20 dry DMF) was added and stirred at RT overnight. The mixture was poured into a container of ice and extracted between saturated NaHCO$_3$ solution and EtOAc. The resulting organic layer was dried over MgSO$_4$, filtered and concentrated in vacuo. The crude material was purified by flash chromatography on silica gel with 7:2 Hexane:EtOAc to afford a yellow gum. MS: 314 (M+1). Calc'd. for C$_{12}$H$_{13}$BrN$_2$O$_3$—313.1.

Preparation CXIII—1-(3,3-dimethyl-6-nitro-2,3-dihydro-indol-1-yl)ethanone

N-(2-Bromo-5-nitrophenyl)-N-(2-methylprop-2-enyl) acetamide (4.5 g) was dissolved in 50 mL anhydrous DMF, 2.5 g tetraethyl-ammonium chloride, 1.2 g sodium formate, 3 g sodium acetate were added, the resulting mixture was bubbled with N$_2$ gas for 10 min. Pd(OAc)$_2$ (350 mg) was added and the mixture was heated at 80° C. under N$_2$ overnight. After the mixture was concentrated in vacuo, it was extracted between saturated NaHCO$_3$ solution and EtOAc, the resulting organic layer was dried over MgSO$_4$, filtered and concentrated in vacuo. The crude material was purified by flash chromatography on silica gel with 2:1 Hexane:EtOAc to afford a yellow gum. MS: 235 (M+1). Calc'd. for C$_{12}$H$_{14}$N$_2$O$_3$—234.2.

Preparation CXIV—3,3-dimethyl-6-nitroindoline 1-(3,3-Dimethyl-6-nitro-2,3-dihydro-indol-1-yl)ethanone (1.8 g) was dissolved in 50 mL EtOH, 50 mL 12N HCl was added and the resulting mixture was heated at 70° C. overnight. After the mixture was concentrated in vacuo, it was extracted between saturated NaHCO$_3$ solution and EtOAc. The resulting organic layer was dried over MgSO$_4$, filtered and concentrated in vacuo to afford a yellow solid. MS: 193 (M+1). Calc'd. for C$_{10}$H$_{12}$N$_2$O$_2$—192.2.

Preparation CXV—3,3-dimethyl-1-(4-methyl-piperazin-1-yl)-6-nitro-2,3-dihydro-1H-indole 3,3-Dimethyl-6-nitroindoline (0.8 g) was dissolved in 50 mL of DCE, and N-methyl-4-piperidone (1 g) was added to the mixture, followed by 2.5 g NaHB(OAc)$_3$ and 1 mL of glacial AcOH. The mixture was stirred at RT overnight. Saturated NaHCO$_3$ solution (50 mL) was added and stirred for 1 h. The resulting mixture was separated by separation funnel, the organic layer was extracted once with saturated NaHCO$_3$ solution and once with brine, the resulting organic layer was dried over MgSO$_4$, filtered and concentrated in vacuo. The crude material was purified by flash chromatography on silica gel with 9:1 EtOAc:MeOH to afford an orange oil. MS: 290 (M+1). Calc'd. for C$_{16}$H$_{23}$N$_3$O$_2$—289.4.

Preparation CXVI—3,3-dimethyl-1-(1-methyl(4-piperidyl)) indoline-6-ylamine 3,3-Dimethyl-1-(4-methyl-piperazin-1-yl)-6-nitro-2,3-dihydro-1H-indole (600 mg) was dissolved in 20 mL MeOH, the mixture was bubbled with H$_2$ for 10 min. 10% Pd/C (100 mg) was added and the mixture was stirred under H$_2$. The mixture was filtered through Celite® and concentrated in vacuo to afford an oil. MS: 260 (M+1). Calc'd. for C$_{16}$H$_{25}$N$_3$—259.4.

Preparation CXVII—3-(1-methyl-1,2,3,6-tetrahydro-pyridin-4-yl)-5-nitro-1H-indole 5-Nitroindole (2.6 g) was dissolved in 100 mL anhydrous MeOH, followed by 5 g N-methyl-4-piperidone and NaOMe (5 g) powder. The mixture was heated to reflux under N$_2$ overnight. The mixture was concentrated in vacuo, and was extracted between saturated NaHCO$_3$ solution and EtOAc. The resulting organic layer was dried over MgSO$_4$, filtered and concentrated in vacuo to afford a yellow solid. This solid was washed with 5 mL EtOAc and 2 mL MeOH to afford a bright yellow solid. MS: 258 (M+1). Calc'd. for C$_{14}$H$_{15}$N$_3$O$_2$—257.29.

Preparation CXVIII—3-(1-methyl-4-piperidyl)indole-5-ylamine 3-(1-Methyl-1,2,3,6-tetrahydro-pyridin-4-yl)-5-nitro-1H-indole (2.7 g) was dissolved in 50 mL MeOH, the mixture was bubbled with H$_2$ for 10 min. 10% Pd/C (150 mg) was added and the mixture and stirred under H$_2$ overnight. The mixture was filtered through Celite® and concentrated in vacuo to afford a yellow oil. MS: 230 (M+1). Calc'd. for C$_{14}$H$_{19}$N$_3$—229.3.

Preparation CXIX—{3-[3-amino-5-(trifluoromethyl) phenyl]propynyl}dimethylamine

A mixture of 3-bromo-5-trifluoromethylaniline (1.4 g, 5.9 mmol), 1-dimethylamino-2-propyne (1.3 mL, 0.76 mmol), PdCl$_2$(PPh$_3$)$_2$ (0.26 g, 0.29 mmol) and CuI (114 mg, 0.60 mmol) in 10 mL of TEA was heated at 100° C. in a sealed tube for 3 h. The resulting mixture was filtered over Celite®. The filtrate was concentrated, and the residue was purified by prep-HPLC (reverse phase) to give the aniline. MS (ES+): 243 (M+H)$^+$; (ES−): 241 (M−H)$^−$. Calc'd C$_{12}$H$_{13}$F$_3$N$_2$—242.24.

Preparation CXX—{3-[3-amino-5-(trifluoromethyl)phenyl] propyl}dimethylamine

A mixture of {3-[3-amino-5-(trifluoromethyl)-phenyl] propyl}dimethylamine (7 g, 29 mmol) and Pd(OH)$_2$ (0.5 g) in 250 mL of MeOH was stirred under 50 psi H$_2$. After 2 h, the resulting mixture was filtered over Celite®. The filtrate was concentrated, and the residue was diluted with aq. 1N HCl. The aq. layer was washed with Et$_2$O, made basic with aq. 5N NaOH, and extracted with CH$_2$Cl$_2$. The organic solution was dried over Na$_2$SO$_4$ and concentrated to give the titled compound. MS (ES+): 386 (M+H)$^+$; (ES−): 384 (M−H)$^−$. Calc'd C$_{18}$H$_{19}$ClF$_3$N$_3$O—385.8.

Preparation CXXI—4,4,5,5-tetramethyl-2-(1-methyl(4-1,2,5,6-tetrahydropyridyl))-1,3,2-dioxaborolane To a solution of LiHMDS (25 mL, 25 mmol, 1.0 M in THF) in 35 mL of THF was added 1-methyl-4-piperidinone (3.0 mL, 25 mmol) at −78° C. The resulting solution was stirred for 2 h, then Tf$_2$NPh (8.9 g, 25 mmol) was added. The resulting solution was warmed to RT and stirred for 2 h. The mixture was concentrated, and the residue was purified by alumina (neutral) chromatography to give 1-methyl-4-(1,2,5,6-tetrahydro)pyridyl-(trifluoromethyl) sulfonate. A mixture of above triflate (5.0 g, 20 mmol), bis(pinacolato) diboron (5.6 g, 22 mmol), potassium acetate (6.5 g, 66 mmol), PdCl$_2$dppf (0.44 g, 0.6 mmol), and (dppf)2 (0.33 g, 0.6 mmol) in 60 mL of dioxane was heated at 80° C. for 4 h. The resulting mixture was cooled to RT, diluted with Et$_2$O (150 mL). The ethereal solution was washed with H$_2$O followed by brine. The organic layer dried over Na$_2$SO$_4$, concentrated, and recrystallized in hexane-Et$_2$O to give the title intermediate.

Preparation CXXII—5-(1-methyl(4-1,2,5,6-tetrahydropyridyl))-3-(trifluoro-methyl)phenylamine To a mixture of 4,4,5,5-tetramethyl-2-(1-methyl(4-1,2,5,6-tetrahydropyridyl))-1,3,2-dioxaborolane (1.0 g, 4.4 mmol), PdCl$_2$pddf (0.16 g, 0.2 mmol) and K$_2$CO$_3$ (1.8 g, 13.2 mmol) and 3-amino-5-bromobenzotrifluoride (0.8 g, 3.3 mmol) in DMF (25 mL) was heated at 80° C. for 16 h. The resulting mixture was diluted with EtOAc, washed with H$_2$O, dried over Na$_2$SO$_4$, and concentrated. The residue was purified by SiO$_2$ chromatography to give the title intermediate. MS (ES+): 257 (M+H)$^+$. Calc'd C$_{13}$H$_{15}$F$_3$N$_2$—256.3.

Preparation CXXIII—4-phenylpiperidine

4-Cyano-4-phenylpiperidine HCl (10.0 g, 45.0 mmol) was combined with KOH pellets and stirred vigorously under Ar at 160° C. for 4 h. The reaction mix was cooled to RT and dissolved into toluene (100 ml) and H$_2$O (100 ml). After separation of the layers, the aqueous layer was back-extracted two times with toluene. The combined organic layer was dried over Na$_2$SO$_4$, concentrated in vacuo, and dried under high vacuum, yielding a white solid.

Preparation CXXIV—1-methyl-4-phenylpiperidine

To a stirring mixture at RT of 4-phenylpiperidine (5.24 g, 32.48 mmol) in CH$_3$CN (95 ml) was added a 37% solution of HCHO in H$_2$O (13 ml). To this mixture was added NaCNBH$_3$ (3.27 g, 51.97 mmol). AcOH was added dropwise every 10 min over the next h to maintain the reaction pH near 7. The reaction volume was then reduced in vacuo. The reaction mix was diluted with CH$_2$Cl$_2$ and washed with 2N NaOH and then brine. The crude was concentrated in vacuo and eluted through a silica gel column with 10% MeOH/CH$_2$Cl$_2$. The 1-methyl-4-phenylpiperidine was concentrated in vacuo, yielding a clear oil.

Preparation CXXV—4-(1-methyl-4-piperidyl)phenylamine

To 1-methyl-4-phenylpiperidine (2.663 g, 15.19 mmol) was added carefully H$_2$SO$_4$ (15.2 ml). The reaction was cooled in an ice bath and a solution of H$_2$SO$_4$ (1.66 ml) and fuming HNO$_3$ (0.67 ml, 15.95 mmol) was added dropwise over 45 min. The mix was stirred at 0° C. for 3 h then at RT for 1.5 h before being poured over about 90 g ice and basified with 24 g solid NaOH. The mix was extracted with CH$_2$Cl$_2$. The organic layer was washed with H$_2$O, dried over Na$_2$SO$_4$, and concentrated in vacuo. The crude was eluted on a silica gel column with a MeOH/CH$_2$Cl$_2$ gradient to yield 1-methyl-4-(4-nitrophenyl)piperidine which was hydrogenated under H$_2$ to furnish the title compound.

Preparation CXXVI—1-piperidylprop-2-en-1-one

To a 0° C. solution of acryloyl chloride (4.576 g, 50.558 mmol) in CH$_2$Cl$_2$ (50 ml) was added dropwise and very carefully piperidine (4.305 g, 50.558 mmol). The reaction flask was vented during the exothermic addition. After the addition was completed, the white slurry was stirred at 0° C. for 40 min and at RT for 1 h. The reaction was diluted with 70 ml CH$_2$Cl$_2$ and washed first with about 60 ml 2N HCl and then with about 60 ml of a mix of 2N NaOH and brine. The organic layer was dried over Na$_2$SO$_4$. The solution was evaporated by heating in a H$_2$O bath at 60° C. without vacuum. Once most solvent had been evaporated off, dried the clear oil under high vacuum at RT for 30 min.

Preparation CXXVII—1-(tert-butyl)-2-bromo-4-nitrobenzene

Bromine (17.4 ml) was added dropwise over 40 min to a stirred mixture of 4-tert-butylnitrobenzene (59.5 g, 332 mmol), silver(II)sulfate (56.5 g, 181 mmol), H$_2$SO$_4$ (300 ml), and H$_2$O (33 ml) at RT. The mixture was stirred for a further 3 h and then poured into 0.1 M Na$_2$S$_2$O$_5$/H$_2$O (1L). The solid was filtered, washed with H$_2$O, Et$_2$O, and CH$_2$Cl$_2$. The filtrate layers were separated. The aqueous fraction was extracted with Et$_2$O. The combined organic layers were combined, dried over Na$_2$SO$_4$, and concentrated in vacuo. The yellow solid was triturated with hexanes to give a pale yellow crystalline solid.

Preparation CXXVIII—(2E)-3-[2-(tert-butyl)-5-nitrophenyl]-1-piperidylprop-2-en-1-one 1-(tert-Butyl)-2-bromo-4-nitrobenzene (6.885 g, 26.674 mmol), 1-piperidylprop-2-en-1-one (4.827 g, 34.677 mmol), and TEA (7.44 ml, 53.35 mmol) were dissolved in toluene (70 ml). To this solution was added Pd(OAc)$_2$ (60 mg, 0.267 mmol) and Pd(PPh$_3$)$_4$ (617 mg, 0.5335 mmol). The mix was degassed with N$_2$ and heated in a sealed vessel at 120° C. for 15 h. The reaction mixture was cooled to RT, filtered, and concentrated in vacuo. The dark crude oil was eluted through a silica gel column with 15% to 22% EtOAc/hexanes gradient system to yield a thick amber oil as the title compound.

Preparation CXXIX—3-(5-amino-2-tert-butylphenyl)-1-piperidin-1-yl-propenone (2E)-3-[2-(tert-Butyl)-5-nitrophenyl]-1-piperidylprop-2-en-1-one (3.22 g, 10.177 mmol) was dissolved in dioxane (20 ml) and IpOH (40 ml). To the N$_2$-degassed solution was added Pd/C 10% by weight catalyst (2 g). The mix was placed in a Parr hydrogenator and stirred for 18 h under 60 psi H$_2$. The reaction was not complete the next day, so the reaction was continued for an additional 20 h with fresh catalyst. The mix was filtered through Celite® and concentrated in vacuo to give a foamy oil.

Preparation CXXX—4-(tert-butyl)-3-(3-piperidylpropyl)phenylamine 3-(5-Amino-2-tert-butylphenyl)-1-piperidin-1-yl-propenone (2.312 g, 7.619 mmol) was dissolved in THF (100 ml) at RT. To this solution was added LiAlH$_4$ (434 mg, 11.43 mmol). After the reaction stopped exotherming, it was heated at reflux at about 80° C. for 4 h. The reaction mix was cooled to 0° C. and treated by dropwise addition of 0.458 ml H$_2$O, 0.730 ml 10% aqueous NaOH, and 1.19 ml H$_2$O, respectively. The mix was stirred at RT for 1 h. After 40 min about 3 g of Na$_2$SO$_4$ was added. The mix was filtered through Celite® and concentrated in vacuo. The crude was eluted through silica gel column with a gradient system of 95:5 to 90:10 CH$_2$Cl$_2$/MeOH, to yield an amber thick oil as the title compound.

The following compounds were prepared similarly to the procedure outlined above:

a) 3-((1E)-4-Pyrrolidinylbut-1-enyl)-4-(tert-butyl)phenylamine.
b) 4-(tert-Butyl)-3-(3-pyrrolidinylpropyl)phenylamine.
c) 4-(tert-Butyl)-3-(3-morpholin-4-ylpropyl)phenylamine.
d) 3-[3-(4-methylpiperazinyl)propyl]phenylamine.
e) 4-[3-(4-methylpiperazinyl)propyl]phenylamine.

Preparation CXXXI—3-(3-nitrophenyl)-1-(4-methylpiperazinyl)propan-1-one

A slurry consisting of CH$_2$Cl$_2$ (15 ml), 3-nitrocinnamic acid (3.154 g, 16.329 mmol), 1-methylpiperazine (1.487 g, 14.845 mmol) and EDC (3.557 g, 18.556 mmol) were stirred at RT for 60 h. The reaction was diluted with H$_2$O and EtOAc. The aqueous layer was back-extracted with EtOAc. The combined organic layers were washed with 2N NaOH and then brine, dried over Na$_2$SO$_4$, and concentrated in vacuo. The crude was eluted through a silica gel column with 5% MeOH/CH$_2$Cl$_2$, to yield an off-white solid, mostly trans-olefin compound.

Preparation CXXXII—3-(3-aminophenyl)-1-(4-methylpiperazinyl)propan-1-one

To a N$_2$-degassed solution of 3-(3-nitrophenyl)-1-(4-methylpiperazinyl)propan-1-one (3.67 g, 13.330 mmol) in MeOH (50 ml) was added 10% by weight Pd/C (500 mg). The mix was stirred under H$_2$ atmosphere for 18 h, filtered through Celite® and concentrated in vacuo, yielding a thick amber oil which eventually solidified into a dark pink solid.

The following compounds were prepared similarly to the procedure outlined above:
a) 4-[3-(4-methylpiperazinyl)-3-oxopropyl]phenylamine.

Preparation CXXXIII—1-(2-morpholin-4-ylethyl)indol-6-ylamine

K$_2$CO$_3$ (5.08 g, 36.726 mmol) was added to a slurry of 6-nitroindole (1.985 g, 12.242 mmol), 4-(2-chloroethyl) morpholine HCl (2.278 g, 12.242 mmol), and CH$_3$CN (100 ml). The mix was heated to reflux for 18 h, then cooled to RT, filtered, and concentrated in vacuo. The crude was eluted through a silica gel column with a gradient of 3:97 to 5:95 and finally 8:92 MeOH/CH$_2$Cl$_2$, to yield upon drying the desired intermediate which was hydrogenated under conditions previously described.

Preparation CXXXIV—methyl 2-methyl-2-(4-nitrophenyl) propanoate

To a stirred solution of 2-(4-nitrophenyl)propionic acid (9 g, 46 mmol, 1 eq) in MeOH (300 mL) was added HCl (4M in Dioxane, 11.5 mL, 46 mmol, 1 eq). The mixture was stirred at RT overnight and was quenched with aqueous NaHCO$_3$. The mixture was extracted with EtOAc. The organic layer was dried over MgSO$_4$ and evaporated under reduced pressure and to the partial residue (4.34 g, 20.7 mmol, 1 eq) at 0° C. in THF (100 mL) was added NaH (1.66 g, 41.5 mmol, 2 eq). Mixture was stirred at RT for 1 h and CH$_3$I (2.58 g, 41.5 mmol, 2 eq) was added. Reaction was stirred at RT overnight and was quenched with H$_2$O. Mixture was extracted with EtOAc. The organic layer was dried over MgSO$_4$ and evaporated under reduced pressure and used for the next step without further purification to give title compound.

Preparation CXXXV—3-methyl-3-(4-nitrophenyl)butan-1-one

To a stirred solution of methyl 2-methyl-2-(4-nitrophenyl) propionate (5.32 g, 23.8 mmol) in THF (200 mL) at 0° C. was added a solution of 1M BH$_3$ in THF (25.8 mL, 45.8 mmol). The reaction was stirred at RT overnight and was quenched with MeOH. THF was evaporated under reduced pressure and the residue was diluted in EtOAc and aqueous HCl (1M) was added. The mixture was extracted with EtOAc, the organic layer was dried over MgSO$_4$ and evaporated under reduced pressure. Purification by flash chromatography using 40% EtOAc-hexane gave a yellow solid. To the yellow solid (2.08 g, 10.8 mmol) at 0° C. in CH$_2$Cl$_2$ was added NMO (1.9 g, 16.1 mmol), molecular sieves 4 Å and TPAP (76 mg, 0.2 mmol). The reaction was stirred for 1 h and filtered on a silica pad. Solvent was evaporated under reduced pressure, forming the crude aldehyde which was used as is. To a suspension of methoxymethyltriphenylphosphonium chloride (6.4 g, 18.6 mmol) in THF (150 mL) was added a solution of KHMDS 0.5 M in toluene (37 mL, 18.5 mmol). The mixture was stirred for 30 min and crude aldehyde was added. The reaction was stirred at RT for 1 h and quenched with H$_2$O. The mixture was extracted with EtOAc, dried and evaporated under reduced pressure. Et$_2$O was added and a precipitate formed, which was filtered on a silica pad and rinsed with 40% EtOAc-hexane. The solvent was removed and crude material was dissolved in CH$_2$Cl$_2$. A solution of TFA-H$_2$O (1:1, 10 mL) was added and the reaction was stirred for 2 h at RT Aqueous NaHCO$_3$ was added until pH 7 and the mixture was extracted with CH$_2$Cl$_2$. The organic layer was dried, filtered and evaporated. Crude compound was purified by flash chromatography (40% EtOAc-hexane) to give the title compound as a yellow oil.

Preparation CXXXVI—4-(1,1-dimethyl-3-morpholin-4-ylpropyl)phenylamine

To a stirred solution of 3-methyl-3-(4-nitrophenyl)butan-1-one (509 mg, 2.4 mmol) and morpholine (0.21 mL, 2.4 mmol) in THF (30 mL) was added NaBH(OAc)$_3$ (0.73 g, 3.4 mmol). The mixture was stirred at RT overnight and washed with HCl (1M). CH$_2$Cl$_2$ was added and the layers were separated. The aqueous layer was basified to pH 9 using NaOH 1M and extracted with CH$_2$Cl$_2$. The organic layer was dried and evaporated the nitro compound. To a solution of the nitro compound (0.50 g, 1.8 mmol) in THF (40 mL) was added AcOH (1.97 mmol, 34.5 mmol) followed by zinc (9.1 g, 137 mmol). The mixture was stirred for 1 h, filtered on Celite®, diluted with H$_2$O and aqueous NaHCO$_3$, and the THF layer was evaporated. The residue was extracted with EtOAc, dried and evaporated to give the title compound.

Preparation CXXXVII—4-{2,2,2-trifluoro-1-[2-(2-methoxy)ethoxy]-1-(trifluoromethyl)ethyl}phenylamine Diethyl azodicarboxylate (366 mg, 2.1 mmol) was added drop-wise to a solution of 2-(4-aminophenyl)-1,1,1,3,3,3-hexafluoropropan-2-ol (520 mg, 2 mmol), 2-(2-methoxyethoxy)ethan-1-ol (240 mg, 2 mmol) and PPh$_3$ (550 mg, 2.1 mmol) in THF (10 mL). The mixture was stirred for 2 h, then partitioned between EtOAc and aqueous NaHCO$_3$ solution. The organic phase was washed with brine. After concentration in vacuo, the organic residue was purified by flash chromatography on silica to give the compound. MS: 362 (M+1). Calc'd. for C$_{14}$H$_{17}$F$_6$NO$_3$—361.29.

Preparation CXXXVIII—2-fluoropyridine-3-carbonyl chloride

To a solution of 2-fluoropyridine (10 g, 100 mmol) in THF (150 mL) under −78° C. was added an LDA solution (2M in heptane/THF/ethylbenzene, 60 mL) dropwise. The mixture was stirred at −78° C. for 3 h, then was quenched with a stream of dry CO$_2$. After warming to RT, the mixture was partitioned between EtOAc (100 mL) and H$_2$O (200 mL). The aqueous layer was acidified to pH between 3–4, and extracted with EtOAc. The organic solution was collected and washed with brine and dried over Na$_2$SO$_4$. After removing the solvent in vacuum, 2-fluoropyridine-3-carboxylic acid was obtained as a brown oil. MS: 140 (M−H). Calc'd. for C$_6$H$_4$FNO$_2$—141.10. 2-Fluoropyridine-3-carboxylic acid (7 g) was suspended in SOCl$_2$ (100 mL). After heating under reflux for 2 h, the mixture became homogeneous. Access SOCl$_2$ was removed in vacuo to afford a brown solid as desired compound.

Preparation CXXXIX—N-(3-Amino-5-chloro-phenyl)-2-dimethylamino-acetamide

To a solution of 5-chloro-benzene-1,3-diamine (3 g, 21 mmol) and dimethylamino-acetic acid (2.2 g, 21 mmol) in CH$_2$Cl$_2$ (300 mL) was added EDC (5 g, 25 mmol), HOBt (2.9 g, 21 mmol), and DIEA (5 mL). The reaction mixture was stirred at RT for overnight. Solvent was removed in vacuum and the residue was purified through flash chromatography on silica gel (0–8% MeOH in EtOAc) to give the desired compound.

Preparation CXL—2-amino-4-nitro-benzamide

To a solution of 2-amino-4-nitro-benzoic acid (9.1 g, 50 mmol) in CH$_2$Cl$_2$ (500 mL) was added EDC (12 gram, 60 mmol), HOBt (6.8 g, 50 mmol), DIEA (12 mL), and NH$_3$ in MeOH (2M, 40 mL). The reaction was stirred at RT for overnight, and a precipitation formed. The solid was isolated via vacuum filtration.

Preparation CXLI—6-nitro-3H-quinazolin-4-one

2-Amino-4-nitro-benzamide was suspended in triethyl orthoformate (50 mL) and the mixture was heated to 140° C. for 5 h. Excess reagent was removed in vacuum. The residue was washed in hexanes to give the compound as a yellow solid.

Preparation CXLII—6-amino-3H-quinazolin-4-one

Hydrogenation of 6-nitro-3H-quinazolin-4-one (2 g) in EtOH (200 mL) was catalyzed by Pd/C (10%, 200 mg) under a $H_2$ balloon for 1 h. MeOH (200 mL) was added to the mixture. The suspension was filtered through a layer of Celite® and the filtrate was concentrated in vacuum to give the desired compound.

Preparation CXLIII—(2,4-dinitro-phenyl)-acetic acid methyl ester

To a solution of (2,4-dinitro-phenyl)-acetic acid (5 g) in MeOH (100 mL) was added concentrated $H_2SO_4$ (1 mL) and the resulting solution was heated at reflux for overnight. After removing solvent in vacuum, the residue was partitioned between EtOAc and aqueous $NaHCO_3$ (sat.). The organic solution was concentrated in vacuum to give the desired compound which was used without further purification.

Preparation CXLIV—6-amino-1,3-dihydro-indol-2-one

An EtOH solution of (2,4-dinitro-phenyl)-acetic acid methyl ester was treated with H2 balloon and catalyzed with Pd/C (10%, 500 mg) at RT. The resulting mixture was filtered through a layer of Celite® and concentrated in vacuum to afford the desired compound.

Preparation CXLV—3-Methyl-but-2-enoic Acid (6-bromo-pyridin-2-yl)-amide

To a solution of 2-amino-6-bromopyridine (3.015 g, 0.017 mol) and $Et_3N$ (2.40 mL, 0.017 mol) in $CH_2Cl_2$ (20.0 mL), was added 3,3-dimethylacryloylchloride (1.96 mL, 0.017 mol) under $N_2$ at 0° C. The mixture was slowly warmed to RT and stirred for 12 h. The reaction was quenched by the addition of $H_2O$ (20.0 mL), the organic layer was separated, dried over $Na_2SO_4$ and evaporated to dryness to yield crude compound which was used without purification.

Preparation CXLVI—3-Methyl-but-2-enoic Acid (6-amino-pyridin-2-yl)-amide

To a solution of 3-methyl-but-2-enoic acid (6-bromo-pyridin-2-yl)-amide (4.30 g, 0.017 mol) and copper (0.214 g, 3.372 mmol) in IpOH (20.0 mL), was added $NH_4OH$ (20.0 mL) in a sealed vessel under $N_2$. The reaction was sealed and heated to 90° C. for 12 h. The reaction mixture was cooled to RT and EtOAc (50.0 mL) was added. The organic layer was separated, and then the aq layer was washed with EtOAc (50.0 mL). Combined organic layers were evaporated to dryness, the resulting residue was dissolved in $CH_2Cl_2$ (50.0 mL) and washed with $H_2O$ (4×30 mL). The organic layer was dried over $Na_2SO_4$ and evaporated to dryness to yield crude aminopyridine which was used without purification.

Preparation CXLVII—7-Amino-4,4-dimethyl-3,4-dihydro-1H-[1,8]naphthyridin-2-one

To a mixture of aminopyridine (1.12 g, 5.833 mmol) and $AlCl_3$ (3.11 g, 0.023 mol) was added chlorobenzene (10.0 mL) in a sealed vessel under Ar. The reaction was sealed and heated to 120° C. for 12 h. The reaction mixture was cooled to RT and the mixture was poured over ice/HCl mixture and extracted with EtOAc (3×50.0 mL). The aqueous layer was neutralized via addition of solid $NaHCO_3$ and extracted with EtOAc (5×50 mL). Combined organic layers were dried over $Na_2SO_4$ and evaporated to dryness to yield crude compound. Chromatography (Silica gel, $CH_2Cl_2$:MeOH, 99:1) yielded pure naphthyridin.

Preparation CXLVIII—2-[1-(3-Amino-phenyl)-2,2,2-trifluoro-1-trifluoromethyl-ethoxymethyl]-pyrrolidine-1-carboxylic acid tert-butyl ester To a mixture of 2-(3-amino-phenyl)-1,1,1,3,3,3-hexafluoro-propan-2-ol (1.30 g), 2-hydroxymethyl-pyrrolidine-1-carboxylic acid tert-butyl ester (1.04 g), $PPh_3$ (2.64 g) and molecular sieves 4 Å in THF (100 mL) was added diethyl diazocarboxylate (1.55 mL) slowly. The reaction was stirred at RT for 4 h and at reflux for overnight. After filtration to remove solids, the filtrate was concentrated and the residue was taken into $Et_2O$. The organic phase was washed with saturated $NaHCO_3$ and brine. The organic layer was dried over $MgSO_4$ and evaporated to give a crude compound as very viscous brown oil, which was purified by chromatography through silica gel (500 g, 30% to 50% EtOAc in hexanes) to afford 2-[1-(3-amino-phenyl)-2,2,2-trifluoro-1-trifluoromethyl-ethoxymethyl]-pyrrolidine-1-carboxylic acid tert-butyl ester as a light brown oil.

Preparation CXLIX—Pyrimidine-4-carbaldehyde oxime 9.14 g (97.11 mmol) of 4-methylpyrimidine was slowly added to a 0° C. solution of 8.75 g HCl in 40 ml EtOH. To this white suspension was added, over 5 min, 61 ml of a 10–20% by weight solution of ethyl nitrite in EtOH. The reaction was stirred at 0° C. for 10 min and at RT for 2.5 h. The white salt was filtered and dried under vacuum. The salt was dissolved into 20 ml $H_2O$ and very slowly treated with about 200 ml sat. aq. $KHCO_3$. A white solid precipitated out of the purple solution. The solid was filtered and dried under vacuum to yield the titled compound.

Preparation CL—C-Pyrimidin-4-yl-methylamine dihydrogen chloride

To a solution of 3.549 g (28.82 mmol) pyrimidine-4-carbaldehyde oxime in 200 ml MeOH was added after degassing with Ar, 800 mg of 10% by weight Pd/C. The mix was stirred under $H_2$ for 4 h, then filtered through a Celite® plug. The solution was concentrated under vacuum to a volume of about 50 ml and then treated carefully with 30 ml of 4N HCl in dioxane. The mix was concentrated and dried under vacuum to yield the titled compound as a pink solid.

Preparation CLI—2-(2,4-Dinitro-phenyl)-3,3,3-trifluoro-2-trifluoromethyl-propionic acid methyl ester A mixture of 7.08 g (38.07 mmol) 2,4-dinitrofluorobenzene, 2.43 g (41.88 mmol) KF, and 0.58 g (2.21 mmol) 18-crown-6-ether in 37 ml sulfolane was added 4.00 g (19.04 mmol) methyl 2-(trifluoromethyl)-3,3,3-trifluoropropionate dropwise over about 7 h via syringe pump. After the addition was complete, another 2.43 g KF, 0.58 g 18-Crown-6-ether were added and then 4.00 g Methyl 2-(trifluoromethyl)-3,3,3-trifluoropropionate were added dropwise over 12 h. The next day, repeated additions using same amounts and setting syringe pump addition over 14 h. The following day, the additions were again repeated, this time using half the amounts as above additions and setting syringe pump addition at 12 h. After addition was completed, the reaction mix was cooled to RT and diluted into $Et_2O$ and 0.5N aqueous HCl. The layers were separated, and the organic layer was washed with brine, dried over $Na_2SO_4$, filtered and concentrated under vacuum. The crude was eluted on a silica gel column with EtOAc/hexanes gradient, to yield the titled compound, as a yellow solid. [See Vlasov et al.; J.Org. Chemistry USSR (Engl. Trans.); 15; 1979; 1953–1964).]

Preparation CLII—6-Amino-1-hydroxy-3,3-bis-trifluoromethyl-1,3-dihydro-indol-2-one To an argon-degassed solution of 5.13 g (13.64 mmol) 2-(2,4-dinitro-phenyl)-3,3,3-trifluoro-2-trifluoromethyl-propionic acid methyl ester in 300 ml EtOH was added 0.5 g of 10% by weight Pd/C. The reaction was stirred under $H_2$ overnight and filtered through Celite®, concentrated down, and dried under vacuum, yielding the titled compound.

Preparation CLIII—6-Amino-3,3-bis-trifluoromethyl-1,3-dihydro-indol-2-one

To a solution of 1.245 g (4.151 mmol) 6-amino-1-hydroxy-3,3-bis-trifluoromethyl-1,3-dihydro-indol-2-one in 80 ml THF was added 3.565 ml (62.27 mmol) glacial AcOH and 19 g (290.6 mmol) Zinc dust (100 mesh). The reaction was stirred 40 min at RT and then 5 h at reflux. The reaction was cooled to RT. The solvent was decanted and concentrated, then dissolved in EtOAc and filtered through Celite®. The EtOAc solution was then washed with saturated aqueous $NaHCO_3$ and brine, dried over $Na_2SO_4$, filtered, and concentrated and dried under vacuum, to yield the titled compound, as a yellow solid.

Preparation CLIV—N-[3-(2-Amino-ethoxy)-4-pentafluoroethyl-phenyl]-2-chloro-nicotinamide To a solution of 500 mg (0.98 mmol) Boc-N-[3-(2-Amino-ethoxy)-4-pentafluoroethyl-phenyl]-2-chloro-nicotinamide in 10 ml $CH_2Cl_2$ was added 10 ml TFA and stirred for 2 h. The reaction was concentrated down, treated with 6N NaOH, and extracted 3 times with $CH_2Cl_2$. The combined organic extracts were dried over $Na_2SO_4$, filtered, concentrated down, and dried under vacuum, yielding the titled compound.

Preparation CLV—2-Chloro-N-[3-(2-methanesulfonyl-amino-ethoxy)-4-pentafluoroethyl-phenyl]-nicotinamide To a solution of 381 mg (0.93 mmol) N-[3-(2-amino-ethoxy)-4-pentafluoroethyl-phenyl]-2-chloro-nicotinamide in 10 ml $CH_2Cl_2$ at 0° C. was added 0.389 ml $Et_3N$ and 0.072 ml (0.93 mmol) methanesulfonylchloride. After 5 min, the reaction was stirred at RT for 30 min. The reaction was diluted with $CH_2Cl_2$, washed with brine, dried over $Na_2SO_4$, filtered, concentrated, and dried under vacuum, yielding the titled compound as a white foamy solid.

Preparation CLVI—2-Methyl-2-(4-nitro-phenyl)-propionic acid

To a solution of 2-(4-nitro-phenyl)-propionic acid (50 g, 0.26 mole) in 250 mL of MeOH was added 6 mL of concentrated HCl. The resulting solution was heated at reflux for 16 h. Then the resultant mixture was diluted with 200 mL of aq. $NaHCO_3$ and 500 mL of EtOAc. The organic layer was separated, dried over $Na_2SO_4$, and concentrated. The residue was diluted with 100 mL of THF and added to a suspension of NaH (11.2 g, 0.28 mole, 60% in mineral oil) in 600 mL of THF. To the resulting mixture was added $CH_3I$ (18.3 mL, 0.29 mole) in one portion. The resulting mixture was stirred for 48 h at 40° C., then diluted with aq. $NH_4Cl$ solution and EtOAc. The organic layer was separated, dried over $Na_2SO_4$, and concentrated. The residue was used without further purification.

To a solution of the residue (54 g, 0.24 mole) in 500 ml of MeOH was added 5N aq. NaOH (144 mL, 0.72 mole). The mixture was stirred for 16 h at 40° C. The resulting mixture was concentrated, the residue was diluted with $H_2O$ (500 mL), and acidified with 2N HCl to give a precipitate. The precipitate was filtered and dried to give the titled compound as a yellowish solid. MS: 210 (M+1), Calc'd for $C_{10}H_{12}NO_4$—210.20.

Preparation CLVII—2-Methyl-5-[1-methyl-1-(4-nitro-phenyl)-ethyl]-[1,3,4]oxadiazole A mixture of 2-methyl-2-(4-nitro-phenyl)-propionic acid (5 g, 24 mmol.) and a few drops of DMF in $SOCl_2$ was stirred at reflux for 16 h. The resulting solution was concentrated to give corresponding acid chloride as a brown solid. To a mixture of the acid chloride (2.33 g, 10.2 mmol), acetic acid hydrazide (0.91 g, 12.2 mmol.), $Et_3N$ (2.86 mL, 20.2 mmol.) in $CH_2Cl_2$ (50 mL) was added 2 crystals of DMAP at RT. The mixture was stirred for 16 h and concentrated. A solution of the residue in 50 mL of phosphorous oxychloride was heated at 95° C. for 16 h. The mixture was concentrated and diluted with ice-water and EtOAc. The organic layer was washed with saturated aq. $NaHCO_3$ solution twice, dried over $Na_2SO_4$, and concentrated. The residue was purified by $SiO_2$ chromatography (hexane:EtOAc=1:1) to give the titled compound as a pale yellow crystal. MS: 248 (M+1), Calc'd for $C_{12}H_{14}N_3O_3$—248.10.

Preparation CLVIII—2-Methyl-5-[1-methyl-1-(4-amino-phenyl)-ethyl]-[1,3,4]oxadiazole A mixture of 2-methyl-5-[1-methyl-1-(4-nitro-phenyl)-ethyl]-[1,3,4]oxadiazole (1.36 g, 5.5 mmol.) and Pd/C (68 mg) in EtOAc (50 mL), was stirred under 1 atm of $H_2$ for 16 h. The resultant was filtered over Celite®, and the filtrate was concentrated to give the titled compound as a pale yellow crystalline. MS: 218 (M+1) calc'd for $C_{12}H_{16}N_3O$—218.12.

Preparation CLIX—4-[1-Methyl-1-(4-nitro-phenyl)-ethyl]-pyrimidine

To a mixture of 1-(4-nitro-phenyl)-propan-2-one (5.32 g, 29.7 mmol.), triethylbenzylammonium chloride (0.34 g, 1.5 mmol.), and 13 mL of aq. 5N KOH solution (65.3 mmol.) in $CH_2Cl_2$ was added $CH_3I$ (4.06 mL, 65.3 mmol.). The resulting mixture was stirred at 40° C., and then diluted with EtOAc and $H_2O$. The organic layer was dried and concentrated. To the residue (1.0 g, 4.8 mmol.) in toluene (30 mL) was added dimethylformamide dimethylacetal (1.27 mL, 9.6 mmol.). The resulting mixture was heated at reflux for 6 h then concentrated to give 1-dimethylamino-4-methyl-4-(4-nitro-phenyl)-pent-1-en-3-one as a yellow solid (MS 263 (M+1) Calc'd for $C^{14}H_{19}N_2O_3$—263.13).

A mixture of 1-dimethylamino-4-methyl-4-(4-nitro-phenyl)-pent-1-en-3-one (0.5 g, 1.9 mmol.), formamidine HCl (0.305 g, 3.8 mmol.), and NaOEt (1.29 g, 4.0 mmol) was heated in Smith synthesizer under microwave for 10 min at 150° C. The resultant mixture was diluted with $H_2O$ and EtOAc. The organic layer was dried, and the residue was used without further purification. MS: 244 (M+1) Calc'd for $C_{13}H_{14}N_3O_2$—244.10.

Preparation CLX—5-[1-Methyl-1-(4-nitro-phenyl)-ethyl]-1H-pyrazole

A mixture of 1-dimethylamino-4-methyl-4-(4-nitro-phenyl)-pent-1-en-3-one (0.36 g, 1.4 mmol.) and hydrazine hydrate (1.0 g, 6.25 mmol.) in EtOH was heated at 50° C. for 3 h. The mixture was concentrated, and the residue was diluted with $H_2O$ and EtOAc. The organic layer was dried over $Na_2SO_4$ and concentrated to give the titled compound as a yellow solid. MS: 232 (M+1) Calc'd for $C_{12}H_{14}N_3O_2$—232.10.

Preparation CLXI—2-tert-Butyl-5-nitro-phenylamine

Concentrated $H_2SO_4$ (1 L) was cooled to −10° C. with a dry ice IpOH bath in a 2 L 3-neck round bottom flask fitted with a mechanical stirrer and temperature probe. 2-t-Butylaniline (109 g, 730 mmol) was added, giving a clumpy solid. Once the temperature of the mixture was stabilized at −10° C., $KNO_3$ (101 g, 1001 mmol) was added portion-wise, as the solid, over 4 h, maintaining the temperature between −20 and −5° C. Once all of the $KNO_3$ was added, the reaction was stirred overnight with gradual warming to RT. The reaction was quenched by diluting with $H_2O$ and extracting 3× with EtOAc. The EtOAc extracts were washed multiple times with saturated $NaHCO_3$(aq), until gas evolution ceased, then with brine. The EtOAc extracts were combined, dried over anhydrous $Na_2SO_4$, filtered and concentrated under reduced pressure giving a black oil. The oil was eluted through a 36×7 cm column of silica gel with a 5%; 10%; 15%; 25%; and 50% EtOAc:Hexanes step gradient (2 L each step) giving 2-tert-butyl-5-nitro-phenylamine as a red solid.

Preparation CLXII—2-Bromo-N-(2-tert-butyl-5-nitro-phenyl)-acetamide 2-tert-Butyl-5-nitro-phenylamine (70 g, 359 mmol) and a catalytic amount of DMAP were dissolved in THF (1.5 L) under $N_2$. TEA (109 g, 1077 mmol) was added and the solution was cooled to 0° C. Bromoacetyl bromide (207 g, 1023 mmol) was added and the reaction was gradually warmed to RT with stirring overnight. The reaction was partially concentrated under reduced pressure, treated with $H_2O$ and extracted with EtOAc (3x). The EtOAc extracts were washed with brine, combined, dried over anhydrous $Na_2SO_4$, filtered and concentrated under reduced pressure giving a black oil. This oil was eluted through a 38×7 cm column of silica gel with 95:5:0.5 $CH_2Cl_2$:MeOH:$NH_4OH_{(aq)}$ eluant giving 2-bromo-N-(2-tert-butyl-5-nitro-phenyl)-acetamide as a brown solid.

Preparation CLXIII—N-(2-tert-Butyl-5-nitro-phenyl)-2-dimethylamino-acetamide

2-Bromo-N-(2-tert-butyl-5-nitro-phenyl)-acetamide (80 g, 253 mmol) and $K_2CO_3$ (70 g, 506 mmol) were combined in a 3-L 3-neck round bottom flask fitted with a mechanical stirrer, $N_2$ inlet, and pressure equalizing addition funnel. THF (1.75 L) was added and the mixture was cooled to 0° C. under $N_2$. DMA (400 mL of a 2 M solution in THF, 800 mmol) was added to the mixture through the pressure equalizing addition funnel over 30 min. The mixture was gradually warmed to RT with stirring overnight. The reaction was quenched by filtering it under vacuum and then concentrating the filtrate under reduced pressure. The recovered material was eluted through a 36×7 cm column of silica gel with 50% EtOAc:Hexanes giving N-(2-tert-butyl-5-nitro-phenyl)-2-dimethylamino-acetamide as a brown solid.

The pyrolidino and morpholino analogs are prepared by substituting the dimethylamine with respectively pyrolidine or morpholine and using the same chemistry as described.
a) N-(2-tert-Butyl-5-nitro-phenyl)-2-pyrrolidin-1-yl-acetamide.
b) N-(2-tert-Butyl-5-nitro-phenyl)-2-morpholin-4-yl-acetamide.

Preparation CLXIV—N-(5-Amino-2-tert-butyl-phenyl)-2-dimethylamino-acetamide

N-(2-tert-Butyl-5-nitro-phenyl)-2-dimethylamino-acetamide (25.8 g, 92 mmol) was dissolved in EtOH (1.4 L) and 1,4-dioxane (200 mL). The solution was degassed under vacuum with stirring. 10% Pd/C (2.5 g) was added (as a slurry in EtOH). The mixture was degassed again, then the reaction vessel was charged with $H_2$ gas (balloon) and stirred overnight at RT. The reaction was filtered through Celite® with MeOH and the filtrate was concentrated under reduced pressure. The recovered material was eluted through a 36×7 cm column of silica gel with a 97.5:2.5:0.25 and 95:5:0.5 $CH_2Cl_2$:MeOH:$NH_4OH$(aq) step gradient giving N-(5-amino-2-tert-butyl-phenyl)-2-dimethylamino-acetamide as a brown solid.

Preparation CLXV—5-Chloro-1-methyl-1H-pyrazole-4-carboxylic Acid (4-tert-butyl-phenyl)-amide 5-Chloro-1-methyl-1H-pyrazole-4-carbonyl chloride (1.0 g, 5.6 mmol) was dissolved in $CH_2Cl_2$ (100 mL) under $N_2$ and cooled to 0° C. 4-L-Butylaniline was added and the reaction was stirred with gradual warming to RT overnight. The reaction was quenched with saturated $NaHCO_3$(aq) and extracted 3x with fresh $CH_2Cl_2$. The $CH_2Cl_2$ extracts were washed with brine, combined, dried over anhydrous $Na_2SO_4$, filtered and concentrated under reduced pressure giving 5-chloro-1-methyl-1H-pyrazole-4-carboxylic acid (4-tert-butyl-phenyl)-amide as a foamy pink solid.

Preparation CLXVI—1,2-dihydro-3-spiro-1'-cyclopropyl-1H-indole

A solution of 3-(2-bromo-ethyl)-1H-indole (5 g) in anhydrous $CH_3CN$ (100 mL) was suspended with oven dried $K_2CO_3$ (20 g) and heated to reflux for 10 h. After cooling to RT, the mixture was filtered and the filter cake was washed with EtOH (50 mL). The combined filtrate was treated with $NaBH_4$ (300 mg) and stirred for 3 h at RT. Solvents were removed in vacuo and the residue was partitioned between $H_2O$ (160 mL) and EtOAc (60 mL). The organic layer was extracted with aqueous HCl (0.5N, 30 mL×2). The acid layer was basified with $NH_4OH$ (aq. Conc.) and extracted with EtOAc. The organic phase was washed with brine and dried over $Na_2SO_4$ and concentrated to give the desired compound as a colorless thin oil.

Preparation CLXVII—6-nitro-1,2-dihydro-3-spiro-1'-cyclopropyl-1H-indole

1',2'-Dihydrospiro(cyclopropane-1,3'-[3H]indole) (1.8 g 12.4 mmol) was added in dropwise over a period of 20 min to a cooled (−5 to −10° C.) solution of $NaNO_3$ (1.3 g) in $H_2SO_4$ (conc., 30 mL). After the addition, the reaction was stirred for another 40 min., then the mixture was poured onto crushed ice (200 g) and the resulting mixture was basified with $NH_4OH$ (aq., conc.) with cooling. The basified mixture was extracted with EtOAc twice and the organic layer was washed with brine then dried over $Na_2SO_4$. After concentration in vacuo, the compound was isolated as a dark gray solid.

Preparation CLXVIII—Ethyl 6-nitro-1,2-dihydro-3-spiro-1'-cyclopropyl-1H-indole-1-carbamate A solution of 6-nitro-1,2-dihydro-3-spiro-1'-cyclopropyl-1H-indole (2.7 g) in $CH_2CL_2$ (100 mL) was suspended with $NaHCO_3$ (5 g), and ethyl chloroformate was added dropwise with vigorous stirring. After the addition, the reaction was stirred overnight. The mixture was washed with $H_2O$ (100 mL), then dried over $Na_2SO_4$ and concentrated in vacuo. The residue was recrystalized in MeOH to give the title compound as a dark gray crystalline.

Preparation CLXIX—Ethyl 6-amino-1,2-dihydro-3-spiro-1'-cyclopropyl-1H-indole-1-carbamate Ethyl 6-nitro-1,2-dihydro-3-spiro-1'-cyclopropyl-1H-indole-1-carbamate (2.1 g) was dissolved in EtOH (200 mL), suspended with Pd/C (10%, 560 mg) and equipped with a balloon filled with $H_2$. The hydrogenation was finished in 3 h. The reaction mixture was filtered through a layer of Celite®. The filtrate was concentrated in vacuo to give the desired product as a white solid.

Preparation CLXX—4-[1-Methyl-1-(4-nitro-phenyl)-ethyl]-3,6-dihydro-2H-pyridine-1-carboxylic acid ethyl ester 1-Methyl-4-[1-methyl-1-(4-nitro-phenyl)-ethyl]-1,2,3,6-tetrahydro-pyridine (5.2 g) was dissolved in toluene (100 mL) and ethyl chloroformate (2.4 g). The mixture was heated at reflux for overnight and cooled to RT. The toluene solution was washed with $NaHCO_3$ (aq., sat., 100 mL) then brine (100 mL) and dried over $Na_2SO_4$. The organic phase was concentrated in vacuo to give the desired compound which was used without purification.

Preparation CLXXI—4-[1-Methyl-1-(4-amino-phenyl)-ethyl]-3,6-dihydro-2H-pyridine-1-carboxylic Acid Ethyl Ester 4-[1-Methyl-1-(4-nitro-phenyl)-ethyl]-3,6-dihydro-2H-pyridine-1-carboxylic acid ethyl ester was dissolved in EtOH (150 mL) and suspended with Pd/C (10%, 1 g). The reaction flask was equipped with a balloon filled with $H_2$. The hydrogenation was continued for 3 days. The mixture was filtered through a layer of Celite® and concentrated in vacuo to provide the desired compound as a light brown oil.

Preparation CLXXII: 3,3-dimethyl-6-nitroindoline 3-Methyl-but-2-enoic Acid (3-acetylamino-phenyl)-amide 3,3-Dimethylacryloyl chloride (3.3 ml, 29.3 mmol) was added to a mixture of 3'-aminoacetanilide (4.40 g, 29.3 mmol) and Et$_3$N (4.5 ml, 32.2 mmol) in 50 ml of CH$_2$Cl$_2$ and 25 ml of THF at 0° C. under N$_2$. The mixture was stirred at RT overnight, diluted with 100 ml of CH$_2$Cl$_2$, washed with aqueous Na$_2$CO$_3$, then brine, condensed, and purified by flash column chromatography (15 to 30% of EtOAc in CH$_2$Cl$_2$). The titled compound was obtained as an off-white solid. MS (ES$^+$): 233.1 (M+H)$^+$. Calc'd for C$_{13}$H$_{16}$N$_2$O$_2$—232.28.

The following compounds were prepared similarly to the procedure outlined above:
a) 3-Methyl-but-2-enoic acid phenylamide. MS (ES$^+$): 176.1 (M+H)$^+$. Calc'd for C$_{11}$H$_{13}$NO—175.23.

Preparation CLXXIII—N-(4,4-Dimethyl-2-oxo-1,2,3,4-tetrahydro-quinolin-7-yl)-acetamide The mixture of 3,3-dimethyl-6-nitroindoline 3-methyl-but-2-enoic acid (3-acetylamino-phenyl)-amide (1.05 g, 4.52 mmol) and AlCl$_3$ (5.0 g, 37.5 mmol, Aldrich, 99.99%) in 50 ml of anhydrous chlorobenzene was stirred at 120° C. (oil bath temperature) under N$_2$ overnight, cooled to RT, poured into 10 ml of ice cold HCl, stirred for 30 min, and extracted with EtOAc. The organic portions were combined, washed with brine, dried with Na$_2$SO$_4$, filtered, condensed, and purified by flash column chromatography (1% of MeOH in CH$_2$Cl$_2$). The title compound was obtained as an off-white solid. MS (ES$^+$): 233.2 (M+H)$^+$. Calc'd for C$_{13}$H$_{16}$N$_2$O$_2$—232.28.

The following compounds were prepared similarly to the procedure outlined above:
a) 4,4-Dimethyl-3,4-dihydro-1H-quinolin-2-one MS (ES$^+$): 175.6 (M+H)$^+$. Calc'd for C$_{11}$H$_{13}$NO—175.23.

Preparation CLXXIV: 7-Amino-4,4-dimethyl-3,4-dihydro-1H-quinolin-2-one

N-(4,4-Dimethyl-2-oxo-1,2,3,4-tetrahydro-quinolin-7-yl)-acetamide (1.50 g, 6.46 mmol) in 10 ml of HCl (concentrated, 37%) and 30 ml of EtOH was stirred at 75° C. for 4 h. The solvents were removed under reduced pressure. The residue was dissolved in EtOAc/H$_2$O, neutralized with NaHCO$_3$, washed with brine, dried with Na$_2$SO$_4$, filtered, and condensed to give the titled compound as an off-white solid. MS (ES$^+$): 191.2 (M+H)$^+$. Calc'd for C$_{11}$H$_{14}$N$_2$O—190.24.

Preparation CLXXV—4,4-Dimethyl-1,2,3,4-tetrahydro-quinolin-7-ylamine

The mixture of 7-amino-4,4-dimethyl-3,4-dihydro-1H-quinolin-2-one (1.07 g, 5.62 mmol) and borane dimethylsulfide complex (1.60 ml, 16.9 mmol) in 40 ml of anhydrous THF was heated at reflux under N$_2$ for 15 h. The solvents were removed under reduced pressure. The residue was heated at reflux in 20 ml of MeOH for 2 h, then 0.80 g of NaHCO$_3$ was added, and the mixture was heated at reflux for 2 h. The mixture was filtered, condensed, and the residue was purified by flash column chromatography (5 to 10% of EtOAc in CH$_2$Cl$_2$). The titled compound was obtained as a viscous oil. MS (ES$^+$): 176.9 (M+H)$^+$. Calc'd for C$_{11}$H$_{16}$N—176.26.

The following compounds were prepared similarly to the procedure outlined above:
a) 4,4-Dimethyl-1,2,3,4-tetrahydroquinoline MS (ES$^+$): 162.5 (M+H)$^+$. Calc'd for C$_{11}$H$_{15}$N—161.24.

Preparation CLXXVI—N-(4,4-Dimethyl-1,2,3,4-tetrahydro-quinolin-7-yl)-2-fluoronicotinamide The mixture of 4,4-dimethyl-1,2,3,4-tetrahydro-quinolin-7-ylamine (0.20 g, 1.13 mmol), 2-fluoronicotinic acid (0.16 g, 1.13 mmol), TBTU (0.36 g, 1.13 mmol), and DIEA (0.24 ml, 1.36 mmol) in 5 ml of DMF was stirred at RT for 3 h, then partitioned between EtOAc and Na$_2$CO$_3$ (aq). The organic layer was washed with H$_2$O, brine, dried with MgSO$_4$, filtered, condensed, and the residue was purified by flash column chromatography (20 to 30% of EtOAc in CH$_2$Cl$_2$). The titled compound was obtained as an off-white solid. MS (ES$^+$): 300.1 (M+H)$^+$. Calc'd for C$_{17}$H$_{18}$FN$_3$O—299.34.

The following compounds were prepared similarly to the procedure outlined above:
a) N-(4,4-Dimethyl-2-oxo-1,2,3,4-tetrahydro-quinolin-7-yl)-2-fluoronicotinamide, as an off-white solid. MS (ES$^+$): 314.2 (M+H)$^+$. Calc'd for C$_{17}$H$_{16}$FN$_3$O$_2$—313.33.
b) N-(1-Ethyl-4,4-dimethyl-1,2,3,4-tetrahydro-quinolin-7-yl)-2-fluoronicotinamide, MS (ES$^+$): 328.3 (M+H)$^+$. Calc'd for C$_{19}$H$_{22}$FN$_3$O—327.40.

Preparation CLXXVII—4,4-Dimethyl-7-nitro-1,2,3,4-tetrahydro-quinoline

To 13 ml of H$_2$SO$_4$ (96%) cooled in a salt ice bath was added dropwise 4,4-dimethyl-1,2,3,4-tetrahydro-quinoline (5.80 g, 36.0 mmol). The resulting slurry was stirred for 30 min, upon when concomitant addition of HNO$_3$ (90%, 1.70 ml, 36.0 mmol) and H$_2$SO$_4$ (96%, 7 ml) was started, the addition was finished in 20 min, the mixture was stirred at 0° C. to 15° C. for 2 h, poured into ice, and extracted with EtOAc. The organic portion was washed with brine, condensed, and purified by flash column chromatography (0 to 10% of EtOAc in hexanes). The titled compound was obtained as a yellow oil. MS (ES$^+$): 206.9 (M+H)$^+$. Calc'd for C$_{11}$H$_{14}$N$_2$O$_2$—206.24.

Preparation CLXXVIII—1-Ethyl-4,4-dimethyl-7-nitro-1,2,3,4-tetrahydroquinoline

The mixture of 4,4-dimethyl-7-nitro-1,2,3,4-tetrahydro-quinoline (0.48 g, 2.33 mmol), iodoethane (0.21 ml, 2.56 mmol), and NaH (60%, 0.10 g, 2.5 mmol) in 10 ml of DMF was stirred at RT overnight, and partitioned between EtOAc and H$_2$O. The combined organic portions were washed with brine, dried with MgSO$_4$, filtered, and condensed. The crude compound was purified by flash column chromatography (5 to 10% of CH$_2$Cl$_2$ in hexanes). The titled compound was obtained as a yellow oil. MS (ES$^+$): 235.3 (M+H)$^+$. Calc'd for C$_{13}$H$_{18}$N$_2$O$_2$— 234.29.

Preparation CLXXIX: 1-Ethyl-4,4-dimethyl-1,2,3,4-tetrahydro-quinolin-7-ylamine

The mixture of 1-ethyl-4,4-dimethyl-7-nitro-1,2,3,4-tetrahydro-quinoline (0.28 g) and Pd/C (0.060 g, 10% wt) in 10 ml of EtOAc was placed under H$_2$ which was provided by a balloon and stirred at RT overnight. Then the mixture was filtered through Celite®, condensed, and the residue was purified by flash column chromatography (2% of EtOAc in CH$_2$Cl$_2$). The titled compound was obtained as a pink oil. MS (ES$^+$): 204.8 (M+H)$^+$. Calc'd for C$_{11}$H$_{16}$N—204.31.

Preparation CLXXX—1-(4-Nitro-phenyl)-cyclopropanecarbonitrile

NaOH (5.0 N, 80 ml) was added to a mixture of 4-nitrophenylacetonitrile (10.0 g, 61.7 mmol), 1,2-dibromoethane (8.0 ml, 92.5 mmol), and tetraethylammonium chloride hydrate (10.2 g, 61.7 mmol) in 200 ml of CH$_2$Cl$_2$ at RT. The resulting mixture was stirred at RT for 24 h, diluted with CH$_2$Cl$_2$, and acidified with HCl (10%, aq). The organic layer was separated, washed with brine, condensed, and the crude was purified by flash column chromatography. The titled compound was obtained as a light yellowish solid.

Preparation CLXXXI—C-[1-(4-Nitro-phenyl)-cyclopropyl]-methylamine

The mixture of 1-(4-nitro-phenyl)-cyclopropanecarbonitrile (3.0 g, 15.9 mmol) and borane THF complex (1.0 M solution in THF, 32 ml, 32 mmol) in 50 ml of anhydrous THF was heated at reflux overnight. The mixture was cooled to RT, quenched with 2.5 ml of 50% AcOH aqueous solution, then partitioned between EtOAc and NaHCO$_3$ (aq). The combined organic portions were washed with brine, dried with MgSO$_4$, filtered, and condensed. The crude was purified by flash column chromatography (1 to 2% of MeOH in CH$_2$Cl$_2$). The titled compound was obtained as a light brownish solid. MS (ES$^+$): 192.9. Calc'd for C$_{10}$H$_{12}$N$_2$O$_2$—192.2.

Preparation CLXXXII—2,2,2-Trifluoro-N-[1-(4-nitro-phenyl)-cyclopropylmethyl]-acetamide Trifluoroacetic anhydride (5.26 ml, 36.9 mmol) was added to a mixture of C-[1-(4-nitro-phenyl)-cyclopropyl]-methylamine (2.37 g, 12.3 mmol) and triethyl amine (8.6 ml, 61.5 mmol) in 50 ml of CH$_2$Cl$_2$ at RT. The resulting mixture was stirred for 2 h. The volatiles were removed under reduced pressure and the residue was partitioned between EtOAc and aqueous NaHCO$_3$. The organic layer was washed with brine, dried with MgSO$_4$, filtered, and condensed. The crude compound was purified by flash column chromatography (10 to 20% of EtOAc in hexanes), and the titled compound was obtained as an off-white solid.

Preparation CLXXXIII—1-(7-Nitro-4-spiro-1'-cyclopropane-3,4-dihydro-1H-isoquinolin-2-yl)-2,2,2-trifluoroethanone A mixture of 2,2,2-trifluoro-N-1-(4-nitro-phenyl)-cyclopropylmethyl]-acetamide (3.10 g, 10.7 mmol) and paraformaldehyde (0.54 g, 17.2 mmol) was added to a mixture of 12 ml of glacial AcOH and 20 ml of H$_2$SO$_4$ at RT. The resulting mixture was stirred at 40° C. for 12 h, poured into ice-water and extracted with EtOAc. The combined organic portion was washed with NaHCO$_3$ (aq), H$_2$O, brine, then dried with MgSO$_4$, and condensed. The crude compound was purified by flash column chromatography (10 to 20% of EtOAc in hexanes), and the titled compound was obtained as a white solid.

Preparation CLXXXIV—7-Nitro-4-spiro-1'-cyclopropane-1,2,3,4-tetrahydroisoquinoline A mixture of 1-(7-nitro-4-spiro-1'-cyclopropane-3,4-dihydro-1H-isoquinolin-2-yl)-2,2,2-trifluoroethanone (0.32 g, 1.07 mmol) and K$_2$CO$_3$ (1.50 g, 14.2 mmol) in 7 ml of MeOH and 2 ml of H$_2$O was stirred at RT overnight. The mixture was filtered, and the filtrate was concentrated. The residue was dissolved in EtOAc, washed with NH$_4$Cl (aq), brine, dried with MgSO$_4$, filtered, and condensed to give the titled compound as a light yellowish solid. MS (ES$^+$): 204.9 (M+H)$^+$. Calc'd for C$_{11}$H$_{12}$N$_2$O$_2$—204.23.

Preparation CLXXXV—tert-Butyl N-[7-nitro-4-spiro-1'-cyclopropane-3,4-dihydro-1H-isoquinoline-2-carbamate The mixture of 7-nitro-4-spiro-1'-cyclopropane-1,2,3,4-tetrahydroisoquinoline (0.20 g, 0.98 mmol), BOC$_2$O (0.24 g, 1.08 mmol), DMAP (0.025 g, 0.20 mmol), DIEA (0.51 ml, 2.94 mmol) in 10 ml of CH$_2$Cl$_2$ was stirred at RT for 2 h. The solvent was removed, the residue was purified by flash column chromatography (5 to 10% of EtOAc in hexanes), and the titled compound was obtained as a white solid.

Preparation CLXXXVI: tert-Butyl N-[7-amino-4-spiro-1'-cyclopropane-3,4-dihydro-1H-isoquinoline]carbamate A mixture of tert-butyl N-[7-nitro-4-spiro-1'-cyclopropane-3,4-dihydro-2H-isoquinoline-2-carbamate (0.27 g, 0.89 mmol) and Pd/C (0.05 g, 10% wt) in 15 ml of MeOH was placed under H$_2$ which was provided by a balloon and stirred at RT for 1.5 h. The mixture was filtered through Celite®, and condensed to give the titled compound as a white solid. MS (ES$^+$): 274.8 (M+H)$^+$. Calc'd for C$_{16}$H$_{22}$N$_2$O$_2$—274.36.

Preparation CLXXXVII—4-methyl-6-[2-(1-methyl-ppyrrolidin-2-yl)-ethyl]-pyrimidin-2-ylamine To a solution of (S)-(−)-1-methyl-2-pyrrolidine (320 mg, 2.78 mmol) in dry THF (10 mL) at 0° C. was added NaH (167 mg, 4.16 mmol). After stirring at RT for 1 h, 2-amino-4-chloro-6-methylpyrimidine (600 mg, 4.16 mmol) in dry THF (10 mL) was added dropwise via the addition funnel. The resulting mixture was heated to reflux under Ar gas for 20 h. The reaction was cooled to RT and quenched with sat. NH$_4$Cl. Solvent was removed and the residue was partitioned between H$_2$O and CHCl$_3$. The organic layer was washed with H$_2$O, brine, dried over MgSO$_4$, and evaporated to dryness. This crude compound was purified in column eluted with CH$_2$Cl$_2$:MeOH=95%:5% to yield the title compound. MS m/z: 223.2 (M+H). Calc'd. for C$_{12}$H$_{20}$N$_4$—222.2.

Preparation CLXXXVIII—(6-bromo-pyridin-2-yl)3-Methyl-but-2-enoic-amide

To a solution of 2-amino-6-bromopyridine (4, 3.015 g, 0.017 mol) and Et$_3$N (2.40 mL, 0.017 mol) in CH$_2$Cl$_2$ (20.0 mL), was added 3,3-dimethylacryloylchloride (1.96 mL, 0.017 mol) under N$_2$ at 0° C. The reaction mixture was slowly warmed to RT and stirred for 12 h. The reaction was quenched by the addition of H$_2$O (20.0 mL). The organic layer was separated, dried over Na$_2$SO$_4$ and evaporated to dryness to yield crude compound which was used without purification.

Preparation CLXXXIX—(6-amino-pyridin-2-yl) 3-Methyl-but-2-enoic-amide

To a solution of 2-amino-6-bromopyridine (4.30 g, 0.017 mol) and copper (0.214 g, 3.372 mmol) in IPOH (20.0 mL), was added NH$_4$OH (20.0 mL) in a sealed vessel under N$_2$. The reaction was sealed and heated to 90° C. for 12 h. The mixture was cooled to RT and EtOAc (50.0 mL) was added. The organic layer was separated, and the aq layer was washed with EtOAc (50.0 mL). The combined organic layers were evaporated to dryness, the resulting residue was dissolved in CH$_2$Cl$_2$ (50.0 mL) and washed with H$_2$O (4×30 mL). The organic layer was dried over Na$_2$SO$_4$ and evaporated to dryness to yield crude compound which was used without purification.

Preparation CXC—7-Amino-4,4-dimethyl-3,4-dihydro-1H-[1,8]naphthyridin-2-one

To a mixture of aminopyridine 6 (1.12 g, 5.833 mmol) and AlCl$_3$ (3.11 g, 0.023 mol) was added chlorobenzene (10.0 mL) in a sealed vessel under Ar. The reaction was sealed and heated to 120° C. for 12 h. The reaction mixture was cooled to RT and the mixture was poured over ice/HCl mixture and extracted with EtOAc (3×50.0 mL). The Aq layer was neutralized with solid NaHCO$_3$ and extracted with EtOAc (5×50 mL). The combined organic layers were dried over Na$_2$SO$_4$ and evaporated to dryness to yield crude compound which was purified by chromatography (Silica gel, CH$_2$Cl$_2$:MeOH, 99:1) yielding the title compound.

Preparation CXCI—2-[1-(3-Amino-phenyl)-2,2,2-trifluoro-1-trifluoromethyl-ethoxymethyl]-pyrrolidine-1-carboxylic acid tert-butyl ester To a mixture of 2-(3-amino-phenyl)-1,1,1,3,3,3-hexafluoro-propan-2-ol (1.30 g), 2-hydroxymethyl-pyrrolidine-1-carboxylic acid tert-butyl ester (1.04 g), PPh$_3$ (2.64 g) and molecular sieves 4 Å in THF (100 mL) was added DEAD (1.55 mL) slowly. The reaction was stirred at RT for 4 h and at reflux overnight. After filtration to remove solids, the filtrate was concentrated and the residue was taken up into Et$_2$O. The organic phase was washed with saturated NaHCO$_3$ and brine. The organic layer was dried over MgSO$_4$ and evaporated to give a very viscous brown oil, which was purified by chromatography through silica gel (500 g, 30% to 50% EtOAc in hexanes) to afford 2-[1-(3-amino-phenyl)-2,2,2-trifluoro-1-trifluoromethyl-ethoxymethyl]-pyrrolidine-1-carboxylic acid tert-butyl ester as a light brown oil.

Preparation CXCII—N-(3-Amino-5-chloro-phenyl)-2-dimethylamino-acetamide

To a solution of 5-chloro-benzene-1,3-diamine (3 g, 21 mmol) and dimethylamino-AcOH (2.2 g, 21 mmol) in $CH_2Cl_2$ (300 mL) was added EDC (5 g, 25 mmol), HOBt (2.9 g, 21 mmol), and DIEA (5 mL). The reaction mixture was stirred at RT overnight. Solvent was removed in vacuo and the residue was purified through flash chromatography on silica gel (0–8% MeOH in EtOAc) to give the desired compound.

General Procedure for the preparation of 2,6-diamonipyridines

To a solution of 2-amino-6-bromopyridine (1.070 g, 6.061 mmol) in 2,4-dimethylphenol (2.0 mL) was added amine (6.667 mmol) and the reaction mixture was heated to 150° C. for 12 h. The mixture was cooled to RT and aq. HCl (2.0 M, 30 mL) was added. EtOAc (50 mL) was added and the organic layer was separated. The Aq layer was washed with EtOAc (2×40 mL) and the combined organic layers were washed with $H_2O$ (50 mL), dried over $Na_2SO_4$, concentrated under vacuo to yield crude compound which was used without purification.

The following compounds were prepared similarly to the procedure outlined above:
a) 3,4,5,6-Tetrahydro-2H-[1,2']bipyridinyl-6'-ylamine:
b) 6-(4-Methyl-piperazin-1-yl)-pyridin-2-ylamine:

Preparation CXCIII—2-Methyl-2-(4-nitrophenyl)propionic acid

To a solution of 2-(4-nitrophenyl)propionic acid (50 g, 0.26 mol) in 250 mL of MeOH was added 6 mL of concentrated HCl. The resulting solution was heated at reflux for 16 h. The reaction was diluted with 200 mL of aq. $NaHCO_3$ and 500 mL of EtOAc. The organic layer was separated, dried over $Na_2SO_4$, and concentrated. The residue was diluted with 100 mL of THF and added to a suspension of NaH (11.2 g, 0.28 mol, 60% in mineral oil) in 600 mL of THF. To the resulting mixture was added $CH_3I$ (18.3 mL, 0.29 mol) in one portion. The resulting mixture was stirred for 48 h at 40° C. and diluted with aq. $NH_4Cl$ solution and EtOAc. The organic layer was separated, dried over $Na_2SO4$, and concentrated. The residue was used without further purification.

To a solution of the residue (54 g, 0.24 mol) in 500 mL of MeOH was added 5 N aq. NaOH solution (144 mL, 0.72 mol). The mixture was stirred for 16 h at 40° C., then, concentrated, and the residue was diluted with $H_2O$ (500 mL). The aq. solution was acidified with 2N HCl to give a precipitate which was filtered and dried to give the titled compound as a yellowish solid. MS: (ES+) 210 (M+H). Calc'd for $C_{10}H_{12}NO_4$—210.20.

Preparation CXCIV—2-Methyl-5-[1-methyl-1-(4-nitrophenyl)-ethyl]-[1,3,4]oxadiazole A mixture of 2-methyl-2-(4-nitro-phenyl)-propionic acid (5 g, 24 mmol) and a few drops DMF in $SOCl_2$ was stirred at reflux for 16 h. The resulting solution was concentrated to give corresponding acid chloride as a brown solid.

To a mixture of the acid chloride (2.33 g, 10.2 mmol), acetic acid hydrazide (0.91 g, 12.2 mmol), $Et_3N$ (2.86 mL, 20.2 mmol) in $CH_2Cl_2$ (50 mL) was added 2 crystals of DMAP at RT. The resulting mixture was stirred for 16 h and concentrated. A solution of the residue in 50 mL of $POCl_3$ was heated at 95° C. for 16 h. The resulting mixture was concentrated and diluted with ice-$H_2O$ and EtOAc. The organic layer was washed with saturated aq. $NaHCO_3$ solution twice, dried over $Na_2SO_4$, and concentrated. The residue was purified by $SiO_2$ chromatography (hexane:EtOAc= 1:1) to give the titled compound as a pale yellow crystalline solid. MS: (ES+) 248 (M+H). Calc'd for $C_{12}H_{14}N_3O_3$—248.10.

Preparation CXCV—2-Methyl-5-[1-methyl-1-(4-amino-phenyl)-ethyl]-[1,3,4]oxadiazole A mixture of 2-methyl-5-[1-methyl-1-(4-nitro-phenyl)-ethyl]-[1,3,4]oxadiazole (1.36 g, 5.5 mmol) and Pd/C (68 mg) in EtOAc (50 mL) was stirred under 1 atm of $H_2$ for 16 h. The resulting slurry was filtered over Celite®, and the filtrate was concentrated to give the titled compound as a pale yellow crystalline solid. MS: (ES+) 218 (M+H). Calc'd for $C_{12}H_{16}N_3O$—218.12.

Preparation CXCVI—4-[1-Methyl-1-(4-nitro-phenyl)-ethyl]-pyrimidine

To a mixture of 1-(4-nitro-phenyl)-propan-2-one (5.32 g, 29.7 mmol), triethylbenzylammonium chloride (0.34 g, 1.5 mmol), and 13 mL of aq. 5N KOH solution (65.3 mmol) in $CH_2Cl_2$ was added $CH_3I$ (4.06 mL, 65.3 mmol). The resulting mixture was stirred at 40° C. then diluted with EtOAc and $H_2O$. The organic layer was dried and concentrated.

To the residue (1.0 g, 4.8 mmol) in toluene (30 mL) was added dimethylformamide dimethylacetal (1.27 mL, 9.6 mmol). The resulting mixture was heated at reflux for 6 h, then concentrated to give 1-dimethylamino-4-methyl-4-(4-nitro-phenyl)-pent-1-en-3-one as a yellow solid. MS: (ES+) 263 (M+H). Calc'd for $C_{14}H_{19}N_2O_3$—263.13.

A mixture of 1-dimethylamino-4-methyl-4-(4-nitro-phenyl)-pent-1-en-3-one (0.5 g, 1.9 mmol), formamidine hydrochloride (0.305 g, 3.8 mmol), and NaOEt (1.29 g, 4.0 mmol) was heated in Smith synthesizer under microwave for 10 min at 150° C. The resultant was diluted with $H_2O$ and EtOAc. The organic layer was dried, and the residue was used without further purification MS: (ES+) 244 (M+H). Calc'd for $C_{13}H_{14}N_3O_2$—244.10.

Preparation CXCVII—5-[1-Methyl-1-(4-nitro-phenyl)-ethyl]-1H-pyrazole

A mixture of 1-dimethylamino-4-methyl-4-(4-nitro-phenyl)-pent-1-en-3-one (0.36 g, 1.4 mmol) and hydrazine hydrate (1.0 g, 6.25 mmol) in EtOH was heated at 50° C. for 3 h. The mixture was concentrated, and the residue was diluted with $H_2O$ and EtOAc. The organic layer was dried over $Na_2SO_4$ and concentrated to give the titled compound as a yellow solid. MS: (ES+) 232 (M+H.) Calc'd for $C_{12}H_{14}N_3O_2$—232.10.

Preparation CXCVIII—2-Methyl-2-(4-nitro-phenyl)-1-pyrrolidin-yl-propan-1-one

To a round bottom flask charged with 2-methyl-2-(4-nitro-phenyl)-propionic acid, was added 6.5 ml of $SOCl_2$. The mixture was heated to 80° C., with stirring under inert atmosphere for 3.5 h. The mixture was cooled to RT, and dried in-vacuo, and placed under high vac. After completely dry, the residue was used without further purification.

To the residue was added 10 ml of $CH_2Cl_2$, along with $Et_3N$ and the mixture was cooled to 0° C. on an ice/$H_2O$ bath. Pyrrolidine 0.46 mL (1.25 eq.) was added into the mixture, then stirred to RT under inert atmosphere. After 3 h of stirring, the mixture was quenched with $H_2O$, diluted with $CH_2Cl_2$, and transferred to a separatory funnel. The organics were collected, combined, dried over $Na_2SO_4$ and filtered. The crude was concentrated in vacuo. After drying, the title compound was produced as an amorphous solid. MS: 263 (M+1); calc'd for $C_{14}H_{18}N_2O_3$—262

Preparation CXCIX—4-(1,1-Dimethyl-2-pyrrolidin-1-yl-ethyl-phenylamine

To a 3-neck round bottom flask, charged with 2-Methyl-2-(4-nitro-phenyl)-1-pyrrolidin-yl-propan-1-one was added 66 ml of 1M $BH_3$/THF soln, while the mixture was maintained at 0° C. on an ice/$H_2O$ bath. The mixture was stirred under inert atmosphere overnight. A couple drops of 5N NaOH was added slowly to the reaction mixture for quenching. After stirring an additional 5 min, 22 ml of 5N NaOH was added into the reaction mixture, then stirred vigorously for 3 h. The mixture was diluted with 50 ml of 1N NaOH and 100 ml of EtOAc, then transferred into a sep. funnel. The organics were collected and concentrated in vacuo. The residue was dissolved in $CH_2CL_2$, then $NaHCO_3$ soln. was added into the mixture the organic extracts were dried over $Na_2SO_4$, filtered, then concentrated in vacuo.

To a round bottom flask charged with Pd/C in MeOH under inert atmosphere, was added 1-[2-methyl-2-(4-nitro-phenyl)-propyl]-pyrrolidine in MeOH and $H_2$ was added while stirring vigorously overnight. The mixture was filtered through Celite® and concentrated in vacuo to yield a light yellow oil. MS: 219 (M+1); calc'd for $C_{14}H_{22}N_2$.

Preparation CC—1-methyl-1-(4-nitro-phenyl)-ethylamine

To a round bottom flask charged with 2-methyl-2-(4-nitro-phenyl)-propionic acid (10 g; 0.0440 mole), was added $SOCl_2$ (32 ml). The mixture was heated to reflux, until completion of the reaction. After heating, the residual $SOCl_2$ was removed by in vacuo, then placed the residue on high vac. The crude was used without further purification.

To the residue, was added 20 ml toluene and stirred. Then slowly $NaN_3$ (7.14 g; 0.1099 mole) was added into the mixture, and stirred vigorously under inert atmosphere for 1.5 h. The mixture was poured into 50 ml $H_2O$ and transferred into a sep. funnel, with 50 ml EtOAc. The organics were collected, dried, filtered, and concentrated in-vacuo. The residue was dissolved in toluene and heated to 100° C. while stirring vigorously under inert atmosphere for 1 h. The solvent was removed in-vacuo, 20% HCl aq was added and the mixture stirred vigorously under reflux conditions at 100° C. for 9 h. The mixture was evaporated in-vacuo and to the residue was added 50 ml of 5N NaOH and 80 ml EtOAc, then transferred the mixture to a sep. funnel. The organic layer was collected, dried, filtered, and conc. in-vacuo. The residue was purified on silica-gel column in a solvent gradient of 80% EtOAc/Hexanes to 10% MeOH/$CH_2CL_2$ yielding a brown solid resulted. MS: 181 (M+1); calc'd for $C_9H_{12}N_2O_2$—180.

Preparation CCI—[1-(4-Amino-phenyl)-1-methyl-ethyl]-(2-methylsulfanyl-pyrimidin-4-yl)-amine To a Personal Chemistry reaction tube, was added 1-methyl-1-(4-nitro-phenyl)-ethylamine, along with 4-chloro-2-methylsulfanyl-pyrimidine, DIEA (2.0 eq) and t-BuOH (0.6 ml). The tube was heated by microwave to 150° C. for 10 min. After heating, the crude was diluted with $CH_2CL_2$ and $H_2O$, then transferred into a sep. funnel. The organics were collected, dried over $Na_2SO_4$, then concentrated in vacuo. The crude was used without further purification.

To a round bottom flask charged with $PtO_2$ (12% wt.) in MeOH (5 ml), was added crude nitro-intermediate (0.170 g.; 0.6 mmole). The mixture was stirred vigorously under $H_2$ for 2.5 h. The mixture was filtered through Celite® and concentrated in-vacuo. The residue was purified by silica-gel chromatography in a solvent gradient of 80% EtOAc/Hexanes to 5% MeOH/$CH_2CL_2$. After drying in high vac, the title compound resulted as a light yellow amorphous solid.

Preparation CCII—2-(2,2,2-Trifluoro-ethoxy)-isonicotinonitrile

To the suspension of NaH (2.78 g, 0.11 mole) in THF 100 mL) 2,2,2-trifluoroethanol (10 g, 0.1 mol) was added slowly. The mixture was stirred at RT till it turned clear. A solution of 2-chloro-isonicotinonitrile (13.8 g, 0.1 mol) in THF (100 mL) was slowly added and stirred at reflux for 3 h. After filtration and concentration, the crude oily compound was purified through column chromatography providing pure compound as an oil.

Preparation CCIII—C-[2-(2,2,2-Trifluoro-ethoxy)-pyridin-4-yl]-methylamine hydrogen chloride A mixture of 2-(2,2,2-trifluoro-ethoxy)-isonicotinonitrile (3.90 g, 19.40 mmol), 12N HCl (8.0 mL) and 10% Pd/C (800 mg) in MeOH (100 ml) was stirred under a balloon of $H_2$ for 7 h. After filtration, the filtrate was concentrated to give compound as a white solid. MS (ES+): 206.9 $(M+H)^+$. Calc'd. for $C_8H_9F_3N_2O$—206.07.

Preparation CCIV—2-Bromomethyl-3-nitro-benzoic acid methyl ester

The mixture of methyl 2-methyl-3-nitro benzoate (5.06 g, 25.9 mmol), NBS (5.54 g, 31.1 mmol), and AIBN (0.43 g, 2.59 mmol) in 100 ml of anhydrous $CCl_4$ was heated at reflux under $N_2$ for 22 h, cooled to RT, diluted with EtOAc, and washed with $Na_2CO_3$ (aq). The organic portion was separated, washed with brine, dried with $Na_2SO_4$, filtered, and condensed. The crude material was purified by flash column chromatography to yield pure product, which was used without further purification.

Preparation CCV—4-Nitro-2,3-dihydro-isoindol-1-one $NH_3$ (2.0 M in MeOH, 50 ml) was slowly added to the solution of 2-bromomethyl-3-nitro-benzoic acid methyl ester (4.46 g, contaminated with a small amount of assumed starting material, 16.3 mmol) in 30 ml of MeOH at RT. The resulting mixture was stirred at RT overnight, to provide the title compound as a white solid. MS $(ES^+)$: 179.2 $(M+H)^+$. Calc'd for $C_8H_6N_2O_3$—178.14.

Preparation CCVI—4-Amino-2,3-dihydro-isoindol-1-one

To the suspension of 4-nitro-2,3-dihydro-isoindol-1-one (2.40 g, 13.5 mmol) in 100 ml of MeOH was added Pd/C (10%, 0.36 g). The mixture was placed under $H_2$ from a balloon, stirred at RT for 24 h, filtered through Celite®, and condensed to give the titled compound as a light greenish solid. MS $(ES^+)$: 149.1 $(M+H)^+$. Calc'd for $C_8H_8N_2O$—148.16.

Preparation CCVII—Pyridin-4-ylmethyl-carbamic acid tert-butyl ester $Boc_2O$ (23 g, 105 mmol) was carefully added to a solution of pyridin-4-yl-methylamine (11 g, 102 mmol) and DMAP (0.5 g, 4 mmole) in $CH_2Cl_2$ (150 mL). The reaction was extended for 1 h after the addition. The reaction mixture was concentrated in vacuo and the residue was recrystallized in EtOAc to afford an off white crystal as the desired compound.

Preparation CCVIII—(1-Oxy-pyridin-4-ylmethyl)-carbamic acid tert-butyl ester

Pyridin-4-ylmethyl-carbamic acid tert-butyl ester (2.1 g, 10 mmol) was dissolved in a one to one mixture of aqueous MeOH (200 mL) with $NaHCO_3$ (5 g, 60 mmol) and Oxone® (12.3 g, 20 mmol). The mixture was stirred overnight then concentrated in vacuo to remove MeOH. The resulted aqueous mixture was diluted with $H_2O$ (150 mL) and filtered. The filter cake was washed with $H_2O$ and dried to afford a white solid as the desired compound.

Preparation CCIX—C-(1-Oxy-pyridin-4-yl)-methylamine

Oxy-pyridin-4-ylmethyl)-carbamic acid tert-butyl ester (2.1 g, 9.4 mmol) was dissolved in a 4N HCl in dioxane solution (50 mL) and heated to 50 C for 2 h. After removing solvent in vacuo, a white solid was received as an HCl salt of the desired compound.

Preparation CCX—2-(4-Methoxy-benzylamino)-isonicotinonitrile

To pyridine (500 mL) were added 2-chloroisonicotinonitrile (22.0 g, 159 mmole), para-methoxybenzylamine (25 g, 114% Meq.), and $NaHCO_3$ (30 g). The mixture was heated under reflux overnight. After cooling to RT, the mixture was filtered and the filter cake was rinsed with $CH_2Cl_2$. The combined filtrate was concentrated to dryness in vacuum to form a yellow solid. This solid was recrystalized in EtOAc to give a light yellow crystalline compound and the mother liquor was concentrated and subjected to EtOAc again (3×) to yield the desired compound.

Preparation CCXI—(4-Aminomethyl-pyridin-2-yl)-(4-methoxy-benzyl)-amine 2-(4-Methoxy-benzylamino)-isonicotinonitrile (12 g, 50 mmole) was dissolved in a mixed solvent of EtOH (800 mL) $Et_3N$ (200 mL) and suspended with 2 g of Pd/C (10%). After removing air with vacuum, the flask was charged with $H_2$ with a balloon. The $H_2$ balloon was refilled every morning and evening. Pd/C was recharged twice (1.3 g each) on days 2 and 3. Reaction was completed on the $4^{th}$ day and the reaction mixture was filtered through a pad of Celite®. The filter cake was rinsed with MeOH and the combined filtrate was concentrated in vacuo to give the desired compound as a light brown solid.

Preparation CCXII—4-Aminomethyl-pyridin-2-ylamine (4-Aminomethyl-pyridin-2-yl)-(4-methoxy-benzyl)-amine (12 g, 50 mmole) was dissolved in TFA (150 mL) and heated to reflux for 1 h. After cooling, the mixture was concentrated in vacuo and the residue was partitioned between HCl (1N, aq.) and EtOAc. The aqueous layer was washed with EtOAc then hexanes and concentrated to dryness in vacuum to give an off white solid as a dihydrochloric salt.

Preparation CCXIII—2-Methylamino-isonicotinonitrile

To a solution of 2-chloroisonicotinonitrile (22.0 g, 159 mmole) in pyridine (500 mL) was added methylamine in THF (2N, 160 mL), and $NaHCO_3$ (54 g). The mixture was heated to 120° C. in a sealed vessel for 40 h. After cooled to RT, the mixture was filtered and the filter cake was washed with $CH_2Cl_2$. The combined filtrated was concentrated in vacuo to give a yellow solid as the desired compound.

Preparation CCXIV—(4-Aminomethyl-pyridin-2-yl)-methyl-amine

A suspension of 2-Methylamino-isonicotinonitrile (5.6 g) and Pd/C (10%, 4 g) in EtOH (150 mL) and TEA (40 mL) was placed in a 500 mL Parr Hydrogenation bottle and hydrogenated under 60 psi of $H_2$ over night. After filtering through a pad of Celite®, the reaction mixture was concentrated in vacuo to give a yellow oil as the desired compound.

Preparation CCXV—3-Fluoro-pyridine 1-oxide

3-Chloroperoxybenzoic acid (70%, 35.0 g, 142 mmol) was added to the solution of 3-fluoropyridine (6.90 g, 71.1 mmol) in 200 ml of $CH_2Cl_2$, the mixture was stirred at RT overnight, washed with a small amount of saturated $NaHCO_3$ solution, dried with $Na_2SO_4$, filtered, condensed, the crude compound was purified by flash column chromatography (1 to 2% of MeOH in $CH_2Cl_2$), the titled compound was obtained as a light yellowish solid. MS (ES+): 114.1 (M+H)+. Calc'd for $C_5H_4FNO$—113.09.

Preparation CCXVI—3-Fluoro-pyridine-2-carbonitrile

The mixture of 3-fluoro-pyridine 1-oxide (0.99 g, 8.75 mmol), trimethylsilyl cyanide (4.80 ml, 35.0 mmol), and $Et_3N$ (1.84 ml, 13.2 mmol) in 100 ml of $CH_3CN$ was heated at reflux overnight. The solvents were removed, under reduced pressure and the residue was partitioned between EtOAc and saturated $NaHCO_3$. The organic portion was separated, dried with $Na_2SO_4$, filtered, condensed, the crude compound was purified by flash column chromatography (10 to 20% of EtOAc in hexanes). The titled compound was obtained as a light yellowish solid. MS (ES+): 123.1 (M+H)+. Calc'd for $C_6H_3FN_2$—122.10.

Preparation CCXVII—C-(3-Fluoro-pyridin-2-yl)-methylamine

The mixture of 3-fluoro-pyridine-2-carbonitrile (0.81 g, 6.63 mmol) and Pd/C (0.20 g, 10% wt) in 10 ml of MeOH and 2.7 ml of concentrated HCl was placed under $H_2$ which was provided by a balloon and stirred at RT for 4 h, filtered through Celite®, condensed, the residue was purified by flash column chromatography. The titled compound was obtained as a light yellowish oil. MS (ES+): 127.1 (M+H)+. Calc'd for $C_6H_7FN_2$—126.13.

Preparation CCXVIII: 5-Bromo-pyridine-2-carbonitrile

The mixture of 2,5-dibromopyridine (4.74 g, 20.0 mmol), zinc cyanide (1.40 g, 12.0 mmol), zinc dust (0.059 g, 0.90 mmol), and Pd(dppf)$Cl_2$.$CH_2Cl_2$ (0.36 g, 0.44 mmol) in 25 ml of DMF was heated at reflux for 5 h, cooled to RT, diluted with $H_2O$, extracted with EtOAc, the organic portion was washed with brine, the solvents were removed, the crude compound was purified by flash column chromatography (5 to 15% of EtOAc in hexanes), the titled compound was obtained as an off-white solid.

Preparation CCXIX—5-Fluoro-pyridine-2-carbonitrile

The mixture of 5-bromo-pyridine-2-carbonitrile (0.50 g, 2.73 mmol), and KF (0.48 g, 8.20 mmol) in 10 ml of 1-methyl-2-pyrrolidinone was stirred at 175° C. for 18 h, cooled to RT, diluted with $H_2O$, extracted with EtOAc, the combined organic portions were washed with $H_2O$, brine, dried with $Na_2SO_4$, filtered, condensed, the crude compound was purified by flash column chromatography (5 to 20% of EtOAc in hexanes). The titled compound was obtained as an off-white solid.

Preparation CCXX—C-(5-Fluoro-pyridin-2-yl)-methylamine

The mixture of 5-fluoro-pyridine-2-carbonitrile (0.16 g, 1.27 mmol) and Pd/C (0.030 g, 10% wt) in 15 ml of MeOH and 0.50 ml of concentrated HCl was placed under $H_2$ which was provided by a balloon and stirred at RT for 4 h, filtered through Celite®, condensed, the residue was purified by flash column chromatography. The titled compound was obtained as a light yellowish solid. MS (ES+): 127.2 (free base) (M+H)+. Calc'd for $C_6H_7FN_2$ (free base)—126.13.

Preparation CCXXI—1H-Pyrrolo[2,3-b]pyridine 7-oxide

To a suspension of 1H-pyrrolo[2,3-b]pyridine (10.0 g) and $NaHCO_3$ (45.2 g) in 1:1 MeOH/$H_2O$ (1000 mL) was added Oxone® (106 g) in potions during 40 min period. The mixture was stirred at RT for 5 h. The sold was removed by filtration and the filtrate was concentrated to 200 mL in volume. This aqueous phase was extracted with $CH_2Cl_2$ (200 mL×7) to afford 1H-pyrrolo[2,3-b]pyridine 7-oxide.

Preparation CCXXII—4-chloro-1H-pyrrolo[2,3-b]pyridine

To a cooled POCl$_3$ (50 mL) in a dried round bottom flask, 1H-pyrrolo[2,3-b]pyridine 7-oxide (5.73 g) was added in potions. The mixture was heated to reflux for 5 h. After cooled down to RT, POCl$_3$ was evaporated under high vacuum under gentle heating (40–50° C.) to obtain black residue. 50 mL of $H_2O$ was added slowly and pH was adjusted to 8–9 with $Na_2CO_3$ (first with solid, then saturated aqueous solution) The resulting priticipate was collected by filtration, washed with cold $H_2O$ and dried in a vacuum oven (50° C.) to give 4-chloro-1H-pyrrolo[2,3-b]pyridine as tan powder.

Preparation CCXXIII—1-(4-iodo-pyrrolo[2,3-b]pyridin-1-yl)-ethanone

To a suspension of 4-chloro-1H-pyrrolo[2,3-b]pyridine (3.80 g) and NaI (19.15 g) in CH$_3$CN (40 mL) was added acetyl chloride (5.0 mL) slowly. The mixture was heated to reflux for overnight. After cooled to RT, 40 mL of 10% Na$_2$CO$_3$ and 40 mL of 10% NaHSO$_3$ were added. After stirring for 15 min, the mixture was extracted with EtOAc 4 times. The combined organic phases were washed with brine, dried over MgSO$_4$ and concentrated to give a brown residue as the crude compound, which was purified by chromatography through silica gel (220 g, 5 to 15% EtOAc/hexanes to afford 1-(4-iodo-pyrrolo[2,3-b]pyridin-1-yl)-ethanone as white solid.

Preparation CCXXIV—1-acetyl-1H-pyrrolo[2,3-b]pyridine-4-carbonitrile

A mixture of 1-(4-iodo-pyrrolo[2,3-b]pyridin-1-yl)-ethanone (4.30 g), CuCN (6.841 g), Pd$_2$dba$_3$ (0.729 g), and dppf (1.636 g) in 85 mL of dioxane was heated to reflux for 2 h. Solid was removed by filtration through a pad of Celite®. The filtrate was concentrated to give a yellow solid as crude compound, which was purified by chromatography through silica gel (250 g, 5–30% EtOAc/hexanes, stepwise gradient) to afford 1-acetyl-1H-pyrrolo[2,3-b]pyridine-4-carbonitrile as a white fluffy solid.

Preparation CCXXV—1-(4-aminomethyl-pyrrolo[2,3-b]pyridin-1-yl)-ethanone

A mixture of 1-acetyl-1H-pyrrolo[2,3-b]pyridine-4-carbonitrile (0.872 g), 10% Pd/C (0.882 g), 20 mL of Et$_3$N, and 80 mL of EtOH was stirred at RT under balloon pressure of H$_2$ for overnight. Solid was removed by filtration through a pad of Celite® and the filtrate was concentrated to yield a cream color residue, which was purified by chromatography through silica gel (70 g, 2 to 5% MeOH/CHCl$_3$ with 1% NH$_4$OH) to afford 1-(4-aminomethyl-pyrrolo[2,3-b]pyridin-1-yl)-ethanone as a white solid.

Preparation CCXXVI—N-(1-acetyl-2,3-dihydro-1H-pyrrolo[2,3-b]pyridin-4-ylmethyl)-acetamide To a mixture of 1-acetyl-1H-pyrrolo[2,3-b]pyridine-4-carbonitrile (0.691 g, example 15), 10% Pd/C (0.702 g), 5 mL of Et$_3$N, and 20 mL of EtOAc was added acetic anhydride (1.0 mL). The mixture was stirred at RT under balloon pressure of H$_2$ for overnight. Solid was removed by filtration through a pad of Celite® and the filtrate was concentrated to yield a white residue, which was purified by chromatography through silica gel (150 g, 1 to 5% MeOH/CHCl$_3$ with 1% NH$_4$OH, stepwise gradient) to afford N-(1-acetyl-2,3-dihydro-1H-pyrrolo[2,3-b]pyridin-4-ylmethyl)-acetamide as a white solid.

Preparation CCXXVII—C-(2,3-dihydro-1H-pyrrolo[2,3-b]pyridin-4-yl)-methylamine hydrogen chloride salt A mixture of N-(1-acetyl-2,3-dihydro-1H-pyrrolo[2,3-b]pyridin-4-ylmethyl)-acetamide (0.50 g), HCl (conc., 3 mL) and EtOH (12 mL) was heated to 70° C. for overnight. Additional 3 mL of conc. HCl was added to the reaction and the heating was continued for 3 more days. Solvent was evaporated to give a white residue as crude C-(2,3-dihydro-1H-pyrrolo[2,3-b]pyridin-4-yl)-methylamine HCl salt, which was used without further purification.

General Procedure for the Preparation of 2-amino-4-methylaminopyridines

Preparation CCXXVIII—2-aminoisonicotinonitrile

To a slurry of 2-chloro-4-cyanopyridine (10.00 g, 0.079 mol) and Na$_2$CO$_3$ (19.92 g, 0.237 mol) in amine (0.174 mol) was added pyridine (35.0 mL) and the reaction was heated to 90° C. for 3 h. The reaction was cooled to RT, diluted with the addition of CH$_2$Cl$_2$ (100 mL) and filtered. The solid was washed with EtOAc. Combined washes were concentrated in vacuo. A mixture of MeOH/hexanes was added and kept in the fridge for 12 h. The crystals that formed were filtered and washed with hexanes.

Preparation CCXXIX—2-amino-4-methylaminopyridine

To a mixture of 2-aminoisonicotinonitrile (0.043 mol) and Pd/C (10%, 6.00 g) was added Et$_3$N (40.0 mL) and EtOH (160.0 mL) in a Parr bottle and hydrogenated at 50 psi for 12 h. Crude mixture was filtered through Celite®, concentrated under vacuo and dried under high vacuum to yield compound.

Preparation CCXXX—(2-Pyrrolidin-1-yl-pyridin-4-yl)-methylamine

Prepared according to the general procedure with pyrrolidine as the amine.

Preparation CCXXXI—(2-Morpholin-4-yl-pyridin-4-yl)-methylamine

Prepared according to the general procedure with morpholine as the amine.

Preparation CCXXXII—3,9,9-Trimethyl-6-nitro-4,9-dihydro-3H-3-aza-fluorene

4-[1-(2-Bromo-4-nitro-phenyl)-1-methyl-ethyl]-1-methyl-1,2,3,6-tetrahydro-pyridine (9 g), Pd(OAc)$_2$ (900 mg), and DIEA (15 mL) was dissolved in DMF (300 mL), and heated to 80° C. overnight. Solvents were removed in vacuo. The residue was partitioned between CH$_2$Cl$_2$/NaHCO$_3$(sat, aq.). The CH$_2$Cl$_2$ layer was washed with brine, dried over Na$_2$SO$_4$ and concentrated in vacuo. The residue was purified via flash chromatography on silica to give the desired compound. (MS: M+H=257).

Preparation CCXXXIII—3,9,9-Trimethyl-2,3,4,4a,9,9a-hexahydro-1H-3-aza-fluoren-6-ylamine (156)

3,9,9-Trimethyl-6-nitro-4,9-dihydro-3H-3-aza-fluorene (700 mg) was dissolved in EtOH (20 mL) with aqueous HCl (1N, 5 mL) and suspended with Pd/C (10%, 100 mg). The flask was capped with a balloon filled with H$_2$. The reaction was completed in 6 h at RT. The reaction mixture was filtered through a layer of Celite® with MeOH. The combined filtrate was concentrated to give desired compound. (MS: M+H=231).

Preparation CCXXXIV—2-Chloro-5-nitro-phenol

A mixture of 2-chloro-4-nitroanisole (10 g, 53.3 mmol) and pyridinium chloride (50 g, 426 mmol) was heated at 200° C. for 3 h. After cooling to RT, the mixture was dissolved in 150 mL of aqueous 2N HCl and 150 mL of EtOAc. The organic phase was separated and was washed with aqueous 2N HCl (2×100 mL). The resulting organic phase was dried over MgSO$_4$ and concentrated in vacuo. The title compound was obtained via chromatography (silica gel, 10:1 hexane/EtOAc) as a yellow solid.

Preparation CCXXXV—3-(5-Amino-2-chloro-phenoxymethyl)-azetidine-1-carboxylic acid tert-butyl ester To a solution of 3-(2-chloro-5-nitro-phenoxymethyl)-azetidine-1-carboxylic acid tert-butyl ester (2.5 g, 7.29 mmol) in 60 mL of MeOH/H$_2$O (1:1) and 3 mL of acetic acid (J. T. Baker) was added Zn powder (2.3 g, 36.47 mmol, Aldrich) at 0° C. The reaction mixture was stirred at 0° C. for 2 h then stirred at 10° C. for 2 h. The resulting mixture was filtered through a Celite® pad and the filtrate was concentrated in vacuo. The residue was treated with 60 mL of saturated aqueous NaHCO$_3$ and extracted with EtOAc (3×50 mL). The combined organic layers were washed with brine and dried with MgSO$_4$. The resulting solution was concentrated in vacuo and the title compound was obtained by column chromatography (silica gel, EtOAc) as a yellow solid.

Preparation CCXXXVI: 3-(Benzotriazol-1-yloxy)-6-chloro-pyridazine-4-carboxylic acid (4-tert-butyl-phenyl)-amide A mixture of 3,6-dichloropyridazine-4-carboxylic acid (1.00 g, 5.18 mmol), 4-tert-butylaniline (0.92 ml, 5.60 mmol), TBTU (1.75 g, 5.44 mmol), and DIEA (1.80 ml, 10.4 mmol) in 7.5 ml of anhydrous DMF was stirred at RT under $N_2$ overnight. The mixtrue was diluted with $H_2O$, extracted with EtOAc, and the combined organic portions were washed with brine, dried with $Na_2SO_4$, filtered, and condensed. The crude compound was purified by flash column chromatography (hexanes/EtOAc/$CH_2Cl_2$, 9:0:1 to 7:2:1), to provide the desired compound as a light yellowish solid. MS (ES$^+$): 423.0 (M+H)$^+$. Calc'd for $C_{21}H_{19}ClN_6O_2$—422.87.

Preparation CCXXXVII—3-Hydroxymethyl-azetidine-1-carboxylic acid benzyl ester

To a mixture of azetidine-1,3-dicarboxylic acid monobenzyl ester (6.4 g) in THF (200 mL) was added $BH_3$.THF (6 eq, 163 mL, 1M solution) dropwise via an addition funnel at −40 C. under an $N_2$ atmosphere. The solution was warmed to RT and stirred overnight. To the reaction, 5N NaOH (50 mL) was added and then concentrated under vacuum. The resulting aqueous solution was extracted with $Et_2O$ (3×100 mL). The organic layer was dried over $Na_2SO_4$ and evaporated to give the title compound which was used without further purification.

Preparation CCXXXVIII—3-Methanesulfonyloxymethyl-azetidine-1-carboxylic acid benzyl ester 3-Hydroxymethyl-azetidine-1,3-dicarboxylic acid monobenzyl ester (6.6 g) was dissolved in $CH_2Cl_2$ (100 mL) and brought to −15 C. While stirring, TEA was added (3 eq, 9.43 g) followed by methanesulphonic chloride (2.0 eq, 7.69 g) and allowed to come to RT and stirred for 1 h. The resulting organic solution was extracted with water (3×100 mL). The organic layer was dried over $Na_2SO_4$ and evaporated to give the desired product as a clear oil which was used without further purification.

Preparation CCXXXIX—3-Nitro-5-trifluoromethyl-phenol

A flask containing 1-Methoxy-3-nitro-5-trifluoromethyl-benzene (10 g) and hydrochloride pyridine (10 eq, 52.0 g) was heated to 210 C. and stirred for 12 h. Once complete, the reaction was cooled and the residue was dissolved in $CH_2Cl_2$ and washed twice with water (100 mL). The organic layer was concentrated under vacuum and then set in the freezer overnight. The resulting crystals were filtered off and washed with ether and used as is.

Preparation CCXL—3-(3-Nitro-5-trifluoromethyl-phenoxymethyl)-azetidine-1-carboxylic acid benzyl ester A mixture of 3-nitro-5-trifluoromethyl-phenol (750 mg), $K_2CO_3$ (3 eq., 1.5 g) and 3-hydroxymethyl-azetidine-1-carboxylic acid benzyl ester (1.1 eq., 1.2 g) in DMF was heated to 80 C. for 1 h. The solution was cooled to RT, filtered and concentraced under vacuum. The residue was dissolved in $CH_2Cl_2$ and washed with $H_2O$ twice, followed by brine. The organic layer was dried over $Na_2SO_4$ and evaporated under reduced pressure. The residue was purified by column chromatography using 5% MeOH/$CH_2Cl_2$ to provide the desired compound as a colorless solid.

Preparation CCXLI—3-(3-amino-5-trifluoromethyl-phenoxymethyl)-azetidine-1-carboxylic acid benzyl ester To a solution of 3-(3-nitro-5-trifluoromethyl-mg) and $NH_4Cl$ (1.1 eq., 80 mg) was added iron dust (3 eq., 220 mg) in a 10% water/EtOH solution. The solution was heated to reflux for 6 h. The solution was cooled, then filtered through a pad of Celite®. The resulting solution was concentrated under vacuum to provide the desired compound as a dark yellow solid and used as is.

Preparation CCXLII—2-Methylamino-pyrimidine-4-carbonitrile

2-Chloro-4-pyrimidinecarbonitrile (14.1 g, 101 mmol, prepared according to the procedure of Daves et. al *J. Het. Chem.* 1964, 1, 130–132) in 100 ml THF was cooled to 0° C. Reaction progress was monitored as aliquots of methylamine solution (in THF, 2.0 M, Aldrich) were added dropwise over the course of 1 h (58 ml+15 ml+15 ml). The mixture was stirred overnight. Additional methylamine solution (15 ml) was added very slowly, and the reaction was stirred 10 min. After concentration, the residue was extracted with EtOAc (400 ml) and saturated aqueous $NaHCO_3$ (15 ml), and the organic layer was washed with 100 ml brine. The combined aqueous layers were extracted with EtOAc again (200 ml), and this organic layer was washed with brine. The combined organic layers were dried over $Na_2SO_4$, filtered, and concentrated. The orange solid was packed into a filtration apparatus, and submerged in just enough MeOH to cover the material (15 ml). Orange liquid was allowed to drain by gravity, then under high vacuum. The solid was washed in the same manner with t-BuOMe (15 ml). 2-Methylamino-pyrimidine-4-carbonitrile was obtained as peach-colored "fly-away" crystals. MS: 135.0 (M+1); Calc'd. for $C_6H_6N_4$—134.14.

Preparation CCXLIII—(4-Aminomethyl-pyrimidin-2-yl) methylamine

2-Methylamino-pyrimidine-4-carbonitrile (8.7 g, 64.0 mmol) was suspended in 450 ml MeOH and 77 ml $Et_3N$. Four cycles of quick high vacuum application and $N_2$ flushing were followed by addition of 10% Pd/C (1.4 g). $H_2$ was rapidly bubbled through the mixture, and the reaction was stirred under $H_2$-balloon pressure overnight. The next day, a full balloon of $H_2$ was bubbled through the mixture, and stirring continued for another day under the pressure of an $H_2$-balloon. The mixture was filtered through a large pad of diatomaceous earth, rinsing with MeOH, and was concentrated. The residue was purified by silica gel chromatography (95:5:0.5 to 10:1:0.1 $CH_2Cl_2$/MeOH/$NH_4OH$), and placed under high vacuum overnight, becoming an off-white crumbly solid MS: 138.8 (M+1); Calc'd. for $C_6H_{10}N_4$—138.17.

Preparation CCXLIV—6-Hydroxy-pyrimidine-4-carbaldehyde oxime

6-Dimethoxymethyl-pyrimidin-4-ol (12.5 g, 73 mmol, prepared according to the procedure of J. Adams et al *Biorg. Med. Chem. Lett.* 8, 22, 1998, 3111–3116) was dissolved in 0.5% aqueous $H_2SO_4$ (100 ml) and stirred at 67° C. for about 30 min. 10% aqueous $H_2SO_4$ (5 ml) was added, and the reaction was stirred at 70° C. for 1.5 h. The mixture was cooled to 5° C. and stirred. NaOH solution was added (1 N, 33 ml) followed by saturated aqueous $NaHCO_3$ (to adjust the pH to 7.5). Hydroxylamine hydrochloride was added carefully, portionwise (50.7 g, 730 mmol), producing a peach suspension. Saturated aqueous $NaHCO_3$ was added to bring the total reaction volume to about 700 ml and the pH back to 7.5. The mixture was stirred overnight and filtered, rinsing with $H_2O$ and then t-BuOMe to obtain 6-hydroxy-pyrimidine-4-carbaldehyde oxime as a light tan solid. MS: 140.0 (M+1), 137.9 (M−1); Calc'd. for $C_5H_5N_3O_2$—139.11.

Preparation CCXLV—6-Chloro-pyrimidine-4-carbonitrile

6-Hydroxy-pyrimidine-4-carbaldehyde oxime (9.3 g, 67 mmol) was stirred in 37 ml $POCl_3$ under $N_2$ at 40° C. for 30 min, 60° C. for 30 min, and 80° C. for one h. N,N,-Dimethylaniline was added very slowly by syringe, and stirred for one h at 80° C. After cooling to 0° C., the mixture was poured into a separatory funnel containing 300 g of ice. The mixture was carefully swirled, then extracted with 500 ml t-BuOMe. The organic layer was washed with 1 N HCl (4×100 ml), then several times with $NaHCO_3$, then brine.

Acidic and basic aqueous layers were separately back-extracted with t-BuOMe, and the organics again washed with 1 N HCl, saturated aqueous NaHCO$_3$, and brine. The combined organic layers were dried with Na$_2$SO$_4$ and concentrated by rotary evaporator. The residue was filtered through a pad of silica gel, applying in CH$_2$Cl$_2$ and eluting with 10:1 hexanes/t-BuOMe. Fractions were carefully concentrated to obtain 6-chloro-pyrimidine-4-carbonitrile as a (volatile) pale yellow, semi-crystalline solid.

Preparation CCXLVI—6-Methylamino-pyrimidine-4-carbonitrile

To 6-chloro-pyrimidine-4-carbonitrile (1.37 g, 9.84 mmol) stirring in 10 ml THF under N$_2$ was added a methylamine solution (2.0 M in THF, Aldrich) in aliquots, causing immediate precipitation. Reaction progress was monitored after addition of 5 ml methylamine solution, then 3 ml, then 2 ml. The mixture was concentrated and filtered through a pad of silica, eluting with 2%->5% MeOH in CH$_2$Cl$_2$ to obtain 6-methylamino-pyrimidine-4-carbonitrile as a pale yellow solid. MS: 135.0 (M+1); Calc'd. for C$_6$H$_6$N$_4$—134.14.

The following compounds were prepared similarly to the procedure outlined above:

a) 2-Methylamino-pyrimidine-4-carbonitrile from 2-chloro-4-pyrimidinecarbonitrile (prepared according to the procedure of Daves et. al *J. Het. Chem.* 1964, 1, 130–132) was obtained as peach-colored "fly-away" crystals. MS: 135.0 (M+1); Calc'd. for C$_6$H$_6$N$_4$—134.14.

Preparation CCXLVII—(6-Aminomethyl-pyrimidin-4-yl)-methyl-amine

6-Methylamino-pyrimidine-4-carbonitrile (1.2 g, 8.6 mmol) was stirred in 100 ml DMF and 8 ml Et$_3$N under N$_2$. 10% Pd/C was added (300 mg). H$_2$ was bubbled through the mixture, which was then stirred under balloon pressure of H$_2$ overnight. The mixture was diluted with methanol and filtered through a bed of Celite, concentrated, and purified by flash chromatography (10:1:0.1 CH$_2$Cl$_2$/MeOH/NH$_4$OH) to obtain a white solid, which contained about 70% (6-aminomethyl-pyrimidine-4-yl)methyl-amine; MS: 137.6 (M+1); Calc'd. for C$_6$H$_{10}$N$_4$—138.17. It also contained 30% dimeric impurity [MS: 260.4 (M+1)].

The following compounds were prepared similarly to the procedure outlined above:

a) (4-Aminomethyl-pyrimidin-2-yl)methylamine MS: 138.8 (M+1); Calc'd. for C$_6$H$_{10}$N$_4$—138.17.

Preparation CCXLVIII—6-aminomethyl quinoline

Similar to the method described by C. Kaslow and W. Clark, (JOC 18, 55, 1953), to a stirred solution of methyl quinoline-6-carboxylate (10 g, 53 mmol) in THF (200 mL) at 0° C. was added LiAlH$_4$ (1.3 g, 14.9 mmol) by small portion. The resulting mixture was stirred at 0° C. for 2 h then warmed to RT and stirred for 3 h. Acetone (10 mL) was added followed by MgSO$_4$×10H$_2$O. The resulting mixture was stirred for 1.5 h at RT and filtered over a silica pad. Solvents were removed to give the crude quinolin-6-yl-methanol.

Quinolin-6-yl-methanol (7.7 g, 48 mmol) was dissolved in benzene (3 mL) and SOCl$_2$ (20 mL) was added at 0° C. The mixture was stirred at RT for 1 h, then heated to reflux and stirred an additional 1 h. The mixture was cooled to RT and the solid was filtered to give the 6-chloromethyl-quinoline.

Similar to that described in ZH. OBSHCHKHIM OR (ENGLAUSFS 1325–1326) 1959, the crude 6-chloromethyl-quinoline (4.9 g) was carefully dissolved in NH$_4$OH (700 mL) and stirred overnight at RT (the solution became orange). The mixture was filtered and the ammonia was evaporated on rotavap (bath at 34° C.). The solution was saturated with K$_2$CO$_3$. The yellow oil was removed and the aqueous phase was extracted with CHCl$_3$. The organic phase was dried with K$_2$CO$_3$, filtered and evaporated to give quinolin-6-yl-methylamine.

Preparation CCXLIX—3-nitro-5-(trifluoromethyl) phenylamine

To a solution of 3,5-dinitrobenzotrifluoride (10 g, 42 mmols, 1 eq.) in 150 mL of EtOH was added 17.6 mL (258.3 mmols, 6.15 eq.) of ammonium sulfide in water (50% by weight, Aldrich). The reaction was heated to reflux for 16 h during which time it became orange and a yellow precipitate formed. After cooling the volume was reduced to approximately 50 mL. The solid was removed by filtration and the filtrate evaporated to dryness in vacuo. The resulting orange solid was purified by column chromatography eluting with a step gradient of 20–30% EtOAc:hexane to provide the compound as a yellow/orange solid.

Preparation CCL—N-(3-nitro-5-(trifluoromethyl)phenyl) methanesulfonamide

3-Nitro-5-(trifluoromethyl)phenylamine (2 g, 9.7 mmols, 1 eq) was dissolved in 100 mL of CH$_2$Cl$_2$. The yellow solution was cooled to 0° C. Et$_3$N (2 mL, 14.55 mmols, 1.5 eq) was added followed by mesyl chloride (0.75 mL, 9.7 mmols, 1 eq). The reaction was stirred for 2 h at 0° C. and warmed to RT. Pyridine (0.785 mL, 9.7 mmols, 1 eq) and a catalytic amount of dimethylamine pyridine were added. The reaction was stirred at RT for 16 h. An additional equivalent of mesyl chloride was added and the reaction was heated to reflux for 24 h. After cooling, the solvent was removed in vacuo, and the residue redissolved in CH$_2$Cl$_2$. The solution was washed twice with 2 N HCl and once with brine. After drying over Na$_2$SO$_4$, the solution was filtered and the solvent removed. The resulting solid was triturated briefly with 10% EtOAc:hexane to provide a white solid that was a mixture of sulfonimide and sulfonimide.

The above mixture was dissolve in 20 mL of MeOH that had been saturated with K$_2$CO$_3$. After 30 min, the reaction was stripped and the resulting solid portioned between 2 N HCl and CH$_2$Cl$_2$. The CH$_2$Cl$_2$ was dryed over Na$_2$SO$_4$ and stripped to provide an off-white solid.

Preparation CCLI—(3S)-tetrahydro-3-furanyl 3-nitro-5-(trifluoromethyl)phenylcarbamate 3-(S)-Hydroxytetrahydrofuran (4.8 mL, 60.7 mmols, 5 eq) was dissolved in 60 mL of toluene. The solution was cooled to 0° C. and Et$_3$N (5.1 mL, 36.4 mmols, 3 eq) was added. Trichloromethyl chloroformate (3.65 mL, 30.33 mmols, 2.5 eq) was added slowly. The solurion was stirred at 0° C. for 45 min. 3-Amino-5-ntrobenzotrifluoride (2.5 g, 12.13 mmols, 1 eq) was added dropwise in 20 mL of toluene. The reaction was stirred at 0° C. for 1 h. An additional 5 eq of 3-(S)-hydroxytetrahydrofuran was converted to the chloroformate as described above, and added to the reaction mixture. After an additional h at 0° C., the reaction was heated to 60° C. for 1 h. The reaction was cooled to RT and concentrated. The residue was dissolved in EtOAc, washed twice with saturated NH$_4$Cl and once with brine. After being dried over Na$_2$SO$_4$ the solution was filtered and the solvent removed in vacuo. The crude product was purified using a Biotage chromatography system eluting with a gradient of 5% to 35% EtOAc:hexane to yield the desired compound.

Preparation CCLII—N-(2-((3-nitro-5-(trifluoromethyl) phenyl)oxy)ethyl)-methanesulfonamide 2-((3-Nitro-5-(trifluoromethyl)phenyl)oxy)ethylamine (4.05 g, 16.2 mmols, 1 eq) was dissolved in 100 mL of CH$_2$Cl$_2$. The solution was cooled to 0° C. Pyridine (2.6 mL, 32.4 mmols, 2 eq) was added followed by mesyl chloride (1.25 mL, 16.2 mmols, 1 eq). The reaction was stirred for 18 h during which time it was warmed slowly to RT. The solvent was removed in vacuo, and the residue dissolved in EtOAc. The resulting solution was washed twice with 2 N HCl, once with water, and 3× with brine. After being dried over $Na_2SO_4$ the solution was filtered and concentrated. The crude was purified by silica gel chromatography eluting with 50% to 60% EtOAc:hexane to yield the desired compound.

Preparation CCLIII—N-(2-((3-amino-5-(trifluoromethyl) phenyl)oxy)ethyl)methanesulfonamide N-(2-((3-Nitro-5-(trifluoromethyl)phenyl)oxy)ethyl)-methanesulfonamide (1.7 g, 5.2 mmols, 1 eq) was dissolved in 50 L of MeOH. 10% Pd/C (170 mg, 10 weight %) was added and the reaction sparged with $H_2$. The suspension was stirred for 5 h, then filtered trough Celite. The filtrate was stripped to yield the title compound.

The following compounds were prepared similarly to the procedure outlined above:

a) 3-((((2R)-1-acetyl-2-pyrrolidinyl)methyl)oxy)-5-(trifluoromethyl)phenylamine.
b) (3S)-tetrahydro-3-furanyl 3-amino-5-(trifluoromethyl) phenylcarbamate.
c) N-(3-amino-5-(trifluoromethyl)phenyl)-methanesulfonamide Preparation CCLIV—(2R)-1-acetyl-2-(((3-nitro-5-(trifluoromethyl)phenyl)oxy)methyl)pyrrolidine (2R)-2-(((3-nitro-5-(trifluoromethyl)phenyl)oxy)methyl) pyrrolidine (3.46 g, 11.9 mmols, 1 eq) was dissolved in 100 mL of $CH_2Cl_2$. $Et_3N$ (5 mL, 35.7 mmols, 3 eq) was added followed by $Ac_2O$ (1.2 mL, 13.1 mmols, 1.1 eq). The reaction was stirred at RT for 1.5 h. The solvent was removed in vacuo and the residue disolved in EtOAc. The solution was washed once each with saturated $NH_4Cl$, 1 N HCl, and twice with brine. The organic layer was dried over $Na_2SO_4$ filtered and concentrated in vacuo. The crude material was purified on a Biotage chromatography system eluting with a gradient of 10% to 75% EtOAc:hexane to yield the title compound.

Preparation CCLV—3-(2-Chloro-5-nitro-phenoxymethyl)-azetidine-1-carboxylic acid tert-butyl ester To the mixture of 2-chloro-5-nitro-phenol (1.31 g, 7.54 mmol) and $K_2CO_3$ (1.57 g, 11.31 mmol) in 20 mL of DMF was added 3-methanesulfonyloxymethyl-azetidine-1-carboxylic acid tert-butyl ester (2.0 g, 7.54 mol). The reaction mixture was stirred at 50° C. for 1 h. After cooling to room temperature, the reaction mixture was diluted in 100 mL of EtOAc and quenched with 50 mL of water. The organic layer was separated and the aqueous layer was extracted with EtOAc (2×50 mL). The combined organic phases were washed with brine, dried over $MgSO_4$ and concentrated in vacuum. The title compound was obtained via column chromatography (silica gel, 1;1 hexane/EtOAc) as yellow oil with 93% yield.

EXAMPLE 1

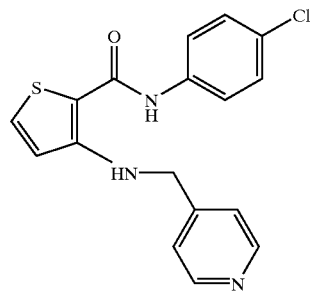

N-(4-Chlorophenyl){3-[(4-pyridylmethyl)amino](2-thienyl)}carboxamide

Step A—Preparation of 3-[(tert-butoxy)carbonylamino] thiophene-2-carboxylic acid To a mixture of methyl 3-amino-2-thiophenecarboxylate (8 g, 51 mmol) and $BOC_2O$ (11 g, 50 mmol) in $CH_2Cl_2$ (400 ml) was added 4-(dimethylamino)pyridine (1 g, 8.1 mmol).

The reaction was stirred at RT overnight and washed with 1N HCl (100 ml), followed by water and brine. The organic layer was dried over $Na_2SO_4$ and evaporated under reduced pressure and used for the next step without further purification. To the residue (2 g, ~7 mmol) in EtOH (50 ml) was added 1N NaOH (25 ml), the reaction was stirred at RT for 1 h and the solvent was evaporated under reduced pressure. Water (5 ml) was added and the solution was acidified with HOAc. The precipitate was filtered and used in the next step without further purification. MS (ES−): 242 (M−H)⁻.

Step B—Preparation of {3-[(tert-butoxy)carbonylamino](2-thienyl)}-N-(4-chlorophenyl)carboxamide To a mixture of the thienyl carboxylic acid from Step A (300 mg, 1.23 mmol) and 4-chloroaniline (160 mg, 1.25 mmol) and DIEA (300 µl, 1.6 mmol) was added EDC (300 mg, 1.6 mmol) and HOBt (170 mg, 1.25 mmol) in $CH_2Cl_2$, the reaction was stirred at RT overnight. The solution was washed with 1N HCl and saturated $NaHCO_3$, followed by $H_2O$ and brine. The organic layer was dried over $Na_2SO_4$ and evaporated under reduced pressure and purified with preparative TLC to give the amide. MS (ES+): 353 (M+H)⁺; (ES−): 351 (M−H)⁻.

Step C—Preparation of N-(4-chlorophenyl){3-[(4-pyridylmethyl)amino](2-thienyl)}carboxamide The amide from Step B was mixed with 25% TFA/$CH_2Cl_2$ and stirred at RT for 1 h (monitored by HPLC). The solvent was evaporated under reduced pressure and the residue was mixed with 4-pyridine carboxaldehyde (260 mg, 2.5 mmol) and $NaCNBH_3$ (160 mg, 2.5 mmol) in MeOH (40 ml). The reaction was stirred at RT overnight and evaporated under reduced pressure. The final product was purified by prep-HPLC as TFA salt. MS (ES+): 344 (M+H)⁺; (ES−): 342 (M−H)⁻. Calc'd. for $C_{17}H_{14}ClN_3OS$—343.84.

EXAMPLE 2

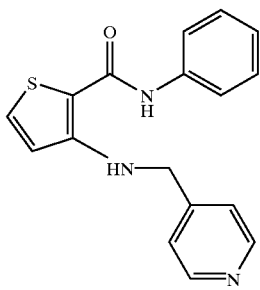

N-Phenyl{3-[(4-pyridylmethyl)amino](2-thienyl)}carboxamide

The title compound was analogously synthesized by method described in Example 1. The final product was purified by preparative HPLC as TFA salt. MS (ES+): 310 (M+H)$^+$; (ES−): 308 (M−H)$^−$. Calc'd. for $C_{17}H_{15}N_3OS$—309.4.

EXAMPLE 3

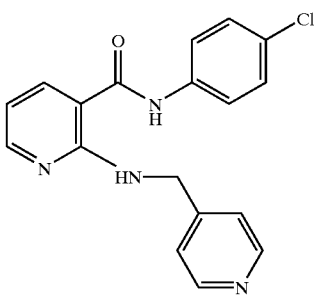

N-(4-Chlorophenyl){2-[(4-pyridylmethyl)amino](3-pyridyl)}carboxamide

Step A—Preparation of (2-amino(3-pyridyl))-N-(4-chlorophenyl)carboxamide

To a mixture of 2-aminonicotinic acid (5.3 g, 38 mmol) and 4-chloroaniline (4.9 g, 38 mmol) and DIEA (9 ml, 48 mmol) at 0° C. in $CH_2Cl_2$ was added EDC (9.5 g, 48 mmol) and HOBt (5.1 g, 38 mmol), the reaction was warmed to RT and stirred overnight. The solvent was evaporated under reduced pressure and quenched with 2N NaOH solution (60 ml) and stirred for 20 min. The precipitate was filtered to give the titled compound. MS (ES+): 248 (M+H)$^+$; (ES−): 246 (M−H)$^−$.

Step B—Preparation of N-(4-chlorophenyl){2-[(4-pyridylmethyl)amino](3-pyridyl)}carboxamide To a mixture of the pyridyl carboxamide (400 mg, 1.6 mmol) from Step A and 4-pyridinecarboxaldehyde (200 µl, 2 mmol) and HOAc (200 µl) in $CH_2Cl_2$ was added NaBH(OAc)$_3$ (600 mg, 2.8 mmol), the reaction was stirred at RT overnight. The reaction mixture was washed with $H_2O$ and brine and dried over $Na_2SO_4$. The solution was evaporated and purified by prep-TLC to give the title compound. MS (ES+): 339 (M+H)$^+$; (ES−): 337 (M−H)$^−$. Calc'd for $C_{18}H_{15}ClN_4O$—338.796.

EXAMPLE 4

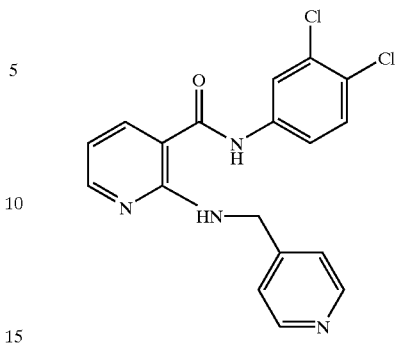

N-(3,4-Dichlorophenyl){2-[(4-pyridylmethyl)amino](3-pyridyl)}-carboxamide

The title compound was analogously synthesized by the method described in Example 3. MS (ES+): 373 (M+H)$^+$; (ES−): 370.9 (M−H)$^−$. Calc'd for $C_{18}H_{14}Cl_2N_4O$—373.24.

EXAMPLE 5

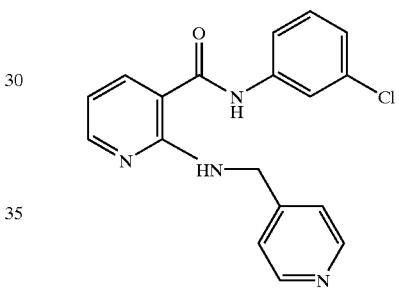

N-(3-Chlorophenyl){2-[(4-pyridylmethyl)amino](3-pyridyl)}carboxamide

The title compound was analogously synthesized by the method described in Example 3. MS (ES+): 339 (M+H)$^+$; (ES−): 337 (M−H)$^−$. Calc'd. for $C_{18}H_{15}ClN_4O$—338.1.

EXAMPLE 6

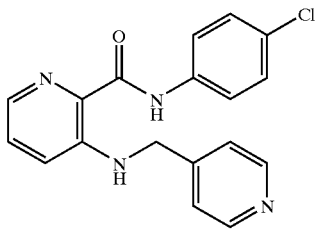

N-(4-Chlorophenyl){3-[(4-pyridylmethyl)amino](2-pyridyl)}carboxamide

The title compound was analogously synthesized by method described in Example 3. MS (ES+): 339 (M+H)$^+$; (ES−): 337 (M−H)$^−$. Calc'd. for $C_{18}H_{15}ClN_4O$—338.8.

EXAMPLE 7

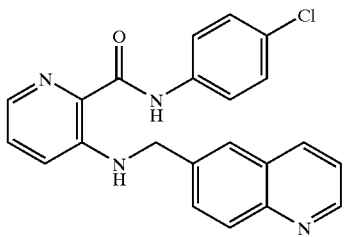

N-(4-Chlorophenyl) {3-[(6-quinolylmethyl)amino](2-pyridyl)}carboxamide

The title compound was analogously synthesized by the method described in Example 3. MS (ES+): 389 (M+H)$^+$; (ES−): 387 (M−H)$^−$. Calc'd. for $C_{22}H_{17}ClN_4O$—388.86.

EXAMPLE 8

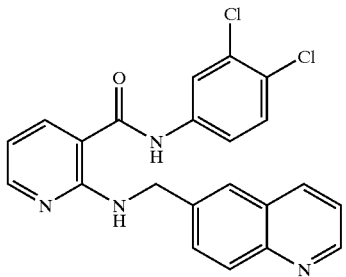

N-(3,4-Dichlorophenyl){2-[(6-quinolylmethyl)amino](3-pyridyl)}-carboxamide

The title compound was analogously synthesized by the method described in Example 3. MS (ES+): 423 (M+H)$^+$; (ES−): 421 (M−H)$^−$. Calc'd. for $C_{22}H_{16}Cl_2N_4O$—423.30.

EXAMPLE 9

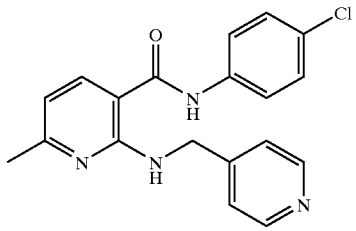

N-(4-Chlorophenyl){6-methyl-2-[(4-pyridylmethyl)amino](3-pyridyl)}carboxamide

Step A—Preparation of 6-methyl-2-[(4-pyridylmethyl)amino]pyridine-3-carboxylic acid The mixture of 2-chloro-6-methyl-nicotinic acid (1.0 eq.) and 4-aminomethyl-pyridine (2.0 eq.) was stirred in a sealed tube at 130° C. overnight. The resulted mixture was cooled to RT, diluted with $CH_2Cl_2$, filtered to collected the brown solid. The brown solid was recrystallized in ethanol to give the substituted amine as light brown solid. MS (ES+): 244 (M+H)$^+$.

Step B—Preparation of N-(4-chlorophenyl){6-methyl-2-[(4-pyridylmethyl)amino](3-pyridyl)}-carboxamide To the mixture of the substituted amine from Step A (1.0 eq.) and 4-chloroaniline (2.0 eq) in $CH_2Cl_2$ was added bis(2-oxo-3-oxazolidinyl)phosphinic chloride (1.1 eq.) and TEA (1.1 eq.). The mixture was stirred overnight, diluted with $CH_2Cl_2$, washed with saturated $NH_4Cl$ solution, dried over $Na_2SO_4$, filtered and concentrated, purified by flash chromatography (4% MeOH/$CH_2Cl_2$) to give the title compound as an white solid. MS (ES+): 353 (M+H); (ES−): 351 (M−H). Calc'd. for $C_{19}H_{17}ClN_4O$—352.82.

EXAMPLE 10

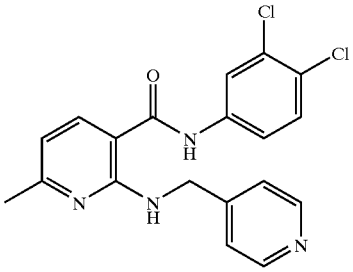

N-(3,4-Dichlorophenyl){6-methyl-2-[(4-pyridylmethyl)amino](3-pyridyl)}carboxamide The title compound was analogously synthesized by the method described in Example 9. MS (ES+): 387 (M+H); (ES−): 385 (M−H). Calc'd. for $C_{19}H_{16}Cl_2N_4O$—387.27.

EXAMPLE 11

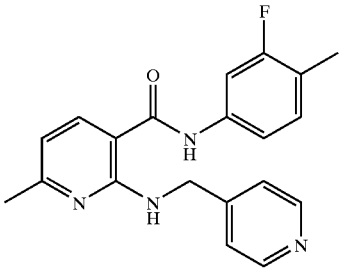

N-(3-Fluoro-4-methylphenyl){6-methyl-2-[(4-pyridylmethyl)amino](3-pyridyl)}carboxamide The title compound was analogously synthesized by the method described in Example 9. MS (ES+): 351 (M+H); (ES−): 349 (M−H). Calc'd. for $C_{20}H_{19}FN_4O$—350.39.

EXAMPLE 12

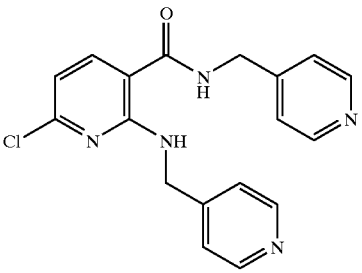

{6-Chloro-2-[(4-pyridylmethyl)amino](3-pyridyl)}-N-(4-pyridylmethyl)carboxamide

The title compound was analogously synthesized by the method described in Example 9. MS (ES+): 354 (M+H); (ES−): 352 (M−H). Calc'd. for $C_{18}H_{16}ClN_5O$—353.81.

EXAMPLE 13

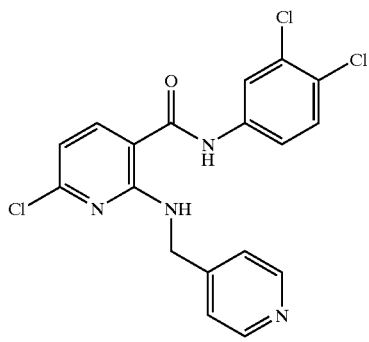

N-(3,4-Dichlorophenyl){6-chloro-2-[(4-pyridylmethyl)amino](3-pyridyl)}carboxamide The title compound was analogously synthesized by the method described in Example 9. MS (ES+): 409 (M+H). Calc'd. for $C_{18}H_{19}Cl_3N_4O$—407.7.

EXAMPLE 14

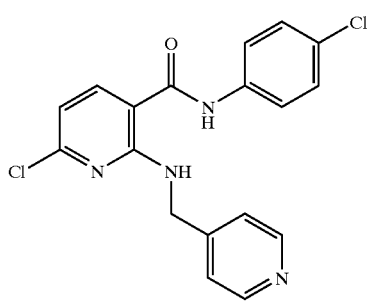

N-(4-Chlorophenyl){6-chloro-2-[(4-pyridylmethyl)amino](3-pyridyl)}carboxamide

The title compound was analogously synthesized by method described in Example 9. MS (ES+): 374 (M+H); (ES−): 372 (M−H). Calc'd. for $C_{18}H_{14}Cl_2N_4O$—373.24.

EXAMPLE 15

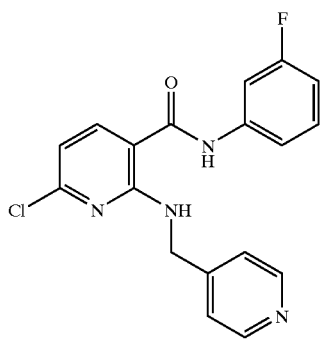

{6-Chloro-2-[(4-pyridylmethyl)amino](3-pyridyl)}-N-(3-fluorophenyl)carboxamide

The title compound was analogously synthesized by the method described in Example 9. MS (ES+): 357 (M+H); (ES−): 355 (M−H). Calc'd. for $C_{18}H_{19}FN_4OCl$—356.5.

EXAMPLE 16

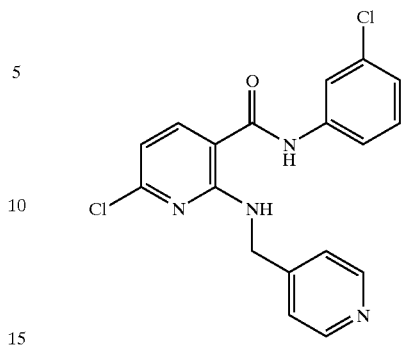

N-(3-Chlorophenyl){6-chloro-2-[(4-pyridylmethyl)amino](3-pyridyl)}carboxamide

The title compound was analogously synthesized by the method described in Example 9. MS (ES+): 374 (M+H); (ES−): 372 (M−H). Calc'd. for $C_{18}H_{14}Cl_2N_4O$—373.24.

EXAMPLE 17

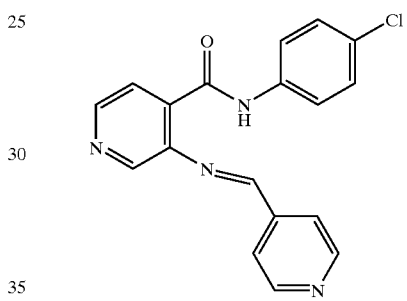

N-(4-Chlorophenyl) {3-[(4-pyridylmethylene)amino](4-pyridinecarboxamide

A mixture of (2-amino(4-pyridyl))-N-(4-chlorophenyl)carboxamide (350 mg, 1.4 mmol) (similar procedure to Example 3, Step A) and 4-pyridine carboxaldehyde (200 µl, 2 mmol) and 4-toluenesulfonic acid monohydrate (50 mg) in EtOH (50 ml) was heated to reflux overnight. The solvent was evaporated and the residue was purified by prep-TLC. MS (ES+): 337 (M+H)⁺; (ES−): 335 (M−H)⁻. Calc'd. for $C_{18}H_{13}ClN_4O$—336.8.

EXAMPLE 18

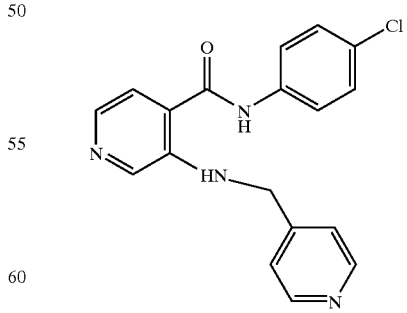

N-(4-Chlorophenyl){3-[(4-pyridylmethyl)amino](4-pyridyl)}carboxamide

The compound from Example 17 was mixed with NaBH₄ (100 mg) in EtOH (20 ml) and heated to reflux for 5 min.

The solvent was evaporated under reduced pressure and the residue was purified by prep-TLC to give the titled compound. MS (ES+): 339 (M+H)+; (ES-): 337 (M-H)-. Calc'd. for $C_{18}H_{15}ClN_4O$—338.8.

EXAMPLE 19

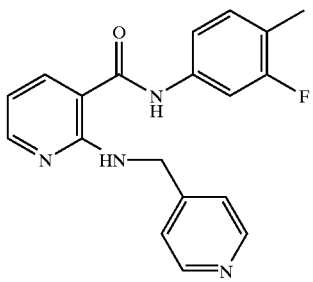

N-(3-Fluoro-4-methylphenyl){2-[(4-pyridylmethyl)amino](3-pyridyl)}carboxamide

The title compound was analogously synthesized by the method in Examples 17–18. MS (ES-): 337 (M-H)-. Calc'd. for $C_{19}H_{17}FN_4O$—336.37.

EXAMPLE 20

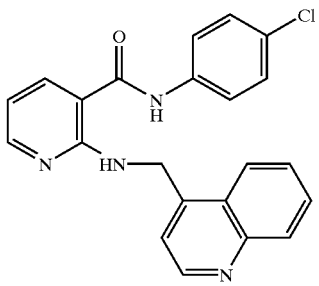

N-(4-Chlorophenyl){2-[(4-quinolylmethyl)amino](3-pyridyl)}carboxamide

The title compound was analogously synthesized by the method described in Examples 17–18. MS (ES+): 389 (M+H)+; (ES-): 387 (M-H)-. Calc'd. for $C_{22}H_{17}ClN_4O$—388.86.

EXAMPLE 21

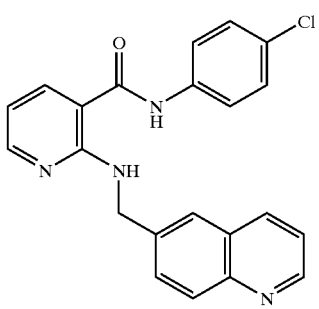

N-(4-Chlorophenyl){2-[(6-quinolylmethyl)amino](3-pyridyl)}carboxamide

The title compound was analogously synthesized by the method described in Examples 17–18. MS (ES+): 389 (M+H)+; (ES-): 387 (M-H)-. Calc'd. for $C_{22}H_{17}ClN_4O$—388.86.

EXAMPLE 22

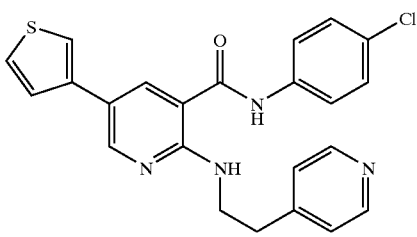

N-(4-Chlorophenyl){2-[(4-pyridylethyl)amino]-5-(3-thienyl)-(3-pyridyl)}carboxamide Step A—Preparation of 5-bromo-2-hydroxynicotinic acid A solution of sodium hypobromide was made by adding $Br_2$ (1.01 ml, 39.5 mmol, 1.1 eq) slowly over a period of 5 min to NaOH (5N, 40 ml) that was previously cooled to 0° C. in an ice bath. The solution was stirred for 10 min before adding 2-hydroxynicotinic acid (5.0 g, 35.9 mmol) and placed in a 50° C. oil bath and stirred. Concurrently, a second pot of sodium hypobromide solution was made by slowly adding $Br_2$ (1.01 ml, 39.5 mmol, 1.1 eq) to a NaOH solution (5N, 40 ml) in an ice bath. The second pot of sodium hypobromide was added to the solution of 2-hydroxynicotinic acid after 24 h of heating then was stirred for an additional 24 h. The solution was cooled to RT, placed in an ice bath and acidified with concentrated HCl while stirring. The precipitate which formed was filtered, washed and dried to afford the desired compound as an off-white solid.

Step B—Preparation of 5-bromo-2-chloronicotinic acid

A solution of 5-bromo-2-hydroxynicotinic acid, from Step A (8.3 g, 38.1 mmol) and $SOCl_2$ (40 ml) in a 150 ml round bottom flask was placed in an 80° C. oil bath and stirred while adding 10 ml of DMF. The solution was heated at reflux for 4 h at 80° C. before cooling to RT. Excess $SOCl_2$ was stripped off under reduced pressure forming a yellow-brown residue. The yellow-brown residue was placed in an ice bath and cooled to 0° C. Residual $SOCl_2$ was neutralized and the chloro compound was precipitated by the dropwise addition of water. Precipitate was filtered, washed and dried to afford the desired chloro compound as a light yellow solid.

Step C—Preparation of 5-bromo-2-chloro-N-(4-chlorophenyl)nicotinamide

To a mixture of 4-chloroanaline (594 mg, 4.7 mmol, 1. eq.), EDC (1.62 g, 8.5 mmol, 2 eq.), HOBT (572 mg, 4.2 mmol, 1 eq.), and DIEA (1.1 ml, 6.3 mmol, 1.5 eq.) in $CH_2Cl_2$ (50 ml) was added 5-bromo-2-chloronicotinic acid from Step B (1.0 g, 4.2 mmol). The reaction was stirred at RT overnight. The solution was quenched with water and the organic layer was purified by chromatography (50% EtOAc in hexane) to afford a light-yellow compound. MS (ES+): 347.0, 349.0 (M+H)+; (ES-): 345.0, 347.0 (M-H)-.

Step D—Preparation of 5-(3-thiophene)-2-chloro-N-(4-chlorophenyl)nicotinamide

3-Thiophene boronic acid (204 mg, 1.6 mmol, 1.1 eq), $Pd(OAc)_2$ (33 mg, 0.2 mmol, 0.2 eq.), and $K_2CO_3$ (505 mg, 4.3 mmol, 3 eq.) were added to a solution of 5-bromo-2-chloro-N-(4-chlorophenyl)nicotinamide from Step C (500 mg, 1.4 mmol) in DMF (20 ml). The reaction was placed in a 50° C. oil bath and stirred overnight. The reaction was filtered and purified by medium pressure chromatography (30% EtOAc in hexane) to afford the desired thienyl compound as an off white solid.

Step E—Preparation of N-(4-chlorophenyl){2-[(4-pyridylethyl)amino]-5-(3-thienyl)-(3-pyridyl)}carboxamide 4-(Aminoethyl)pyridine (10 ml) was added to a 25 ml round-bottom flask containing 5-(3-thiophene)-2-chloro-N-(4-chlorophenyl)nicotinamide from Step D (200 mg, 0.6 mmol). The solution was placed in an 80° C. oil bath and stirred overnight. The reaction was cooled to RT, and after an aqueous work-up, was purified by medium-pressure chromatography (80% EtOAc in hexane) to afford the title compound as a light yellow solid. MS: (ES+) 435.1 (M+H); (ES−) 432.8 (M−H). Calc'd. for $C_{23}H_{19}ClN_4OS$—434.95.

EXAMPLE 23

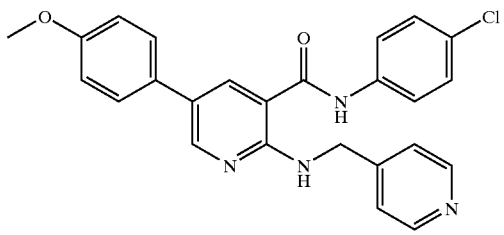

N-(4-Chlorophenyl) {5-(4-methoxyphenyl)-2-[(4-pyridylmethyl)amino]-(3-pyridyl)}carboxamide The title compound was prepared analogously to Example 22. MS: (ES+) 445.1 (M+H). Calc'd. for $C_{25}H_{21}ClN_4O$—444.92.

EXAMPLE 24

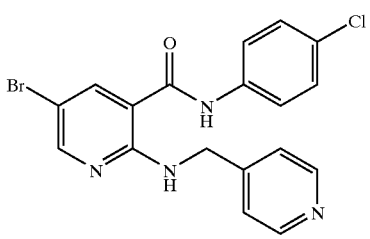

N-(4-Chlorophenyl){5-bromo-2-[(4-pyridylmethyl)amino]-(3-pyridyl)}carboxamide

The title compound was prepared analogously to Example 22, Steps A, B, C and E. MS: (ES+) 419 (M+H) (ES−) 417 (M−H). Calc'd. for $C_{18}H_{14}BrClN_4O$—417.69.

EXAMPLE 25

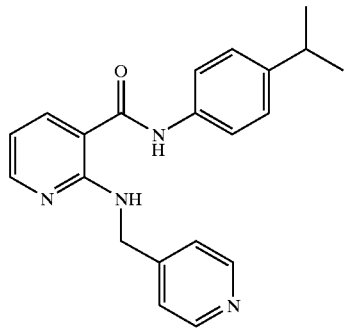

N-(4-Isopropylphenyl){2-[(4-pyridylmethyl)amino] (3-pyridyl)}carboxamide

Step A: Preparation of (2-chloro-3-pyridyl)-N-(4-isopropylphenyl)carboxamide

To a mixture of 2-chloronicotinic acid (6.3 g) and 4-isopropylaniline (5.26 ml) and DIEA (10 ml) in $CH_2Cl_2$ (200 ml) was added EDC (10 g) and HOBt (5.4 g). The reaction was stirred at RT overnight and washed with 2 N NaOH (100 ml), $H_2O$ (250 ml) and brine (100 ml). The organic layer was dried over $Na_2SO_4$ and evaporated to give (2-chloro-3-pyridyl)-N-(4-isopropylphenyl)-carboxamide.

Step B: Preparation of N-[4-(isopropyl)phenyl]{2-[(4-pyridylmethyl)amino](3-pyridyl)}carboxamide hydrochloride A mixture of (2-chloro(3-pyridyl))-N-(4-isopropylphenyl)carboxamide (1.5 g, from Step A) and 4-aminomethylpyridine (0.71 ml) was heated at 130° C. neat for 3 h. The reaction was cooled and diluted with $CH_2Cl_2$ and washed with $H_2O$ twice followed by brine. The organic layer was dried with $Na_2SO_4$ and evaporated under reduced pressure. The residue was purified by column chromatography with EtOAc and further mixed with MeOH and 1 N $HCl/Et_2O$ (2 ml). The solution was evaporated to furnish the titled compound. MS (ES+): 347 (M+H)$^+$; (ES−): 345 (M−H). Calc'd. for $C_{21}H_{22}N_4O$—346.18.

The following compounds (Examples 26–81) were synthesized by the method described in Example 25 unless specifically described. Detailed intermediate preparations are included.

TABLE 1
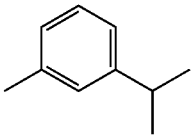
| # | Y | R¹ | R² | M + H | calc'd |
|---|---|---|---|---|---|
| 26 | —NH—CH₂— | 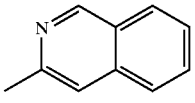 | H | 347 | 346.2 |
| 27 | NH—CH₂— | 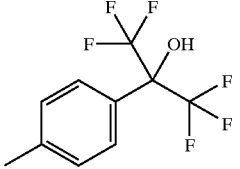 | H | 356 | 355.1 |
| 28 | NH—CH₂— | 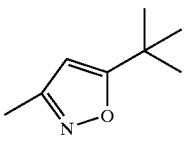 | H | 471 | 470.1 |
| 29 | NH—CH₂— | 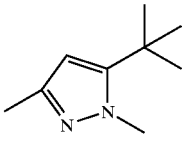 | H | 352 | 351.4 |
| 30 | NH—CH₂— | 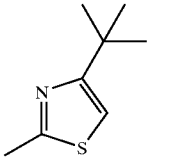 | H | 365 | 364.2 |
| 31 | NH—CH₂— | 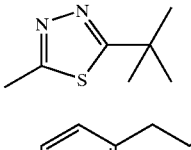 | H | 368 | 367.5 |
| 32 | NH—CH₂— |  | H | 369 | 368.5 |
| 33 | NH—CH₂— | 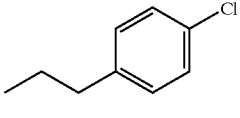 | H | 377 | 376.2 |
| 34 | NH—CH₂— |  | H | 366.8 | 366.8 |

TABLE 1-continued
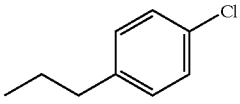
| # | Y | R¹ | R² | M + H | calc'd |
|---|---|---|---|---|---|
| 35 | NH—CH₂— | 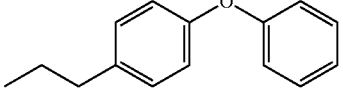 (4-Cl-phenylpropyl) | 5-Br | 447.0 | 445.7 |
| 36 | NH—CH₂— | 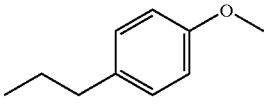 (4-phenoxyphenylpropyl) | H | 425.0 | 424.5 |
| 37 | NH—CH₂— | 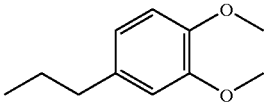 (4-methoxyphenylpropyl) | H | 363.2 | 362.4 |
| 38 | NH—CH₂— | 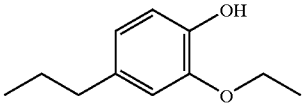 (3,4-dimethoxyphenylpropyl) | H | 393.2 | 392.4 |
| 39 | NH—CH₂— | 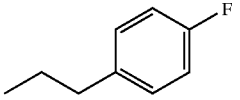 (4-OH-3-ethoxyphenylpropyl) | H | 393.2 | 392.4 |
| 40 | NH—CH₂— | 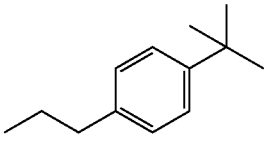 (4-F-phenylpropyl) | H | 350.8 | 350.4 |
| 41 | NH—CH₂— | 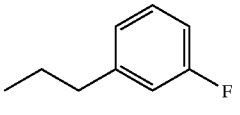 (4-tBu-phenylpropyl) | H | 389.2 | 388.5 |
| 42 | NH—CH₂— | (3-F-phenylpropyl) | H | 351.0 | 350.4 |
| 43 | NH—CH₂— | 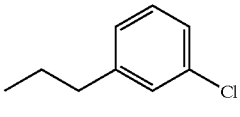 (3-Cl-phenylpropyl) | H | 367.1 | 366.8 |
| 44 | NH—CH₂— | 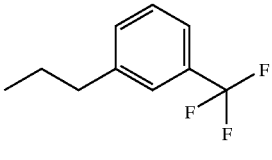 (3-CF₃-phenylpropyl) | H | 401.3 | 400.4 |

TABLE 1-continued
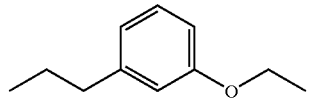
| # | Y | R¹ | R² | M + H | calc'd |
|---|---|---|---|---|---|
| 45 | NH—CH₂— | 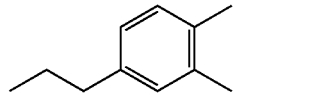 | H | 377.2 | 376.5 |
| 46 | NH—CH₂— | 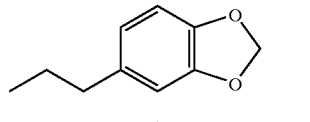 | H | 361.4 | 360.4 |
| 47 | NH—CH₂— | 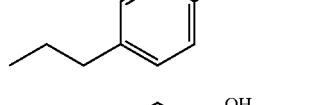 | H | 377.1 | 376.4 |
| 48 | NH—CH₂— | 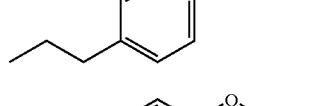 | H | 347.1 | 346.4 |
| 49 | NH—CH₂— | 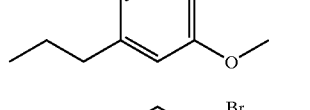 | H | 349.1 | 348.4 |
| 50 | NH—CH₂— | 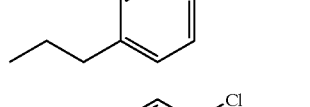 | H | 393.2 | 392.4 |
| 51 | NH—CH₂— | 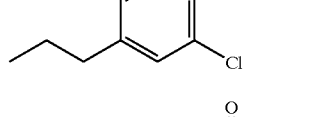 | H | 411.2 | 411.3 |
| 52 | NH—CH₂— | 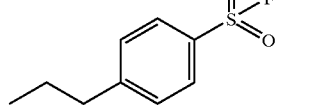 | H | 403.1 | 401.3 |
| 53 | NH—CH₂— | 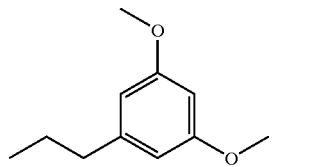 | H | 415.2 | 414.4 |
| 54 | NH—CH₂— |  | H | 393.2 | 392.4 |

TABLE 1-continued
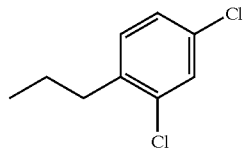
| # | Y | R¹ | R² | M + H | calc'd |
|---|---|---|---|---|---|
| 55 | NH—CH₂— | 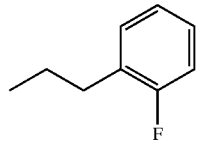 | H | 403.2 | 401.3 |
| 56 | NH—CH₂— | 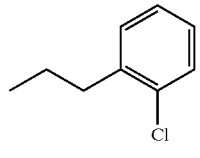 | H | 351.0 | 350.4 |
| 57 | NH—CH₂— | 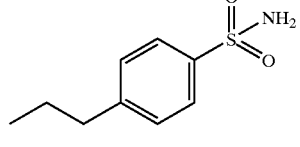 | H | 369.1 | 366.8 |
| 58 | NH—CH₂— | 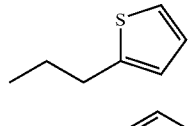 | H | 412.3 | 411.5 |
| 59 | NH—CH₂— | 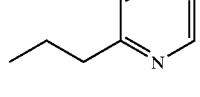 | H | 338.8 | 338.4 |
| 60 | NH—CH₂— | 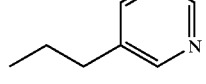 | H | 334.1 | 333.4 |
| 61 | NH—CH₂— | 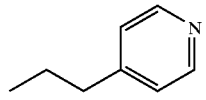 | H | 333.6 | 333.4 |
| 62 | NH—CH₂— | 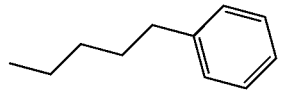 | H | 333.6 | 333.4 |
| 63 | NH—CH₂— | 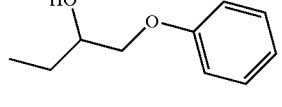 | H | 361.1 | 360.4 |
| 64 | NH—CH₂— |  | H | 379.0 | 378.4 |

TABLE 1-continued

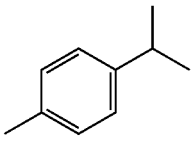

| # | Y | R¹ | R² | M + H | calc'd |
|---|---|---|---|---|---|
| 65 | NH—CH₂— | 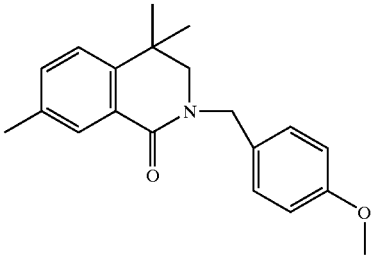 | H | 399 | 398.9 |
| 66 | NH—CH₂— | 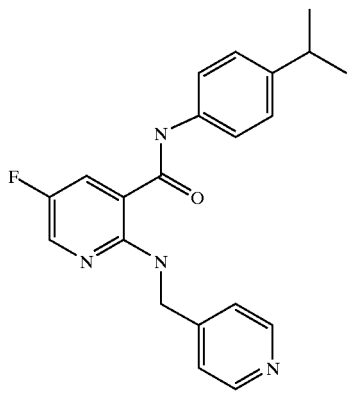 | H | 522.3 | 521 |

EXAMPLE 67

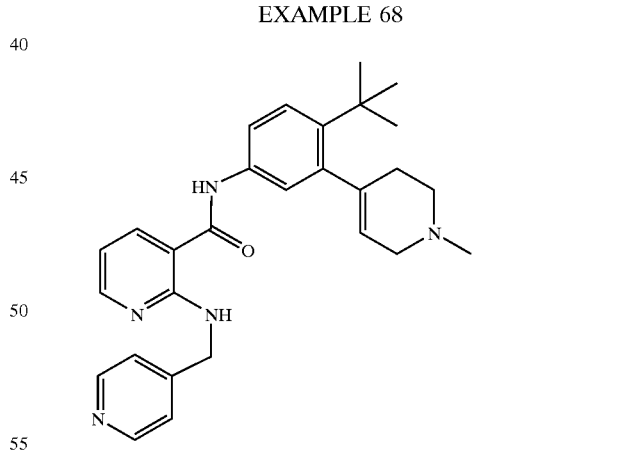

{5-Fluoro-2-[(4-pyridylmethyl)amino](3-pyridyl)}-
N-[4-(isopropyl)phenyl]carboxamide {6-Chloro-5-fluoro-2-[(4-pyridylmethyl)amino](3-pyridyl)}-N-[4-(methylethyl)phenyl]carboxamide (50 mg, 0.125 mmol, from Example 66) dissolved in EtOH (10 mL) with TEA (0.5 mL) and suspended with Pd/C (10%, 5 mg). The mixture was stirred at RT under a H₂ balloon for 45 min. The mixture was filtered through a layer of Celite® and the filtrate was concentrated in vacuo. The residue was partitioned between CH₂Cl₂ and aq. NaHCO₃ (sat.). The organic solution was dried over Na₂SO₄ and concentrated in vacuo to give the title compound. MS: 365 (M+1). Calc'd. for C₂₁H₂₁FN₄O—364.42.

EXAMPLE 68

2-[(Pyridin-4-ylmethyl)amino]-N-[4-tert-butyl-3-(1,2,3,6-tetrahydropyridin-4-yl)phenyl](3-pyridyl)carboxamide Step A Preparation of 2-bromo-1-tert-butyl-4-nitrobenzene NBS (125.0 g, 697.5 mmol) was slowly added to a solution of TFA:H₂SO₄ (5:1, 750 mL) and tert-butyl-4-nitrobenzene (100.0 g, 558.0 mmol) at RT. The solution was stirred for 24 h then poured over 5 kg of ice. The resulting suspension was filtered and washed with a 1:1 MeOH:H₂O solution (200 mL) and dried in a vacuum oven. MS (ES+): 258.1, 260.1 (M+H)⁺. Calc'd for C₁₀H₁₂BrNO₂: 257.01.

Step B Preparation of 4-(2-tert-butyl-5-nitrophenyl)pyridine

To a solution of 2-bromo-1-tert-butyl-4-nitrobenzene (8.6 g, 33.3 mmol) and toluene (70 mL) in a 150 mL round bottom flask, 4-pyridylboronic acid (4.5 g, 36.6 mmol), Pd(PPh₃)₄ (3.8 g, 3.3 mmol) and K₂CO₃ (13.8 g, 99.9 mmol) were added. The solution was stirred for 24 h at 80° C. before cooling to RT. The solution was filtered through a pad of Celite® and purified by silica flash chromatography (30% EtOAc/Hexanes). This afforded the desired compound as a yellow solid. MS (ES+): 257.2 (M+H)⁺; (ES–): 255.2 (M–H)⁻. Calc'd for C₁₅H₁₆N₂O₂: 256.12.

Step C Preparation of 4-(2-tert-butyl-5-nitrophenyl)-1-methylpyridinium 4-(2-tert-Butyl-5-nitrophenyl)pyridine (2.0 g, 7.8 mmol, Step B) was added to a round-bottom flask and dissolved in EtOH (10 mL). MeI (30 mL) was added and the flask was placed in an 80° C. sand bath and heated to reflux. After 6 h the solution was cooled to RT and the excess MeI and EtOH was concentrated in vacuo resulting in the desired compound as a light brown solid. MS (ES+): 271.2 (M+H)⁺; (ES–): 269.2 (M–H)⁻. Calc'd for C₁₆H₁₉N₂O₂⁺: 271.14.

Step D Preparation of 4-tert-butyl-3-(1-methyl-1,2,3,6-tetrahydropyridin-4-yl)aniline 4-(2-tert-Butyl-5-nitrophenyl)-1-methylpyridinium (2.1 g, 7.8 mmol, Step C) was added to a 100 mL round-bottom flask and dissolved in a 10% H₂O/EtOH mixture. To the flask iron dust (1.31 g, 23.4 mmol) and NH₄Cl (460 mg, 8.6 mmol) were added. The flask was placed in a 100° C. sand bath and heated to reflux. After 2 h the solution was cooled to RT and filtered through a pad of Celite®. The resulting solution was concentrated in vacuo to a yellow solid and re-dissolved in MeOH (20 mL, anhydrous). The solution was cooled to 0° C. by placing it in an ice bath and slowly adding NaBH₄ (450 mg, 11.7 mmol). After addition of the NaBH₄, the solution was cooled to RT and stirred for 30 min. The solvent was concentrated in vacuo and the solid was re-dissolved in CH₂Cl₂ and filtered. The solution was again concentrated in vacuo to afford an amorphous clear yellow solid. MS (ES+): 245.2 (M+H)⁺. Calc'd for C₁₆H₂₄N₂: 244.19.

Step E Preparation of 2-[(pyridin-4-ylmethyl)amino]-N-[4-tert-butyl-3-(1,2,3,6-tetrahydropyridin-4-yl)phenyl](3-pyridyl)carboxamide The titled compound was prepared from 4-tert-butyl-3-(1-methyl-1,2,3,6-tetrahydropyridin-4-yl)aniline (Step D) by the method described in Example 25. MS: (ES+) 456.3 (M+H); (ES–) 454.4 (M–H). Calc'd for C₂₈H₃₃N₅O—455.59.

EXAMPLE 69

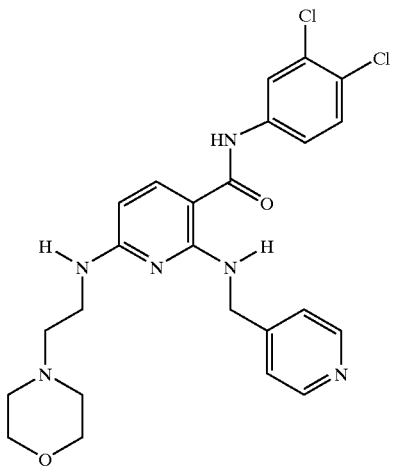

N-(3,4-Dichlorophenyl){6-[(2-morpholin-4-ylethyl)amino]-2-[(4-pyridylmethyl)amino](3-pyridyl)}carboxamide A mixture of N-(3,4-dichlorophenyl){6-chloro-2-[(4-pyridylmethyl)amino](3-pyridyl)}carboxamide (18 mg, 0.044 mmol, made from 2,6-dichloronicotinic acid) and 2-morpholin-4-ylethylamine (300 μL) was stirred at 80° C. for 20 h. The reaction mixture was purified on silica gel chromatography to yield N-(3,4-dichlorophenyl){6-[(2-morpholin-4-ylethyl)amino]-2-[(4-pyridylmethyl)-amino](3-pyridyl)}carboxamide. MS (ES+): 501 (M+H)⁺; (ES–): 499 (M–H)⁻. Calc'd for C₂₄H₂₆Cl₂N₆O₂—500.15.

EXAMPLE 70

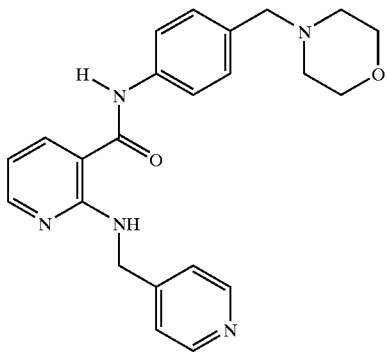

N-[4-(Morpholin-4-ylmethyl)phenyl]{2-[(4-pyridylmethyl)amino](3-pyridyl)}carboxamide Step A Preparation of 4-[(4-nitrophenyl)methyl]morpholine A mixture of nitrobenzyl bromide (648 mg, 3.0 mmol) and morpholine (522 mg, 6.0 mmol) in CH₂Cl₂ was stirred for 5 h at RT. Filtration to remove the white solid, and the filtrate was concentrated to give 4-[(4-nitrophenyl)-methyl] morpholine as a solid, which was used in next step without further purification.

Step B Preparation of 4-(morpholin-4-ylmethyl) phenylamine

A mixture of 4-[(4-nitrophenyl)methyl]morpholine (220 mg, 1.0 mmol, Step A), iron powder (279 mg, 5.0 mmol) and $NH_4Cl$ (39 mg, 0.7 mmol) in EtOH (3 mL) and $H_2O$ (3 mL) was stirred for 4 h at 80° C. Filtration and concentration gave the crude 4-(morpholin-4-ylmethyl)-phenylamine, which was used in next step without further purification.

Step C Preparation of N-[4-(morpholin-4-ylmethyl)phenyl] {2-[(4-pyridylmethyl)amino](3-pyridyl)}carboxamide The titled compound was prepared from 4-(morpholin-4-ylmethyl)phenylamine (Step B) by the method described in Example 25. MS (ES+): 404 (M+H); (ES−): 402 (M−H). Calc'd. for $C_{22}H_{24}N_4O_2$—403.20.

EXAMPLE 71

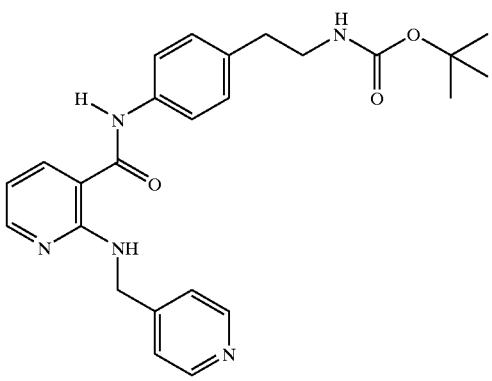

N-(4-{2-[(tert-Butoxy)carbonylamino]ethyl}phenyl) {2-[(4-pyridylmethyl)amino](3-pyridyl) }carboxamide Step A Preparation of (tert-butoxy)-N-[2-(4-nitrophenyl) ethyl]carboxamide A mixture of 2-(4-nitrophenyl)ethylamine (1.01 g, 5.0 mmol), and di-tert-butyl dicarbonate (1.09 g, 5.0 mmol) in $CH_2Cl_2$ (20 mL) and 1N NaOH (20 mL) was stirred for 20 h at RT. The mixture was extracted with $CH_2Cl_2$, washed with brine, and dried with $MgSO_4$. Filtration and concentration yielded (tert-butoxy)-N-[2-(4-nitrophenyl)ethyl] carboxamide, which was used in next step without further purification.

Step B Preparation of N-[2-(4-aminophenyl)ethyl](tert-butoxy)carboxamide

A mixture of (tert-butoxy)-N-[2-(4-nitrophenyl)ethyl]-carboxamide (570 mg, 2.15 mmol, Step A), iron powder (602 mg, 10.75 mmol) and $NH_4Cl$ (82 mg, 1.5 mmol) in EtOH (6 mL) and $H_2O$ (6 ml) was stirred for 4 h at 80° C. Filtration and concentration gave the crude compound, which was used in next step without further purification.

Step C Preparation of N-[4-(morpholin-4-ylmethyl)phenyl] {2-[(4-pyridylmethyl)amino](3-pyridyl)}carboxamide The titled compound was prepared from N-[2-(4-aminophenyl)ethyl](tert-butoxy)carboxamide (Step B) by the method described in Example 25. MS (ES+): 448 (M+H); (ES−): 446 (M−H). Calc'd. for $C_{25}H_{29}N_5O_3$—447.23.

EXAMPLE 72

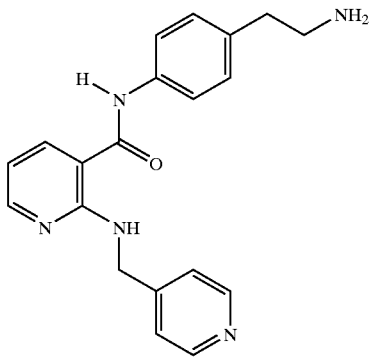

N-[4-(2-Aminoethyl)phenyl]{2-[(4-pyridylmethyl) amino](3-pyridyl)}carboxamide

To the solution of N-(4-{2-[(tert-butoxy)carbonylamino]-ethyl}phenyl){2-[(4-pyridylmethyl)amino](3-pyridyl) }carboxamide (96 mg, 0.22 mmol, Example 71) in $CH_2Cl_2$ (3 mL) was added TFA (3 mL). The mixture was stirred for 3 h at RT. The reaction mixture was concentrated and dried in vacuo to yield N-[4-(2-aminoethyl)phenyl]{2-[(4-pyridylmethyl)-amino](3-pyridyl)}carboxamide. MS (ES+): 348 (M+H); (ES−): 346 (M−H). Calc'd. for $C_{20}H_{21}N_5O$—347.17.

The following compounds (Example a–m) were synthesized by the method described above, unless specifically described.

a) N-[3-(azetidin-3-ylmethoxy)-5-trifluoromethyl-phenyl]-2-[(pyridin-4-ylmethyl)-amino]-nicotinamide.

b) 2-[(2,3-Dihydro-benzofuran-5-ylmethyl)-amino]-N-[3,3-dimethyl-1-(piperidin-4-ylmethyl)-2,3-dihydro-1H-indol-6-yl]-nicotinamide. M+H 512.3; Calc'd 511.7.

c) N-[3-(piperazine-1-carbonyl)-5-trifluoromethyl-phenyl]-2-[(pyridin-4-ylmethyl)-amino]-nicotinamide. M+H 485.3.

d) N-[3-(piperazine-1-methyl)-4-pentafluoroethyl-phenyl]-2-[(pyridin-4-ylmethyl)-amino]-nicotinamide. M+H 521.4.

c) N-[3-(piperazine-1-methyl)-5-trifluoromethyl-phenyl]-2-[(pyridin-4-ylmethyl)-amino]-nicotinamide. M+H 471.2; Calc'd 470.

d) N-[1-(2-Amino-acetyl)-3,3-dimethyl-2,3-dihydro-1H-indol-6-yl]-2-[(2-methoxy-pyridin-4-ylmethyl)-amino] nicotinamide. M+H 461.1.

e) N-[1-(2-Amino-acetyl)-3,3-dimethyl-2,3-dihydro-1H-indol-6-yl]-2-[(pyridin-4-ylmethyl)-amino]nicotinamide. M+H 431.4.

f) (S) N-[3-(pyrrolidin-2-yl-methoxy)-4-pentafluoroethyl-phenyl]-2-[(pyridin-4-ylmethyl)-amino]-nicotinamide. M+H 522.6; Calc'd 521.5.

g) (R) N-[3-(pyrrolidin-2-yl-methoxy)-4-trifluoromethyl-phenyl]-2-[(pyridin-4-ylmethyl)-amino]-nicotinamide. M+H 472.6; Calc'd 471.5.

h) (R) N-[3-(pyrrolidin-2-yl-methoxy)-4-pentafluoroethyl-phenyl]-2-[(pyridin-4-ylmethyl)-amino]-nicotinamide. M+H 522.3; Calc'd 521.5.

i) (S) N-[3-(pyrrolidin-2-yl-methoxy)-5-trifluoromethyl-phenyl]-2-[(pyridin-4-yl-methyl)-amino]-nicotinamide. M+H 472; Calc'd 471.5.

j) (S) N-[3-(4-piperdinyloxy)-5-trifluoromethyl-phenyl]-2-[(pyridin-4-ylmethyl)-amino]-nicotinamide. M+H 472; Calc'd 471.5.
k) 2-[(2-Methoxy-pyridin-4-yl-methyl)-amino]-N-[3-(piperidin-4-yloxy)-5-trifluoromethyl-phenyl]-nicotinamide.
l) N-(4-tert-Butyl-3-[2-(piperidin-4-yl)-methoxy]-phenyl)-2-[(pyridin-4-ylmethyl)-amino]-nicotinamide. M+H 474.
m) N-[4-tert-Butyl-3-(pyrrolidin-2-ylmethoxy)-phenyl]-2-[(pyridin-4-ylmethyl)-amino]-nicotinamide. M+H 460.
n) 2-[(2-Methoxy-pyridin-4-ylmethyl)-amino]-N-[3-(pyrrolidin-2-ylmethoxy)-5-trifluoromethyl-phenyl]-nicotinamide.
o) N-(3,3-Dimethyl-1-pyrrolidin-2-ylmethyl-2,3-dihydro-1H-indol-6-yl)-2-[(pyridin-4-ylmethyl)-amino]-nicotinamide.

EXAMPLE 73

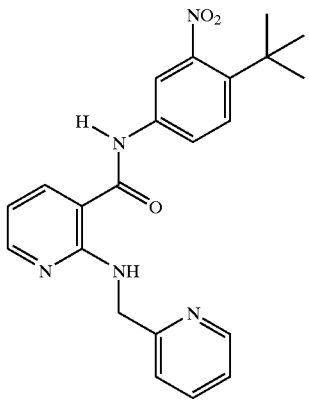

N-[4-(tert-Butyl)-3-nitrophenyl]{2-[(2-pyridylmethyl)amino](3-pyridyl)}carboxamide MS (ES+): 406 (M+H); (ES−): 405 (M−H). Calc'd. for $C_{22}H_{23}N_5O_3$— 405.18.

EXAMPLE 74

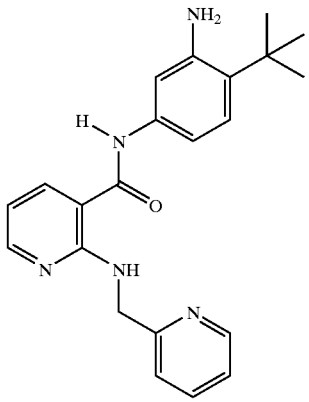

N-[3-Amino-4-(tert-butyl)phenyl]{2-[(2-pyridylmethyl)amino](3-pyridyl)}carboxamide A mixture of N-[4-(tert-butyl)-3-nitrophenyl]{2-[(2-pyridylmethyl)amino](3-pyridyl)}carboxamide (100 mg, 0.25 mmol, Example 73), iron powder (69 mg, 1.25 mmol) and NH$_4$Cl (10 mg, 0.17 mmol) in EtOH (0.5 mL) and H$_2$O (0.5 ml) was stirred for 4 h at 80° C. The reaction mixture was filtered, concentrated, and purified through column chromatography to give the product. MS (ES+):376 M+H; (ES−):374(M−H). Calc'd. for $C_{22}H_{25}N_5O$—375.21.

EXAMPLE 75

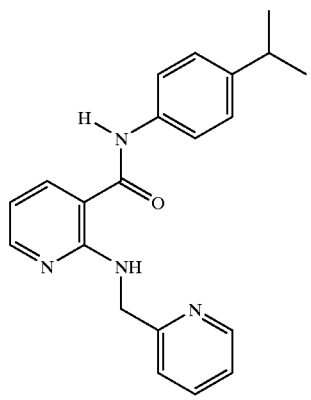

N-[4-(Isopropyl)phenyl]{2-[(2-pyridylmethyl)amino](3-pyridyl)}carboxamide

MS (ES+): 347 (M+H); (ES−): 345 (M−H). Calc'd. for $C_{21}H_{22}N_4O$—346.18.

EXAMPLE 76

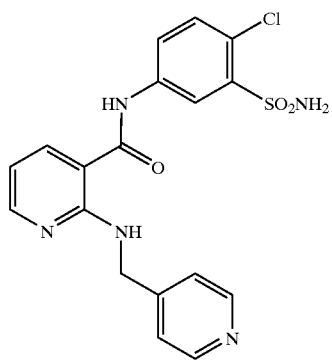

N-(3-Aminosulfonyl-4-chlorophenyl){2-[(4-pyridylmethyl)amino](3-pyridyl)}carboxamide MS (ES+): 418 (M+H); (ES−): 416 (M−H). Calc'd. for $C_{18}H_{16}N_5O_3S$—417.07.

EXAMPLE 77

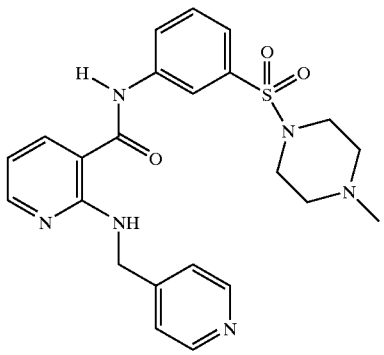

N-{3-[(4-Methylpiperazinyl)sulfonyl]phenyl}{2-[(4-pyridylmethyl)amino](3-pyridyl)}carboxamide Step A Preparation of 3-[(4-methylpiperazinyl)sulfonyl]-1-nitrobenzene A mixture of 3-nitrobezenesulfonyl chloride (664 mg, 3.0 mmol) and methylpiperazine (600 mg, 6.0 mmol) in EtOH was stirred for 2 h at RT. The reaction was concentrated and triturated in $Et_2O$ to yield a yellowish solid, 3-[(4-methylpiperazinyl)sulfonyl]-1-nitrobenzene, and was used in next step without further purification.

Step B Preparation of 3-[(4-methylpiperazinyl)sulfonyl]phenylamine

3-[(4-Methylpiperazinyl)sulfonyl]phenylamine was analogously synthesized from 3-[(4-methylpiperazinyl)sulfonyl]-1-nitrobenzene (Step A) by the method described in Example 74, which was used in next step without further purification. MS (ES+): 256 (M+H). Calc'd. for $C_{11}H_{17}N_3O_2S$—255.10.

Step C Preparation of N-[4-(morpholin-4-ylmethyl)phenyl]{2-[(4-pyridylmethyl)amino](3-pyridyl)}carboxamide The titled compound was prepared from 3-[(4-methylpiperazinyl)sulfonyl]phenylamine (Step B) by the method described in Example 25. MS (ES+): 467 (M+H); (ES−): 465 (M−H). Calc'd. for $C_{23}H_{26}N_6O_3S$—466.18.

EXAMPLE 78

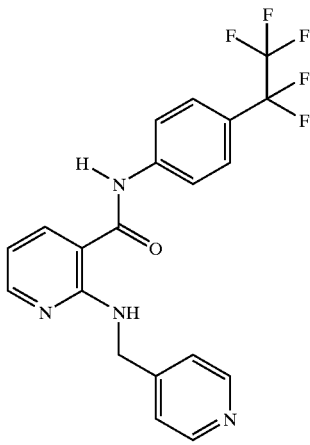

N-[4-(1,1,2,2,2-Pentafluoroethyl)phenyl]{2-[(4-pyridylmethyl)amino](3-pyridyl)}carboxamide Step A Preparation of 4-(1,1,2,2,2-pentafluoroethyl)phenylamine 1-Nitro-4-(1,1,2,2,2-pentafluoroethyl)benzene was synthesized by the method described in the reference [John N. Freskos, Synthetic Communications, 18(9), 965–972 (1988)]. It was reduced with Fe similar to that described in Example 74. It was used in next step without further purification.

Step B Preparation of N-[4-(1,1,2,2,2-Pentafluoroethyl)phenyl]{2-[(4-pyridylmethyl)amino](3-pyridyl)}carboxamide The titled compound was prepared from 4-(1,1,2,2,2-pentafluoroethyl)phenylamine (Step A) by the method described in Example 25. MS (ES+): 423 (M+H); (ES−): 421 (M−H). Calc'd. for $C_{20}H_{15}FN_4O$—422.12.

EXAMPLE 79

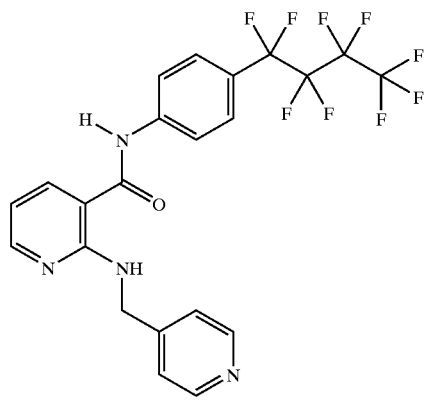

N-[4-(1,1,2,2,3,3,4,4,4-Nonafluorobutyl)phenyl]{2-[(4-pyridylmethyl)amino](3-pyridyl)}carboxamide Step A Preparation of 4-(1,1,2,2,3,3,4,4,4-nonafluorobutyl)phenylamine The title intermediate was analogously synthesized by the method described of W. A. Gregory, et al. [J. Med. Chem., 1990, 33, 2569–2578]. 1-nitro-4-(1,1,2,2,3,3,4,4-monofluorobutyl)benzene was reduced with Fe described in Example 68, Step D, and used in next step without further purification.

Step B Preparation of N-[4-(1,1,2,2,3,3,4,4,4-nonafluorobutyl)phenyl]{2-[(4-pyridylmethyl)amino](3-pyridyl)}carboxamide The titled compound was prepared from 4-(1,1,2,2,3,3,4,4,4-nonafluorobutyl)phenylamine (Step A) by the method described in Example 25. MS (ES+): 523 (M+H); (ES−): 521 (M−H). Calc'd. for $C_{22}H_{15}F_9N_4O$—522.37.

EXAMPLE 80

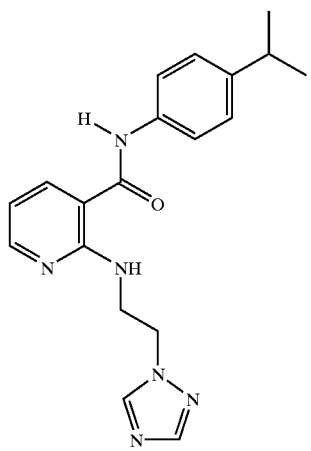

N-[4-(Isopropyl)phenyl]{2-[(2-(1,2,4-triazolyl)ethyl) amino](3-pyridyl)}carboxamide Step A Preparation of 2-(1,2,4-triazolyl)ethylamine A mixture of (tert-butoxy)-N-(2-chloroethyl)-carboxamide (900 mg, 5 mmol), 1,2,4-triazole (690 mg, 10 mmol) and $Na_2CO_3$ (1.06 g, 10 mmol) in DMF (3 mL) was stirred overnight at 100° C. The mixture was filtered and concentrated to give an oil. The oil was treated with TFA (10 mL) and stirred for 3 h. The reaction was concentrated to give the titled intermediate, which was used in next step without further purification.

Step B Preparation of N-[4-(methylethyl)phenyl]{2-[(2-(1,2,4-triazolyl)ethyl)amino](3-pyridyl)}carboxamide The titled compound was prepared from 2-(1,2,4-triazolyl)ethylamine (Step A) by the method described in Example 25. MS (ES+): 351 (M+H); (ES−): 349 (M−H). Calc'd. for $C_{19}H_{22}N_6O$—350.19.

EXAMPLE 81

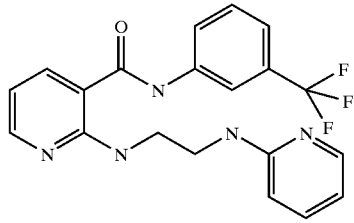

(2-{[2-(2-Pyridylamino)ethyl]amino}(3-pyridyl))-N-[3-(trifluoromethyl)phenyl]carboxamide Step A Preparation of 2-(2-pyridylamino)ethylamine Ethylenediamine (6 g, 0.1 mol) and 2-fluoropyridine (10 g, 0.1 mol) were heated neat at 120° C. overnight. The reaction was cooled and the residue was used in next step without further purification.

Step B Preparation of (2-{[2-(2-pyridylamino)ethyl]amino}-(3-pyridyl))-N-[3-(trifluoromethyl)phenyl]carboxamide The titled compound was prepared from 2-(2-pyridylamino)ethylamine (Step A) by the method described in Example 25. MS (ES+): 402 (M+H); (ES−): 400 (M−H). Calc'd. for $C_{20}H_{18}F_3N_5O$—401.15.

EXAMPLE 82

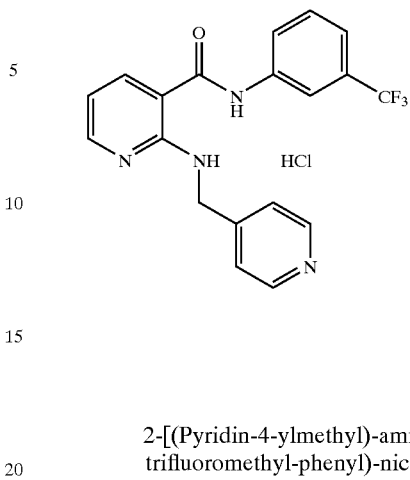

2-[(Pyridin-4-ylmethyl)-amino]-N-(3-trifluoromethyl-phenyl)-nicotinamide

Step A: Preparation of (2-chloro(3-pyridyl))-N-(3-trifluoromethylphenyl)carboxamide 2-Chloropyridine-3-carbonyl chloride (18.02 g, 0.102 mol) in $CH_2Cl_2$ (100 ml) was added dropwise (via an addition funnel) to a stirred solution of 3-(trifluoromethyl)-aniline (15.00 g, 0.093 mol) and DIEA (24.39 ml, 0.14 mol) in $CH_2Cl_2$ (500 ml) at 0° C. The mixture gradually was warmed to RT. The reaction continued for 18 h before washing several times with saturated $NaHCO_3$ aqueous solution and brine, respectively. The organic layer was dried over $Na_2SO_4$ and evaporated. The resulting oil was purified over silica gel with EtOAc/hexane (2:1) as eluant to leave the amide as a white solid (26.08 g). MS: (ES+) 301 (M+1)$^+$; (ES−): 299 (M−1)$^−$. Calc'd for $C_{13}H_8ClF_3N_2O$: 300.03.

Step B: Preparation of N-[3-trifluoromethylphenyl phenyl]{2-[(4-pyridylmethyl)amino](3-pyridyl)}carboxamide hydrochloride The amide (10.0 g 0.033 mol, Step A) and 4-aminomethylpyridine (10.81 g, 0.10 mol) were combined and heated at 120° C. for 4 h. After cooling to RT, the residue was dissolved in EtOAc and washed several times with saturated $NaHCO_3$ aqueous solution and brine, respectively. The organic layer was dried over $Na_2SO_4$ and evaporated. The crude yellow oil was purified over silica gel with EtOAc as eluant to leave an amber oil (10.9 g). The free base was dissolved in MeOH (20 ml) and treated with a HCl ethereal solution (1.0 eq.). The solvent was evaporated to leave the salt as a white solid. The HCl salt was dried in vacuo at 30° C. for 24 h. MS: (ES+) 373 (M+1)$^+$; (ES−): 371 (M−1)$^−$. Calc'd. for $C_{19}H_{15}F_3N_4O$—372.12.

The following compounds (Examples 83–138) were analogously synthesized by the method described in Example 82 unless specifically described. Detailed intermediate preparations are included.

TABLE 2

| # | Y | R¹ | R² | M + H | calc'd |
|---|---|---|---|---|---|
| 83 | —NH—CH₂— | 8-methylquinoline | H | 356 | 355.14 |
| 84 | —NH—CH₂— | 4-(4-chlorophenoxy)-methylphenyl | H | 431 | 430.12 |
| 85 | —NH—CH₂— | 2,3,4-trifluoromethylphenyl | H | 359 | 358.1 |
| 86 | —NH—CH₂— | 2-methylnaphthalene | H | 355 | 354.15 |
| 87 | —NH—CH₂— | 5-methyl-1,2,3,4-tetrahydronaphthalene | H | 359 | 358.18 |
| 88 | —NH—CH₂— | 5-methylbenzo[1,3]dioxole | H | 349 | 348.128 |
| 89 | —NH—CH₂— | 1-methylnaphthalene | H | 355 | 354.15 |
| 90 | —NH—CH₂— | 3-benzylmethylphenyl | H | 395 | 394.18 |
| 91 | —NH—CH₂— | (S)-1-cyclohexylethyl | H | 339 | 338.12 |

TABLE 2-continued
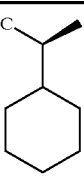
| # | Y | R¹ | R² | M + H | calc'd |
|---|---|---|---|---|---|
| 92 | —NH—CH₂— | 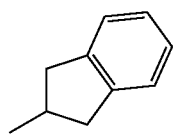 | H | 339 | 338.12 |
| 93 | —NH—CH₂— | 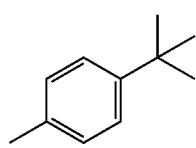 | H | 345 | 344.16 |
| 94 | —NH—CH₂— | 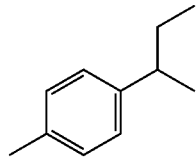 | H | 361 | 360.20 |
| 95 | —NH—CH₂— | 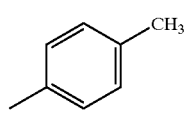 | H | 361 | 360.20 |
| 96 | —NH—CH₂— | 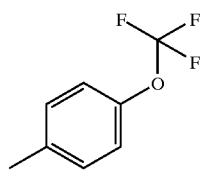 | H | 319 | 318.5 |
| 97 | —NH—CH₂— | 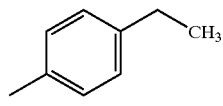 | H | 389 | 388.11 |
| 98 | —NH—CH₂— | 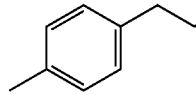 | H | 333 | 332.16 |
| 99 | —NH—CH₂— | 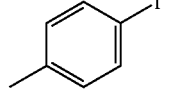 | H | 361 | 360.2 |
| 100 | —NH—CH₂— | | H | 431 | 430 |

TABLE 2-continued
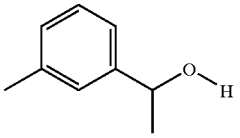
| # | Y | R¹ | R² | M + H | calc'd |
|---|---|---|---|---|---|
| 101 | —NH—CH₂— | 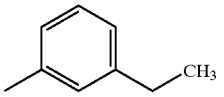 | H | 349 | 348.16 |
| 102 | —NH—CH₂— | 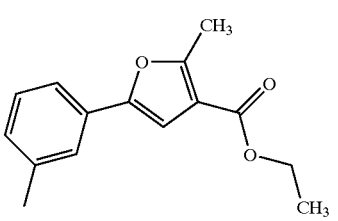 | H | 333 | 332.16 |
| 103 | —NH—CH₂— | 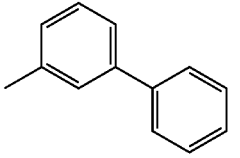 | H | 457 | 456.18 |
| 104 | —NH—CH₂— | 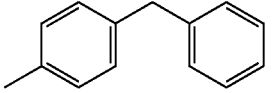 | H | 381 | 380.16 |
| 105 | —NH—CH₂— | 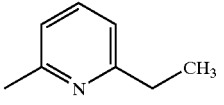 | H | 395 | 394.18 |
| 106 | —NH—CH₂— | 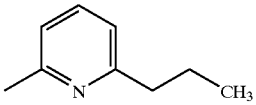 | H | 334 | 333.16 |
| 107 | —NH—CH₂— | 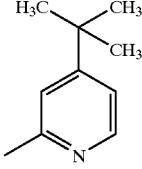 | H | 348 | 347.17 |
| 108 | —NH—CH₂— | H₃C  CH₃<br>   \\ /<br>   C—CH₃<br>   |<br>  (2-methylpyridin-4-yl) | H | 362 | 361.19 |

TABLE 2-continued
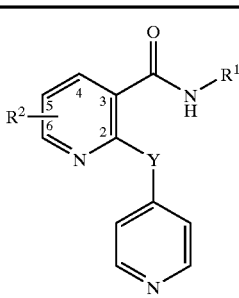
| # | Y | R¹ | R² | M + H | calc'd |
|---|---|---|---|---|---|
| 109 | —NH—CH₂— | 3-hydroxymethylphenyl | H | 321 | 320.13 |
| 110 | —NH—CH₂— | 4-isopropyl-2-methylpyridinyl | H | 348 | 347.17 |
| 111 | —NH—CH₂— | 3,5-bis(trifluoromethyl)phenyl | H | 441 | 440.11 |
| 112 | —NH—CH₂— | 4-chloro-3-(trifluoromethyl)phenyl | H | 407 | 406.08 |
| 113 | —NH—CH₂— | 3-chlorophenyl | H | 353 | 352.11 |
| 114 | —NH—CH₂— | 4-(methylsulfonyl)phenyl | H | 383 | 382.11 |
| 115 | —NH—CH₂— | 1-acetyl-6-methylindolinyl | H | 388 | 387.43 |
| 116 | —NH—CH₂— | 6-methylindolinyl | H | 346 | 345.00 |

TABLE 2-continued

[Structure shown: pyridine-3-carboxamide with R¹ on amide N, R² at position 5/6, and Y-linked 4-pyridyl at position 2]

| # | Y | R¹ | R² | M + H | calc'd |
|---|---|---|---|---|---|
| 117 | —NH—CH₂— | 6-methylindol-3-yl | H | 344 | 343.38 |
| 118 | —NH—CH₂— | 5-methylindol-3-yl | H | 344 | 343.38 |
| 119 | —NH—CH₂— | 7-methylindol-3-yl | H | 344 | 343.38 |
| 120 | —NH—CH₂— | 3-tert-butyl-5-methyl-1H-pyrazol-... | H | 351 | 350.43 |
| 121 | —NH—CH₂— | 3-phenyl-5-methyl-1H-pyrazol-... | H | 371 | 370.43 |

EXAMPLE 122

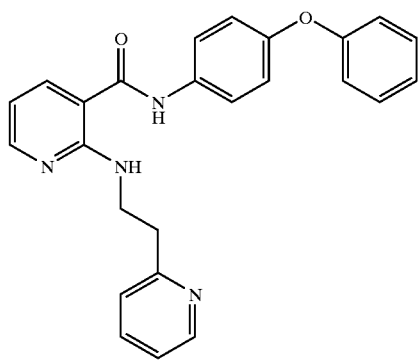

N-(4-Phenoxyphenyl){2-[(2-(2-pyridyl)ethyl)amino](3-pyridyl)}carboxamide

MS: 411 (M+1); 409 (M−1). Calc'd. for $C_{25}H_{22}N_4O_2$—410.17.

EXAMPLE 123

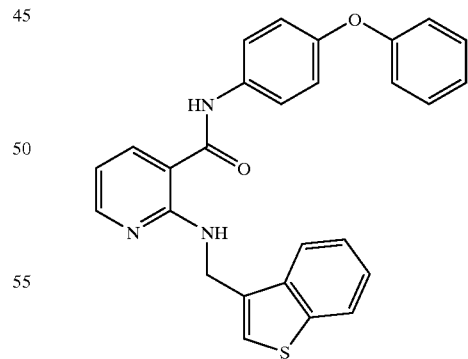

2-[(Benzo[b]thiophen-3-ylmethyl)amino](3-pyridyl)}-N-(4-phenoxyphenyl)carboxamide MS: (ES+) 452 (M+1)⁺; (ES−): 450 (M−1)⁻. Calc'd. for $C_{27}H_{21}N_3O_2S$—451.14.

EXAMPLE 124

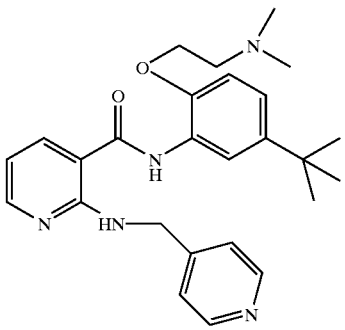

N-{2-[2-(Dimethylamino)ethoxy]-5-(tert-butyl)phenyl}{2-[(4-pyridylmethyl)amino](3-pyridyl)}carboxamide Step A—Preparation of {2-[4-(tert-butyl)-2-nitrophenoxy]-ethyl}dimethylamine To a mixture of 2-nitro-4-tert-butylphenol (2 g) and N,N-dimethylethanolamine (1.3 g) and PPh$_3$ (4 g) in THF (50 ml) was added DEAD (2.6 ml). The reaction was stirred at RT for 1 h, diluted with EtOAc (50 ml) and washed with 1 N HCl twice. The aqueous layer was basified with NaHCO$_3$, extracted with EtOAc twice and washed with H$_2$O and brine. The organic layer was dried over Na$_2$SO$_4$ and evaporated to give {2-[4-(tert-butyl)-2-nitrophenoxy]-ethyl}dimethylamine, was used in next step without further purification.

Step B—Preparation of {2-[4-(tert-butyl)-2-aminophenoxy]-ethyl}dimethylamine

{2-[4-(tert-Butyl)-2-nitrophenoxy]-ethyl}dimethylamine (Step A) was hydrogenated under H$_2$ atmosphere to give {2-[4-(tert-butyl)-2-aminophenoxy]-ethyl}dimethylamine, and used in next step without further purification.

Step C—Preparation of N-{2-[2-(dimethylamino)ethoxy]-5-(tert-butyl)phenyl}{2-[(4-pyridylmethyl)amino](3-pyridyl)}carboxamide The titled compound was prepared from {2-[4-(tert-butyl)-2-aminophenoxy]-ethyl}dimethylamine (Step B) by the method described in Example 82. MS (ES+): 448 (M+H); (ES−): 446 (M−H). Calc'd. for C$_{26}$H$_{33}$N$_5$O$_2$—447.26.

EXAMPLE 125

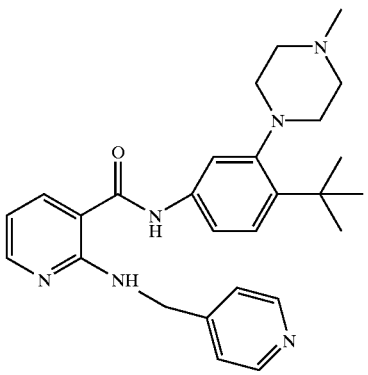

N-[4-(tert-Butyl)-3-(4-methylpiperazinyl)phenyl]{2-[(4-pyridylmethyl)amino](3-pyridyl)}carboxamide Step A—Preparation of 1-[2-(tert-butylphenyl]-4-methylpiperazine A mixture of 2-tert-butylaniline (5.4 g) and N-methylbis(2-chloroethyl)amine hydrochloride (7 g) and K$_2$CO$_3$ (5 g) in NaI (2 g) in diglyme (150 ml) was heated at 170° C. for 8 h. The reaction was filtered and the filtrate was evaporated under high vacuum. The residue was mixed with EtOAc (200 ml) and H$_2$O (200 ml) and extracted with EtOAc twice. The combined organic layer was washed with brine, dried over Na$_2$SO$_4$ and evaporated to give crude 1-[2-(tert-butylphenyl]-4-methyl-piperazine, which was used in next step without further purification.

Step B—Preparation of 1-[2-(tert-butyl)-5-aminophenyl]-4-methylpiperazine

The crude 1-[2-(tert-butylphenyl]-4-methylpiperazine (260 mg, Step A) was stirred with H$_2$SO$_4$ (3 ml) at 0° C. and HNO$_3$ (1.2 ml) was slowly added to the reaction. The reaction was warmed to RT, stirred for 30 min. and poured on ice and basified with K$_2$CO$_3$ slowly. The solution was extracted with EtOAc three times, washed with H$_2$O, followed by brine, dried over Na$_2$SO$_4$, and evaporated under reduced pressure. The residue was purified by column chromatography to give 1-[2-(tert-butyl)-5-nitrophenyl]-4-methylpiperazine (260 mg), which was hydrogenated under H$_2$ atmosphere to give 1-[2-(tert-butyl)-5-aminophenyl]-4-methylpiperazine.

Step C—Preparation of N-[4-(tert-Butyl)-3-(4-methylpiperazinyl)phenyl]{2-[(4-pyridylmethyl)amino](3-pyridyl)}carboxamide The titled compound was prepared from 1-[2-(tert-butyl)-5-aminophenyl]-4-methylpiperazine (Step B) by the method described in Example 82. MS (ES+): 459 (M+H); (ES−): 457 (M−H). Calc'd. for C$_{27}$H$_{34}$N$_6$O—458.28.

EXAMPLE 126

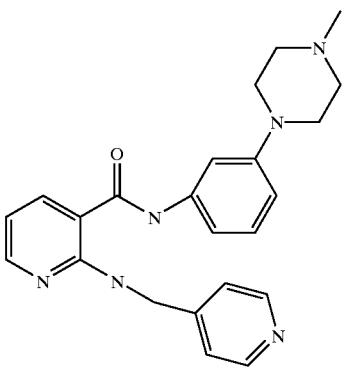

N-[3-(4-Methylpiperazinyl)phenyl]{2-[(4-pyridylmethyl)amino](3-pyridyl)}carboxamide Step A—Preparation of 3-(4-methylpiperazinyl)phenylamine The intermediate was analogously synthesized from 3-nitroaniline by the method described in Example 130.

Step B—Preparation of N-[3-(4-methylpiperazinyl)phenyl]{2-[(4-pyridylmethyl)amino](3-pyridyl)}carboxamide The titled compound was prepared from 3-(4-methylpiperazinyl)phenylamine (Step A) by the method described in Example 82. MS (ES+): 403 (M+H); (ES−): 401 (M−H). Calc'd. for C$_{23}$H$_{26}$N$_6$O—402.22.

EXAMPLE 127

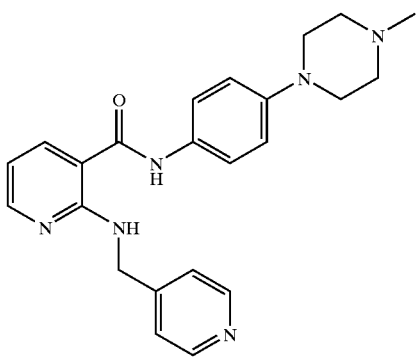

N-[4-(4-Methylpiperazinyl)phenyl]{2-[(4-pyridylmethyl)amino](3-pyridyl)}formamide Step A—Preparation of 4-methyl-1-(4-nitrophenyl)piperazine 1-Fluoro-4-nitrobenzene (3.0 g, 0.021 mol) and 1-methylpiperazine (6.98 ml, 0.63 mol) were combined and heated neat at 90° C. for 48 h. Upon cooling to RT, the resulting brown oil solidified. The crude material was purified by re-crystallization from EtOAc/Hexane mixtures to leave the title compound as an orange solid (3.59 g). MS: (ES+) 222 (M+1)$^+$; (ES−): 220 (M−1)$^−$. Calc'd for $C_{11}H_{15}N_3O_2$: 221.12.

Step B—Preparation of 4-methyl-1-(4-aminophenyl)piperazine

4-Methyl-1-(4-nitrophenyl)piperazine (2.0 g, 9 mmol, Step A) and 10% Pd/C (200 mg) were added to EtOH/MeOH (1:1) (50 ml) at RT. The reaction stirred under a H$_2$ atmosphere (via balloon) overnight. The mixture was filtered through a plug of Celite® and the filtrate was concentrated under reduced pressure to leave the desired material as a light yellow oil. The material was used in subsequent reaction without purification. MS: (ES+) 192 (M+1)$^+$; (ES−): 190 (M−1)$^−$. Calc'd for $C_{11}H_{17}N_3$: 191.14.

Step C Preparation of N-[4-(4-methylpiperazinyl)phenyl]{2-[(4-pyridylmethyl)amino](3-pyridyl)}formamide The titled compound was prepared from 4-methyl-1-(4-aminophenyl)piperazine (Step B) by the method described in Example 82. MS (ES+): 403 (M+H); (ES−): 401 (M−H). Calc'd. for $C_{23}H_{26}N_6O$—402.22.

EXAMPLE 128

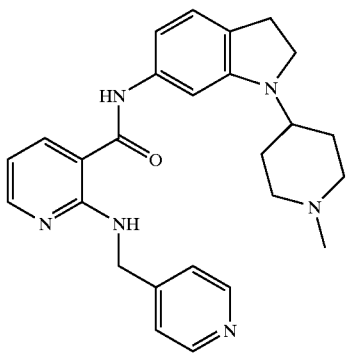

N-[1-(1-Methyl-(4-piperidyl))indolin-6-yl]{2-[(4-pyridylmethyl)amino](3-pyridyl)}carboxamide Step A—Preparation of 1-(1-methyl(4-piperidyl))-6-nitroindoline 6-Nitroindoline (5 g) was dissolved in 200 mL of dichloroethane, N-methyl-4-piperidone (5 g) was added to the mixture, followed by 12 g NaBH(OAc)$_3$ and 1 mL of glacial AcOH. The mixture was stirred at RT overnight. Saturated NaHCO$_3$ solution (200 mL) was added to the reaction mixture and stirred for 1 h. The resulting mixture was separated by separation funnel, the organic layer was extracted once with saturated NaHCO$_3$ solution and once with brine. The resulting organic layer was dried over MgSO$_4$, filtered and concentrated in vacuo. The crude material was purified by flash chromatography on silica gel with 2:1 EtOAc:MeOH to afford an orange oil. MS: 262 (M+1). Calc'd. for $C_{14}H_{19}N_3O_2$— 261.32.

Step B—Preparation of 1-(1-methyl-4-piperidyl)indoline-6-ylamine 1-(1-Methyl(4-piperidyl))-6-nitroindoline (3 g, Step A) was dissolved in 100 mL MeOH, and the mixture was bubbled with N$_2$ for 10 min. 10% Pd/C (200 mg) was added and the mixture was stirred under H$_2$ overnight. The mixture was filtered through Celite® and concentrated in vacuo to afford a light yellow oil. MS: 232 (M+1). Calc'd. for $C_{14}H_{21}N_3$— 231.34.

Step C—Preparation of N-[1-(1-methyl(4-piperidyl))indolin-6-yl]{2-[(4-pyridylmethyl)amino](3-pyridyl)}carboxamide The titled compound was prepared from 1-(1-methyl-4-piperidyl)indoline-6-ylamine (Step B) by the method described in Example 82. MS: 443 (M+1). Calc'd. for $C_{26}H_{30}N_6O$—442.56.

EXAMPLE 129

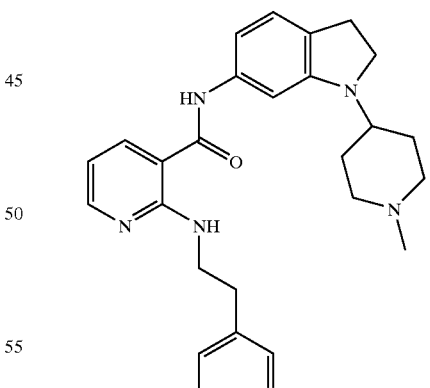

N-[1-(1-Methyl-(4-piperidyl))indolin-6-yl]{2-[(2-(3-pyridyl)ethyl)amino](3-pyridyl)}carboxamide MS: 457 (M+1). Calc'd. for $C_{27}H_{32}N_6O$—456.58.

EXAMPLE 130

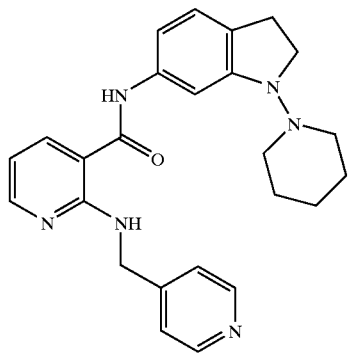

N-[1-(2-Piperidylethyl)indolin-6-yl]{2-[(4-pyridylmethyl)amino](3-pyridyl)}carboxamide Step A—Preparation of 1-(6-nitroindolinyl)-2-piperidylethan-1-one 6-Nitroindoline (2.5 g) was dissolved in 200 mL of CH$_2$Cl$_2$, followed by DIEA (2.5 g). The mixture was cooled down to 0° C. in ice bath. Chloroacetyl chloride (1.7 g) in 20 mL CH$_2$Cl$_2$ was added dropwise to the mixture over 10 min and the mixture was stirred at RT overnight. The mixture was extracted once with saturated NaHCO$_3$ solution and once with brine, the resulting organic layer was dried over MgSO$_4$, filtered and concentrated in vacuo. The crude material was purified by flash chromatography on silica gel with 3:2 Hexane:EtOAc to afford a yellow oil (1.4 g) which was added to piperidine (5 mL), followed by NaI (100 mg). The mixture was heated at 70° C. overnight then concentrated in vacuo and extracted between EtOAc and saturated NaHCO$_3$ solution, the organic layer was washed with brine, the resulting organic layer was dried over MgSO$_4$, filtered and concentrated in vacuo. The crude material was purified by flash chromatography on silica gel with 9:1 EtOAc:MeOH to afford a yellow oil. MS: 290 (M+1). Calc'd. for C$_{15}$H$_{19}$N$_3$O$_3$—289.33.

Step B—Preparation of 1-(2-piperidylethyl)indoline-6-ylamine 1-(6-Nitroindolinyl)-2-piperidylethan-1-one (1.6 g, Step A) was dissolved in 100 mL MeOH, the mixture was bubbled with N$_2$ for 10 min. 10% Pd/C (200 mg) was added and the mixture was stirred under H$_2$ overnight. The mixture was filtered through Celite® and concentrated in vacuo to afford a yellow solid. 400 mg was dissolved in 20 mL anhydrous THF, 5 mL borane-THF (1 M) solution was added dropwise and the mixture was stirred at RT overnight. The mixture was quenched with MeOH, 100 mg NaOH added and heated at 70° C. for 30 min. The resulting mixture was concentrated in vacuo and extracted between EtOAc and saturated NaHCO$_3$ solution, the organic layer was washed with brine, the resulting organic layer was dried over MgSO$_4$, filtered and concentrated in vacuo to afford a yellow oil. MS: 246 (M+1). Calc'd. for C$_{15}$H$_{23}$N$_3$—246.36.

Step C—Preparation of N-[1-(2-piperidylethyl)indolin-6-yl]{2-[(4-pyridylmethyl)amino](3-pyridyl)}carboxamide The titled compound was prepared from 1-(2-piperidylethyl)indoline-6-ylamine (Step B) by the method described in Example 82. MS: 457 (M+1). Calc'd. for C$_{27}$H$_{32}$N$_6$O—456.58.

EXAMPLE 131

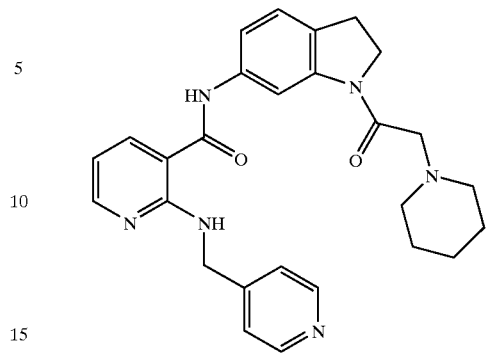

N-[1-(2-Piperidylacetyl)indolin-6-yl]{2-[(4-pyridylmethyl)amino](3-pyridyl)}carboxamide MS: 471 (M+1). Calc'd. for C$_{27}$H$_{30}$N$_6$O$_2$—470.57.

EXAMPLE 132

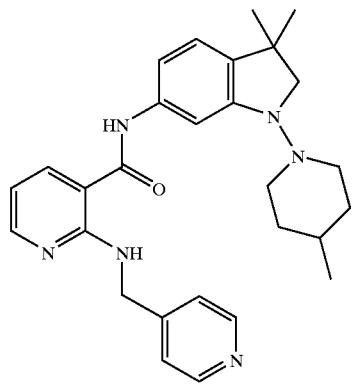

N-[3,3-Dimethyl-1-(1-methyl(piperid-4-yl)indolin-6-yl]{2-[(4-pyridylmethyl)amino](3-pyridyl)}carboxamide Step A—Preparation of N-(2-bromo-5-nitrophenyl)acetamide 2-Bromo-5-nitroaniline (10 g) was dissolved in 500 mL of CH$_2$Cl$_2$, DIEA (6.6 g) was added to the mixture, followed by DMAP (100 mg). The mixture was cooled to 0° C. in ice bath. Acetyl chloride (4 g in 50 mL CH$_2$Cl$_2$) was added dropwise to the reaction mixture. After the mixture was stirred at RT over 3 h, extracted once with saturated NaHCO$_3$ solution and once with brine, the resulting organic layer was dried over MgSO$_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M−1). Calc'd. for C$_8$H$_7$BrN$_2$O$_3$—259.06.

Step B—Preparation of N-(2-bromo-5-nitrophenyl)-N-(2-methylprop-2-enyl)acetamide A suspension of 2 g NaH (95% powder) in anhydrous DMF (100 mL) was cooled to −78° C., N-(2-bromo-5-nitrophenyl)acetamide (7 g, Step A) in dry DMF (50 mL) was added to the mixture under N$_2$ atmosphere. After the mixture was warmed to 0° C., 3-bromo-2-methylpropene (7.3 g in 20 dry DMF) was added to the mixture. The mixture was stirred at RT overnight. Next morning, the mixture was poured into a container of ice and extracted between saturated NaHCO$_3$ solution and EtOAc. The resulting organic layer was dried over MgSO$_4$, filtered and concentrated in vacuo. The crude material was purified by flash chromatography on silica gel with 7:2 hexane:EtOAc to afford the title compound as a yellow gum. MS: 314 (M+1). Calc'd. for C$_{12}$H$_{13}$BrN$_2$O$_3$—313.15.

Step C—Preparation of 1-(3,3-dimethyl-6-nitro-2,3-dihydro-indol-1-yl)ethanone

N-(2-Bromo-5-nitrophenyl)-N-(2-methylprop-2-enyl) acetamide (4.5 g, Step B) was dissolved in anhydrous DMF (50 mL), tetraethyl-ammonium chloride (2.5 g), sodium formate (1.2 g), NaOAc (3 g) were added, and the resulting mixture was bubbled with N$_2$ gas for 10 min. Pd(OAc)$_2$ (350 mg) was added and the mixture was heated at 80° C. under N$_2$ atmosphere overnight. After the mixture was concentrated in vacuo, it was partitioned between saturated NaHCO$_3$ solution and EtOAc, the resulting organic layer was dried over MgSO$_4$, filtered and concentrated in vacuo. The crude material was purified by flash chromatography on silica gel with 2:1 Hexane:EtOAc to afford the title compound as a yellow gum. MS: 235 (M+1). Calc'd. for C$_{12}$H$_{14}$N$_2$O$_3$—234.25.

Step D—Preparation of 3,3-dimethyl-6-nitroindoline 1-(3,3-Dimethyl-6-nitro-2,3-dihydro-indol-1-yl)ethanone (1.8 g, Step C) was dissolved in EtOH (50 mL), 12N HCl (50 mL) was added and the resulting mixture was heated at 70° C. overnight. After the mixture was concentrated in vacuo, it was partitioned between saturated NaHCO$_3$ solution and EtOAc, the resulting organic layer was dried over MgSO$_4$, filtered and concentrated in vacuo to afford a yellow solid. MS: 193 (M+1). Calc'd. for C$_{10}$H$_{12}$N$_2$O$_2$—192.21.

Step E—Preparation of 3,3-dimethyl-1-(1-methyl-piperidin-4-yl)-6-nitro-2,3-dihydro-1H-indole 3,3-Dimethyl-6-nitroindoline (0.8 g) was dissolved in CH$_2$Cl$_2$ (50 mL), N-methyl-4-piperidone (1 g) was added to the mixture, followed by 2.5 g NaBH(OAc)$_3$ and glacial AcOH (1 mL). The mixture was stirred at RT overnight. Saturated NaHCO$_3$ solution (50 ml) was added to the reaction mixture and stirred for 1 h. The resulting mixture was separated by separation funnel, the organic layer was extracted once with saturated NaHCO$_3$ solution and once with brine, the resulting organic layer was dried over MgSO$_4$, filtered and concentrated in vacuo. The crude material was purified by flash chromatography on silica gel with 9:1 EtOAc:MeOH to afford the title compound as an orange oil. MS: 290 (M+1). Calc'd. for C$_{16}$H$_{23}$N$_3$O$_2$—289.37.

Step F—Preparation of 3,3-dimethyl-1-(1-methyl(4-piperidyl))indoline-6-ylamine 3,3-Dimethyl-1-(1-methyl-piperidin-4-yl)-6-nitro-2,3-dihydro-1H-indole (600 mg, Step E) was dissolved in MeOH (20 mL), the mixture was bubbled with H$_2$ for 10 min. 10% Pd/C (100 mg) was added and the mixture was stirred under H$_2$ overnight. The mixture was filtered through Celite® and concentrated in vacuo to afford the title compound as an oil. MS: 260 (M+1). Calc'd. for C$_{16}$H$_{25}$N$_3$—259.39.

Step G—Preparation of N-[3,3-dimethyl-1-(1-methyl(4-piperidyl))indolin-6-yl]{2-[(4-pyridylmethyl)amino](3-pyridyl)}carboxamide The titled compound was prepared from 3,3-dimethyl-1-(1-methyl(4-piperidyl))indoline-6-ylamine (Step E) by the method described in Example 82. MS: 471 (M+1). Calc'd. for C$_{28}$H$_{34}$N$_6$O—470.61.

EXAMPLE 133

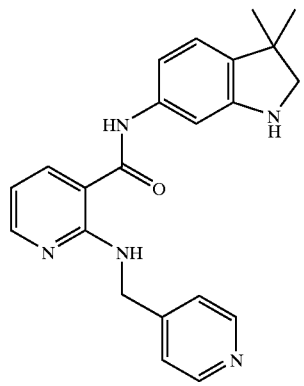

N-(3,3-Dimethylindolin-6-yl){2-[(4-pyridylmethyl)amino](3-pyridyl)}carboxamide

Step A—Preparation of 1-acetyl-6-amino-3,3-dimethylindoline

1-Acetyl-3,3-dimethyl-6-nitroindoline (250 mg) was dissolved in MeOH (20 mL), the mixture was bubbled with H$_2$ for 10 min. 10% Pd/C (50 mg) was added and the mixture was stirred under H$_2$ overnight. The mixture was filtered through Celite® and concentrated in vacuo. The crude material was purified by flash chromatography on silica gel with 1:1 EtOAc:CH$_2$Cl$_2$ to afford the title compound as a white crystalline material. MS: 205 (M+1). Calc'd. for C$_{12}$H$_{16}$N$_2$O—204.27.

Step B—Preparation of N-(1-acetyl-3,3-dimethylindolin-6-yl){2-[(4-pyridylmethyl)amino](3-pyridyl)}carboxamide The titled compound was prepared from 1-acetyl-6-amino-3,3-dimethylindoline (Step A) by the method described in Example 82.

Step C—Preparation of N-(3,3-dimethylindolin-6-yl){2-[(4-pyridylmethyl)amino](3-pyridyl)}carboxamide The titled compound was prepared from N-(1-acetyl-3,3-dimethylindolin-6-yl){2-[(4-pyridylmethyl)amino](3-pyridyl)}carboxamide (Step B) by the deacylation method described in Example 993. MS: 374 (M+1). Calc'd. for C$_{22}$H$_{23}$N$_5$O—373.45.

EXAMPLE 134

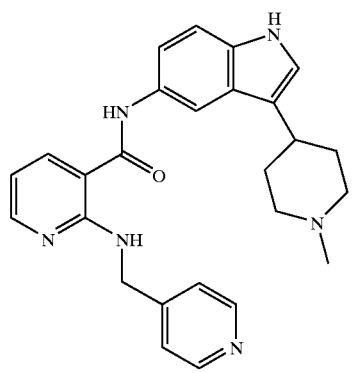

N-[3-(1-Methyl-(4-piperidyl))indol-5-yl]{2-[(4-pyridylmethyl)amino](3-pyridyl)}carboxamide Step A—Preparation of 3-(1-methyl-1,2,3,6-tetrahydro-pyridin-4-yl)-5-nitro-1H-indole 5-Nitroindole (2.6 g) was dissolved in anhydrous MeOH (100 ml), followed by N-methyl-4-piperidone (5 g) and NaOMe powder (5 g). The mixture was heated to reflux under N₂ overnight. The mixture was concentrated in vacuo. The crude was partitioned between saturated NaHCO₃ solution and EtOAc, the resulting organic layer was dried over MgSO₄, filtered and concentrated in vacuo to afford a yellow solid. This solid was washed with EtOAc (5 mL) and MeOH (2 ml) to afford the title compound as a bright yellow solid. MS: 258 (M+1). Calc'd. for $C_{14}H_{15}N_3O_2$—257.29.

Step B—Preparation of 3-(1-methyl-4-piperidyl)indole-5-ylamine 3-(1-Methyl-1,2,3,6-tetrahydro-pyridin-4-yl)-5-nitro-1H-indole (2.7 g, Step A) was dissolved in MeOH (50 mL), the mixture was bubbled with H₂ for 10 min. 10% Pd/C (150 mg) was added and the mixture was stirred under H₂ overnight. The mixture was filtered through Celite® and concentrated in vacuo to afford 3-(1-methyl-4-piperidyl) indole-5-ylamine as a yellow oil. MS: 230 (M+1). Calc'd. for $C_{14}H_{19}N_3$—229.32.

Step C—Preparation of N-[3-(1-methyl-(4-piperidyl))indol-5-yl]{2-[(4-pyridylmethyl)amino](3-pyridyl)}carboxamide The titled compound was prepared from 3-(1-methyl-4-piperidyl)indole-5-ylamine (Step B) by the method described in Example 82. MS: 441 (M+1). Calc'd. for $C_{26}H_{28}N_6O$—440.54.

EXAMPLE 135

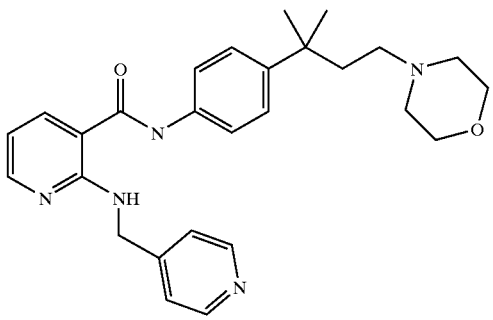

N-[4-(1,1-Dimethyl-3-morpholin-4-ylpropyl)phenyl]
{2-[(4-pyridylmethyl)amino](3-pyridyl)
}carboxamide Step A—Preparation of methyl 2-methyl-2-(4-nitrophenyl) propionate To a stirred solution of 2-(4-nitrophenyl)-propionic acid (9 g, 46 mmol) in MeOH (300 mL) was added HCl (4M in dioxane, 11.5 mL, 46 mmol). The mixture was stirred at RT overnight and quenched with aqueous NaHCO₃. The mixture was extracted with EtOAc. The organic layer was dried over MgSO₄, evaporated under reduced pressure and to the partial residue at 0° C. in THF (100 mL) was added NaH (1.66 g, 41.5 mmol). The mixture was stirred at RT for 1 h and MeI (2.58 g, 41.5 mmol) was added. The reaction was stirred at RT overnight and was quenched with H₂O. The mixture was extracted with EtOAc, the organic layer was dried over MgSO₄, evaporated under reduced pressure to give the title compound which was used in the next step without further purification. Calc'd for $C_{11}H_{13}NO_4$: 223.08.

Step B—Preparation of 2-methyl-2-(4-nitro-phenyl)-propan-1-ol

To a stirred solution of methyl 2-methyl-2-(4-nitrophenyl) propionate (5.32 g, 23.8 mmol, Step A) in THF (200 mL) at 0° C. was added a solution of BH₃ 1M in THF (25.8 mL, 45.8 mmol). The reaction was stirred at RT overnight and quenched with MeOH. THF was evaporated under reduced pressure and the residue was diluted in EtOAc and aqueous 1M HCl was added. The mixture was extracted with EtOAc, the organic layer was dried over MgSO₄ and evaporated under reduced pressure. The product was purified by flash chromatography using 40% EtOAc-hexane to give the title compound as a yellow solid.

Step C—Preparation of 2-methyl-2-(4-nitro-phenyl)-propionaldehyde

To a stirred solution of the alcohol (2.08 g, 10.8 mmol, Step B) at 0° C. in CH₂Cl₂ was added NMO (1.9 g, 16.1 mmol), molecular sieves 4 Å and TPAP (76 mg, 0.2 mmol). The reaction was stirred for 1 h and was filtered on silica pad. Solvent was evaporated under reduced pressure. Crude aldehyde was used without further purification in the next step.

Step D—Preparation of 3-methyl-3-(4-nitrophenyl)butan-1-aldehyde

To a suspension of methoxymethyltriphenyl-phosphonium chloride (6.4 g, 18.6 mmol) in THF (150 mL) was added a solution of KHMDS 0.5 M in toluene (37 mL, 18.5 mmol). The mixture was stirred for 30 min and crude aldehyde (Step C) was added. The reaction was stirred at RT for 1 h and quenched with H₂O. Mixture was extracted with EtOAc, dried and evaporated under reduced pressure. Et₂O was added and the formed precipitate was filtered on silica pad (rinsed with 40% EtOAc-hexane). The solvent was removed and crude product was dissolved in CH₂Cl₂. A solution of TFA—H₂O (1:1, 10 mL) was added and the reaction was stirred for 2 h at RT. Aqueous NaHCO₃ was added until pH 7 and residue was extracted with CH₂Cl₂. Organic layer was dried, filtered and evaporated. Crude compound was purified by flash chromatography (40% EtOAc-hexane) to give the title compound as a yellow oil. Calc'd for $C_{11}H_{13}NO_3$: 207.09.

Step E—Preparation of 4-[3-methyl-3-(4-nitro-phenyl)-butyl]-morpholine

To a stirred solution of 3-methyl-3-(4-nitrophenyl)butan-1-aldehyde (509 mg, 2.4 mmol, Step D) and morpholine (0.21 mL, 2.4 mmol) in THF (30 mL) was added NaBH (OAc)₃ (0.73 g, 3.4 mmol). The mixture was stirred at RT overnight and was washed with 1M HCl. CH₂Cl₂ was added and the layers were separated. The aqueous layer was basified to pH 9 using 1M NaOH and extracted with CH₂Cl₂. This organic layer was dried and evaporated yielding the morpholino compound. Calc'd for $C_{15}H_{22}N_2O_3$: 278.16.

Step F Preparation of 4-(1,1-dimethyl-3-morpholin-4-ylpropyl)phenylamine

To a solution of 4-[3-methyl-3-(4-nitro-phenyl)-butyl]-morpholine (0.50 g, 1.8 mmol, Step E) in THF (40 mL) was added AcOH (1.97 mmol, 34.5 mmol) followed by zinc (9.1 g, 137 mmol). The mixture was stirred for 1 h and filtered on Celite®. The mixture was diluted with H₂O, and aqueous NaHCO₃ and the THF was evaporated. The residue was extracted with EtOAc, dried and evaporated to give the title intermediate. Calc'd for $C_{15}H_{24}N_2O$: 248.19.

Step G—Preparation of N-[4-(1,1-dimethyl-3-morpholin-4-ylpropyl)phenyl]{2-[(4-pyridylmethyl)amino](3-pyridyl) }carboxamide The titled compound was prepared from 4-(1,1-dimethyl-3-morpholin-4-ylpropyl)phenylamine (Step F) by the method described in Example 82. MS: 460.0 (M+1). Calc'd. for $C_{27}H_{33}N_5O_2$—459.60.

EXAMPLE 136

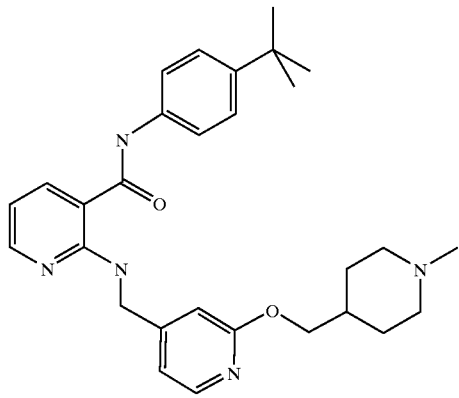

N-[4-(tert-Butyl)phenyl]{2-[({2-[(1-methyl(4-piperidyl))-methoxy](4-pyridyl)}methyl)amino](3-pyridyl)}carboxamide Step A—Preparation of 4-hydroxymethyl-1-methylpiperidine To a solution of 4-piperidylmethanol (1.0 g, 8.7 mmol) and HCHO (2 mL, 25 mmol, 37% in $H_2O$) in $CH_3CN$ was added $NaCNBH_3$ (0.5 g, 12.5 mmol). The resulting mixture was stirred for 1 h and filtered. The filtrate was concentrated and the residue was distilled (105° C., 40 torr) to give the title intermediate.

Step B—Preparation of {2-[(1-methyl-4-piperidyl)methoxy]-4-pyridyl}methylamine

To a suspension of NaH (0.44 g, 12.7 mmol, 60% in mineral oil) in DMF (25 mL) was added a solution of alcohol (1.1 g, 8.5 mmol, Step A) in 3 mL of DMF. After 20 min, a solution of 2-chloro-4-cyanopyridine (1.2 g, 8.5 mmol) in 2 mL of DMF was added. The resulting mixture was stirred for 2 h, diluted with $CH_2Cl_2$, and washed with $H_2O$ twice. The organic layer was dried over $Na_2SO_4$ and concentrated to give 2-[(1-methyl-4-piperidyl)methoxy]pyridine-4-carbonitrile, which was hydrogenated under regular conditions to furnish the title intermediate. MS (ES+): 236 (M+H)$^+$. Calc'd $C_{13}H_{21}N_3O$—235.33.

Step C—Preparation of N-[4-(tert-butyl)phenyl]{2-[({2-[(1-methyl(4-piperidyl))-methoxy](4-pyridyl)}methyl)amino](3-pyridyl)}carboxamide The title compound was prepared from {2-[(1-methyl-4-piperidyl)methoxy]-4-pyridyl}methylamine (Step B) by the method described in Example 82. MS (ES+): 488 (M+H)$^+$; (ES−): 486 (M−H)$^-$. Calc'd $C_{29}H_{37}N_5O_2$—487.64.

EXAMPLE 137

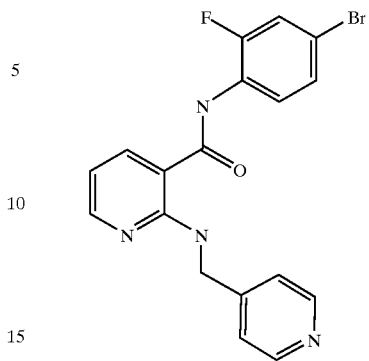

N-(4-Bromo-2-fluorophenyl){2-[(4-pyridylmethyl)amino](3-pyridyl)}carboxamide

MS (ES+): 402 (M+H)$^+$; (ES−): 400. Calc'd $C_{18}H_{14}BrFN_4O$—401.238.

EXAMPLE 138

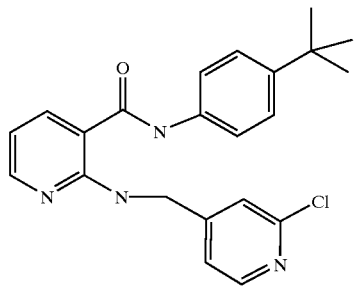

N-[4-(tert-Butyl)phenyl](2-{[(2-chloro(4-pyridyl))methyl]amino}(3-pyridyl))carboxamide MS (ES+): 395 (M+H)$^+$; (ES−): 393(M−H)$^-$. Calc'd $C_{22}H_{23}ClN_4O$—394.90.

EXAMPLE 139

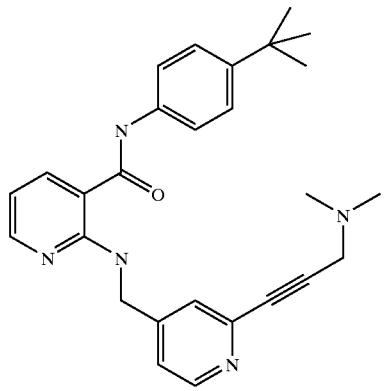

{2-[({2-[3-(Dimethylamino)prop-1-ynyl](4-pyridyl)}methyl)amino](3-pyridyl)}-N-[4-(tert-butyl)phenyl]carboxamide A mixture of N-[4-(tert-butyl)phenyl](2-{[(2-chloro(4-pyridyl))methyl]amino}(3-pyridyl))carboxamide (0.15 g, 0.38 mmol, Example 139), 1-dimethylamino-2-propyne (62 mg, 0.76 mmol), PdCl₂(PPh₃)₂ (13 mg, 0.0019 mmol) and CuI (7 mg, 0.019 mmol) in 1 mL of TEA was heated at 100° C. in a sealed tube for 3 h. The resulting mixture was filtered over Celite®. The filtrate was concentrated, and the residue was purified by prep-HPLC (reverse phase) to give the title compound. MS (ES+): 442 (M+H)⁺; (ES−): 440(M−H)⁻. Calc'd C₂₇H₃₁N₅O—441.58.

EXAMPLE 140

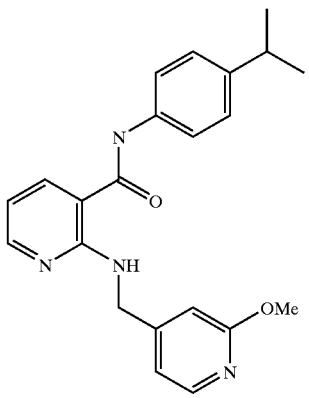

(2-{[(2-Methoxy(4-pyridyl))methyl]amino}(3-pyridyl))-N-[4-(methylethyl)phenyl]carboxamide Step A—Preparation of (2-methoxy-4-pyridyl)methylamine A solution of 2-methoxyisonicotinylcarboxamide (1.0 g, 6.5 mmol) and BH₃—THF complex (35 mmol) in 35 mL of THF was stirred at RT for 16 h. The reaction was quenched by addition of MeOH, and the resulting mixture was concentrated. The residue was diluted with 1N aq. NaOH and CH₂Cl₂. The organic layer was separated, dried over Na₂SO₄, and concentrated.

Step B—Preparation of (2-{[(2-methoxy(4-pyridyl))methyl]-amino}(3-pyridyl))-N-[4-(methylethyl)phenyl]carboxamide The title compound was prepared from (2-methoxy-4-pyridyl)methylamine (Step A) by the method described in Example 82. MS (ES+): 377 (M+H)⁺; (ES−): 375 (M−H)⁻. Calc'd C₂₂H₂₄N₄O₂—376.46.

EXAMPLE 141

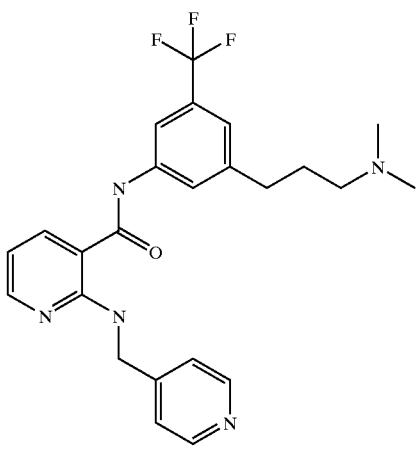

N-{3-[3-(Dimethylamino)propyl]-5-(trifluoromethyl)phenyl}-{2-[(4-pyridylmethyl)amino](3-pyridyl)}carboxamide Step A—Preparation of {3-[3-amino-5-(trifluoromethyl)phenyl]propyn-2-yl}dimethylamine A mixture of 3-bromo-5-trifluoromethylaniline (1.4 g, 5.9 mmol), 1-dimethylamino-2-propyne (1.3 mL, 0.76 mmol), PdCl₂(PPh₃)₂ (0.26 g, 0.29 mmol) and CuI (114 mg, 0.60 mmol) in 10 mL of TEA was heated at 100° C. in a sealed tube for 3 h. The resulting mixture was filtered over Celite®. The filtrate was concentrated, and the residue was purified by prep-HPLC (reverse phase) to give the titled compound. MS (ES+): 243 (M+H)⁺; (ES−): 241 (M−H)³¹. Calc'd C₁₂H₁₃F₃N₂—242.24.

Step B—Preparation of {3-[3-amino-5-(trifluoromethyl)phenyl]propyl}dimethylamine A mixture of the propynyl-aniline (7 g, 29 mmol, Step A) and Pd(OH)₂ (0.5 g) in MeOH (250 mL) was stirred under 50 psi H₂. After 2 h, the resulting mixture was filtered over Celite®. The filtrate was concentrated, and the residue was diluted with aq. 1N HCl. The aq. layer was washed with Et₂O, made basic with aq. 5N NaOH, and extracted with CH₂Cl₂. The organic solution was dried over NaSO₄ and concentrated to give the titled compound. MS (ES+): 386 (M+H)⁺; (ES−): 384 (M−H)⁻. Calc'd C₁₈H₁₉ClF₃N₃O—385.81.

Step C—Preparation of N-{3-[3-(dimethylamino)propyl]-5-(trifluoromethyl)phenyl}-{2-[(4-pyridylmethyl)amino](3-pyridyl)}carboxamide The title compound was prepared by the method described in Example 82. MS (ES+): 458(M+H)⁺; (ES−): 456(M−H)⁻. Calc'd C₂₄H₂₆F₃N₅O—457.497.

EXAMPLE 142

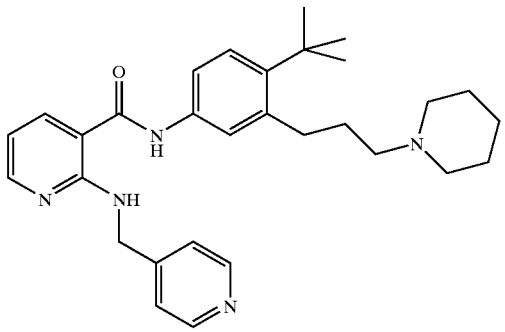

N-[4-(tert-Butyl)-3-(3-piperidylpropyl)phenyl]{2-[(4-pyridylmethyl)amino](3-pyridyl)}carboxamide Step A—Preparation of 1-piperidylprop-2-en-1-one To a 0° C. solution of acryloyl chloride (4.576 g, 50.558 mmol) in 50 ml of CH₂Cl₂ was added dropwise and very carefully piperidine (4.305 g, 50.558 mmol). The reaction flask was vented during the exothermic addition. After the addition was completed, the white slurry was stirred at 0° C. for 40 min and at RT for 1 h. The reaction was diluted with 70 ml CH₂Cl₂ and washed first with about 60 ml 2N HCl and then with about 60 ml of a mix of 2N NaOH and brine. The organic layer was dried over Na₂SO₄. The solution was evaporated by heating in a H₂O bath at 60° C. without vacuum. Once most solvent had been evaporated off, it was furthered dried to a clear oil under high vacuum at RT for 30 min.

Step B—Preparation of 1-bromo-2-(tert-butyl)-5-nitrophenyl

Br$_2$ (17.4 ml) was added dropwise over 40 min to a stirred mixture of 4-tert-butylnitrobenzene (59.5 g, 332 mmol), AgSO$_4$ (56.5 g, 181 mmol), H$_2$SO$_4$ (300 ml), and H$_2$O (33 ml) at RT. The mixture was stirred for 3 h, then poured into 0.1 M Na$_2$S$_2$O$_5$/H$_2$O (1 L). The solid was filtered, washed with H$_2$O, Et$_2$O, and CH$_2$Cl$_2$. The filtrate layers were separated. The aqueous fraction was extracted with Et$_2$O. The combined organic layers were combined, dried over Na$_2$SO$_4$, and concentrated in vacuo. The yellow solid was triturated with hexanes to give a pale yellow crystalline solid.

Step C—Preparation of (2E)-3-[2-(tert-butyl)-5-nitrophenyl]-1-piperidylprop-2-en-1-one 1-(tert-Butyl)-2-bromo-4-nitrobenzene (6.885 g, 26.674 mmol, Step B), 1-piperidylprop-2-en-1-one (4.827 g, 34.677 mmol, Step A), and TEA (7.44 ml, 53.35 mmol) were dissolved into toluene (70 ml). To this solution was added Pd(OAc)$_2$ (60 mg, 0.267 mmol) and Pd(PPh$_3$)$_4$ (617 mg, 0.5335 mmol). The mix was degassed with N$_2$ and heated in a sealed vessel at 120° C. for 15 h. The reaction mixture was cooled to RT, filtered, and concentrated in vacuo. The dark crude oil was eluted through a silica gel column with 15% to 22% EtOAc/hexanes gradient system to yield a thick amber oil as the title intermediate.

Step D—Preparation of (2E)-3-[2-(tert-butyl)-5-aminophenyl]-1-piperidylprop-2-en-1-one (2E)-3-[2-(tert-Butyl)-5-nitrophenyl]-1-piperidylprop-2-en-1-one (3.22 g, 10.177 mmol, step C) was dissolved in dioxane (20 ml) and IpOH (40 ml). To the N$_2$-degassed solution was added 10% by weight Pd/C catalyst (2 g). The mix was placed into a Parr hydrogenator and stirred for 18 h under 60 psi H$_2$. The reaction was not complete the next day, so the reaction was continued for an additional 20 h with fresh catalyst. The mix was filtered through Celite® and concentrated in vacuo to give a foamy oil.

Step E—Preparation of 4-(tert-butyl)-3-(3-piperidylpropyl)phenylamine (2E)-3-[2-(tert-Butyl)-5-aminophenyl]-1-piperidylprop-2-en-1-one (2.312 g, 7.619 mmol, step D) was dissolved in THF (100 ml) at RT. To this solution was added LiAlH$_4$ (434 mg, 11.43 mmol). After the reaction mixture stopped exotherming, it was heated at reflux at about 80° C. for 4 h. The reaction was cooled to 0° C. and treated by dropwise addition of 0.458 ml H$_2$O, 0.730 ml 10% aqueous NaOH, and 1.19 ml H$_2$O, respectively The mix was stirred at RT for 40 min. Na$_2$SO$_4$ (3 g) was added and the mix was stirred for 20 min. The mix was filtered through Celite® and concentrated in vacuo. The crude was eluted through silica gel column with a gradient system of 95:5 to 90:10 CH$_2$Cl$_2$:MeOH, to yield an amber thick oil as the title compound.

Step F—Preparation of N-[4-(tert-butyl)-3-(3-piperidylpropyl)phenyl]{2-[(4-pyridylmethyl)amino](3-pyridyl)}carboxamide The title compound was prepared from 4-(tert-butyl)-3-(3-piperidylpropyl)phenylamine (Step E) similar to the method described in Example 82. MS: 486.2 (M+1). Calc'd. for C$_{30}$H$_{39}$N$_5$O—485.68.

EXAMPLE 143

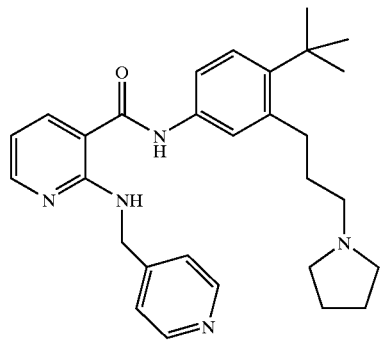

N-[4-(tert-Butyl)-3-(3-pyrrolidinylpropyl)phenyl]{2-[(4-pyridylmethyl)amino](3-pyridyl)}carboxamide MS: 472.5 (M+1). Calc'd. for C$_{29}$H$_{37}$N$_5$O—471.65.

EXAMPLE 144

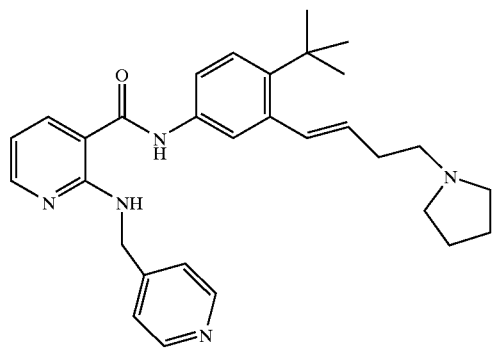

N-[3-((1E)-4-Pyrrolidinylbut-1-enyl)-4-(tert-butyl)phenyl]{2-[(4-pyridylmethyl)amino](3-pyridyl)}carboxamide MS: 484.0 (M+1) Calc'd. for C$_{30}$H$_{37}$N$_5$O—483.66.

EXAMPLE 145

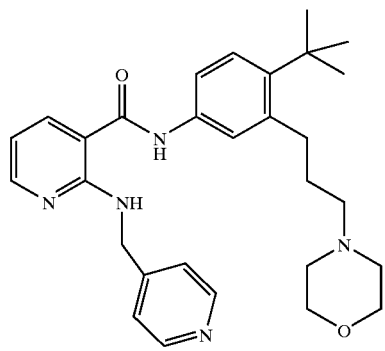

N-[4-(tert-Butyl)-3-(3-morpholin-4-ylpropyl)phenyl]{2-[(4-pyridylmethyl)amino](3-pyridyl)}carboxamide MS: 488.4 (M+1). Calc'd. for C$_{29}$H$_{37}$N$_5$O$_2$—487.65.

EXAMPLE 146

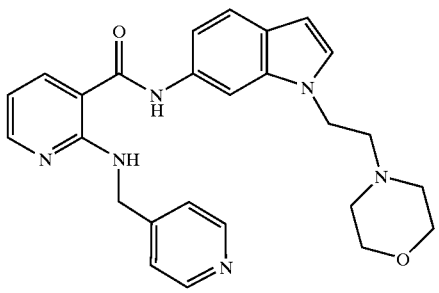

N-[1-(2-Morpholin-4-ylethyl)indol-6-yl]{2-[(4-pyridylmethyl)amino](3-pyridyl)}carboxamide Step A—Preparation of 1-(2-morpholin-4-ylethyl)indole-6-ylamine $K_2CO_3$ (5.08 g, 36.726 mmol) was added to a slurry of 6-nitroindole (1.985 g, 12.242 mmol), 4-(2-chloroethyl) morpholine hydrochloride (2.278 g, 12.242 mmol), and $CH_3CN$ (100 ml). The mix was heated at reflux for 18 h, then cooled to RT, filtered, and concentrated in vacuo. The crude was eluted through a silica gel column with a gradient of 3:97 to 5:95 and finally 8:92 $MeOH:CH_2Cl_2$, to yield upon drying 1-(2-morpholin-4-yl-ethyl)-6-nitro-1H-indole which was hydrogenated at regular condition described early to yield the title compound.

Step B—Preparation of N-[1-(2-morpholin-4-ylethyl)indol-6-yl]{2-[(4-pyridylmethyl)amino](3-pyridyl)}carboxamide The title compound was prepared from 1-(2-morpholin-4-ylethyl)indole-6-ylamine (Step A) similar to the method described in Example 82. MS: 457.3 (M+1). Calc'd. for $C_{26}H_{28}N_6O_2$—456.55.

EXAMPLE 147

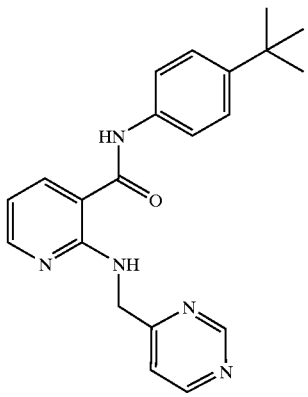

N-[4-(tert-Butyl)phenyl]{2-[(pyrimidin-4-ylmethyl)amino](3-pyridyl)}carboxamide

Step A—Preparation of pyrimidine-4-yl formaldehyde

Pyrimidine-4-yl formaldehyde was prepared from 4-methyl pyrimidine through a reference described in M. C. Liu et al., J Med Chem., 1995, 38 (21), 4234–4243.

Step B—Preparation of N-[4-(tert-butyl)phenyl]{2-[(pyrimidin-4-ylmethyl)amino](3-pyridyl)}carboxamide The title compound was prepared from pyrimidine-4-yl formaldehyde (Step A) similar to the method described in Example 82. MS (ES+): 362(M+H);(ES−): 360(M−H). Calc'd. for $C_{21}H_{23}N_5O$—361.19.

EXAMPLE 148

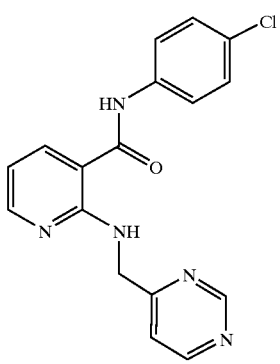

N-(4-Chlorophenyl){2-[(pyrimidin-4-ylmethyl)amino](3-pyridyl)}carboxamide

MS (ES+): 340 (M+H); (ES−): 338 (M−H). Calc'd. for $C_{17}H_{14}ClN_5O$—339.09.

EXAMPLE 149

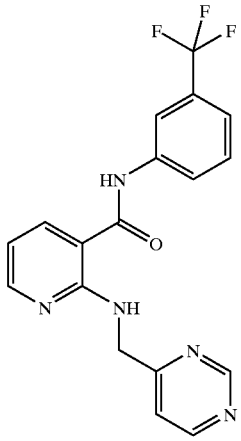

{2-[(Pyrimidin-4-ylmethyl)amino](3-pyridyl)}-N-[3-(trifluoromethyl)phenyl]carboxamide MS (ES+): 374 (M+H); (ES−): 372 (M−H). Calc'd. for $C_{18}H_{14}F_3N_5O$—373.12.

EXAMPLE 150

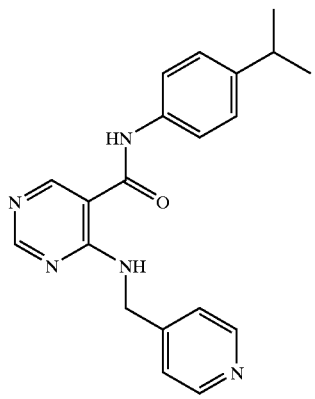

N-[4-(Isopropyl)phenyl]{4-[(4-pyridylmethyl)amino]pyrimidin-5-yl}carboxamide

Step A—Preparation of ethyl 2-methylthio-4-[benzylamino]pyrimidine-5-carboxylate A solution of ethyl 4-chloro-2-methylthio-pyrimidine-5-carboxylate (2.8 g, 12.2 mmol) and 4-aminomethylpyridine (1.24 mL, 12.2 mmol) in EtOH (20 mL) was heated at 70° C. for 2 h. The resulting suspension was concentrated, and the residue was purified by $SiO_2$ chromatography to give ethyl 2-methylthio-4-[benzylamino]pyrimidine-5-carboxylate. MS (ES+): 305 (M+H)$^+$; (ES−): 303 (M−H)$^−$. Calc'd $C_{15}H_{17}N_3O_2S$: 303.38.

Step B—Preparation of N-[4-(isopropyl)phenyl]{2-methylthio-4-[(4-pyridylmethyl)amino]pyrimidin-5-yl}carboxamide To a solution of ethyl 2-methylthio-4-[benzylamino]-pyrimidine-5-carboxylate (0.1 g, 0.3 mmol, Step A) in EtOH (3 mL) was added 1 mL of aq. 1N NaOH solution. The resulting mixture was stirred at 45° C. for 2 h. The resulting mixture was neutralized with aq. 1N HCl and concentrated. To the residue in 3 mL of $CH_2Cl_2$ was added 4-isopropylaniline (90 mg, 0.66 mmol), HATU (0.18 g, 0.45 mmol), and 0.5 mL of TEA (0.36 g, 3.5 mmol). The resulting mixture was stirred at RT for 4 h and diluted with $CH_2Cl_2$. The organic solution was washed with $H_2O$, dried over $Na_2SO_4$ and concentrated. The residue was purified by $SiO_2$ chromatography to give N-[4-(isopropyl)phenyl]{2-methylthio-4-[(4-pyridylmethyl)amino]pyrimidin-5-yl}carboxamide. MS (ES+): 394 (M+H)$^+$; (ES−): 392 (M−H)$^−$. Calc'd $C_{21}H_{23}N_5OS$—393.51.

Step C—Preparation of N-[4-(isopropyl)phenyl]{4-[(4-pyridylmethyl)amino]pyrimidin-5-yl}carboxamide A mixture of N-[4-(isopropyl)phenyl]{2-methylthio-4-[(4-pyridylmethyl)amino]pyrimidin-5-yl}carboxamide (50 mg, 0.13 mmol, Step B) and Raney-Ni in EtOH (10 mL) was heated at reflux for 2 h. The resulting mixture was filtered, and the filtrate was concentrated to give the titled compound. MS (ES+): 348 (M+H)$^+$; (ES−): 346 (M−H)$^−$. Calc'd $C_{20}H_{21}N_5O$—347.42.

EXAMPLE 151

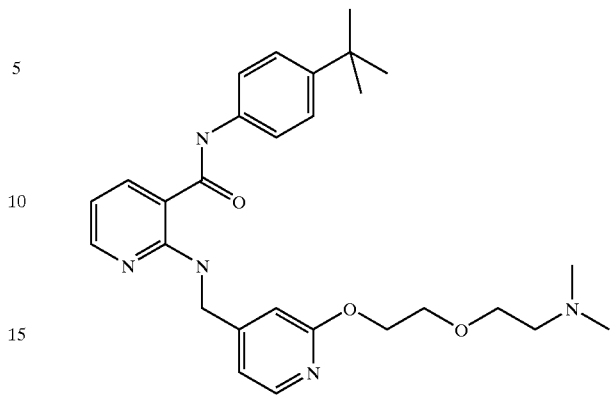

(2-{[(2-{2-[2-(Dimethylamino)ethoxy]ethoxy}(4-pyridyl))methyl]amino}(3-pyridyl))-N-[4-(tert-butyl)phenyl]carboxamide Step A—Preparation of 2-{2-[2-(dimethylamino)ethoxy]ethoxy}pyridine-4-carbonitrile To a DMF (30 mL) solution of 2-[2-(dimethylamino)ethoxy]ethan-1-ol (3.33 g, 25 mmol) was added NaH (60% in mineral oil, 900 mg, 22.5 mmol, hexane washed) and heated at 50° C. for 2 h. The warm sodium alkoxide solution was added to 2-chloro-4-cyanopyridine (3.12 g, 22.5 mmol) in DMF (10 mL). After the addition, the reaction mixture was heated to 70° C. for 2 h, then DMF was removed in vacuo. The residue was partitioned between $CH_2Cl_2/H_2O$. The organic layer was washed with brine, dried over $Na_2SO_4$, and concentrated in vacuo to give a light yellow oil (5.6 g). MS: 236 (M+1). Calc'd. for $C_{12}H_{17}N_3O_2$—235.29.

Step B—Preparation of (2-{2-[4-(aminomethyl)(2-pyridyloxy)]ethoxy}ethoxy)dimethylamine 2-{2-[2-(Dimethylamino)ethoxy]ethoxy}pyridine-4-carbonitrile (330 mg 1.4 mmol, Step A) was dissolved in EtOH (10 mL) along with TEA (2 mL) and suspended with Pd/C (10%, 40 mg). The reaction mixture was stirred overnight at RT under balloon filled with $H_2$. After removing the balloon, the reaction suspension was filtered through a layer of Celite®. The Celite® layer was rinsed with MeOH. The combined filtrate was concentrated in vacuo to give a light yellow oil. MS: 240 (M+1). Calc'd. for $C_{12}H_{21}N_3O_2$—239.32.

Step C—Synthesis of 2-fluoropyridine-3-carboxylic Acid

To a solution of 2-fluoropyridine (10 g, 100 mmol) in THF (150 mL) under −78° C. was dropwise added an LDA solution (2M in heptane/THF/ethylbenzene, 60 mL). The mixture was stirred at −78° C. for 3 h after the addition of LDA then quenched with $N_2$ dried solid $CO_2$. After warming to RT, the reaction was partitioned between EtOAc (100 mL) and $H_2O$ (200 mL). The aqueous layer was acidified to pH between 3–4 and extracted with EtOAc. The organic solution was collected and washed with brine and dried over $Na_2SO_4$. After removing solvent in vacuum, a brown oil was received as the desired compound. MS: 140 (M−H). Calc'd. for $C_6H_4FNO_2$—141.10.

Step D—Synthesis of 2-fluoropyridine-3-carbonyl Chloride

2-Fluoropyridine-3-carboxylic acid (7 g, Step C) was suspended in $SOCl_2$ (100 mL). After heating under reflux for 2 h, the mixture became homogeneous. Excess $SOCl_2$ was removed in vacuo to afford a brown solid as desired product.

Step E—Synthesis of N-[4-(tert-butyl)phenyl] 2-fluoropyridine-3-carboxamide

To a suspension of 2-fluoropyridine-3-carbonyl chloride (3.2 g, 20 mmol, Step D) and NaHCO$_3$ (4 g, 48 mmol) in CH$_2$Cl$_2$ added in dropwise a solution of 4-tert butylaniline (3.0 g, 20 mmol). After the addition, the suspension was stirred at RT for 5 h. Solid inorganic salts were removed via filtration. The filtrate was concentrated to afford a brown solid as desired compound. MS: 273 (M+H). Calc'd. for C$_{16}$H$_{17}$FN$_2$O—272.33.

Step F—Synthesis of {2-[({2-[2-(2-N,N-dimethylaminoethoxy)ethoxy]-4-pyridyl}methyl)amino](3-pyridyl)}-N-(4-tert-butylphenyl)carboxamide N-[4-(tert-Butyl)phenyl] 2-fluoropyridine-3-carboxamide (544 mg, 2 mmol, Step E) was dissolved in pyridine (5 mL) along with (2-{2-[4-(aminomethyl)(2-pyridyloxy)]ethoxy}ethoxy)dimethylamine (570 mg, 2.38 mmol, Step A). The reaction was heated to 85° C. for 48 h. After removal of pyridine in vacuo, the residue was dissolved in CH$_2$Cl$_2$ and washed with NaHCO$_3$ (Sat. aq), then brine. After drying over Na$_2$SO$_4$, the CH$_2$Cl$_2$ solution was concentrated in vacuo and purified via prep. HPLC (H$_2$O/CH$_3$CN: 5%–95% gradient) to give the title product. MS: 492 (M+1). Calc'd. for C$_{28}$H$_{37}$N$_5$O$_3$—491.63

The following compounds (Examples 152–157) were analogously synthesized by the method described in Example 151 unless specifically described. Detailed intermediate preparations are included.

EXAMPLE 152

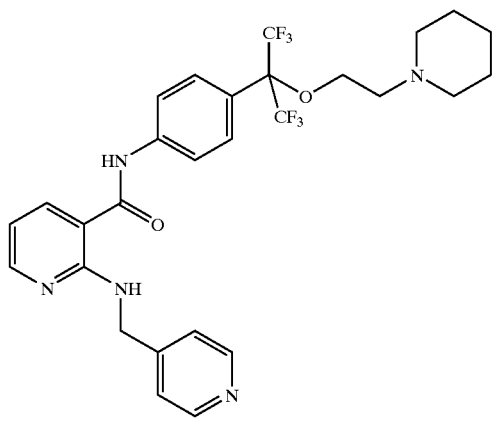

{2-[(4-Pyridylmethyl)amino](3-pyridyl)}-N-{4-[2,2,2-trifluoro-1-(2-piperidylethoxy)-1-(trifluoromethyl)ethyl]phenyl}carboxamide Step A—Preparation of 4-[2,2,2-trifluoro-1-(2-piperidin-1-yl-ethoxy)-1-trifluoromethyl-ethyl]-phenylamine DEAD (366 mg, 2.1 mmol) was added drop-wise to the solution of 2-(4-aminophenyl)-1,1,1,3,3,3-hexafluoropropan-2-ol (520 mg, 2 mmol), 2-piperidylethan-1-ol (260 mg, 2 mmol) and PPh$_3$ (550 mg, 2.1 mmol) in THF (10 mL). The mixture was stirred for 2 h. The reaction was partitioned between EtOAc and aqueous NaHCO$_3$ solution and the organic phase was washed with brine. After concentrated in vacuo, the organic residue was purified by flash chromatography on silica to give the title intermediate.

Step B—Preparation of {2-[(4-pyridylmethyl)amino](3-pyridyl)}-N-{4-[2,2,2-trifluoro-1-(2-piperidylethoxy)-1-(trifluoromethyl)ethyl]phenyl}carboxamide The title compound was synthesized by the method described in Example 151. MS: 582 (M+1). Calc'd. for C$_{28}$H$_{29}$F$_6$N$_5$O$_2$—581.56.

EXAMPLE 153

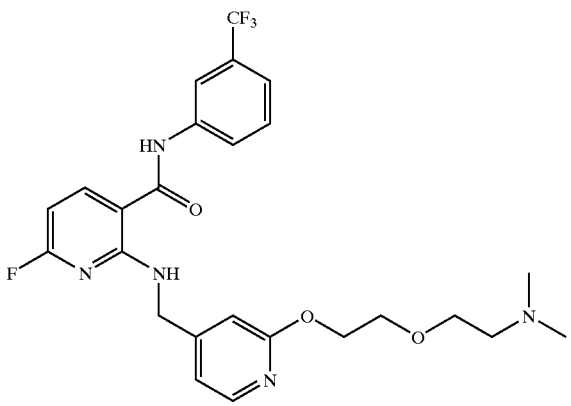

(2-{[(2-{2-[2-(Dimethylamino)ethoxy]ethoxy}(4-pyridyl))methyl]amino}-6-fluoro(3-pyridyl))-N-[3-(trifluoromethyl)phenyl]carboxamide Step A Preparation of 2,6-difluoropyridine-3-carbonyl Chloride The title compound was prepared similar to that described in Example 151, Step D.

Step B—Preparation of (2-{[(2-{2-[2-(dimethylamino)ethoxy]ethoxy}(4-pyridyl))methyl]amino}-6-fluoro(3-pyridyl))-N-[3-(trifluoromethyl)phenyl]carboxamide The title compound was synthesized by the method described in Example 151. MS: 522 (M+1). Calc'd. for C$_{25}$H$_{27}$F$_4$N$_5$O$_3$—521.51.

EXAMPLE 154

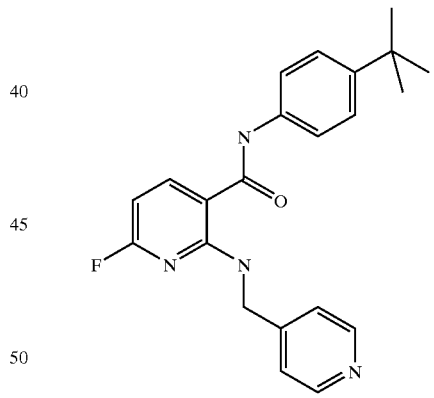

N-[4-(tert-Butyl)phenyl]{6-fluoro-2-[(4-pyridylmethyl)amino](3-pyridyl)}carboxamide Step A—Preparation of N-(4-tert-butyl-phenyl)-2,6-difluoro-nicotinamide A solution of 2,6-difluoropyridine-3-carboxylic acid (3.2 g, 20 mmol), t-butylaniline (3.0 g, 20 mmol), HOBt (2.6 g, 20 mmol), EDAC (8 g, 40 mmol), and DIEA (8 mL) in CH$_2$Cl$_2$ (80 mL) was stirred at RT for 1 h. The mixture was washed with aq. NaHCO$_3$ and brine. The organic solution was dried over Na$_2$SO$_4$ and concentrated in vacuo The residue was purified via flash chromatography on silica (Hex:EtOAc=4:1) to give a light yellow flaky crystal as desired product.

Step B—Preparation of N-[4-(tert-butyl)phenyl]{6-fluoro-2-[(4-pyridylmethyl)amino](3-pyridyl)}carboxamide The title compound was synthesized similar to that described in Example 151 except that it was synthesized at RT. MS: 379 (M+1). Calc'd. for $C_{22}H_{23}FN_4O$—378.45.

The following compounds were analogously synthesized by the method described in Example 154. Detailed intermediate preparations are described.

EXAMPLE 155

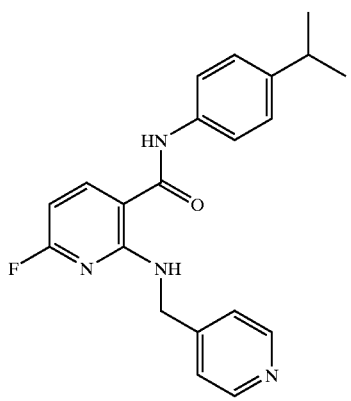

{6-Fluoro-2-[(4-pyridylmethyl)amino](3-pyridyl)}-N-[4-(isopropyl)phenyl]carboxamide MS: 365 (M+1). Calc'd. for $C_{21}H_{21}FN_4O$—364.42.

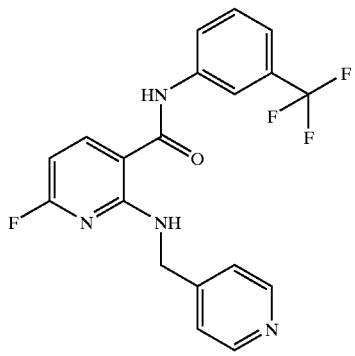

{6-Fluoro-2-[(4-pyridylmethyl)amino](3-pyridyl)}-N-[3-(trifluoromethyl)phenyl]carboxamide MS: 391 (M+1). Calc'd. for $C_{19}H_{14}F_4N_4O$—390.34.

EXAMPLE 157

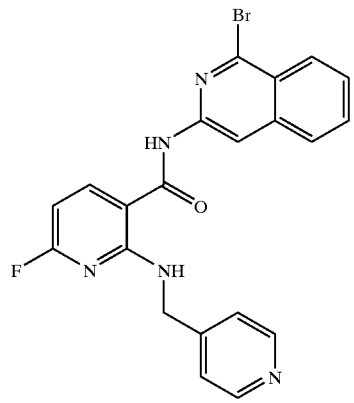

N-(1-Bromo(3-isoquinolyl)){6-fluoro-2-[(4-pyridylmethyl)amino](3-pyridyl)}-carboxamide MS: 452/454 (M+1). Calc'd. for $C_{21}H_{15}BrFN_5O$—452.29.

EXAMPLE 158

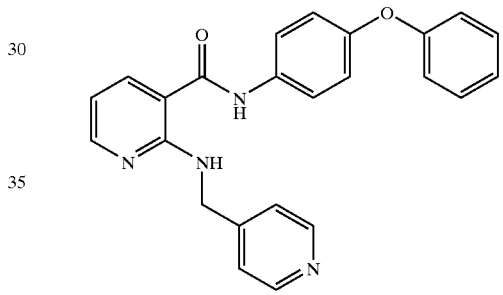

N-(4-Phenoxyphenyl){2-[(4-pyridylmethyl)amino](3-pyridyl)}carboxamide

Step A—Preparation of (2-chloro(3-pyridyl))-N-(4-phenoxy-phenyl)carboxamide

2-Chloronicotinic acid (0.78 g, 5.0 mmol) and TEA (1.6 ml, 10.0 mmol) were added to anhydrous THF (50 ml) under a $N_2$ atmosphere at 0° C. After stirring for 5 min, ethyl chloroformate (0.54 g, 5.0 mmol) was added dropwise and the mixture gradually came to RT over a period of 1 h. 4-Phenoxyaniline (0.83 g, 5.0 mmol) was added and the mixture was stirred for 14 h. The mixture was partitioned between $H_2O$ and EtOAc. The aqueous layer was extracted two additional times with EtOAc (50 ml). The combined organic layers were then washed with brine, dried over $Na_2SO_4$, and evaporated. The resulting brown oil was used directly in the subsequent reaction without further purification. MS m/z: 325 (M+1). Calc'd for $C_{18}H_{13}ClN_2O_2$: 324.07.

Step B—Preparation of N-(4-phenoxyphenyl){2-[(4-pyridylmethyl)amino](3-pyridyl)}carboxamide hydrochloride The amide (0.500 g, 1.5 mmol, Step A) and 4-aminomethylpyridine (0.486 g, 4.5 mmol) were combined and heated neat at 90° C. for 48 h. After cooling to RT, the mixture was poured into a saturated $NaHCO_3$ solution and extracted with EtOAc. The combined organic layers were washed with brine, dried over Na$_2$SO$_4$, and evaporated. The resulting brown oil was purified by column chromatography with EtOAc/hexanes (2:1) as eluant to leave N-(4-phenoxyphenyl){2-[(4-pyridylmethyl)amino](3-pyridyl)}formamide as a clear oil. This material was converted directly into the HCl salt by dissolution in MeOH (5 ml), treatment with 3 equivalents of an HCl ethereal solution, and evaporation of solvent to leave the titled product as a light yellow solid. MS (ES+): 397 (M+H)$^+$; (ES−): 395 (M−H). Calc'd. for C$_{24}$H$_{20}$N$_4$O$_2$—396.16.

The following compounds (Examples 159–161) were prepared similar to the method described in Example 158.

EXAMPLE 159

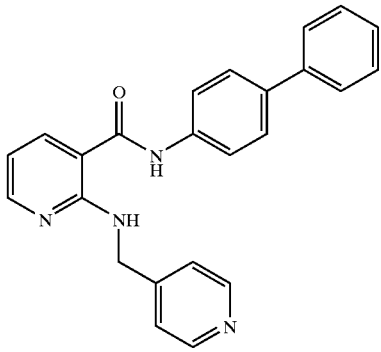

N-(4-Biphenyl){2-[(4-pyridylmethyl)amino](3-pyridyl)}carboxamide

MS: 381 (M+1); 379 (M−1). Calc'd. for C$_{24}$H$_{20}$N$_4$O—380.16.

EXAMPLE 160

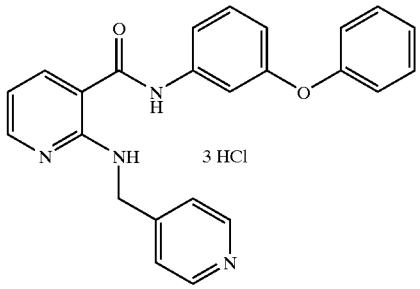

N-(3-Phenoxyphenyl){2-[(4-pyridylmethyl)amino](3-pyridyl)}carboxamide hydrochloride MS: 397 (M+1); 395 (M−1). Calc'd. for C$_{24}$H$_{20}$N$_4$O$_2$—396.16.

EXAMPLE 161

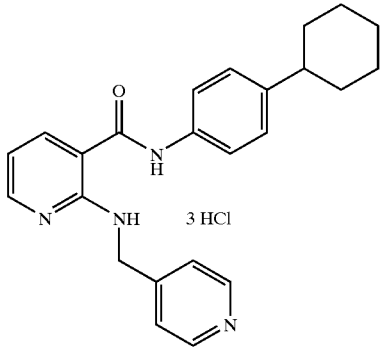

N-(4-Cyclohexylphenyl){2-[(4-pyridylmethyl)amino](3-pyridyl)}carboxamide

MS: 387 (M+1); 385 (M−1). Calc'd. for C$_{24}$H$_{26}$N$_4$O—386.21.

EXAMPLE 162

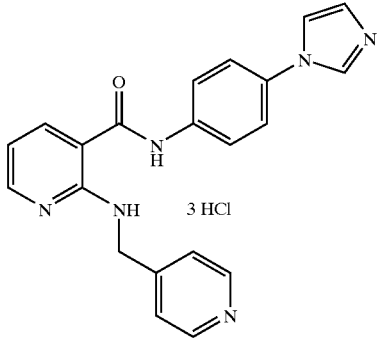

N-(4-Imidazol-1-ylphenyl){2-[(4-pyridylmethyl)amino](3-pyridyl)}carboxamide

Step A—Preparation of (2-Chloro(3-pyridyl))-N-(4-imidazolylphenyl)carboxamide

A slurry of 4-imidazolylphenylamine (15.9 mg, 0.100 mmol), polymer-supported DIPEA (0.100 g, 0.362 mmol, 3.62 mmol/g loading) in CH$_2$Cl$_2$ (2 ml) was treated with a 2-chloropyridine-3-carbonyl chloride solution (0.10 M, 0.200 mmol, 2.0 ml, 2.0 eq) in CH$_2$Cl$_2$. The mixture was vortexed at RT for 14 h. Afterwards, the excess acid chloride was removed by treating the reaction mixture with polymer-supported trisamine resin (0.100 g, 0.375 mmol, 3.75 mmol/g loading). The slurry was shaken at RT for an additional 18 h. The reaction mixture was filtered, rinsed with CH$_2$Cl$_2$ (1 ml), and the filtrate was concentrated under reduced pressure. The resulting brown oil was used directly in the subsequent reaction.

Step B—Synthesis of N-(4-imidazolylphenyl){2-[(4-pyridylmethyl)amino](3-pyridyl)}carboxamide hydrochloride (2-Chloro-(3-pyridyl))-N-(4-imidazolylphenyl)-carboxamide was treated with 4-aminomethylpyridine (0.100 g, 0.93 mmol) and heated neat at 120° C. for 18 h. After cooling to RT, the material was purified by preparative HPLC. The final product was converted into an HCl salt by dissolution in a minimum of MeOH, treatment with an HCl ethereal solution, and evaporation of solvent. MS: (ES+) 371 (M+1)$^+$; (ES−): 369 (M−1). Calc'd. for C$_{21}$H$_{18}$N$_6$O—370.15.

The following compounds (Examples 163–166) were analogously synthesized by the method described in Example 162.

EXAMPLE 163

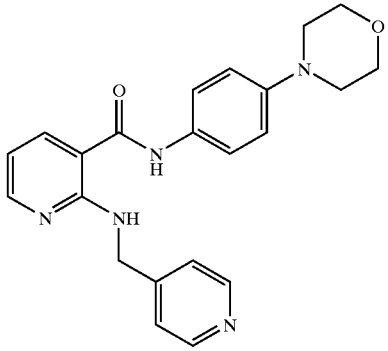

N-(4-Morpholin-4-ylphenyl){2-[(4-pyridylmethyl)amino](3-pyridyl)}carboxamide

The title compound was isolated as the HCl salt. MS: 390 (M+1); 388 (M−1). Calc'd. for $C_{22}H_{23}N_5O_2$—389.19.

EXAMPLE 164

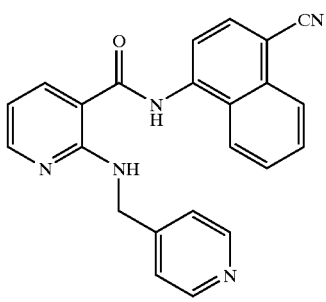

N-(4-Cyanonaphthyl){2-[(4-pyridylmethyl)amino](3-pyridyl)}carboxamide

The title compound was isolated as the HCl salt. MS: 380 (M+1); 378 (M−1). Calc'd. for $C_{23}H_{17}N_5O$—379.14.

EXAMPLE 165

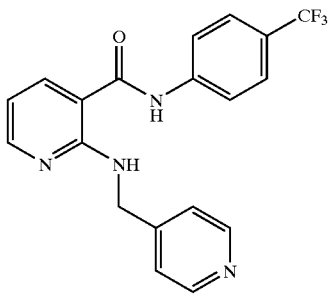

{2-[(4-Pyridylmethyl)amino](3-pyridyl)}-N-[4-(trifluoromethyl)phenyl]carboxamide The title compound was isolated as the HCl salt. MS: 373 (M+1); 371 (M−1). Calc'd. for $C_{19}H_{15}F_3N_4O$—372.12.

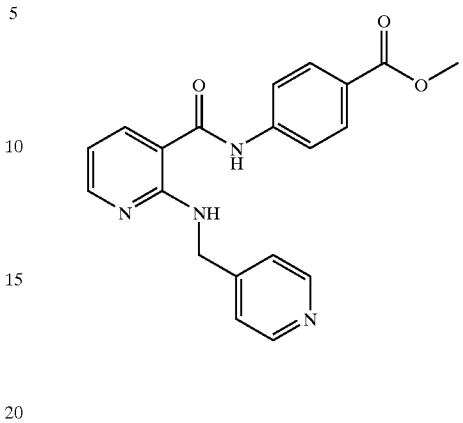

Methyl-({2-[(4-pyridylmethyl)amino]-3-pyridyl}carbonylamino)benzoate

The title compound was isolated as the HCl salt. MS: 363 (M+1); 361 (M−1). Calc'd. for $C_{20}H_{18}N_4O_3$—362.14.

The following compounds were synthesized by a procedure similar to the method described in Example 3, using an aldehyde to react with the aminopyridine core via reductive amination.

EXAMPLE 167

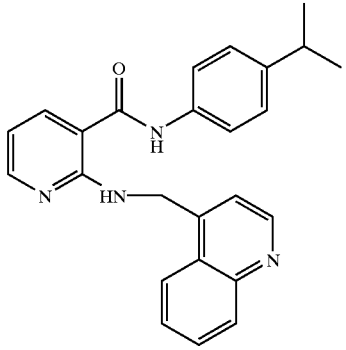

N-[4-(Isopropyl)phenyl]{2-[(4-quinolylmethyl)amino](3-pyridyl)}carboxamide

MS: (ES+) 397 (M+H); (ES−) 395 (M−H). Calc'd. for $C_{25}H_{24}N_4O$—396.20.

EXAMPLE 168

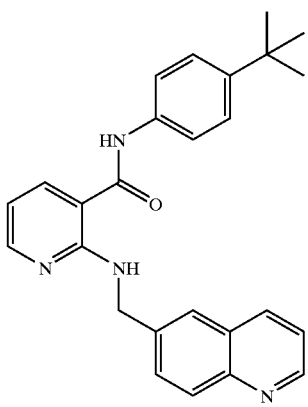

N-[4-(tert-Butyl)phenyl]{2-[(6-quinolylmethyl)amino](3-pyridyl)}carboxamide

MS (ES+): 411 (M+H); (ES−): 409 (M−H). Calc'd. for $C_{26}H_{26}N_4O$—410.51.

EXAMPLE 169

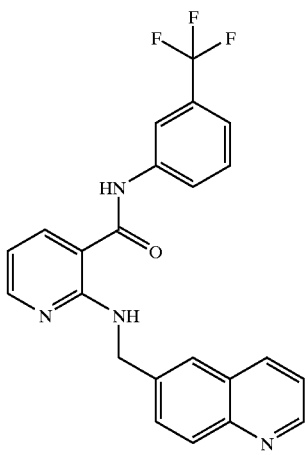

{2-[(6-Quinolylmethyl)amino](3-pyridyl)}-N-[3-(trifluoromethyl)phenyl]carboxamide MS (ES+): 423 (M+H); (ES−): 421 (M−H). Calc'd. for $C_{23}H_{17}F_3N_4O$: 422.14.

Other compounds included in this invention are set forth in Tables 3–9 below.

TABLE 3

| # | R¹ | R² | n |
|---|---|---|---|
| 170. | 2-chlorophenyl | H | 1 |
| 171. | 4-benzimidazolyl | H | 1 |
| 172. | 5-benzimidazolyl | H | 1 |
| 173. | 7-benzimidazolyl | H | 1 |
| 174. | 2-chlorophenyl | 5-Br | 1 |
| 175. | 3-isoquinolinyl | 5-Br | 1 |
| 176. | 2-quinolinyl | 5-Br | 1 |
| 177. | 2-benzthiazolyl | 5-Br | 1 |
| 178. | 2-benzimidazolyl | 5-Br | 1 |
| 179. | 4-benzimidazolyl | 5-Br | 1 |
| 180. | 5-benzimidazolyl | 5-Br | 1 |
| 181. | 6-benzimidazolyl | 5-Br | 1 |
| 182. | 7-benzimidazolyl | 5-Br | 1 |
| 183. | 4-chlorophenyl | H | 3 |
| 184. | 4-chlorophenyl | 3-pyridyl | 1 |
| 185. | 4-pyridyl | H | 1 |
| 186. | 4-pyridyl | 6-CH₃ | 1 |
| 187. | 4-chlorophenyl- | 5-Cl | 1 |
| 188. | 3,4-dichlorophenyl- | 5-Br | 1 |
| 189. | 4-fluorophenyl | 6-CH₃ | 1 |
| 190. | 3-chlorophenyl | 6-CH₃ | 1 |
| 191. | 3-fluorophenyl | 6-CH₃ | 1 |
| 192. | 3-fluoro-4-methoxyphenyl | 6-CH₃ | 1 |
| 193. | 3-fluoro-4-methylphenyl | 6-Cl | 1 |
| 194. | 4-phenoxyphenyl | H | 1 |
| 195. | 3-phenoxyphenyl | H | 1 |
| 196. | 4-biphenyl | H | 1 |
| 197. | 4-cyclohexylphenyl | H | 1 |
| 198. | 2-quinolyl | H | 1 |
| 199. | 3-isoquinolyl | H | 1 |
| 200. | 3-quinolyl | H | 1 |
| 201. | 1-isoquinolyl | H | 1 |
| 202. | 5-quinolyl | H | 1 |
| 203. | 5-isoquinolyl | H | 1 |
| 204. | 6-quinolyl | H | 1 |
| 205. | 6-isoquinolyl | H | 1 |
| 206. | 7-quinolyl | H | 1 |
| 207. | 7-isoquinolyl | H | 1 |
| 208. | 4-quinolyl | H | 1 |
| 209. | 4-isoquinolyl | H | 1 |
| 210. | 4-pyridyl | H | 1 |
| 211. | 4-pyrimidinyl | H | 1 |
| 212. | 2-pyrimidinyl | H | 1 |
| 213. | 6-pyrimidinyl | H | 1 |
| 214. | 4-pyridazinyl | H | 1 |
| 215. | 5-pyridazinyl | H | 1 |
| 216. | 4-indolyl | H | 1 |
| 217. | 5-isoindolyl | H | 1 |
| 218. | 5-naphthyridinyl | H | 1 |
| 219. | 6-quinozalinyl | H | 1 |
| 220. | 6-isoquinolyl | H | 1 |
| 221. | 4-naphthyridinyl | H | 1 |
| 222. | 5-quinozalinyl | H | 1 |
| 223. | 4-naphthyridinyl | H | 1 |
| 224. | 7-tetrahydroquinolinyl | H | 1 |
| 225. | 6-indazolyl | H | 1 |
| 226. | 6-isoindolyl | H | 1 |
| 227. | 5-indazolyl | H | 1 |
| 228. | 5-isoindolyl | H | 1 |
| 229. | 6-benzothienyl | H | 1 |
| 230. | 6-benzofuryl | H | 1 |
| 231. | 5-benzothienyl | H | 1 |

TABLE 3-continued

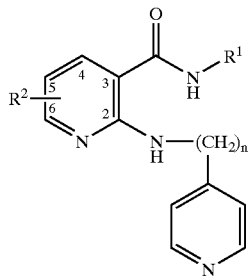

| # | R¹ | R² | n |
|---|---|---|---|
| 232. | 5-benzofuryl | H | 1 |
| 233. | 2-benzimidazolyl | H | 1 |
| 234. | 2-benzoxazolyl | H | 1 |
| 235. | 2-benzthiazolyl | H | 1 |
| 236. | 6-benzimidazolyl | H | 1 |
| 237. | 6-benzoxazolyl | H | 1 |
| 238. | 6-benzthiazolyl | H | 1 |
| 239. | 2-quinazolinyl | H | 1 |
| 240. | 3-(phenoxy)-6-pyridyl | H | 1 |
| 241. | 4-(phenylcarbonyl)phenyl | H | 1 |
| 242. | 4-(phenylamino)phenyl | H | 1 |
| 243. | 4-cyclohexyloxyphenyl | H | 1 |
| 244. | 4-(3-thienyl)phenyl | H | 1 |
| 245. | 4-(pyrazol-3-yl)phenyl | H | 1 |
| 246. | 4-chlorophenyl | 6-F | 2 |
| 247. | 4-pyridyl | 6-Cl | 1 |
| 248. | 3-methoxyphenyl | 6-F | 1 |
| 249. | 4-hydroxyphenyl | 6-Cl | 1 |
| 250. | 3-hydroxyphenyl | H | 1 |
| 251. | 2-hydroxyphenyl | H | 1 |
| 252. | 4-chlorophenyl | 6-F | 1 |
| 253. | 4-phenoxyphenyl | 6-F | 1 |
| 254. | 4-biphenyl | 6-phenyl | 1 |
| 255. | 4-hydroxyphenyl | 6-phenyl | 1 |
| 256. | 4-cyclohexylphenyl | 6-F | 1 |
| 257. | 3-isoquinolyl | 6-phenyl | 1 |
| 258. | 4-piperidinylmethylphenyl | H | 1 |
| 259. | 4-morpholinylmethylphenyl | H | 1 |

TABLE 4a

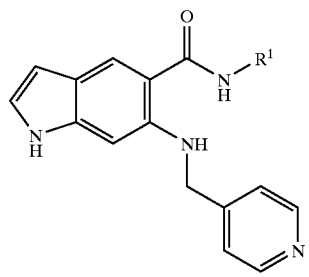

| # | R¹ |
|---|---|
| 260. | 4-chlorophenyl |
| 261. | 3,4-dichlorophenyl |
| 262. | 4-phenoxyphenyl |
| 263. | 4-biphenyl |
| 264. | 4-cyclohexylphenyl |
| 265. | 3-isoquinolyl |

TABLE 4b

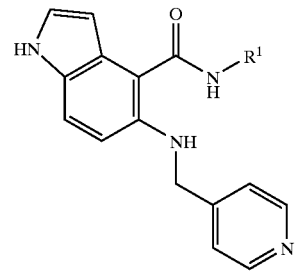

| # | R¹ |
|---|---|
| 266. | 4-chlorophenyl |
| 267. | 3,4-dichlorophenyl |
| 268. | 4-phenoxyphenyl |
| 269. | 4-biphenyl |
| 270. | 4-cyclohexylphenyl |
| 271. | 3-isoquinolyl |

TABLE 4c

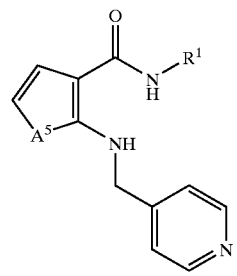

| # | R¹ | A⁵ |
|---|---|---|
| 272. | 4-chlorophenyl | NH |
| 273. | 3,4-dichlorophenyl | NH |
| 274. | 4-phenoxyphenyl | NH |
| 275. | 4-biphenyl | NH |
| 276. | 4-cyclohexylphenyl | NH |
| 277. | 3-isoquinolyl | NH |
| 278. | 4-chlorophenyl | O |
| 279. | 3,4-dichlorophenyl | O |
| 280. | 4-phenoxyphenyl | O |
| 281. | 4-biphenyl | O |
| 282. | 4-cyclohexylphenyl | O |
| 283. | 3-isoquinolyl | O |
| 284. | 3,4-dichlorophenyl | S |
| 285. | 4-phenoxyphenyl | S |
| 286. | 4-biphenyl | S |
| 287. | 4-cyclohexylphenyl | S |
| 288. | 3-isoquinolyl | S |

TABLE 4d

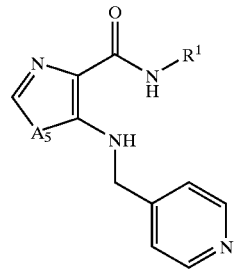

| # | R¹ | A⁵ |
|---|---|---|
| 289. | 4-chlorophenyl | NH |
| 290. | 3,4-dichlorophenyl | NH |
| 291. | 4-phenoxyphenyl | NH |
| 292. | 4-biphenyl | NH |
| 293. | 4-cyclohexylphenyl | NH |
| 294. | 3-isoquinolyl | NH |
| 295. | 4-chlorophenyl | O |
| 296. | 3,4-dichlorophenyl | O |
| 297. | 4-phenoxyphenyl | O |
| 298. | 4-biphenyl | O |
| 299. | 4-cyclohexylphenyl | O |
| 300. | 3-isoquinolyl | O |
| 301. | 3,4-dichlorophenyl | S |
| 302. | 4-phenoxyphenyl | S |
| 303. | 4-biphenyl | S |
| 304. | 4-cyclohexylphenyl | S |
| 305. | 3-isoquinolyl | S |

TABLE 4e

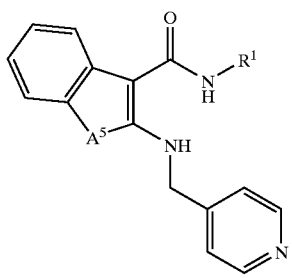

| # | R¹ | A⁵ |
|---|---|---|
| 306. | 4-chlorophenyl | NH |
| 307. | 3,4-dichlorophenyl | NH |
| 308. | 4-phenoxyphenyl | NH |
| 309. | 4-biphenyl | NH |
| 310. | 4-cyclohexylphenyl | NH |
| 311. | 3-isoquinolyl | NH |
| 312. | 4-chlorophenyl | O |
| 313. | 3,4-dichlorophenyl | O |
| 314. | 4-phenoxyphenyl | O |
| 315. | 4-biphenyl | O |
| 316. | 4-cyclohexylphenyl | O |
| 317. | 3-isoquinolyl | O |
| 318. | 3,4-dichlorophenyl | S |
| 319. | 4-phenoxyphenyl | S |
| 320. | 4-biphenyl | S |
| 321. | 4-cyclohexylphenyl | S |
| 322. | 3-isoquinolyl | S |

TABLE 4f

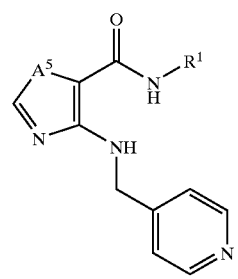

| # | R¹ | A⁵ |
|---|---|---|
| 323. | 4-chlorophenyl | NH |
| 324. | 3,4-dichlorophenyl | NH |
| 325. | 4-phenoxyphenyl | NH |
| 326. | 4-biphenyl | NH |
| 327. | 4-cyclohexylphenyl | NH |
| 328. | 3-isoquinolyl | NH |
| 329. | 4-chlorophenyl | O |
| 330. | 3,4-dichlorophenyl | O |
| 331. | 4-phenoxyphenyl | O |
| 332. | 4-biphenyl | O |
| 333. | 4-cyclohexylphenyl | O |
| 334. | 3-isoquinolyl | O |
| 335. | 3,4-dichlorophenyl | S |
| 336. | 4-phenoxyphenyl | S |
| 337. | 4-biphenyl | S |
| 338. | 4-cyclohexylphenyl | S |
| 339. | 3-isoquinolyl | S |

TABLE 4g

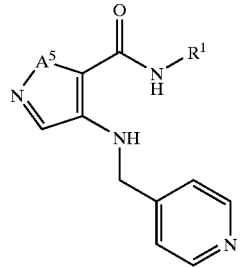

| # | R¹ | A⁵ |
|---|---|---|
| 340. | 4-chlorophenyl | NH |
| 341. | 3,4-dichlorophenyl | NH |
| 342. | 4-phenoxyphenyl | NH |
| 343. | 4-biphenyl | NH |
| 344. | 4-cyclohexylphenyl | NH |
| 345. | 3-isoquinolyl | NH |
| 346. | 4-chlorophenyl | O |
| 347. | 3,4-dichlorophenyl | O |
| 348. | 4-phenoxyphenyl | O |
| 349. | 4-biphenyl | O |
| 350. | 4-cyclohexylphenyl | O |
| 351. | 3-isoquinolyl | O |

TABLE 4h

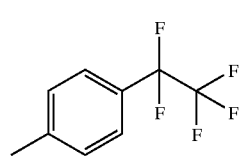

| # | R¹ | A⁵ | M + H |
|---|---|---|---|
| 352. | 4-chlorophenyl | NCH₃ | 364 |
| 353. | 3,4-dichlorophenyl | NCH₃ | |
| 354. | 4-phenoxyphenyl | NCH₃ | |
| 355. | 4-biphenyl | NH | |
| 356. | 4-cyclohexylphenyl | NH | |
| 357. | 4-tert-butylphenyl | NCH₃ | |

TABLE 4h-continued

| # | R¹ | A⁵ | M + H |
|---|---|---|---|
| 358. | 4-chlorophenyl | O | |
| 359. | 3,4-dichlorophenyl | O | |
| 360. | 4-phenoxyphenyl | O | |
| 361. | 4-biphenyl | O | |
| 362. | 4-cyclohexylphenyl | O | |
| 363. | 3-isoquinolyl | O | |

TABLE 5

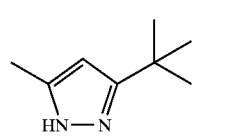

| # | R | Y | R¹ | R² |
|---|---|---|---|---|
| 364. | 4-pyridyl | —NHSO₂— | 4-chlorophenyl | H |
| 365. | 4-pyridyl | —NHSO₂— | 4-chlorophenyl | 5-Br |
| 366. | 4-pyridyl | —NHSO₂— | 3-chlorophenyl | H |
| 367. | 4-pyridyl | —NHSO₂— | 3-chlorophenyl | 5-Br |
| 368. | 4-pyridyl | —NHSO₂— | 4-phenoxyphenyl | H |
| 369. | 4-pyridyl | —NHSO₂— | 4-biphenyl | H |
| 370. | 4-pyridyl | —NHSO₂— | 3-isoquinolyl | H |
| 371. | 4-pyridyl | —NHSO₂— | 3-isoquinolyl | 5-Br |
| 372. | 5-quinolyl | —NHSO₂— | 4-chlorophenyl | H |
| 373. | 5-quinolyl | —NHSO₂— | 4-chlorophenyl | 5-Br |
| 374. | 5-quinolyl | —NHSO₂— | 3-chlorophenyl | H |
| 375. | 5-quinolyl | —NHSO₂— | 3-chlorophenyl | 5-Br |
| 376. | 5-quinolyl | —NHSO₂— | 4-phenoxyphenyl | H |
| 377. | 6-quinolyl | —NHSO₂— | 4-biphenyl | H |
| 378. | 5-quinolyl | —NHSO₂— | 3-isoquinolyl | H |
| 379. | 6-quinolyl | —NHSO₂— | 3-isoquinolyl | 5-Br |
| 380. | 4-pyridyl | —NHCH₂— | 4-(pentafluoroethyl)tolyl | H |
| 381. | 4-methyl-2-(1-methylpiperidin-4-yloxy)pyridyl | —NHCH₂— | 3-tert-butyl-5-methyl-1H-pyrazolyl | H |

TABLE 5-continued

| # | R | Y | R¹ | R² |
|---|---|---|----|----|
| 382. | 4-methylpyridin-2-yloxymethyl-(1-methylpiperidin-4-yl) | —NHCH₂— | 3-tert-butyl-5-methyl-1H-pyrazole | H |
| 383. | 4-methylpyridin-2-yloxyethyl-(1-methylpiperidin-4-yl) | —NHCH₂— | 3-tert-butyl-5-methyl-1H-pyrazole | H |
| 384. | 4-methylpyridin-2-yloxyethyl-(1-methylpiperidin-4-yl) | —NHCH₂— | 4-(1,1,1,2,2-pentafluoroethyl)phenyl | H |
| 385. | 4-methylpyridin-2-yloxyethyl-(1-methylpiperidin-4-yl) | —NHCH₂— | 4-CF₃-phenyl | H |
| 386. | 4-methylpyridin-2-yloxypropyl-(1-methylpiperidin-4-yl) | —NHCH₂— | 3-tert-butyl-5-methylisoxazole | H |
| 387. | 4-methylpyridin-2-yloxypropyl-(1-methylpiperidin-4-yl) | —NHCH₂— | 3-tert-butyl-5-methyl-1H-pyrazole | H |
| 388. | 4-methylpyridin-2-yloxypropyl-(1-methylpiperidin-4-yl) | —NHCH₂— | 4-(1,1,1,2,2-pentafluoroethyl)phenyl | H |

TABLE 5-continued
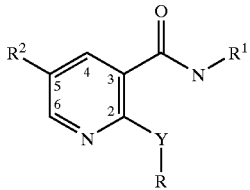
| # | R | Y | R¹ | R² |
|---|---|---|----|----|
| 389. | 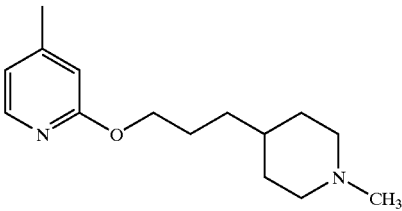 | —NHCH$_2$— | 3-CF$_3$-phenyl | H |
| 390. | 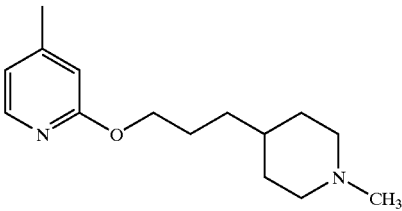 | —NHCH$_2$— | 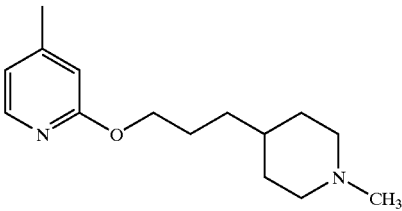 | H |
| 391. | 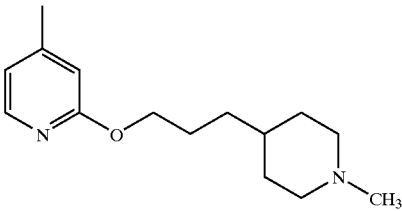 | —NHCH$_2$— | 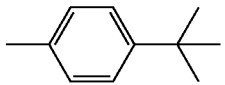 | H |
| 392. | 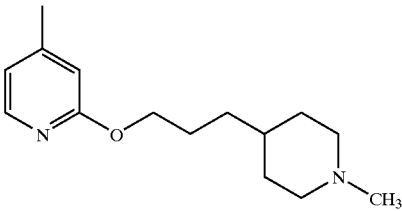 | —NHCH$_2$— | 4-CF$_3$-phenyl | H |
| 393. | 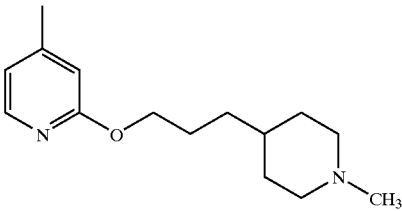 | —NHCH$_2$— | 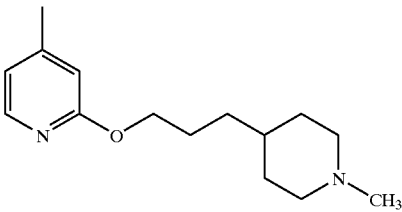 | H |
| 394. | 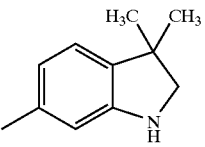 | —NHCH$_2$— | 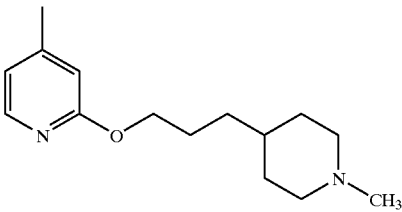 | H |

TABLE 5-continued

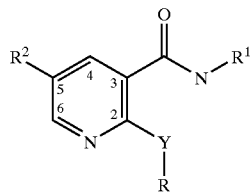

| # | R | Y | R¹ | R² |
|---|---|---|---|---|
| 395. | 6-methyl-pyrimidin-4-yl-O-(CH₂)₃-(1-methylpiperidin-4-yl) | —NHCH₂— | 4-(1,1,2,2,2-pentafluoroethyl)phenyl | H |
| 396. | 6-methyl-pyrimidin-4-yl-O-(CH₂)₃-(1-methylpiperidin-4-yl) | —NHCH₂— | 3-CF₃-phenyl | H |
| 397. | 6-methyl-pyrimidin-4-yl-O-(CH₂)₃-(1-methylpiperidin-4-yl) | —NHCH₂— | 4-tert-butyl-phenyl | H |
| 398. | 6-methyl-pyrimidin-4-yl-O-(CH₂)₃-(1-methylpiperidin-4-yl) | —NHCH₂— | 3,3,6-trimethyl-2,3-dihydro-1H-indol-yl | H |
| 399. | 4-methyl-pyrimidin-2-yl-O-(CH₂)₂-(1-methylpiperidin-4-yl) | —NHCH₂— | 3-tert-butyl-5-methyl-isoxazol-yl | H |
| 400. | 6-methyl-pyrimidin-4-yl-O-(CH₂)₃-(1-methylpiperidin-4-yl) | —NHCH₂— | 4-CF₃-phenyl | H |

TABLE 5-continued
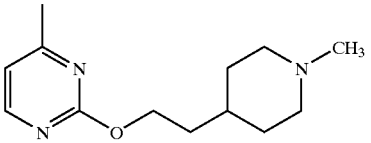
| # | R | Y | R¹ | R² |
|---|---|---|----|----|
| 401. | 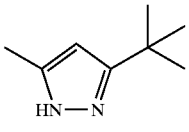 | —NHCH₂— | 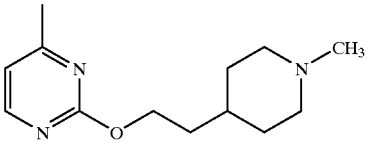 | H |
| 402. | 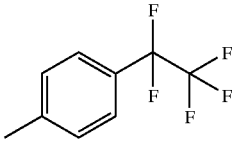 | —NHCH₂— | 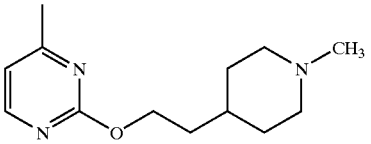 | H |
| 403. | 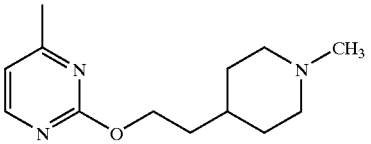 | —NHCH₂— | 3-CF₃-phenyl | H |
| 404. | 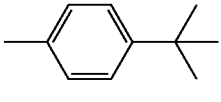 | —NHCH₂— | 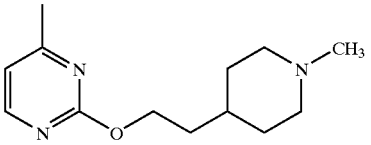 | H |
| 405. | 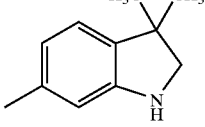 | —NHCH₂— | 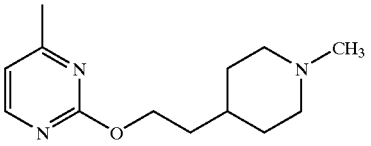 | H |
| 406. | 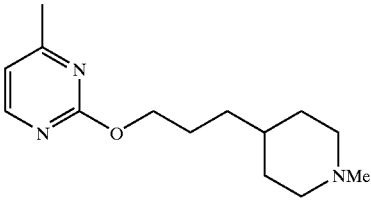 | —NHCH₂— | 4-CF₃-phenyl | H |
| 407. | 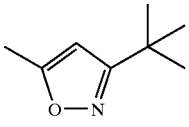 | —NHCH₂— | 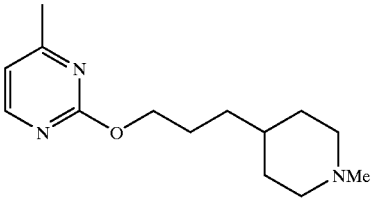 | H |
| 408. | 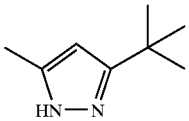 | —NHCH₂— | 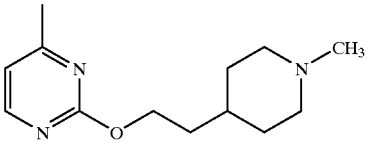 | H |

TABLE 5-continued
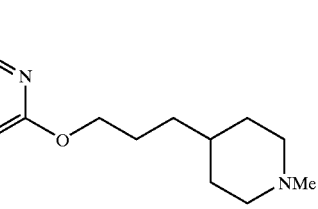
| # | R | Y | R¹ | R² |
|---|---|---|----|----|
| 409. |  | —NHCH₂— | 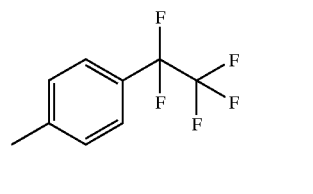 | H |
| 410. | 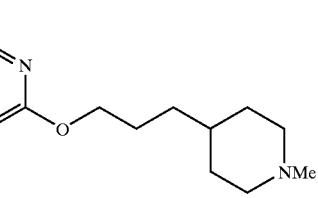 | —NHCH₂— | 3-CF₃-phenyl | H |
| 411. |  | —NHCH₂— | 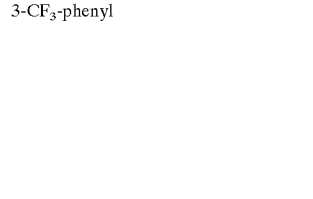 | H |
| 412. | 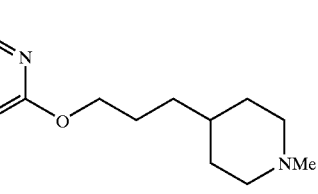 | —NHCH₂— |  | H |
| 413. | 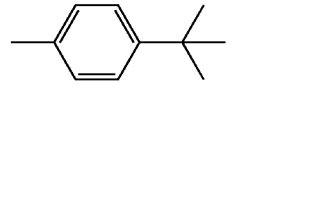 | —NHCH₂— | 4-CF₃-phenyl | H |
| 414. | 4-pyridyl | —NHCH₂— | 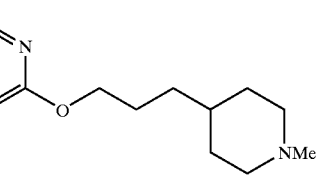 | H |

TABLE 5-continued

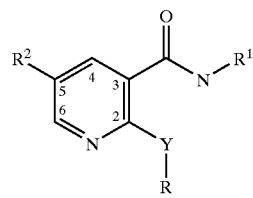

| # | R | Y | R¹ | R² |
|---|---|---|---|---|
| 415. | 4-pyridyl | —NHCH₂— | [2-tert-butyl-5-methylphenyl with O-CH₂CH₂-piperidine] | H |
| 416. | 4-pyridyl | —NHCH₂— | [2-tert-butyl-5-methylphenyl with O-CH₂-piperidine] | H |
| 417. | 4-pyridyl | —NHCH₂— | [2-tert-butyl-5-methylphenyl with NH-CH₂CH₂-morpholine] | H |
| 418. | 4-pyridyl | —NHCH₂— | [2-tert-butyl-5-methylphenyl with NH-4-piperidinyl] | H |
| 419. | 4-pyrimidinyl | —NHCH₂— | [2-tert-butyl-5-methylphenyl with NH-CH₂CH₂-morpholine] | H |
| 420. | 4-pyrimidinyl | —NHCH₂— | [2-tert-butyl-5-methylphenyl with NH-4-piperidinyl] | H |
| 421. | 4-pyrimidinyl | —NHCH₂— | [2-tert-butyl-5-methylphenyl with O-CH₂-piperidine] | H |

TABLE 5-continued

| # | R | Y | R¹ | R² |
|---|---|---|---|---|
| 422. | 4-pyrimidinyl | —NHCH₂— | 2-tert-butyl-5-methylphenyl group with NH-CH₂CH₂-piperidinyl substituent | H |
| 423. | 4-pyrimidinyl | —NHCH₂— | 2-tert-butyl-5-methylphenyl group with O-CH₂CH₂-piperidinyl substituent | H |
| 424. | 4-pyrimidinyl | —NHCH₂— | 2-tert-butyl-5-methylphenyl group with CH₂CH₂-piperidinyl substituent | H |
| 425. | 4-pyrimidinyl | —NHCH₂— | 2-tert-butyl-5-methylphenyl group with 4-methylpiperazin-1-yl substituent | H |
| 426. | 4-pyrimidinyl | —NHCH₂— | 2-tert-butyl-5-methylphenyl group with CH₂CH₂CH₂-piperidinyl substituent | H |
| 427. | 4-pyrimidinyl | —NHCH₂— | 2-tert-butyl-5-methylphenyl group with O-CH₂-(1-methylpiperidin-4-yl) substituent | H |
| 428. | 4-pyrimidinyl | —NHCH₂— | 4-methylphenyl group with C(CH₃)-(1-methylpiperidin-4-yl) substituent | H |

TABLE 5-continued

| # | R | Y | R¹ | R² |
|---|---|---|---|---|
| 429. | 3-pyridyl | —NH(CH₂)₂— | 2-tert-butyl-5-methylphenyl-O-CH₂-piperidinyl | H |
| 430. | 3-pyridyl | —NH(CH₂)₂— | 2-tert-butyl-5-methylphenyl-NH-CH₂CH₂-piperidinyl | H |
| 431. | 3-pyridyl | —NH(CH₂)₂— | 2-tert-butyl-5-methylphenyl-O-CH₂CH₂-piperidinyl | H |
| 432. | 3-pyridyl | —NH(CH₂)₂— | 2-tert-butyl-5-methylphenyl-CH₂CH₂-piperidinyl | H |
| 433. | 3-pyridyl | —NH(CH₂)₂— | 2-tert-butyl-5-methylphenyl-(4-methylpiperazin-1-yl) | H |
| 434. | 3-pyridyl | —NH(CH₂)₂— | 2-tert-butyl-5-methylphenyl-CH₂CH₂CH₂-piperidinyl | H |
| 435. | 3-pyridyl | —NH(CH₂)₂— | 2-tert-butyl-5-methylphenyl-O-CH₂-(1-methylpiperidin-4-yl) | H |

TABLE 5-continued

| # | R | Y | R¹ | R² |
|---|---|---|---|---|
| 436. | 3-pyridyl | —NH(CH₂)₂— | 2-tert-butyl-5-methyl-phenyl-NH-(piperidin-4-yl) | H |
| 437. | 3-pyridyl | —NH(CH₂)₂— | 2-tert-butyl-5-methyl-phenyl-NH-CH₂CH₂-morpholinyl | H |
| 438. | 2-methoxy-4-pyridyl | —NHCH₂— | 2-tert-butyl-5-methyl-phenyl-NH-CH₂CH₂-morpholinyl | H |
| 439. | 2-methoxy-4-pyridyl | —NHCH₂— | 2-tert-butyl-5-methyl-phenyl-NH-(piperidin-4-yl) | H |
| 440. | 2-methoxy-4-pyridyl | —NHCH₂— | 2-tert-butyl-5-methyl-phenyl-(CH₂)₃-piperidinyl | H |
| 441. | 2-methoxy-4-pyridyl | —NHCH₂— | 2-tert-butyl-5-methyl-phenyl-O-CH₂-(1-methylpiperidin-4-yl) | H |
| 442. | 2-methoxy-4-pyridyl | —NHCH₂— | 2-tert-butyl-5-methyl-phenyl-O-CH₂-piperidinyl | H |

TABLE 5-continued

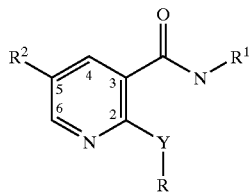

| # | R | Y | R¹ | R² |
|---|---|---|---|---|
| 443. | 4-(2-OMe-pyridyl) | —NHCH₂— | 2-tert-butyl-5-methylphenyl-NH-CH₂CH₂-piperidine | H |
| 444. | 4-(2-OMe-pyridyl) | —NHCH₂— | 2-tert-butyl-5-methylphenyl-O-CH₂CH₂-piperidine | H |
| 445. | 4-(2-OMe-pyridyl) | —NHCH₂— | 2-tert-butyl-5-methylphenyl-CH₂CH₂-piperidine | H |
| 446. | 4-(2-OMe-pyridyl) | —NHCH₂— | 2-tert-butyl-5-methylphenyl-(4-methylpiperazin-1-yl) | H |
| 447. | 4-(2-SMe-pyridyl) | —NHCH₂— | 2-tert-butyl-5-methylphenyl-O-CH₂-piperidine | H |
| 448. | 4-(2-SMe-pyridyl) | —NHCH₂— | 2-tert-butyl-5-methylphenyl-NH-CH₂CH₂-piperidine | H |
| 449. | 4-(2-SMe-pyridyl) | —NHCH₂— | 2-tert-butyl-5-methylphenyl-O-CH₂CH₂-piperidine | H |

TABLE 5-continued

| # | R | Y | R¹ | R² |
|---|---|---|---|---|
| 450. | 4-pyridyl, 2-SMe | —NHCH₂— | 2-tert-butyl-5-methylphenyl with CH₂-piperidine | H |
| 451. | 4-pyridyl, 2-SMe | —NHCH₂— | 2-tert-butyl-5-methylphenyl with N-methylpiperazine | H |
| 452. | 4-pyridyl, 2-CH₃ | —NHCH₂— | 2-tert-butyl-5-methylphenyl with O-CH₂-piperidine | H |
| 453. | 4-pyridyl, 2-CH₃ | —NHCH₂— | 2-tert-butyl-5-methylphenyl with NH-CH₂CH₂-piperidine | H |
| 454. | 4-pyridyl, 2-CH₃ | —NHCH₂— | 2-tert-butyl-5-methylphenyl with O-CH₂CH₂-piperidine | H |
| 455. | 4-pyridyl, 2-CH₃ | —NHCH₂— | 2-tert-butyl-5-methylphenyl with CH₂CH₂-piperidine | H |
| 456. | 4-pyridyl, 2-CH₃ | —NHCH₂— | 2-tert-butyl-5-methylphenyl with N-methylpiperazine | H |

TABLE 5-continued

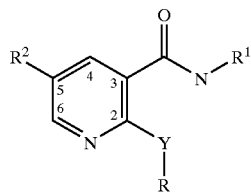

| # | R | Y | R¹ | R² |
|---|---|---|---|---|
| 457. | 4-(2-N(CH₃)₂)pyridyl | —NHCH₂— | 2-tert-butyl-5-methyl-phenyl with -OCH₂-(piperidin-1-yl) | H |
| 458. | 4-(2-N(CH₃)₂)pyridyl | —NHCH₂— | 2-tert-butyl-5-methyl-phenyl with -NH-CH₂CH₂-(piperidin-1-yl) | H |
| 459. | 4-(2-N(CH₃)₂)pyridyl | —NHCH₂— | 2-tert-butyl-5-methyl-phenyl with -O-CH₂CH₂-(piperidin-1-yl) | H |
| 460. | 4-(2-N(CH₃)₂)pyridyl | —NHCH₂— | 2-tert-butyl-5-methyl-phenyl with -CH₂CH₂-(piperidin-1-yl) | H |
| 461. | 4-(2-N(CH₃)₂)pyridyl | —NHCH₂— | 2-tert-butyl-5-methyl-phenyl with (4-methylpiperazin-1-yl) | H |
| 462. | 4-pyridyl | —NHCH₂— | 2-CF₂CF₃-5-methyl-phenyl with (4-methylpiperazin-1-yl) | H |
| 463. | 4-pyridyl | —NHCH₂— | 2-CF₂CF₃-5-methyl-phenyl with -CH₂-(morpholin-4-yl) | H |
| 464. | 4-pyridyl | —NHCH₂— | 2-CF₂CF₃-5-methyl-phenyl with -CH₂-(1-methylpiperidin-4-yl) | H |

TABLE 5-continued
| # | R | Y | R¹ | R² |
|---|---|---|---|---|
| 465. | 4-pyridyl | —NHCH₂— | 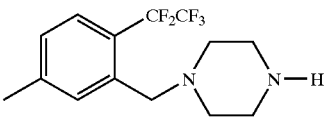 | H |
| 466. | 4-pyridyl | —NHCH₂— | 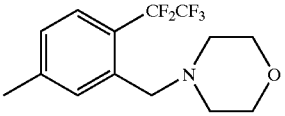 | H |
| 467. | 4-pyridyl | —NHCH₂— | 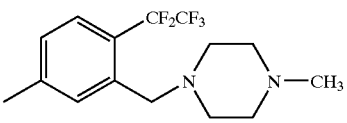 | H |
| 468. | 4-pyridyl | —NHCH₂— | 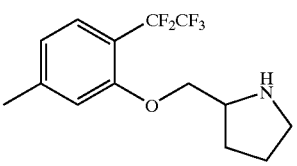 | H |
| 469. | 4-pyridyl | —NHCH₂— | 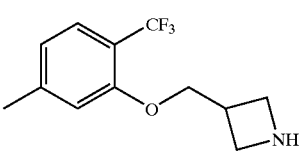 | H |
| 470. | 3-pyridyl | —NH(CH₂)₂— | 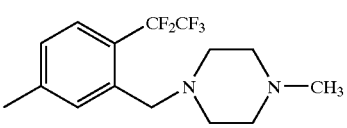 | H |
| 471. | 3-pyridyl | —NH(CH₂)₂— | 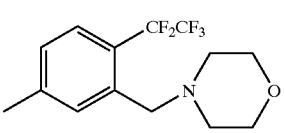 | H |
| 472. | 3-pyridyl | —NH(CH₂)₂— | 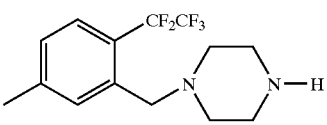 | H |
| 473. | 3-pyridyl | —NH(CH₂)₂— | 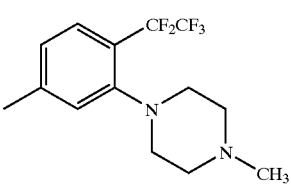 | H |

TABLE 5-continued

| # | R | Y | R¹ | R² |
|---|---|---|---|---|
| 474. | 3-pyridyl | —NH(CH₂)₂— | 5-methyl-2-(pentafluoroethyl)benzyl-morpholine | H |
| 475. | 3-pyridyl | —NH(CH₂)₂— | 5-methyl-2-(pentafluoroethyl)benzyl-(1-methylpiperidin-4-yl) | H |
| 476. | 3-pyridyl | —NH(CH₂)₂— | 4-methylphenyl-C(CF₃)₂-O-CH₂CH₂-piperidine | H |
| 477. | 3-pyridyl | —NH(CH₂)₂— | 5-methyl-2-(pentafluoroethyl)phenoxy-methyl-pyrrolidin-2-yl | H |
| 478. | 3-pyridyl | —NH(CH₂)₂— | 5-methyl-2-(trifluoromethyl)phenoxy-methyl-azetidin-3-yl | H |
| 479. | 4-pyrimidinyl | —NHCH₂— | 5-methyl-2-(trifluoromethyl)phenoxy-methyl-azetidin-3-yl | H |
| 480. | 4-pyrimidinyl | —NHCH₂— | 5-methyl-2-(pentafluoroethyl)phenyl-(4-methylpiperazin-1-yl) | H |
| 481. | 4-pyrimidinyl | —NHCH₂— | 5-methyl-2-(pentafluoroethyl)phenoxy-methyl-(1-methylpiperidin-4-yl) | H |

TABLE 5-continued

| # | R | Y | R¹ | R² |
|---|---|---|---|---|
| 482. | 4-pyrimidinyl | —NHCH₂— | 2-(CF₂CF₃), 5-methyl benzyl-morpholine | H |
| 483. | 4-pyrimidinyl | —NHCH₂— | 2-(CF₂CF₃), 5-methyl benzyl-(1-methylpiperidin-4-yl) | H |
| 484. | 4-pyrimidinyl | —NHCH₂— | 2-(CF₂CF₃), 5-methyl phenoxy-ethyl-piperidine | H |
| 485. | 4-pyrimidinyl | —NHCH₂— | 2-(CF₂CF₃), 5-methyl phenoxy-(2-hydroxy-3-pyrrolidinyl)propyl | H |
| 486. | 4-pyrimidinyl | —NHCH₂— | 4-methyl phenyl-C(CF₃)₂-O-ethyl-piperidine | H |
| 487. | 4-pyrimidinyl | —NHCH₂— | 2-(CF₂CF₃), 5-methyl benzyl-piperazine | H |
| 488. | 4-pyrimidinyl | —NHCH₂— | 2-(CF₂CF₃), 5-methyl benzyl-morpholine | H |
| 489. | 4-pyrimidinyl | —NHCH₂— | 2-(CF₂CF₃), 5-methyl benzyl-(4-methylpiperazine) | H |
| 490. | 4-pyrimidinyl | —NHCH₂— | 2-(CF₂CF₃), 5-methyl phenoxy-methyl-pyrrolidine | H |

TABLE 5-continued
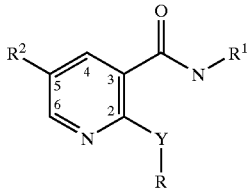
| # | R | Y | R[1] | R[2] |
|---|---|---|---|---|
| 491. | 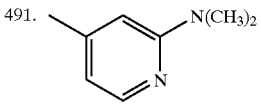 | —NHCH$_2$— | 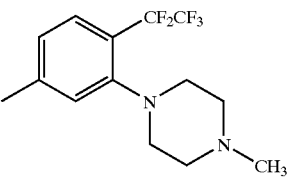 | H |
| 492. | 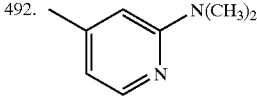 | —NHCH$_2$— | 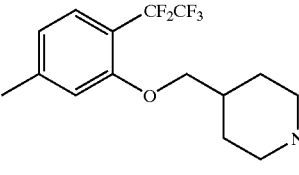 | H |
| 493. | 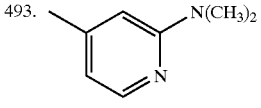 | —NHCH$_2$— | 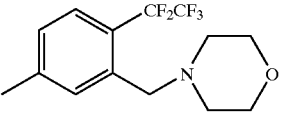 | H |
| 494. | 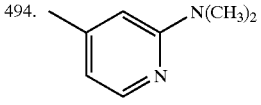 | —NHCH$_2$— | 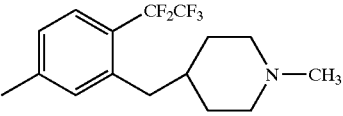 | H |
| 495. | 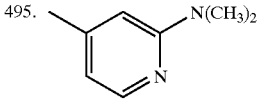 | —NHCH$_2$— | 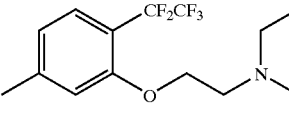 | H |
| 496. | 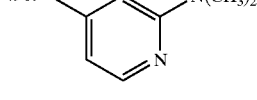 | —NHCH$_2$— | 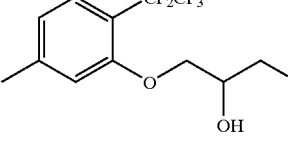 | H |
| 497. | 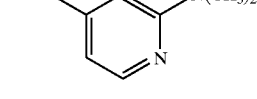 | —NHCH$_2$— | 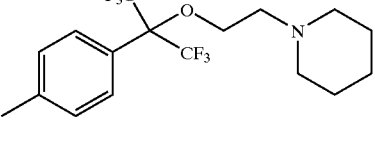 | H |
| 498. | 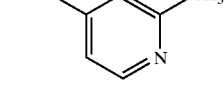 | —NHCH$_2$— | 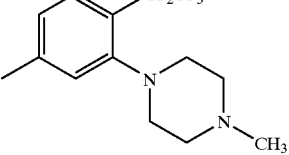 | H |

TABLE 5-continued

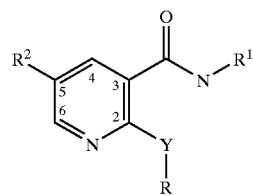

| # | R | Y | R¹ | R² |
|---|---|---|----|----|
| 499. | 4-(2-methyl)pyridyl | —NHCH₂— | 4-methyl-2-(1-methylpiperidin-4-ylmethoxy)phenyl with CF₂CF₃ | H |
| 500. | 4-(2-methyl)pyridyl | —NHCH₂— | 4-methyl-2-(morpholin-4-ylmethyl)phenyl with CF₂CF₃ | H |
| 501. | 4-(2-methyl)pyridyl | —NHCH₂— | 4-methyl-2-(1-methylpiperidin-4-ylmethyl)phenyl with CF₂CF₃ | H |
| 502. | 4-(2-methyl)pyridyl | —NHCH₂— | 4-methyl-2-(2-piperidin-1-ylethoxy)phenyl with CF₂CF₃ | H |
| 503. | 4-(2-methyl)pyridyl | —NHCH₂— | 4-methyl-2-(2-hydroxy-3-pyrrolidin-1-ylpropoxy)phenyl with CF₂CF₃ | H |
| 504. | 4-(2-methyl)pyridyl | —NHCH₂— | 4-methylphenyl-C(CF₃)₂-O-CH₂CH₂-piperidin-1-yl | H |
| 505. | 4-(2-SMe)pyridyl | —NHCH₂— | 4-methyl-2-(4-methylpiperazin-1-yl)phenyl with CF₂CF₃ | H |
| 506. | 4-(2-SMe)pyridyl | —NHCH₂— | 4-methyl-2-(1-methylpiperidin-4-ylmethoxy)phenyl with CF₂CF₃ | H |

TABLE 5-continued

| # | R | Y | R¹ | R² |
|---|---|---|---|---|
| 507. | 4-pyridyl, 2-SMe | —NHCH₂— | phenyl with CF₂CF₃, Me, and CH₂-morpholine | H |
| 508. | 4-pyridyl, 2-SMe | —NHCH₂— | phenyl with CF₂CF₃, Me, and CH₂-(1-methylpiperidin-4-yl) | H |
| 509. | 4-pyridyl, 2-SMe | —NHCH₂— | phenyl with CF₂CF₃, Me, and O-CH₂CH₂-piperidine | H |
| 510. | 4-pyridyl, 2-SMe | —NHCH₂— | phenyl with CF₂CF₃, Me, and O-CH₂-CH(OH)-CH₂-pyrrolidine | H |
| 511. | 4-pyridyl, 2-OMe | —NHCH₂— | phenyl with Me, and C(CF₃)₂-O-CH₂CH₂-piperidine | H |
| 512. | 4-pyridyl, 2-OMe | —NHCH₂— | phenyl with CF₂CF₃, Me, and 4-methylpiperazin-1-yl | H |
| 513. | 4-pyridyl, 2-OMe | —NHCH₂— | phenyl with CF₂CF₃, Me, and O-CH₂-(1-methylpiperidin-4-yl) | H |
| 514. | 4-pyridyl, 2-OMe | —NHCH₂— | phenyl with CF₃, Me, and O-CH₂-azetidin-3-yl | H |
| 515. | 4-pyridyl, 2-OMe | —NHCH₂— | phenyl with CF₂CF₃, Me, and CH₂-morpholine | H |

TABLE 5-continued

| # | R | Y | R¹ | R² |
|---|---|---|----|----|
| 516. | 4-methyl-2-methoxypyridyl | —NHCH₂— | 2-(CF₂CF₃)-5-methyl-benzyl-(1-methylpiperidin-4-yl) | H |
| 517. | 4-methyl-2-methoxypyridyl | —NHCH₂— | 2-(CF₂CF₃)-5-methyl-phenoxyethyl-piperidine | H |
| 518. | 4-methyl-2-methoxypyridyl | —NHCH₂— | 2-(CF₂CF₃)-5-methyl-phenoxy-2-hydroxypropyl-pyrrolidine | H |
| 519. | 4-methyl-2-methoxypyridyl | —NHCH₂— | 4-methylphenyl-C(CF₃)₂-O-ethyl-piperidine | H |
| 520. | 4-methyl-2-methoxypyridyl | —NHCH₂— | 2-(CF₂CF₃)-5-methyl-benzyl-(4-methylpiperazin-1-yl) | H |
| 521. | 4-methyl-2-methoxypyridyl | —NHCH₂— | 2-(CF₂CF₃)-5-methyl-benzyl-piperazine | H |
| 522. | 4-methyl-2-methoxypyridyl | —NHCH₂— | 2-(CF₂CF₃)-5-methyl-benzyl-morpholine | H |
| 523. | 4-methyl-2-methoxypyridyl | —NHCH₂— | 2-(CF₂CF₃)-5-methyl-phenoxymethyl-pyrrolidine | H |
| 524. | 4-methyl-2-methoxypyridyl | —NHCH₂— | 3,3,6-trimethyl-2,3-dihydrobenzo[d]isothiazole-1,1-dioxide | H |
| 525. | 4-pyridyl | —NHCH₂— | 3-CF₃-phenyl | H |

TABLE 5-continued

| # | R | Y | R¹ | R² |
|---|---|---|---|---|
| 526. | 4-pyridyl | —NHCH₂— | 3-CF₃-5-methyl-phenyl with propyl-morpholine | H |
| 527. | 4-pyridyl | —NHCH₂— | 3-CF₃-5-methyl-phenyl with propyl-piperidine | H |
| 528. | 4-pyridyl | —NHCH₂— | 3-CF₃-5-methyl-phenyl with CH₂-(4-methylpiperazine) | H |
| 529. | 4-pyridyl | —NHCH₂— | 3-CF₃-5-methyl-phenyl with 4-methylpiperazine | H |
| 530. | 4-pyridyl | —NHCH₂— | 3-CF₃-5-methyl-phenyl with O-CH₂-piperidine | H |
| 531. | 4-pyridyl | —NHCH₂— | 3-CF₃-5-methyl-phenyl with O-CH₂-pyrrolidine | H |
| 532. | 4-pyridyl | —NHCH₂— | 3-CF₃-5-methyl-phenyl with O-azetidine | H |

TABLE 5-continued

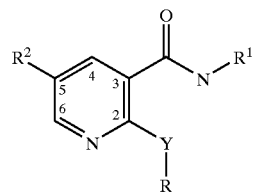

| # | R | Y | R¹ | R² |
|---|---|---|----|----|
| 533. | 4-pyridyl | —NHCH₂— | 3-CF₃, 5-methyl phenyl-O-(piperidin-4-yl) | H |
| 534. | 3-pyridyl | —NH(CH₂)₂— | 3-CF₃, 5-methyl phenyl-O-CH₂-(piperidin-4-yl) | H |
| 535. | 3-pyridyl | —NH(CH₂)₂— | 3-CF₃, 5-methyl phenyl-O-CH₂-(pyrrolidin-2-yl) | H |
| 536. | 3-pyridyl | —NH(CH₂)₂— | 3-CF₃, 5-methyl phenyl-O-(azetidin-3-yl) | H |
| 537. | 3-pyridyl | —NH(CH₂)₂— | 3-CF₃, 5-methyl phenyl-CH₂-(4-methylpiperazin-1-yl) | H |
| 538. | 3-pyridyl | —NH(CH₂)₂— | 3-CF₃, 5-methyl phenyl-(CH₂)₃-morpholin-4-yl | H |
| 539. | 4-pyridyl | —NHCH₂— | 3,6-dimethyl-3-(hydroxymethyl)-3H-indole | H |

TABLE 5-continued

| # | R | Y | R¹ | R² |
|---|---|---|---|---|
| 540. | 4-pyrimidinyl | —NHCH₂— | 3-CF₃-5-methyl-phenyl-O-CH₂-(piperidin-4-yl) | H |
| 541. | 4-pyrimidinyl | —NHCH₂— | 3-CF₃-5-methyl-phenyl-O-CH₂-(pyrrolidin-2-yl) | H |
| 542. | 4-pyrimidinyl | —NHCH₂— | 3-CF₃-5-methyl-phenyl-O-(azetidin-3-yl) | H |
| 543. | 4-pyrimidinyl | —NHCH₂— | 3-CF₃-5-methyl-phenyl-O-(piperidin-4-yl) | H |
| 544. | 4-pyrimidinyl | —NHCH₂— | 3-CF₃-5-methyl-phenyl-(CH₂)₃-morpholin-4-yl | H |
| 545. | 4-pyrimidinyl | —NHCH₂— | 3-CF₃-5-methyl-phenyl-(CH₂)₃-piperidin-1-yl | H |
| 546. | 4-pyrimidinyl | —NHCH₂— | 3-CF₃-5-methyl-phenyl-CH₂-(1-methyl-piperidin-4-yl) | H |

TABLE 5-continued

| # | R | Y | R[1] | R[2] |
|---|---|---|---|---|
| 547. | 4-pyrimidinyl | —NHCH$_2$— | 3-CF$_3$-5-methyl-phenyl-CH$_2$-(4-methylpiperazin-1-yl) | H |
| 548. | 4-pyrimidinyl | —NHCH$_2$— | 3-CF$_3$-5-methyl-phenyl-(4-methylpiperazin-1-yl) | H |
| 549. | 4-pyrimidinyl | —NHCH$_2$— | 3-CF$_3$-5-methyl-phenyl-(1-methylpiperidin-4-yl) | H |
| 550. | 4-(2-N(CH$_3$)$_2$)pyridinyl | —NHCH$_2$— | 3-CF$_3$-phenyl | H |
| 551. | 4-(2-N(CH$_3$)$_2$)pyridinyl | —NHCH$_2$— | 3-CF$_3$-5-methyl-phenyl-(1-methylpiperidin-4-yl) | H |
| 552. | 4-(2-N(CH$_3$)$_2$)pyridinyl | —NHCH$_2$— | 3-CF$_3$-5-methyl-phenyl-(4-methylpiperazin-1-yl) | H |
| 553. | 4-(2-N(CH$_3$)$_2$)pyridinyl | —NHCH$_2$— | 3-CF$_3$-5-methyl-phenyl-CH$_2$-(4-methylpiperazin-1-yl) | H |

TABLE 5-continued
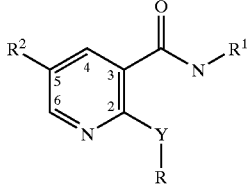
| # | R | Y | R¹ | R² |
|---|---|---|----|----|
| 554. | 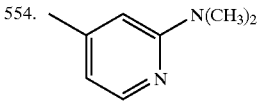 | —NHCH₂— | 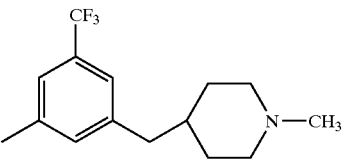 | H |
| 555. | 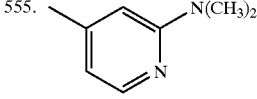 | —NHCH₂— | 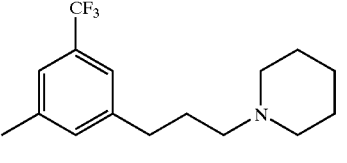 | H |
| 556. | 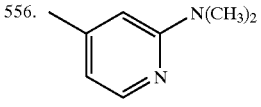 | —NHCH₂— | 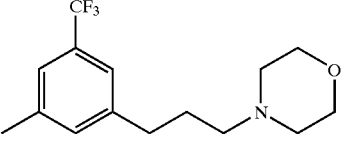 | H |
| 557. | 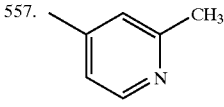 | —NHCH₂— | 3-CF₃-phenyl | H |
| 558. | 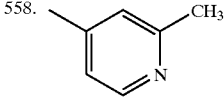 | —NHCH₂— | 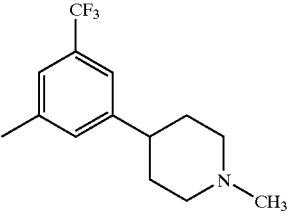 | H |
| 559. | 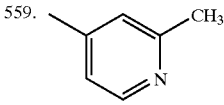 | —NHCH₂— | 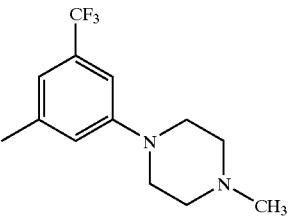 | H |
| 560. | 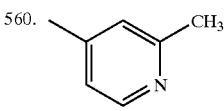 | —NHCH₂— | 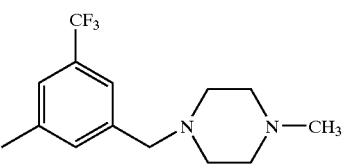 | H |

TABLE 5-continued
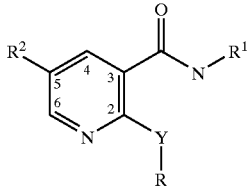
| # | R | Y | R¹ | R² |
|---|---|---|---|---|
| 561. | 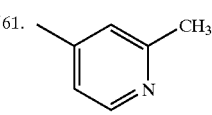 | —NHCH₂— | 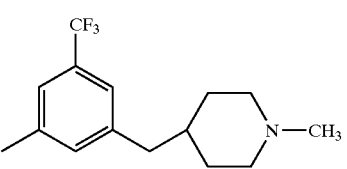 | H |
| 562. | 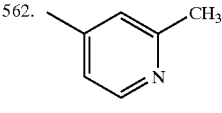 | —NHCH₂— | 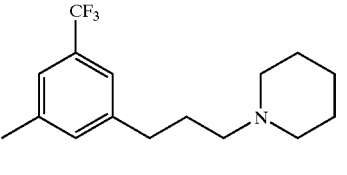 | H |
| 563. | 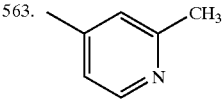 | —NHCH₂— | 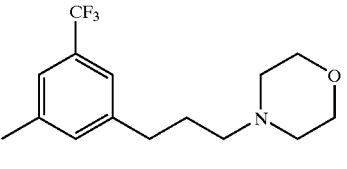 | H |
| 564. | 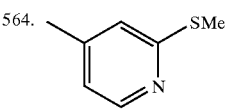 | —NHCH₂— | 3-CF₃-phenyl | H |
| 565. | 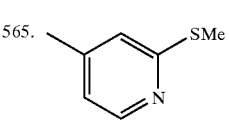 | —NHCH₂— | 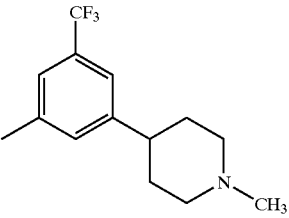 | H |
| 566. | 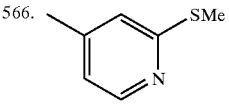 | —NHCH₂— | 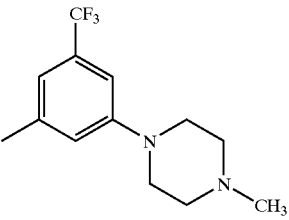 | H |
| 567. | 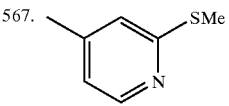 | —NHCH₂— | 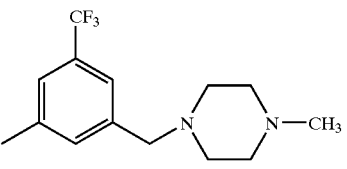 | H |

TABLE 5-continued
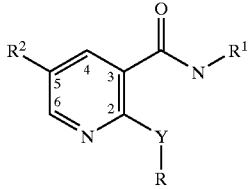
| # | R | Y | R¹ | R² |
|---|---|---|---|---|
| 568. | 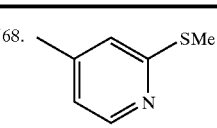 | —NHCH₂— | 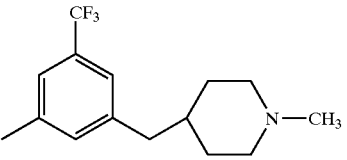 | H |
| 569. | 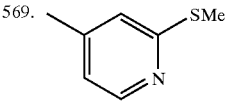 | —NHCH₂— | 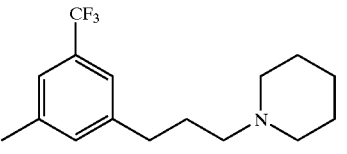 | H |
| 570. | 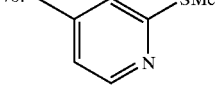 | —NHCH₂— | 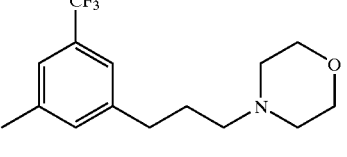 | H |
| 571. | 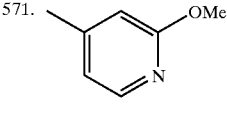 | —NHCH₂— | 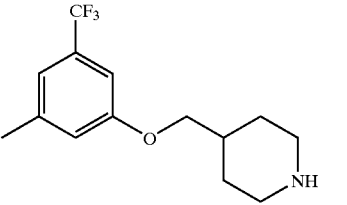 | H |
| 572. | 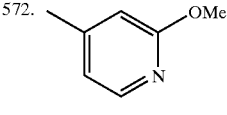 | —NHCH₂— | 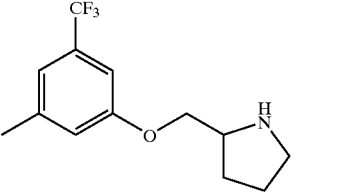 | H |
| 573. | 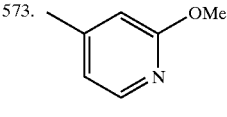 | —NHCH₂— | 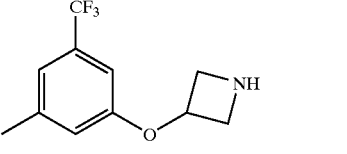 | H |
| 574. | 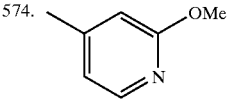 | —NHCH₂— | 3-CF₃-phenyl | H |

TABLE 5-continued
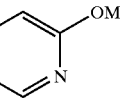
| # | R | Y | R¹ | R² |
|---|---|---|----|----|
| 575. | 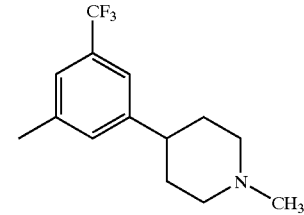 4-methyl-2-methoxypyridinyl | —NHCH₂— | 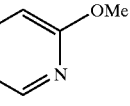 | H |
| 576. | 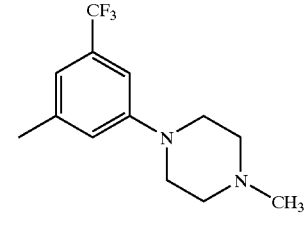 4-methyl-2-methoxypyridinyl | —NHCH₂— | 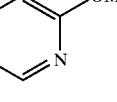 | H |
| 577. | 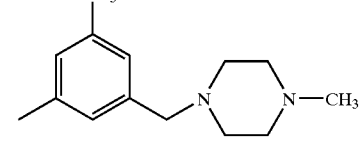 4-methyl-2-methoxypyridinyl | —NHCH₂— | 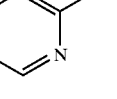 | H |
| 578. | 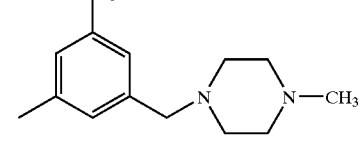 4-methyl-2-methoxypyridinyl | —NHCH₂— | 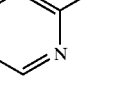 | H |
| 579. | 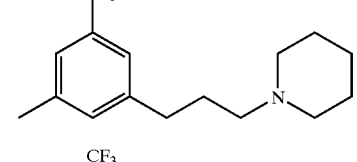 4-methyl-2-methoxypyridinyl | —NHCH₂— | 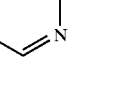 | H |
| 580. | 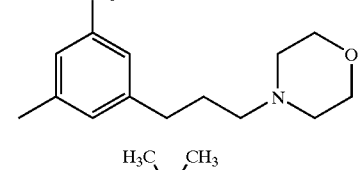 4-methyl-2-methoxypyridinyl | —NHCH₂— | 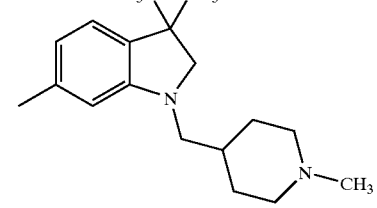 | H |
| 581. | 4-pyrimidinyl | —NHCH₂— | | H |

TABLE 5-continued
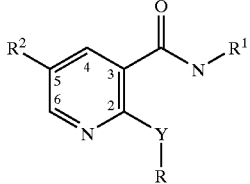
| # | R | Y | R¹ | R² |
|---|---|---|----|----|
| 582. | 4-pyrimidinyl | —NHCH₂— | 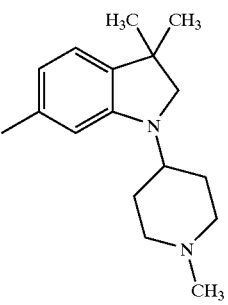 | H |
| 583. | 4-pyrimidinyl | —NHCH₂— | 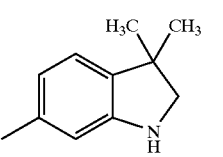 | H |
| 584. | 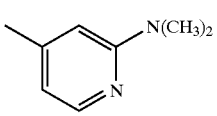 | —NHCH₂— | 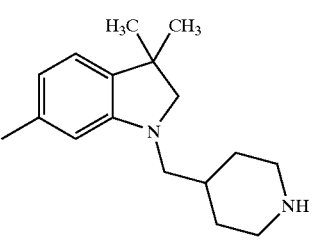 | H |
| 585. | 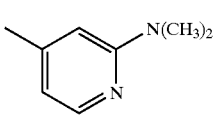 | —NHCH₂— | 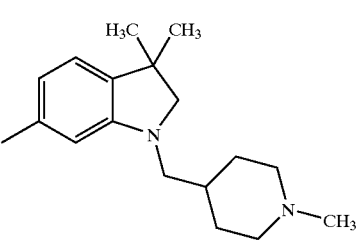 | H |
| 586. | 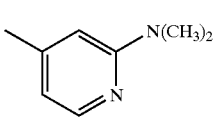 | —NHCH₂— | 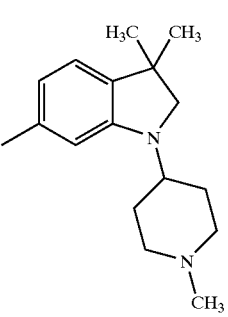 | H |

TABLE 5-continued

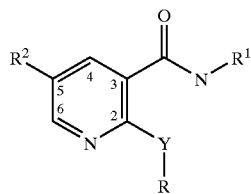

| # | R | Y | R¹ | R² |
|---|---|---|---|---|
| 587. | 4-(2-N(CH₃)₂-pyridyl) | —NHCH₂— | 3,3,6-trimethylindoline | H |
| 588. | 4-(2-methylpyridyl) | —NHCH₂— | 3,3,6-trimethyl-1-(piperidin-4-ylmethyl)indoline | H |
| 589. | 4-(2-methylpyridyl) | —NHCH₂— | 3,3,6-trimethyl-1-((1-methylpiperidin-4-yl)methyl)indoline | H |
| 590. | 4-(2-methylpyridyl) | —NHCH₂— | 3,3,6-trimethyl-1-(1-methylpiperidin-4-yl)indoline | H |
| 591. | 4-(2-methylpyridyl) | —NHCH₂— | 3,3,6-trimethylindoline | H |
| 592. | 4-(2-SMe-pyridyl) | —NHCH₂— | 3,3,6-trimethyl-1-(piperidin-4-ylmethyl)indoline | H |

TABLE 5-continued

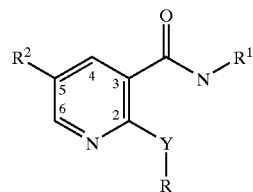

| # | R | Y | R¹ | R² |
|---|---|---|----|----|
| 593. | 4-methyl-2-(SMe)-pyridine | —NHCH₂— | 3,3,6-trimethyl-1-[(1-methylpiperidin-4-yl)methyl]indoline | H |
| 594. | 4-methyl-2-(SMe)-pyridine | —NHCH₂— | 3,3,6-trimethyl-1-(1-methylpiperidin-4-yl)indoline | H |
| 595. | 4-methyl-2-(SMe)-pyridine | —NHCH₂— | 3,3,6-trimethylindoline | H |
| 596. | 4-methyl-2-(OMe)-pyridine | —NHCH₂— | 3,3,6-trimethyl-1-[(1-methylpiperidin-4-yl)methyl]indoline | H |
| 597. | 4-methyl-2-(2-morpholinoethoxy)-pyridine | —NHCH₂— | 3-tert-butyl-5-methyl-1H-pyrazole | H |
| 598. | 4-methyl-2-(2-pyrrolidinoethoxy)-pyridine | —NHCH₂— | 3,3,6-trimethylindoline | H |

TABLE 5-continued
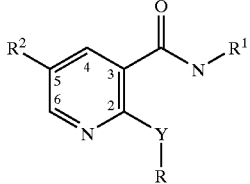
| # | R | Y | R¹ | R² |
|---|---|---|---|---|
| 599. | 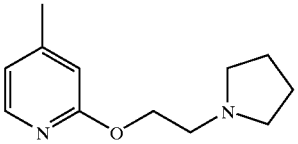 | —NHCH₂— | 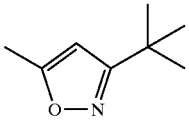 | H |
| 600. | 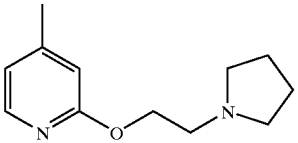 | —NHCH₂— | 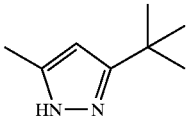 | H |
| 601. | 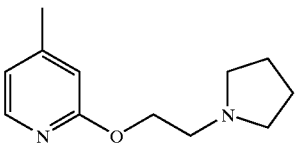 | —NHCH₂— | 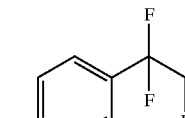 | H |
| 602. | 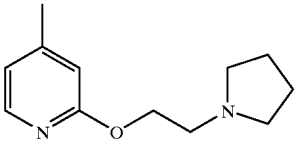 | —NHCH₂— | 3-CF₃-phenyl | H |
| 603. | 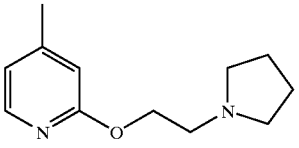 | —NHCH₂— | 4-CF₃-phenyl | H |
| 604. | 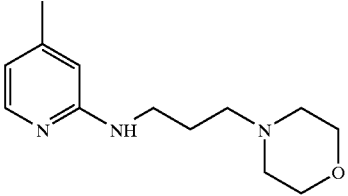 | —NHCH₂— | 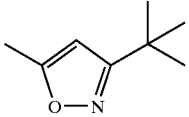 | H |
| 605. | 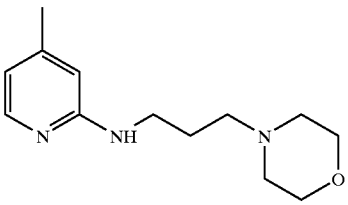 | —NHCH₂— | 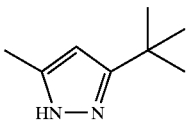 | H |

TABLE 5-continued

| # | R | Y | R¹ | R² |
|---|---|---|---|---|
| 606. | 4-methyl-2-(3-morpholinopropylamino)pyridine | —NHCH₂— | 4-methyl-phenyl-C(F)(F)CF₃ | H |
| 607. | 4-methyl-2-(3-morpholinopropylamino)pyridine | —NHCH₂— | 3-CF₃-phenyl | H |
| 608. | 4-methyl-2-(3-morpholinopropylamino)pyridine | —NHCH₂— | 4-tert-butyl-phenyl | H |
| 609. | 4-methyl-2-(3-morpholinopropylamino)pyridine | —NHCH₂— | 4-CF₃-phenyl | H |
| 610. | 4-methyl-2-(3-morpholinopropoxy)pyridine | —NHCH₂— | 3,3,6-trimethyl-indoline | H |
| 611. | 4-methyl-2-(3-morpholinopropoxy)pyridine | —NHCH₂— | 3-tert-butyl-5-methyl-1H-pyrazole | H |

US 6,878,714 B2

311                                                                                                   312

TABLE 5-continued

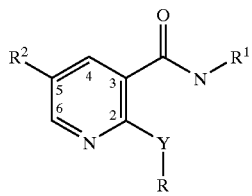

| # | R | Y | R¹ | R² |
|---|---|---|---|---|
| 612. | <br>4-methylpyridin-2-yloxy-propyl-morpholine | —NHCH₂— | 3-CF₃-phenyl | H |
| 613. | <br>4-methylpyridin-2-yloxy-propyl-morpholine | —NHCH₂— | 4-CF₃-phenyl | H |
| 614. | <br>4-methylpyridin-2-yloxy-azetidine | —NHCH₂— | 3,3,6-trimethylindoline | H |
| 615. | <br>4-methylpyridin-2-yloxy-azetidine | —NHCH₂— | 3-tert-butyl-5-methylisoxazole | H |
| 616. | <br>4-methylpyridin-2-yloxy-azetidine | —NHCH₂— | 3-tert-butyl-5-methyl-1H-pyrazole | H |
| 617. | <br>4-methylpyridin-2-yloxy-azetidine | —NHCH₂— | 4-(pentafluoroethyl)-methylphenyl | H |
| 618. | <br>4-methylpyridin-2-yloxy-azetidine | —NHCH₂— | 3-CF₃-phenyl | H |
| 619. | <br>4-methylpyridin-2-yloxy-azetidine | —NHCH₂— | 4-CF₃-phenyl | H |

TABLE 5-continued
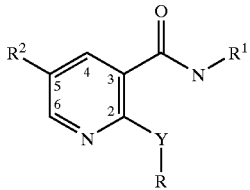
| # | R | Y | R¹ | R² |
|---|---|---|---|---|
| 620. | 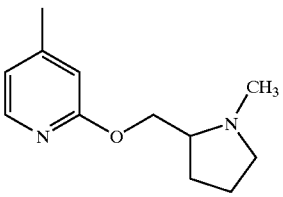 | —NHCH₂— | 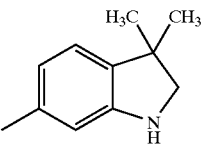 | H |
| 621. | 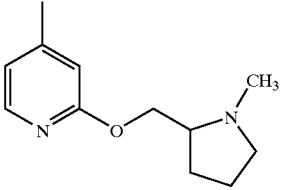 | —NHCH₂— | 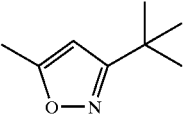 | H |
| 622. | 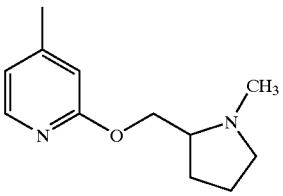 | —NHCH₂— | 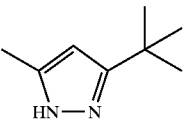 | H |
| 623. | 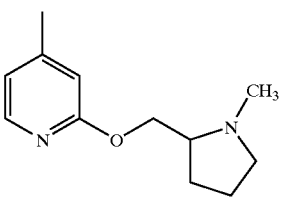 | —NHCH₂— | 3-CF₃-phenyl | H |
| 624. | 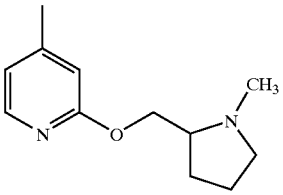 | —NHCH₂— | 4-CF₃-phenyl | H |
| 625. | 4-pyridyl | —NHCH₂— | 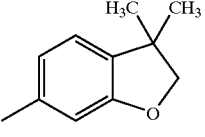 | H |
| 626. | 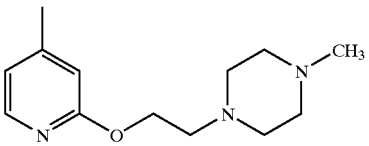 | —NHCH₂— | 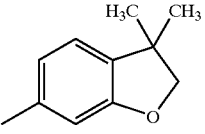 | H |

TABLE 5-continued

| # | R | Y | R¹ | R² |
|---|---|---|----|-----|
| 627. | 4-methylpyridin-2-yl-oxymethyl-(1-methylpiperidin-4-yl) | —NHCH₂— | 3,3,6-trimethyl-2,3-dihydrobenzofuran-5-yl | H |
| 628. | 4-methylpyridin-2-yl-oxy-propyl-(4-methylpiperazin-1-yl) | —NHCH₂— | 3,3,6-trimethyl-2,3-dihydrobenzofuran-5-yl | H |
| 629. | 2-OMe-4-methylpyridine | —NHCH₂— | 3-CF₃-5-methyl-phenyl-C(O)-(4-methylpiperazin-1-yl) | H |
| 630. | 2-CH₃-4-methylpyridine | —NHCH₂— | 3-CF₃-5-methyl-phenyl-C(O)-(4-methylpiperazin-1-yl) | H |
| 631. | 2-SMe-4-methylpyridine | —NHCH₂— | 3-CF₃-5-methyl-phenyl-C(O)-(4-methylpiperazin-1-yl) | H |
| 632. | 2-N(CH₃)₂-4-methylpyridine | —NHCH₂— | 3-CF₃-5-methyl-phenyl-C(O)-(4-methylpiperazin-1-yl) | H |

TABLE 5-continued

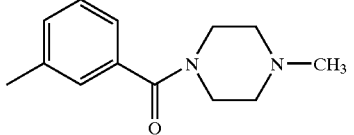

| # | R | Y | R¹ | R² |
|---|---|---|----|----|
| 633. | 3-pyridyl | —NH(CH₂)₂— | 3-CF₃-5-methyl-benzoyl-(4-methylpiperazinyl) | H |
| 634. | 4-pyrimidinyl | —NHCH₂— | 3-CF₃-5-methyl-benzoyl-(4-methylpiperazinyl) | H |
| 635. | 4-pyridyl | —NHCH₂— | 3-CF₃-5-methyl-benzoyl-(4-methylpiperazinyl) | H |

TABLE 6

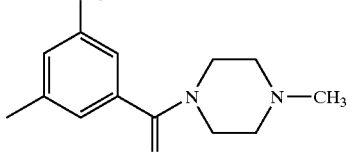

| # | R¹ | n | R² |
|---|----|---|----|
| 636. | 4-chlorophenyl | 1 | 6-F |
| 637. | 3,4-dichlorophenyl | 1 | H |
| 638. | 4-fluorophenyl | 1 | H |
| 639. | 3-chlorophenyl | 1 | H |
| 640. | 3-fluorophenyl | 1 | H |
| 641. | 3-fluoro-4-methoxyphenyl | 1 | H |
| 642. | 3-fluoro-4-methylphenyl | 2 | H |
| 643. | 4-phenoxyphenyl | 1 | H |
| 644. | 3-phenoxyphenyl | 1 | H |
| 645. | 4-biphenyl | 1 | H |
| 646. | 4-cyclohexylphenyl | 1 | H |
| 647. | 2-quinolyl | 1 | H |
| 648. | 3-isoquinolyl | 1 | H |
| 649. | 3-quinolyl | 1 | H |
| 650. | 1-isoquinolyl | 1 | H |

TABLE 6-continued

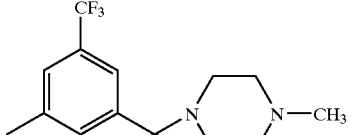

| # | R¹ | n | R² |
|---|----|---|----|
| 651. | 5-quinolyl | 1 | H |
| 652. | 5-isoquinolyl | 1 | H |
| 653. | 6-quinolyl | 1 | H |
| 654. | 6-isoquinolyl | 1 | H |
| 655. | 7-quinolyl | 1 | H |
| 656. | 7-isoquinolyl | 1 | H |
| 657. | 4-quinolyl | 1 | H |
| 658. | 4-isoquinolyl | 1 | H |
| 659. | 4-pyridyl | 1 | 6-F |
| 660. | 4-pyrimidinyl | 1 | H |
| 661. | 2-pyrimidinyl | 1 | H |
| 662. | 6-pyrimidinyl | 1 | H |
| 663. | 4-pyridazinyl | 1 | H |
| 664. | 5-pyridazinyl | 1 | H |
| 665. | 4-indolyl | 1 | H |

TABLE 6-continued

| # | R¹ | n | R² |
|---|---|---|---|
| 666. | 5-isoindolyl | 1 | H |
| 667. | 5-naphthyridinyl | 1 | H |
| 668. | 6-quinozalinyl | 1 | H |
| 669. | 6-isoquinolyl | 1 | H |
| 670. | 4-naphthyridinyl | 1 | H |
| 671. | 5-quinozalinyl | 1 | H |
| 672. | 4-naphthyridinyl | 1 | H |
| 673. | tetrahydroquinolinyl | 1 | H |
| 674. | 6-indazolyl | 1 | H |
| 675. | 6-isoindolyl | 1 | H |
| 676. | 5-indazolyl | 1 | H |
| 677. | 5-isoindolyl | 1 | H |
| 678. | 6-benzothienyl | 1 | H |
| 679. | 6-benzofuryl | 1 | H |
| 680. | 5-benzothienyl | 1 | H |
| 681. | 5-benzofuryl | 1 | H |
| 682. | 2-benzimidazolyl | 1 | H |
| 683. | 2-benzoxazolyl | 1 | H |
| 684. | 2-benzthiazolyl | 1 | H |
| 685. | 6-benzimidazolyl | 1 | H |
| 686. | 6-benzoxazolyl | 1 | H |
| 687. | 6-benzthiazolyl | 1 | H |
| 688. | 2-quinazolinyl | 1 | H |
| 689. | 3-(phenoxy)-6-pyridyl | 1 | H |
| 690. | 4-(phenylcarbonyl)phenyl | 1 | H |
| 691. | 4-(phenylamino)phenyl | 1 | H |
| 692. | cyclohexyloxyphenyl | 1 | H |
| 693. | 4-(3-thienyl)phenyl | 1 | H |
| 694. | 4-(pyrazol-3-yl)phenyl | 1 | 6-CH₃ |

TABLE 7

| # | R¹ | n | R² |
|---|---|---|---|
| 695. | 4-chlorophenyl | 1 | 6-Cl |
| 696. | 3,4-dichlorophenyl | 1 | 5-Cl |
| 697. | 4-fluorophenyl | 1 | H |
| 698. | 3-chlorophenyl | 1 | H |
| 699. | 3-fluorophenyl | 1 | H |
| 700. | 3-fluoro-4-methoxyphenyl | 1 | H |
| 701. | 3-fluoro-4-methylphenyl | 1 | H |
| 702. | 4-phenoxyphenyl | 1 | H |
| 703. | 3-phenoxyphenyl | 1 | H |

TABLE 7-continued

| # | R¹ | n | R² |
|---|---|---|---|
| 704. | 4-biphenyl | 1 | H |
| 705. | 4-cyclohexylphenyl | 1 | H |
| 706. | 2-quinolyl | 1 | H |
| 707. | 3-isoquinolyl | 1 | H |
| 708. | 3-quinolyl | 1 | H |
| 709. | 1-isoquinolyl | 1 | H |
| 710. | 5-quinolyl | 1 | H |
| 711. | 5-isoquinolyl | 1 | H |
| 712. | 6-quinolyl | 1 | H |
| 713. | 6-isoquinolyl | 1 | H |
| 714. | 7-quinolyl | 1 | H |
| 715. | 7-isoquinolyl | 1 | H |
| 716. | 4-quinolyl | 1 | H |
| 717. | 4-isoquinolyl | 1 | H |
| 718. | 4-pyridyl | 1 | H |
| 719. | 4-pyrimidinyl | 1 | H |
| 720. | 2-pyrimidinyl | 1 | H |
| 721. | 6-pyrimidinyl | 1 | H |
| 722. | 4-pyridazinyl | 1 | H |
| 723. | 5-pyridazinyl | 1 | H |
| 724. | 4-indolyl | 1 | H |
| 725. | 5-isoindolyl | 1 | H |
| 726. | 5-naphthyridinyl | 1 | H |
| 727. | 6-quinozalinyl | 1 | H |
| 728. | 6-isoquinolyl | 1 | H |
| 729. | 4-naphthyridinyl | 1 | H |
| 730. | 5-quinozalinyl | 1 | H |
| 731. | 4-naphthyridinyl | 1 | H |
| 732. | tetrahydroquinolinyl | 1 | H |
| 733. | 6-indazolyl | 1 | H |
| 734. | 6-isoindolyl | 1 | H |
| 735. | 5-indazolyl | 1 | H |
| 736. | 5-isoindolyl | 1 | H |
| 737. | 6-benzothienyl | 1 | H |
| 738. | 6-benzofuryl | 1 | H |
| 739. | 5-benzothienyl | 1 | H |
| 740. | 5-benzofuryl | 1 | H |
| 741. | 2-benzimidazolyl | 1 | H |
| 742. | 2-benzoxazolyl | 1 | H |
| 743. | 2-benzthiazolyl | 1 | H |
| 744. | 6-benzimidazolyl | 1 | H |
| 745. | 6-benzoxazolyl | 1 | H |
| 746. | 6-benzthiazolyl6-benzoxazolyl | 1 | H |
| 747. | 2-quinazolinyl6-benzoxazolyl | 1 | H |
| 748. | 3-(phenoxy)-6-pyridyl | 1 | H |
| 749. | 4-(phenylcarbonyl)phenyl | 1 | H |
| 750. | 4-(phenylamino)phenyl | 1 | H |
| 751. | cyclohexyloxyphenyl | 1 | H |
| 752. | 4-(3-thienyl)phenyl | 1 | H |
| 753. | 4-(pyrazol-3-yl)phenyl | 1 | H |
| 754. | 4-chlorophenyl | 1 | EtO₂CCH=CH— |
| 755. | 4-chlorophenyl | 1 | 5-Br |

TABLE 8

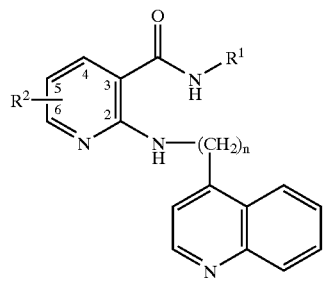

| # | R¹ | n | R² |
|---|---|---|---|
| 756. | 4-pyridyl | 1 | H |
| 757. | 4-pyridyl | 1 | H |
| 758. | 4-chlorophenyl | 1 | 6-F |
| 759. | 3,4-dichlorophenyl- | 1 | 6-CH₃ |
| 760. | 4-fluorophenyl | 1 | H |
| 761. | 3-chlorophenyl | 1 | H |
| 762. | 3-fluorophenyl | 1 | H |
| 763. | 3-fluoro-4-methoxyphenyl | 1 | H |
| 764. | 3-fluoro-4-methylphenyl | 1 | H |
| 765. | 4-phenoxyphenyl | 1 | H |
| 766. | 3-phenoxyphenyl | 1 | H |
| 767. | 4-biphenyl | 1 | H |
| 768. | 4-cyclohexylphenyl | 1 | H |
| 769. | 2-quinolyl | 1 | H |
| 770. | 3-isoquinolyl | 1 | H |
| 771. | 3-quinolyl | 1 | H |
| 772. | 1-isoquinolyl | 1 | H |
| 773. | 5-quinolyl | 1 | H |
| 774. | 5-isoquinolyl | 1 | H |
| 775. | 6-quinolyl | 1 | H |
| 776. | 6-isoquinolyl | 1 | H |
| 777. | 7-quinolyl | 1 | H |
| 778. | 7-isoquinolyl | 1 | H |
| 779. | 4-quinolyl | 1 | H |
| 780. | 4-isoquinolyl | 1 | H |
| 781. | 4-pyridyl | 1 | H |
| 782. | 4-pyrimidinyl | 1 | H |
| 783. | 2-pyrimidinyl | 1 | H |
| 784. | 6-pyrimidinyl | 1 | H |
| 785. | 4-pyridazinyl | 1 | H |
| 786. | 5-pyridazinyl | 1 | H |
| 787. | 4-indolyl | 1 | H |
| 788. | 5-isoindolyl | 1 | H |
| 789. | 5-naphthyridinyl | 1 | H |
| 790. | 6-quinozalinyl | 1 | H |
| 791. | 6-isoquinolyl | 1 | H |
| 792. | 4-naphthyridinyl | 1 | H |
| 793. | 5-quinozalinyl | 1 | H |
| 794. | 4-naphthyridinyl | 1 | H |
| 795. | 7-tetrahydroquinolinyl | 1 | H |
| 796. | 6-indazolyl | 1 | H |
| 797. | 6-isoindolyl | 1 | H |
| 798. | 5-indazolyl | 1 | H |
| 799. | 5-isoindolyl | 1 | H |
| 800. | 6-benzothienyl | 1 | H |
| 801. | 6-benzofuryl | 1 | H |
| 802. | 5-benzothienyl | 1 | H |
| 803. | 5-benzofuryl | 1 | H |
| 804. | 2-benzimidazolyl | 1 | H |
| 805. | 2-benzoxazolyl | 1 | H |
| 806. | 2-benzthiazolyl | 1 | H |
| 807. | 6-benzimidazolyl | 1 | H |
| 808. | 6-benzoxazolyl | 1 | H |
| 809. | 6-benzthiazolyl | 1 | H |
| 810. | 2-quinazolinyl | 1 | H |
| 811. | 3-(phenoxy)-6-pyridyl | 1 | H |
| 812. | 4-(phenylcarbonyl)phenyl | 1 | H |
| 813. | 4-(phenylamino)phenyl | 1 | H |
| 814. | 4-cyclohexyloxyphenyl | 1 | H |
| 815. | 4-(3-thienyl)phenyl | 1 | H |

TABLE 8-continued

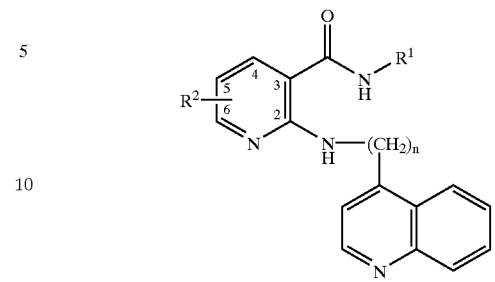

| # | R¹ | n | R² |
|---|---|---|---|
| 816. | 4-(pyrazol-3-yl)phenyl | 1 | H |
| 817. | 3,4-dichlorophenyl | 1 | H |

TABLE 9

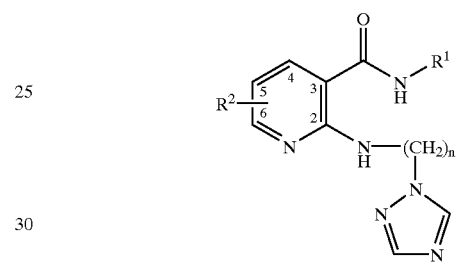

| # | R¹ | n | R² |
|---|---|---|---|
| 818. | 4-chlorophenyl | 1 | 6-F |
| 819. | 3-fluoro-4-methoxyphenyl | 1 | H |
| 820. | 4-phenoxyphenyl | 1 | H |
| 821. | 4-biphenyl | 1 | H |
| 822. | 4-cyclohexylphenyl | 1 | H |
| 823. | 2-quinolyl | 1 | H |
| 824. | 3-isoquinolyl | 1 | H |
| 825. | 3-quinolyl | 1 | H |

EXAMPLE 826

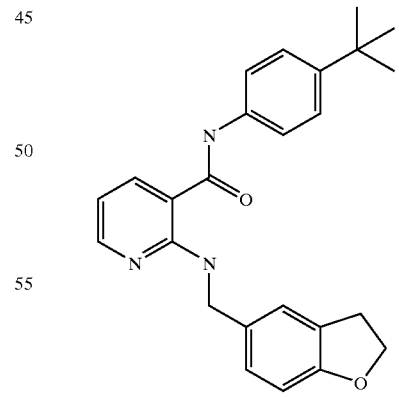

N-[4-(tert-Butyl)phenyl]{2-[(2,3-dihydrobenzo[b]furan-5-ylmethyl)amino](3-pyridyl)}carboxamide The titled compound was prepared from 2,3-dihydrobenzo[b]furan-5-ylmethylamine by the method described in Example 25. MS: (ES+) 402 (M+1)⁺; (ES−): 400 (M−1)⁻. Calc'd. for $C_{25}H_{27}N_3O_2$: 401.21.

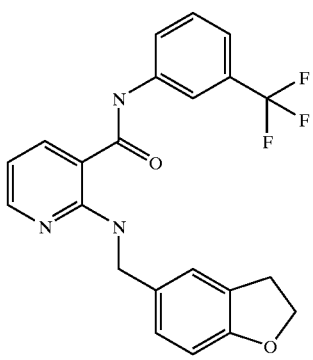

{2-[(2,3-Dihydrobenzo[b]furan-5-ylmethyl)amino](3-pyridyl)}-N-[3-(trifluoromethyl)phenyl] carboxamide The titled compound was prepared from 2,3-dihydrobenzo[b]furan-5-ylmethylamine by the method described in Example 25. MS: (ES+) 414 (M+1)$^+$; (ES−): 412 (M−1)$^-$. Calc'd. for $C_{22}H_{18}F_3N_3O_2$: 413.14.

The following compounds (Examples 828–864) were synthesized by the method described in Example 25 or Example 82 unless specifically described.

TABLE 10

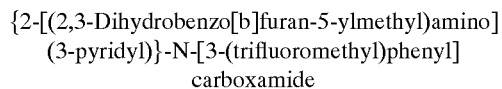

| # | Y | R$^1$ | M + H | calc'd |
|---|---|---|---|---|
| 828. | —NH(CH$_2$)$_2$— | 4-tert-butylphenyl | 375 | 374.2 |
| 829. | —NH(CH$_2$)$_2$— | 4-sec-butylphenyl | 375 | 374.2 |
| 830. | —NH(CH$_2$)$_2$— | 4-phenoxyphenyl | 411 | 410.2 |
| 831. | —NH(CH$_2$)$_2$— | 3-(trifluoromethyl)phenyl | 387 | 386.1 |
| 832. | —NH(CH$_2$)$_2$— | 4-isopropylphenyl | 361 | 360.2 |
| 833. | —NH(CH$_2$)$_2$— | 6-methyl-1-(1-methylpiperidin-4-yl)indolin-yl | 457 | 456.6 |

TABLE 10-continued
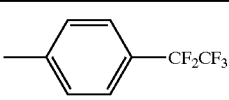
| # | Y | R¹ | M + H | calc'd |
|---|---|---|---|---|
| 834. | —NH(CH$_2$)$_2$— | 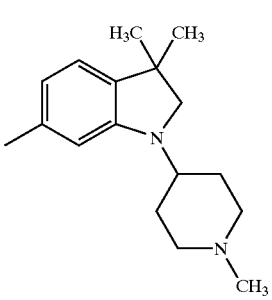 | 437 | 436.4 |
| 835. | —NH(CH$_2$)$_2$— | 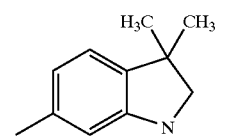 | 485.3 | 484.7 |
| 836. | —NH(CH$_2$)$_2$— | 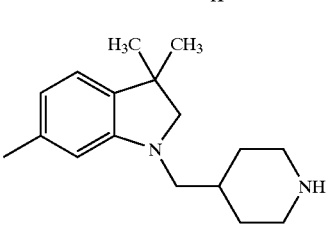 | 388.3 | 387.5 |
| 837. | —NH(CH$_2$)$_2$— | 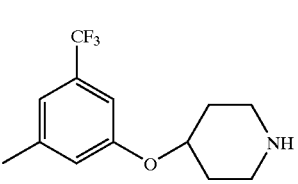 | 485.3 | 484.6 |
| 838. | —NH(CH$_2$)$_2$— | 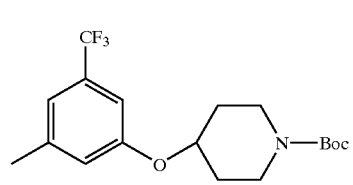 | 486 | 485.5 |
| 839. | —NH(CH$_2$)$_2$— | 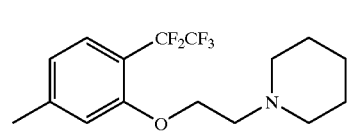 | 586.4 | 585.6 |
| 840. | —NH(CH$_2$)$_2$— | | 564 | 563.6 |

TABLE 10-continued
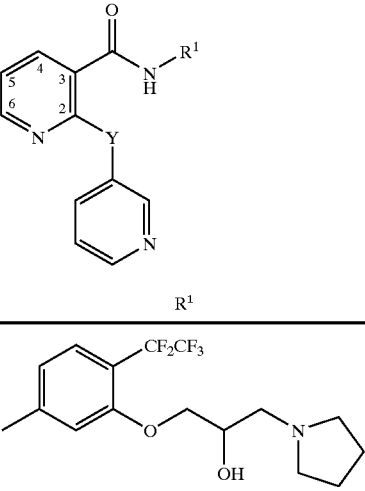
| # | Y | R¹ | M + H | calc'd |
|---|---|----|-------|--------|
| 841. | —NH(CH₂)₂— | 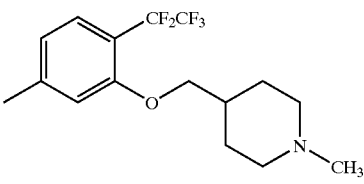 | 580 | 579.6 |
| 842. | —NH(CH₂)₂— | 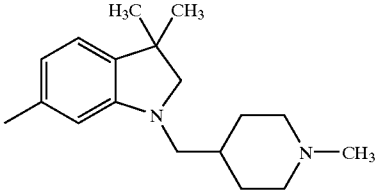 | 564 | 563.6 |
| 843. | —NH(CH₂)₂— | 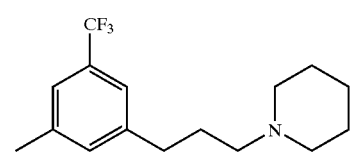 | 499.2 | 498.7 |
| 844. | —NH(CH₂)₂— | 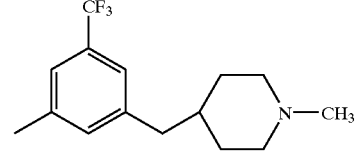 | 512.1 | 511.6 |
| 845. | —NH(CH₂)₂— | 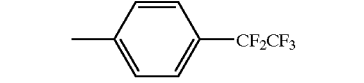 | | 497.6 |
| 846. | —NHCH₂—CH(4-morpholino) | 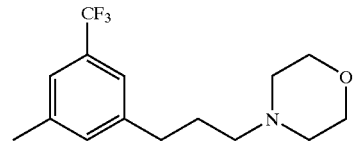 | | 521.5 |
| 847. | —NH(CH₂)₂— | 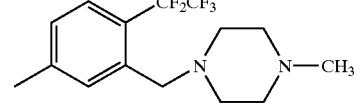 | 514 | 513.6 |
| 848. | —NH(CH₂)₂— | | | 548.6 |

TABLE 10-continued
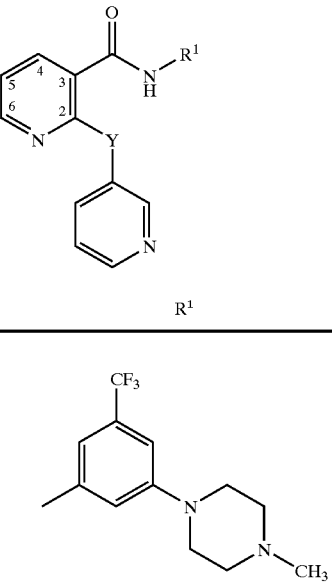
| # | Y | R¹ | M + H | calc'd |
|---|---|---|---|---|
| 849. | —NH(CH₂)₂— | 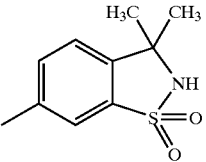 | 484.1 | 483.2 |
| 850. | —NH(CH₂)₂— | 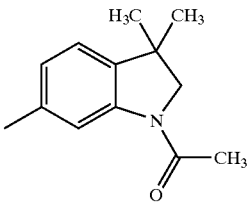 | 438 | 437 |
| 851. | —NH(CH₂)₂— | 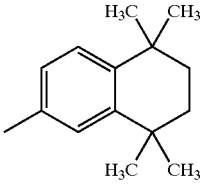 | 430.2 | 429.5 |
| 852. | —NH(CH₂)₂— | 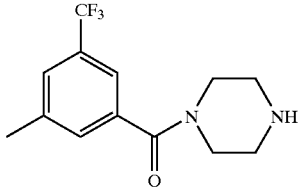 | 429 | 428.6 |
| 853. | —NH(CH₂)₂— | 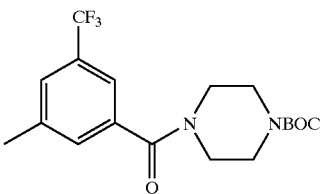 | 498.5 | |
| 854. | —NH(CH₂)₂— | 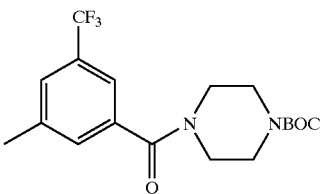 | 599 | 598.6 |

TABLE 10-continued
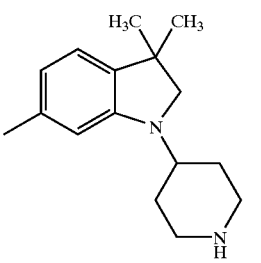
| # | Y | R¹ | M + H | calc'd |
|---|---|---|---|---|
| 855. | —NH(CH₂)₂— | 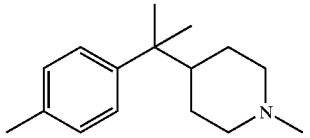 | 471.3 | 470.7 |
| 856. | —NH(CH₂)₂— | 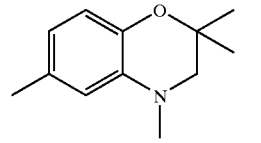 | 458 | 457.3 |
| 857. | —NH(CH₂)₂— | 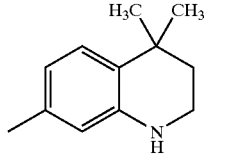 | 418.1 | 417.2 |
| 858. | —NH(CH₂)₂— | 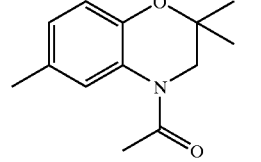 | 402 | 401.1 |
| 859. | —NH(CH₂)₂— | 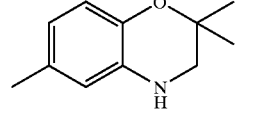 | 445.9 | 445.5 |
| 860. | —NH(CH₂)₂— | 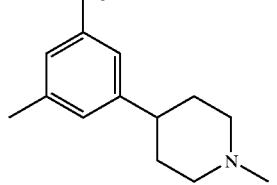 | 432.1 | 431.5 |
| 861. | —NH(CH₂)₂— |  | 472.0 | 471.2 |

TABLE 10-continued

[Structure: pyridine-3-carboxamide with NHR¹ group and 2-Y-linked pyridin-3-yl]

| # | Y | R¹ | M + H | calc'd |
|---|---|---|---|---|
| 862. | —NH(CH₂)₂— | 4,4,7-trimethyl-3,4-dihydroisoquinolin-1(2H)-one | 416.3 | 415.2 |
| 863. | —NH(CH₂)₂— | 3-hydroxy-5-methyl-(trifluoromethyl)phenyl | 403.1 | 402.1 |
| 864. | —NH(CH₂)₂— | 3-(azetidin-3-ylmethoxy)-5-methyl-(trifluoromethyl)phenyl | 472.1 | 471.2 |

EXAMPLE 865

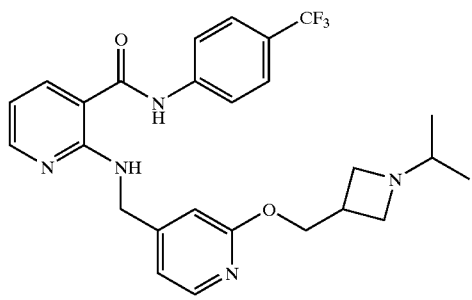

2-{[2-(1-Isopropyl-azetidin-3-ylmethoxy)-pyridin-4-ylmethyl]-amino}-N-(4-trifluoromethyl-phenyl)-nicotinamide A solution of 2-fluoro-N-(4-trifluoromethyl-phenyl)-nicotinamide (107 mg) and [2-(1-isopropyl-azetidin-3-ylmethoxy)-pyridin-4-yl]-methylamine (89 mg) and NaHCO₃ (95 mg) was dissolved in IpOH (10 ml) and heated to 80° C. for 18 h. After cooling to RT, the mixture was diluted with EtOAc (50 ml) forming a precipitate which was filtered. The filtrate was concentrated in vacuo. The residue was purified by silica gel column chromatography (20% (12 N NH₃/MeOH)/EtOAc) to give the product as a light yellow oil. M+H 500.1; Calc'd 499.2.

The following compounds (Example 866–939) were synthesized by the method described above.

866) N-(4-tert-Butyl-phenyl)-2-{[2-(1-isopropyl-azetidin-3-ylmethoxy)-pyridin-4-ylmethyl]-amino}-nicotinamide. M+H 488.1; Calc'd—487.3

867) 2-[(2,3-Dihydro-benzofuran-5-ylmethyl)-amino]-N-{4-[1-methyl-1-(1-methyl-piperidin-4-yl)-ethyl]-phenyl}-nicotinamide. M+H 485.3; Calc'd 484.6.

868) N-(1-Acetyl-3,3-dimethyl-2,3-dihydro-1H-indol-6-yl)-2-[(2,3-dihydro-benzofuran-5-ylmethyl)-amino]-nicotinamide. M+H 457.1; Calc'd 456.5.

869) 2-[(2,3-Dihydro-benzofuran-5-ylmethyl)-amino]-N-[3,3-dimethyl-1-(1-Boc-piperidin-4-ylmethyl)-2,3-dihydro-1H-indol-6-yl]-nicotinamide. M+H 612.6; Calc'd 611.8.

870) 2-[(2,3-Dihydro-benzofuran-5-ylmethyl)-amino]-N-[3,3-dimethyl-1-(1-methylpiperidin-4-ylmethyl)-2,3-dihydro-1H-indol-6-yl]-nicotinamide. M+H 526.3; Calc'd 525.7.

871) N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide. M+H Calc'd 556.

872) 2-({2-[2-(1-Methyl-piperidin-4-yl)-ethoxy]-pyridin-4-ylmethyl}-amino)-N-(3-trifluoromethyl-phenyl)-nicotinamide. M+H Calc'd 513.

873) N-(4-tert-Butyl-phenyl)-2-{[2-ethylpyridin-4-ylmethyl]-amino}-nicotinamide.

874) N-(4-tert-Butyl-phenyl)-2-({2-[2-(1-methyl-pyrrolidin-2-yl)-ethoxy]-pyridin-4-ylmethyl}-amino)-nicotinamide. M+H Calc'd 487.

875) 2-({2-[2-(1-Methyl-pyrrolidin-2-yl)-ethoxy]-pyridin-4-ylmethyl}-amino)-N-(4-pentafluoroethyl-phenyl)-nicotinamide. M+H Calc'd 549.

876) N-(4-Pentafluoroethyl-phenyl)-2-{[2-(2-pyrrolidin-1-yl-ethoxy)-pyridin-4-ylmethyl]-amino}-nicotinamide. M+H Calc'd 535.

877) N-(4-tert-Butyl-phenyl)-2-{[2-(2-pyrrolidin-1-yl-ethoxy)-pyridin-4-ylmethyl]-amino}-nicotinamide. M+H Calc'd 473.

878) N-[3-(4-Boc-piperazin-1-ylmethyl)-5-trifluoromethyl-phenyl]-2-[(pyridin-4-ylmethyl)-amino]-nicotinamide. M+H 571.4; Calc'd 570.3.

879) N-[3-(4-Boc-piperazine-1-carbonyl)-5-trifluoromethyl-phenyl]-2-[(pyridin-4-ylmethyl)-amino]-nicotinamide. M+H Calc'd 584.

880) N-[3-(4-Boc-piperazine-1-carbonyl)-5-trifluoromethyl-phenyl]-2-(2-pyridin-4-yl-ethylamino)-nicotinamide. M+H Calc'd 598.

881) N-[3-(4-Methyl-piperazin-1-ylmethyl)-4-pentafluoroethyl-phenyl]-2-[(pyridin-4-ylmethyl)-amino]-nicotinamide. M+H Calc'd 534.

882) N-[3-(4-Boc-piperazin-1-ylmethyl)-4-pentafluoroethyl-phenyl]-2-[(pyridin-4-ylmethyl)-amino]-nicotinamide. M+H 621.4; Calc'd 620.

883) 2-{[2-(1-Methyl-piperidin-4-ylmethoxy)-pyridin-4-ylmethyl]-amino}-N-(4-trifluoromethyl-phenyl)-nicotinamide.

884) N-(4-tert-Butyl-phenyl)-2-{[2-(1-methyl-piperidin-4-ylmethoxy)-pyridin-4-ylmethyl]-amino}-nicotinamide.

885) 2-({2-[3-(1-Methyl-piperidin-4-yl)-propoxy]-pyridin-4-ylmethyl}-amino)-N-(4-pentafluoroethyl-phenyl)-nicotinamide. M+H 578.3. Calc'd 577.2.

886) N-(1-Acetyl-3,3-dimethyl-2,3-dihydro-1H-indol-6-yl)-2-[(2-methoxy-pyridin-4-ylmethyl)-amino]-nicotinamide.

887) N-[3,3-Dimethyl-1-(1-methyl-piperidin-4-yl)-2,3-dihydro-1H-indol-6-yl]-2-[(2-methoxy-pyridin-4-ylmethyl)-amino]-nicotinamide. M+H 501.2; Calc'd 500.3.

888) N-(1-Boc-3,3-dimethyl-2,3-dihydro-1H-indol-6-yl)-2-[(2-methoxy-pyridin-4-ylmethyl)-amino]-nicotinamide.

889) N-[3,3-Dimethyl-1-(1-Boc-piperidin-4-ylmethyl)-2,3-dihydro-1H-indol-6-yl]-2-[(2-methoxy-pyridin-4-ylmethyl)-amino]-nicotinamide. M+H 601.6; Calc'd 600.34.

890) N-[3,3-Dimethyl-1-(1-methyl-piperidin-4-yl)-2,3-dihydro-1H-indol-6-yl]-2-[(pyridin-4-ylmethyl)-amino]-nicotinamide.

891) N-[1-(2-Dimethylamino-acetyl)-3,3-dimethyl-2,3-dihydro-1H-indol-6-yl]-2-[(2-methoxy-pyridin-4-ylmethyl)-amino]-nicotinamide.

892) N-[1-(2-Dimethylamino-acetyl)-3,3-dimethyl-2,3-dihydro-1H-indol-6-yl]-2-[(pyridin-4-ylmethyl)-amino]-nicotinamide.

893) 2-[(2-Methoxy-pyridin-4-ylmethyl)-amino]-N-[3-{1-Boc-piperidin-4-ylmethoxy)-5-trifluoromethyl-phenyl]-nicotinamide 894) N-[3,3-Dimethyl-1-(1-Boc-pyrrolidin-2-ylmethoxy)-2,3-dihydro-1H-indol-6-yl]-2-[(2-methoxy-pyridin-4-ylmethyl)-amino]-nicotinamide.

895) N-[3,3-Dimethyl-1-(2-Boc-amino-acetyl)-2,3-dihydro-1H-indol-6-yl]-2-[(2-methoxy-pyridin-4-ylmethyl)-amino]-nicotinamide.

896) N-[3,3-Dimethyl-1-(2-Boc-amino-acetyl)-2,3-dihydro-1H-indol-6-yl]-2-[(pyridin-4-ylmethyl)-amino]-nicotinamide.

897) 2-[(2-Methoxy-pyridin-4-ylmethyl)-amino]-N-[3-(1-methyl-pyrrolidin-2-ylmethoxy)-5-trifluoromethyl-phenyl]-nicotinamide. M+H 516.1.

898) 2-[(2-Methoxy-pyridin-4-ylmethyl)-amino]-N-[3-(1-Boc-piperidin-4-ylmethyl)-5-trifluoromethyl-phenyl]-nicotinamide. M+H 501.3.

899) 2-[(2-Methoxy-pyridin-4-ylmethyl)-amino]-N-[3-(4-Boc-piperazin-1-ylmethyl)-5-trifluoromethyl-phenyl]-nicotinamide.

900) 2-{[2-(3-Morpholin-4-yl-propoxy)-pyridin-4-ylmethyl]-amino}-N-(4-pentafluoroethyl-phenyl)-nicotinamide. M+H 566.

901) (S) 2-{[2-(1-Methyl-pyrrolidin-2-ylmethoxy)-pyridin-4-ylmethyl]-amino}-N-(4-pentafluoroethyl-phenyl)-nicotinamide. M+H 536.

902) N-(3-tert-Butyl-isoxazol-5-yl)-2-{[2-(3-morpholin-4-yl-propoxy)-pyridin-4-ylmethyl]-amino}-nicotinamide. M+H 495. Calc'd 494.

903) N-(1-Acetyl-3,3-dimethyl-2,3-dihydro-1H-indol-6-yl)-2-{[2-(3-morpholin-4-yl-propylamino)-pyridin-4-ylmethyl]-amino}-nicotinamide. M+H 558; Calc'd 557.

904) N-(4-tert-Butyl-phenyl)-2-{[2-(3-morpholin-4-yl-propoxy)-pyridin-4-ylmethyl]-amino}-nicotinamide. M+H 504. Calc'd 503.

905) N-(4-tert-Butyl-phenyl)-2-{[2-(2-morpholin-4-yl-ethoxy)-pyridin-4-ylmethyl]-amino}-nicotinamide. M+H 409; Calc'd 489.

906) 2-{[2-(2-Morpholin-4-yl-ethoxy)-pyridin-4-ylmethyl]-amino}-N-(4-trifluoromethyl-phenyl)-nicotinamide. M+H 502; Calc'd 501.

907) 2-{[2-(2-Morpholin-4-yl-ethoxy)-pyridin-4-ylmethyl]-amino}-N-(3-trifluoromethyl-phenyl)-nicotinamide. M+H 502; Calc'd 501.

908) 2-{[2-(2-Morpholin-4-yl-ethoxy)-pyridin-4-ylmethyl]-amino}-N-(4-pentafluoroethyl-phenyl)-nicotinamide. M+H 552; Calc'd 551.

909) N-(3-tert-Butyl-isoxazol-5-yl)-2-{[2-(2-morpholin-4-yl-ethoxy)-pyridin-4-ylmethyl]-amino}-nicotinamide. M+H 481; Calc'd 480.

910) N-(1-Acetyl-3,3-dimethyl-2,3-dihydro-1H-indol-6-yl)-2-{[2-(2-morpholin-4-yl-ethoxy)-pyridin-4-ylmethyl]-amino}-nicotinamide. M+H 545; Calc'd 544.

911) N-(1-Acetyl-3,3-dimethyl-2,3-dihydro-1H-indol-6-yl)-2-{[2-(1-methyl-piperidin-4-yloxy)-pyridin-4-ylmethyl]-amino}-nicotinamide.

912) 2-{[2-(1-Methyl-piperidin-4-yloxy)-pyridin-4-ylmethyl]-amino}-N-(4-trifluoromethyl-phenyl)-nicotinamide.

913) 2-{[2-(1-Methyl-piperidin-4-yloxy)-pyridin-4-ylmethyl]-amino}-N-(4-pentafluoroethyl-phenyl)-nicotinamide.

914) 2-{[2-(1-Methyl-piperidin-4-yloxy)-pyridin-4-ylmethyl]-amino}-N-(4-tert-butyl-phenyl)-nicotinamide.

915) (R) N-(4-tert-Butyl-phenyl)-2-{[2-(1-methyl-pyrrolidin-2-ylmethoxy)-pyridin-4-ylmethyl]-amino}-nicotinamide. M+H 474; Calc'd 473.

916) (R) N-[3-(1-Boc-pyrrolidin-2-ylmethoxy)-5-trifluoromethyl-phenyl]-2-[(pyridin-4-ylmethyl)-amino]-nicotinamide.

917) (R) N-[3-(1-Methyl-pyrrolidin-2-ylmethoxy)-5-trifluoromethyl-phenyl]-2-[(pyridin-4-ylmethyl)-amino]-nicotinamide. M+H 486; Calc'd 485.5.

918) N-[3-(1-Methyl-piperidin-4-yloxy)-5-trifluoromethyl-phenyl]-2-[(pyridin-4-ylmethyl)-amino]-nicotinamide.

919) N-[3-(1-Methyl-piperidin-4-ylmethyl)-5-trifluoromethyl-phenyl]-2-[(pyridin-4-ylmethyl)-amino]-nicotinamide.

920) N-[4-tert-Butyl-3-(1-Boc-pyrrolidin-2-ylmethoxy)-phenyl]-2-[(pyridin-4-ylmethyl)-amino]-nicotinamide. M+H 560; Calc'd 559.
921) N-(3,3-Dimethyl-2,3-dihydro-benzofuran-6-yl)-2-{[2-(1-methyl-piperidin-4-ylmethoxy)-pyridin-4-ylmethyl]-amino}-nicotinamide.
922) 2-({2-[3-(1-Methyl-piperidin-4-yl)-propoxy]-pyridin-4-ylmethyl}-amino)-N-(4-trifluoromethyl-phenyl)-nicotinamide.
923) 2-({2-[3-(1-Methyl-piperidin-4-yl)-propoxy]-pyridin-4-ylmethyl}-amino)-N-(3-trifluoromethyl-phenyl)-nicotinamide.
924) 2-({2-[3-(1-Methyl-piperidin-4-yl)-propoxy]-pyridin-4-ylmethyl}-amino)-N-(4-tert-butyl-phenyl)-nicotinamide.
925) 2-({2-[3-(1-Methyl-piperidin-4-yl)-propoxy]-pyridin-4-ylmethyl}-amino)-N-(3-tert-butyl-isoxazol-5-yl)-nicotinamide.
926) N-(3,3-Dimethyl-2,3-dihydro-1H-indol-6-yl)-2-({2-[3-(1-methyl-piperidin-4-yl)-propoxy]-pyridin-4-ylmethyl}-amino)-nicotinamide.
927) 2-[(Pyridin-4-ylmethyl)-amino]-N-(3,9,9-trimethyl-2,3,4,4a,9,9a-hexahydro-1H-3-aza-fluoren-6-yl)-nicotinamide.
928) N-[3,3-Dimethyl-1-(1-Boc-piperidin-4-ylmethyl)-2,3-dihydro-1H-indol-6-yl]-2-[(pyridin-4-ylmethyl)-amino]-nicotinamide.
929) N-[3,3-Dimethyl-1-(1-methyl-piperidin-4-ylmethyl)-2,3-dihydro-1H-indol-6-yl]-2-[(pyridin-4-ylmethyl)-amino]-nicotinamide. M+H 485.3; Calc'd 484.6.

The following compounds (Example 930–937) were synthesized by the method described above, substituting $K_2CO_3$ for $NaHCO_3$.

930) 2-{[2-(1-Methyl-piperidin-4-ylmethoxy)-pyridin-4-ylmethyl]-amino}-N-(4-pentafluoroethyl-phenyl)-nicotinamide. M+H 550.2; Calc'd 549.2.
932) N-(1-Acetyl-3,3-dimethyl-2,3-dihydro-1H-indol-6-yl)-2-{[2-(1-methyl-piperidin-4-ylmethoxy)-pyridin-4-ylmethyl]-amino}-nicotinamide. M+H 543.4; Calc'd 542.3.
933) N-(4-tert-Butyl-phenyl)-2-{[2-(3-morpholin-4-yl-propylamino)-pyrimidin-4-ylmethyl]-amino}-nicotinamide. M+H 504.3; Calc'd 503.6.
934) 2-{[2-(3-Morpholin-4-yl-propylamino)-pyrimidin-4-ylmethyl]-amino}-N-(4-pentafluoroethyl-phenyl)-nicotinamide. M+H 566.3; Calc'd 565.55.
935) 2-{[2-(3-Morpholin-4-yl-propylamino)-pyrimidin-4-ylmethyl]-amino}-N-(3-trifluoromethyl-phenyl)-nicotinamide. M+H 516.0; Calc'd 515.5.
936) N-(4-tert-Butyl-phenyl)-2-({2-[2-(1-methyl-pyrrolidin-2-yl)-ethylamino]-pyrimidin-4-ylmethyl}-amino)-nicotinamide. M+H Calc'd 487.6.
937) N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H Calc'd 542.69.

The following compounds (Example 938–939) were synthesized by the method described above, substituting $Cs_2CO_3$ for $NaHCO_3$.

938) 2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide. M H 597.0; Calc'd 596.7.
939) N-(3-tert-Butyl-isoxazol-5-yl)-2-{[2-(1-methyl-piperidin--4-ylmethoxy)-pyridin-4-ylmethyl]-amino}-nicotinamide. M+H 479; Calc'd 478.3.

The following compounds (Example 940–945) were synthesized by the method described above, substituting t-BuOH for IpOH.

940) N-[3-(1-Boc-azetidin-3-ylmethoxy)-5-trifluoromethyl-phenyl]-2-[(pyridin-4-ylmethyl)-amino]-nicotinamide. M+H 558.1. Calc'd 557.6.
941) 2-[(2-Methoxy-pyridin-4-ylmethyl)-amino]-N-[3-(1-Boc-azetidin-3-ylmethoxy)-5-trifluoromethyl-phenyl]-nicotinamide. M+H 588.1. Calc'd 587.2.
942) 2-[(Pyridin-4-ylmethyl)-amino]-N-(2,2,4-trimethyl-3,4-dihydro-2H-benzo[1,4]oxazin-6-yl)-nicotinamide. M+H 404.5; Calc'd 403.2.
943) N-(4-Acetyl-2,2-dimethyl-3,4-dihydro-2H-benzo[1,4]oxazin-6-yl)-2-[(pyridin-4-ylmethyl)-amino]-nicotinamide. M+H 432.1; Calc'd 431.5.
944) N-(2,2-Dimethyl-3-oxo-3,4-dihydro-2H-benzo[1,4]oxazin-6-yl)-2-[(pyridin-4-ylmethyl)-amino]-nicotinamide. M+H 404.5; Calc'd 403.2.
945) 2-{[2-(1-Benzhydryl-azetidin-3-yloxy)-pyridin-4-ylmethyl]-amino}-N-(4-tert-butyl-phenyl)-nicotinamide. M+H 598.4; Calc'd 597.3.

The following compounds (Example 946–993) were synthesized by the method described above, unless specifically described.

946) N-(4,4-Dimethyl-1-oxo-1,2,3,4-tetrahydro-isoquinolin-7-yl)-2-[(pyridin-4-ylmethyl)-amino]-nicotinamide was prepared with MeOH as the solvent at 110° C. M+H 402.3.
947) N-(4-tert-Butyl-phenyl)-2-({2-[2-(1-methyl-piperidin-4-yl)-ethoxy]-pyridin-4-ylmethyl}-amino)-nicotinamide was prepared with pentanol at 95° C. M+H Calc'd 501.
948) N-(3-tert-Butyl-isoxazol-5-yl)-2-({2-[2-(1-methyl-piperidin-4-yl)-ethoxy]-pyridin-4-ylmethyl}-amino)-nicotinamide was prepared with pyridine at 95° C. M+H Calc'd 492.
949) N-(3-trifluoromethylphenyl)-2-({2-[2-(1-methyl-piperidin-4-yl)-ethoxy]-pyridin-4-ylmethyl}-amino)-nicotinamide was prepared with pyridine at 95° C. M+H Calc'd 513.
950) 2-[(2,3-Dihydro-benzofuran-6-ylmethyl)-amino]-N-[3-(1-Boc-pyrrolidin-2-ylmethoxy)-4-pentafluoroethyl-phenyl]-nicotinamide was prepared with DIEA at 120° C. M+H 663.4; Calc'd 662.6.
951) (R) N-[3-(2-Hydroxy-3-pyrrolidin-1-yl-propoxy)-4-pentafluoroethyl-phenyl]-2-[(pyridin-4-ylmethyl)-amino]-nicotinamide was prepared with IpOH as the solvent at 135° C. M+H 566.5; Calc'd 565.5.
952) (S) N-[3-(2-Hydroxy-3-pyrrolidin-1-yl-propoxy)-4-pentafluoroethyl-phenyl]-2-[(pyridin-4-ylmethyl)-amino]-nicotinamide was prepared with IpOH as the solvent at 135° C. M+H 566.5; Calc'd 565.5.
953) N-[4-tert-Butyl-3-(1-methyl-piperidin-4-ylmethoxy)-phenyl]-2-[(pyridin-4-ylmethyl)-amino]-nicotinamide was prepared with IpOH as the solvent at 130° C. M+H 488.3; Calc'd 487.6.
954) N-[3-(1-Methyl-piperidin-4-ylmethoxy)-4-pentafluoroethyl-phenyl]-2-[(pyridin-4-ylmethyl)-amino]-nicotinamide was prepared with IpOH as the solvent at 135° C. M+H 550.2; Calc'd 549.5.
955) N-[4-Pentafluoroethyl-3-(2-piperidin-1-yl-ethoxy)-phenyl]-2-[(pyridin-4-ylmethyl)-amino]-nicotinamide was prepared with IpOH as the solvent at 130° C. M+H 550.1; Calc'd 549.5.
956) N-[4-Trifluoromethyl-3-(2-piperidin-1-yl-ethoxy)-phenyl]-2-[(pyridin-4-ylmethyl)-amino]-nicotinamide was prepared with IpOH as the solvent at 130° C. M+H 486.3; Calc'd 485.5.

957) (S) N-[3-(1-Boc-pyrrolidin-2-ylmethoxy)-4-pentafluoroethyl-phenyl]-2-[(pyridin-4-ylmethyl)-amino]-nicotinamide was prepared with DIEA at 135° C. M+H 572. Calc'd 571.6.

958) (R) N-[3-(1-Boc-pyrrolidin-2-ylmethoxy)-4-trifluoromethyl-phenyl]-2-[(pyridin-4-ylmethyl)-amino]-nicotinamide was prepared with DIEA at 130° C. M+H 622. Calc'd 621.6.

959) (R) N-[3-(1-Boc-pyrrolidin-2-ylmethoxy)-4-pentafluoroethyl-phenyl]-2-[(pyridin-4-ylmethyl)-amino]-nicotinamide was prepared with DIEA at 130° C. M+H 622.4. Calc'd 621.6.

960) N-(4-tert-Butyl-phenyl)-2-{[2-(1-methyl-piperidin-4-yloxy)-pyridin-4-ylmethyl]-amino}-nicotinamide was prepared with pyridine and TEA at 90° C. M+H 474.

961) N-(3-Trifluoromethyl-phenyl)-2-{[2-(1-methyl-piperidin-4-yloxy)-pyridin-4-ylmethyl]-amino}-nicotinamide was prepared with pyridine and TEA at 90° C. M+H 486.

962) N-(3-tert-Butyl-isoxazol-5-yl)-2-{[2-(1-methyl-piperidin-4-yloxy)-pyridin-4-ylmethyl]-amino}-nicotinamide was prepared with pyridine and TEA at 90° C. M+H 465.

963) N-[3-(3-Piperidin-1-yl-propyl)-5-trifluoromethyl-phenyl]-2-[(pyridin-4-ylmethyl)-amino]-nicotinamide was prepared with pyridine at 90° C. M+H 498; Calc'd 497.6.

964) N-[3-(3-Morpholin-4-yl-propyl)-5-trifluoromethyl-phenyl]-2-[(pyridin-4-ylmethyl)-amino]-nicotinamide was prepared at 130° C. neat. M+H 500. Calc'd 499.2.

965) 2-[(2-Methoxy-pyridin-4-ylmethyl)-amino]-N-[3-(1-Boc-piperidin-4-yloxy)-5-trifluoromethyl-phenyl]-nicotinamide was prepared at 130° C. neat. M+H 602. Calc'd for $C_{30}H_{34}F_3N_5O_5$: 601.6.

967) N-{4-tert-Butyl-3-[2-(1-Boc-piperidin-4-yl)-ethoxy]-phenyl}-2-[(pyridin-4-ylmethyl)-amino]-nicotinamide was prepared with DIEA and IpOH at 130° C. M+H 574.6.

968) N-[4-tert-Butyl-3-(1-methyl-azetidin-3-ylmethoxy)-phenyl]-2-[(pyridin-4-ylmethyl)-amino]-nicotinamide was prepared with IpOH and DIEA at 130° C. M+H 546.

969) N-(3,3-Dimethyl-1,1-dioxo-2,3-dihydro-1H-1λ-benzo[d]isothiazol-6-yl)-2-[(pyridin-4-ylmethyl)-amino]-nicotinamide was prepared neat at 130° C. M+H 424; Calc'd 423.

970) N-[1,1,4,4-Tetramethyl-1,2,3,4-tetrahydro-naphth-6-yl]-2-[(pyridin-4-ylmethyl)-amino]-nicotinamide was prepared neat at 130° C. M+H 415; Calc'd 414.

971) N-{4-[1-Methyl-1-(1-methyl-piperidin-4-yl)-ethyl]-phenyl}-2-[(pyridin-4-ylmethyl)-amino]-nicotinamide was prepared with pyridine. M+H 444; Calc'd 443.27.

972) 2-[(2-Methoxy-pyridin-4-ylmethyl)-amino]-N-{4-[1-methyl-1-(1-methyl-piperidin-4-yl)-ethyl]-phenyl}-nicotinamide was prepared with pyridine and NaHCO$_3$ at 110° C. MS: 473 (M+H), Calc'd for $C_{28}H_{35}N_5O_2$—472.6.

973) N-(3,3-Dimethyl-2,3-dihydro-benzofuran-6-yl)-2-[(pyridin-4-ylmethyl)-amino]-nicotinamide was prepared with IpOH at 120° C. M+H 375. Calc'd for $C_{27}H_{32}N_6O$: 374.

974) 2-{[2-(3-Dimethylamino-propoxy)-pyridin-4-ylmethyl]-amino}-N-(4-pentafluoroethyl-phenyl)-nicotinamide. M+H 524; Calc'd 523.2.

975) N-[3-(1-Methyl-piperidin-4-yl)-5-trifluoromethyl-phenyl]-2-[(pyridin-4-ylmethyl)-amino]-nicotinamide. M+H 470.4; Calc'd 469.21.

976) 2-{[2-(1-Methyl-piperidin-4-ylmethoxy)-pyridin-4-ylmethyl]-amino}-N-[3-(1-methyl-piperidin-4-yl)-5-trifluoromethyl-phenyl]-nicotinamide. M+H 597.0; Calc'd 596.31.

977) N-[3-(azetidin-3-ylmethoxy)-5-trifluoromethyl-phenyl]-2-[(pyridin-4-ylmethyl)-amino]-nicotinamide. M+H 458.1; Calc'd 457.2.

978) N-(3-Hydroxy-5-trifluoromethyl-phenyl)-2-[(pyridin-4-ylmethyl)-amino]-nicotinamide. M+H 388.9; Calc'd 388.11.

979) N-(2-Acetyl-4,4-dimethyl-1,2,3,4-tetrahydro-isoquinolin-7-yl)-2-[(pyridin-4-ylmethyl)-amino]-nicotinamide. M+H 430; Calc'd 429.22.

980) N-[2-(4-methoxy-benzyl)-4,4-dimethyl-1-oxo-1,2,3,4-tetrahydro-isoquinolin-7-yl]-2-[(pyridin-4-ylmethyl)-amino]-nicotinamide. M+H 522.3; Calc'd 521.24.

981) N-(2-Acetyl-4,4-dimethyl-1,2,3,4-tetrahydro-isoquinolin-7-yl)-2-[(quinolin-4-ylmethyl)-amino]-benzamide. M+H 479; Calc'd 478.24.

982) 2-[(Pyridin-4-ylmethyl)-amino]-N-[3-(2-pyrrolidin-1-yl-ethoxy)-4-trifluoromethyl-phenyl]-nicotinamide. M+H 486; Calc'd 485.

983) 2-{[2-(1-Methyl-piperidin-4-ylmethoxy)-pyridin-4-ylmethyl]-amino}-N-(3-trifluoromethyl-phenyl)-nicotinamide. M+H 500.5; Calc'd 499.5.

984) N-[3-(1-Boc-azetidin-3-ylmethoxy)-4-tert-butyl-phenyl]-2-[(pyridin-4-ylmethyl)-amino]-nicotinamide. M+H 546. Calc'd 545.

985) 2-Methyl-2-[4-({2-[(pyridin-4-ylmethyl)-amino]-pyridine-3-carbonyl}-amino)-phenyl]-propionic acid methyl ester. M+H 405; Calc'd 404.

986) N-(4-tert-Butyl-phenyl)-2-{[2-(3-morpholin-4-yl-propylamino)-pyrimidin-4-ylmethyl]-amino}-nicotinamide. M+H 504.3; Calc'd 503.

987) N-(4-pentafluoroethyl-phenyl)-2-{[2-(3-morpholin-4-yl-propylamino)-pyrimidin-4-ylmethyl]-amino}-nicotinamide. M+H 566.3; Calc'd 565.

988) N-(4-trifluoromethyl-phenyl)-2-{[2-(3-morpholin-4-yl-propylamino)-pyrimidin-4-ylmethyl]-amino}-nicotinamide. M+H 516.0; Calc'd 515.

989) N-(4-tert-Butyl-phenyl)-2-({2-[2-(1-methyl-pyrrolidin-2-yl)-ethylamino]-pyrimidin-4-ylmethyl}-amino)-nicotinamide. M+H 488.4; Calc'd 487.

990) N-(1-Acetyl-3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H 543.5; Calc'd 542.

991) N-(1-Acetyl-3,3-dimethyl-2,3-dihydro-1H-indol-6-yl)-2-(2,3-dihydro-benzo[1,4]dioxin-6-ylamino)-nicotinamide. M+H 459.3.

992) 2-({2-[2-(1-Methyl-pyrrolidin-2-yl)-ethylamino]-pyrimidin-4-ylmethyl}-amino)-N-(3-trifluoromethyl-phenyl)-nicotinamide. M+H 500.4; Calc'd 499.

EXAMPLE 993

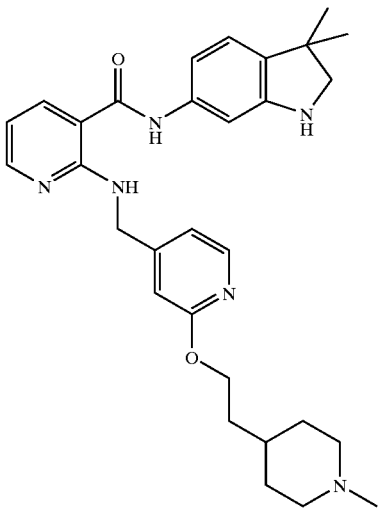

N-(3,3-Dimethyl-2,3-dihydro-1H-indol-6-yl)-2-({2-[2-(1-methyl-piperidin-4-yl)-ethoxy]-pyridin-4-ylmethyl}-amino)-nicotinamide N-(1-Acetyl-3,3-dimethyl-2,3-dihydro-1H-indol-6-yl)-2-({2-[2-(1-methyl-piperidin-4-yl)-ethoxy]-pyridin-4-ylmethyl}-amino)-nicotinamide (300 mg, Example 871) was dissolved in conc. HCl (20 ml) and EtOH (20 ML) and heated at 70° C. for 4 H. The mixture was concentrated and the residue was diluted with sat'd NaHCO$_3$ and CH$_2$Cl$_2$. The organic layer was dried over Na$_2$SO$_4$ and concentrated to obtain the desired compound. M+H 515. Calc'd for C$_{30}$H$_{38}$N$_6$O$_2$: 514.

The following compounds (Example 995–1009) were synthesized by the method described above, unless specifically described.

995) N-(2,2-Dimethyl-3,4-dihydro-2H-benzo[1,4]oxazin-6-yl)-2-[(pyridin-4-ylmethyl)-amino]-nicotinamide. M+H 390.3; Calc'd 389.4.

996) N-(4,4-Dimethyl-1,2,3,4-tetrahydro-isoquinolin-7-yl)-2-[(pyridin-4-ylmethyl)-amino]-nicotinamide. M+H 388.3.

997) N-(3,3-Dimethyl-2,3-dihydro-1H-indol-6-yl)-2-{[2-(1-methyl-piperidin-4-ylmethoxy)-pyridin-4-ylmethyl]-amino}-nicotinamide. M+H 501.3; Calc'd 500.3.

998) N-(3,3-Dimethyl-1-piperidin-4-yl-2,3-dihydro-1H-indol-6-yl)-2-[(pyridin-4-ylmethyl)-amino]-nicotinamide was prepared with 1N HCl in ether and dioxane at RT. M+H 457.2; Calc'd 456.7.

999) N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H Calc'd 500.65.

1000) N-(3,3-dimethyl-2,3-dihydro-1H-indol-6-yl)-2-[(2-methoxy-pyridin-4-ylmethyl)-amino]-nicotinamide. M+H 404.3; Calc'd 403.2.

1001) N-[3,3-Dimethyl-1-(piperidin-4-ylmethyl)-2,3-dihydro-1H-indol-6-yl]-2-[(2-methoxy-pyridin-4-ylmethyl)-amino]-nicotinamide was prepared with HCl in EtOAc. M+H 501.4; Calc'd 500.3.

1002) N-(3,3-Dimethyl-1-piperidin-4-yl-2,3-dihydro-1H-indol-6-yl)-2-[(2-methoxy-pyridin-4-ylmethyl)-amino]-nicotinamide. M+H 487.4; Calc'd 486.3.

1003) 2-[(2-Methoxy-pyridin-4-ylmethyl)-amino]-N-[3-(piperidin-4-ylmethoxy)-5-trifluoromethyl-phenyl]-nicotinamide was prepared with HCl in EtOAc.

1004) N-[3,3-Dimethyl-1-(pyrrolidin-2-ylmethyl)-2,3-dihydro-1H-indol-6-yl]-2-[(2-methoxy-pyridin-4-ylmethyl)-amino]-nicotinamide was prepared with HCl in EtOAc.

1005) 2-[(2-Methoxy-pyridin-4-ylmethyl)-amino]-N-[3-(piperazin-1-ylmethyl)-5-trifluoromethyl-phenyl]-nicotinamide was prepared with HCl in EtOAc. M+H 501.3.

1006) N-(3,3-dimethyl-2,3-dihydro-1H-indol-6-yl)-2-{[2-(2-morpholin-4-yl-ethoxy)-pyridin-4-ylmethyl]-amino}-nicotinamide. M+H 503; Calc'd 502.

1007) N-(3,3-dimethyl-2,3-dihydro-1H-indol-6-yl)-2-{[2-(1-methyl-piperidin-4-yloxy)-pyridin-4-ylmethyl]-amino}-nicotinamide. M+H 529.

1008) N-(3,3-dimethyl-2,3-dihydro-1H-indol-6-yl)-2-{[2-(2-morpholin-4-yl-propylamino)-pyridin-4-ylmethyl]-amino}-nicotinamide. M+H 516; Calc'd 515.

1009) N-(3,3-dimethyl-2,3-dihydro-1H-indol-6-yl)-2-({2-[2-(1-methyl-pyrrolidin-2-yl)-ethylamino]-pyrimidin-4-ylmethyl}-amino)-nicotinamide. M+H 501.4; Calc'd 500.

EXAMPLE 1010

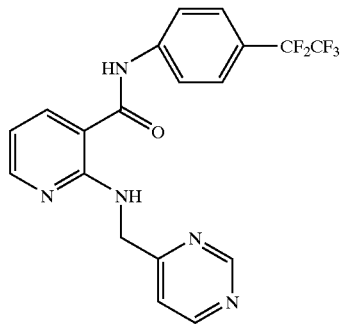

N-(4-Pentafluoroethyl-phenyl)-2-[(pyrimidin-4-ylmethyl)-amino]-nicotinamide

2-Amino-N-(4-pentafluoroethyl-phenyl)-nicotinamide (180 mg), TsOH (40 mg) and a solution of pyrimidine-4-carboxaldehyde in DMSO (10 ml) were stirred at 60 C. for 6 h. Treated with NaBH$_4$ (200 mg) and stirred for 2 h at RT. MS (ES$^+$): 566.3 (M+H)$^+$; Calc'd for C$_{26}$H$_{28}$F$_5$N$_7$O$_2$—565.

EXAMPLE 1011

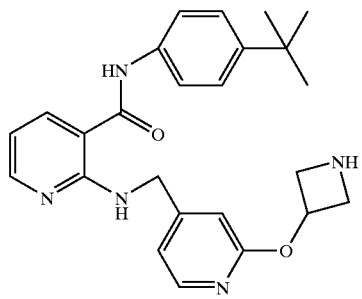

2-{[2-(Azetidin-3-yloxy)-pyridin-4-ylmethyl]-amino}-N-(4-tert-butyl-phenyl)nicotinamide 2-{[2-(1-Benzhydryl-azetidin-3-yloxy)-pyridin-4-ylmethyl]-amino}-N-(4-tert-butyl-phenyl)-nicotinamide (210 mg) was heated at reflux with Et$_3$SiH (5 ml) and TFA

EXAMPLE 1012

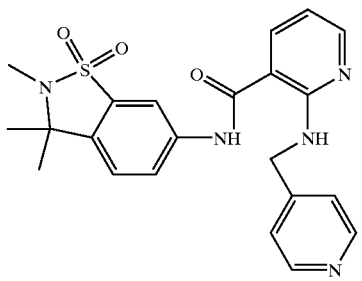

N-(2,3,3-Trimethyl-1,1-dioxo-2,3-dihydro-1H-1λ'-benzo[d]isothiazol-6-yl)-2-[(pyridin-4-ylmethyl)-amino]-benzamide N-(3,3-Dimethyl-1,1-dioxo-2,3-dihydro-1H-1λ'-benzo[d]isothiazol-6-yl)-2-[(pyridin-4-ylmethyl)-amino]-benzamide (110 mg) was dissolved in DMF and added NaH (30 mg). The mix was stirred for 15 min then MeI (18 ul) was added and stirred for 10 min. The Solvent was evaporated and purified by preparative TLC (10% MeOH/EtOAc) to give the product. M+H 438; Calc'd for $C_{22}H_{23}N_5O_3S$: 437.1.

The following compounds (Example 1013–1014) were synthesized by the method described above, unless specifically described.

1013) N-[3,3-Dimethyl-1,1-dioxo-2-(2-piperidin-1-yl-ethyl)-2,3-dihydro-1H-1λ'-benzo[d]isothiazol-6-yl]-2-[(pyridin-4-ylmethyl)-amino]-nicotinamide. M+H 535; Calc'd for $C_{28}H_{34}N_6O_3S$: 534.

1014) N-[2-(2-Dimethylamino-ethyl)-3,3-dimethyl-1,1-dioxo-2,3-dihydro-1H-1λ'-benzo[d]isothiazol-6-yl]-2-[(pyridin-4-ylmethyl)-amino]-nicotinamide. M+H 495; Calc'd 494.

EXAMPLE 1015

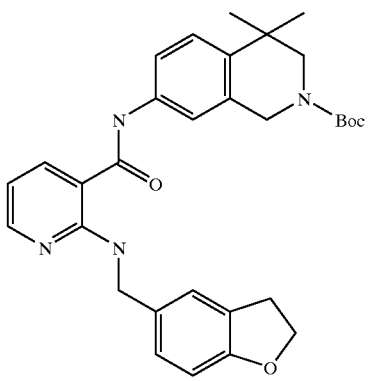

2-[(2,3-Dihydro-benzofuran-5-ylmethyl)-amino]-N-(1-Boc-4,4-dimethyl-1,2,3,4-tetrahydro-isoquinolin-7-yl)-nicotinamide MS: M+H 529.4. Calc'd for $C_{31}H_{36}N_4O_4$—528.3.

EXAMPLE 1016

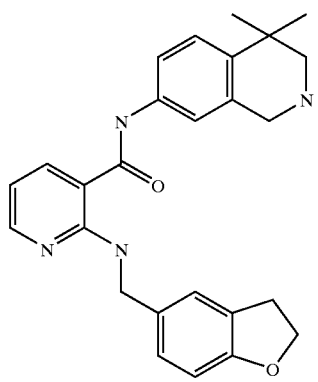

2-[(2,3-Dihydro-benzofuran-5-ylmethyl)-amino]-N-(4,4-dimethyl-1,2,3,4-tetrahydro-isoquinolin-7-yl)-nicotinamide MS: M+H 429.2. Calc'd for $C_{26}H_{28}N_4O_2$—428.2.

EXAMPLE 1017

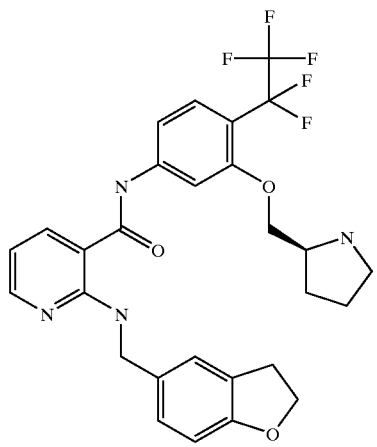

2-[(2,3-Dihydro-benzofuran-5-ylmethyl)-amino]-N-[4-pentafluoroethyl-3-(pyrrolidin-2-ylmethoxy)-phenyl]-nicotinamide MS: M+H 663.4. Calc'd for $C_{28}H_{27}F_5N_4O_3$—662.3.

EXAMPLE 1018

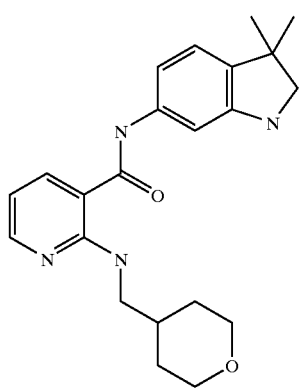

N-(3,3-Dimethyl-2,3-dihydro-1H-indol-6-yl)-2-[(tetrahydro-pyran-4-ylmethyl)-amino]-nicotinamide MS: M+H 381.3. Calc'd for $C_{22}H_{28}N_4O_2$—380.5.

EXAMPLE 1019

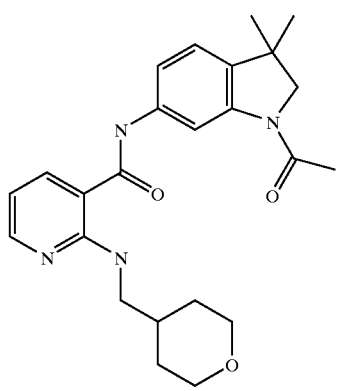

N-(1-Acetyl-3,3-dimethyl-2,3-dihydro-1H-indol-6-yl)-2-[(tetrahydro-pyran-4-ylmethyl)-amino]-nicotinamide MS: M+H 430. Calc'd for $C_{24}H_{30}N_4O_3$—422.5.

EXAMPLE 1020

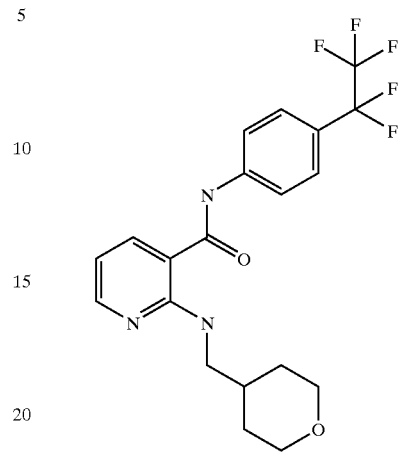

N-(4-Pentafluoroethyl-phenyl)-2-[(tetrahydro-pyran-4-ylmethyl)-amino]-nicotinamide MS: M+H 432.2. Calc'd for $C_{20}H_{20}F_5N_3O_2$—429.387.

EXAMPLE 1021

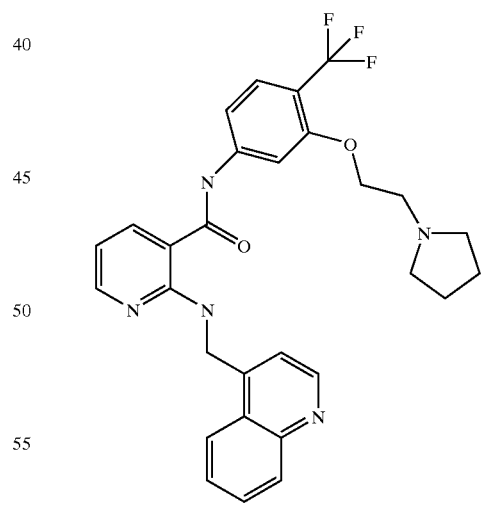

N-(3-((2-(1-pyrrolidinyl)ethyl)oxy)-4-(trifluoromethyl)phenyl)-2-((4-quinolinylmethyl)amino)-3-pyridinecarboxamide MS: M+H—536.7; Calc'd for $C_{29}H_{28}F_3N_5O_2$—535.567.

EXAMPLE 1022

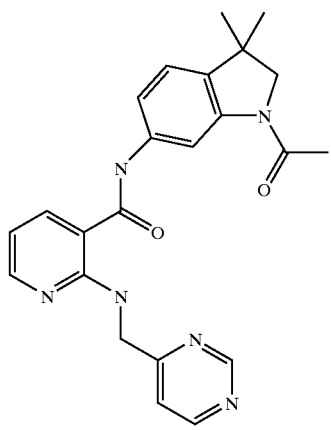

N-(1-Acetyl-3,3-dimethyl-2,3-dihydro-1H-indol-6-yl)-2-((4-pyrimidinylmethyl)amino)-3-pyridinecarboxamide MS: M+H 417.1; Calc'd for $C_{23}H_{24}N_6O_2$—416.483.

EXAMPLE 1023

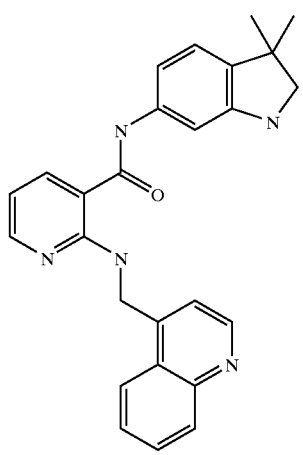

N-(3,3-Dimethyl-2,3-dihydro-1H-indol-6-yl)-2-((4-quinolinylmethyl)amino)-3-pyridinecarboxamide MS: M+H 424.5; Calc'd for $C_{26}H_{25}N_5O$—423.517.

EXAMPLE 1024

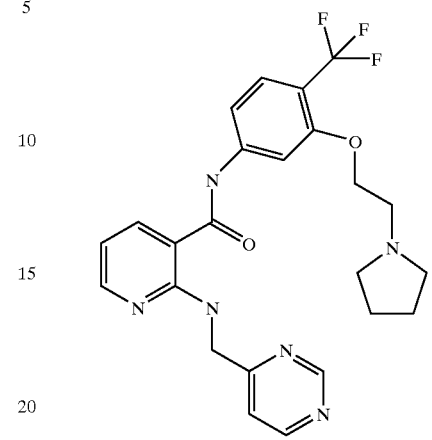

2-((4-Pyrimidinylmethyl)amino)-N-(3-((2-(1-pyrrolidinyl)ethyl)oxy)-4-(trifluoromethyl)phenyl)-3-pyridinecarboxamide MS: M+H 487.2; Calc'd for $C_{24}H_{25}F_3N_6O_2$—486.496.

EXAMPLE 1025

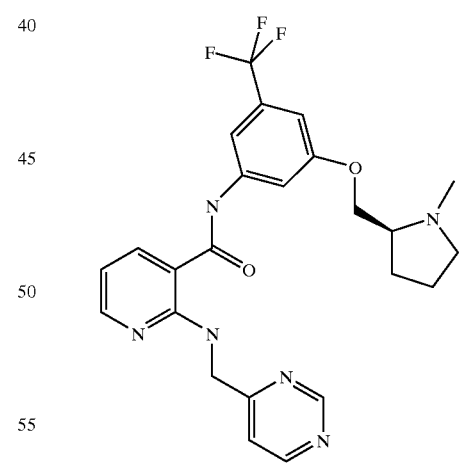

N-(3-((((2S)-1-Methyl-2-pyrrolidinyl)methyl)oxy)-5-(trifluoromethyl)phenyl)-2-((4-pyrimidinylmethyl)amino)-3-pyridinecarboxamide MS: M+H 487.2; Calc'd for $C_{24}H_{25}F_3N_6O_2$—486.495.

EXAMPLE 1026

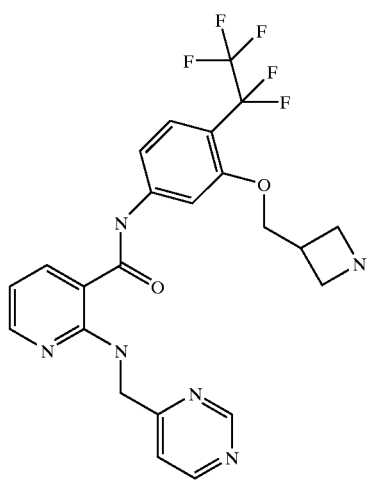

N-(3-((3-Azetidinylmethyl)oxy)-4-(pentafluoroethyl)phenyl)-2-((4-pyrimidinylmethyl)amino)-3-pyridinecarboxamide M+H 509.4; Calc'd for $C_{23}H_{21}F_5N_6O_2$—508.449.

EXAMPLE 1027

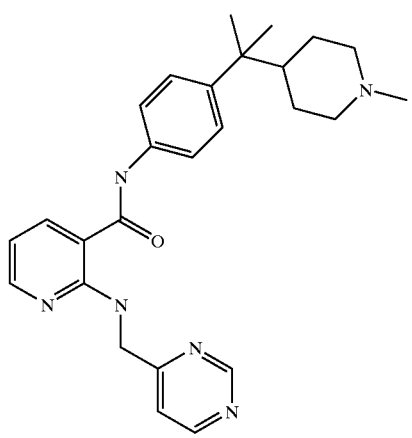

N-(4-(1-Methyl-1-(1-methyl-4-piperidinyl)ethyl)phenyl)-2-((4-pyrimidinylmethyl)amino)-3-pyridinecarboxamide M+H 445.6; Calc'd for $C_{26}H_{32}N_6O$—444.58

EXAMPLE 1028

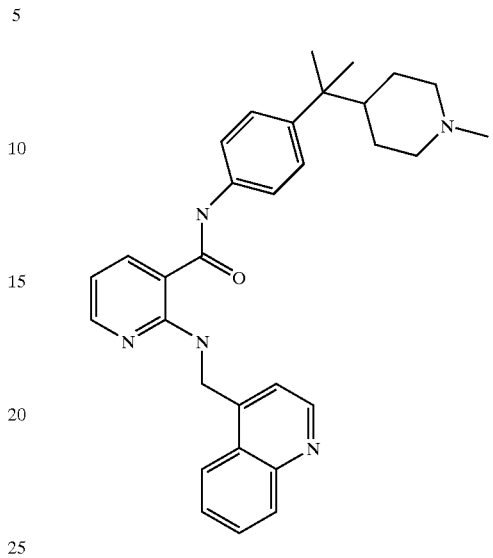

N-(4-(1-Methyl-1-(1-methyl-4-piperidinyl)ethyl)phenyl)-2-((4-quinolinylmethyl)amino)-3-pyridinecarboxamide M+H 494.5; Calc'd for $C_{31}H_{35}N_5O$—493.651.

EXAMPLE 1029

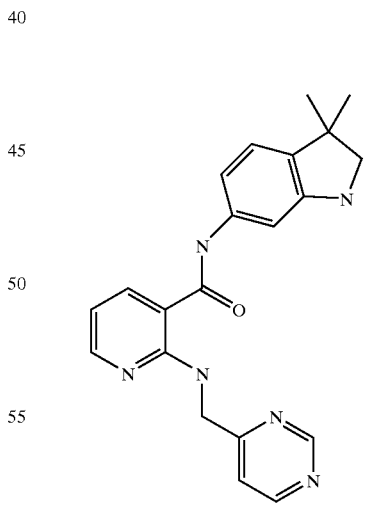

N-(3,3-Dimethyl-2,3-dihydro-1H-indol-6-yl)-2-((4-pyrimidinylmethyl)amino)-3-pyridinecarboxamide M+H 375.6; Calc'd for $C_{21}H_{22}N_6O$—374.446.

EXAMPLE 1030

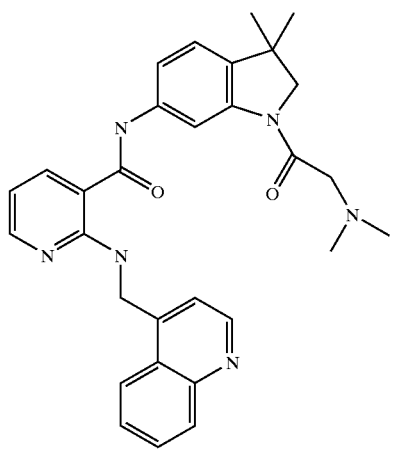

N-(1-(N,N-Dimethylglycyl)-3,3-dimethyl-2,3-dihydro-1H-indol-6-yl)-2-((4-quinolinylmethyl)amino)-3-pyridinecarboxamide M+H 509.5; Calc'd for $C_{30}H_{32}N_6O_2$—508.623.

EXAMPLE 1031

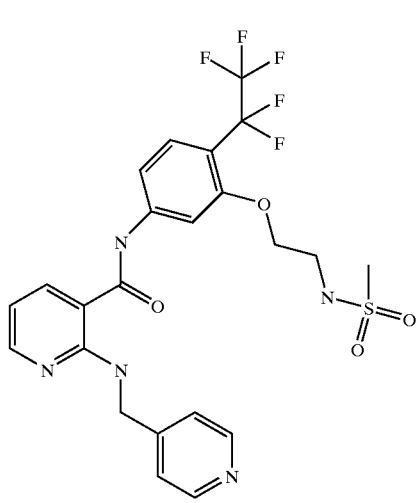

N-(3-((2-((Methylsulfonyl)amino)ethyl)oxy)-4-(pentafluoroethyl)phenyl)-2-((4-pyridinylmethyl)amino)-3-pyridinecarboxamide M+H 560; Calc'd for —$C_{23}H_{22}F_5N_5O_4S$—559.514.

EXAMPLE 1032

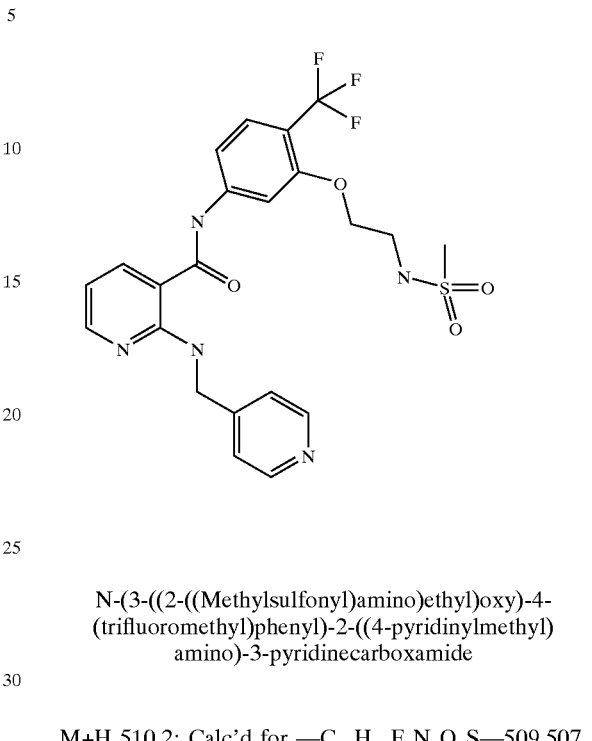

N-(3-((2-((Methylsulfonyl)amino)ethyl)oxy)-4-(trifluoromethyl)phenyl)-2-((4-pyridinylmethyl)amino)-3-pyridinecarboxamide M+H 510.2; Calc'd for —$C_{22}H_{22}F_3N_5O_4S$—509.507.

EXAMPLE 1033

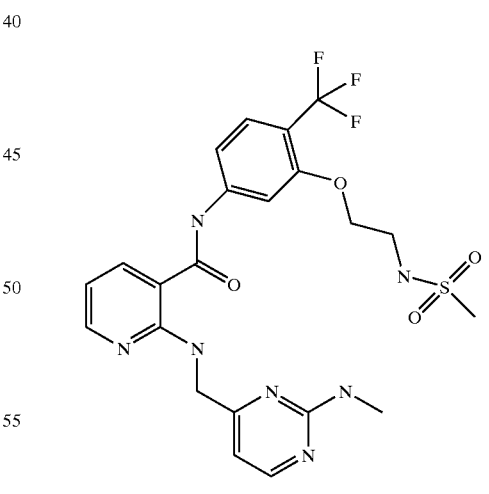

2-(((2-(Methylamino)-4-pyrimidinyl)methyl)amino)-N-(3-((2-((methylsulfonyl)amino)ethyl)oxy)-4-(trifluoromethyl)phenyl)-3-pyridinecarboxamide M+H 539.9; Calc'd for $C_{22}H_{24}F_3N_7O_4S$—539.537.

EXAMPLE 1034

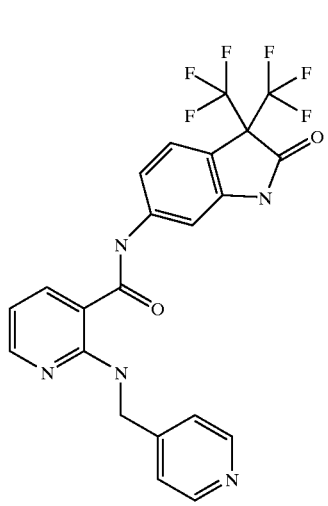

N-(2-oxo-3,3-bis(trifluoromethyl)-2,3-dihydro-1H-indol-6-yl)-2-((4-pyridinylmethyl)amino)-3-pyridinecarboxamide M+H 495.9; Calc'd for $C_{22}H_{15}F_6N_5O_2$—495.382.

EXAMPLE 1035

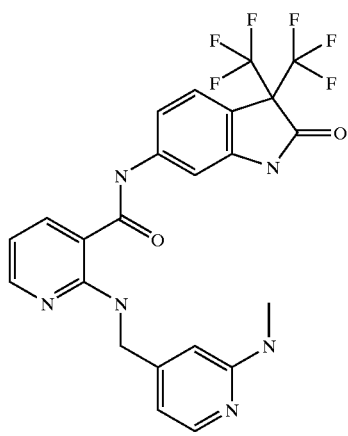

2-(((2-(Methylamino)-4-pyridinyl)methyl)amino)-N-(2-oxo-3,3-bis(trifluoromethyl)-2,3-dihydro-1H-indol-6-yl)-3-pyridinecarboxamide M+H 525.1; Calc'd for —$C_{23}H_{18}F_6N_6O_2$—524.423.

EXAMPLE 1036

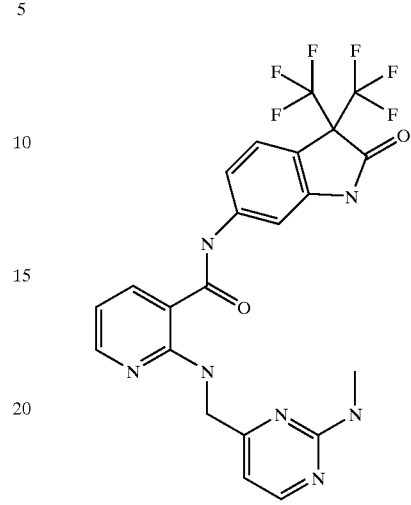

2-(((2-(Methylamino)-4-pyrimidinyl)methyl)amino)-N-(2-oxo-3,3-bis(trifluoromethyl)-2,3-dihydro-1H-indol-6-yl)-3-pyridinecarboxamide M+H 526.1; Calc'd for C22 H17 F6 N7 O2—525.411

EXAMPLE 1037

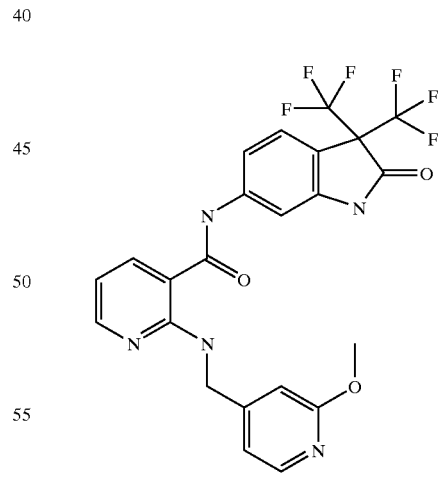

2-(((2-(Methyloxy)-4-pyridinyl)methyl)amino)-N-(2-oxo-3,3-bis(trifluoromethyl)-2,3-dihydro-1H-indol-6-yl)-3-pyridinecarboxamide M+H 526.1; Calc'd for C23 H17 F6 N5 O3—525.407.

EXAMPLE 1038

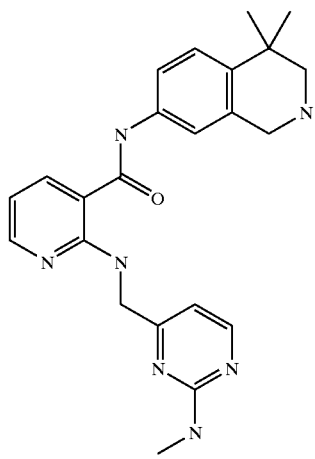

N-(4,4-Dimethyl-1,2,3,4-tetrahydro-7-isoquinolinyl)-2-(((2-(methylamino)-4-pyrimidinyl)methyl)amino)-3-pyridinecarboxamide M+H 418; Calc'd for C23 H27 N7 O—417.514.

EXAMPLE 1040

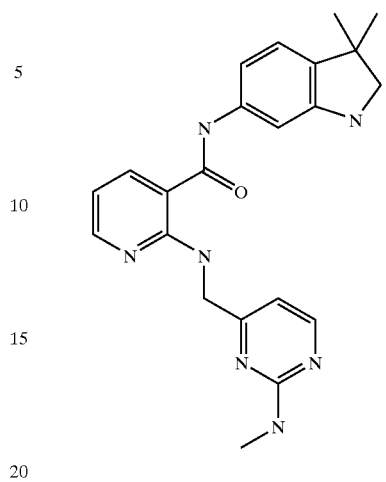

N-(3,3-Dimethyl-2,3-dihydro-1H-indol-6-yl)-2-(((2-(methylamino)-4-pyrimidinyl)methyl)amino)-3-pyridinecarboxamide M+H 404.2; Calc'd for C22 H25 N7 O—403.488.

EXAMPLE 1039

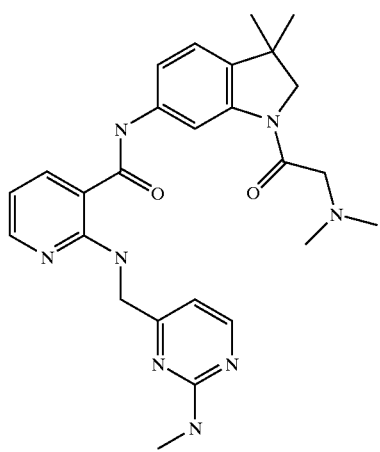

N-(1-(N,N-Dimethylglycyl)-3,3-dimethyl-2,3-dihydro-1H-indol-6-yl)-2-(((2-(methylamino)-4-pyrimidinyl)methyl)amino)-3-pyridinecarboxamide M+H 489.3; Calc'd for C26 H32 N8 O2—488.593.

EXAMPLE 1041

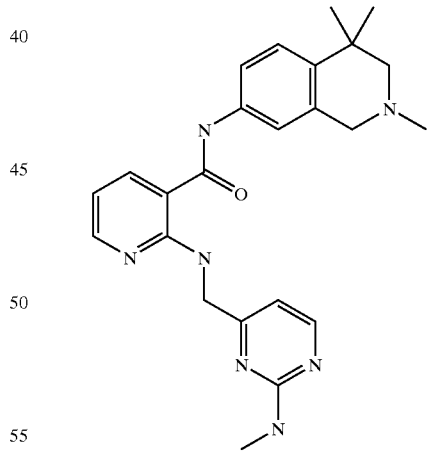

2-(((2-(methylamino)-4-pyrimidinyl)methyl)amino)-N-(2,4,4-trimethyl-1,2,3,4-tetrahydro-7-isoquinolinyl)-3-pyridinecarboxamide M+H 432.3; Calc'd for C24 H29 N7 O—431.541.

EXAMPLE 1042

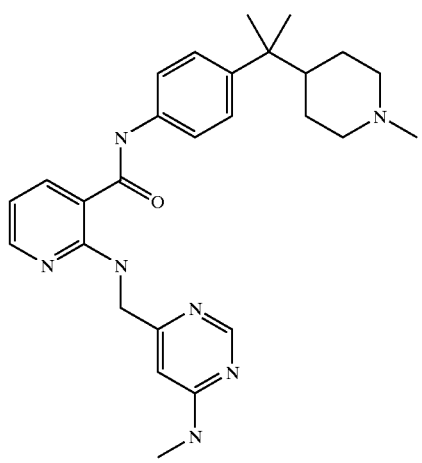

2-(((6-(methylamino)-4-pyrimidinyl)methyl)amino)-
N-(4-(1-methyl-1-(1-methyl-4-piperidinyl)ethyl)
phenyl)-3-pyridinecarboxamide M+H 474.4; Calc'd for C27 H35 N7 O—473.621.

EXAMPLE 1043

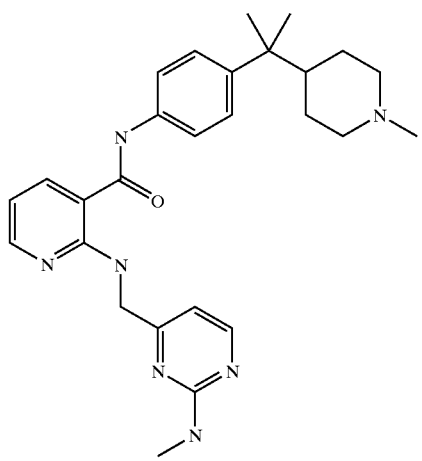

2-(((2-(methylamino)-4-pyrimidinyl)methyl)amino)-
N-(4-(1-methyl-1-(1-methyl-4-piperidinyl)ethyl)
phenyl)-3-pyridinecarboxamide M+H 474.1; Calc'd for C27 H35 N7 O—473.621.

EXAMPLE 1044

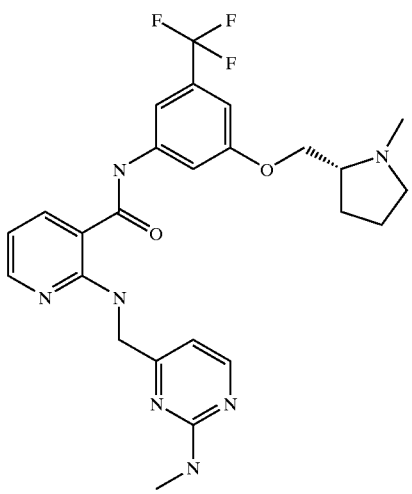

2-(((2-(methylamino)-4-pyrimidinyl)methyl)amino)-
N-(3-((((2R)-1-methyl-2-pyrrolidinyl)methyl)oxy)-
5-(trifluoromethyl)phenyl)-3-pyridinecarboxamide M+H 516.4; Calc'd for C25 H28 F3 N7 O2—515.537.

EXAMPLE 1045

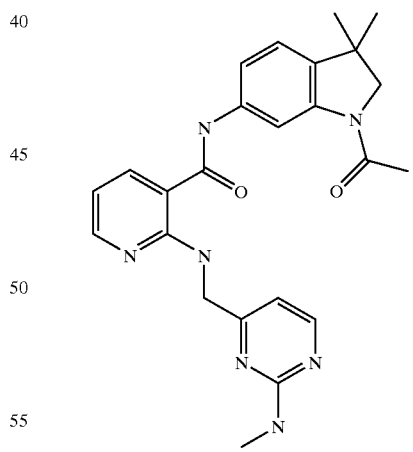

N-(1-acetyl-3,3-dimethyl-2,3-dihydro-1H-indol-6-
yl)-2-(((2-(methylamino)-4-pyrimidinyl)methyl)
amino)-3-pyridinecarboxamide M+H 446.4; Calc'd for C24 H27 N7 O2—445.524.

EXAMPLE 1046

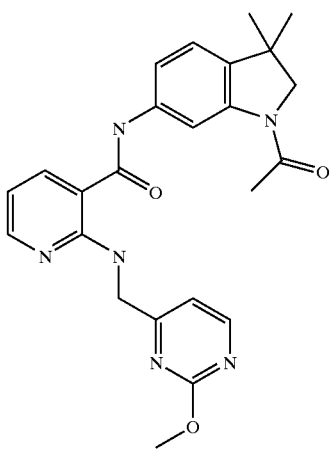

N-(1-acetyl-3,3-dimethyl-2,3-dihydro-1H-indol-6-yl)-2-(((2-(methyloxy)-4-pyrimidinyl)methyl)amino)-3-pyridinecarboxamide M+H 447.0; Calc'd for C24 H26 N6 O3—446.508.

EXAMPLE 1047

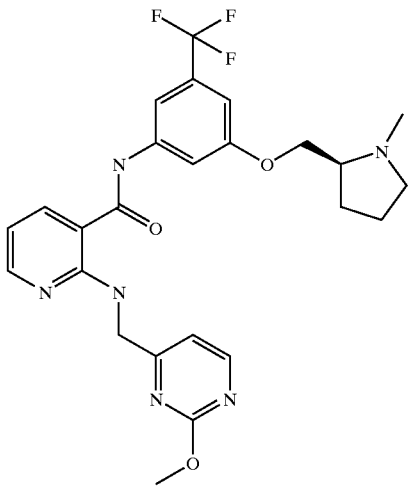

2-(((2-(methyloxy)-4-pyrimidinyl)methyl)amino)-N-(3-((((2S)-1-methyl-2-pyrrolidinyl)methyl)oxy)-5-(trifluoromethyl)phenyl)-3-pyridinecarboxamide M+H 517.7; Calc'd for C25 H27 F3 N6 O3—516.521.

EXAMPLE 1048

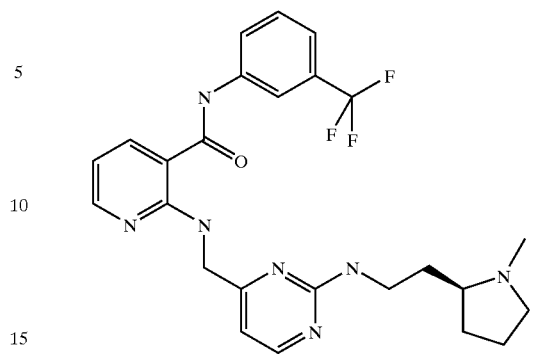

2-(((2-((2-((2R,S)-1-methyl-2-pyrrolidinyl)ethyl)amino)-4-pyrimidinyl)methyl)amino)-N-(3-(trifluoromethyl)phenyl)-3-pyridinecarboxamide M+H 500.4; Calc'd for C25 H28 F3 N7 O—499.538.

EXAMPLE 1049

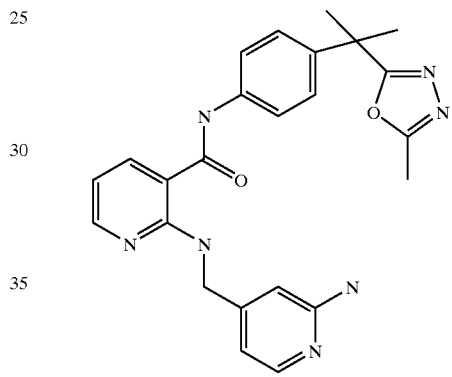

2-[(2-Amino-pyridin-4-ylmethyl)-amino]-N-{4-[1-methyl-1-(5-methyl-[1,3,4]oxadiazol-2-yl)-ethyl]-phenyl}-nicotinamide MS: 444 (M+1) calc'd for C24 H26 N7 O2—443.21.

EXAMPLE 1050

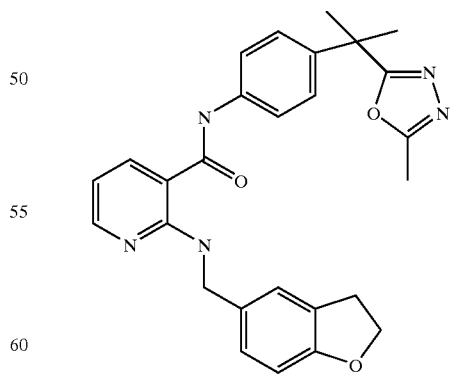

2-[(2,3-Dihydro-benzofuran-5-ylmethyl)-amino]-N-{4-[1-methyl-1-(5-methyl-[1,3,4]oxadiazol-2-yl)-ethyl]-phenyl}-nicotinamide MS: 470 (M+1) calc'd for C27 H28N5 O3—469.21.

EXAMPLE 1051

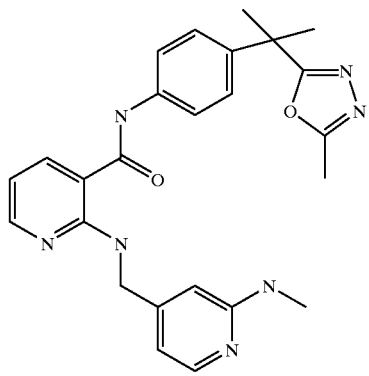

2-[(2-Methylamino-pyridin-4-ylmethyl)-amino]-N-
{4-[1-methyl-1-(5-methyl-[1,3,4]oxadiazol-2-yl)-
ethyl]-phenyl}-nicotinamide
MS: 458 (M+1) calc'd for C25 H28N7 O2—458.22.

EXAMPLE 1052

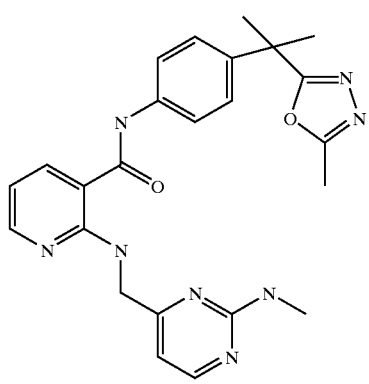

2-(((2-(methylamino)-4-pyrimidinyl)methyl)amino)-
N-(4-(1-methyl-1-(5-methyl-1,3,4-oxadiazol-2-yl)
ethyl)phenyl)-3-pyridinecarboxamide
MS: 459 (M+1) Calc'd for C24 H27N8 O2—459.22.

EXAMPLE 1053

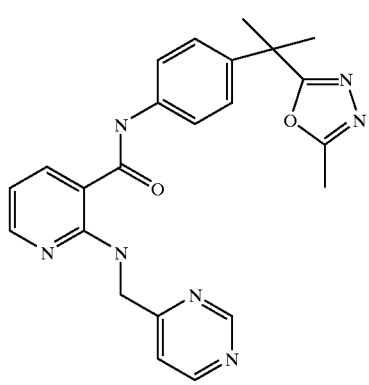

N-(4-(1-methyl-1-(5-methyl-1,3,4-oxadiazol-2-yl)
ethyl)phenyl)-2-((4-pyrimidinylmethyl)amino)-3-
pyridinecarboxamide
MS: 430 (M+1) Calc'd for C23 H24 N7 O2—429.19.

EXAMPLE 1054

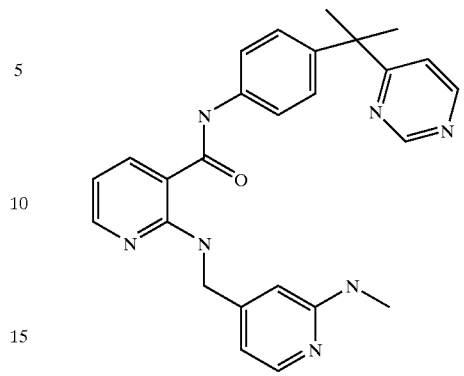

2-(((2-(methylamino)-4-pyridinyl)methyl)amino)-N-
(4-(1-methyl-1-(4-pyrimidinyl)ethyl)phenyl)-3-
pyridinecarboxamide
MS: 454 (M+1) Calc'd for C26 H28 N7 O—454.23.

EXAMPLE 1055

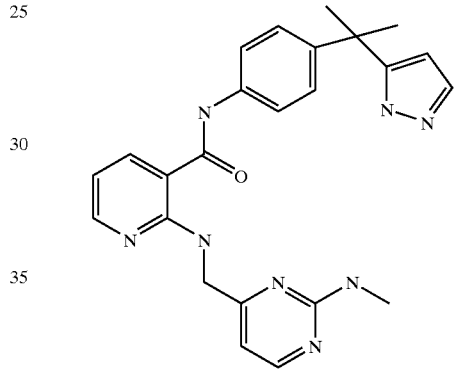

2-[(2-Methylamino-pyrimidin-4-ylmethyl)-amino]-
N-{4-[1-methyl-1-(2H-pyrazol-3-yl)-ethyl]-phenyl}-
nicotinamide
MS: 443 (M+1) Calc'd for C24 H26 N8O—442.22.

EXAMPLE 1056

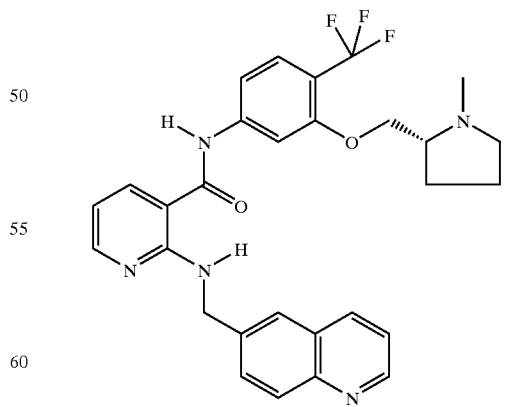

N-(3-((((2R)-1-methyl-2-pyrrolidinyl)methyl)oxy)-
4-(trifluoromethyl)phenyl)-2-((6-quinolinylmethyl)
amino)-3-pyridinecarboxamide
C29 H28 F3 N5 O2—535.567; M+H—536.2.

EXAMPLE 1057

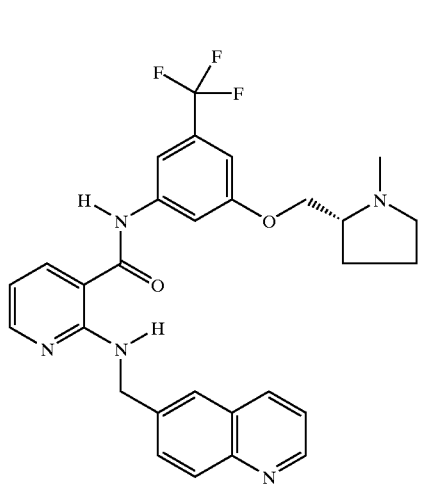

N-(3-((((2R)-1-methyl-2-pyrrolidinyl)methyl)oxy)-5-(trifluoromethyl)phenyl)-2-((6-quinolinylmethyl)amino)-3-pyridinecarboxamide

C29 H28 F3 N5 O2—535.567; M+H—536.2.

EXAMPLE 1058

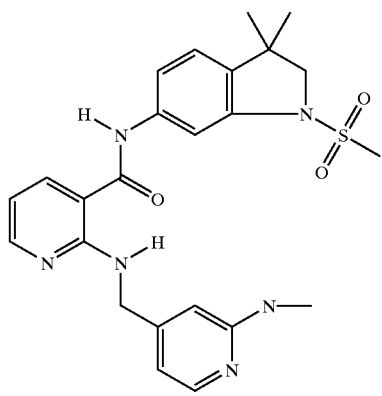

N-(3,3-dimethyl-1-(methylsulfonyl)-2,3-dihydro-1H-indol-6-yl)-2-(((2-(methylamino)-4-pyridinyl)methyl)amino)-3-pyridinecarboxamide Calc'd for C24 H28 N6 O3 S—480.59; M+H 481.2.

EXAMPLE 1059

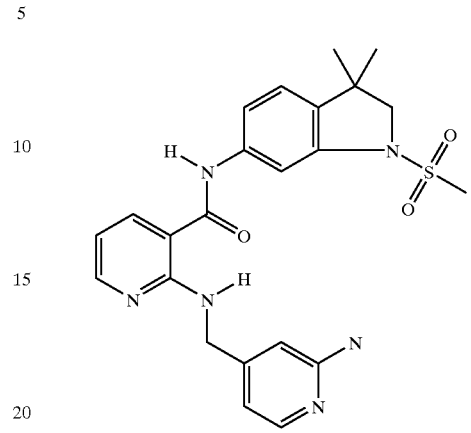

2-(((2-amino-4-pyridinyl)methyl)amino)-N-(3,3-dimethyl-1-(methylsulfonyl)-2,3-dihydro-1H-indol-6-yl)-3-pyridinecarboxamide Calc'd for C23 H26 N6 O3 S—466.563; M+H 467.1.

EXAMPLE 1060

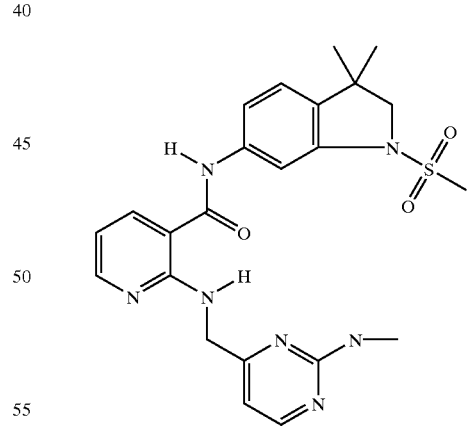

N-(3,3-dimethyl-1-(methylsulfonyl)-2,3-dihydro-1H-indol-6-yl)-2-(((2-(methylamino)-4-pyrimidinyl)methyl)amino)-3-pyridinecarboxamide Calc'd for C23 H27 N7 O3 S—481.578; M+H 482.2.

EXAMPLE 1061

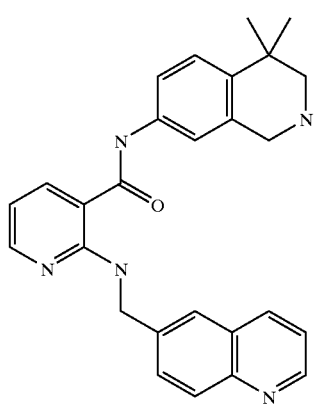

N-(4,4-dimethyl-1,2,3,4-tetrahydro-7-isoquinolinyl)-2-((6-quinolinylmethyl)amino)-3-pyridinecarboxamide Calc'd for C27 H27 N5 O—437.544; M+H 438.4.

EXAMPLE 1062

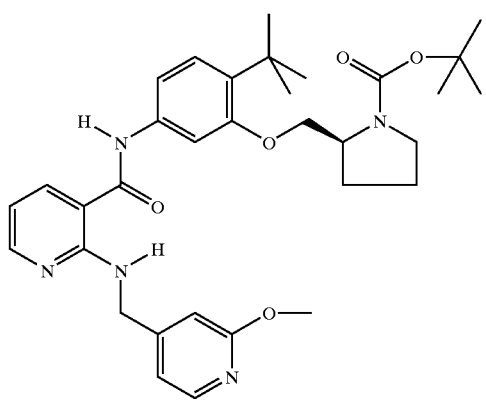

1,1-dimethylethyl (2S)-2-(((2-(1,1-dimethylethyl)-5-(((2-(((2-(methyloxy)-4-pyridinyl)methyl)amino)-3-pyridinyl)carbonyl)amino)phenyl)oxy)methyl)-1-pyrrolidinecarboxylate Calc'd for C33 H43 N5 O5—589.733; M+H 590.6, M-BOC 490.7.

EXAMPLE 1063

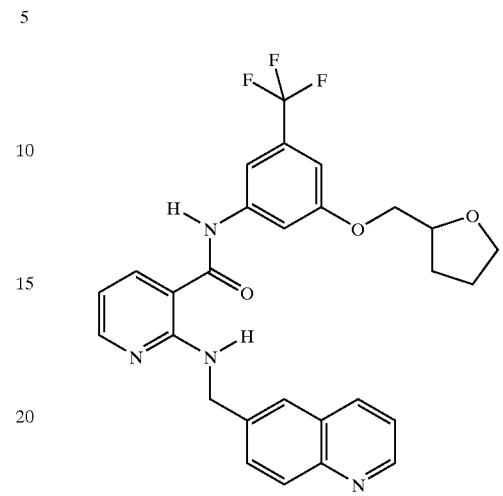

2-((6-quinolinylmethyl)amino)-N-(3-((tetrahydro-2-furanylmethyl)oxy)-5-(trifluoromethyl)phenyl)-3-pyridinecarboxamide Calc'd for C28 H25 F3 N4 O3—522.524; M+H 523.1.

EXAMPLE 1064

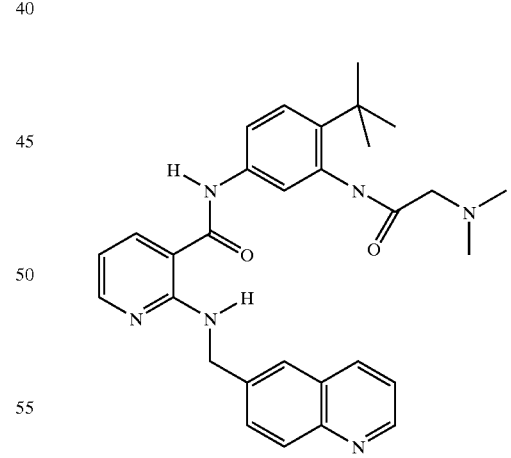

N-(4-(1,1-dimethylethyl)-3-((N,N-dimethylglycyl)amino)phenyl)-2-((6-quinolinylmethyl)amino)-3-pyridinecarboxamide Calc'd for C30 H34 N6 O2—510.639; M+H 511.2.

EXAMPLE 1065

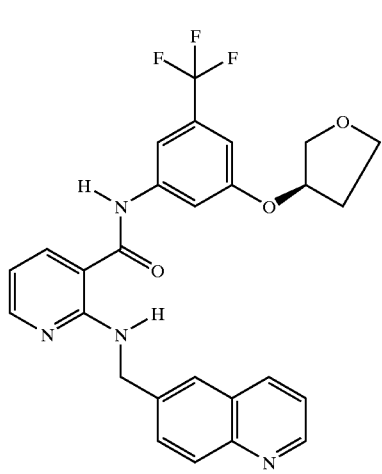

2-((6-quinolinylmethyl)amino)-N-(3-((3R)-tetrahydro-3-furanyloxy)-5-(trifluoromethyl)phenyl)-3-pyridinecarboxamide Calc'd for C27 H23 F3 N4 O3—508.498; M+H 509.1.

EXAMPLE 1066

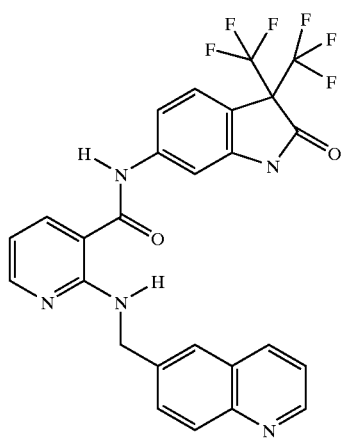

N-(2-oxo-3,3-bis(trifluoromethyl)-2,3-dihydro-1H-indol-6-yl)-2-((6-quinolinylmethyl)amino)-3-pyridinecarboxamide Calc'd for C26 H17 F6 N5 O2—545.441; M+H 546.1.

EXAMPLE 1067

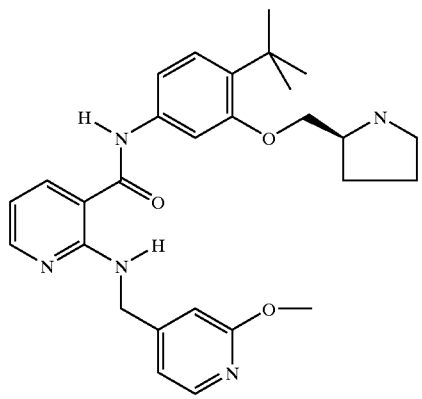

N-(4-(1,1-dimethylethyl)-3-(((2S)-2-pyrrolidinylmethyl)oxy)phenyl)-2-(((2-(methyloxy)-4-pyridinyl)methyl)amino)-3-pyridinecarboxamide Calc'd for C28 H35 N5 O3—489.616; M+H 490.6.

EXAMPLE 1068

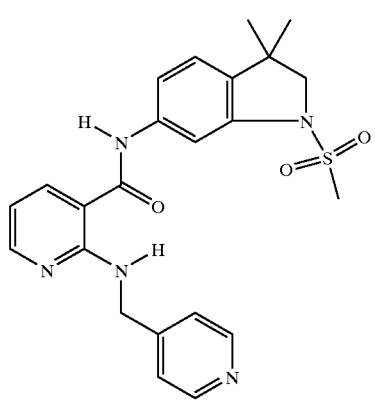

N-(3,3-dimethyl-1-(methylsulfonyl)-2,3-dihydro-1H-indol-6-yl)-2-((4-pyridinylmethyl)amino)-3-pyridinecarboxamide Calc'd for C23 H25 N5 O3 S—451.548; M+H 452.3.

EXAMPLE 1069

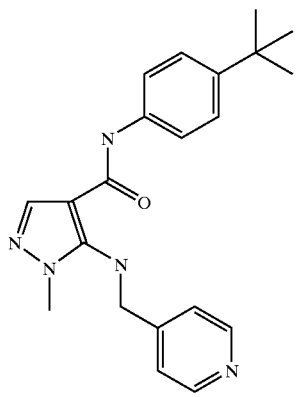

1-methyl-5-[(pyridin-4-ylmethyl)-amino]-1H-pyrazole-4-carboxylic Acid (4-tert-butyl-phenyl)-amide 5-Chloro-1-methyl-1H-pyrazole-4-carboxylic acid (4-tert-butyl-phenyl)-amide (530 mg, 1.80 mmol) and powered 40% KF/Alumina (1.04 g, effective 6.0 mmol of KF) were combined and treated with IpOH (6 mL). 4-(Aminomethyl)pyridine (3.9 g, 36 mmol) was added. The headspace of the reaction vessel was purged with argon and the reaction vessel was sealed. The reaction was then heated to 160° C. overnight with stirring. The reaction was cooled to RT and filtered under vacuum, washing the collected solid with fresh IpOH. The filtrate was concentrated under reduced pressure and the recovered material was eluted through a 17×2.5 cm column of silica gel with a 14:7:7:1 and 7:7:7:1 Hexane:MtBE:$CH_2Cl_2$:MeOH step gradient giving 1-methyl-5-[(pyridin-4-ylmethyl)-amino]-1H-pyrazole-4-carboxylic acid (4-tert-butyl-phenyl)-amide as a white foamy solid. MS: 364 (M+1). Calc'd. for $C_{21}H_{25}N_5O$—363.46.

EXAMPLE 1070

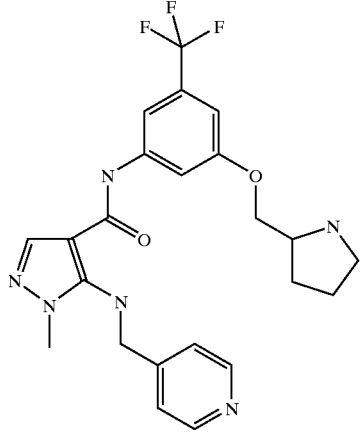

1-Methyl-5-[(pyridin-4-ylmethyl)-amino]-1H-pyrazole-4-carboxylic Acid [3-(pyrrolidin-2-ylmethoxy)-5-trifluoromethyl-phenyl]-amide The Compound was prepared in a similar fashion as described above. MS: 475 (M+1). Calc'd. for $C_{23}H_{25}F_3N_6O_2$—474.48.

EXAMPLE 1071

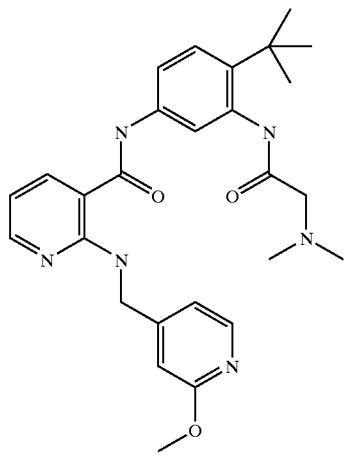

N-(4-(1,1-dimethylethyl)-3-((N,N-dimethylglycyl)amino)phenyl)-2-(((2-(methyloxy)-4-pyridinyl)methyl)amino)-3-pyridinecarboxamide Calc'd for C27 H34 N6 O3—490.605; M+H 491.

EXAMPLE 1072

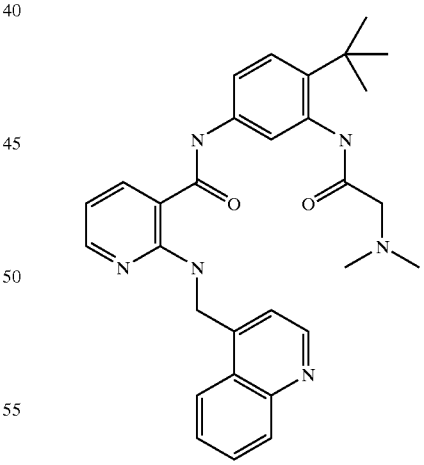

N-(4-(1,1-dimethylethyl)-3-((N,N-dimethylglycyl)amino)phenyl)-2-((4-quinolinylmethyl)amino)-3-pyridinecarboxamide Calc'd for C30 H34 N6 O2—510.639; M+H 511.

EXAMPLE 1073

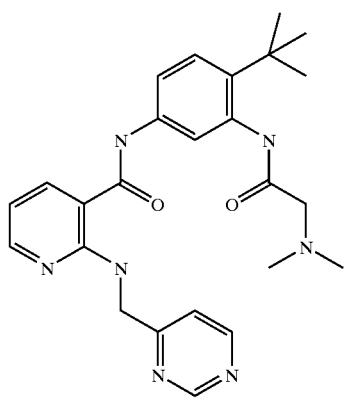

N-(4-(1,1-dimethylethyl)-3-((N,N-dimethylglycyl)amino)phenyl)-2-((4-pyrimidinylmethyl)amino)-3-pyridinecarboxamide Calc'd for C25 H31 N7 O2—461.567; M+H 462.

EXAMPLE 1074

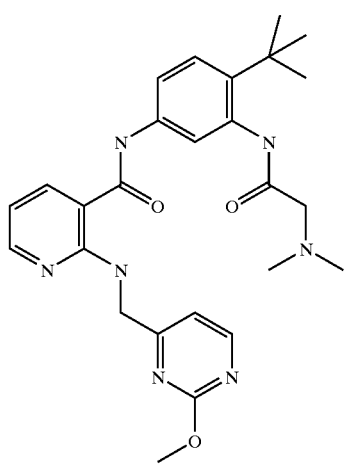

N-(4-(1,1-dimethylethyl)-3-((N,N-dimethylglycyl)amino)phenyl)-2-(((2-(methyloxy)-4-pyrimidinyl)methyl)amino)-3-pyridinecarboxamide Calc'd for C26 H33 N7 O3—491.593; M+H 492.

EXAMPLE 1075

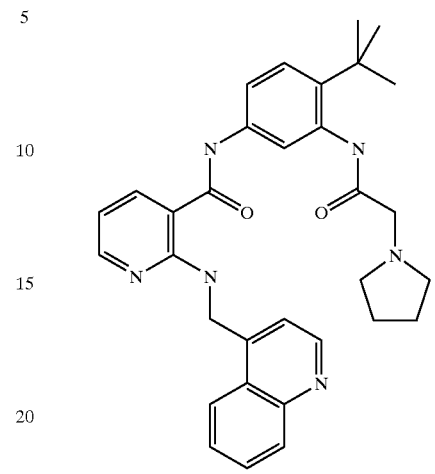

N-(4-(1,1-dimethylethyl)-3-((1-pyrrolidinylacetyl)amino)phenyl)-2-((4-quinolinylmethyl)amino)-3-pyridinecarboxamide Calc'd for C32 H36 N6 O2—536.676; M+H 537.

EXAMPLE 1076

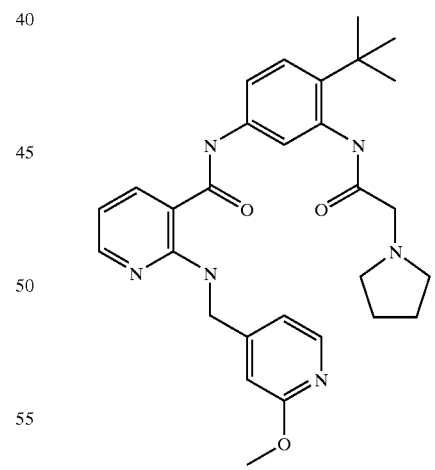

N-(4-(1,1-dimethylethyl)-3-((1-pyrrolidinylacetyl)amino)phenyl)-2-(((2-(methyloxy)-4-pyridinyl)methyl)amino)-3-pyridinecarboxamide Calc'd for C29 H36 N6 O3—516.642; M+H 517.

EXAMPLE 1077

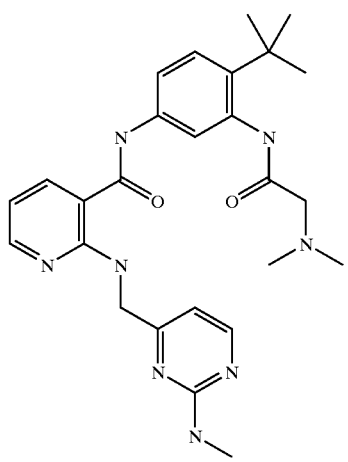

N-(4-(1,1-dimethylethyl)-3-((N,N-dimethylglycyl)amino)phenyl)-2-(((2-(methylamino)-4-pyrimidinyl)methyl)amino)-3-pyridinecarboxamide Calc'd for C26 H34 N8 O2—490.609; M+H 491.

EXAMPLE 1078

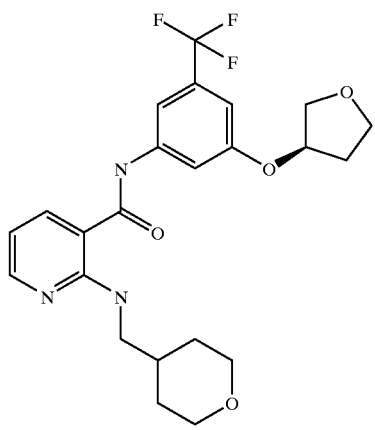

N-(3-((3R)-tetrahydro-3-furanyloxy)-5-(trifluoromethyl)phenyl)-2-((tetrahydro-2H-pyran-4-ylmethyl)amino)-3-pyridinecarboxamide

C23 H26 F3 N3 O4—465.469; M+H 466.

EXAMPLE 1079

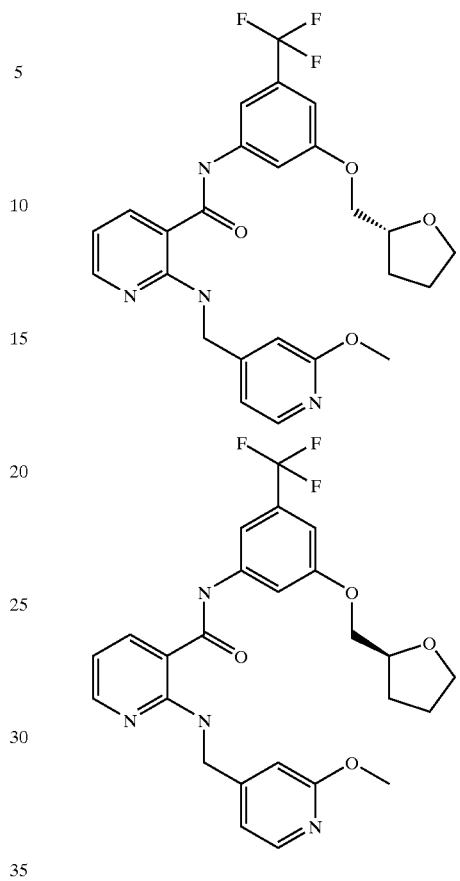

2-(((2-(methyloxy)-4-pyridinyl)methyl)amino)-N-(3-(((2S)-tetrahydro-2-furanylmethyl)oxy)-5-(trifluoromethyl)phenyl)-3-pyridinecarboxamide 2-(((2-(methyloxy)-4-pyridinyl)methyl)amino)-N-(3-(((2R)-tetrahydro-2-furanylmethyl)oxy)-5-(trifluoromethyl)phenyl)-3-pyridinecarboxamide C25 H25 F3 N4 O4—502.49; M+H 503, M+Na 525.

EXAMPLE 1080

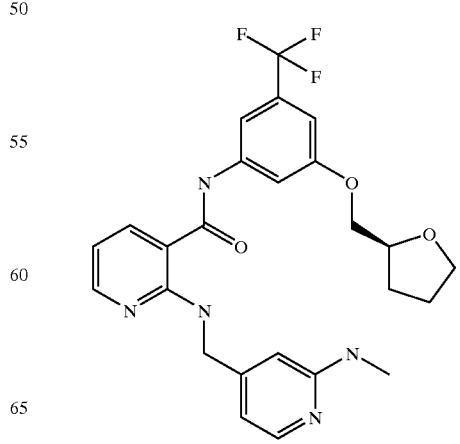

-continued

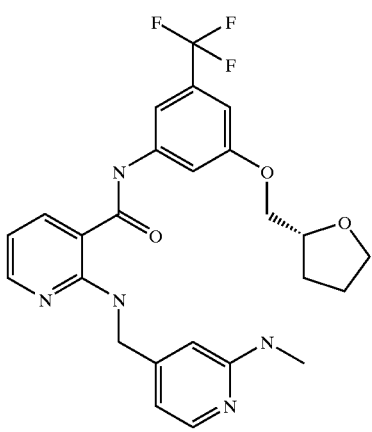

2-(((2-(methylamino)-4-pyridinyl)methyl)amino)-N-(3-(((2S)-tetrahydro-2-furanylmethyl)oxy)-5-(trifluoromethyl)phenyl)-3-pyridinecarboxamide 2-(((2-(methylamino)-4-pyridinyl)methyl)amino)-N-(3-(((2R)-tetrahydro-2-furanylmethyl)oxy)-5-(trifluoromethyl)phenyl)-3-pyridinecarboxamide C25 H26 F3 N5 O3—501.506; M+H 502, M+Na 524.

EXAMPLE 1081

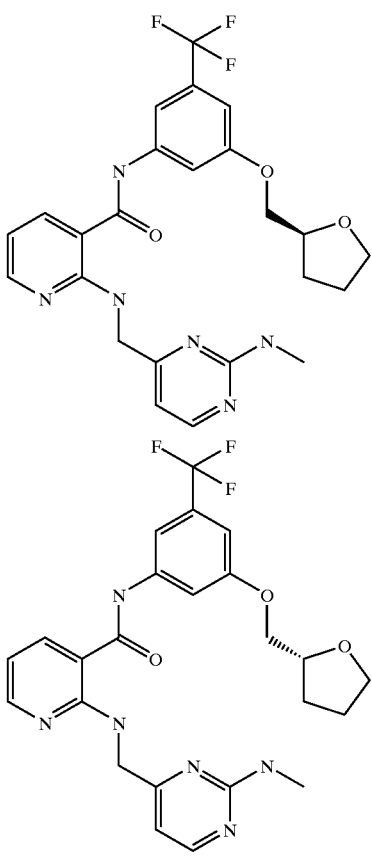

2-(((2-(methylamino)-4-pyrimidinyl)methyl)amino)-N-(3-(((2S)-tetrahydro-2-furanylmethyl)oxy)-5-(trifluoromethyl)phenyl)-3-pyridinecarboxamide 2-(((2-(methylamino)-4-pyrimidinyl)methyl)amino)-N-(3-(((2R)-tetrahydro-2-furanylmethyl)oxy)-5-(trifluoromethyl)phenyl)-3-pyridinecarboxamide C24 H25 F3 N6 O3—502.494; M+H 503, M+Na 525.

EXAMPLE 1082

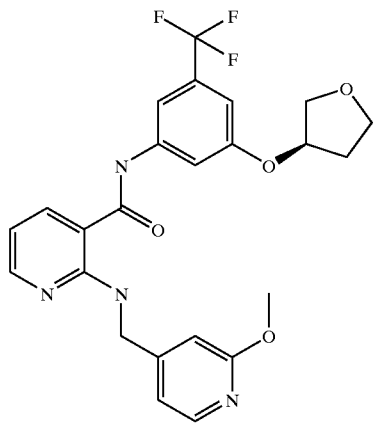

2-(((2-(methyloxy)-4-pyridinyl)methyl)amino)-N-(3-((3R)-tetrahydro-3-furanyloxy)-5-(trifluoromethyl)phenyl)-3-pyridinecarboxamide C24 H23 F3 N4 O4—488.464; M+H 489, M+Na 511.

EXAMPLE 1083

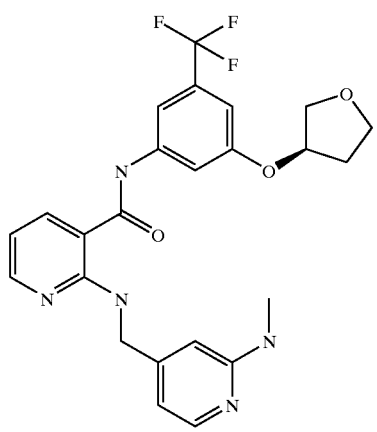

2-(((2-(methylamino)-4-pyridinyl)methyl)amino)-N-(3-((3R)-tetrahydro-3-furanyloxy)-5-(trifluoromethyl)phenyl)-3-pyridinecarboxamide

C24 H24 F3 N5 O3—487.48; M+H 488.

EXAMPLE 1084

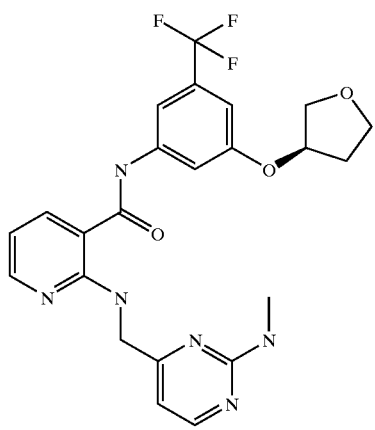

2-(((2-(methylamino)-4-pyrimidinyl)methyl)amino)-
N-(3-((3R)-tetrahydro-3-furanyloxy)-5-
(trifluoromethyl)phenyl)-3-pyridinecarboxamide

C23 H23 F3 N6 O3—488.468; M+H 489.

EXAMPLE 1085

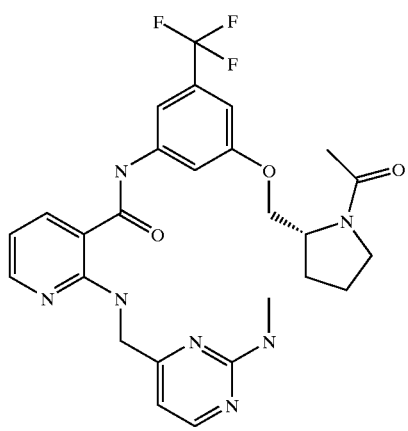

N-(3-((((2R)-1-acetyl-2-pyrrolidinyl)methyl)oxy)-5-
(trifluoromethyl)phenyl)-2-(((2-(methylamino)-4-
pyrimidinyl)methyl)amino)-3-pyridinecarboxamide

C26 H28 F3 N7 O3—543.547; M+H 544.

EXAMPLE 1086

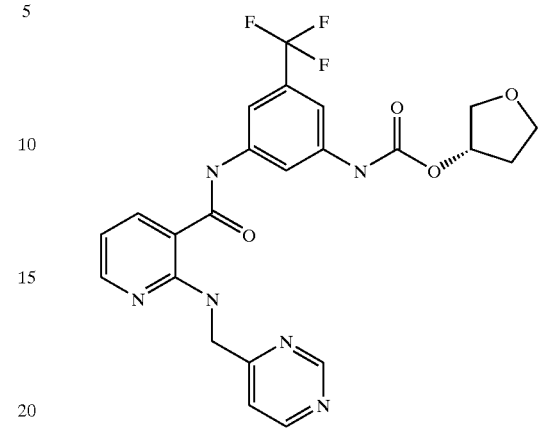

(3S)-tetrahydro-3-furanyl 3-(((2-((4-
pyrimidinylmethyl)amino)-3-pyridinyl)carbonyl)
amino)-5-(trifluoromethyl)phenylcarbamate C23 H21 F3 N6 O4—502.451; M+H 503, M+Na 525.

EXAMPLE 1087

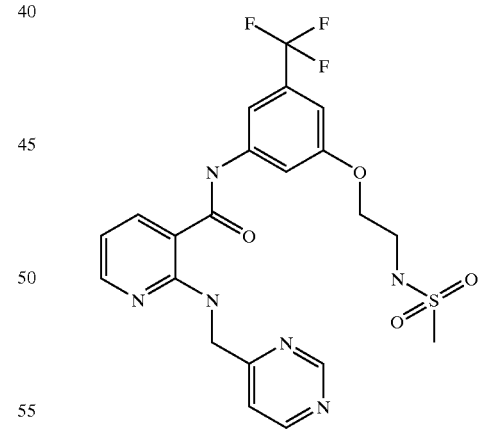

N-(3-((2-((methylsulfonyl)amino)ethyl)oxy)-5-
(trifluoromethyl)phenyl)-2-((4-pyrimidinylmethyl)
amino)-3-pyridinecarboxamide C21 H21 F3 N6 O4 S—510.495; M+H 511, M+Na 533.

EXAMPLE 1088

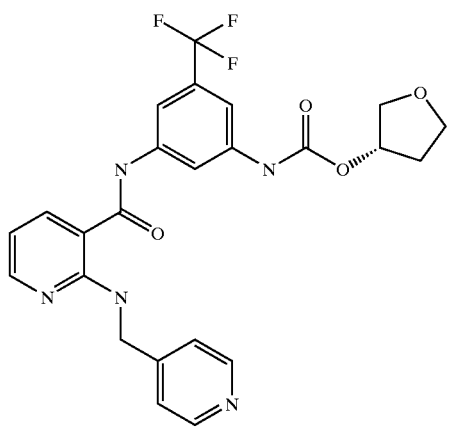

(3S)-tetrahydro-3-furanyl 3-(((2-((4-pyridinylmethyl)amino)-3-pyridinyl)carbonyl)amino)-5-(trifluoromethyl)phenylcarbamate C24 H22 F3 N5 O4—501.463; M+H 501, M+Na 524.

EXAMPLE 1089

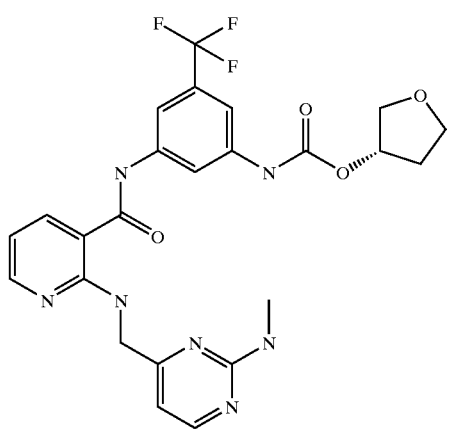

(3S)-tetrahydro-3-furanyl 3-(((2-(((2-(methylamino)-4-pyrimidinyl)methyl)amino)-3-pyridinyl)carbonyl)amino)-5-(trifluoromethyl)phenylcarbamate C24 H24 F3 N7 O4—531.493; M+H 532, M+Na 554.

EXAMPLE 1090

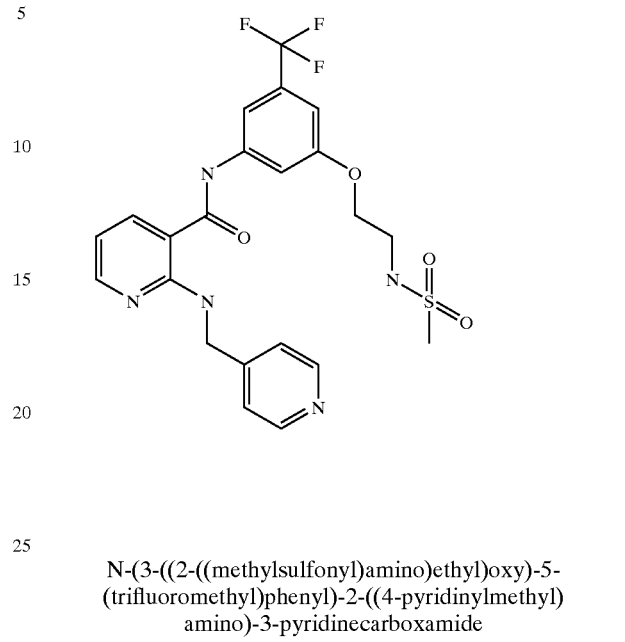

N-(3-((2-((methylsulfonyl)amino)ethyl)oxy)-5-(trifluoromethyl)phenyl)-2-((4-pyridinylmethyl)amino)-3-pyridinecarboxamide C22 H22 F3 N5 O4 S—509.507; M+H 510, M+Na 532.

EXAMPLE 1091

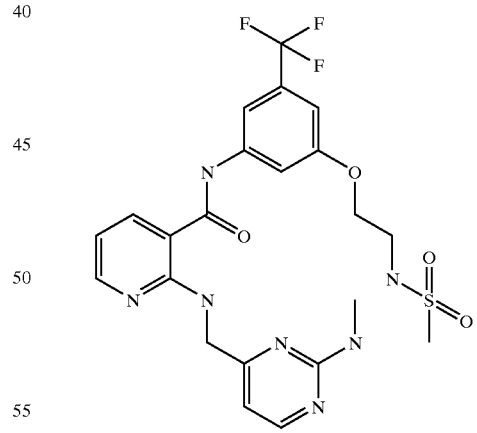

2-(((2-(methylamino)-4-pyrimidinyl)methyl)amino)-N-(3-((2-((methylsulfonyl)amino)ethyl)oxy)-5-(trifluoromethyl)phenyl)-3-pyridinecarboxamide C22 H24 F3 N7 O4 S—539.537; M+H 540, M+Na 562.

EXAMPLE 1092

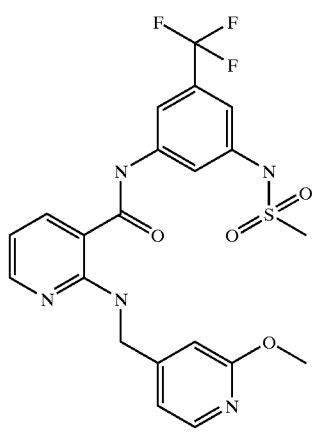

2-(((2-(methyloxy)-4-pyridinyl)methyl)amino)-N-(3-((methylsulfonyl)amino)-5-(trifluoromethyl)phenyl)-3-pyridinecarboxamide

C21 H21 F3 N5 O4 S—495.48; M+H 496.

EXAMPLE 1093

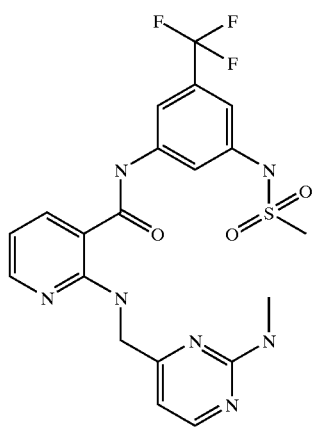

2-(((2-(methylamino)-4-pyrimidinyl)methyl)amino)-N-(3-((methylsulfonyl)amino)-5-(trifluoromethyl)phenyl)-3-pyridinecarboxamide C20 H20 F3 N7 O3 S—495.484; M+H 496, M+Na 518.

EXAMPLE 1094

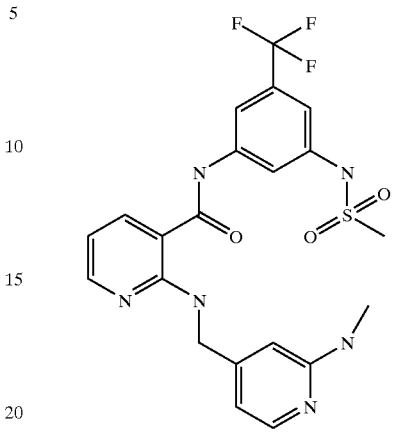

2-(((2-(methylamino)-4-pyridinyl)methyl)amino)-N-(3-((methylsulfonyl)amino)-5-(trifluoromethyl)phenyl)-3-pyridinecarboxamide

C21 H21 F3 N6 O3 S—494.496; M+H 495.

EXAMPLE 1095

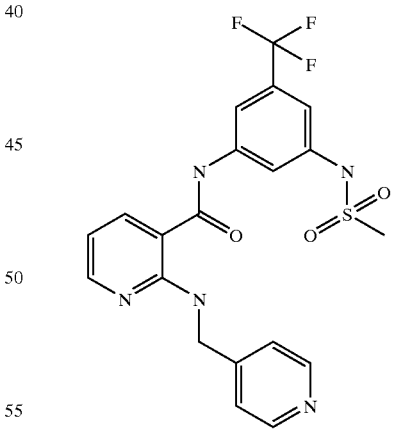

N-(3-((methylsulfonyl)amino)-5-(trifluoromethyl)phenyl)-2-((4-pyridinylmethyl)amino)-3-pyridinecarboxamide

MS: $C_{20}$ $H_{18}$ $F_3$ $N_5$ $O_3$ S—465.454; M+H 466.

EXAMPLE 1096

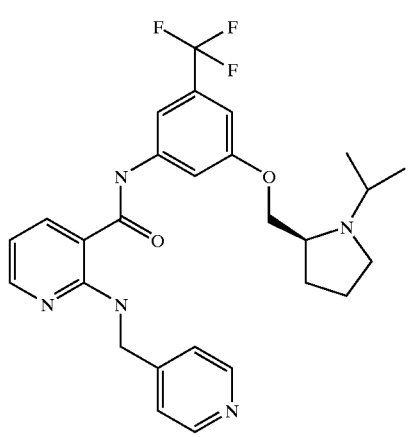

N-(3-((((2S)-1-(1-methylethyl)-2-pyrrolidinyl)methyl)oxy)-5-(trifluoromethyl)phenyl)-2-((4-pyridinylmethyl)amino)-3-pyridinecarboxamide

MS: $C_{27}H_{30}F_3N_5O_2$—513.561; M+H 514.

EXAMPLE 1097

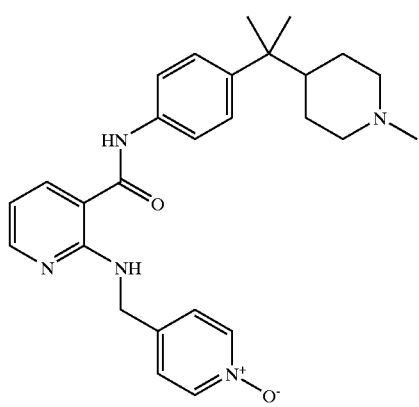

N-{4-[1-Methyl-1-(1-methyl-piperidin-4-yl)-ethyl]-phenyl}-2-[(1-oxy-pyridin-4-ylmethyl)-amino]-nicotinamide MS: (ES+) 460 (M+H). Calc'd. for $C_{27}H_{33}N_5O_2$—459.58.

EXAMPLE 1098

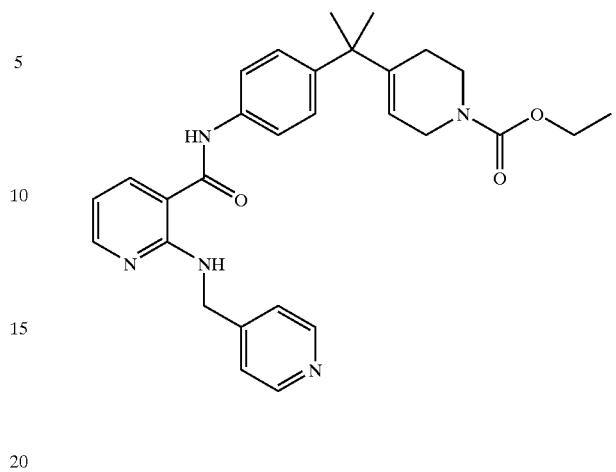

4-{1-Methyl-1-[4-({2-[(pyridin-4-ylmethyl)-amino]-pyridine-3-carbonyl}-amino)-phenyl]-ethyl}-3,6-dihydro-2H-pyridine-1-carboxylic Acid Ethyl Ester MS: (ES+) 500 (M+H). Calc'd. for $C_{29}H_{33}N_5O_3$—499.60.

EXAMPLE 1099

N-[3,3-Dimethyl-1-(1-oxy-pyridin-4-ylmethyl)-2,3-dihydro-1H-indol-6-yl]-2-[(pyridin-4-ylmethyl)-amino]-nicotinamide This compound was prepared via standard reductive amination conditions of N-(3,3-dimethyl-2,3-dihydro-1H-indol-6-yl)-2-[(pyridin-4-ylmethyl)-amino]-nicotinamide with 1-oxy-pyridine-4-carbaldehyde, as previously described.
MS: (ES+) 481 (M+H) Calc'd. for $C_{28}H_{28}N_6O_2$—480.56.

EXAMPLE 1100

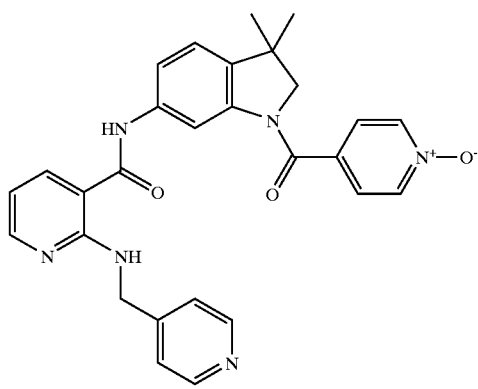

N-[3,3-Dimethyl-1-(1-oxy-pyridine-4-carbonyl)-2,3-dihydro-1H-indol-6-yl]-2-[(pyridin-4-ylmethyl)-amino]-nicotinamide To a solution of N-(3,3-dimethyl-2,3-dihydro-1H-indol-6-yl)-2-[(pyridin-4-ylmethyl)-amino]-nicotinamide (374 mg, 1 mmol) in a mixture of DCM (20 mL) and DMF (10 mL) were added EDC (400 mg, 2 mmol), HOBt (80 mg) and DIEA (0.5 mL). The reaction mixture was stirred at RT overnight. After removing solvents in vacuo, the residue was suspended in water. The mixture was sonicated for 5 min and a precipitation was received after filtration. The filter cake was washed with water and then dried in a vacuum oven at RT. The dried solid was then purified via preparative TLC on silica gel (DCM:EtOH:TEA=100:3:6) to afford the desired product. MS: (ES+) 495 (M+H). Calc'd. for $C_{28}H_{26}N_6O_3$—494.54.

EXAMPLE 1101

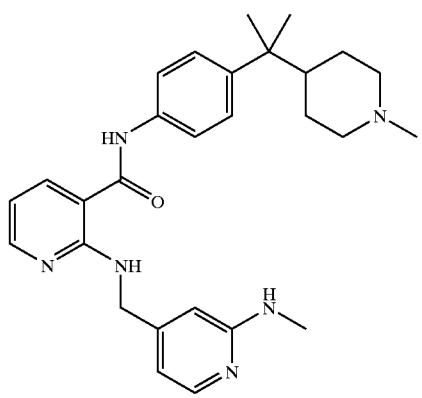

2-[(2-Methylamino-pyridin-4-ylmethyl)-amino]-N-{4-[1-methyl-1-(1-methyl-piperidin-4-yl)-ethyl]-phenyl}-nicotinamide MS: (ES+) 473 (M+H). Calc'd. for $C_{28}H_{36}N_6O$—472.63.

EXAMPLE 1102

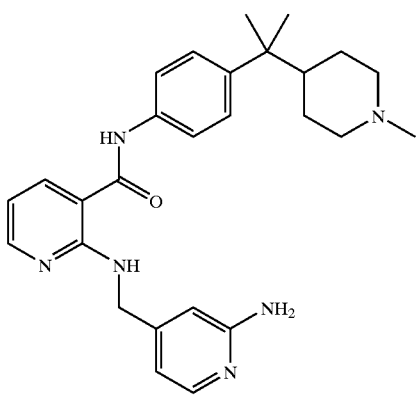

2-[(2-Amino-pyridin-4-ylmethyl)-amino]-N-{4-[1-methyl-1-(1-methyl-piperidin-4-yl)-ethyl]-phenyl}-nicotinamide MS: (ES+) 459 (M+H). Calc'd. for $C_{27}H_{34}N_6O$—458.60.

EXAMPLE 1103

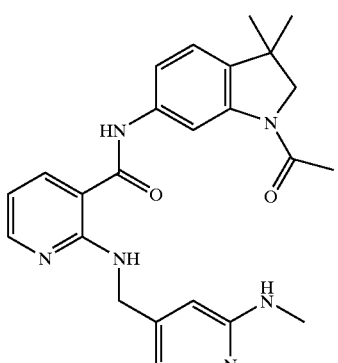

N-(1-Acetyl-3,3-dimethyl-2,3-dihydro-1H-indol-6-yl)-2-[(2-methylamino-pyridin-4-ylmethyl)-amino]-nicotinamide MS: (ES+) 445 (M+H). Calc'd. for $C_{25}H_{28}N_6O_2$—444.53.

EXAMPLE 1104

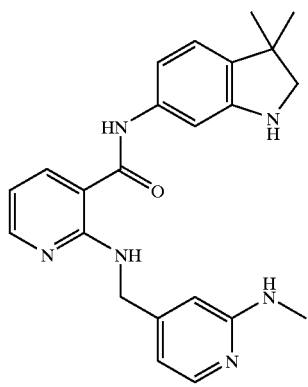

N-(3,3-Dimethyl-2,3-dihydro-1H-indol-6-yl)-2-[(2-methylamino-pyridin-4-ylmethyl)-amino]-nicotinamide MS: (ES+) 403 (M+H). Calc'd. for $C_{23}H_{26}N_6O$—402.49.

EXAMPLE 1105

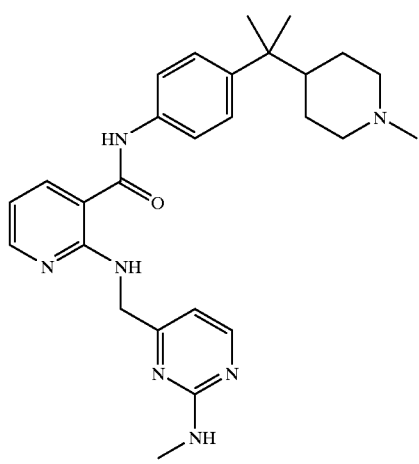

2-[(2-Methylamino-pyrimidin-4-ylmethyl)-amino]-N-{4-[1-methyl-1-(1-methyl-piperidin-4-yl)-ethyl]-phenyl}-nicotinamide MS: (ES+) 474 (M+H). Calc'd. for $C_{27}H_{35}N_7O$—473.61.

EXAMPLE 1106

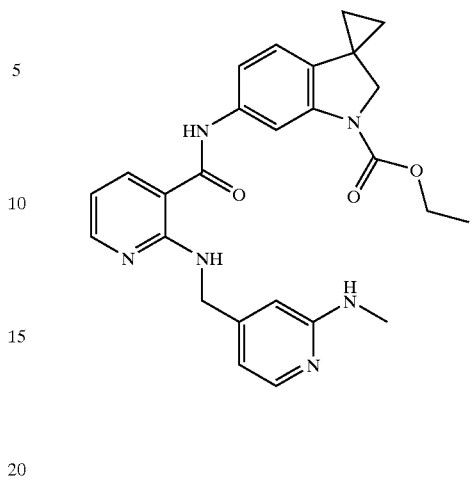

Ethyl[1,2-dihydro-6-({2-[(2-methylamino-pyridin-4-ylmethyl)-amino]-pyridine-3-carbonyl}-amino)-3-spiro-1'-cyclopropyl-1H-indole]-1-carbamate MS: (ES+) 473 (M+H). Calc'd. for $C_{26}H_{28}N_6O_3$—472.54.

EXAMPLE 1107

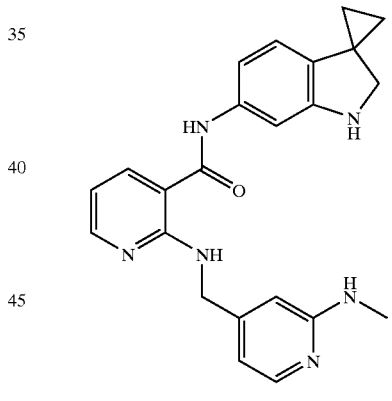

N-(1,2-dihydroindol-3-spiro-1'-cyclopropane-6-yl)-2-[(2-methylaminopyridin-4-ylmethyl)-amino]-nicotinamide A suspension of ethyl[1,2-dihydro-6-({2-[(2-methylamino-pyridin-4-ylmethyl)-amino]-pyridine-3-carbonyl}-amino)-3-spiro-1'-cyclopropyl-1H-indole]-1-carbamate (70 mg) in EtOH (1 mL) with aqueous NaOH (2N, 0.2 mL) and anhydrous hydrazine (0.2 mL) was microwaved in a Smith Synthesizer at 100° C. for 30 min. After cooling to RT, the mixture was filtered to give a white crystalline solid as the desired product. MS: (ES+) 401 (M+H). Calc'd. for $C_{23}H_{24}N_6O$—400.48.

EXAMPLE 1108

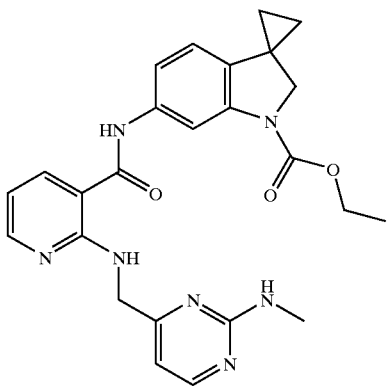

Ethyl[1,2-dihydro-6-({2-[(2-methylamino-pyrimidin-4-ylmethyl)-amino]-pyridine-3-carbonyl}-amino)-3-spiro-1'-cyclopropyl-1H-indole]-1-carbamate MS: (ES+) 474 (M+H). Calc'd. for $C_{25}H_{27}N_7O_3$—473.53.

EXAMPLE 1109

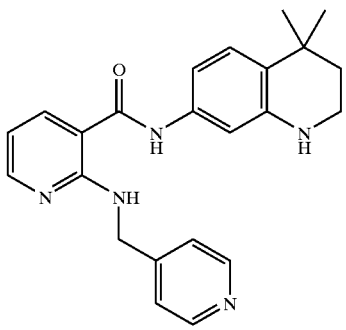

N-(4,4-Dimethyl-1,2,3,4-tetrahydro-quinolin-7-yl)-2-[(pyridin-4-ylmethyl)-amino]-nicotinamide The mixture of N-(4,4-Dimethyl-1,2,3,4-tetrahydro-quinolin-7-yl)-2-fluoro-nicotinamide(0.26 g, 0.87 mmol),4-(aminomethyl) (0.27 ml, 2.61 mmol), and NaHCO$_3$ (0.15 g, 1.74 mmol) in 1.5 ml of 2-propanol was stirred at 85° C. for 24 h and filtered. The filtrate was condensed, and the residue was purified by flash column chromatography (2% of MeOH in CH$_2$Cl$_2$). The titled compound was obtained as an off-white solid. MS (ES$^+$): 388.0 (M+H)$^+$. Calc'd for $C_{23}H_{25}N_5O$—387.48.

EXAMPLE 1110

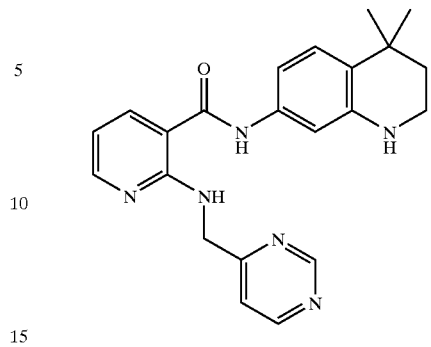

N-(4,4-Dimethyl-1,2,3,4-tetrahydro-quinolin-7-yl)-2-[(pyrimidin-4-ylmethyl)-amino]-nicotinamide MS (ES$^+$): 389.2 (M+H)$^+$. Calc'd for $C_{22}24_6N_6O$—388.47.

EXAMPLE 1111

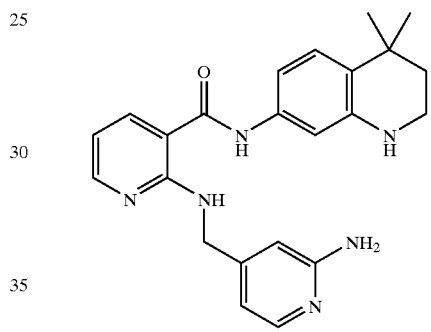

2-[(2-Amino-pyridin-4-ylmethyl)-amino]-N-(4,4-dimethyl-1,2,3,4-tetrahydro-quinolin-7-yl)-nicotinamide MS (ES$^+$): 403.2 (M+H)$^+$. Calc'd for $C_{17}H_{16}FN_3O_2$—402.49.

EXAMPLE 1112

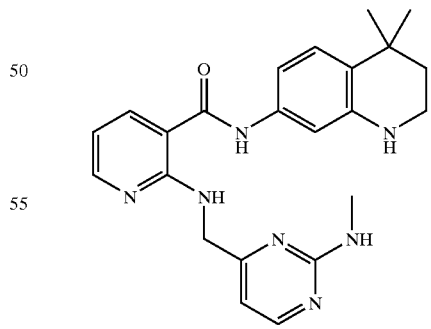

N-(4,4-Dimethyl-1,2,3,4-tetrahydro-quinolin-7-yl)-2-[(2-methylamino-pyrimidin-4-ylmethyl)-amino]-nicotinamide MS: (ES+) 418.2 (M+H). Calc'd. for $C_{23}H_{27}N_7O$—417.51.

EXAMPLE 1113

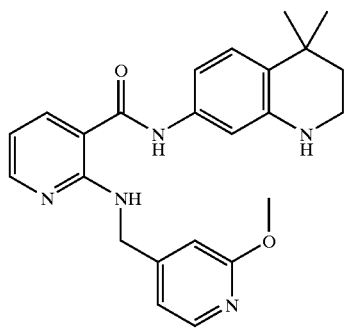

N-(4,4-Dimethyl-1,2,3,4-tetrahydro-quinolin-7-yl)-
2-[(2-methoxy-pyridin-4-ylmethyl)-amino]-
nicotinamide MS: (ES+) 418.1 (M+H). Calc'd. for $C_{24}H_{27}N_5O_2$—417.5.

EXAMPLE 1114

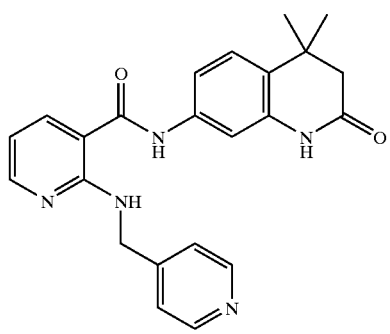

N-(4,4-Dimethyl-2-oxo-1,2,3,4-tetrahydro-quinolin-
7-yl)-2-[(pyridin-4-ylmethyl)-amino]-nicotinamide MS (ES+): 402.6 (M+H)+. Calc'd for $C_{23}H_{23}N_5O_2$—401.47.

EXAMPLE 1115

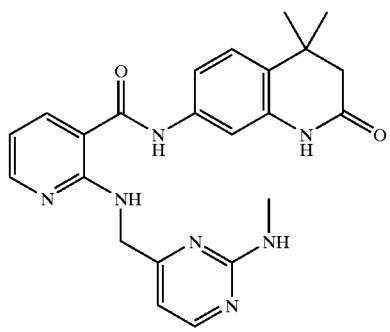

N-(4,4-Dimethyl-2-oxo-1,2,3,4-tetrahydro-quinolin-
7-yl)-2-[(2-methylamino-pyrimidin-4-ylmethyl)-
amino]-nicotinamide MS: (ES+) 432.1(M+H). Calc'd. for $C_{23}H_{25}N_7O_2$—431.49.

EXAMPLE 1116

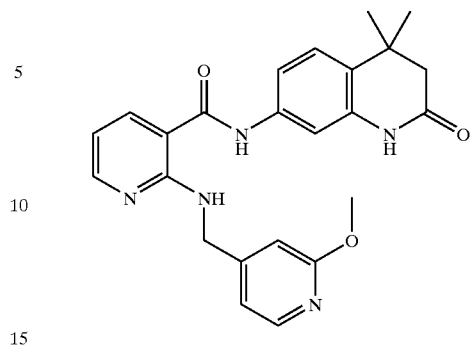

N-(4,4-Dimethyl-2-oxo-1,2,3,4-tetrahydro-quinolin-
7-yl)-2-[(2-methoxy-pyridin-4-ylmethyl)-amino]-
nicotinamide MS: (ES+) 432.3 (M+H). Calc'd. for $C_{24}H_{25}N_5O_3$—431.49.

EXAMPLE 1117

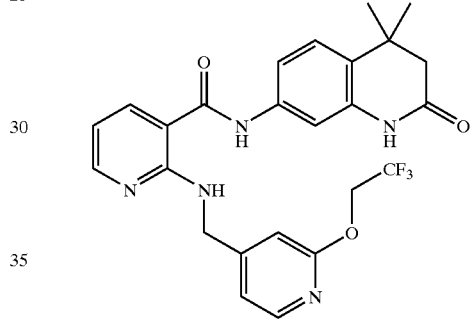

N-(4,4-Dimethyl-2-oxo-1,2,3,4-tetrahydro-quinolin-
7-yl)-2-{[2-(2,2,2-trifluoro-ethoxy)-pyridin-4-
ylmethyl]-amino}-nicotinamide MS: (ES+) 500.1 (M+H). Calc'd. for $C_{25}H_{24}F_3N_5O_3$—499.49.

EXAMPLE 1118

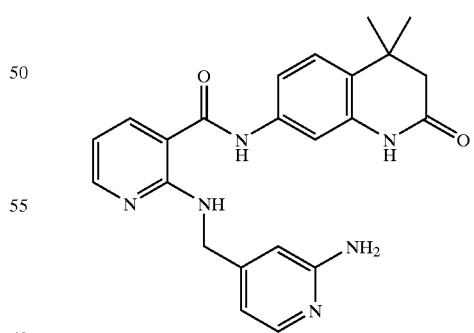

2-[(2-Amino-pyridin-4-ylmethyl)-amino]-N-(4,4-
dimethyl-2-oxo-1,2,3,4-tetrahydro-quinolin-7-yl)-
nicotinamide MS: (ES+) 417.2 (M+H). Calc'd. for $C_{23}H_{24}N_6O_2$—416.48.

EXAMPLE 1119

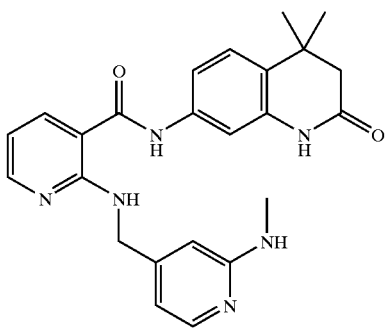

N-(4,4-Dimethyl-2-oxo-1,2,3,4-tetrahydro-quinolin-7-yl)-2-[(2-methylamino-pyridin-4-ylmethyl)-amino]-nicotinamide MS: (ES+) 431.2(M+H). Calc'd. for $C_{24}H_{26}N_6O_2$—430.50.

EXAMPLE 1120

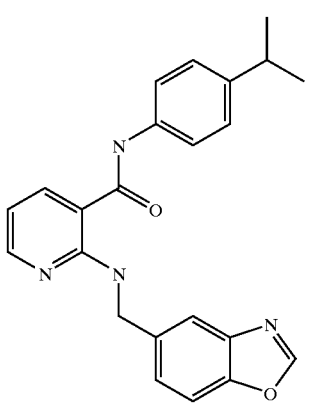

2-((1,3-Benzoxazol-5-ylmethyl)amino)-N-(4-(1-methylethyl)phenyl)-3-pyridinecarboxamide

EXAMPLE 1121

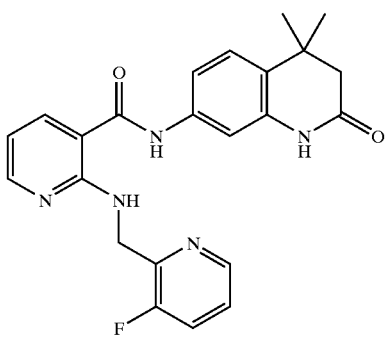

N-(4,4-Dimethyl-2-oxo-1,2,3,4-tetrahydro-quinolin-7-yl)-2-[(3-fluoro-pyridin-2-ylmethyl)-amino]-nicotinamide MS: (ES+) 420.1(M+H). Calc'd. for $C_{24}H_{23}FN_4O$—419.45.

EXAMPLE 1122

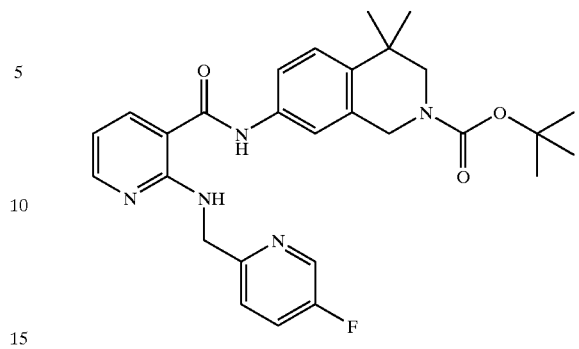

tert-Butyl N-[7-({2-[(5-fluoro-pyridin-2-ylmethyl)-amino]-pyridine-3-carbonyl}-amino)-4,4-dimethyl-3,4-dihydro-1H-isoquinoline]carbamate MS: (ES+) 506.5 (M+H). Calc'd. for $C_{28}H_{32}FN_5O_3$—505.59.

EXAMPLE 1123

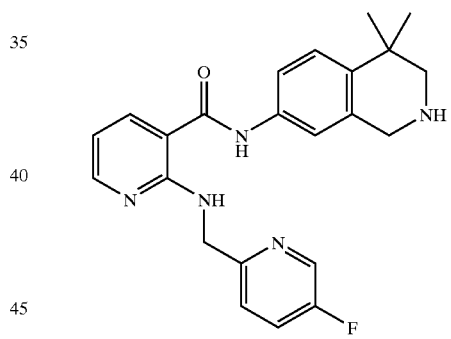

N-(4,4-Dimethyl-1,2,3,4-tetrahydro-isoquinolin-7-yl)-2-[(5-fluoro-pyridin-2-ylmethyl)-amino]-nicotinamide 2.5 ml of TFA was added to a solution of 7-({2-[(5-fluoro-pyridin-2-ylmethyl)-amino]-pyridine-3-carbonyl}-amino)-4,4-dimethyl-3,4-dihydro-1H-isoquinoline-2-carboxylic acid tert-butyl ester (0.20 g, 0.40 mmol) in 2.5 ml of $CH_2Cl_2$. The mixture was stirred at RT for 1 h. The volatiles were removed under reduced pressure, and the residue was purified by flash column chromatography (2 to 5% of MeOH in $CH_2Cl_2$ with 2% of $NH_4OH$). The titled compound was obtained as an off-white solid. MS: (ES+) 406.1 (M+H). Calc'd. for $C_{23}H_{24}FN_5O$—405.47.

EXAMPLE 1124

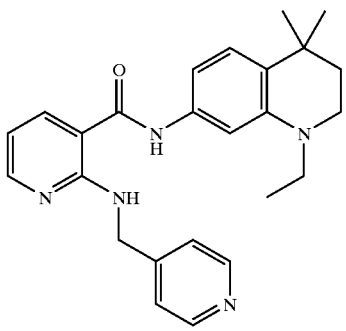

N-(1-Ethyl-4,4-dimethyl-1,2,3,4-tetrahydro-quinolin-7-yl)-2-[(pyridin-4-ylmethyl)-amino]-nicotinamide MS (ES+): 416.3 (M+H)+. Calc'd for $C_{25}H_{29}N_5O$—415.54.

EXAMPLE 1125

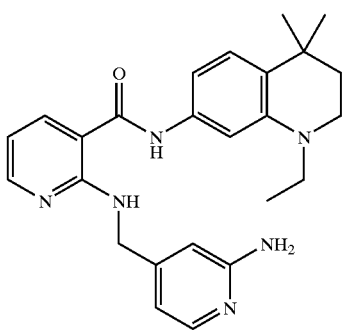

2-[(2-Amino-pyridin-4-ylmethyl)-amino]-N-(1-ethyl-4,4-dimethyl-1,2,3,4-tetrahydro-quinolin-7-yl)-nicotinamide MS (ES+): 431.3 (M+H)+. Calc'd for $C_{25}H_{30}N_6O$—430.55.

EXAMPLE 1126

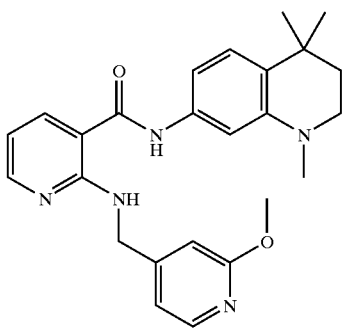

2-[(2-Methoxy-pyridin-4-ylmethyl)-amino]-N-(1,4,4-trimethyl-1,2,3,4-tetrahydro-quinolin-7-yl)-nicotinamide MS (ES+): 432.2(M+H)+. Calc'd for $C_{25}H_{29}N_5O_2$—431.53.

EXAMPLE 1127

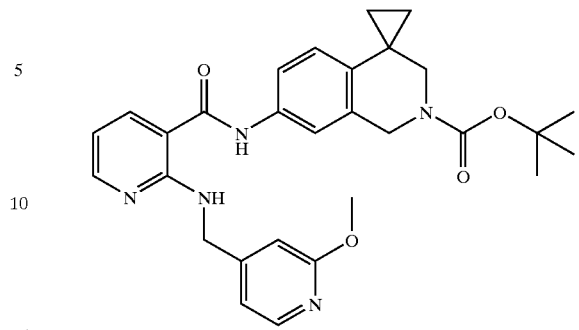

tert-Butyl N-[7-({2-[(2-methoxy-pyridin-4-ylmethyl)-amino]-pyridine-3-carbonyl}-amino)-4-spiro-1'-cyclopropane-3,4-dihydro-1H-isoquinoline] carbamate MS (ES+): 516.3 (M+H)+. Calc'd for $C_{29}H_{33}N_5O_4$—515.59.

EXAMPLE 1128

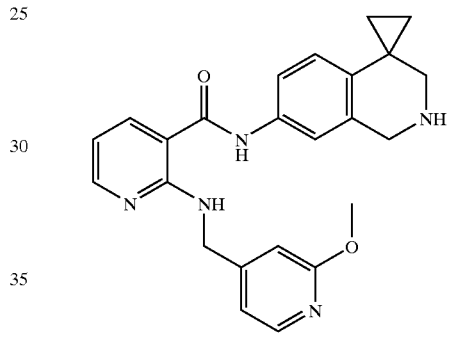

N-(4-Spiro-1'-cyclopropane-1,2,3,4-tetrahydroisoquinolin-7-yl)-2-[(2-methoxy-pyridin-4-ylmethyl)-amino]-nicotinamide MS (ES+): 416.2 (M+H)+. Calc'd for $C_{24}H_{25}N_5O_2$—415.50.

EXAMPLE 1129

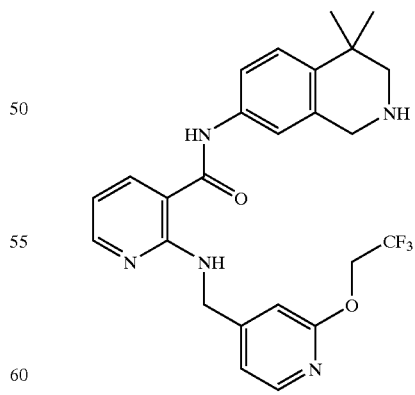

N-(4,4-Dimethyl-1,2,3,4-tetrahydro-isoquinolin-7-yl)-2-{[2-(2,2,2-trifluoro-ethoxy)-pyridin-4-ylmethyl]-amino}-nicotinamide MS (ES+) 486 (M+H)+. Calc'd. for $C_{25}H_{26}F_3N_5O_2$—485.20.

EXAMPLE 1130

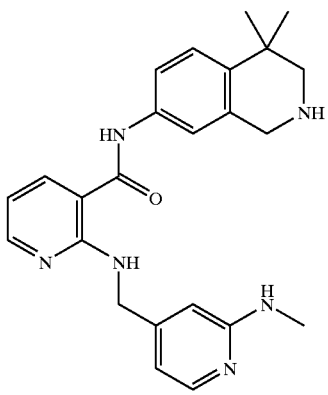

N-(4,4-Dimethyl-1,2,3,4-tetrahydro-isoquinolin-7-yl)-2-[(2-methylamino-pyridin-4-ylmethyl)-amino]-nicotinamide MS (ES+): 417 (M+H)$^+$. Calc'd. for $C_{24}H_{28}N_6O$—416.23.

EXAMPLE 1131

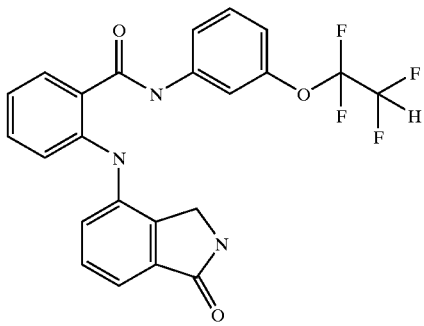

2-((1-Oxo-2,3-dihydro-1H-isoindol-4-yl)amino)-N-(3-((1,1,2,2-tetrafluoroethyl)oxy)phenyl)benzamide

EXAMPLE 1132

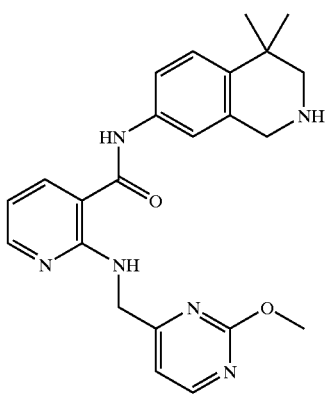

N-(4,4-Dimethyl-1,2,3,4-tetrahydro-isoquinolin-7-yl)-2-[(2-methoxy-pyrimidin-4-ylmethyl)-amino]-nicotinamide MS (ES+): 419 (M+H)$^+$. Calc'd. for $C_{23}H_{26}N_6O_2$—418.21.

EXAMPLE 1133

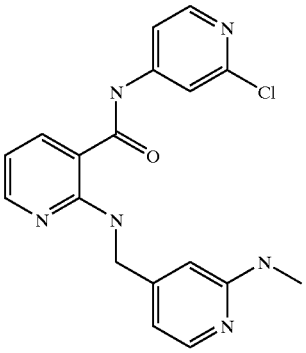

N-(2-Chloro-pyridin-4-yl)-2-[(2-methylamino-pyridin-4-ylmethyl)-amino]-nicotinamide MS m/z: 369.1 (M+H). Calc'd. for $C_{18}H_{17}ClN_6O$—368.12.

EXAMPLE 1134

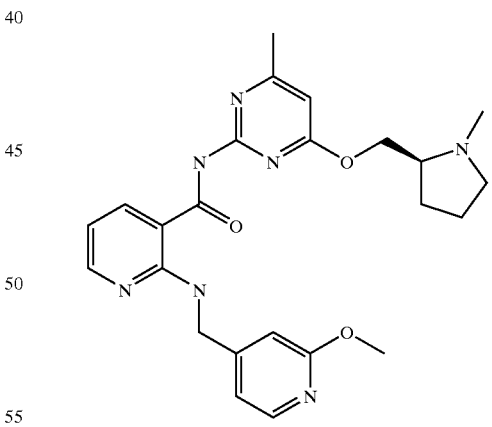

2-[(2-Methoxy-pyridin-4-ylmethyl)-amino]-N-[4-methyl-6-(1-methyl-pyrrolidin-2-ylmethoxy)-pyrimidin-2-yl]-nicotinamide MS m/z: 464.2 (M+H). Calc'd. for $C_{24}H_{29}N_7O_3$—463.2.

EXAMPLE 1135

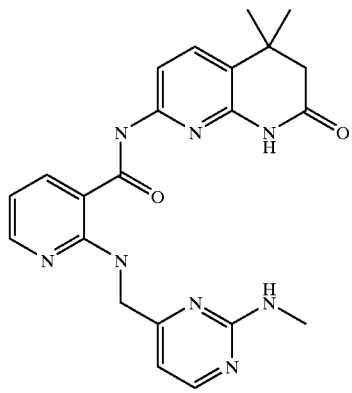

N-(5,5-Dimethyl-7-oxo-5,6,7,8-tetrahydro-[1,8]naphthyridin-2-yl)-2-[(2-methylamino-pyrimidin-4-ylmethyl)-amino]-nicotinamide MS m/z: 433.3 (M+H). Calc'd. for $C_{22}H_{24}N_8O_2$—432.2.

EXAMPLE 1136

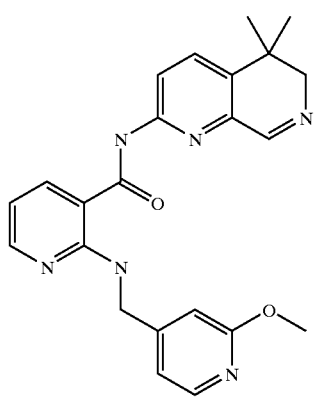

N-(5,5-Dimethyl-5,6-dihydro-[1,7]naphthyridin-2-yl)-2-[(2-methoxy-pyridin-4-ylmethyl)-amino]-nicotinamide MS m/z: 416.3 (M+H). Calc'd. for $C_{23}H_{24}N_6O_2$—415.2.

EXAMPLE 1137

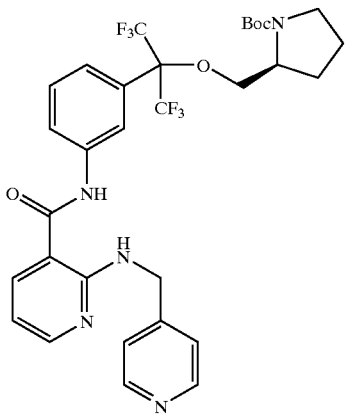

2-{2,2,2-Trifluoro-1-[3-({2-[(pyridin-4-ylmethyl)-amino]-pyridine-3-carbonyl}-amino)-phenyl]-1-trifluoromethyl-ethoxymethyl}-pyrrolidine-1-carboxylic Acid tert-butyl Ester MS: (ES+) 654 (M+H). Calc'd. for $C_{31}H_{33}F_6N_5O_4$—653.62.

EXAMPLE 1138

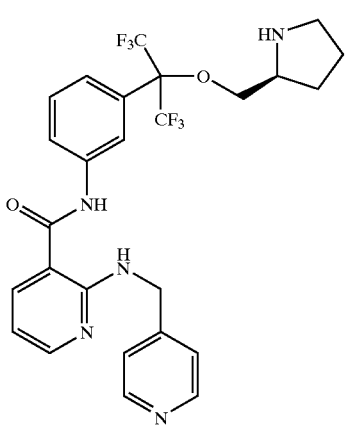

2-[(Pyridin-4-ylmethyl)-amino]-N-{3-[2,2,2-trifluoro-1-(pyrrolidin-2-ylmethoxy)-1-trifluoromethyl-ethyl]-phenyl}-nicotinamide MS: (ES+) 554(M+H). Calc'd. for $C_{26}H_{25}F_6N_5O_2$—553.51.

EXAMPLE 1139

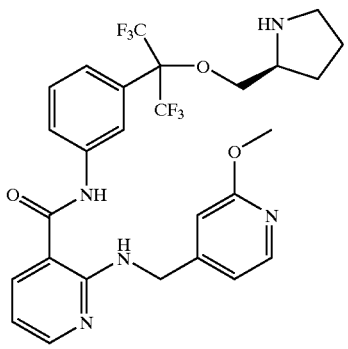

2-[(2-Methoxy-pyridin-4-ylmethyl)-amino]-N-{3-[2,2,2-trifluoro-1-(pyrrolidin-2-ylmethoxy)-1-trifluoromethyl-ethyl]-phenyl}-nicotinamide MS: (ES+) 584 (M+H). Calc'd. for $C_{27}H_{27}F_6N_5O_3$—583.53.

EXAMPLE 1140

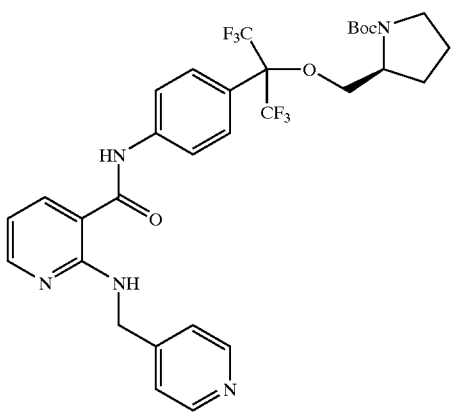

2-{2,2,2-Trifluoro-1-[4-({2-[(pyridin-4-ylmethyl)-amino]-pyridine-3-carbonyl}-amino)-phenyl]-1-trifluoromethyl-ethoxymethyl}-pyrrolidine-1-carboxylic Acid tert-butyl Ester Step A: Preparation of 2-[1-(4-Amino-phenyl)-2,2,2-trifluoro-1-trifluoromethyl-ethoxymethyl]-pyrrolidine-1-carboxylic Acid tert-butyl Ester To a mixture of 2-(4-amino-phenyl)-1,1,1,3,3,3-hexafluoro-propan-2-ol (1.30 g), 2-hydroxymethyl-pyrrolidine-1-carboxylic acid tert-butyl ester (1.00 g), PPh$_3$ (1.56 g) and molecular sieves 4 Å in THF (100 mL) was added DEAD (0.93 mL) slowly. The reaction was stirred at RT for 5 h and at reflux for overnight. After filtration to remove solids, the filtrate was concentrated and the residue was taken into ether. The organic phase was washed with saturated NaHCO$_3$ and brine. The organic layer was dried over MgSO$_4$ and evaporated to give a crude product as a very viscous brown oil which was chromatographed through silica gel (400 g, 2:1:7 to 3:1:6 EtOAc/Et3N/hexanes) to afford 2-[1-(4-amino-phenyl)-2,2,2-trifluoro-1-trifluoromethyl-ethoxymethyl]-pyrrolidine-1-carboxylic acid tert-butyl ester as a light brown oil.

The title compound was synthesized from the above aniline in analogous to what was described previously. MS: (ES+) 654 (M+H). Calc'd. for $C_{31}H_{33}F_6N_5O_4$—653.62.

EXAMPLE 1141

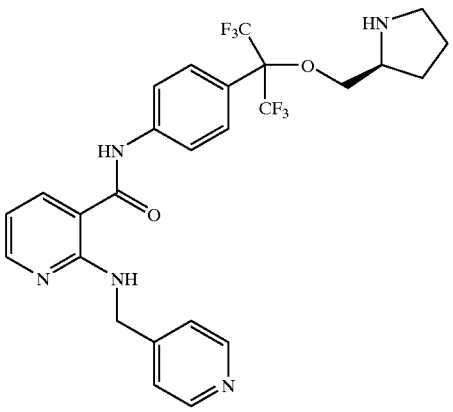

2-[(Pyridin-4-ylmethyl)-amino]-N-{4-[2,2,2-trifluoro-1-(pyrrolidin-2-ylmethoxy)-1-trifluoromethyl-ethyl]-phenyl}-nicotinamide This compound was obtained via standard procedures for deprotecting a Boc group from an amine, in analogous to previously described in this document. MS: (ES+) 554(M+H). Calc'd. for $C_{26}H_{25}F_6N_5O_2$—553.51.

EXAMPLE 1142

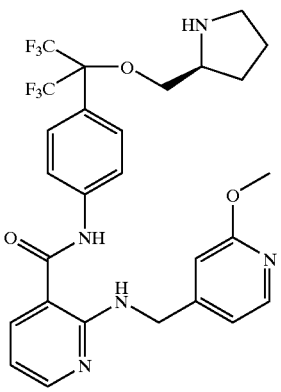

2-[(2-Methoxy-pyridin-4-ylmethyl)-amino]-N-{4-[2,2,2-trifluoro-1-(pyrrolidin-2-ylmethoxy)-1-trifluoromethyl-ethyl]-phenyl}-nicotinamide MS: (ES+) 584 (M+H). Calc'd. for $C_{27}H_{27}F_6N_5O_3$—583.53.

EXAMPLE 1143

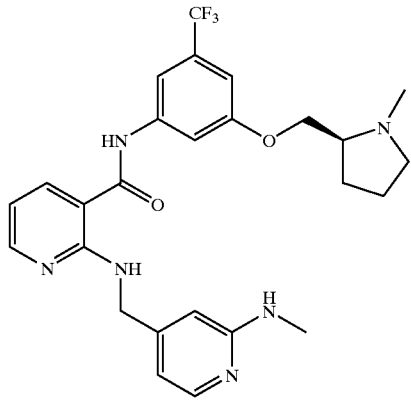

2-[(2-Methylamino-pyridin-4-ylmethyl)-amino]-N-[3-(1-methyl-pyrrolidin-2-ylmethoxy)-5-trifluoromethyl-phenyl]-nicotinamide MS: (ES+) 515 (M+H). Calc'd. for $C_{26}H_{29}F_3N_6O_2$—514.55.

EXAMPLE 1144

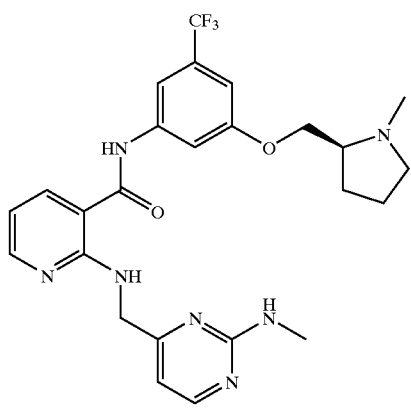

2-[(2-Methylamino-pyrimidin-4-ylmethyl)-amino]-N-[3-(1-methyl-pyrrolidin-2-ylmethoxy)-5-trifluoromethyl-phenyl]-nicotinamide MS: (ES+) 516 (M+H). Calc'd. for $C_{25}H_{28}F_3N_7O_2$—515.53.

EXAMPLE 1145

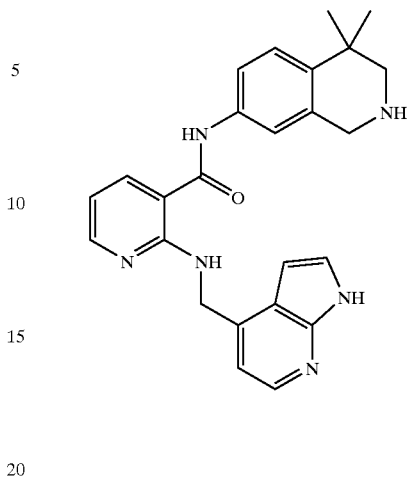

N-(4,4-Dimethyl-1,2,3,4-tetrahydro-isoquinolin-7-yl)-2-[(1H-pyrrolo[2,3-b]pyridin-4-ylmethyl)-amino]-nicotinamide Step A: Preparation of 4,4-Dimethyl-7-({2-[(1H-pyrrolo[2,3-b]pyridin-4-ylmethyl)-amino]-pyridine-3-carbonyl}-amino)-3,4-dihydro-1H-isoquinoline-2-carboxylic Acid tert-butyl Ester A mixture of 7-[(2-fluoro-pyridine-3-carbonyl)-amino]-4,4-dimethyl-3,4-dihydro-1H-isoquinoline-2-carboxylic acid tert-butyl ester (0.24 g), 1-(4-aminomethyl-pyrrolo[2,3-b]pyridin-1-yl)-ethanone (0.14 g), DIEA (0.8 mL) and IpOH (0.8 mL) was subjected to a MicroWave condition (170° C., 1000 s) twice. Evaporation of solvent yielded the crude compound, which was purified by chromatography through silica gel (15 g, 5% MeOH/CH$_2$Cl$_2$) to afford 4,4-dimethyl-7-({2-[(1H-pyrrolo[2,3-b]pyridin-4-ylmethyl)-amino]-pyridine-3-carbonyl}-amino)-3,4-dihydro-1H-isoquinoline-2-carboxylic acid tert-butyl ester.

Step B: Preparation of N-(4,4-dimethyl-1,2,3,4-tetrahydro-isoquinolin-7-yl)-2-[(1H-pyrrolo[2,3-b]pyridin-4-ylmethyl)-amino]-nicotinamide A mixture of 4,4-dimethyl-7-({2-[(1H-pyrrolo[2,3-b]pyridin-4-ylmethyl)-amino]-pyridine-3-carbonyl}-amino)-3,4-dihydro-1H-isoquinoline-2-carboxylic acid tert-butyl ester (0.115 g, step A), HCl (4N, 3 mL) and dioxane (4 mL) was stirred at RT for overnight. Sat'd NaHCO$_3$ was added until the bubbling stopped. The aqueous phase was extracted with EtOAc 3 times. The combined organic phases were dried over Na$_2$SO$_4$ and evaporated to yield a light purple oil as a crude product, which was purified by chromatography through silica gel (10 g, 5% MeOH/CHCl$_3$ with 1% NH$_4$OH) to afford N-(4,4-dimethyl-1,2,3,4-tetrahydro-isoquinolin-7-yl)-2-[(1H-pyrrolo[2,3-b]pyridin-4-ylmethyl)-amino]-nicotinamide. The material was further purified via silica gel column chromatography (10 g, 1% to 5% MeOH/CH$_2$Cl$_2$, stepwise gradient) to afford pure title compound. MS: (ES+) 427 (M+H). Calc'd. for $C_{25}H_{26}N_6O$—426.51.

EXAMPLE 1146

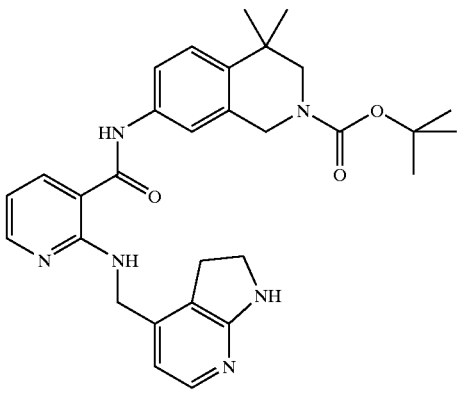

7-({2-[(2,3-Dihydro-1H-pyrrolo[2,3-b]pyridin-4-ylmethyl)-amino]-pyridine-3-carbonyl}-amino)-4,4-dimethyl-3,4-dihydro-1H-isoquinoline-2-carboxylic Acid tert-butyl Ester A mixture of 7-[(2-fluoro-pyridine-3-carbonyl)-amino]-4,4-dimethyl-3,4-dihydro-1H-isoquinoline-2-carboxylic acid tert-butyl ester (0.187 g), C-(2,3-dihydro-1H-pyrrolo[2,3-b]pyridin-4-yl)-methylamine HCl salt (0.098 g, step B), DIEA (1.0 mL) and IpOH (1.5 mL) was subjected to a Microwave condition (170° C., 1000 s). Solvent was removed and the residue was purified by chromatography through silica gel (70 g, 1–4% MeOH/CH$_2$Cl$_2$ with 1% NH$_4$OH, stepwise gradient) to afford 7-({2-[(2,3-dihydro-1H-pyrrolo[2,3-b]pyridin-4-ylmethyl)-amino]-pyridine-3-carbonyl}-amino)-4,4-dimethyl-3,4-dihydro-1H-isoquinoline-2-carboxylic acid tert-butyl ester as cream color solid. MS: (ES+) 529 (M+H). Calc'd. for C$_{30}$H$_{36}$N$_6$O$_3$—528.65.

EXAMPLE 1147

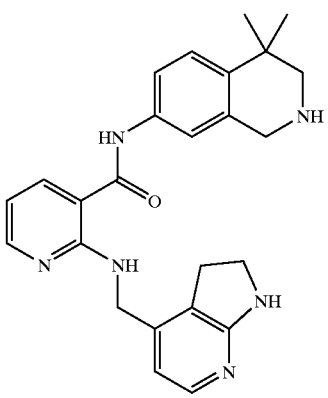

2-[(2,3-Dihydro-1H-pyrrolo[2,3-b]pyridin-4-ylmethyl)-amino]-N-(4,4-dimethyl-1,2,3,4-tetrahydro-isoquinolin-7-yl)-nicotinamide A mixture of 7-({2-[(2,3-dihydro-1H-pyrrolo[2,3-b]pyridin-4-ylmethyl)-amino]-pyridine-3-carbonyl}-amino)-4,4-dimethyl-3,4-dihydro-1H-isoquinoline-2-carboxylic acid tert-butyl ester (0.070 g), HCl (4N, 3.0 mL) and dioxane (4.0 mL) was stirred at RT for overnight. Sat'd NaHCO$_3$ was added until the bubbling stopped. The aqueous phase was extracted with CH$_2$Cl$_2$ 3 times. The combined organic phases were dried over Na$_2$SO$_4$ and evaporated to yield a tan colored residue as a crude product, which was chromatographed through HPLC. The fractions were collected and the solvent was evaporated. The residue was treated with NaHCO$_3$ and the solvent was evaporated. The residue was washed with H$_2$O to remove any inorganics to afford 2-[(2,3-dihydro-1H-pyrrolo[2,3-b]pyridin-4-ylmethyl)-amino]-N-(4,4-dimethyl-1,2,3,4-tetrahydro-isoquinolin-7-yl)-nicotinamide. MS: (ES+) 429 (M+H). Calc'd. for C$_{25}$H$_{28}$N$_6$O—428.54.

EXAMPLE 1148

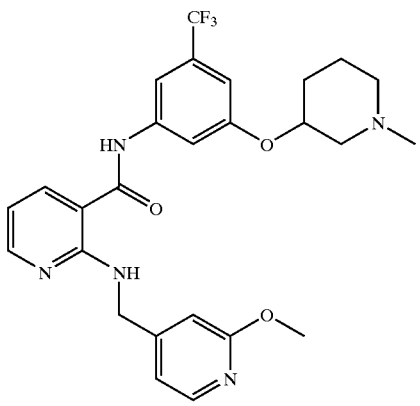

2 2-[(2-Methoxy-pyridin-4-ylmethyl)-amino]-N-[3-(1-methyl-piperidin-3-yloxy)-5-trifluoromethyl-phenyl]-nicotinamide MS: (ES+) 516 (M+H). Calc'd. for C$_{26}$H$_{29}$F$_3$N$_6$O$_2$—515.53.

EXAMPLE 1149

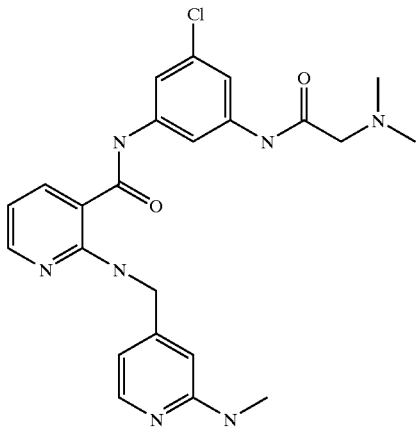

N-[3-Chloro-5-(2-dimethylamino-acetylamino)-phenyl]-2-[(2-methylamino-pyridin-4-ylmethyl)-amino]-nicotinamide MS: (ES+) 468 (M+H). Calc'd. for C$_{23}$H$_{26}$ClN$_7$O$_2$—467.96.

EXAMPLE 1150

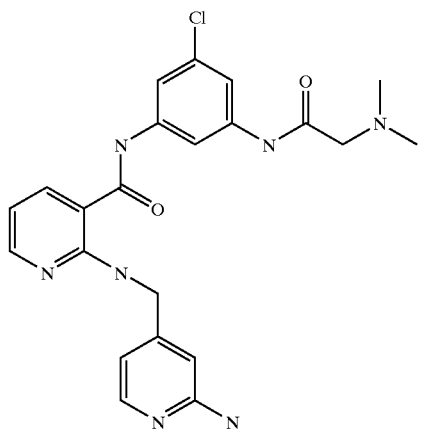

2-[(2-Amino-pyridin-4-ylmethyl)-amino]-N-[3-chloro-5-(2-dimethylamino-acetylamino)-phenyl]-nicotinamide MS: (ES+) 454 (M+H). Calc'd. for $C_{22}H_{24}ClN_7O_2$—453.93.

EXAMPLE 1151

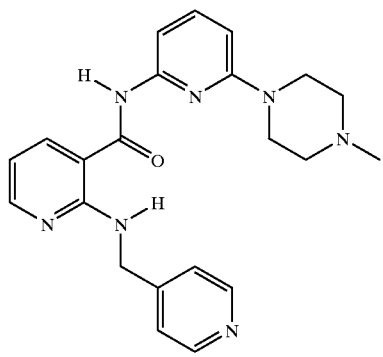

N-[6-(4-Methyl-piperazin-1-yl)-pyridin-2-yl]-2-[(pyridin-4-ylmethyl)-amino]-nicotinamide MS: (ES+) 404.2 (M+H). Calc'd. for $C_{22}H_{25}N_7O$ 403.49.

EXAMPLE 1152

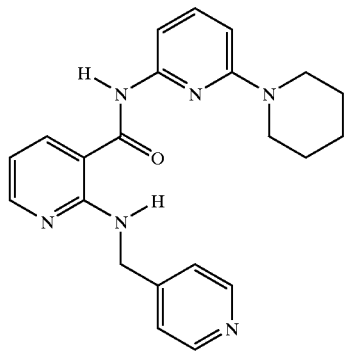

2-[(Pyridin-4-ylmethyl)-amino]-N-(3,4,5,6-tetrahydro-2H-[1,2']bipyridinyl-6'-yl)-nicotinamide MS: (ES+) 389.3 (M+H) Calc'd. for $C_{22}H_{24}N_6O$—388.48.

EXAMPLE 1153

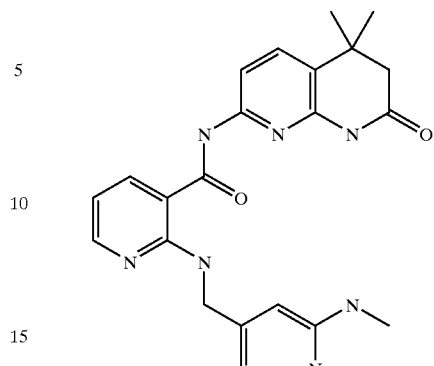

N-(5,5-Dimethyl-7-oxo-5,6,7,8-tetrahydro-[1,8]naphthyridin-2-yl)-2-[(2-methylamino-pyridin-4-ylmethyl)-amino]-nicotinamide MS: (ES+) 432.6 (M+H). Calc'd. for $C_{23}H_{25}N_7O_2$ 431.50.

EXAMPLE 1154

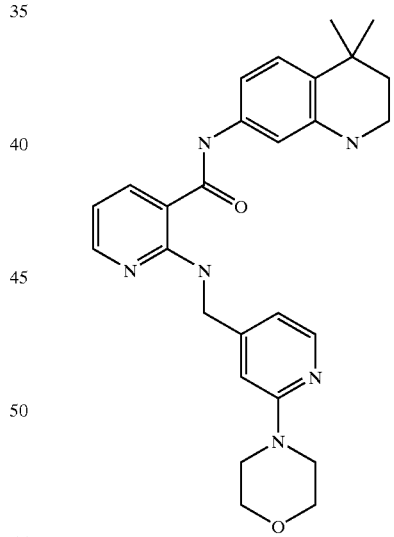

N-(4,4-Dimethyl-1,2,3,4-tetrahydro-quinolin-7-yl)-2-[(2-morpholin-4-yl-pyridin-4-ylmethyl)-amino]-nicotinamide MS: (ES+) 473.7 (M+H). Calc'd. for $C_{27}H_{32}N_6O_2$ 472.59.

EXAMPLE 1155

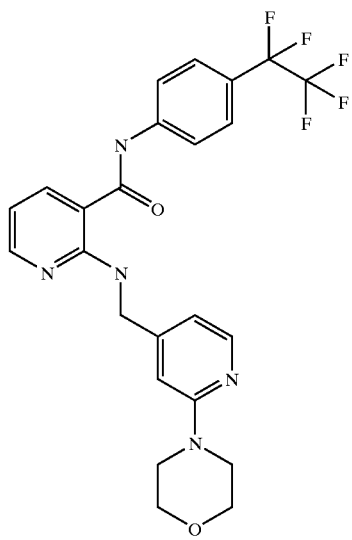

2-[(2-Morpholin-4-yl-pyridin-4-ylmethyl)-amino]-
N-(4-pentafluoroethyl-phenyl)-nicotinamide MS: (ES+) 508.2 (M+H). Calc'd. for $C_{24}H_{22}F_5N_5O_2$ 507.46.

EXAMPLE 1156

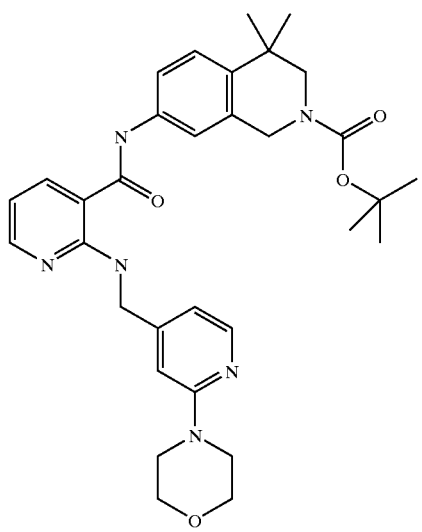

tert-Butyl N-[4,4-Dimethyl-7-({2-[(2-morpholin-4-
yl-pyridin-4-ylmethyl)-amino]-pyridine-3-
carbonyl}-amino)-3,4-dihydro-1H-isoquinoline]
carbamate MS: (ES+) 573.8 (M+H). Calc'd. for $C_{32}H_{40}N_6O_4$ 572.71.

EXAMPLE 1157

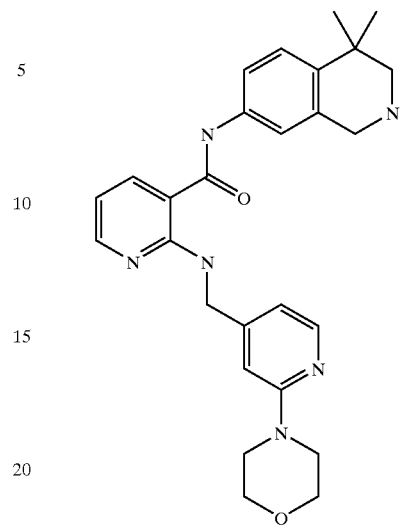

N-(4,4-Dimethyl-1,2,3,4-tetrahydro-isoquinolin-7-
yl)-2-[(2-morpholin-4-yl-pyridin-4-ylmethyl)-
amino]-nicotinamide MS: (ES+) 473.5 (M+H). Calc'd. for $C_{27}H_{32}N_6O_2$ 472.59.

EXAMPLE 1158

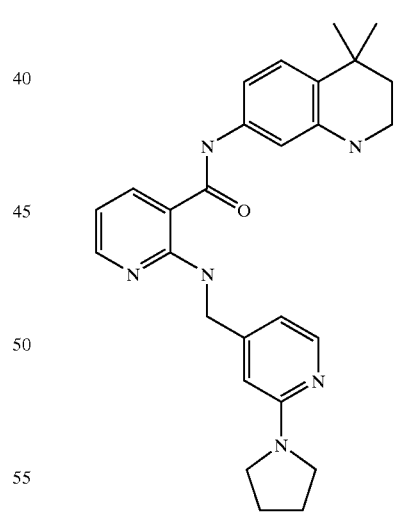

N-(4,4-Dimethyl-1,2,3,4-tetrahydro-quinolin-7-yl)-
2-[(2-pyrrolidin-1-yl-pyridin-4-ylmethyl)-amino]-
nicotinamide MS: (ES+) 457.7 (M+H). Calc'd. for $C_{27}H_{32}N_6O_2$ 456.59.

EXAMPLE 1159

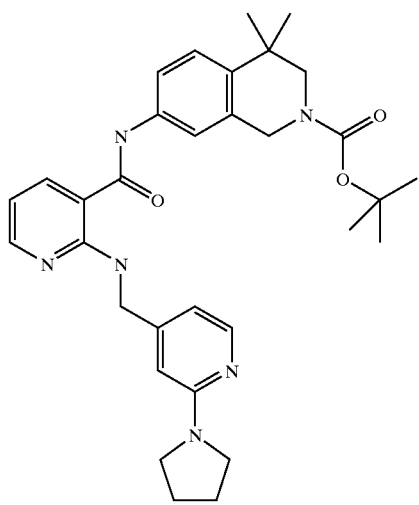

tert-Butyl N-[4,4-Dimethyl-7-({2-[(2-pyrrolidin-1-yl-pyridin-4-ylmethyl)-amino]-pyridine-3-carbonyl}-amino)-3,4-dihydro-1H-isoquinoline] carbamate MS: (ES+) 557.5 (M+H). Calc'd. for $C_{32}H_{40}N_6O_3$ 556.71.

EXAMPLE 1160

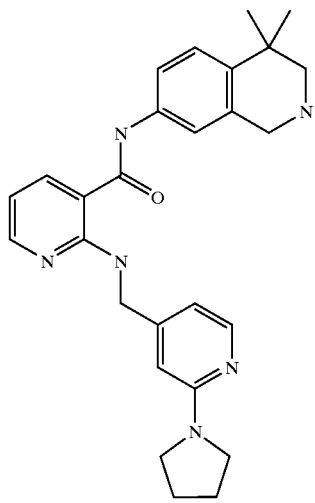

N-(4,4-Dimethyl-1,2,3,4-tetrahydro-isoquinolin-7-yl)-2-[(2-pyrrolidin-1-yl-pyridin-4-ylmethyl)-amino]-nicotinamide MS: (ES+) 457.5 (M+H). Calc'd. for $C_{27}H_{32}N_6O$ 456.59.

EXAMPLE 1161

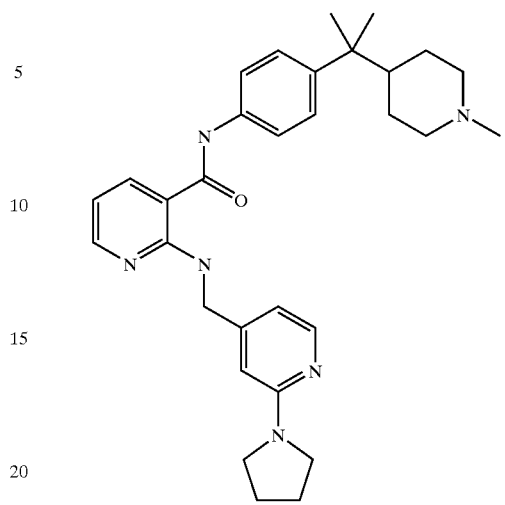

N-{4-[1-Methyl-1-(1-methyl-piperidin-4-yl)-ethyl]-phenyl}-2-[(2-pyrrolidin-1-yl-pyridin-4-ylmethyl)-amino]-nicotinamide MS: (ES+) 513.3 (M+H). Calc'd. for $C_{31}H_{40}N_6O$ 512.70.

EXAMPLE 1162

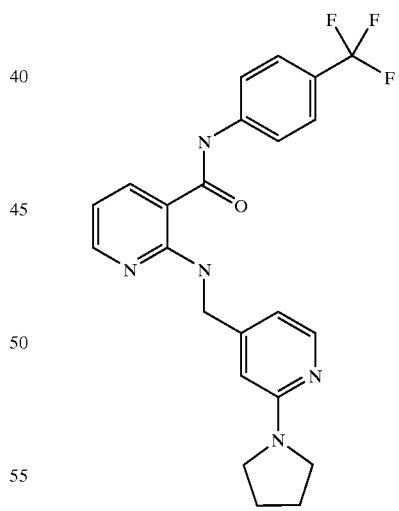

2-[(2-Pyrrolidin-1-yl-pyridin-4-ylmethyl)-amino]-N-(4-trifluoromethyl-phenyl)-nicotinamide MS: (ES+) 442.4 (M+H). Calc'd. for $C_{23}H_{22}F_3N_5O$ 441.45.

EXAMPLE 1163

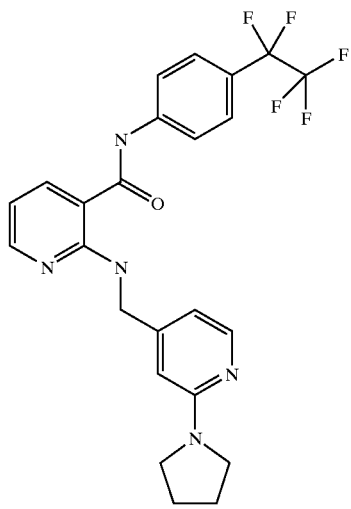

N-(4-Pentafluoroethyl-phenyl)-2-[(2-pyrrolidin-1-yl-pyridin-4-ylmethyl)-amino]-nicotinamide MS: (ES+) 492.4 (M+H). Calc'd. for $C_{24}H_{22}F_5N_5O$ 491.46.

EXAMPLE 1165

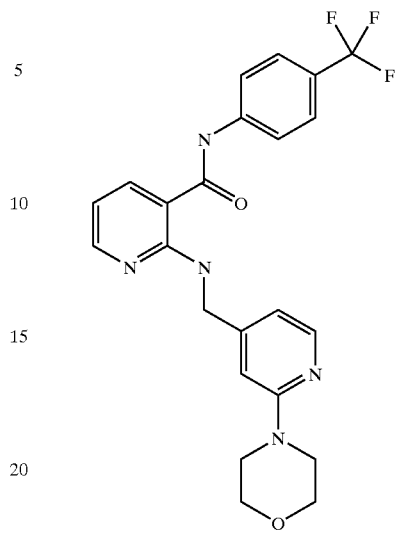

2-[(2-Morpholin-4-yl-pyridin-4-ylmethyl)-amino]-N-(4-trifluoromethyl-phenyl)-nicotinamide MS: (ES+) xxx (M+H). Calc'd. for $C_{23}H_{22}F_3N_5O_2$ 457.45.

EXAMPLE 1164

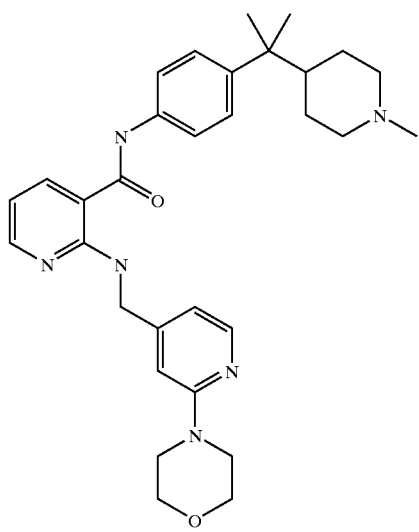

N-{4-[1-Methyl-1-(1-methyl-piperidin-4-yl)-ethyl]-phenyl}-2-[(2-morpholin-4-yl-pyridin-4-ylmethyl)-amino]-nicotinamide MS: (ES+) 529.5 (M+H). Calc'd. for $C_{31}H_{40}N_6O_2$ 528.70.

EXAMPLE 1166

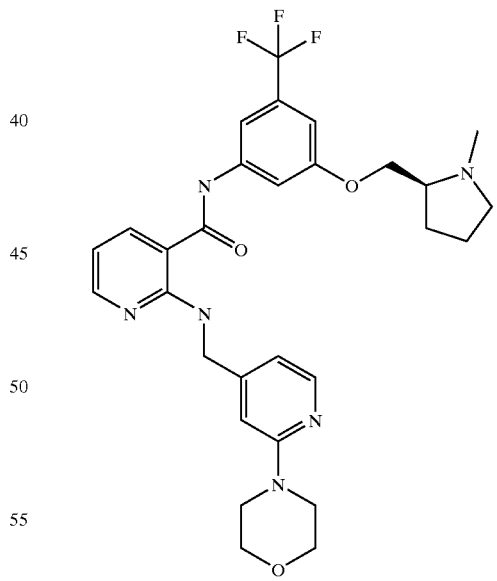

N-[3-(1-Methyl-pyrrolidin-2-ylmethoxy)-5-trifluoromethyl-phenyl]-2-[(2-morpholin-4-yl-pyridin-4-ylmethyl)-amino]-nicotinamide MS: (ES+) 571.5 (M+H). Calc'd. for $C_{29}H_{33}F_3N_6O_3$ 570.61.

EXAMPLE 1167

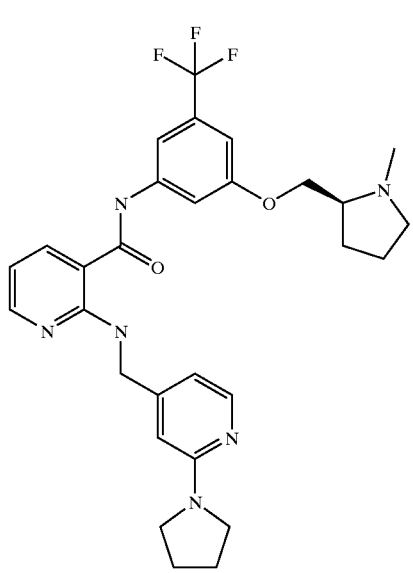

N-[3-(1-Methyl-pyrrolidin-2-ylmethoxy)-5-trifluoromethyl-phenyl]-2-[(2-pyrrolidin-1-yl-pyridin-4-ylmethyl)-amino]-nicotinamide MS: (ES+) 555.4 (M+H). Calc'd. for $C_{29}H_{33}F_3N_6O_2$ 554.61.

EXAMPLE 1168

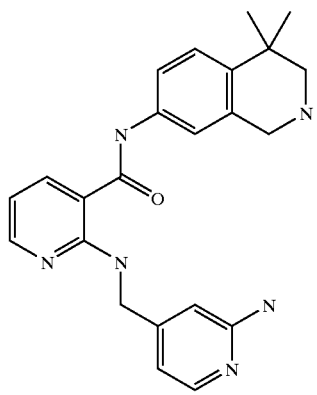

2-(((2-Amino-4-pyridinyl)methyl)amino)-N-(4,4-dimethyl-1,2,3,4-tetrahydro-7-isoquinolinyl)-3-pyridinecarboxamide

EXAMPLE 1169

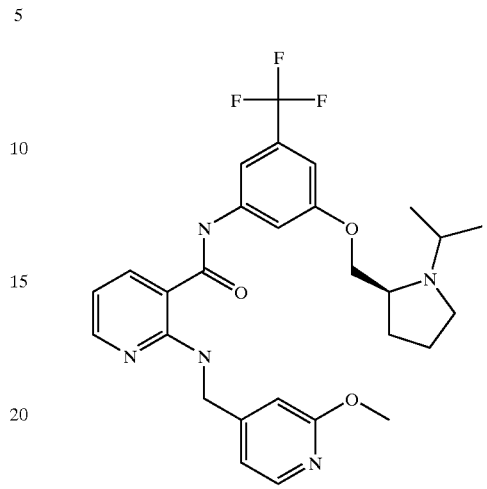

N-(3-((((2S)-1-(1-methylethyl)-2-pyrrolidinyl)methyl)oxy)-5-(trifluoromethyl)phenyl)-2-(((2-(methyloxy)-4-pyridinyl)methyl)amino)-3-pyridinecarboxamide

EXAMPLE 1170

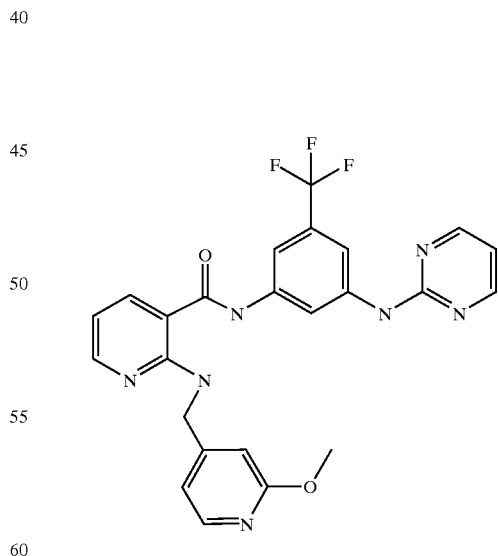

2-[(2-Methoxy-pyridin-4-ylmethyl)-amino]-N-[3-(pyrimidin-2-ylamino)-5-trifluoromethyl-phenyl]-nicotinamide

EXAMPLE 1171

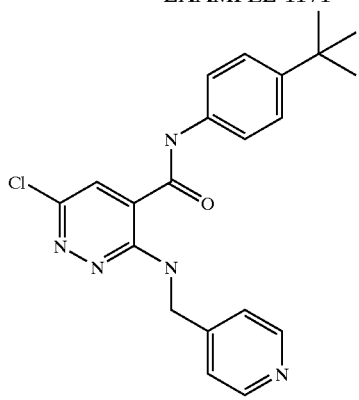

6-Chloro-N-(4-(1,1-dimethylethyl)phenyl)-3-((4-pyridinylmethyl)amino)-4-pyridazinecarboxamide

EXAMPLE 1172

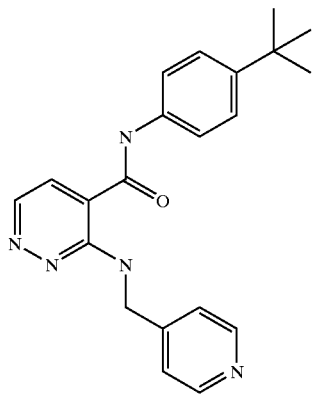

N-(4-(1,1-dimethylethyl)phenyl)-3-((4-pyridinylmethyl)amino)-4-pyridazinecarboxamide

EXAMPLE 1173

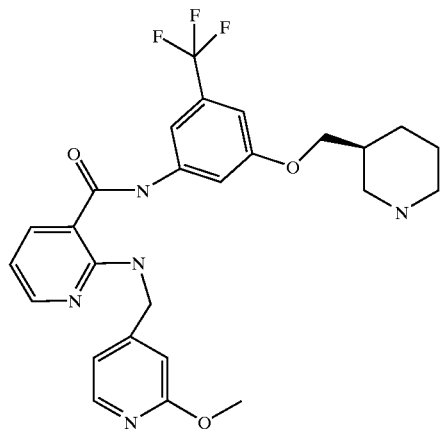

2-(((2-(methyloxy)-4-pyridinyl)methyl)amino)-N-(3-(((3S)-3-piperidinylmethyl)oxy)-5-(trifluoromethyl)phenyl)-3-pyridinecarboxamide

EXAMPLE 1174

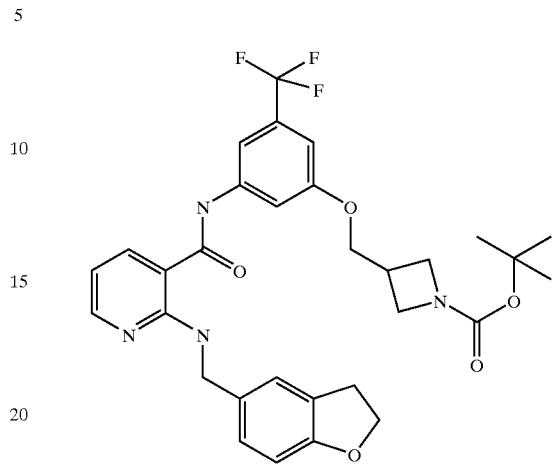

1,1-Dimethylethyl 3-(((3-(((2-((2,3-dihydro-1-benzofuran-5-ylmethyl)amino)-3-pyridinyl)carbonyl)amino)-5-(trifluoromethyl)phenyl)oxy)methyl)-1-azetidinecarboxylate

EXAMPLE 1175

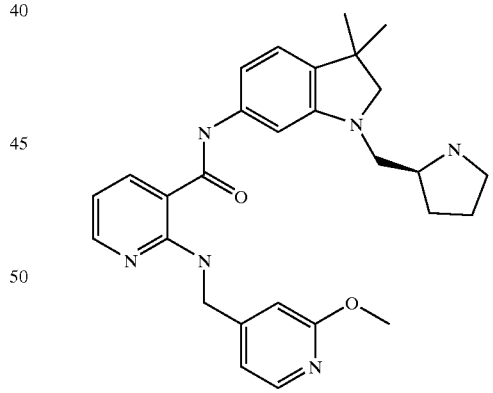

N-(3,3-Dimethyl-1-pyrrolidin-(2S)-ylmethyl-2,3-dihydro-1H-indol-6-yl)-2-[(2-methoxy-pyridin-4-ylmethyl)-amino]-nicotinamide MS: (ES+) 487.1 (M+H). Calc'd for $C_{28}H_{34}N_6O_2$—486.62.

EXAMPLE 1176

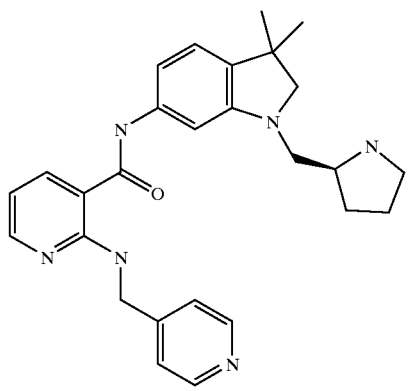

N-(3,3-Dimethyl-1-pyrrolidin-(2S)-ylmethyl-2,3-dihydro-1H-indol-6-yl)-2-[(pyridin-4-ylmethyl)-amino]-nicotinamide MS: (ES+) 457.0 (M+H). Calc'd for $C_{27}H_{32}N_6O$—456.59.

EXAMPLE 1177

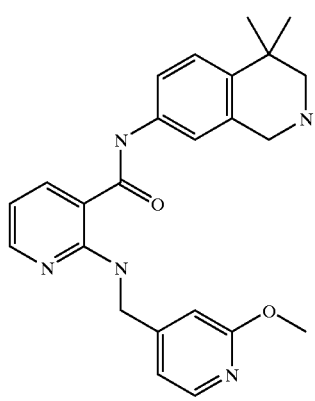

N-(4,4-Dimethyl-1,2,3,4-tetrahydro-isoquinolin-7-yl)-2-[(2-methoxy-pyridin-4-ylmethyl)-amino]-nicotinamide MS: (ES+) 418.2 (M+H). Calc'd for $C_{24}H_{27}N_5O_2$—417.51.

EXAMPLE 1178

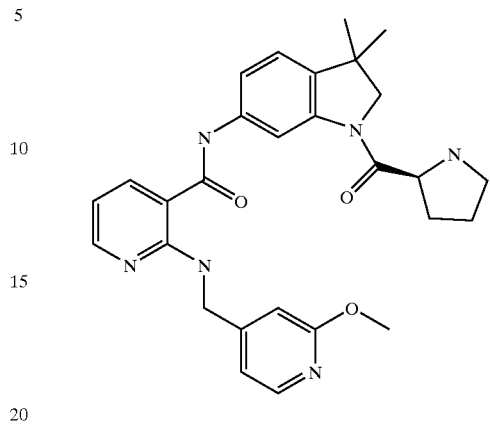

N-[3,3-Dimethyl-1-L-(pyrrolidine-2-carbonyl)-2,3-dihydro-1H-indol-6-yl]-2-[(2-methoxy-pyridin-4-ylmethyl)-amino]-nicotinamide MS: (ES+) 501.0 (M+H). Calc'd for $C_{28}H_{32}N_6O_3$—500.6.

EXAMPLE 1179

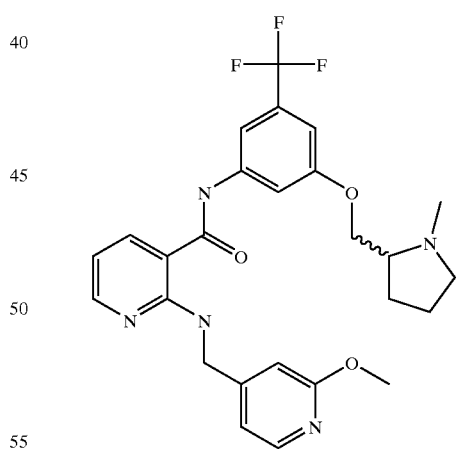

2-[(2-Methoxy-pyridin-4-ylmethyl)-amino]-N-[3-(1-methyl-pyrrolidin-(2R)-ylmethoxy)-5-trifluoromethylphenyl]-nicotinamide MS: (ES+) 516.1 (M+H). Calc'd for $C_{26}H_{28}F_3N_5O_3$—515.53.

EXAMPLE 1180

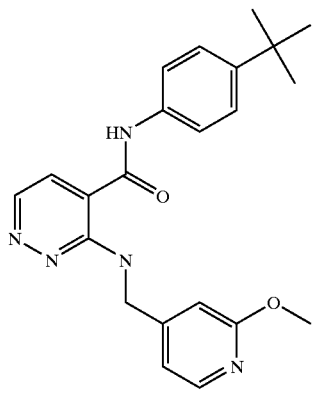

3-[(2-Methoxy-pyridin-4-ylmethyl)-amino]-pyridazine-4-carboxylic Acid (4-tert-butylphenyl)-amide Step A: Preparation of 3,6-Dichloro-pyridazine-4-carboxylic acid (4-tert-butyl-phenyl)-amide: 3,6-Dichloro-pyridazine-4-carboxylic acid (1.93 g, 10 mmol), 4-tert-Butyl-phenylamine (1.49 g, 10 mmol), DIEA (3.5 mL, 20 mmol), and HATU (4.56 g, 12 mmol) were added to DMF (20 mL). The reaction was stirred at rt for 15 h. The resulting dark brown solution was extracted with DCM (2×10 mL), washed with $H_2O$ (2×10 mL), and dried over sodium sulfate. The curde product was further purified using Flash Chromatography (2% MeOH/DCM), affording the desired product as yellow solid.

Step B: Preparation of 6-Chloro-3-[(2-methoxy-pyridin-4-ylmethyl)-amino]-pyridazine-4-carboxylic acid (4-tert-butyl-phenyl)-amide: 3,6-Dichloro-pyridazine-4-carboxylic acid (4-tert-butyl-phenyl)-amide (162 mg, 0.5 mmol), C-(2-Methoxy-pyridin-4-yl)-methylamine (211 mg, 1 mmol), and sodium bicarbonate (840 mg, 20 mmol) were added to IPA (2.5 mL). The reaction was ran in microwave (150° C., 15 min). Water (5 mL) was added to the reaction and the mixture was extracted with DCM (2×5 mL). The organic layer was dried over sodium sulfate and reduced. The crude was subjected to Flash chromatography (2% MeOH/DCM) for further purification.

Step C: 3-[(2-Methoxy-pyridin-4-ylmethyl)-amino]-pyridazine-4-carboxylic acid (4-tert-butyl-phenyl)-amide: 6-Chloro-3-[(2-methoxy-pyridin-4-ylmethyl)-amino]-pyridazine-4-carboxylic acid (4-tert-butyl-phenyl)-amide (150 mg, 0.35 mmol) was dissolved in MeOH (5 mL). 10% Pd/C (50 mg) was added to above under $N_2$ atmosphere. The system was charged with $H_2$ balloon, and the reaction was stirred under $H_2$ gas for 3 h. The crude was subjected to Flash chromatography (5% MeOH/DCM) for further purification, affording desired product as yellow solid. MS (ES+): 392 (M+H). Calc'd. for $C_{22}H_{25}N_5O_2$—391.20.

EXAMPLE 1081

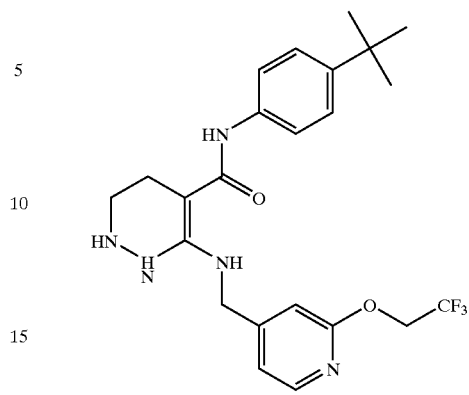

3-{[2-(2,2,2-Trifluoro-ethoxy)-pyridin-4-ylmethyl]-amino}-1,2,5,6-tetrahydro-pyridazine-4-carboxylic Acid (4-tert-butyl-phenyl)-amide Same procedure was used (Steps A, B & C) as AMG 672851. MS: (ES+) 464 (M+H). Calc'd. for $C_{23}H_{28}F_3N_5O_2$—463.22.

EXAMPLE 1182

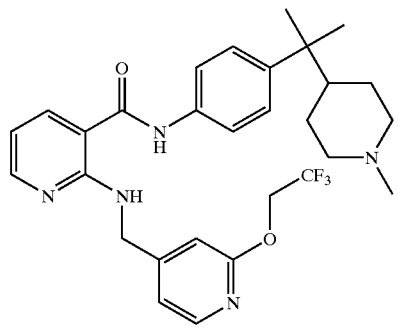

N-{4-[1-Methyl-1-(1-methyl-piperidin-4-yl)-ethyl]-phenyl}-2-{[2-(2,2,2-trifluoro-ethoxy)-pyridin-4-ylmethyl]-amino}-nicotinamide MS: (ES+) 542 (M+H). Calc'd. for $C_{29}H_{34}F_3N_5O_2$—541.3.

EXAMPLE 1183

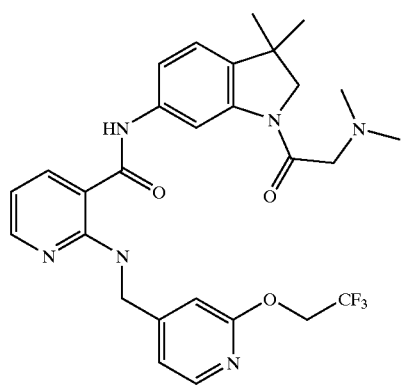

N-[1-(2-Dimethylamino-acetyl)-3,3-dimethyl-2,3-dihydro-1H-indol-6-yl]-2-{[2-(2,2,2-trifluoro-ethoxy)-pyridin-4-ylmethyl]-amino}-nicotinamide MS: (ES+) 557 (M+H). Calc'd. for $C_{28}H_{31}F_3N_6O_3$—556.24.

EXAMPLE 1184

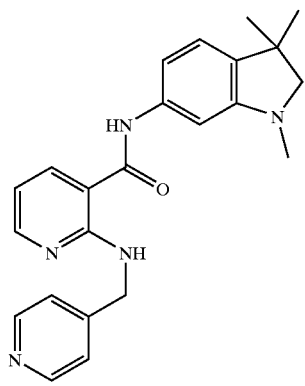

2-[(Pyridin-4-ylmethyl)-amino]-N-(1,3,3-trimethyl-2,3-dihydro-1H-indol-6-yl)-nicotinamide MS: (ES+) 388 (M+H). Calc'd. for $C_{23}H_{25}N_5O$—387.48.

EXAMPLE 1185

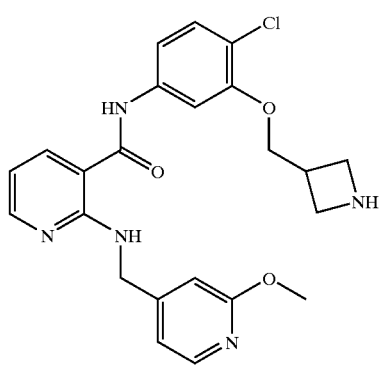

N-[3-(Azetidin-3-ylmethoxy)-4-chloro-phenyl]-2-[(2-methoxy-pyridin-4-ylmethyl)-amino]-nicotinamide MS: (ES+) 454 (M+H). Calc'd. for $C_{23}H_{24}ClN_5O_3$—453.92.

EXAMPLE 1186

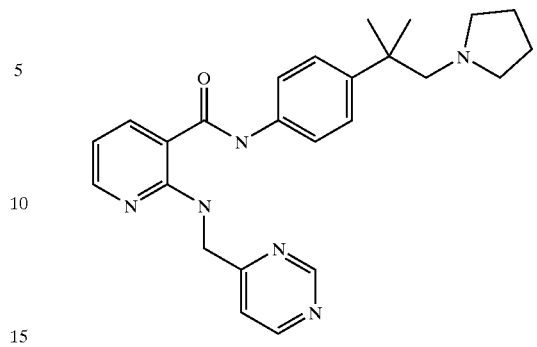

N-[4-(1,1-Dimethyl-2-pyrrolidin-1-yl-ethyl)-phenyl]-2-[(pyrimidin-4-ylmethyl)-amino]-nicotinamide MS: (ES+) 431 (M+H). Calc'd for $C_{25}H_{30}N_6O$—430.55.

EXAMPLE 1187

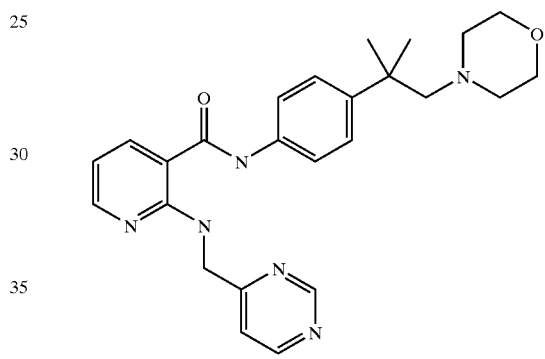

N-[4-(1,1-Dimethyl-2-morpholin-4-yl-ethyl)-phenyl]-2-[(pyrimidin-4-ylmethyl)-amino]-nicotinamide MS: (ES+) 447 (M+H). Calc'd for $C_{25}H_{30}N_6O_2$—446.54.

EXAMPLE 1188

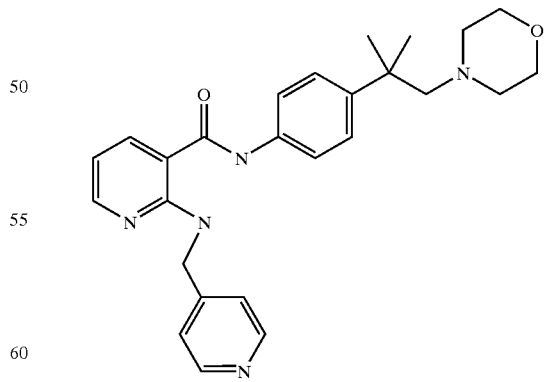

N-[4-(1,1-Dimethyl-2-morpholin-4-yl-ethyl)-phenyl]-2-[(pyridin-4-ylmethyl)-amino]-nicotinamide MS: (ES+) 446 (M+H). Calc'd for $C_{26}H_{31}N_5O_2$—445.56.

EXAMPLE 1189

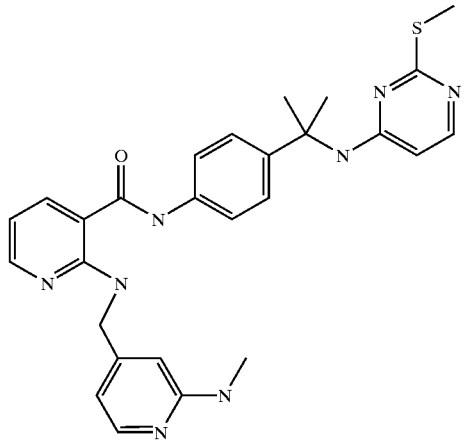

2-[(2-Methylamino-pyridin-4-ylmethyl)-amino]-N-
{4-[1-methyl-1-(2-methylsulfanyl-pyrimidin-4-
ylamino)-ethyl]-phenyl}-nicotinamide MS: (ES+) 515 (M+H). Calc'd for $C_{27}H_{30}N_8OS$—514.65.

EXAMPLE 1190

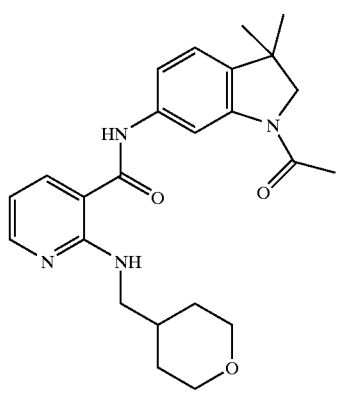

N-(1-Acetyl-3,3-dimethyl-2,3-dihydro-1H-indol-6-
yl)-2-[(tetrahydro-pyran-4-ylmethyl)-amino]-
nicotinamide MS: (ES+) 423 (M+H). Calc'd for $C_{24}H_{30}N_4O_3$—422.52.

EXAMPLE 1191

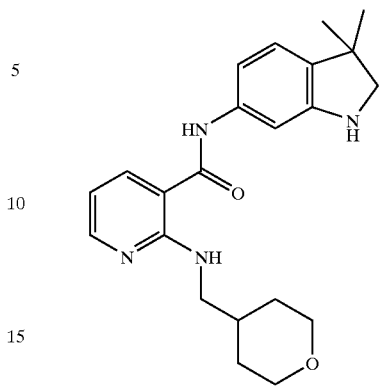

N-(3,3-Dimethyl-2,3-dihydro-1H-indol-6-yl)-2-
[(tetrahydro-pyran-4-ylmethyl)-amino]-nicotinamide
MS: (ES+) 381 (M+H). Calc'd for $C_{22}H_{28}N_4O_2$—380.48.

EXAMPLE 1192

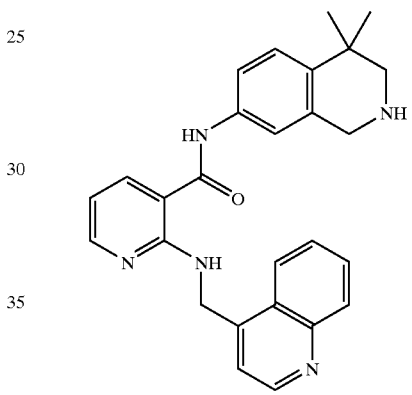

N-(4,4-Dimethyl-1,2,3,4-tetrahydro-isoquinolin-7-
yl)-2-[(quinolin-4-ylmethyl)-amino]-nicotinamide
MS: (ES+) 438 (M+H). Calc'd. for $C_{27}H_{27}F_6N_5O$—437.54.

EXAMPLE 1193

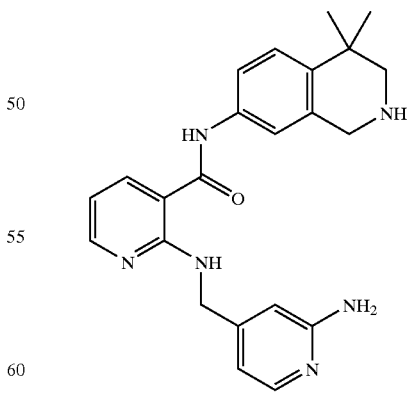

2-[(2-Amino-pyridin-4-ylmethyl)-amino]-N-(4,4-
dimethyl-1,2,3,4-tetrahydro-isoquinolin-7-yl)-
nicotinamide
MS: (ES+) 403 (M+H). Calc'd. for $C_{23}H_{26}F_6N_6O$—402.49.

EXAMPLE 1194

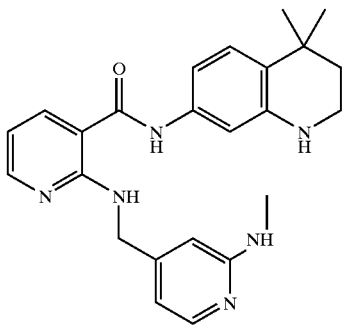

2-[(2-N-(4,4-Dimethyl-1,2,3,4-tetrahydro-quinolin-7-yl)-2-[(2-methylamino-pyridin-4-ylmethyl)-amino]-nicotinamide MS (ES$^+$): 417 (M+H)$^+$. Calc'd for $C_{23}H_{26}N_6O$—416.53.

Although the pharmacological properties of the compounds of Formula I–XIII vary with structural change, in general, activity possessed by compounds of Formula I–XIII may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR kinase at doses less than 50 µM.

Biological Evaluation

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of 3×10$^5$ cells/mL. Another cell count is performed to confirm the cell concentration. The cells are diluted to 3×10$^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+10% FBS+antibiotics (400× dilution). Medium containing 0.25% DMSO is also prepared for the 0 µM compound sample. At the 22-hour timepoint, the medium is removed from the cells, and 100 µL of each compound dilution is added. The cells are incubated at 37° C. for 2–3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. IC$_{50}$ values are then determined.

Examples 4, 7, 20–21, 25–26, 28, 33, 67, 72(f–i, n–o), 78, 82, 84, 86, 94–95, 97–100, 105, 111–112, 115–118, 130, 133, 138, 140, 151, 154–156, 158–159, 165, 167, 169, 817, 826–829, 831–838, 840–844, 845, 847–851, 853, 855–860, 862, 864, 873, 900, 904–905, 916–917, 922–924, 942–944, 946, 951–952, 954–955, 963–964, 973, 977–978, 982, 985, 991, 995, 1000, 1008, 1021–1025, 1028–1033, 1036, 1038–1041, 1043–1047, 1058–1061, 1067–1068, 1072, 1074, 1077, 1080, 1083–1086, 1088–1091, 1093, 1095–1096, 1099–1100, 1103–1116, 1119–1120, 1124–1125, 1128, 1130, 1132, 1135, 1138, 1141, 1143–1145, 1147, 1149, 1154, 1168, 1176–1177, 1184, 1192 and 1194 inhibited VEGF-stimulated HUVEC proliferation at a level below 50 nm.

Angiogenesis Model

To determine the effects of the present compounds on angiogenesis in vivo, selective compounds are tested in the rat corneal neovascularization micropocket model or the angiogenesis assay of Passaniti, Lab. Invest., 67, 519–28 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+ 5% Isofluorane). An otoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-VEGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After twenty-four hours in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A. G. Heinz, Irvine Calif.) mounted on a Nikon SMZ-U stereo microscope (A. G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations: 0.1% BSA in PBS vehicle: 0.025 g of BSA was added to 25.0 ml of sterile 1× phosphate buffered saline, gently shaken until fully dissolved, and filtered at 0.2 $\mu$m. Individual 1.0 ml samples were aliquoted into 25 single use vials, and stored at −20° C. until use. For the rHu-bFGF disks, a vial of this 0.1% BSA solution was allowed to thaw at room temperature. Once thawed, 10 $\mu$l of a 100 mM stock solution of DTT was added to the 1 ml BSA vial to yield a final concentration of 1 mM DTT in 0.1% BSA.

rHu-VEGF Dilutions: Prior to the disk implant surgery, 23.8 $\mu$l of the 0.1% BSA vehicle above was added to a 10 $\mu$g rHu-VEGF lyophilized vial yielding a final concentration of 10 $\mu$M.

rHu-bFGF: Stock concentration of 180 ng/$\mu$l: R&D rHu-bFGF: Added 139 $\mu$l of the appropriate vehicle above to the 25 $\mu$g vial lyophilized vial. 13.3 $\mu$l of the [180 ng/$\mu$l] stock vial and added 26.6 $\mu$l of vehicle to yield a final concentration of 3.75 $\mu$M concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 $\mu$M rHu-VEGF (R&D Systems, Minneapolis, Minn.), or 3.75 $\mu$M rHu-bFGF (R&D Systems, Minneapolis, Minn.) and allowed to soak for 45–60 min before use. Each nitrocellulose filter disk absorbs approximately 0.1 $\mu$l of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5–8 week old female nude mice (CD1 nu/nu, Charles River Labs) (n=5–15). Subsequent administration of compound by oral gavage (10–200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91, 95–101 (1956)) is used to test the anti-arthritic activity of compounds of the formula I, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:
1. A compound of formula XIII:

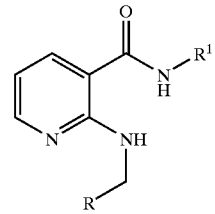

XIII wherein R is selected from
a) unsubstituted or substituted 5- or 6-membered rings selected from 4-pyridyl, 2-pyridyl, 4-pyrimidinyl, and tetrahydro-2H-pyran-4-yl, and
b) unsubstituted or substituted 9- or 10-membered fused rings selected from 4-quinolyl, 6-quinolyl, 2,3-dihydro-5-benzofuryl, 5-benzoxazolyl, 1H-pyrrolo[2,3-b]pyridin-4-yl, and 2,3-dihydro-1H-pyrrolo[2,3-b]pyridin-4-yl,
where substituted R is substituted with one or more substituents selected from halo, amino, hydroxy, oxo, $C_{1-6}$-alkyl, $C_{1-6}$-haloalkyl, $C_{1-6}$-alkylaminocarbonyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl; and
wherein $R^1$ is 4,4-dimethyl-3,4-dihydro-2-oxo-1H-quinolinyl;
or wherein $R^1$ is 4,4-dimethyl-1,2,3,4-tetrahydro-1H-quinolinyl;
or wherein $R^1$ is 4,4-dimethyl-3,4-dihydro-2-oxo-1H-[1,8]naphthyridinyl;
or wherein $R^1$ is 3,3-dimethyl-2,3-dihydro-1H-indolyl optionally substituted with a substituent selected from pyrrolidin-1-yl-carbonyl, methylcarbonyl, and methylsulfonyl;
or wherein $R^1$ is 4,4-dimethyl-1,2,3,4-tetrahydro-1H-isoquinolinyl;
or wherein $R^1$ is 2-oxo-3,3-bis(trifluoromethyl)-2,3-dihydro-1H-indol-6-yl;
or wherein $R^1$ is 1',2'-dihydro-spiro[cyclopropane-1,3'-[3H]indol]-6'-yl;
and pharmaceutically acceptable derivatives thereof.
2. Compound of claim 1 wherein R is selected from 2-methylamino-4-pyrimidinyl, 4-pyrimidinyl, 4-quinolyl, 2-methylamino-4-pyridyl, 1H-pyrrolo[2,3-b]pyridin-4-yl, 4-pyridyl, 2-amino-4-pyridyl, 2-methoxy-4-pyrimidinyl, 6-quinolyl, 2-methoxy-4-pyridyl, 2-methylaminocarbonyl-4-pyridyl, 2-morpholino-4-pyridyl, and 2-trifluoromethoxy-4-pyridyl.
3. Compound of claim 1 wherein R is 4-quinolyl.
4. Compound of claim 1 wherein R is 2-methylamino-4-pyridyl.
5. Compound of claim 1 wherein R is 4-pyridyl and N-oxides thereof.
6. Compound of claim 1 wherein R is 4-pyrimidinyl.
7. Compound of claim 1 wherein R is 2-methoxy-4-pyrimidinyl.
8. Compound of claim 1 wherein R is 2-methoxy-4-pyridyl.

9. Compound of claim 1 wherein R is 2-methylamino-4-pyrimidinyl.

10. Compound of claim 1 wherein $R^1$ is 4,4-dimethyl-3,4-dihydro-2-oxo-1H-quinolinyl; and pharmaceutically acceptable derivatives thereof.

11. Compound of claim 1 wherein $R^1$ is 4,4-dimethyl-1,2,3,4-tetrahydro-1H-quinolinyl; and pharmaceutically acceptable derivatives thereof.

12. Compound of claim 1 wherein $R^1$ is 4,4-dimethyl-3,4-dihydro-2-oxo-1H-[1,8]naphthyridinyl; and pharmaceutically acceptable derivatives thereof.

13. Compound of claim 1 wherein $R^1$ is 3,3-dimethyl-2,3-dihydro-1H-indolyl optionally substituted with a substituent selected from pyrrolidin-1-yl-carbonyl, methylcarbonyl, and methylsulfonyl; and pharmaceutically acceptable derivatives thereof.

14. Compound of claim 1 wherein $R^1$ is 4,4-dimethyl-1,2,3,4-tetrahydro-1H-isoquinolinyl.

15. Compound of claim 1 wherein $R^1$ is 2-oxo-3,3-bis(trifluoromethyl)-2,3-dihydro-1H-indol-6-yl.

16. Compound of claim 1 wherein $R^1$ is 1',2'-dihydro-spiro[cyclopropane-1,3'-[3H]indol]-6'-yl.

17. A compound and pharmaceutically acceptable salts thereof selected from 2-(((2-Amino-4-pyridinyl)methyl)amino)-N-(4,4-dimethyl-1,2,3,4-tetrahydro-7-isoquinolinyl)-3-pyridinecarboxamide;

N-(3-((((2S)-1-(1-methylethyl)-2-pyrrolidinyl)methyl)oxy)-5-(trifluoromethyl)phenyl)-2-(((2-(methyloxy)-4-pyridinyl)methyl)amino)-3-pyridinecarboxamide;

2-[(2-Methoxy-pyridin-4-ylmethyl)-amino]-N-[3-(pyrimidin-2-ylamino)-5-trifluoromethyl-phenyl]-nicotinamide;

6-Chloro-N-(4-(1,1-dimethylethyl)phenyl)-3-((4-pyridinylmethyl)amino)-4-pyridazinecarboxamide;

N-(4-(1,1-dimethylethyl)phenyl)-3-((4-pyridinylmethyl)amino)-4-pyridazinecarboxamide;

2-(((2-(methyloxy)-4-pyridinyl)methyl)amino)-N-(3-(((3S)-3-piperidinylmethyl)oxy)-5-(trifluoromethyl)phenyl)-3-pyridinecarboxamide;

1,1-dimethylethyl 3-(((3-(((2-((2,3-dihydro-1-benzofuran-5-ylmethyl)amino)-3-pyridinyl)carbonyl)amino)-5-(trifluoromethyl)phenyl)oxy)methyl)-1-azetidinecarboxylate;

2-((1,3-Benzoxazol-5-ylmethyl)amino)-N-(4-(1-methylethyl)phenyl)-3-pyridinecarboxamide;

2-((1-oxo-2,3-dihydro-1H-isoindol-4-yl)amino)-N-(3-((1,1,2,2-tetrafluoroethyl)oxy)phenyl)benzamide;

N-{4-[1-Methyl-1-(1-methyl-piperidin-4-yl)-ethyl]-phenyl}-2-[(1-oxy-pyridin-4-ylmethyl)-amino]-nicotinamide;

4-{1-Methyl-1-[4-({2-[(pyridin-4-ylmethyl)-amino]-pyridine-3-carbonyl}-amino)-phenyl]-ethyl}-3,6-dihydro-2H-pyridine-1-carboxylic acid ethyl ester;

Ethyl[1,2-dihydro-6-({2-[(2-methylamino-pyridin-4-ylmethyl)-amino]-pyridine-3-carbonyl}-amino)-3-spiro-1'-cyclopropyl-1H-indole]-1-carbamate;

N-(1,2-dihydroindol-3-spiro-1'-cyclopropane-6-yl)-2-[(2-methylaminopyridin-4-ylmethyl)-amino]-nicotinamide;

Ethyl[1,2-dihydro-6-({2-[(2-methylamino-pyrimidin-4-ylmethyl)-amino]-pyridine-3-carbonyl}-amino)-3-spiro-1'-cyclopropyl-1H-indole]-1-carbamate;

N-(4,4-Dimethyl-1,2,3,4-tetrahydro-quinolin-7-yl)-2-[(pyridin-4-ylmethyl)-amino]-nicotinamide;

N-(4,4-Dimethyl-1,2,3,4-tetrahydro-quinolin-7-yl)-2-[(pyrimidin-4-ylmethyl)-amino]-nicotinamide;

2-[(2-Amino-pyridin-4-ylmethyl)-amino]-N-(4,4-dimethyl-1,2,3,4-tetrahydro-quinolin-7-yl)-nicotinamide;

N-(4,4-Dimethyl-1,2,3,4-tetrahydro-quinolin-7-yl)-2-[(2-methylamino-pyrimidin-4-ylmethyl)-amino]-nicotinamide;

N-(4,4-Dimethyl-1,2,3,4-tetrahydro-quinolin-7-yl)-2-[(2-methoxy-pyridin-4-ylmethyl)-amino]-nicotinamide;

N-(4,4-Dimethyl-2-oxo-1,2,3,4-tetrahydro-quinolin-7-yl)-2-[(pyridin-4-ylmethyl)-amino]-nicotinamide;

N-(4,4-Dimethyl-2-oxo-1,2,3,4-tetrahydro-quinolin-7-yl)-2-[(2-methylamino-pyrimidin-4-ylmethyl)-amino]-nicotinamide;

N-(4,4-Dimethyl-2-oxo-1,2,3,4-tetrahydro-quinolin-7-yl)-2-[(2-methoxy-pyridin-4-ylmethyl)-amino]-nicotinamide;

N-(4,4-Dimethyl-2-oxo-1,2,3,4-tetrahydro-quinolin-7-yl)-2-{[2-(2,2,2-trifluoro-ethoxy)-pyridin-4-ylmethyl]-amino}-nicotinamide;

2-[(2-Amino-pyridin-4-ylmethyl)-amino]-N-(4,4-dimethyl-2-oxo-1,2,3,4-tetrahydro-quinolin-7-yl)-nicotinamide;

N-(4,4-Dimethyl-2-oxo-1,2,3,4-tetrahydro-quinolin-7-yl)-2-[(2-methylamino-pyridin-4-ylmethyl)-amino]-nicotinamide;

N-(4,4-Dimethyl-2-oxo-1,2,3,4-tetrahydro-quinolin-7-yl)-2-[(2-methylamino-pyridin-4-ylmethyl)-amino]-nicotinamide;

N-(4,4-Dimethyl-2-oxo-1,2,3,4-tetrahydro-quinolin-7-yl)-2-[(3-fluoro-pyridin-2-ylmethyl)-amino]-nicotinamide;

N-(1-Ethyl-4,4-dimethyl-1,2,3,4-tetrahydro-quinolin-7-yl)-2-[(pyridin-4-ylmethyl)-amino]-nicotinamide;

2-[(2-Amino-pyridin-4-ylmethyl)-amino]-N-(1-ethyl-4,4-dimethyl-1,2,3,4-tetrahydro-quinolin-7-yl)-nicotinamide;

2-[(2-Methoxy-pyridin-4-ylmethyl)-amino]-N-(1,4,4-trimethyl-1,2,3,4-tetrahydro-quinolin-7-yl)-nicotinamide;

tert-Butyl N-[7-({2-[(2-methoxy-pyridin-4-ylmethyl)-amino]-pyridine-3-carbonyl}-amino)-4-spiro-1'-cyclopropane-3,4-dihydro-1H-isoquinoline]carbamate;

N-(4-Spiro-1'-cyclopropane-1,2,3,4-tetrahydroisoquinolin-7-yl)-2-[(2-methoxy-pyridin-4-ylmethyl)-amino]-nicotinamide;

N-(4,4-Dimethyl-1,2,3,4-tetrahydro-isoquinolin-7-yl)-2-{[2-(2,2,2-trifluoro-ethoxy)-pyridin-4-ylmethyl]-amino}-nicotinamide;

N-(4,4-Dimethyl-1,2,3,4-tetrahydro-isoquinolin-7-yl)-2-[(2-methylamino-pyridin-4-ylmethyl)-amino]-nicotinamide;

N-(4,4-Dimethyl-1,2,3,4-tetrahydro-isoquinolin-7-yl)-2-[(quinolin-6-ylmethyl)-amino]-nicotinamide;

N-(2-Chloro-pyridin-4-yl)-2-[(2-methylamino-pyridin-4-ylmethyl)-amino]-nicotinamide;

2-[(2-Methoxy-pyridin-4-ylmethyl)-amino]-N-[4-methyl-6-(1-methyl-pyrrolidin-2-ylmethoxy)-pyrimidin-2-yl]-nicotinamide;

N-(5,5-Dimethyl-7-oxo-5,6,7,8-tetrahydro-[1,8]naphthyridin-2-yl)-2-[(2-methylamino-pyrimidin-4-ylmethyl)-amino]-nicotinamide;

N-(5,5-Dimethyl-5,6-dihydro-[1,7]naphthyridin-2-yl)-2-[(2-methoxy-pyridin-4-ylmethyl)-amino]-nicotinamide;

2-{2,2,2-Trifluoro-1-[3-({2-[(pyridin-4-ylmethyl)-amino]-pyridine-3-carbonyl}-amino)-phenyl]-1-trifluoromethyl-ethoxymethyl}-pyrrolidine-1-carboxylic acid tert-butyl ester;

2-[(Pyridin-4-ylmethyl)-amino]-N-{3-[2,2,2-trifluoro-1-(pyrrolidin-2-ylmethoxy)-1-trifluoromethyl-ethyl]-phenyl}-nicotinamide;

2-[(2-Methoxy-pyridin-4-ylmethyl)-amino]-N-{3-[2,2,2-trifluoro-1-(pyrrolidin-2-ylmethoxy)-1-trifluoromethyl-ethyl]-phenyl}-nicotinamide;

2-{2,2,2-Trifluoro-1-[4-({2-[(pyridin-4-ylmethyl)-amino]-pyridine-3-carbonyl}-amino)-phenyl]-1-trifluoromethyl-ethoxymethyl}-pyrrolidine-1-carboxylic acid tert-butyl ester;

2-[(Pyridin-4-ylmethyl)-amino]-N-{4-[2,2,2-trifluoro-1-(pyrrolidin-2-ylmethoxy)-1-trifluoromethyl-ethyl]-phenyl}-nicotinamide;

2-[(2-Methoxy-pyridin-4-ylmethyl)-amino]-N-{4-[2,2,2-trifluoro-1-(pyrrolidin-2-ylmethoxy)-1-trifluoromethyl-ethyl]-phenyl}-nicotinamide;

2-[(2-Methylamino-pyridin-4-ylmethyl)-amino]-N-[3-(1-methyl-pyrrolidin-2-ylmethoxy)-5-trifluoromethyl-phenyl]-nicotinamide;

2-[(2-Methylamino-pyrimidin-4-ylmethyl)-amino]-N-[3-(1-methyl-pyrrolidin-2-ylmethoxy)-5-trifluoromethyl-phenyl]-nicotinamide;

N-(4,4-Dimethyl-1,2,3,4-tetrahydro-isoquinolin-7-yl)-2-[(1H-pyrrolo[2,3-b]pyridin-4-ylmethyl)-amino]-nicotinamide;

7-({2-[(2,3-Dihydro-1H-pyrrolo[2,3-b]pyridin-4-ylmethyl)-amino]-pyridine-3-carbonyl}-amino)-4,4-dimethyl-3,4-dihydro-1H-isoquinoline-2-carboxylic acid tert-butyl ester;

2-[(2,3-Dihydro-1H-pyrrolo[2,3-b]pyridin-4-ylmethyl)-amino]-N-(4,4-dimethyl-1,2,3,4-tetrahydro-isoquinolin-7-yl)-nicotinamide;

2 2-[(2-Methoxy-pyridin-4-ylmethyl)-amino]-N-[3-(1-methyl-piperidin-3-yloxy)-5-trifluoromethyl-phenyl]-nicotinamide;

N-[3-Chloro-5-(2-dimethylamino-acetylamino)-phenyl]-2-[(2-methylamino-pyridin-4-ylmethyl)-amino]-nicotinamide;

2-[(2-Amino-pyridin-4-ylmethyl)-amino]-N-[3-chloro-5-(2-dimethylamino-acetylamino)-phenyl]-nicotinamide;

N-[6-(4-Methyl-piperazin-1-yl)-pyridin-2-yl]-2-[(pyridin-4-ylmethyl)-amino]-nicotinamide;

2-[(Pyridin-4-ylmethyl)-amino]-N-(3,4,5,6-tetrahydro-2H-[1,2']bipyridinyl-6'-yl)-nicotinamide;

N-(5,5-Dimethyl-7-oxo-5,6,7,8-tetrahydro-[1,8]naphthyridin-2-yl)-2-[(2-methylamino-pyridin-4-ylmethyl)-amino]-nicotinamide;

N-(4,4-Dimethyl-1,2,3,4-tetrahydro-quinolin-7-yl)-2-[(2-morpholin-4-yl-pyridin-4-ylmethyl)-amino]-nicotinamide;

2-[(2-Morpholin-4-yl-pyridin-4-ylmethyl)-amino]-N-(4-pentafluoroethyl-phenyl)-nicotinamide;

tert-Butyl N-[4,4-Dimethyl-7-({2-[(2-morpholin-4-yl-pyridin-4-ylmethyl)-amino]-pyridine-3-carbonyl}-amino)-3,4-dihydro-1H-isoquinoline]carbamate;

N-(4,4-Dimethyl-1,2,3,4-tetrahydro-isoquinolin-7-yl)-2-[(2-morpholin-4-yl-pyridin-4-ylmethyl)-amino]-nicotinamide;

N-(4,4-Dimethyl-1,2,3,4-tetrahydro-quinolin-7-yl)-2-[(2-pyrrolidin-1-yl-pyridin-4-ylmethyl)-amino]-nicotinamide;

tert-Butyl N-[4,4-Dimethyl-7-({2-[(2-pyrrolidin-1-yl-pyridin-4-ylmethyl)-amino]-pyridine-3-carbonyl}-amino)-3,4-dihydro-1H-isoquinoline]carbamate;

N-(4,4-Dimethyl-1,2,3,4-tetrahydro-isoquinolin-7-yl)-2-[(2-pyrrolidin-1-yl-pyridin-4-ylmethyl)-amino]-nicotinamide;

N-{4-[1-Methyl-1-(1-methyl-piperidin-4-yl)-ethyl]-phenyl}-2-[(2-pyrrolidin-1-yl-pyridin-4-ylmethyl)-amino]-nicotinamide;

2-[(2-Pyrrolidin-1-yl-pyridin-4-ylmethyl)-amino]-N-(4-trifluoromethyl-phenyl)-nicotinamide;

N-(4-Pentafluoroethyl-phenyl)-2-[(2-pyrrolidin-1-yl-pyridin-4-ylmethyl)-amino]-nicotinamide;

N-{4-[1-Methyl-1-(1-methyl-piperidin-4-yl)-ethyl]-phenyl}-2-[(2-morpholin-4-yl-pyridin-4-ylmethyl)-amino]-nicotinamide;

2-[(2-Morpholin-4-yl-pyridin-4-ylmethyl)-amino]-N-(4-trifluoromethyl-phenyl)-nicotinamide;

N-[3-(1-Methyl-pyrrolidin-2-ylmethoxy)-5-trifluoromethyl-phenyl]-2-[(2-morpholin-4-yl-pyridin-4-ylmethyl)-amino]-nicotinamide;

N-[3-(1-Methyl-pyrrolidin-2-ylmethoxy)-5-trifluoromethyl-phenyl]-2-[(2-pyrrolidin-1-yl-pyridin-4-ylmethyl)-amino]-nicotinamide;

2-[(2-Amino-pyridin-4-ylmethyl)-amino]-N-{4-[1-methyl-1-(5-methyl-[1,3,4]oxadiazol-2-yl)-ethyl]phenyl}-nicotinamide;

2-[(2,3-Dihydro-benzofuran-5-ylmethyl)-amino]-N-{4-[1-methyl-1-(5-methyl-[1,3,4]oxadiazol-2-yl)-ethyl]-phenyl}-nicotinamide;

2-[(2-Methylamino-pyridin-4-ylmethyl)-amino]-N-{4-[1-methyl-1-(5-methyl-[1,3,4]oxadiazol-2-yl)-ethyl]-phenyl}-nicotinamide;

2-[(2-Methylamino-pyrimidin-4-ylmethyl)-amino]-N-{4-[1-methyl-1-(2H-pyrazol-3-yl)-ethyl]-phenyl}-nicotinamide;

N-(3,3-Dimethyl-1-pyrrolidin-(2S)-ylmethyl-2,3-dihydro-1H-indol-6-yl)-2-[(2-methoxy-pyridin-4-ylmethyl)-amino]-nicotinamide;

N-(3,3-Dimethyl-1-pyrrolidin-(2S)-ylmethyl-2,3-dihydro-1H-indol-6-yl)-2-[(pyridin-4-ylmethyl)-amino]-nicotinamide;

N-(4,4-Dimethyl-1,2,3,4-tetrahydro-isoquinolin-7-yl)-2-[(2-methoxy-pyridin-4-ylmethyl)-amino]-nicotinamide;

N-[3,3-Dimethyl-1-L-(pyrrolidine-2-carbonyl)-2,3-dihydro-1H-indol-6-yl]-2-[(2-methoxy-pyridin-4-ylmethyl)-amino]-nicotinamide;

2-[(2-Methoxy-pyridin-4-ylmethyl)-amino]-N-[3-(1-methyl-pyrrolidin-(2R)-ylmethoxy)-5-trifluoromethylphenyl]-nicotinamide;

3-[(2-Methoxy-pyridin-4-ylmethyl)-amino]-pyridazine-4-carboxylic acid (4-tert-butylphenyl)-amide;

N-{4-[1-Methyl-1-(1-methyl-piperidin-4-yl)-ethyl]-phenyl}-2-{[2-(2,2,2-trifluoro-ethoxy)-pyridin-4-ylmethyl]-amino}-nicotinamide;

N-[1-(2-Dimethylamino-acetyl)-3,3-dimethyl-2,3-dihydro-1H-indol-6-yl]-2-{[2-(2,2,2-trifluoro-ethoxy)-pyridin-4-ylmethyl]-amino}-nicotinamide;

2-[(Pyridin-4-ylmethyl)-amino]-N-(1,3,3-trimethyl-2,3-dihydro-1H-indol-6-yl)-nicotinamide;

N-[4-(1,1-Dimethyl-2-pyrrolidin-1-yl-ethyl)-phenyl]-2-[(pyrimidin-4-ylmethyl)-amino]-nicotinamide;
N-[4-(1,1-Dimethyl-2-morpholin-4-yl-ethyl)-phenyl]-2-[(pyrimidin-4-ylmethyl)-amino]-nicotinamide;
2-[(2-Methylamino-pyridin-4-ylmethyl)-amino]-N-{4-[1-methyl-1-(2-methylsulfanyl-pyrimidin-4-ylamino)-ethyl]-phenyl}-nicotinamide;
2-[(2-N-(4,4-Dimethyl-1,2,3,4-tetrahydro-quinolin-7-yl)-2-[(2-methylamino-pyridin-4-ylmethyl)-amino]-nicotinamide;
N-(4,4-Dimethyl-1,2,3,4-tetrahydro-isoquinolin-7-yl)-2-[(quinolin-4-ylmethyl)-amino]-nicotinamide.

18. Compound of claim 1 and pharmaceutically acceptable salts thereof selected from N-(3,3-Dimethyl-2,3-dihydro-1H-indol-6-yl)-2-((4-quinolinylmethyl)amino)-3-pyridinecarboxamide;
N-(3,3-Dimethyl-2,3-dihydro-1H-indol-6-yl)-2-[(2-methylamino-pyridin-4-ylmethyl)-amino]-nicotinamide;
N-(4,4-Dimethyl-2-oxo-1,2,3,4-tetrahydro-quinolin-7-yl)-2-[(2-methylamino-pyrimidin-4-ylmethyl)-amino]-nicotinamide;
Ethyl[1,2-dihydro-6-({2-[(2-methylamino-pyridin-4-ylmethyl)-amino]-pyridine-3-carbonyl}-amino)-3-spiro-1'-cyclopropyl-1H-indole]-1-carbamate;
2-[(2-Amino-pyridin-4-ylmethyl)-amino]-N-(4,4-dimethyl-1,2,3,4-tetrahydro-quinolin-7-yl)-nicotinamide;
N-(1-acetyl-3,3-dimethyl-2,3-dihydro-1H-indol-6-yl)-2-(((2-(methylamino)-4-pyrimidinyl)methyl)amino)-3-pyridinecarboxamide;
2-(((2-(methylamino)-4-pyrimidinyl)methyl)amino)-N-(2,4,4-trimethyl-1,2,3,4-tetrahydro-7-isoquinolinyl)-3-pyridinecarboxamide;
N-(3,3-dimethyl-1-(methylsulfonyl)-2,3-dihydro-1H-indol-6-yl)-2-((4-pyridinylmethyl)amino)-3-pyridinecarboxamide;
N-(1-Acetyl-3,3-dimethyl-2,3-dihydro-1H-indol-6-yl)-2-[(2-methylamino-pyridin-4-ylmethyl)-amino]-nicotinamide;
N-(4,4-Dimethyl-1,2,3,4-tetrahydro-quinolin-7-yl)-2-[(pyrimidin-4-ylmethyl)-amino]-nicotinamide;
N-(1-Ethyl-4,4-dimethyl-1,2,3,4-tetrahydro-quinolin-7-yl)-2-[(pyridin-4-ylmethyl)-amino]-nicotinamide;
N-(4,4-Dimethyl-1,2,3,4-tetrahydro-isoquinolin-7-yl)-2-[(quinolin-4-ylmethyl)-amino]-nicotinamide;
N-(3,3-dimethyl-1-(methylsulfonyl)-2,3-dihydro-1H-indol-6-yl)-2-(((2-(methylamino)-4-pyridinyl)methyl)amino)-3-pyridinecarboxamide;
N-(1-(N,N-Dimethylglycyl)-3,3-dimethyl-2,3-dihydro-1H-indol-6-yl)-2-(((2-(methylamino)-4-pyrimidinyl)methyl)amino)-3-pyridinecarboxamide;
N-(3,3-dimethyl-1-(methylsulfonyl)-2,3-dihydro-1H-indol-6-yl)-2-(((2-(methylamino)-4-pyrimidinyl)methyl)amino)-3-pyridinecarboxamide;
2-[(2-Amino-pyridin-4-ylmethyl)-amino]-N-(1-ethyl-4,4-dimethyl-1,2,3,4-tetrahydro-quinolin-7-yl)-nicotinamide;
2-[(Pyridin-4-ylmethyl)-amino]-N-(1,3,3-trimethyl-2,3-dihydro-1H-indol-6-yl)-nicotinamide;
N-(4,4-Dimethyl-1,2,3,4-tetrahydro-isoquinolin-7-yl)-2-[(2-methoxy-pyrimidin-4-ylmethyl)-amino]-nicotinamide;
2-[(2,3-Dihydro-1H-pyrrolo[2,3-b]pyridin-4-ylmethyl)-amino]-N-(4,4-dimethyl-1,2,3,4-tetrahydro-isoquinolin-7-yl)-nicotinamide;
N-(3,3-Dimethyl-1-pyrrolidin-(2S)-ylmethyl-2,3-dihydro-1H-indol-6-yl)-2-[(pyrimidin-4-ylmethyl)-amino]-nicotinamide;
2-(((2-amino-4-pyridinyl)methyl)amino)-N-(3,3-dimethyl-1-(methylsulfonyl)-2,3-dihydro-1H-indol-6-yl)-3-pyridinecarboxamide;
2-(((2-(Methylamino)-4-pyrimidinyl)methyl)amino)-N-(2-oxo-3,3-bis(trifluoromethyl)-2,3-dihydro-1H-indol-6-yl)-3-pyridinecarboxamide;
N-(1-(N,N-Dimethylglycyl)-3,3-dimethyl-2,3-dihydro-1H-indol-6-yl)-2-((4-quinolinylmethyl)amino)-3-pyridinecarboxamide;
N-(4,4-dimethyl-1,2,3,4-tetrahydro-7-isoquinolinyl)-2-((6-quinolinylmethyl)amino)-3-pyridinecarboxamide;
N-(4,4-Dimethyl-1,2,3,4-tetrahydro-isoquinolin-7-yl)-2-[(2-methoxy-pyridin-4-ylmethyl)-amino]-nicotinamide;
2-(((2-Amino-4-pyridinyl)methyl)amino)-N-(4,4-dimethyl-1,2,3,4-tetrahydro-7-isoquinolinyl)-3-pyridinecarboxamide;
N-(4-Spiro-1'-cyclopropane-1,2,3,4-tetrahydroisoquinolin-7-yl)-2-[(2-methoxy-pyridin-4-ylmethyl)-amino]-nicotinamide;
N-[3,3-Dimethyl-1-(1-oxy-pyridine-4-carbonyl)-2,3-dihydro-1H-indol-6-yl]-2-[(pyridin-4-ylmethyl)-amino]-nicotinamide;
N-(1,2-dihydroindol-3-spiro-1'-cyclopropane-6-yl)-2-[(2-methylaminopyridin-4-ylmethyl)-amino]-nicotinamide;
N-(4,4-Dimethyl-1,2,3,4-tetrahydro-isoquinolin-7-yl)-2-[(2-methylamino-pyridin-4-ylmethyl)-amino]-nicotinamide;
N-(1-acetyl-3,3-dimethyl-2,3-dihydro-1H-indol-6-yl)-2-(((2-(methyloxy)-4-pyrimidinyl)methyl)amino)-3-pyridinecarboxamide;
N-(3,3-Dimethyl-2,3-dihydro-1H-indol-6-yl)-2-((4-pyrimidinylmethyl)amino)-3-pyridinecarboxamide;
N-(4,4-Dimethyl-1,2,3,4-tetrahydro-quinolin-7-yl)-2-[(2-methoxy-pyridin-4-ylmethyl)-amino]-nicotinamide;
N-(4,4-Dimethyl-2-oxo-1,2,3,4-tetrahydro-quinolin-7-yl)-2-[(pyridin-4-ylmethyl)-amino]-nicotinamide;
N-(4,4-Dimethyl-1,2,3,4-tetrahydro-quinolin-7-yl)-2-[(2-morpholin-4-yl-pyridin-4-ylmethyl)-amino]-nicotinamide;
N-[3,3-Dimethyl-1-(1-oxy-pyridin-4-ylmethyl)-2,3-dihydro-1H-indol-6-yl]-2-[(pyridin-4-ylmethyl)-amino]-nicotinamide;
N-(4,4-Dimethyl-2-oxo-1,2,3,4-tetrahydro-quinolin-7-yl)-2-[(2-methoxy-pyridin-4-ylmethyl)-amino]-nicotinamide;
N-(4,4-Dimethyl-2-oxo-1,2,3,4-tetrahydro-quinolin-7-yl)-2-[(2-methylamino-pyridin-4-ylmethyl)-amino]-nicotinamide;
N-(1-Acetyl-3,3-dimethyl-2,3-dihydro-1H-indol-6-yl)-2-((4-pyrimidinylmethyl)amino)-3-pyridinecarboxamide;
N-(4,4-Dimethyl-1,2,3,4-tetrahydro-7-isoquinolinyl)-2-(((2-(methylamino)-4-pyrimidinyl)methyl)amino)-3-pyridinecarboxamide;
N-(4,4-Dimethyl-1,2,3,4-tetrahydro-isoquinolin-7-yl)-2-[(1H-pyrrolo[2,3-b]pyridin-4-ylmethyl)-amino]-nicotinamide;

N-(4,4-Dimethyl-1,2,3,4-tetrahydro-quinolin-7-yl)-2-[(pyridin-4-ylmethyl)-amino]-nicotinamide;

Ethyl[1,2-dihydro-6-({2-[(2-methylamino-pyrimidin-4-ylmethyl)-amino]-pyridine-3-carbonyl}-amino)-3-spiro-1'-cyclopropyl-1H-indole]-1-carbamate;

N-(5,5-Dimethyl-7-oxo-5,6,7,8-tetrahydro-[1,8]naphthyridin-2-yl)-2-[(2-methylamino-pyrimidin-4-ylmethyl)-amino]-nicotinamide;

N-(3,3-Dimethyl-2,3-dihydro-1H-indol-6-yl)-2-(((2-(methylamino)-4-pyrimidinyl)methyl)amino)-3-pyridinecarboxamide; and N-(4,4-Dimethyl-1,2,3,4-tetrahydro-quinolin-7-yl)-2-[(2-methylamino-pyrimidin-4-ylmethyl)-amino]-nicotinamide.

19. A compound of Formula XIII:

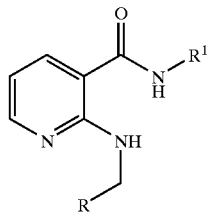

XIII wherein R is selected from
   a) unsubstituted or substituted 5- or 6-membered rings selected from 4-pyridyl, 2-pyridyl, 4-pyrimidinyl, and tetrahydro-2H-pyran-4-yl, and
   b) unsubstituted or substituted 9- or 10-membered fused rings selected from 4-quinolyl, 6-quinolyl, 2,3-dihydro-5-benzofuryl, 5-benzoxazolyl, 1H-pyrrolo[2,3-b]pyridin-4-yl, and 2,3-dihydro-1H-pyrrolo[2,3-b]pyridin-4-yl,
   where substituted R is substituted with one or more substituents selected from halo, amino, hydroxy, oxo, $C_{1-6}$-alkyl, $C_{1-6}$-haloalkyl, $C_{1-6}$-alkylaminocarbonyl, $C_{1-6}$-alkoxy, optionally substituted heterocyclyl-$C_{1-6}$-alkoxy, optionally substituted heterocyclyl-$C_{1-6}$-alkylamino, optionally substituted heterocyclyl-$C_{1-6}$-alkyl, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl; and
   wherein $R^1$ is phenyl substituted with one or more substituents selected from chloro, 2-methyl-2-(1-methylpiperidin-4-yl)ethyl, 2-methyl-2-(5-methyloxadiazol-2-yl)ethyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, isopropyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolindin-2-ylmethoxy, pyrrolindin-1-ylethoxy, 1-isopropyl-pyrrolindin-2-ylmethoxy, 3-tetrahydrofurylmethoxy, azetidin-3-ylmethoxy, and methylsulfonylaminoethoxy;
   provided $R^1$ is phenyl substituted with at least one substituent selected from 2-methyl-2-(1-methylpiperidin-4-yl)ethyl, 2-methyl-2-(5-methyloxadiazol-2-yl)ethyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolindin-2-ylmethoxy, pyrrolindin-1-ylethoxy, 1-isopropyl-pyrrolindin-2-ylmethoxy, 3-tetrahydrofurylmethoxy, azetidin-3-ylmethoxy, and methylsulfonylaminoethoxy when R is 4-pyridyl, 2-pyridyl, 4-pyrimidinyl, 4-quinolyl, 6-quinolyl, 5-benzoxazolyl, or 1H-pyrrolo[2,3-b]pyridin-4-yl;
and pharmaceutically acceptable derivatives thereof.

20. Compound of claim 19 wherein $R^1$ is phenyl substituted with one or more substituents selected from chloro, 2-methyl-2-(1-methylpiperidin-4-yl)ethyl, 2-methyl-2-(5-methyloxadiazol-2-yl)ethyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, isopropyl, tert-butyl, trifluoromethyl, pentafluoroethyl, 1,1-di(trifluoromethyl)-1-hydroxymethyl, 1,1-di(trifluoromethyl)-1-(pyrrolidin-2-ylmethoxy)methyl, 3-tetrahydrofuryloxy, 1-methylcarbonyl-pyrrolidin-2-ylmethoxy, 1-methyl-pyrrolindin-2-ylmethoxy, pyrrolindin-1-ylethoxy, 1-isopropyl-pyrrolindin-2-ylmethoxy, 3-tetrahydrofurylmethoxy, azetidin-3-ylmethoxy, and methylsulfonylaminoethoxy; and pharmaceutically acceptable derivatives thereof.

21. Compound of claim 19 wherein R is selected from 2-methylamino-4-pyrimidinyl, 4-pyrimidinyl, 4-quinolyl, 2-methylamino-4-pyridyl, 1H-pyrrolo[2,3-b]pyridin-4-yl, 4-pyridyl, 2-amino-4-pyridyl, 2-methoxy-4-pyrimidinyl, 6-quinolyl, 2-methoxy-4-pyridyl, 2-methylaminocarbonyl-4-pyridyl, 2-morpholino-4-pyridyl, and 2-trifluoromethoxy-4-pyridyl.

22. Compound of claim 19 wherein R is 4-quinolyl.

23. Compound of claim 19 wherein R is 2-methylamino-4-pyridyl.

24. Compound of claim 19 wherein R is 4-pyridyl and N-oxides thereof.

25. Compound of claim 19 wherein R is 4-pyrimidinyl.

26. Compound of claim 19 wherein R is 2-methoxy-4-pyrimidinyl.

27. Compound of claim 19 wherein R is 2-methoxy-4-pyridyl.

28. Compound of claim 19 wherein R is 2-methylamino-4-pyrimidinyl.

29. Compound of claim 19 and pharmaceutically acceptable salts thereof selected from 2-[(2-Methylamino-pyrimidin-4-ylmethyl)-amino]-N-[3-(1-methyl-pyrrolidin-2-ylmethoxy)-5-trifluoromethyl-phenyl]-nicotinamide;

2-(((2-(methylamino)-4-pyrimidinyl)methyl)amino)-N-(3-((2-((methylsulfonyl)amino)ethyl)oxy)-5-(trifluoromethyl)phenyl)-3-pyridinecarboxamide;

(3S)-tetrahydro-3-furanyl 3-(((2-(((2-(methylamino)-4-pyrimidinyl)methyl)amino)-3-pyridinyl)carbonyl)amino)-5-(trifluoromethyl)phenylcarbamate;

2-[(Pyridin-4-ylmethyl)-amino]-N-{3-[2,2,2-trifluoro-1-(pyrrolidin-2-ylmethoxy)-1-trifluoromethyl-ethyl]-phenyl}-nicotinamide;

N-[3-Chloro-5-(2-dimethylamino-acetylamino)-phenyl]-2-[(2-methylamino-pyridin-4-ylmethyl)-amino]-nicotinamide;

N-(4-(1,1-dimethylethyl)-3-((N,N-dimethylglycyl)amino)phenyl)-2-(((2-(methylamino)-4-pyrimidinyl)methyl)amino)-3-pyridinecarboxamide;

2-(((2-(methylamino)-4-pyrimidinyl)methyl)amino)-N-(3-((3R)-tetrahydro-3-furanyloxy)-5-(trifluoromethyl)phenyl)-3-pyridinecarboxamide;

N-(3-((2-(1-pyrrolidinyl)ethyl)oxy)-4-(trifluoromethyl)phenyl)-2-((4-quinolinylmethyl)amino)-3-pyridinecarboxamide;

N-(3-((2-((Methylsulfonyl)amino)ethyl)oxy)-4-(trifluoromethyl)phenyl)-2-((4-pyridinylmethyl)amino)-3-pyridinecarboxamide;

2-(((2-(methylamino)-4-pyrimidinyl)methyl)amino)-N-(4-(1-methyl-1-(1-methyl-4-piperidinyl)ethyl)phenyl)-3-pyridinecarboxamide;

2-[(2-Methylamino-pyridin-4-ylmethyl)-amino]-N-[3-(1-methyl-pyrrolidin-2-ylmethoxy)-5-trifluoromethyl-phenyl]-nicotinamide;

N-(3-((((2S)-1-Methyl-2-pyrrolidinyl)methyl)oxy)-5-(trifluoromethyl)phenyl)-2-((4-pyrimidinylmethyl)amino)-3-pyridinecarboxamide;

N-(3-((2-((Methylsulfonyl)amino)ethyl)oxy)-4-(pentafluoroethyl)phenyl)-2-((4-pyridinylmethyl)amino)-3-pyridinecarboxamide;

(3S)-tetrahydro-3-furanyl 3-(((2-((4-pyridinylmethyl)amino)-3-pyridinyl)carbonyl)amino)-5-(trifluoromethyl)phenylcarbamate;

2-((4-Pyrimidinylmethyl)amino)-N-(3-((2-(1-pyrrolidinyl)ethyl)oxy)-4-(trifluoromethyl)phenyl)-3-pyridinecarboxamide;

N-(4-(1-Methyl-1-(1-methyl-4-piperidinyl)ethyl)phenyl)-2-((4-quinolinylmethyl)amino)-3-pyridinecarboxamide;

2-[(2-Methylamino-pyrimidin-4-ylmethyl)-amino]-N-{4-[1-methyl-1-(1-methyl-piperidin-4-yl)-ethyl]-phenyl}-nicotinamide;

N-(4-(1,1-dimethylethyl)-3-((N,N-dimethylglycyl)amino)phenyl)-2-((4-quinolinylmethyl)amino)-3-pyridinecarboxamide;

N-(3-((methylsulfonyl)amino)-5-(trifluoromethyl)phenyl)-2-((4-pyridinylmethyl)amino)-3-pyridinecarboxamide;

N-(4-(1,1-dimethylethyl)-3-(((2S)-2-pyrrolidinylmethyl)oxy)phenyl)-2-(((2-(methyloxy)-4-pyridinyl)methyl)amino)-3-pyridinecarboxamide;

N-(3-((((2R)-1-acetyl-2-pyrrolidinyl)methyl)oxy)-5-(trifluoromethyl)phenyl)-2-(((2-(methylamino)-4-pyrimidinyl)methyl)amino)-3-pyridinecarboxamide;

N-(3-((2-((methylsulfonyl)amino)ethyl)oxy)-5-(trifluoromethyl)phenyl)-2-((4-pyridinylmethyl)amino)-3-pyridinecarboxamide;

2-[(Pyridin-4-ylmethyl)-amino]-N-{4-[2,2,2-trifluoro-1-(pyrrolidin-2-ylmethoxy)-1-trifluoromethyl-ethyl]-phenyl}-nicotinamide;

2-(((2-(Methylamino)-4-pyrimidinyl)methyl)amino)-N-(3-((2-((methylsulfonyl)amino)ethyl)oxy)-4-(trifluoromethyl)phenyl)-3-pyridinecarboxamide;

2-(((2-(methyloxy)-4-pyrimidinyl)methyl)amino)-N-(3-((((2S)-1-methyl-2-pyrrolidinyl)methyl)oxy)-5-(trifluoromethyl)phenyl)-3-pyridinecarboxamide;

N-(4-(1,1-dimethylethyl)-3-((N,N-dimethylglycyl)amino)phenyl)-2-(((2-(methyloxy)-4-pyrimidinyl)methyl)amino)-3-pyridinecarboxamide;

(3S)-tetrahydro-3-furanyl 3-(((2-((4-pyrimidinylmethyl)amino)-3-pyridinyl)carbonyl)amino)-5-(trifluoromethyl)phenylcarbamate;

2-(((2-(methylamino)-4-pyrimidinyl)methyl)amino)-N-(3-((methylsulfonyl)amino)-5-(trifluoromethyl)phenyl)-3-pyridinecarboxamide;

N-(3-((((2S)-1-(1-methylethyl)-2-pyrrolidinyl)methyl)oxy)-5-(trifluoromethyl)phenyl)-2-((4-pyridinylmethyl)amino)-3-pyridinecarboxamide;

2-(((2-(methylamino)-4-pyrimidinyl)methyl)amino)-N-(3-((((2R)-1-methyl-2-pyrrolidinyl)methyl)oxy)-5-(trifluoromethyl)phenyl)-3-pyridinecarboxamide; and N-(4-(1-Methyl-1-(1-methyl-4-piperidinyl)ethyl)phenyl)-2-((4-quinolinylmethyl)amino)-3-pyridinecarboxamide.

30. A pharmaceutical composition comprising a pharmaceutically-acceptable carrier and a compound as in any of claims 1–9, 20–16, 17 and 19–28.

31. A method of treating cancer in a subject, said method comprising administering an effective amount of a compound as in any of claims 1–17.

32. The method of claim 31 comprising a combination with a compound selected from antibiotic-type agents, alkylating agents, antimetabolite agents, hormonal agents, immunological agents, interferon-type agents and miscellaneous agents.

33. A method of treating angiogenesis in a subject, said method comprising administering an effective amount of a compound as in any of claims 1–17.

34. A method of treating KDR-related disorders in a mammal, said method comprising administering an effective amount of a compound of claims 1–17.

35. A method of treating proliferation-related disorders in a mammal, said method comprising administering an effective amount of a compound of any of claim 1–17.

36. Method of claim 35 wherein the disorder is inflammation or an inflammation-related disorder.

37. A method of reducing blood flow in a tumor in a subject, said method comprising administering an effective amount of a compound as in any of claims 1–17.

38. A method of reducing tumor size in a subject, said method comprising administering an effective amount of a compound as in any of claims 1–17.

39. A method of treating diabetic retinopathy in a subject, said method comprising administering an effective amount of a compound as in any of claims 1–17.

* * * * *